United States Patent
Barbour et al.

(10) Patent No.: US 11,414,404 B2
(45) Date of Patent: Aug. 16, 2022

(54) COMPOUNDS FOR THE TREATMENT OF BRAF-ASSOCIATED DISEASES AND DISORDERS

(71) Applicant: Array BioPharma Inc., Boulder, CO (US)

(72) Inventors: Patrick Michael Barbour, Westminster, CO (US); Katie Keaton Brown, Niwot, CO (US); Adam Wade Cook, Broomfield, CO (US); Erik James Hicken, Longmont, CO (US); Dean Russell Kahn, Longmont, CO (US); Ellen Ruth Laird, Longmont, CO (US); Andrew Terrance Metcalf, Erie, CO (US); David Austin Moreno, Centennial, CO (US); Bradley Jon Newhouse, Broomfield, CO (US); Spencer Phillip Pajk, Boulder, CO (US); Brett Joseph Prigaro, Broomfield, CO (US); Li Ren, Superior, CO (US); Eugene Tarlton, Lafayette, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 16/910,688

(22) Filed: Jun. 24, 2020

(65) Prior Publication Data
US 2020/0407344 A1   Dec. 31, 2020

Related U.S. Application Data

(60) Provisional application No. 63/021,410, filed on May 7, 2020, provisional application No. 62/868,581, filed on Jun. 28, 2019.

(51) Int. Cl.
| | | |
|---|---|---|
| *C07D 403/12* | (2006.01) | |
| *C07D 239/90* | (2006.01) | |
| *C07D 239/91* | (2006.01) | |
| *A61K 31/4184* | (2006.01) | |
| *A61K 45/06* | (2006.01) | |

(52) U.S. Cl.
CPC ......... *C07D 403/12* (2013.01); *C07D 239/90* (2013.01); *C07D 239/91* (2013.01); *A61K 31/4184* (2013.01); *A61K 45/06* (2013.01)

(58) Field of Classification Search
CPC .. C07D 239/90; C07D 239/91; C07D 401/12; C07D 403/12; A61K 31/517
See application file for complete search history.

(56) References Cited

FOREIGN PATENT DOCUMENTS

| WO | 2006/024834 | 3/2006 |
| WO | 2007/113557 | 4/2007 |
| WO | 2007/113558 | 10/2007 |
| WO | 2007/119055 | 10/2007 |
| WO | 2009/012283 | 1/2009 |
| WO | 2012/118492 | 9/2012 |
| WO | 2013/070996 | 5/2013 |
| WO | 2019060611 | 3/2019 |

OTHER PUBLICATIONS

Ulrich, Crystallization, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
International Searching Authority, Search Report dated Sep. 28, 2020, PCT/IB2020/055992 Filing date Jun. 24, 2020, Array BioPharma Inc.
Achrol A.S., et al., Brain metastases, Nature Reviews (2019), 5:5, pp. 1-26.
Behling, F., et al., Frequency of BRAF V600E mutations in 969 central nervous system neoplasms, Diagnostic Pathol 11(1):55, 2016.
Berghoff, AS, Preusser M., BRAF alterations in brain tumours: molecular pathology and therapeutic opportunities, Curr Opin Neurol (2014) 27(6):689-696.
Brastianos et al., Exome sequencing identifies BRAF mutations in papillary craniopharyngiomas, Nat Genet 46 (2):161-165, 2014.
Davies H., et al., Mutations of the BRAF gene in human cancer, Nature 417(6892):949-954, 2002.
Dagogo-Jack, I., et al., Impact of BRAF Mutation Class on Disease Characteristics and Clinical Outcomes in BRAF-Mutant Lung Cancer, Clin Cancer Res. 2018.
Dankner, et al., Dual MAPK Inhibition Is an Effective Therapeutic Strategy for a Subset of Class II BRAF Mutant Melanomas, Clin. Cancer Research, 2018.
Dougherty, M.J., et al., Activating mutations in BRAF characterize a spectrum of pediatric low-grade gliomas, Neuro Oncol, 12(7):621-630, 2010.
Eleveld, TF, et al., Relapsed neuroblastomas show frequent RAS-MAPK pathway mutations, Nat Genet 47(8):864-871, 2015.
Flaherty KT, et al., From genes to drugs: targeted strategies for melanoma, Nat Rev Cancer (2012) 12(5):349-361.

(Continued)

*Primary Examiner* — Deepak R Rao
(74) *Attorney, Agent, or Firm* — Zhigang Rao

(57) ABSTRACT

Provided herein are compounds of the Formula I:

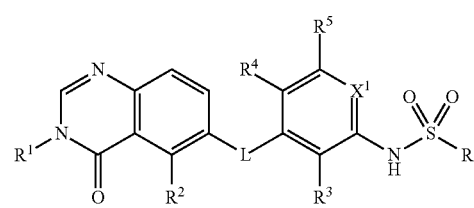

and pharmaceutically acceptable salts, solvates and polymorphs thereof, wherein L, $X^1$, $R^1$, $R^2$, $R^3$, $R^4$, $R^5$ and $R^6$ are as defined herein, for the treatment of BRAF-associated diseases and disorders, including BRAF-associated tumors, including malignant and benign BRAF-associated tumors of the CNS and malignant extracranial BRAF-associated tumors.

14 Claims, 17 Drawing Sheets

(56) References Cited

OTHER PUBLICATIONS

Grisham, R.N., et al., BRAF Mutation is Associated with Early Stage Disease and Improved Outcome in Patients with Low-Grade Serous Ovarian Cancer, Cancer, 2013; 119(3): 548-554.

Johnson, B. E., et al., Mutational Analysis Reveals the Origin and Therapy-driven Evolution of Recurrent Glioma, Science, 343(6167): 189-193 (2014).

Kaley, et al., BRAF Inhibition in BRAFV600-Mutant Gliomas: Results From the VE-BASKET Study, J Clin Oncol, vol. 36, No. 35, 2018.

Kim, WW et al., Clinical implications of the BRAF mutation in papillary thyroid carcinoma and chronic lymphocytic thyroiditis, J Otolaryngol Head Neck Surg. 2018; 47:4, 1-6.

Lehman, N.L., et al., Morphological and molecular features of astroblastoma, including BRAFV600E mutations, suggest an ontological relationship to other cortical-based gliomas of children and young adults, Neuro Oncol 19 (1):31-42, 2017.

Levy, et al., Autophagy Inhibition Improves Chemosensitivity in BRAF V600E Brain TumorsJM et al. Cancer Discov 4 (7):773-780, 2014.

Ma, XH et al., Targeting ER stress-induced autophagy overcomes BRAF inhibitor resistance in melanoma, J Clin Invest 124(3):1406-1417, 2014.

Mittapalli, RK, et al., Mechanisms Limiting Distribution of the Threonine-Protein Kinase B-RaFV600E Inhibitor Dabrafenib to the Brain: Implications for the Treatment of Melanoma Brain MetastasessJ Pharmacol. Exp Ther 344:655-664, Mar. 2013.

Mittapalli, RK. et al., Impact of P-Glycoprotein (ABCB1) and Breast Cancer Resistance Protein (ABCG2) on the Brain Distribution of a Novel BRAF Inhibitor: Vemurafenib (PLX4032)J Pharmacol. Exp Ther 342:33-40, Mar. 2012.

Montero-Conde et al., Relief of Feedback Inhibition of HER3 Transcription by RAF and MEK Inhibitors Attenuates Their Antitumor Effects in BRAF—Mutant Thyroid CarcinomasCancer Discov 3(5):520-533, 2013.

Mordechai, O., et al., Metastatic Rhabdoid Meningioma with BRAF V600E Mutation and Good Response to Personalized Therapy: Case Report and Review of the LiteraturePediatr Hematol Oncol 32(3):207-211, 2015.

Myung et al., Analysis of the BRAFV600E Mutation in Central Nervous System Tumors1Transl Oncol 5(6):430-436, 2012.

Oliva I.C.G, et al., Advances in the systemic treatment of melanoma brain metastases, Annals of Oncology, 29: 1509-1520 (2018).

Schindler, G., et al., Analysis of BRAF V600E mutation in 1,320 nervous system tumors reveals high mutation frequencies in pleomorphic xanthoastrocytoma, ganglioglioma and extra-cerebellar pilocytic astrocytoma, Acta Neuropathol 121(3):397-405, 2011.

Schreck, et al. BRAF Mutations and the Utility of RAF and MEK Inhibitors in Primary Brain Tumors, Cancers 2019, 11, 1262.

Yao, TW et al., Acquired resistance to BRAF inhibition in BRAFV600E mutant gliomas, Oncotarget, 8(1):583-595, 2017.

Ywo, Z., et al., BRAF mutants evade ERK dependent feedback by different mechanisms that determine their sensitivity to pharmacologic inhibition, Cancer Cell, 28(3):370-383, 2015.

Wenglowsky, et al., Highly potent and selective 3-N-methylquinazoline-4(3H)-one based inhibitors of B-Raf V600E Kinase, Bioorg Med Chem Lett, 1923-1927, 2014.

* cited by examiner

COMPOUNDS FOR THE TREATMENT OF BRAF-ASSOCIATED DISEASES AND DISORDERS

CROSS-REFERENCE TO RELATED APPLICATIONS

This application claims priority to U.S. Provisional Application Ser. No. 63/021,410, filed May 7, 2020 and U.S. Provisional Application Ser. No. 62/868,581, filed Jun. 28, 2019, each of which is incorporated by reference in their entireties herein.

BACKGROUND

The present disclosure relates to 5-substituted quinazolinones for the treatment of BRAF-associated diseases and disorders, including BRAF-associated tumors, including malignant and benign BRAF-associated tumors of the CNS and malignant extracranial BRAF-associated tumors.

BRAF protein, a member of the RAF family of serine/threonine kinases, participates in the cascade of the Ras-Raf-MEK-extracellular signal-regulated kinase (ERK) pathway or mitogen-activated protein kinase (MAPK)/ERK signaling pathway that affects cell division and differentiation. Mutations in the BRAF gene can lead to uncontrolled growth and subsequent tumor formation. It has been shown that BRAF is mutated and/or overactivated in common human cancers such as melanoma, colorectal cancer, thyroid cancer, non-small cell lung cancer, and ovarian cancer and metastatic cancers thereof, and primary brain tumors. Although certain BRAF inhibitors produce excellent extracranial responses, a cancer may still develop brain metastases during, or subsequent to, therapy with BRAF inhibitors (Oliva I. C. G, et al., Annals of Oncology, 29: 1509-1520 (2018)). An estimated 20% of all subjects with cancer will develop brain metastases, with the majority of brain metastases occurring in those with melanoma, colorectal cancer, lung cancer, and renal cell carcinoma (Achrol A. S., et al., Nature Reviews (2019), 5:5, pp 1-26). Although these are the most likely types to do so, any type of cancer could spread to the brain. Development of brain metastases remains a substantial contributor to overall cancer mortality in subjects with advance-stage cancer because prognosis remains poor despite multimodal treatments and advances in systemic therapies, which includes combinations of surgery, radiotherapy, chemotherapy, immunotherapy, and/or targeted therapies.

Additionally, BRAF has been identified as a potential target for treating primary brain tumors. The prevalence of the BRAF-V600E mutation in primary brain tumors has been reported by Schindler et al. (Acta Neuropathol 121(3): 397-405, 2011) from the analysis of 1,320 central nervous system (CNS) tumors and by Behling et al. (Diagn Pathol 11(1):55, 1-10, 2016), who analyzed 969 CNS tumors in pediatric and adult populations. These studies, in combination with others, report the presence of BRAF-V600E mutations in various cancers, including papillary craniopharyngiomas, pleomorphic xanthoastrocytomas (PXAs), gangliogliomas, astroblastomas, and others. (Behling et al., Diagn Pathol 11(1):55, 1-10, 2016; Brastianos et al., Nat Genet 46(2):161-165, 2014; Dougherty et al., Neuro Oncol 12(7):621-630, 2010; Lehman et al., Neuro Oncol 19(1):31-42, 2017; Mordechai et al., Pediatr Hematol Oncol 32(3): 207-211, 2015; Myung et al., Transl Oncol 5(6):430-436, 2012; Schindler et al., Acta Neuropathol 121(3):397-405, 2011).

The blood brain barrier (BBB) is a highly selective physical, transport and metabolic barrier that divides the CNS from the blood. The BBB may prevent certain drugs from entering brain tissue and is a limiting factor in the delivery of many peripherally-administered agents to the CNS. Many drugs commonly used to treat cancer are not able to cross the BBB. This means the drugs are not able to penetrate the brain, and therefore cannot effectively kill cancer cells in the brain. Current treatments for subjects with brain tumors include surgical resection, radiotherapy, and/or chemotherapy with agents such as temozolomide and/or bevacizumab. However, treatment of brain cancers by surgery is not always possible or desirable, for example, the tumor may be inaccessible, or the subject may be incapable of withstanding the trauma of neurosurgery. In addition, radiotherapy and treatment with cytotoxic agents are known to have undesirable side effects. For example, there is increasing evidence that the use of temozolomide may itself induce mutations and worsen prognosis in a significant fraction of subjects (B. E. Johnson et al., Science 343: 189-193 (2014)), and bevacizumab labeling has boxed warnings for gastrointestinal perforation, surgery and wound healing complications, and hemorrhage. Kinase inhibitors are useful for treating many peripheral cancers. However, due to their structural characteristics, many kinase inhibitors such as BRAF inhibitors (e.g., vemurafenib and dabrafenib) are substrates of active transporters such as P-glycoproteins (P-gp) or breast cancer resistance protein (BCRP). For example, dabrafenib has been reported to have an MDR1 efflux ratio of 11.4, a BCRP efflux ratio of 21.0, and a total brain-to-plasma ratio of 0.023; a free brain-to-plasma ratio was not reported (Mittapalli, R K, et al., J Pharmacol. Exp Ther 344:655-664, March 2013), and vemurafenib has been reported to have an MDR1 efflux ratio of 83, a BCRP efflux ratio of 495, and a total brain-to-plasma ratio of 0.004; a free brain-to-plasma ratio was not reported (Mittapalli, R K. et al., J Pharmacol. Exp Ther 342:33-40 (March 2012).

Given that both P-gp and BCRP are expressed in the endothelial cells lining the blood brain capillaries, the activity of both P-gp and BCRP in the BBB play a critical role in preventing the distribution of most kinase inhibitors to the brain parenchyma. Therefore, kinase inhibitors are not generally suitable to be used for the treatment of tumors or cancers in the brain, which is protected by the BBB.

Thus, there remains a need for treatment of tumors bearing BRAF mutations. In addition, treatments for CNS tumors, including CNS tumors bearing BRAF mutations, remain an unmet need.

SUMMARY OF THE INVENTION

Accordingly, provided herein is a compound of the Formula I:

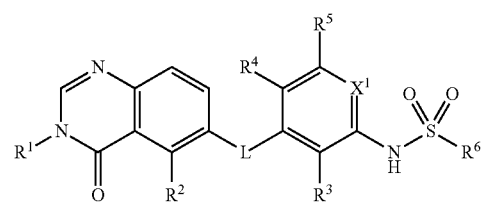

or a pharmaceutically acceptable salt, solvate or polymorph thereof, wherein L, $X^1$, $R^1$, $R^2$, $R^3$, $R^4$, $R^5$ and $R^6$ are as defined herein. Certain compounds of Formula I (i.e. compounds of Formula II and Formula III as defined herein) exhibit central nervous system (CNS) penetration and may be useful for treating BRAF-associated tumors of the CNS.

Also provided herein is a pharmaceutical composition comprising a compound of Formula I, Formula II or Formula III, or a pharmaceutically acceptable salt, solvate or polymorph thereof, in admixture with a pharmaceutically acceptable diluent or carrier.

Also provided herein is a method of treating a BRAF-associated tumor in a subject in need of such treatment, the method comprising administering to the subject a therapeutically effective amount of a compound of Formula I, Formula II or Formula III or a pharmaceutically acceptable salt, solvate or polymorph thereof or a pharmaceutical composition thereof as defined herein.

Also provided herein is a method of inhibiting metastasis associated with a BRAF-associated tumor in a subject in need of such treatment, the method comprising administering to the subject a therapeutically effective amount of a compound of Formula I, Formula II or Formula III or a pharmaceutically acceptable salt, solvate or polymorph thereof or a pharmaceutical composition thereof as defined herein.

Also provided herein is a method of inhibiting BRAF kinase activity, in vitro or in vivo, the method comprising contacting a cell with a therapeutically effective amount of a compound of Formula I, Formula II or Formula III or a pharmaceutically acceptable salt, solvate or polymorph thereof, or a pharmaceutical composition thereof as defined herein.

Also provided herein is a method of inhibiting cell proliferation, in vitro or in vivo, the method comprising contacting a cell with a therapeutically effective amount of a compound of Formula I, Formula II or Formula III or a pharmaceutically acceptable salt, solvate or polymorph thereof, or a pharmaceutical composition thereof as defined herein.

Also provided herein is a compound of Formula I, Formula II or Formula III or a pharmaceutically acceptable salt, solvate or polymorph thereof, or a pharmaceutical composition thereof as defined herein for use in therapy.

Also provided herein is a compound of Formula I, Formula II or Formula III or a pharmaceutically acceptable salt, solvate or polymorph thereof or a pharmaceutical composition thereof as defined herein for use in the treatment of tumors.

Also provided herein is a compound of Formula I, Formula II or Formula III or a pharmaceutically acceptable salt, solvate or polymorph thereof or a pharmaceutical composition thereof as defined herein for use in inhibiting metastasis associated with a BRAF-associated tumor.

Also provided herein is a compound of Formula I, Formula II or Formula III or a pharmaceutically acceptable salt, solvate or polymorph thereof for use in the inhibition of BRAF kinase activity.

Also provided herein is a compound of Formula I, Formula II or Formula III or a pharmaceutically acceptable salt, solvate or polymorph thereof or a pharmaceutical composition thereof as defined herein, for use in the treatment of a BRAF-associated disease or disorder (e.g., a BRAF-associated tumor).

Also provided herein is the use of a compound of Formula I, Formula II or Formula III or a pharmaceutically acceptable salt, solvate or polymorph thereof, as defined herein in the manufacture of a medicament for the treatment of a BRAF-associated tumor (e.g., a BRAF-associated malignant tumor or a BRAF-associated benign tumor).

Also provided herein is the use of a compound of Formula I, Formula II or Formula III or a pharmaceutically acceptable salt, solvate or polymorph thereof, as defined herein in the manufacture of a medicament for inhibiting metastasis associated with a BRAF-associated tumor.

Also provided herein is a use of a compound of Formula I, Formula II or Formula III or a pharmaceutically acceptable salt, solvate or polymorph thereof, as defined herein in the manufacture of a medicament for the inhibition of BRAF kinase activity.

Also provided herein is the use of a compound of Formula I, Formula II or Formula III or a pharmaceutically acceptable salt, solvate or polymorph thereof, as defined herein, in the manufacture of a medicament for the treatment of a BRAF-associated disease or disorder.

Also provided herein is a method for treating a BRAF-associated tumor in a subject in need thereof, the method comprising (a) determining that the tumor is associated with a BRAF mutation; and (b) administering to the subject a therapeutically effective amount of a compound of Formula I, Formula II or Formula III or a pharmaceutically acceptable salt, solvate or polymorph thereof, or a pharmaceutical composition thereof.

Also provided herein is a pharmaceutical combination for treating a BRAF-associated tumor in a subject in need thereof, which comprises (a) a compound of Formula I, Formula II or Formula III or a pharmaceutically acceptable salt, solvate or polymorph thereof, and (b) an additional anticancer agent, wherein the compound of Formula I, Formula II or Formula III or the pharmaceutically acceptable salt or solvate thereof and the additional anticancer agent are formulated as separate compositions or dosages for separate or sequential use for the treatment of the BRAF-associated tumor, wherein the amounts of the compound of Formula I, Formula II or Formula III or a pharmaceutically acceptable salt, solvate or polymorph thereof and of the additional anticancer agent are together effective in treating the BRAF-associated tumor. Also provided herein is the use of such a combination for use in the treatment of a BRAF-associated tumor. Also provided herein is a commercial package or product comprising such a combination as a combined preparation for separate or sequential use in the treatment of a BRAF-associated tumor a subject in need thereof.

Also provided are methods of treating a subject with a BRAF-associated tumor that include administering a compound of Formula I, Formula II or Formula III or a pharmaceutically acceptable salt, solvate or polymorph thereof, before, during, or after administration of another anticancer therapy (e.g., surgery, radiotherapy and/or another anticancer drug).

Also provided herein is a process for preparing a compound of Formula I, Formula II or Formula III or a pharmaceutically acceptable salt, solvate or polymorph thereof.

Also provided herein is a compound of Formula I, Formula II or Formula III or a pharmaceutically acceptable salt, solvate or polymorph thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Figure 1:
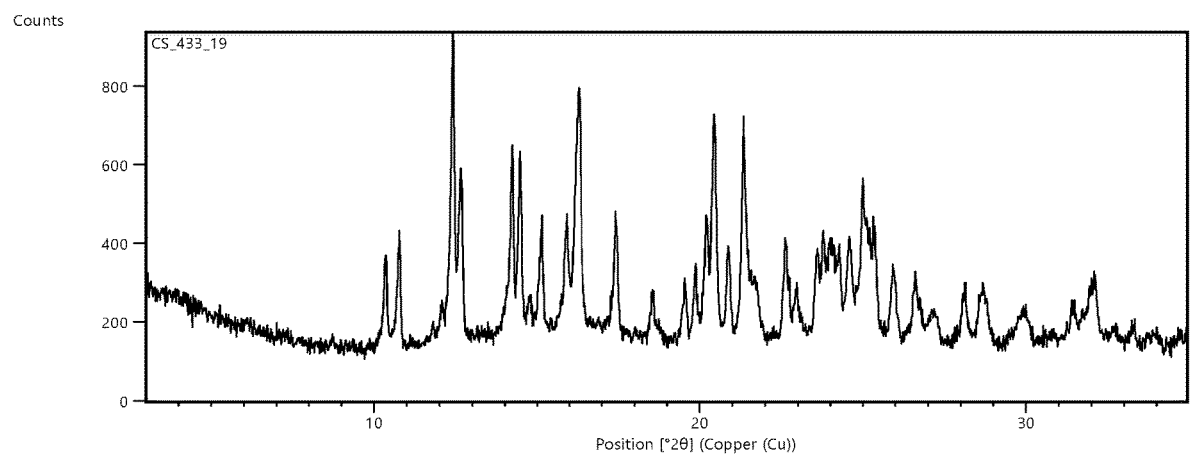
FIG. 1 illustrates an X-ray powder diffraction (XRPD) pattern of crystalline form N-(2-chloro-3-((3,5-dimethyl-4-oxo-3,4-dihydroquinazolin-6-yl)amino)-4-fluorophenyl)-3-fluoropropane-1-sulfonamide Form A anhydrous, according to one embodiment.

Provided herein is a compound of Formula I:

and pharmaceutically acceptable salts, solvates and polymorphs thereof, wherein:

L is O, NH or S;

$X^1$ is CH or N;

$R^1$ is C1-C6 alkyl, C1-C6 deuteroalkyl, C1-C6 fluoroalkyl, C3-C6 cycloalkyl, (C3-C6 cycloalkyl)CH$_2$—, (C1-C6 alkoxy)C1-C6 alkyl-, $Ar^1$, $Ar^1CH_2$—, $hetAr^1$ or $hetCyc^1$;

$Ar^1$ is phenyl which is optionally substituted with 1-5 substituents independently selected from halogen and C1-C3 alkyl;

$hetAr^1$ is a 5-6 membered heteroaryl ring having 1-2 ring nitrogen atoms and optionally substituted with 1-3 substituents independently selected from halogen and C1-C3 alkyl;

$hetCyc^1$ is a 4-6 membered saturated monocyclic heterocyclic ring having one ring oxygen atom;

$R^2$ is methyl, —CD$_3$ or HC≡C—;

$R^3$ is F, Cl, CN or methyl;

$R^4$ is H, F or Cl;

$R^5$ is H, F, Cl or methyl;

$R^6$ is C1-C6 alkyl, C1-C6 fluoroalkyl, $(Cyc^1)$C1-C6 alkyl-, (C1-C3 alkoxy)C1-C6 alkyl-, hetAr$^2$, Ar$^2$ or $R^aR^bN$—;

Cyc$^1$ is a 3-6 membered saturated carbocyclic ring;

hetAr$^2$ is a 5-6 membered heteroaryl having 1-2 ring heteroatoms independently selected from N, O and S and optionally substituted with 1-3 substituents independently selected from halogen and C1-C3 alkyl;

Ar$^2$ is phenyl optionally substituted with 1-5 substituents independently selected from halogen and C1-C6 alkyl; and $R^a$ and $R^b$ are independently C1-C3 alkyl, or $R^a$ and $R^b$ together with the nitrogen atom to which they are attached form a 5-6 membered saturated monocyclic heterocyclic ring optionally substituted with 1-2 halogens.

For complex chemical names employed herein, a substituent group is typically named before the group to which it attaches. For example, methoxyethyl comprises an ethyl backbone with a methoxy substituent.

The term "halogen" means —F (sometimes referred to herein as "fluoro" or "fluoros"), —Cl, —Br and —I.

The terms "C1-C3 alkyl" and "C1-C6 alkyl" as used herein refer to saturated linear or branched-chain monovalent hydrocarbon radicals of one to three or one to six carbon atoms, respectively. Examples of alkyl groups include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "C1-C6 fluoroalkyl" as used herein refers to a C1-C6 alkyl radical as defined herein, wherein one to three hydrogen atoms is replaced with one to three fluoro atoms, respectively. Examples include, but are not limited to, fluoromethyl, difluoromethyl, trifluoromethyl, 2-fluoroethyl, 2,2-difluoroethyl, 2,2,2-and trifluoroethyl.

The term "C1-C6 deuteroalkyl" as used herein refers to a C1-C6 alkyl radical as defined herein, which is substituted with one to six deuterium atoms. An example includes, but is not limited to, —CD$_3$.

The terms "C1-C3 alkoxy" and "C1-C6 alkoxy" as used herein refer to saturated linear or branched-chain monovalent alkoxy radicals of one to three or one to six carbon atoms, respectively, wherein the radical is on the oxygen atom. Examples of alkoxy groups include methoxy, ethoxy, propoxy, and isopropoxy.

The terms "(C1-C3 alkoxy)C1-C6 alkyl" and "(C1-C6 alkoxy)C1-C6 alkyl" as used herein refer to saturated linear or branched-chain monovalent radicals of one to six carbon atoms, wherein one of the carbon atoms is substituted with a C1-C3 alkoxy group or C1-C6 alkoxy group, respectively, as defined herein. Examples of include methoxymethyl (CH$_3$OCH$_2$—) and methoxyethyl (CH$_3$OCH$_2$CH$_2$—).

The term "C3-C6 cycloalkyl" as used herein refers to cyclopropyl, cyclobutyl, cyclopentyl or cyclohexyl.

The term "(Cyc$^1$)C1-C6 alkyl" as used herein refers to a C1-C6 alkyl radical as defined herein, wherein one of the carbon atoms is substituted with a Cyc$^1$ group as defined herein. An example is cyclopropylmethyl.

The term "5-6 membered saturated monocyclic heterocyclic ring" when referring to the ring formed by $R^aR^bN$— wherein $R^a$ and $R^b$ together with the nitrogen atom to which they are attached form a 5-6 membered saturated monocyclic heterocyclic ring" refers to a heterocyclic ring having one ring nitrogen atom.

The term "Boc" as used herein refers to a tert-butyloxycarbonyl group, i.e., (CH$_3$)$_3$COC(=O)—.

Throughout the disclosure, it will be understood that the number and nature of optional substituent groups will be limited to the extent that such substitutions make chemical sense.

The term "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

It will be appreciated that certain compounds provided herein may contain one or more centers of asymmetry and may therefore be prepared and isolated in a mixture of isomers such as a racemic mixture, or in an enantiomerically pure form.

In one embodiment of Formula I, $X^1$ is CH.
In one embodiment of Formula I, $X^1$ is N.
In one embodiment of Formula I, L is NH.
In one embodiment of Formula I, L is O.
In one embodiment of Formula I, L is S.
In one embodiment of Formula I, $R^1$ is C1-C6 alkyl. Non-limiting examples include methyl, ethyl and isopropyl.
In one embodiment of Formula I, $R^1$ is C1-C6 deuteroalkyl. A non-limiting example includes —CD$_3$.
In one embodiment of Formula I, $R^1$ is C1-C6 fluoroalkyl. A non-limiting example includes 2,2,2-trifluoroethyl.
In one embodiment of Formula I, $R^1$ is C3-C6 cycloalkyl. Non-limiting examples include cyclopropyl, cyclobutyl and cyclopentyl.
In one embodiment of Formula I, $R^1$ is (C3-C6 cycloalkyl)CH$_2$—. A non-limiting example includes cyclopropylmethyl.
In one embodiment of Formula I, $R^1$ is (C1-C6 alkoxy)C1-C6 alkyl-. A non-limiting example includes methoxyethyl.
In one embodiment of Formula I, $R^1$ is Ar$^1$. In one embodiment, Ar$^1$ is phenyl which is optionally substituted with 1-3 substituents independently selected from halogen and C1-C3 alkyl. A non-limiting example of Ar$^1$ is phenyl.
In one embodiment of Formula I, $R^1$ is Ar$^1$CH$_2$—. In one embodiment, the Ar$^1$ portion is optionally substituted with 1-2 substituents independently selected from halogen and C1-C3 alkyl. A non-limiting example of Ar$^1$CH$_2$— is benzyl.
In one embodiment of Formula I, $R^1$ is hetAr$^1$. In one embodiment, hetAr$^1$ is a 5-6 membered heteroaryl ring having 1-2 ring nitrogen atoms and optionally substituted with 1-2 substituents independently selected from halogen and C1-C3 alkyl. In one embodiment, hetAr$^1$ is unsubstituted. A non-limiting example is pyridyl.
In one embodiment of Formula I, $R^1$ is hetCyc$^1$. A non-limiting example includes tetrahydrofuranyl.
In one embodiment of Formula I, $R^2$ is methyl.
In one embodiment of Formula I, $R^2$ is —CD$_3$.
In one embodiment of Formula I, $R^2$ is HC≡C—.
In one embodiment of Formula I, $R^3$ is F.
In one embodiment of Formula I, $R^3$ is Cl.
In one embodiment of Formula I, $R^3$ is CN.
In one embodiment of Formula I, $R^3$ is methyl.

In one embodiment of Formula I, $R^4$ is H.
In one embodiment of Formula I, $R^4$ is F.
In one embodiment of Formula I, $R^4$ is Cl.
In one embodiment of Formula I, $R^5$ is H.
In one embodiment of Formula I, $R^5$ is F.
In one embodiment of Formula I, $R^5$ is Cl.
In one embodiment of Formula I, $R^5$ is methyl.

In one embodiment of Formula I, $R^6$ is C1-C6 alkyl. Non-limiting examples include ethyl, propyl, 2-methylpropyl and 1-methylpropyl.

In one embodiment of Formula I, $R^6$ is C1-C6 fluoroalkyl. A non-limiting example includes 3-fluoropropyl.

In one embodiment of Formula I, $R^6$ is $(Cyc^1)$C1-C6 alkyl-. A non-limiting example includes cyclopropylmethyl.

In one embodiment of Formula I, $R^6$ is (C1-C3 alkoxy)C1-C6 alkyl-. A non-limiting example includes 2-methoxyethyl.

In one embodiment of Formula I, $R^6$ is $hetAr^2$. In one embodiment, $hetAr^2$ is a 5-6 membered heteroaryl having 1-2 ring heteroatoms independently selected from N, O and S and optionally substituted with 1-2 substituents independently selected from halogen and C1-C3 alkyl.

In one embodiment, $hetAr^2$ is a 5-6 membered heteroaryl having 1 ring heteroatoms independently selected from N and O and optionally substituted with 1-2 substituents independently selected from halogen and C1-C3 alkyl. In one embodiment, $hetAr^2$ is an unsubstituted 5-6 membered heteroaryl having 1 ring heteroatom selected from N and O. Non-limiting examples include pyridyl and furanyl.

In one embodiment of Formula I, $R^6$ is $Ar^2$. In one embodiment, $Ar^2$ is phenyl optionally substituted with 1-2 substituents independently selected from halogen and C1-C6 alkyl. In one embodiment, $Ar^2$ is phenyl optionally substituted with 1-2 halogens. In one embodiment, $Ar^2$ is phenyl optionally substituted with 1-2 fluoros. Non-limiting examples include phenyl and 2,4-difluorophenyl.

In one embodiment of Formula I, $R^6$ is $R^aR^bN-$.

In one embodiment of Formula I, $R^6$ is $R^aR^bN-$, wherein $R^a$ and $R^b$ are independently C1-C3 alkyl. A non-limiting example is N-ethyl-N-methylamino.

In one embodiment of Formula I, $R^6$ is $R^aR^bN-$, wherein $R^a$ and $R^b$ together with the nitrogen atom to which they are attached form a 5-6 membered saturated monocyclic heterocyclic ring optionally substituted with 1-2 halogens. In one embodiment of Formula I, $R^6$ is $R^aR^bN-$, wherein $R^a$ and $R^b$ together with the nitrogen atom to which they are attached form a 5-membered saturated monocyclic heterocyclic ring optionally substituted with 1-2 halogens. In one embodiment of Formula I, $R^6$ is $R^aR^bN-$, wherein $R^a$ and $R^b$ together with the nitrogen atom to which they are attached form a 5-membered saturated monocyclic heterocyclic ring optionally substituted with 1-2 fluoros. In one embodiment of Formula I, $R^6$ is $R^aR^bN-$, wherein $R^a$ and $R^b$ together with the nitrogen atom to which they are attached form a 5-membered saturated monocyclic heterocyclic ring optionally substituted with fluoro. A non-limiting example is 3-fluoropyrrolidinyl.

In one embodiment of Formula I, $R^6$ is C1-C6 alkyl, C1-C6 fluoroalkyl, $(Cyc^1)$C1-C6 alkyl-, (C1-C3 alkoxy)C1-C6 alkyl-, $hetAr^2$ or $Ar^2$.

In one embodiment, $X^1$ is CH and L is NH.
In one embodiment of Formula I, $X^1$ is CH and L is O.
In one embodiment of Formula I, $X^1$ is CH and L is S.
In one embodiment of Formula I, $X^1$ is N and L is NH.
In one embodiment of Formula I, $X^1$ is N and L is O.
In one embodiment of Formula I, $X^1$ is N and L is S.

In one embodiment of Formula I, $X^1$ is CH, L is NH, $R^2$ is methyl, and $R^1$, $R^3$, $R^4$, $R^5$ and $R^6$ are as defined for Formula I.

In one embodiment of Formula I, $X^1$ is CH, L is NH, $R^2$ is methyl, $R^3$ is F, Cl, CN or methyl, $R^4$ is H, F or Cl, $R^5$ is H, F, Cl or methyl, and $R^1$ and $R^6$ are as defined for Formula I.

In one embodiment of Formula I, $X^1$ is CH, L is NH, $R^2$ is methyl, $R^3$ is F, $R^4$ is H, F or C, $R^5$ is H, F, C or methyl, and $R^1$ and $R^6$ are as defined for Formula I.

In one embodiment of Formula I, $X^1$ is CH, L is NH, $R^2$ is methyl, $R^3$ is F, $R^4$ is H, F or Cl, $R^5$ is H, F, Cl or methyl, $R^6$ is C1-C6 alkyl or C1-C6 fluoroalkyl, and $R^1$ is as defined for Formula I.

In one embodiment of Formula I, $X^1$ is CH, L is NH, $R^2$ is methyl, $R^3$ is F, $R^4$ is H, F or Cl, $R^5$ is H, F, Cl or methyl, $R^6$ is C1-C6 alkyl or C1-C6 fluoroalkyl, and $R^1$ is C1-C6 alkyl.

In one embodiment of Formula I, $X^1$ is CH, L is NH, $R^2$ is methyl, $R^3$ is Cl, $R^4$ is H or F, $R^5$ is H, F or Cl, and $R^1$ and $R^6$ are as defined for Formula I.

In one embodiment of Formula I, $X^1$ is CH, L is NH, $R^2$ is methyl, $R^3$ is Cl, $R^4$ is H or F, $R^5$ is H, F or Cl, $R^6$ is C1-C6 alkyl or C1-C6 fluoroalkyl, and $R^1$ is as defined for Formula I.

In one embodiment of Formula I, $X^1$ is CH, L is NH, $R^2$ is methyl, $R^3$ is Cl, $R^4$ is H or F, $R^5$ is H, F or Cl, $R^6$ is C1-C6 alkyl or C1-C6 fluoroalkyl, and $R^1$ is C1-C6 alkyl or C1-C6 deuteroalkyl.

In one embodiment of Formula I, $X^1$ is CH, L is NH, $R^2$ is methyl, $R^3$ is CN, $R^4$ is H or F, $R^5$ is H, and $R^1$ and $R^6$ are as defined for Formula I.

In one embodiment of Formula I, $X^1$ is CH, L is NH, $R^2$ is methyl, $R^3$ is CN, $R^4$ is H or F, $R^5$ is H, $R^6$ is C1-C6 alkyl, and $R^1$ is as defined for Formula I.

In one embodiment of Formula I, $X^1$ is CH, L is NH, $R^2$ is methyl, $R^3$ is CN, $R^4$ is H or F, $R^5$ is H, $R^6$ is C1-C6 alkyl, and $R^1$ is C1-C6 alkyl.

In one embodiment of Formula I, $X^1$ is CH, L is NH, $R^2$ is methyl, $R^3$ is methyl, $R^4$ is F, $R^5$ is H, and $R^1$ and $R^6$ are as defined for Formula I.

In one embodiment of Formula I, $X^1$ is CH, L is NH, $R^2$ is methyl, $R^3$ is methyl, $R^4$ is F, $R^5$ is H, $R^6$ is C1-C6 alkyl, and $R^1$ is as defined for Formula I.

In one embodiment of Formula I, $X^1$ is CH, L is NH, $R^2$ is methyl, $R^3$ is methyl, $R^4$ is F, $R^5$ is H, $R^6$ is C1-C6 alkyl, and $R^1$ is C1-C6 alkyl.

In one embodiment of Formula I, $X^1$ is CH, L is NH, $R^2$ is HC≡C—, $R^3$ is F, Cl, CN or methyl, $R^4$ is H, F or Cl, $R^5$ is H, F, Cl or methyl, and $R^1$ and $R^6$ are as defined for Formula I In one embodiment of Formula I, $X^1$ is CH, L is NH, $R^2$ is HC≡C—, $R^3$ is Cl, $R^4$ is F, $R^5$ is H, and $R^1$ and $R^6$ are as defined for Formula I.

In one embodiment of Formula I, $X^1$ is CH, L is NH, $R^2$ is HC≡C—, $R^3$ is Cl, $R^4$ is F, $R^5$ is H, $R^6$ is C1-C6 alkyl, and $R^1$ is as defined for Formula I.

In one embodiment of Formula I, $X^1$ is CH, L is NH, $R^2$ is HC≡C—, $R^3$ is Cl, $R^4$ is F, $R^5$ is H, $R^6$ is C1-C6 alkyl, and $R^1$ is C1-C6 alkyl.

In one embodiment of Formula I, $X^1$ is N, L is NH, $R^2$ is methyl, and $R^1$, $R^3$, $R^4$, $R^5$ and $R^6$ are as defined for Formula I.

In one embodiment of Formula I, $X^1$ is N, L is NH, $R^2$ is methyl, $R^3$ is F, $R^4$ is F, $R^5$ is H, and $R^1$ and $R^6$ are as defined for Formula I.

In one embodiment of Formula I, $X^1$ is N, L is NH, $R^2$ is methyl, $R^3$ is F, $R^4$ is F, $R^5$ is H, $R^6$ is C1-C6 alkyl, C1-C6 fluoroalkyl or $(Cyc^1)$C1-C6 alkyl-, and $R^1$ is as defined for Formula I.

In one embodiment of Formula I, $X^1$ is N, L is NH, $R^2$ is methyl, $R^3$ is F, $R^4$ is F, $R^5$ is H, $R^6$ is C1-C6 alkyl, C1-C6 fluoroalkyl or $(Cyc^1)$C1-C6 alkyl-, and $R^1$ is C1-C6 alkyl.

In one embodiment of Formula I, $X^1$ is N, L is NH, $R^2$ is methyl, $R^3$ is Cl, $R^4$ is F or Cl, $R^5$ is H, and $R^1$ and $R^6$ are as defined for Formula I.

In one embodiment of Formula I, $X^1$ is N, L is NH, $R^2$ is methyl, $R^3$ is Cl, $R^4$ is F or Cl, $R^5$ is H, $R^6$ is C1-C6 alkyl, C1-C6 fluoroalkyl, or $(Cyc^1)$C1-C6 alkyl-, and $R^1$ is as defined for Formula I.

In one embodiment of Formula I, $X^1$ is N, L is NH, $R^2$ is methyl, $R^3$ is Cl, $R^4$ is F or Cl, $R^5$ is H, $R^6$ is C1-C6 alkyl, C1-C6 fluoroalkyl, or $(Cyc^1)$C1-C6 alkyl-, and $R^1$ is C1-C6 alkyl.

In one embodiment of Formula I, $X^1$ is CH, L is O, $R^2$ is methyl, and $R^1$, $R^3$, $R^4$, $R^5$ and $R^6$ are as defined for Formula I.

In one embodiment of Formula I, $X^1$ is CH, L is O, $R^2$ is methyl $R^3$ is F, $R^4$ is H or F, $R^5$ is H, and $R^1$ and $R^6$ are as defined for Formula I.

In one embodiment of Formula I, $X^1$ is CH, L is O, $R^2$ is methyl, $R^3$ is F, $R^4$ is H or F, $R^5$ is H, $R^6$ is C1-C6 alkyl or C1-C6 fluoroalkyl, and $R^1$ is as defined for Formula I.

In one embodiment of Formula I, $X^1$ is CH, L is O, $R^2$ is methyl, $R^3$ is F, $R^4$ is H or F, $R^5$ is H, $R^6$ is C1-C6 alkyl or C1-C6 fluoroalkyl, and $R^1$ is C1-C6 alkyl.

In one embodiment of Formula I, $X^1$ is CH, L is O, $R^2$ is methyl, $R^3$ is Cl, $R^4$ is F, $R^5$ is H, and $R^1$ and $R^6$ are as defined for Formula I.

In one embodiment of Formula I, $X^1$ is CH, L is O, $R^2$ is methyl, $R^3$ is Cl, $R^4$ is F, $R^5$ is H, $R^6$ is C1-C6 alkyl or C1-C6 fluoroalkyl, and $R^1$ is as defined for Formula I.

In one embodiment of Formula I, $X^1$ is CH, L is O, $R^2$ is methyl, $R^3$ is Cl, $R^4$ is F, $R^5$ is H, $R^6$ is C1-C6 alkyl, and $R^1$ is C1-C6 alkyl.

In one embodiment of Formula I, $X^1$ is CH, L is O, $R^2$ is methyl, $R^3$ is CN, $R^4$ is H or F, $R^5$ is H, and $R^1$ and $R^6$ are as defined for Formula I.

In one embodiment of Formula I, $X^1$ is CH, L is O, $R^2$ is methyl, $R^3$ is CN, $R^4$ is H or F, $R^5$ is H, $R^1$ is C1-C6 alkyl, and $R^1$ is as defined for Formula I.

In one embodiment of Formula I, $X^1$ is CH, L is O, $R^2$ is methyl, $R^3$ is CN, $R^4$ is H or F, $R^5$ is H, $R^6$ is C1-C6 alkyl, and $R^1$ is C1-C6 alkyl.

In one embodiment of Formula I, $X^1$ is N, L is O, $R^2$ is methyl, and $R^1$, $R^3$, $R^4$, $R^5$ and $R^6$ are as defined for Formula I.

In one embodiment of Formula I, $X^1$ is N, L is O, $R^2$ is methyl, $R^3$ is Cl, $R^4$ is H or F, $R^5$ is H, and $R^1$ and $R^6$ are as defined for Formula I.

In one embodiment of Formula I, $X^1$ is N, L is O, $R^2$ is methyl, $R^3$ is Cl, $R^4$ is H or F, $R^5$ is H, $R^6$ is C1-C6 alkyl, and $R^1$ is as defined for Formula I.

In one embodiment of Formula I, $X^1$ is N, L is O, $R^2$ is methyl, $R^3$ is Cl, $R^4$ is H or F, $R^5$ is H, $R^6$ is C1-C6 alkyl, and $R^1$ is methyl.

In one embodiment of Formula I, is $X^1$ is N, L is O, $R^2$ is methyl, $R^3$ is F, $R^4$ is F, $R^5$ is F, and $R^1$ and $R^6$ are as defined for Formula I.

In one embodiment of Formula I, is $X^1$ is N, L is O, $R^2$ is methyl, $R^3$ is F, $R^4$ is F, $R^5$ is F, $R^6$ is C1-C6 alkyl or fluoroC1-C6 alkyl, and $R^1$ is as defined for Formula I.

In one embodiment of Formula I, is $X^1$ is N, L is O, $R^2$ is methyl, $R^3$ is F, $R^4$ is F, $R^5$ is F, $R^6$ is C1-C6 alkyl or fluoroC1-C6 alkyl, and $R^1$ is C1-C6 alkyl.

In one embodiment of Formula I, $X^1$ is CH, L is S, $R^2$ is methyl, and $R^1$, $R^3$, $R^4$, $R^5$ and $R^6$ are as defined for Formula I.

In one embodiment of Formula I, $X^1$ is CH, L is S, $R^2$ is methyl, $R^3$ is Cl, $R^4$ is F, $R^5$ is H, and $R^1$ and $R^6$ are as defined for Formula I.

In one embodiment of Formula I, $X^1$ is CH, L is S, $R^2$ is methyl, $R^3$ is Cl, $R^4$ is F, $R^5$ is H, $R^6$ is C1-C6 alkyl, and $R^1$ is as defined for Formula I.

In one embodiment of Formula I, $X^1$ is CH, L is S, $R^2$ is methyl, $R^3$ is Cl, $R^4$ is F, $R^5$ is H, $R^6$ is C1-C6 alkyl, and $R^1$ is C1-C6 alkyl.

Any of the aforementioned embodiments of Formula I may be combined with each other.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The term "pharmaceutically acceptable salt" refers to a conventional acid addition or base addition salt which preserves the biological efficacy and properties of the compounds of formula (I) and which can be formed with suitable non-toxic organic or inorganic acids or organic or inorganic bases. Examples of acid addition salts include salts derived from inorganic acids, such as, but not limited to, hydrochloric acid, hydrobromic acid, hydroiodic acid, sulfuric acid, sulphamic acid, phosphoric acid, nitric acid and perchloric acid and derived from various organic acids, such as, but not limited to, acetic acid, propionic acid, benzoic acid, glycolic acid, phenylacetic acid, salicylic acid, malonic acid, maleic acid, oleic acid, pamoic acid, palmitic acid, benzenesulfonic acid, toluenesulfonic acid, methanesulfonic acid, oxalic acid, tartaric acid, succinic acid, citric acid, malic acid, lactic acid, glutamic acid, fumaric acid and the like. Examples of base addition salts are salts derived from ammonium-, potassium-, sodium- and quaternary ammonium hydroxides such as tetramethylammonium hydroxide. These salts often exhibit more favorable solubility properties than the compounds used for their preparation and are therefore more suitable for use in the preparation of various pharmaceutical formulations. In one embodiment, pharmaceutically acceptable salts of compounds of Formula I include acid salts such as trifluoroacetate salts.

It will further be appreciated that the compounds of Formula I, Formula II, and Formula III, or their salts, may be isolated in the form of solvates, and accordingly that any such solvate is included within the scope of the present invention.

The term "solvate" refers to non-covalent stoichiometric or nonstoichiometric combinations of solvent and solute. The term "hydrate" refers to non-covalent stoichiometric or nonstoichiometric combinations of water and solute. For example, compounds of Formula I, Formula II, and Formula III, and pharmaceutically acceptable salts and polymorphs thereof, can exist in unsolvated as well as solvated forms with pharmaceutically acceptable solvents such as anisole, dichloromethane, toluene, 1,4-dioxane, water, and the like.

The compounds of Formula I, Formula II, and Formula III may exist in various geometric isomeric forms. In addition, certain compounds of Formula I, Formula II, and Formula III may contain one or more asymmetric centers, thus exist in stereoisomeric and diastereomeric forms. The term "stereoisomer" denotes a compound that possesses identical molecular connectivity and bond multiplicity, but which differs in the arrangement of its atoms in space. All of these compounds, such as cis isomers, trans isomers, diastereomeric mixtures, racemates, non-racemic mixtures of enantiomers, substantially pure and pure enantiomers are within the scope of the invention. In one embodiment, the substantially pure enantiomers contain up to 5 wt % of the corresponding opposite enantiomer. In one embodiment, the substantially pure enantiomers contain up to 2 wt % of the corresponding opposite enantiomer. In one embodiment, the substantially pure enantiomers contain up to 1 wt %, of the corresponding opposite enantiomer.

Optical isomers can be prepared by resolving the racemic mixtures by known methods, for example, by using an optically active acid or base to form diastereoisomeric salts or by forming covalent diastereomers. Suitable acids include, for example, tartaric acid, diacetyltartaric acid, dibenzoyltartaric acid, ditoluoyltartaric acid and camphorsulfonic acid. Diastereoisomeric mixtures can be separated into individual diastereomers based on their physical and/or chemical differences, by methods known to those skilled in the art, such as chromatography or fractional crystallization. Subsequently, the optically active bases or acids are liberated from the separated diastereoisomeric salts. Various methods of separating optical isomers include chiral chromatography (e.g., chiral HPLC columns) optionally used by derivatization with the aim to maximize the separation of enantiomers. Appropriate chiral HPLC columns are Diacel columns, such as CHIRALPAK or CHIRALCEL columns, which can be routinely chosen as desired. Where applicable, enzymatic separations carried out by derivatization may also be used. The optically active compounds of Formula II, and Formula III can also be prepared using optically active starting materials using chiral synthesis without racemization reaction conditions.

In one embodiment, the compounds of Formula I include the compounds of Examples 1-80, and pharmaceutically acceptable salts, solvates and polymorphs (e.g., Examples 81-86) thereof. In one embodiment, the compounds of Examples 1-80 are in the free base form. In one embodiment, the compounds of Examples 1-80 are in the acid salt form. In one embodiment, one or more of the compounds of Examples 1-80 are trifluoroacetate salts.

The term "pharmaceutically acceptable" indicates that the compound, or salt or composition thereof is compatible chemically and/or toxicologically with the other ingredients comprising a formulation and/or the subject being treated therewith.

Compounds provided herein may also contain unnatural proportions of atomic isotopes at one or more of the atoms that constitute such compounds. That is, an atom, in particular when mentioned in relation to a compound according to Formula I, Formula II, and Formula III, comprise all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C, $^{14}$C or mixtures thereof; when nitrogen is mentioned, it is understood to refer to $^{13}$N, $^{14}$N, $^{15}$N or mixtures thereof; when oxygen is mentioned, it is understood to refer to $^{14}$, $^{15}$O, $^{16}$O, $^{17}$O, $^{18}$O or mixtures thereof; and when fluoro is mentioned, it is understood to refer to $^{18}$F, $^{19}$F or mixtures thereof. As noted above, the compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

The compounds of Formula I, Formula II and Formula II may exist in various polymorphic forms. The terms "polymorph", "polymorphic form" and "crystalline form" refer to different crystalline forms of a single compound. That is, polymorphs are distinct solids sharing the same molecular formula, yet each polymorph may have distinct solid state physical properties. Therefore, a single compound may give rise to a variety of polymorphic forms where each form has different and distinct solid state physical properties, such as different solubility profiles, dissolution rates, melting point temperatures, flowability, and/or different X-ray diffraction peaks. The differences in physical properties may affect pharmaceutical parameters such as storage stability, compressibility and density (which can be important in formulation and product manufacturing), and dissolution rate (which can be an important factor in bioavailability). Techniques for characterizing polymorphic forms include, but are not limited to, X-ray powder diffractometry (XRPD), differential scanning calorimetry (DSC), thermal gravimetric analysis (TGA), single-crystal X-ray diffractometry (XRD), vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis.

In one embodiment, provided herein are crystalline forms of N-(2-chloro-3-((3,5-dimethyl-4-oxo-3,4-dihydroquinazolin-6-yl)amino)-4-fluorophenyl)-3-fluoropropane-1-sulfonamide or solvates thereof.

In one embodiment, one or more crystalline forms of N-(2-chloro-3-((3,5-dimethyl-4-oxo-3,4-dihydroquinazolin-6-yl)amino)-4-fluorophenyl)-3-fluoropropane-1-sulfonamide disclosed herein are anhydrous.

In one embodiment, one or more crystalline forms of N-(2-chloro-3-((3,5-dimethyl-4-oxo-3,4-dihydroquinazolin-6-yl)amino)-4-fluorophenyl)-3-fluoropropane-1-sulfonamide disclosed herein may be isolated as a solvate. In one embodiment, the crystalline form is isolated as an anisole solvate, e.g., a mono-anisole solvate. In one embodiment, the crystalline form is isolated as a dichloromethane solvate, e.g., a hemi-dichloromethane solvate. In one embodiment, the crystalline form is isolated as a toluene solvate. In one embodiment, the crystalline form is isolated as a 1,4-dioxane solvate.

In one embodiment, provided herein are crystalline forms of N-(2-chloro-3-((3,5-dimethyl-4-oxo-3,4-dihydroquinazolin-6-yl)amino)-4-fluorophenyl)-3-fluoropropane-1-sulfonamide selected from N-(2-chloro-3-((3,5-dimethyl-4-oxo-3,4-dihydroquinazolin-6-yl)amino)-4-fluorophenyl)-3-fluoropropane-1-sulfonamide Form A anhydrous, N-(2-chloro-3-((3,5-dimethyl-4-oxo-3,4-dihydroquinazolin-6-yl)amino)-4-fluorophenyl)-3-fluoropropane-1-sulfonamide Form B anhydrous, N-(2-chloro-3-((3,5-dimethyl-4-oxo-3, 4-dihydroquinazolin-6-yl)amino)-4-fluorophenyl)-3-fluoropropane-1-sulfonamide Form C mono-anisole, N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane, N-(2-chloro-3-((3,5-dimethyl-4-oxo-3,4-dihydroquinazolin-6-yl)amino)-4-fluorophenyl)-3-fluoropropane-1-sulfonamide Form E toluene, and N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane.

In some embodiments, the crystalline forms may be characterized by their X-ray powder diffraction (XRPD) patterns. XRPD analysis was carried out on a PANalytical X'pert pro with PIXcel detector (128 channels), scanning the samples between 3 and 35° 2θ. The material was gently ground to release any agglomerates and loaded onto a multi-well plate with Mylar polymer film to support the sample. The multi-well plate was then placed into the diffractometer and analyzed using Cu K radiation (CuK$_\alpha$=1.5418Å) running in transmission mode (step size 0.0130° 2θ, step time 18.87 s) using 40 kV/40 mA generator settings. Data were visualized and images generated using the HighScore Plus 4.7 desktop application (PANalytical, 2017). The Tables below include the analysis and are provided with the following approximate data: 2θ measured in degrees±0.2 degrees; d measured in angstroms±0.2 angstroms; and relative intensity using peak height to measure height % (H %) in counts per second.

It will be understood that the 2-theta values of the X-ray powder diffraction patterns for crystalline forms of N-(2-chloro-3-((3,5-dimethyl-4-oxo-3,4-dihydroquinazolin-6-yl)amino)-4-fluorophenyl)-3-fluoropropane-1-sulfonamide may vary slightly from one instrument to another and also depending on variations in sample preparation and batch to batch variation, and so the values quoted are not to be construed as absolute. It will also be understood that the relative intensities of peaks may vary depending on orientation effects so that the intensities shown in the XRPD trace included herein are illustrative and not intended to be used for absolute comparison. Accordingly, it is to be understood that the phrase "substantially the same XRPD pattern as shown in FIG. 1" means that for comparison purposes, at least 90% of the peaks shown in FIG. 1 are present. It is to be understood that the relative peak positions may vary ±0.2 degrees from the peak positions shown in FIG. 1. It is to be further understood that for comparison purposes some variability in peak intensities from those shown in FIG. 1 is allowed. The same applies to the descriptions of FIGS. 4, 7, 9, 11 and 13.

In some embodiments, the crystalline forms may be characterized by their DSC scans. Thermal transition values were measured by differential scanning calorimetry ("DSC"). Approximately 1-5 mg of material was weighed into an aluminum DSC pan and sealed non-hermetically with an aluminum lid. The sample pan was loaded into a TA Instruments Discovery DSC 2500 differential scanning calorimeter equipped with a RC90 cooler. The sample and reference were heated to various temperatures at a scan rate of 10° C./min and the resulting heat flow response monitored. The sample was re-cooled to 20° C. and then reheated at 10° C./min. Nitrogen was used as the purge gas at a flow rate of 50 cm$^3$/min.

In some embodiments, the crystalline forms may be characterized by thermogravimetric (TG)/differential scanning calorimetry scans (DSC). TG/DSC analysis was carried out using Approximately 5-10 mg of material was added into a pre-tared open aluminum pan and loaded into a TA Instruments Discovery SDT 650 Auto-Simultaneous DSC and held at room temperature. The sample was then heated at a rate of 10° C./min from 30° C. to 400° C. during which time the change in sample weight was recorded along with the heat flow response (DSC). Nitrogen was used as the purge gas, at a flow rate of 300 cm$^3$/min.

N-(2-chloro-3-((3,5-dimethyl-4-oxo-3,4-dihydroquinazolin-6-yl)amino)-4-fluorophenyl)-3-fluoropropane-1-sulfonamide Form A Anhydrous In one embodiment, provided herein is crystalline form N-(2-chloro-3-((3,5-dimethyl-4-oxo-3,4-dihydroquinazolin-6-yl)amino)-4-fluorophenyl)-3-fluoropropane-1-sulfonamide Form A anhydrous.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form A anhydrous may be characterized by its XRPD pattern as illustrated in FIG. 1.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form A anhydrous has an XRPD pattern with at least the 20 characteristic peaks (2θ degrees±0.2), as listed in Table 3.

TABLE 3

XRPD peaks of crystalline Form A anhydrous

| Peak No. | Position [°2θ] | Relative Intensity [%] |
|---|---|---|
| 1 | 10.4 | 29.0 |
| 2 | 10.8 | 31.7 |
| 3 | 12.4 | 100 |
| 4 | 12.7 | 52.8 |
| 5 | 14.2 | 64.3 |
| 6 | 14.5 | 58.0 |
| 7 | 15.1 | 39.1 |
| 8 | 15.9 | 36.7 |
| 9 | 16.3 | 67.9 |
| 10 | 17.4 | 43.4 |
| 11 | 20.2 | 39.9 |
| 12 | 20.5 | 71.4 |
| 13 | 20.9 | 29.1 |
| 14 | 21.3 | 72.7 |
| 15 | 22.6 | 32.3 |
| 16 | 23.6 | 29.2 |
| 17 | 24.3 | 30.0 |
| 18 | 24.6 | 33.0 |
| 19 | 25.0 | 49.6 |
| 20 | 25.4 | 36.5 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form A anhydrous has an XRPD pattern with at least 8 of the characteristic peaks (2θdegrees±0.2) listed in Table 3.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form A anhydrous has an XRPD pattern with at least 5 of the characteristic peaks (2θdegrees±0.2) listed in Table 3.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form A anhydrous has an XRPD pattern with at least the 8 characteristic peaks (2θdegrees±0.2) as listed in Table 3A.

TABLE 3A

| XRPD peaks of crystalline Form A anhydrous | | |
|---|---|---|
| Peak No. | Position [°2θ] | Relative Intensity [%] |
| 1 | 10.4 | 29.0 |
| 2 | 10.8 | 31.7 |
| 3 | 12.4 | 100 |
| 5 | 14.2 | 64.3 |
| 6 | 14.5 | 58.0 |
| 9 | 16.3 | 67.9 |
| 12 | 20.5 | 71.4 |
| 16 | 23.6 | 29.2 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form A anhydrous has an XRPD pattern with at least the 5 characteristic peaks (2θdegrees±0.2) as listed in Table 3B.

TABLE 3B

| XRPD peaks of crystalline Form A anhydrous | | |
|---|---|---|
| Peak No. | Position [°2θ] | Relative Intensity [%] |
| 3 | 12.4 | 100 |
| 5 | 14.2 | 64.3 |
| 9 | 16.3 | 67.9 |
| 12 | 20.5 | 71.4 |
| 14 | 21.3 | 72.7 |

Figure 2:
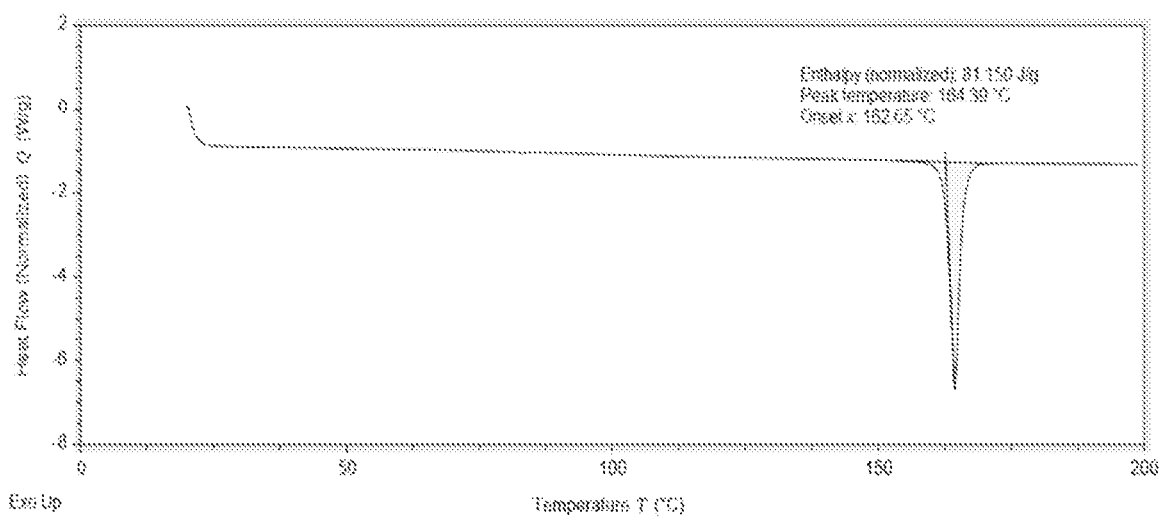
FIG. 2 illustrates a differential scanning calorimetry (DSC) profile of N-(2-chloro-3-((3,5-dimethyl-4-oxo-3,4-dihydroquinazolin-6-yl)amino)-4-fluorophenyl)-3-fluoropropane-1-sulfonamide Form A anhydrous, according to one embodiment.

In some embodiments, crystalline N-(2-chloro-3-((3,5-dimethyl-4-oxo-3,4-dihydroquinazolin-6-yl)amino)-4-fluorophenyl)-3-fluoropropane-1-sulfonamide Form A anhydrous has a DSC thermogram as shown in FIG. 2, having an onset temperature of melting of 162.65 and a melt maxima temperature of 164.39° C.

Figure 3:
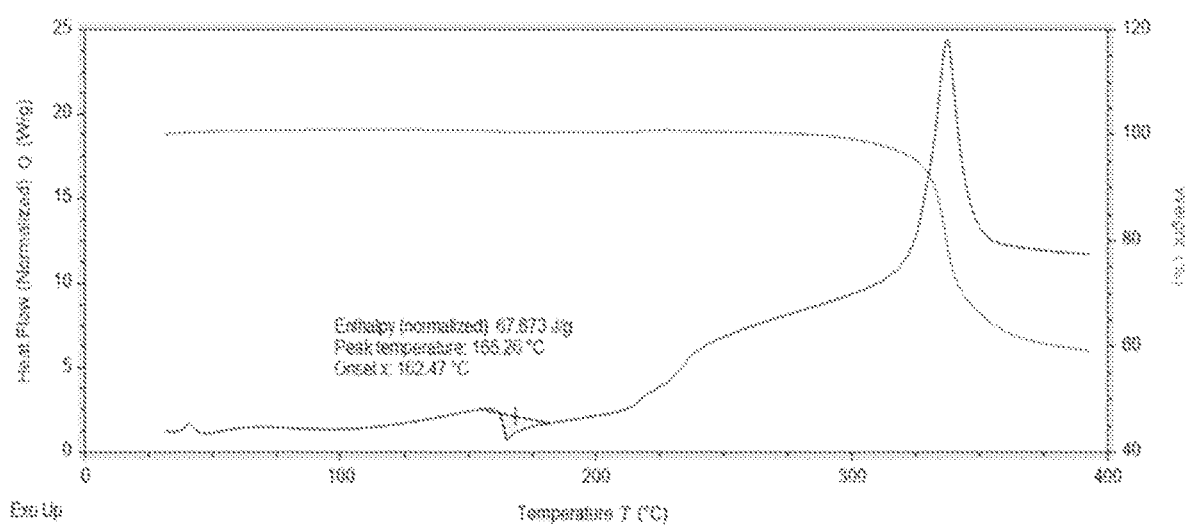
FIG. 3 is an overlay of a differential scanning calorimetry (DSC) scan and a thermogravimetric (TG) analysis scan of N-(2-chloro-3-((3,5-dimethyl-4-oxo-3,4-dihydroquinazolin-6-yl)amino)-4-fluorophenyl)-3-fluoropropane-1-sulfonamide Form A.

In some embodiments, crystalline N-(2-chloro-3-((3,5-dimethyl-4-oxo-3,4-dihydroquinazolin-6-yl)amino)-4-fluorophenyl)-3-fluoropropane-1-sulfonamide Form A anhydrous has a TG/DSC profile as shown in FIG. 3.

N-(2-chloro-3-((3,5-dimethyl-4-oxo-3,4-dihydroquinazolin-6-yl)amino)-4-fluorophenyl)-3-fluoropropane-1-sulfonamide Form B Anhydrous In one embodiment, provided herein is crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Figure 4:
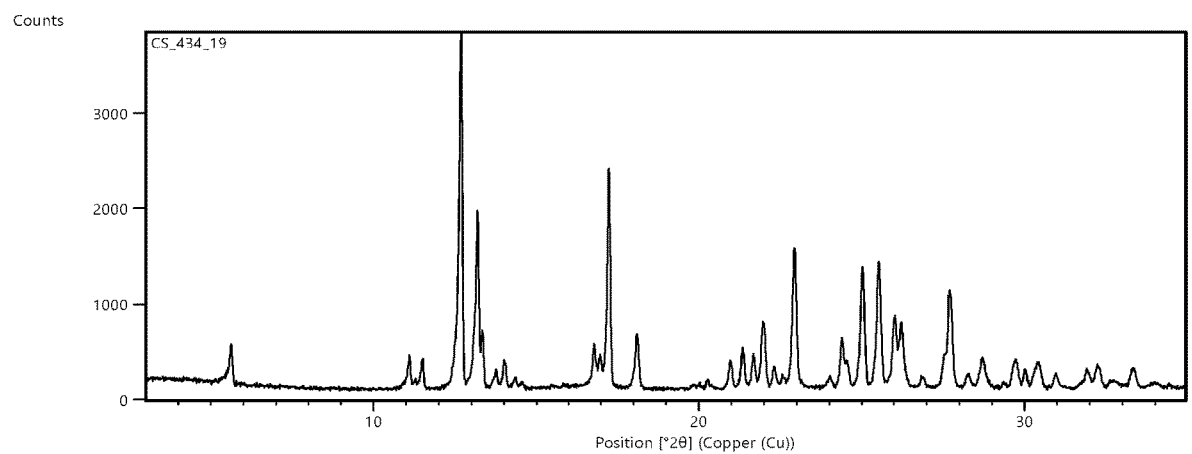
FIG. 4 illustrates an X-ray powder diffraction (XRPD) pattern of crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous, according to one embodiment.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous may be characterized by its XRPD pattern as illustrated in FIG. 4.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous has an XRPD pattern with at least the 20 characteristic peaks (2θdegrees±0.2), as listed in Table 4.

TABLE 4

| XRPD peaks of crystalline Form B anhydrous | | |
|---|---|---|
| Peak No. | Position [°2θ] | Relative Intensity [%] |
| 1 | 5.6 | 10.7 |
| 2 | 11.1 | 9.6 |

TABLE 4-continued

| XRPD peaks of crystalline Form B anhydrous | | |
|---|---|---|
| Peak No. | Position [°2θ] | Relative Intensity [%] |
| 3 | 12.7 | 100 |
| 4 | 13.2 | 50.7 |
| 5 | 13.4 | 15.9 |
| 6 | 16.8 | 12.9 |
| 7 | 17.0 | 9.6 |
| 8 | 17.2 | 63.7 |
| 9 | 18.1 | 15.8 |
| 10 | 21.3 | 11.3 |
| 11 | 21.7 | 9.8 |
| 12 | 21.9 | 17.4 |
| 13 | 22.9 | 40.6 |
| 14 | 24.4 | 14.7 |
| 15 | 25.0 | 35.0 |
| 16 | 25.5 | 36.1 |
| 17 | 26.0 | 19.9 |
| 18 | 26.2 | 19.2 |
| 19 | 27.7 | 26.3 |
| 20 | 27.8 | 25.9 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous has an XRPD pattern with at least 8 of the characteristic peaks (2θ degrees±0.2) listed in Table 4.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous has an XRPD pattern with at least 5 of the characteristic peaks (2θdegrees±0.2) listed in Table 4.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous has an XRPD pattern with at least the 8 characteristic peaks (2θdegrees±0.2) as listed in Table 4A.

TABLE 4A

| XRPD peaks of crystalline Form B anhydrous | | |
|---|---|---|
| Peak No. | Position [°2θ] | Relative Intensity [%] |
| 3 | 12.7 | 100 |
| 4 | 13.2 | 50.7 |
| 8 | 17.2 | 63.7 |
| 13 | 22.9 | 40.6 |
| 15 | 25.0 | 35.0 |
| 16 | 25.5 | 36.1 |
| 19 | 27.7 | 26.3 |
| 20 | 27.8 | 25.9 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous has an XRPD pattern with at least the 6 characteristic peaks (2θdegrees±0.2) as listed in Table 4B.

TABLE 4B

| XRPD peaks of crystalline Form B anhydrous | | |
|---|---|---|
| Peak No. | Position [°2θ] | Relative Intensity [%] |
| 1 | 5.6 | 10.7 |
| 2 | 11.1 | 9.6 |
| 4 | 13.2 | 50.7 |

TABLE 4B-continued

XRPD peaks of crystalline Form B anhydrous

| Peak No. | Position [°2θ] | Relative Intensity [%] |
|---|---|---|
| 5 | 13.4 | 15.9 |
| 8 | 17.2 | 63.7 |
| 19 | 27.7 | 26.3 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous has an XRPD pattern with at least the 5 characteristic peaks (2θdegrees±0.2) as listed in Table 4C.

TABLE 4C

XRPD peaks of crystalline Form B anhydrous

| Peak No. | Position [°2θ] | Relative Intensity [%] |
|---|---|---|
| 8 | 17.2 | 63.7 |
| 13 | 22.9 | 40.6 |
| 16 | 25.5 | 36.1 |
| 18 | 26.2 | 19.2 |
| 19 | 27.7 | 26.3 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous has an XRPD pattern with at least the 3 characteristic peaks (2θdegrees±0.2) as listed in Table 4D.

TABLE 4D

XRPD peaks of crystalline Form B anhydrous

| Peak No. | Position [°2θ] | Relative Intensity [%] |
|---|---|---|
| 8 | 17.2 | 63.7 |
| 13 | 22.9 | 40.6 |
| 16 | 25.5 | 36.1 |

Figure 5:
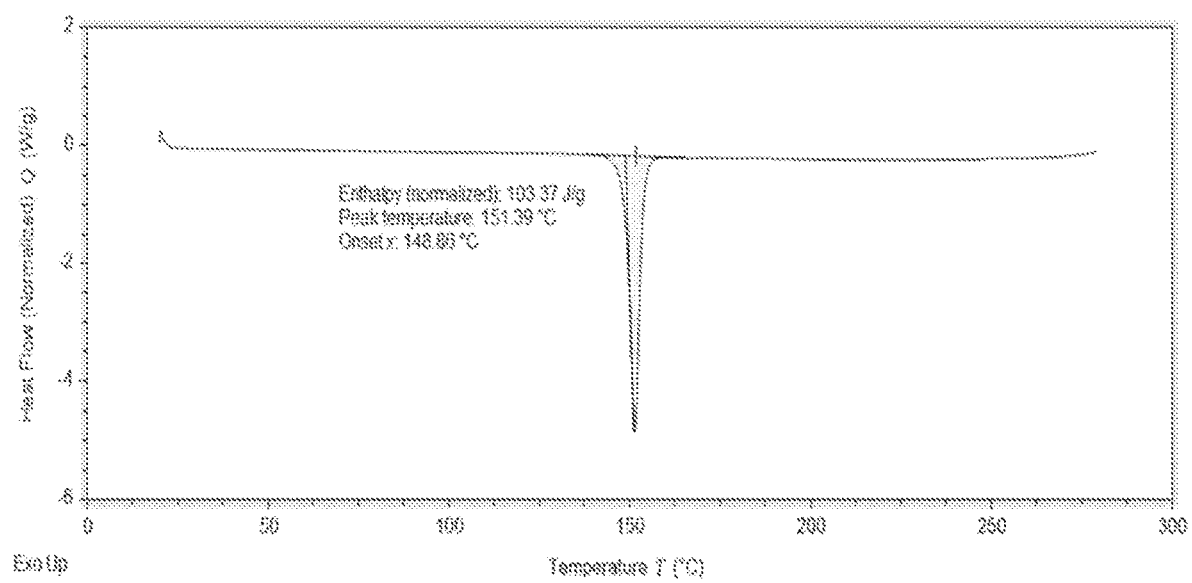
FIG. 5 illustrates a differential scanning calorimetry (DSC) profile of crystalline form N-(2-chloro-3-((3,5-dimethyl-4-oxo-3,4-dihydroquinazolin-6-yl)amino)-4-fluorophenyl)-3-fluoropropane-1-sulfonamide Form B anhydrous, according to one embodiment.

In some embodiments, crystalline N-(2-chloro-3-((3,5-dimethyl-4-oxo-3,4-dihydroquinazolin-6-yl)amino)-4-fluorophenyl)-3-fluoropropane-1-sulfonamide Form B anhydrous has a DSC thermogram as shown in FIG. 5, having an onset temperature of melting of 148.8° C. and a melt maxima temperature of 151.39° C.

Figure 6:
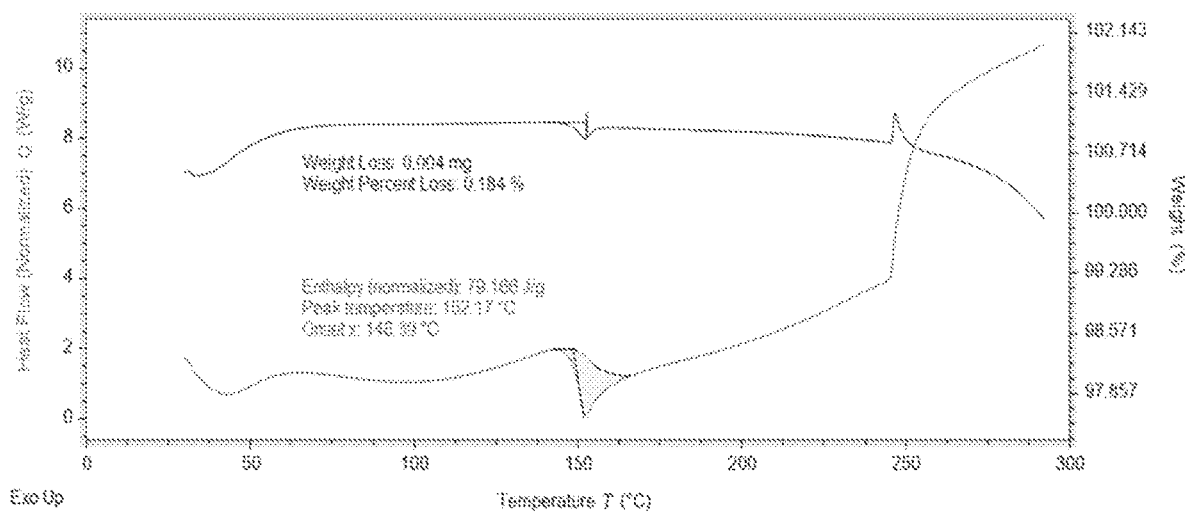
FIG. 6 is an overlay of a differential scanning calorimetry scan and a thermogravimetric analysis scan of N-(2-chloro-3-((3,5-dimethyl-4-oxo-3,4-dihydroquinazolin-6-yl)amino)-4-fluorophenyl)-3-fluoropropane-1-sulfonamide Form B anhydrous, according to one embodiment.

In some embodiments, crystalline N-(2-chloro-3-((3,5-dimethyl-4-oxo-3,4-dihydroquinazolin-6-yl)amino)-4-fluorophenyl)-3-fluoropropane-1-sulfonamide Form B anhydrous has a TG/DSC profile as shown in FIG. 6.

N-(2-chloro-3-((3,5-dimethyl-4-oxo-3,4-dihydroquinazolin-6-yl)amino)-4-fluorophenyl)-3-fluoropropane-1-sulfonamide Form C Mono-anisole In one embodiment, provided herein is crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole.

Figure 7:
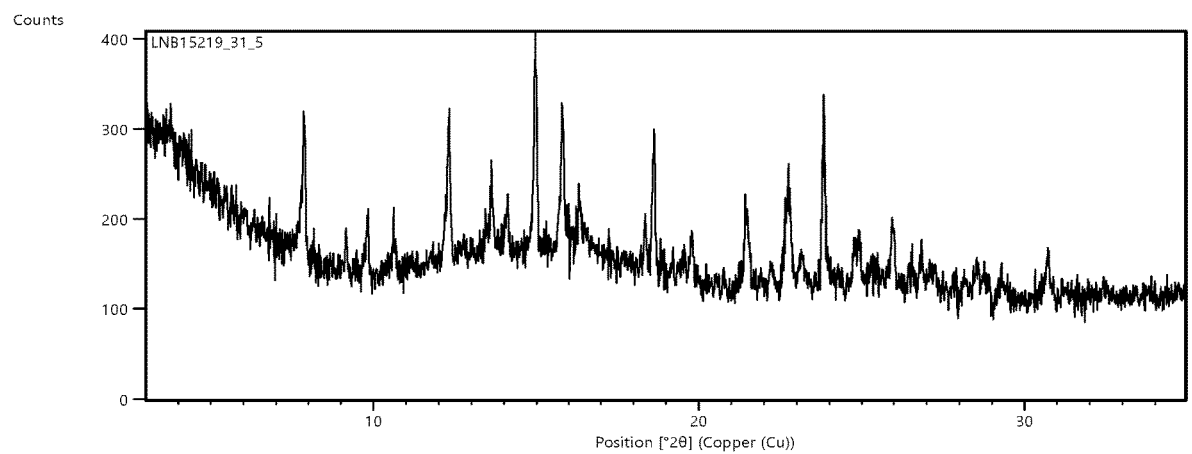
FIG. 7 illustrates an X-ray powder diffraction (XRPD) pattern of crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole, according to one embodiment.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole may be characterized by its XRPD pattern as illustrated in FIG. 7.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole has an XRPD pattern with at least the 20 characteristic peaks (2θdegrees±0.2), as listed in Table 5.

TABLE 5

XRPD peaks of crystalline Form C mono-anisole

| Peak No. | Position [°2θ] | Relative Intensity [%] |
|---|---|---|
| 1 | 7.9 | 50.5 |
| 2 | 9.8 | 14.6 |
| 3 | 10.6 | 19.8 |
| 4 | 12.3 | 67.4 |
| 5 | 13.6 | 39.5 |
| 6 | 14.1 | 28.6 |
| 7 | 15.0 | 100 |
| 8 | 15.8 | 67.3 |
| 9 | 16.3 | 28.3 |
| 10 | 18.4 | 21.8 |
| 11 | 18.6 | 61.9 |
| 12 | 19.7 | 13.6 |
| 13 | 21.4 | 31.8 |
| 14 | 22.8 | 41.7 |
| 15 | 23.8 | 69.2 |
| 16 | 24.8 | 17.8 |
| 17 | 26.0 | 26.7 |
| 18 | 26.6 | 14.7 |
| 19 | 26.9 | 21.4 |
| 20 | 30.7 | 18.1 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole has an XRPD pattern with at least 8 of the characteristic peaks (2θdegrees±0.2) listed in Table 5.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole has an XRPD pattern with at least 5 of the characteristic peaks (2θdegrees±0.2) listed in Table 5.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole has an XRPD pattern with at least the 8 characteristic peaks (2θdegrees±0.2) as listed in Table 5A.

TABLE 5A

XRPD peaks of crystalline Form C mono-anisole

| Peak No. | Position [°2θ] | Relative Intensity [%] |
|---|---|---|
| 1 | 7.9 | 50.5 |
| 4 | 12.3 | 67.4 |
| 5 | 13.6 | 39.5 |
| 7 | 15.0 | 100 |
| 8 | 15.8 | 67.3 |
| 11 | 18.6 | 61.9 |
| 14 | 22.8 | 41.7 |
| 15 | 23.8 | 69.2 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole has an XRPD pattern with at least the 6 characteristic peaks (2θdegrees±0.2) as listed in Table 5B.

TABLE 5B

XRPD peaks of crystalline
Form C mono-anisole

| Peak No. | Position [°2θ] | Relative Intensity [%] |
|---|---|---|
| 1 | 7.9 | 50.5 |
| 4 | 12.3 | 67.4 |
| 7 | 15.00 | 100 |
| 8 | 15.8 | 67.3 |
| 11 | 18.6 | 61.9 |
| 15 | 23.8 | 69.2 |

Figure 8:
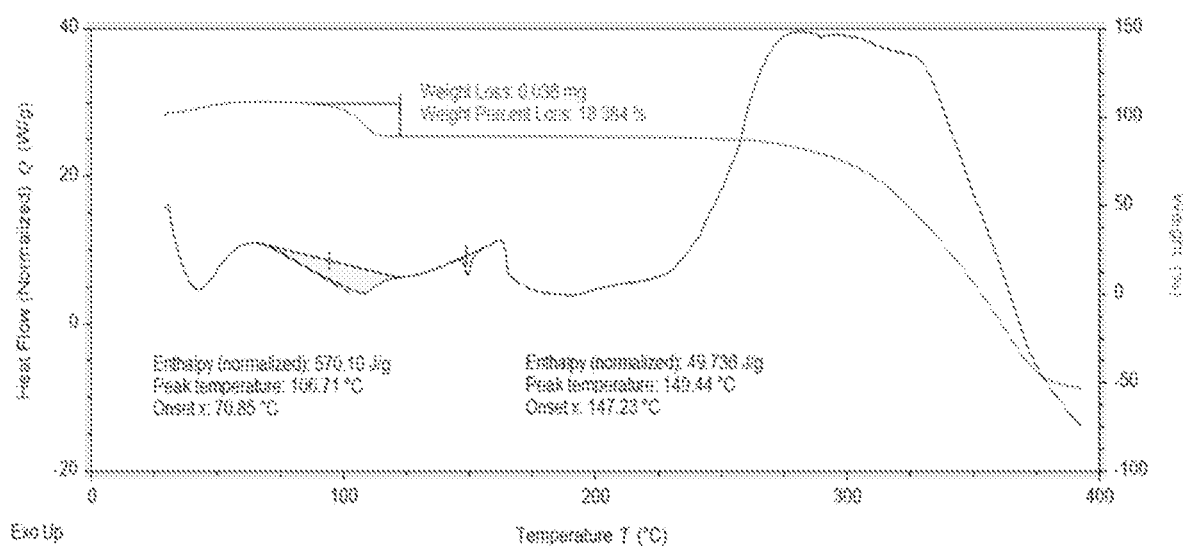
FIG. 8 is an overlay of a differential scanning calorimetry (DSC) scan and a thermogravimetric (TG) analysis scan of N-(2-chloro-3-((3,5-dimethyl-4-oxo-3,4-dihydroquinazolin-6-yl)amino)-4-fluorophenyl)-3-fluoropropane-1-sulfonamide Form C mono-anisole, according to one embodiment.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form C mono-anisole has a TG/DSC profile as shown in FIG. 8.

N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane In one embodiment, provided herein is crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane.

Figure 9:
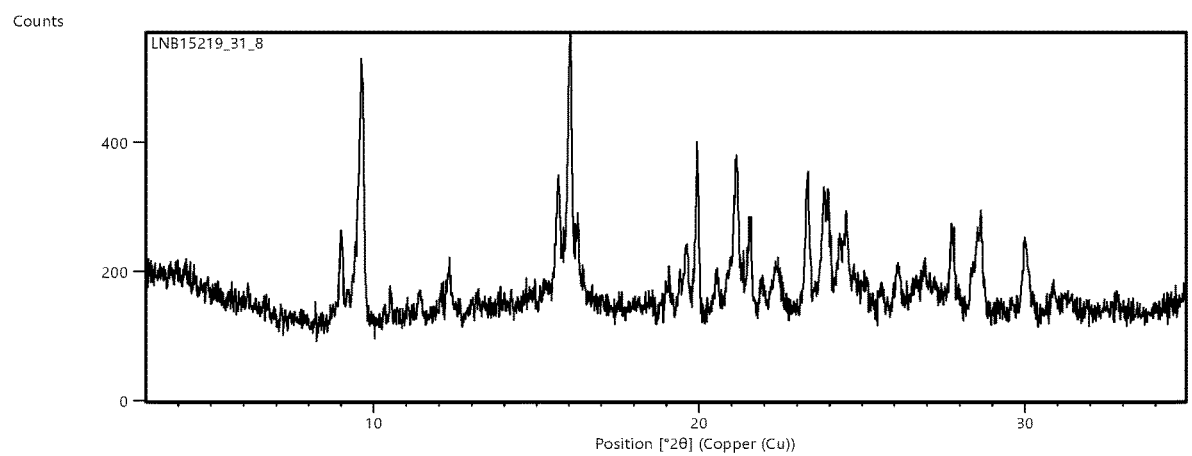
FIG. 9 illustrates an X-ray powder diffraction (XRPD) pattern of crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane, according to one embodiment.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane may be characterized by its XRPD pattern as illustrated in FIG. 9.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane has an XRPD pattern with at least the 20 characteristic peaks (2θdegrees±0.2) as listed in Table 6.

TABLE 6

XRPD peaks of crystalline
Form D hemi-dichloromethane

| Peak No. | Position [°2θ] | Relative Intensity [%] |
|---|---|---|
| 1 | 9.0 | 29.9 |
| 2 | 9.7 | 76.9 |
| 3 | 12.3 | 14.1 |
| 4 | 15.7 | 44.5 |
| 5 | 16.0 | 100 |
| 6 | 16.3 | 29.4 |
| 7 | 19.6 | 21.1 |
| 8 | 20.00 | 57.6 |
| 9 | 21.2 | 52.8 |
| 10 | 21.6 | 27.8 |
| 11 | 22.4 | 14.8 |
| 12 | 23.3 | 48.1 |
| 13 | 23.9 | 37.9 |
| 14 | 24.2 | 14.9 |
| 15 | 24.5 | 31.9 |
| 16 | 24.7 | 12.3 |
| 17 | 26.1 | 14.9 |
| 18 | 27.8 | 25.5 |
| 19 | 28.6 | 29.6 |
| 20 | 30.0 | 25.5 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane has an XRPD pattern with at least 8 of the characteristic peaks (2θdegrees±0.2) listed in Table 6.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane has an XRPD pattern with at least 5 of the characteristic peaks (2θdegrees±0.2) listed in Table 6.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane has an XRPD pattern with at least the 8 characteristic peaks (2θdegrees±0.2) as listed in Table 6A.

TABLE 6A

XRPD peaks of crystalline Form
D hemi-dichloromethane

| Peak No. | Position [°2θ] | Relative Intensity [%] |
|---|---|---|
| 2 | 9.7 | 76.9 |
| 4 | 15.7 | 44.5 |
| 5 | 16.0 | 100 |
| 8 | 20. | 57.6 |
| 9 | 21.2 | 52.8 |
| 12 | 23.3 | 48.1 |
| 13 | 23.9 | 37.9 |
| 15 | 24.5 | 31.9 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane has an XRPD pattern with at least the 6 characteristic peaks (2θdegrees±0.2) as listed in Table 68.

TABLE 6B

XRPD peaks of
crystalline Form
D hemi-dichloromethane

| Peak No. | Position [°2θ] | Relative Intensity [%] |
|---|---|---|
| 2 | 9.7 | 76.9 |
| 4 | 15.7 | 44.5 |
| 5 | 16.0 | 100 |
| 8 | 20.0 | 57.6 |
| 9 | 21.2 | 52.8 |
| 12 | 23.3 | 48.1 |

Figure 10:
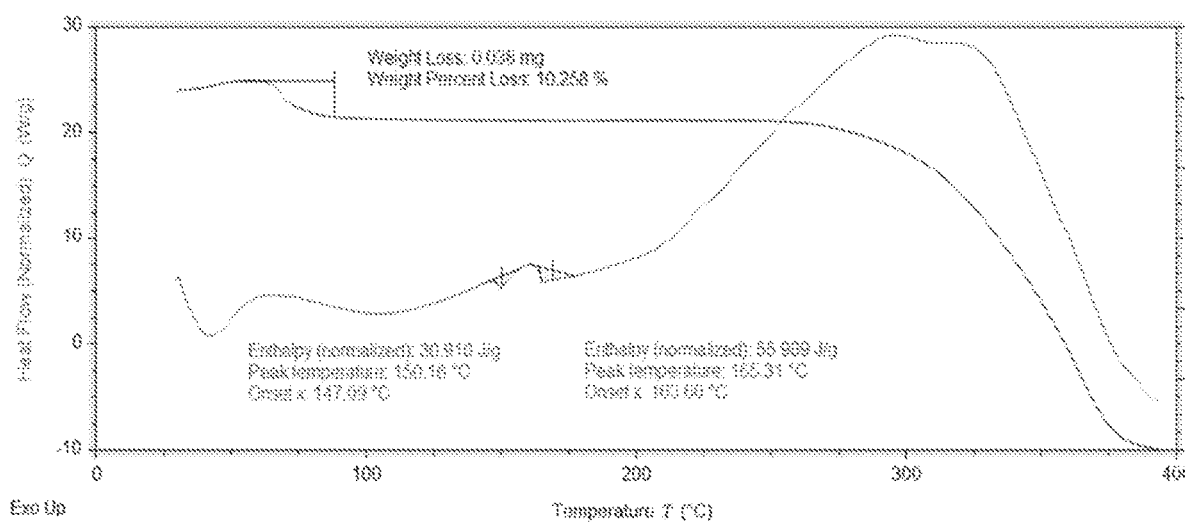
FIG. 10 is an overlay of a differential scanning calorimetry scan and a thermogravimetric analysis scan of N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane, according to one embodiment.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane has a TG/DSC profile as shown in FIG. 10.

N-(2-chloro-3-((3,5-dimethyl-4-oxo-3,4-dihydroquinazolin-6-yl)amino)-4-fluorophenyl)-3-fluoropropane-1-sulfonamide Form E Toluene In one embodiment, provided herein is crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene.

Figure 11:
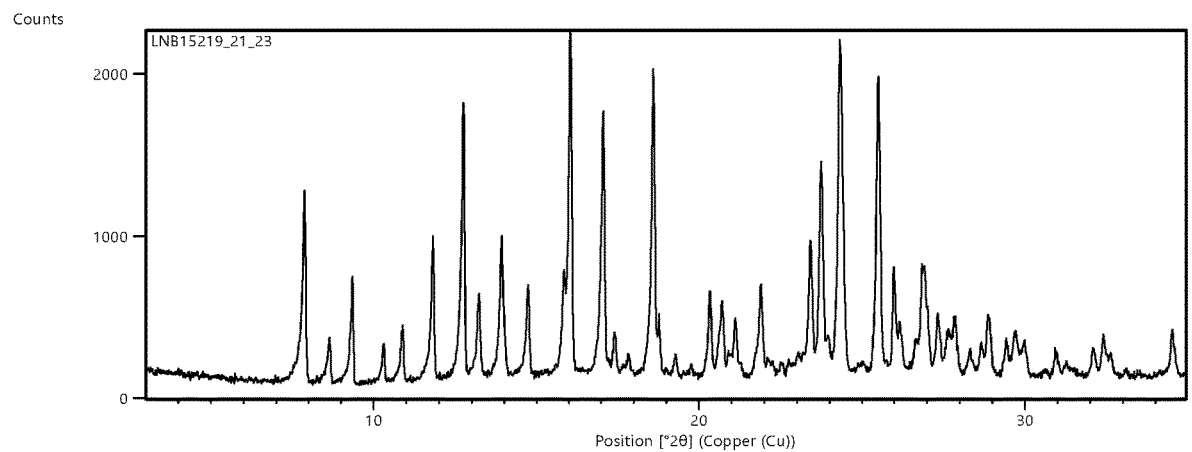
FIG. 11 illustrates an X-ray powder diffraction (XRPD) pattern of crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene, according to one embodiment.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene may be characterized by its XRPD pattern as illustrated in FIG. 11.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene has an XRPD pattern with at least the 20 characteristic peaks (2θdegrees±0.2) as listed in Table 7.

TABLE 7

XRPD peaks of crystalline Form E toluene

| Peak No. | Position [°2θ] | Relative Intensity [%] |
|---|---|---|
| 1 | 7.9 | 52.6 |
| 2 | 9.4 | 29.0 |
| 3 | 11.8 | 40.0 |
| 4 | 12.8 | 78.1 |
| 5 | 13.2 | 24.7 |
| 6 | 13.9 | 41.0 |
| 7 | 14.7 | 27.4 |
| 8 | 15.8 | 30.5 |
| 9 | 16.0 | 100 |
| 10 | 17.0 | 76.2 |
| 11 | 18.6 | 88.3 |
| 12 | 20.3 | 25.6 |
| 13 | 20.7 | 22.6 |
| 14 | 21.9 | 27.4 |
| 15 | 23.4 | 39.9 |
| 16 | 23.7 | 62 |
| 17 | 24.3 | 90.9 |
| 18 | 25.5 | 86.0 |
| 19 | 26.0 | 32.5 |
| 20 | 26.8 | 30.7 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene has an XRPD pattern with at least 8 of the characteristic peaks (2θdegrees±0.2) listed in Table 7.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene has an XRPD pattern with at least 5 of the characteristic peaks (2θdegrees±0.2) listed in Table 7.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene has an XRPD pattern with at least the 8 characteristic peaks (2θdegrees±0.2) as listed in Table 7A.

TABLE 7A

XRPD peaks of crystalline Form E toluene

| Peak No. | Position [°2θ] | Relative Intensity [%] |
|---|---|---|
| 1 | 7.9 | 52.6 |
| 4 | 12.8 | 78.1 |
| 9 | 16.0 | 100 |
| 10 | 17.1 | 76.2 |
| 11 | 18.6 | 88.3 |
| 16 | 23.7 | 62 |
| 17 | 24.3 | 90.9 |
| 18 | 25.5 | 86.0 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene has an XRPD pattern with at least the 6 characteristic peaks (2θdegrees±0.2) as listed in Table 7B.

TABLE 7B

XRPD peaks of crystalline Form E toluene

| Peak No. | Po. [°2θ] | Rel. Int. [%] |
|---|---|---|
| 4 | 12.8 | 78.1 |
| 9 | 16.0 | 100 |
| 10 | 17.1 | 76.2 |
| 11 | 18.6 | 88.3 |
| 17 | 24.3 | 90.9 |
| 18 | 25.5 | 86.0 |

Figure 12:
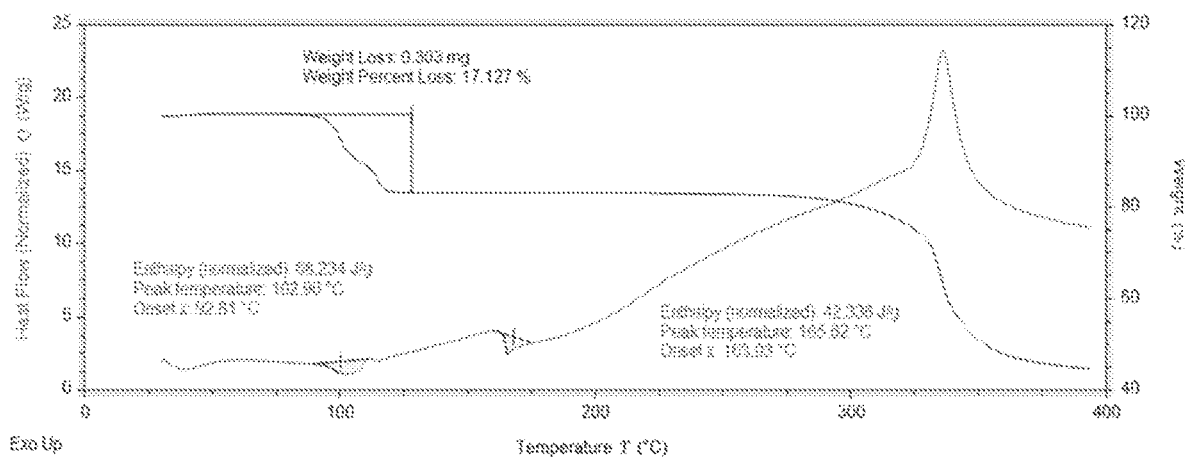
FIG. 12 is an overlay of a differential scanning calorimetry scan and a thermogravimetric analysis scan of N-(2-chloro-3-((3,5-dimethyl-4-oxo-3,4-dihydroquinazolin-6-yl)amino)-4-fluorophenyl)-3-fluoropropane-1-sulfonamide Form E, according to one embodiment.

In certain embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form E toluene has a TG/DSC profile as shown in FIG. 12.

N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane In one embodiment, provided herein is crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane.

Figure 13:
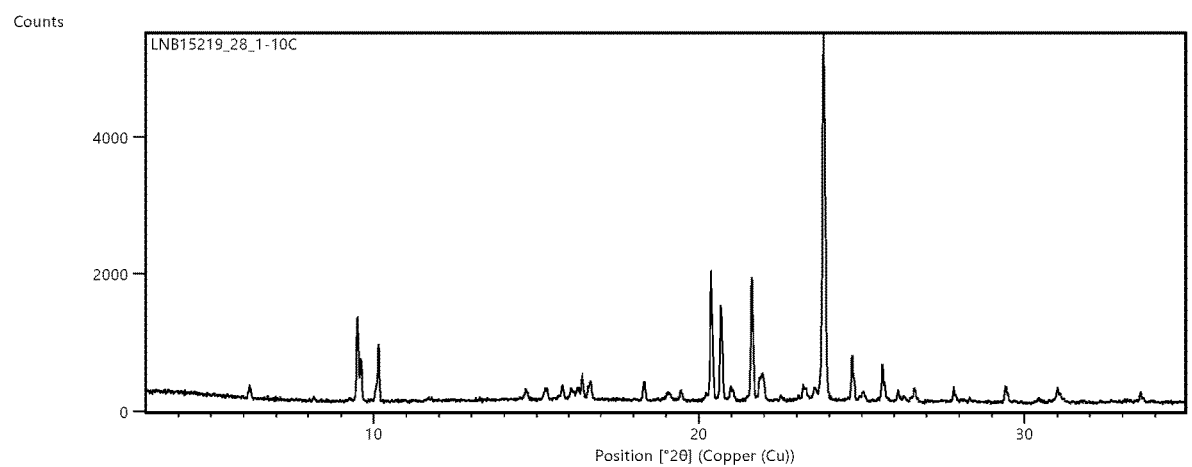
FIG. 13 illustrates an X-ray powder diffraction (XRPD) pattern of crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane, according to one embodiment.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane may be characterized by its XRPD pattern as illustrated in FIG. 13.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane has an XRPD pattern with at least the 20 characteristic peaks (2θ degrees±0.2) as listed in Table 8.

TABLE 8

XRPD peaks of crystalline Form F 1,4-dioxane

| Peak No. | Position [°2θ] | Relative Intensity [%] |
|---|---|---|
| 1 | 9.5 | 23.2 |
| 2 | 9.6 | 11.4 |
| 3 | 10.2 | 15.5 |
| 4 | 15.8 | 4.0 |
| 5 | 16.4 | 7.3 |
| 6 | 16.7 | 5.2 |
| 7 | 18.3 | 5.3 |
| 8 | 20.4 | 34.9 |
| 9 | 20.7 | 25.7 |
| 10 | 21.6 | 34.4 |
| 11 | 21.9 | 5.9 |
| 12 | 23.2 | 4.5 |
| 13 | 23.6 | 3.8 |
| 14 | 23.8 | 100 |
| 15 | 24.7 | 12.7 |
| 16 | 25.7 | 10.5 |
| 17 | 26.6 | 3.8 |
| 18 | 27.8 | 4.2 |
| 19 | 29.4 | 4.4 |
| 20 | 31.0 | 4.0 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane has an XRPD pattern with at least 8 of the characteristic peaks (2θdegrees±0.2) listed in Table 8.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane has an XRPD pattern with at least 5 of the characteristic peaks (2θdegrees±0.2) listed in Table 8.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane has an XRPD pattern with at least the 8 characteristic peaks (2θdegrees±0.2) as listed in Table 8A.

TABLE 8A

| \multicolumn{3}{c}{XRPD peaks of crystalline Form F 1,4-dioxane} | | |
|---|---|---|
| Peak No. | Position [°2θ] | Relative Intensity [%] |
| 1 | 9.5 | 23.2 |
| 2 | 9.6 | 11.4 |
| 3 | 10.2 | 15.5 |
| 8 | 20.4 | 34.9 |
| 9 | 20.7 | 25.7 |
| 10 | 21.6 | 34.4 |
| 14 | 23.8 | 100 |
| 15 | 24.7 | 12.7 |

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane has an XRPD pattern with at least the 6 characteristic peaks (2θdegrees±0.2) as listed in Table 8B.

TABLE 8B

| \multicolumn{3}{c}{XRPD peaks of crystalline Form F 1,4-dioxane} | | |
|---|---|---|
| Peak No. | Pos. [°2θ] | Rel. Int. [%] |
| 1 | 9.5 | 23.2 |
| 3 | 10.2 | 15.5 |
| 8 | 20.4 | 34.9 |
| 9 | 20.7 | 25.7 |
| 10 | 21.6 | 34.4 |
| 14 | 23.8 | 100 |

Figure 14:
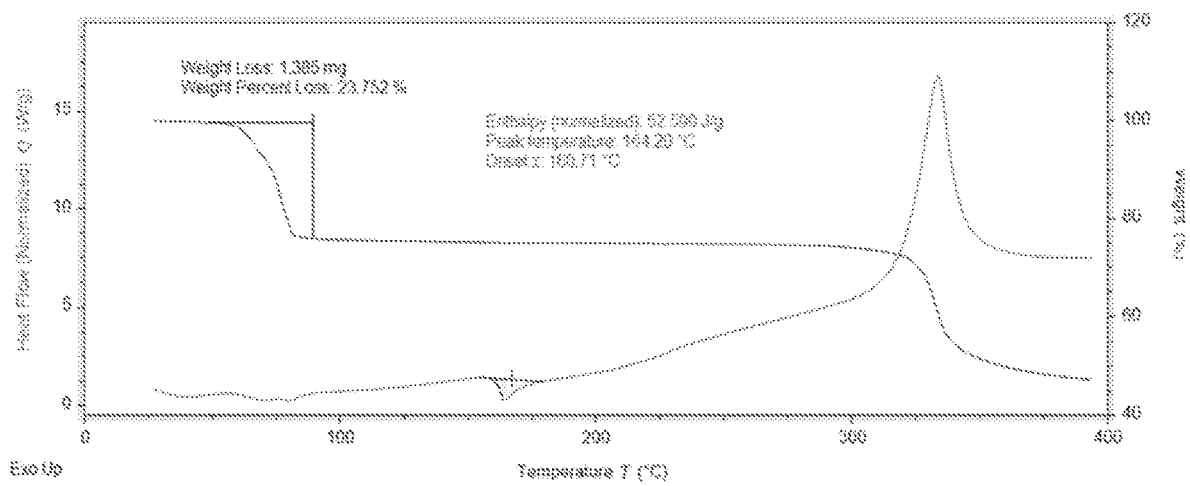
FIG. 14 is an overlay of a differential scanning calorimetry scan and a thermogravimetric analysis scan of N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane, according to one embodiment.

In some embodiments, crystalline form N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane has a TG/DSC profile as shown in FIG. 14.

For illustrative purposes, Schemes 1-15 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

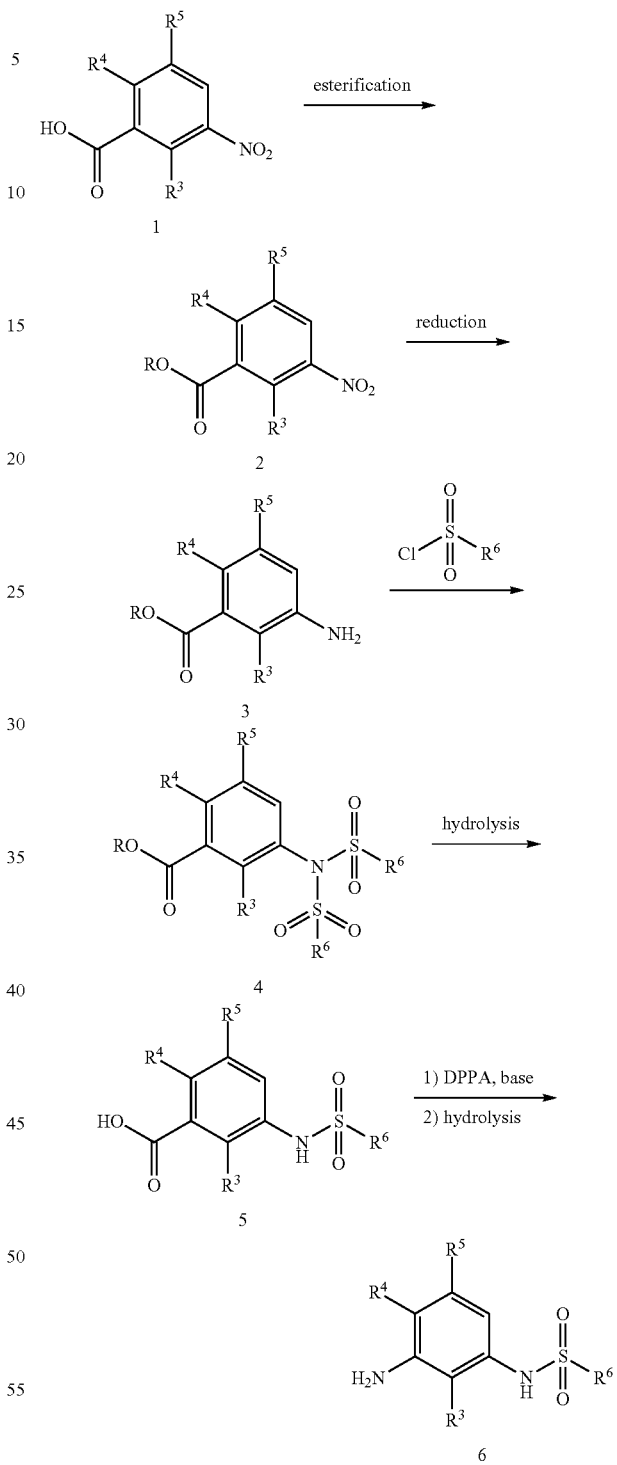

Scheme 1

Scheme 1 shows a general method for preparing intermediate compound 6 which is useful for preparing compounds of Formula I wherein $R^3$, $R^4$, $R^5$ and $R^6$ are as defined for Formula I, $X^1$ is CH, and L is NH. A benzoic acid 1 (wherein $R^3$, $R^4$ and $R^5$ are as defined for Formula I) may be esterified to provide compound 2 (wherein R is alkyl), e.g., by treatment with trimethylsilyl diazomethane in MeOH or by Fischer esterification conditions, such as treatment with trimethylsilyl chloride in MeOH. The nitro group of intermediate 2 may be reduced to an amino group using standard conditions, such as treatment with Pd/C and H₂ to provide compound 3. Compound 3 may be treated with a sulfonyl chloride reagent having the formula R⁶SO₂Cl, wherein R⁶ is as defined for Formula I, in the presence of a base, such as NEt₃, in an organic solvent such as dichloromethane, to provide compound 4. Compound 4 may be hydrolyzed under basic conditions, such as aqueous NaOH, in the appropriate solvent system, such as THF and/or MeOH, to provide compound 5. Compound 5 may be treated with DPPA (diphenylphosphonic azide) and a base such as triethylamine in a suitable solvent, such as THF followed by hydrolysis to provide compound 6.

Scheme 2

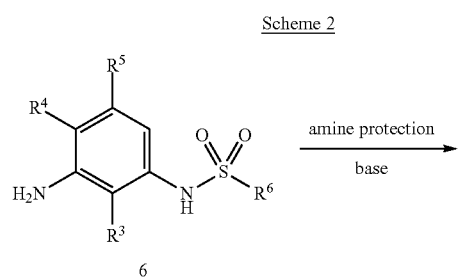

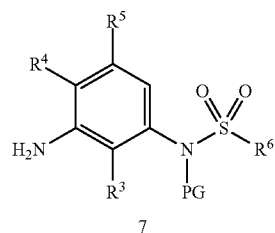

Scheme 2 shows a procedure for preparing compound 7 which is useful for preparing compounds of Formula I wherein R³, R⁴, R⁵ and R⁶ are as for Formula I, X¹ is CH, and L is NH. Compound 6, prepared according to Scheme 1, may be treated with an amine protecting reagent, (e.g., 2-(chloromethoxy)ethyl)trimethylsilane or p-methoxybenzyl bromide) in the presence of a base (e.g., sodium hydride) to provide compound 7, wherein PG is an amine protecting group protecting group (PG) (e.g., trimethylsilylethoxymethyl or p-methoxybenzyl).

Scheme 3

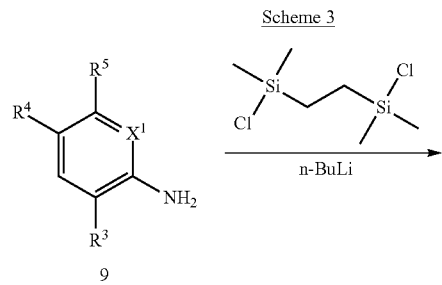

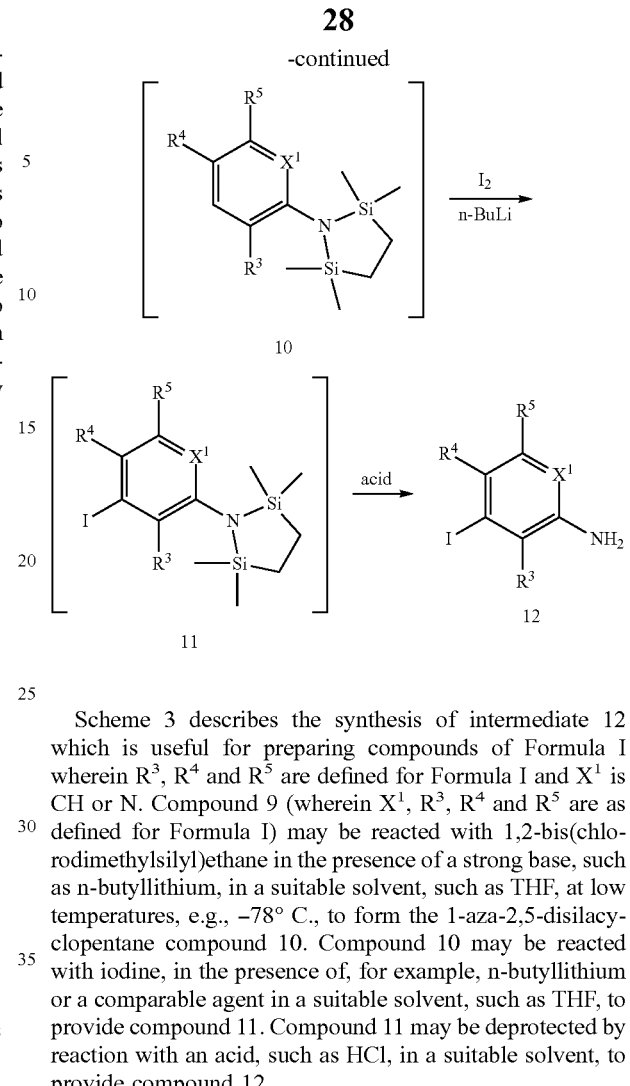

Scheme 3 describes the synthesis of intermediate 12 which is useful for preparing compounds of Formula I wherein R³, R⁴ and R⁵ are defined for Formula I and X¹ is CH or N. Compound 9 (wherein X¹, R³, R⁴ and R⁵ are as defined for Formula I) may be reacted with 1,2-bis(chlorodimethylsilyl)ethane in the presence of a strong base, such as n-butyllithium, in a suitable solvent, such as THF, at low temperatures, e.g., −78° C., to form the 1-aza-2,5-disilacyclopentane compound 10. Compound 10 may be reacted with iodine, in the presence of, for example, n-butyllithium or a comparable agent in a suitable solvent, such as THF, to provide compound 11. Compound 11 may be deprotected by reaction with an acid, such as HCl, in a suitable solvent, to provide compound 12.

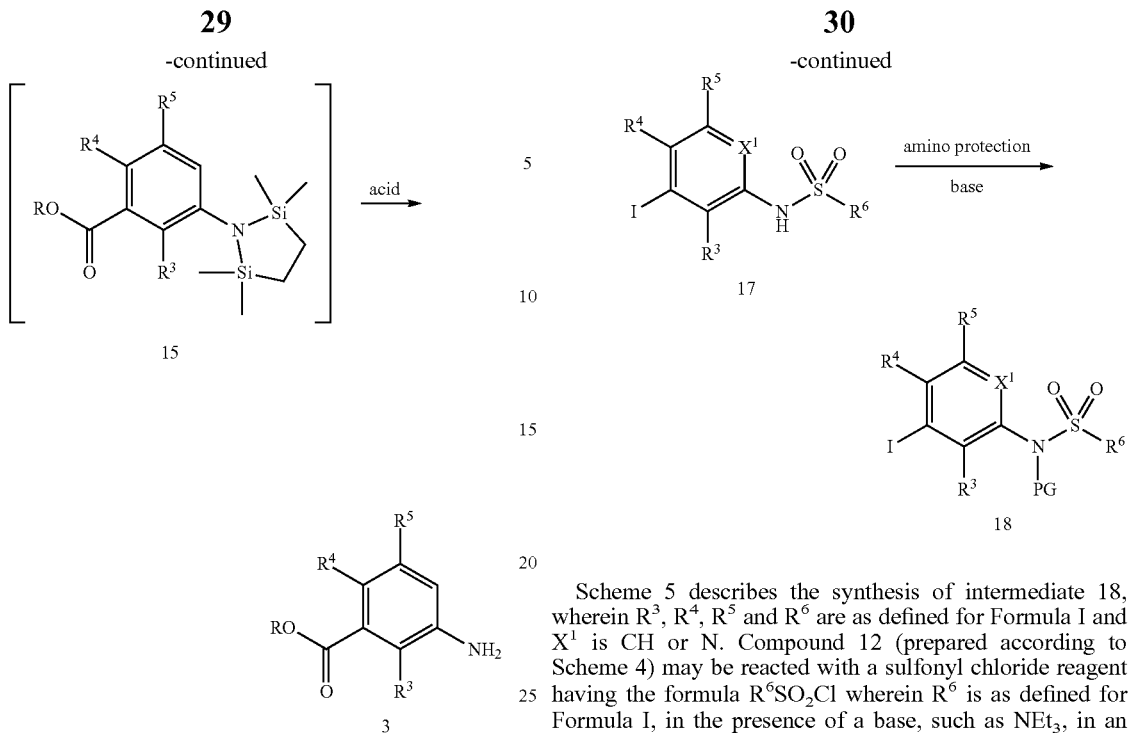

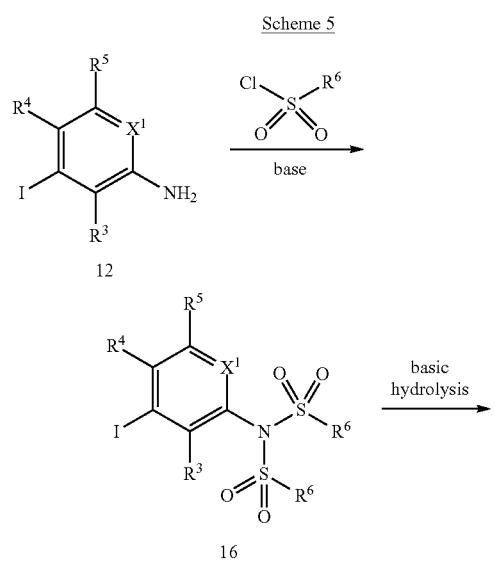

Scheme 4 describes an alternative synthesis of compound 3 wherein $X^1$ is CH, and wherein $R^3$, $R^4$ and $R^5$ are defined for Formula I. Compound 13 (wherein $R^3$, $R^4$ and $R^5$ are as defined for Formula I) may be reacted with 1,2-bis(chlorodimethylsilyl)ethane in the presence of a strong base, such as n-butyllithium, in a suitable solvent, such as THF, at low temperatures, e.g., −78° C., to provide compound 14. Compound 14 may be reacted with a carbamoyl chloride, RO(C=O)Cl wherein R is a small alkyl, such as methyl or ethyl, or a benzyl group, in the presence of, for example n-butyllithium, in a suitable solvent; such as THF, to provide compound 15. Compound 15 may be deprotected by reaction with an acid, such as HCl, in a suitable solvent, to provide compound 3.

Scheme 5 describes the synthesis of intermediate 18, wherein $R^3$, $R^4$, $R^5$ and $R^6$ are as defined for Formula I and $X^1$ is CH or N. Compound 12 (prepared according to Scheme 4) may be reacted with a sulfonyl chloride reagent having the formula $R^6SO_2Cl$ wherein $R^6$ is as defined for Formula I, in the presence of a base, such as $NEt_3$, in an organic solvent, such as dichloromethane to provide compound 16. Compound 16 may be hydrolyzed, e.g., under basic conditions such as aqueous NaOH, in the appropriate solvent system such as THF and/or MeOH, to provide the compound 17. Compound 17 may be reacted with an amino group protecting reagent, for example (2-(chloromethoxy)ethyl)trimethylsilane (SEM-Cl), under standard conditions (e.g., in the presence of a base, such as sodium hydride, in a suitable solvent, such as DMF) to provide compound 18 wherein PG is an amine protecting group (e.g., a SEM group).

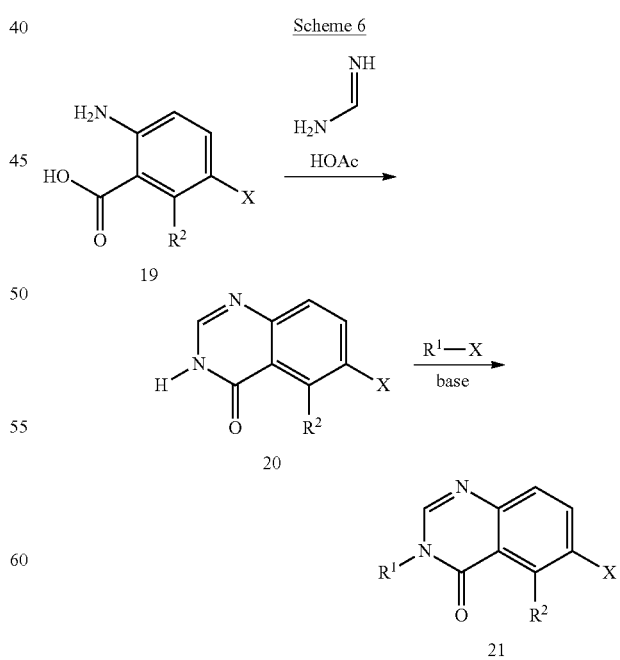

Scheme 6 describes the synthesis of intermediate 21 wherein X is halogen, which is useful for preparing compounds of Formula I wherein $R^1$ and $R^2$ are as defined for Formula I and $X^1$ is CH. Compound 19 may be cyclized with formamidine acetate in an organic solvent, such as EtOH, at elevated temperature to provide compound 20. Compound 20 may be alkylated with a reagent having the formula $R^1X$ wherein $R^1$ is as defined for Formula I and X is halogen, in the presence of a base such as $Cs_2CO_3$, in a solvent, such as DMF to provide compound 21.

wherein PG is an amine protecting group (such as p-methoxybenzyl (PMB)) in the presence of a catalyst, such as a palladium catalyst (e.g., $Pd_2(dba)_3$) and a ligand (e.g., Xantphos) to provide compound 22. Compound 22 may be deprotected under standard conditions, for example using TFA, to provide compound 23.

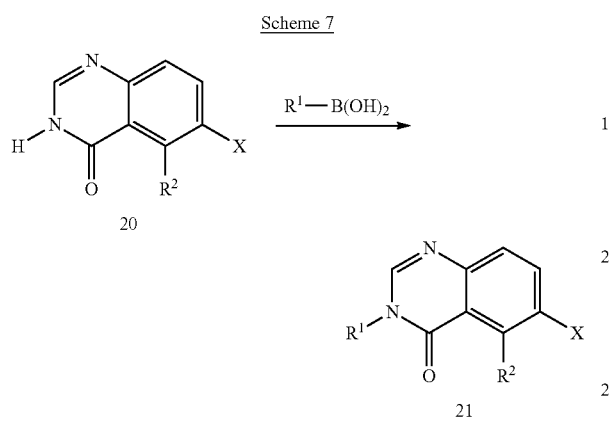

Scheme 7 describes an alternative route for synthesizing intermediate 21, wherein $R^1$ and $R^2$ are as defined for Formula I, $X^1$ is CH and X is halogen, which is useful for preparing compounds of Formula I. Compound 20 may be coupled with a boronic acid reagent $R^1B(OH)_2$ wherein $R^1$ is as defined for Formula I, in the presence of a catalyst, such as $Cu(OAc)_2$ and a ligand, such as pyridine, to provide compound 21.

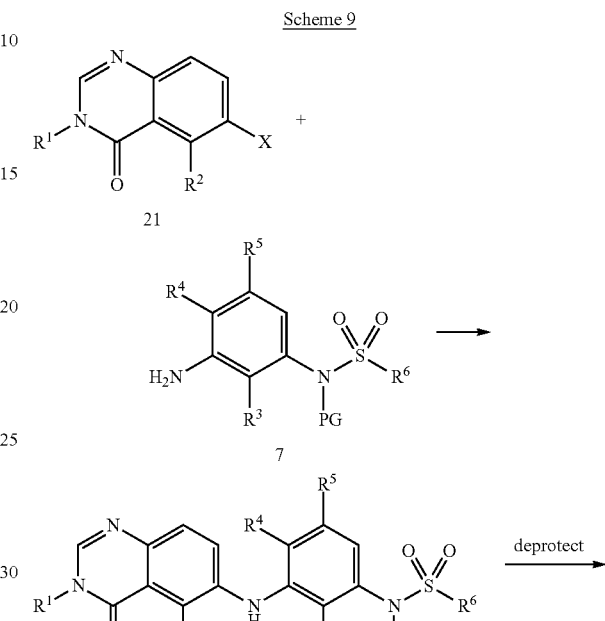

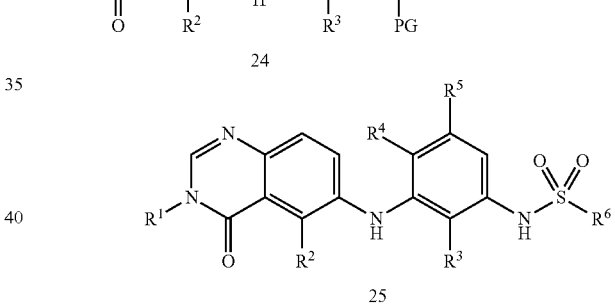

Scheme 9 describes the synthesis of compound 25, which is a compound of Formula I wherein $R^1$, $R^2$, $R^3$, $R^4$, $R^5$ and $R^6$ are as defined for Formula I, $X^1$ is CH, and L is NH. Compound 25 may be obtained by coupling compound 21 (prepared, e.g., according to Scheme 6 or 7) with compound 7 (prepared, e.g., according to Scheme 2) in the presence of a catalyst (e.g., a palladium catalyst, e.g., $Pd_2(dba)_3$) and a ligand (e.g., Xantphos) followed by deprotection under standard conditions (e.g. with TFA), to provide compound 25.

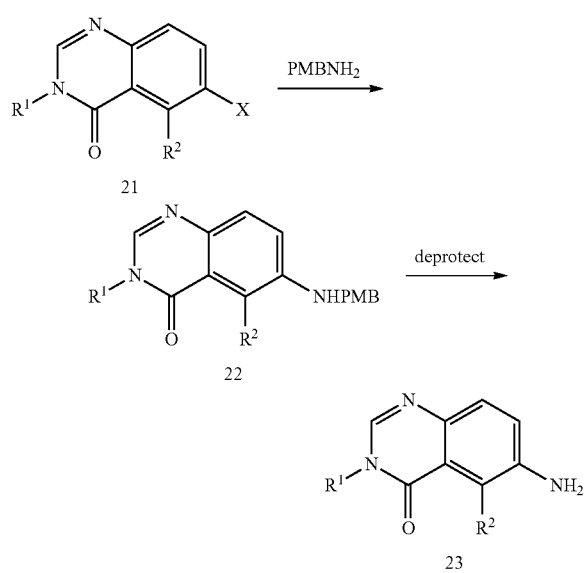

Scheme 8 describes the synthesis of intermediate 23 wherein $R^1$ and $R^2$ are as defined for Formula I and $X^1$ is CH, which is useful for preparing compounds of Formula I compound 21 (prepared e.g., according to Scheme 6 or 7) may be coupled with a reagent having the formula $(PG)NH_2$

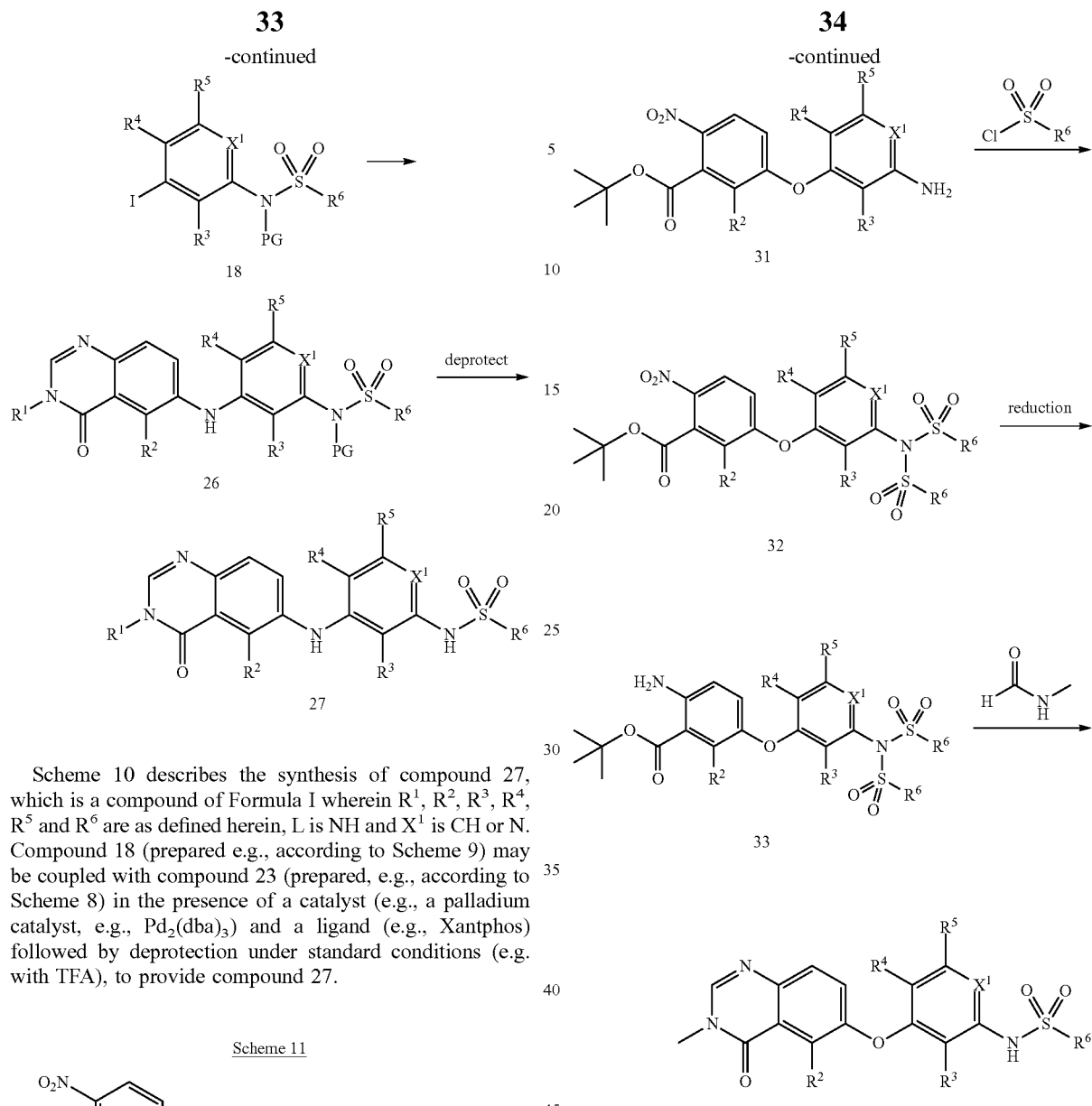

Scheme 10 describes the synthesis of compound 27, which is a compound of Formula I wherein $R^1$, $R^2$, $R^3$, $R^4$, $R^5$ and $R^6$ are as defined herein, L is NH and $X^1$ is CH or N. Compound 18 (prepared e.g., according to Scheme 9) may be coupled with compound 23 (prepared, e.g., according to Scheme 8) in the presence of a catalyst (e.g., a palladium catalyst, e.g., $Pd_2(dba)_3$) and a ligand (e.g., Xantphos) followed by deprotection under standard conditions (e.g. with TFA), to provide compound 27.

Scheme 11 describes the synthesis of a compound of Formula 34, which is a compound of Formula I wherein $R^3$, $R^4$, $R^5$ and $R^6$ are as defined for Formula I, $R^1$ is methyl, L is O and $X^1$ is CH. Compound 28 (wherein $R^2$ is as defined for Formula I) may be reacted with $(Boc)_2O$ in a mixture of organic solvents, such as t-BuOH and DCM, in the presence of a catalyst (e.g., DMAP) to provide compound 29. Compound 29 may be coupled with compound 30 in a suitable solvent, such as DMF, in the presence of a base, such as $Cs_2CO_3$, at elevated temperature to provide compound 31. Compound 31 may be reacted with a sulfonyl chloride reagent having the formula $ClSO_2R^6$, in the presence of a base, such as $NEt_3$, in an organic solvent, such as DCM, to provide compound 32. The nitro group of compound 32 may be reduced under standard nitro reduction conditions, such as treatment with Pd/C and $H_2$ to provide compound 33. Compound 33 may be cyclized with N-methylformamide in the presence of an acid, such as formic acid, at elevated temperatures, to provide compound 34.

Scheme 12

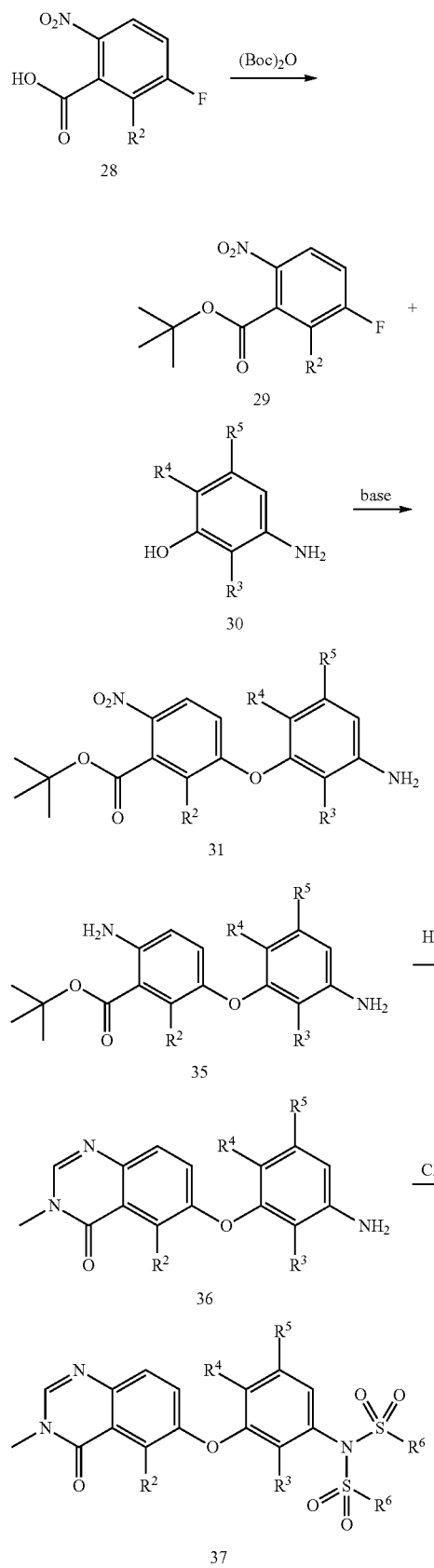

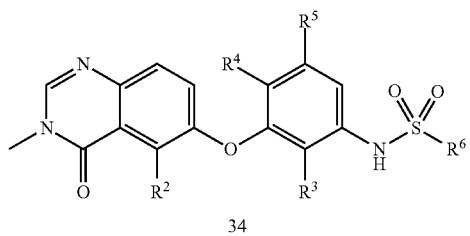

Scheme 12 describes the synthesis of a compound of Formula 34, which is a compound of Formula I wherein $R^3$, $R^4$, $R^5$ and $R^6$ are as defined for Formula I, $R^1$ is methyl, L is O and $X^1$ is CH. Compound 28 (wherein $R^2$ is as defined for Formula I) may be reacted with $(Boc)_2O$ in a mixture of organic solvents, such as t-BuOH and DCM, in the presence of a catalyst (e.g., DMAP) to provide compound 29. Compound 29 may be coupled with compound 30 in a suitable solvent, such as DMF, in the presence of a base, such as $Cs_2CO_3$, at elevated temperature to provide compound 31. The nitro group of compound 31 may be reduced under standard nitro reduction conditions, such as treatment with Pd/C and $H_2$ to provide compound 35. Compound 35 may be cyclized with N-methylformamide in the presence of an acid, such as formic acid, at elevated temperatures, to provide compound 36. Compound 36 may be reacted with a sulfonyl chloride reagent having the formula $ClSO_2R^6$, in the presence of a base, such as an amine base (e.g., $NEt_3$), in a suitable organic solvent (e.g., DCM) to provide compound 37. Compound 37 may be hydrolyzed, e.g., under basic conditions such as aqueous NaOH, in the appropriate solvent system such as THF and/or MeOH, to provide the compound 34.

Scheme 13

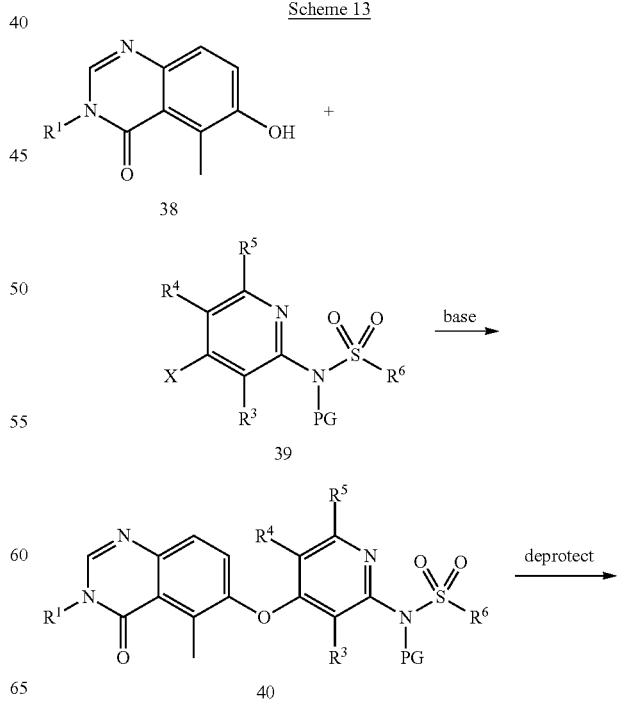

-continued

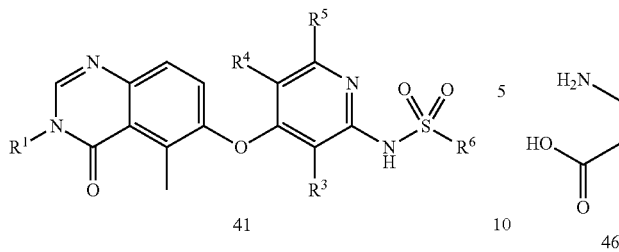

41

Scheme 13 describes the synthesis of a compound of Formula 41, which is a compound of Formula I wherein $R^3$, $R^4$, $R^5$ and $R^6$ are as defined for Formula I, $R^1$ is methyl, $R^2$ is methyl, L is O and $X^1$ is N. Compound 38, wherein $R^1$ is as defined for Formula I, may be coupled with compound 39, wherein X is a halogen, PG is an amine protecting group, and $R^3$, $R^4$ and $R^5$ are as defined for Formula I, in a suitable solvent, such as DMF, in the presence of a base, e.g., an alkaline carbonate base (e.g., $Cs_2CO_3$) at elevated temperature to provide compound 40. Compound 40 may be deprotected under standard conditions, for example using TFA, to provide compound 41.

Scheme 14

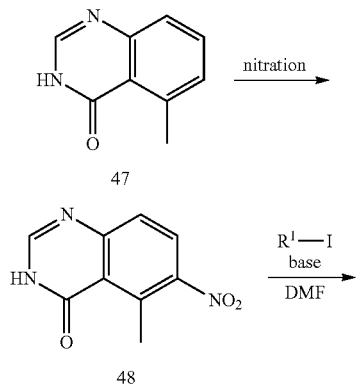

Scheme 14 shows a general method for preparing intermediate compound 45, which is useful for preparing compounds Formula I wherein $R^3$ is chloro, $R^4$ is fluoro and $R^5$ is hydrogen. Commercially available 2-chloro-4-fluoroaniline may be treated with n-butyllithium at a reduced temperature, followed by treatment with 1,2-(bis(chlorodimethylsilyl)ethane to form a 1-(2-chloro-4-fluorophenyl)-2,2,5,5-tetramethyl-1,2,5-azadisilolidine intermediate (not shown), which may be treated with n-butyllithium followed by addition of iodine to provide intermediate 43. The amino group of intermediate 43 may be treated with di-tert-butyl-dicarbonate to provide the bis-Boc protected intermediate 44. Intermediate 44 may be treated with a base, e.g., an alkaline carbonate base, e.g., potassium carbonate, to provide the Boc-protected intermediate 45.

Scheme 15

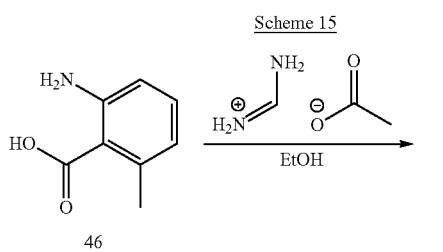

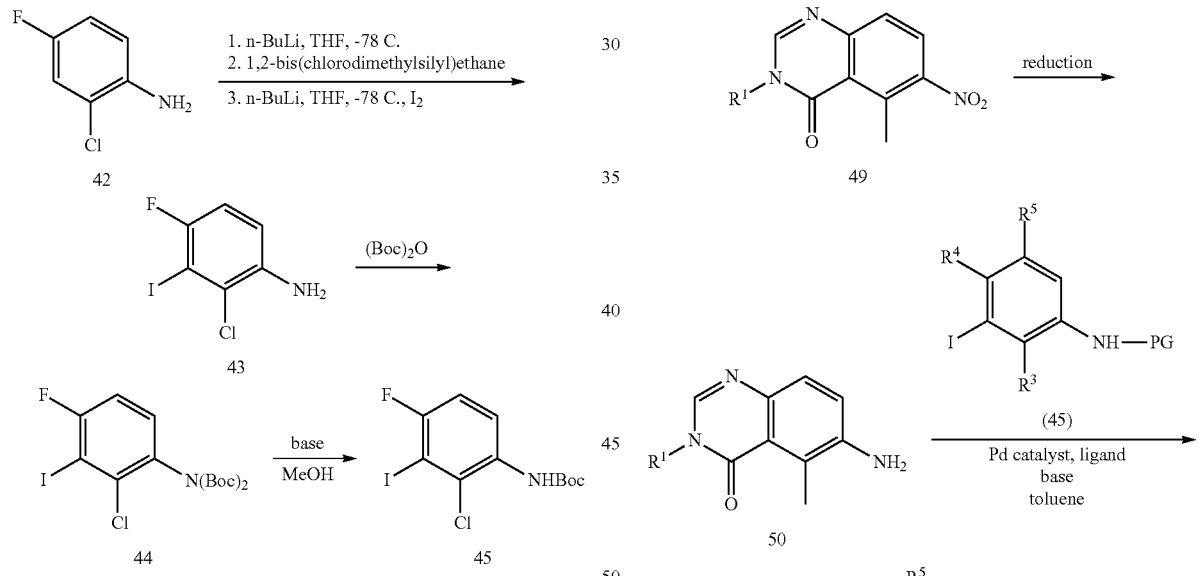

-continued

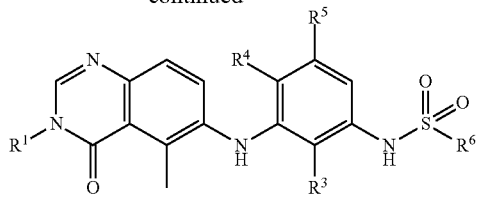

53

Scheme 15 describes the synthesis of compound 53, which is a compound of Formula I wherein $X^1$ is CH, $R^1$ is methyl, and $R^2$, $R^3$, $R^4$, $R^5$ and $R^6$ are as defined for Formula I. Commercially available compound 46 may be reacted with formamidine acetate at elevated temperatures to provide compound 47. Compound 47 may be nitrated under standard conditions, e.g., in the presence of nitric acid and sulfuric acid, to provide compound 48. Compound 48 may be alkylated with MeI, in the presence of a base such as $Cs_2CO_3$, in a solvent, such as DMF to provide compound 49. The nitro group of compound 49 may be reduced to an amino group using standard conditions, such as treatment with Pd/C and $H_2$ to provide compound 50. Compound 50 may be coupled with compound 45 wherein PG is an amine protecting group and $R^3$, $R^4$ and $R^5$ are as defined for Formula I (prepared, e.g., as described in Scheme 14) in the presence of a catalyst (e.g., a palladium catalyst, e.g., $Pd_2(dba)_3$), a ligand (e.g., Xantphos) and a base (e.g., an alkaline carbonate base, e.g., $Cs_2CO_3$) to provide compound 51. Compound 51 may be reacted with a sulfonyl chloride reagent having the formula $R^6SO_2Cl$ (wherein $R^6$ is as defined for Formula I), in the presence of a base, such as NaHMDS, in an organic solvent such as THF, to provide compound 52. Removal of the amino protecting group of compound 52 under standard conditions (e.g. with TFA), provides compound 53.

The synthetic intermediates having formulas 21, 23, 24, 26, 31, 32, 33, 35, 36, 37, 40, 45, 49, 50, 51 and 52 as defined in the above Schemes are provided as further aspects of this invention.

In one embodiment, provided herein is a compound having the formula (23)

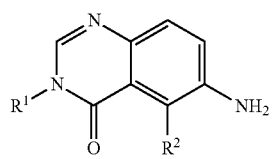

(23)

wherein:
$R^1$ is C1-C6 alkyl, C1-C6 deuteroalkyl, C1-C6 fluoroalkyl, C3-C6 cycloalkyl, (C3-C6 cycloalkyl)$CH_2$—, (C1-C6 alkoxy)C1-C6 alkyl-, $Ar^1$, $Ar^1CH_2$—, $hetAr^1$ or $hetCyc^1$;

$Ar^1$ is phenyl which is optionally substituted with 1-5 substituents independently selected from halogen and C1-C3 alkyl;

$hetAr^1$ is a 5-6 membered heteroaryl ring having 1-2 ring nitrogen atoms and optionally substituted with 1-3 substituents independently selected from halogen and C1-C3 alkyl;

$hetCyc^1$ is a 4-6 membered saturated monocyclic heterocyclic ring having one ring oxygen atom; and $R^2$ is methyl, —$CD_3$ or HC≡C—.

In one embodiment of formula (23), $R^1$ is C1-C6 alkyl. In one embodiment of formula (23), $R^1$ is methyl.

In one embodiment of formula (23), $R^1$ is C1-C6 alkyl and $R^2$ is methyl. In one embodiment of formula (23), $R^1$ is methyl and $R^2$ is methyl.

In one embodiment, provided herein is a compound having the formula (24)

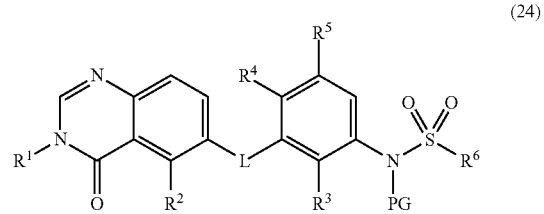

(24)

wherein:
$R^1$ is C1-C6 alkyl, C1-C6 deuteroalkyl, C1-C6 fluoroalkyl, C3-C6 cycloalkyl, (C3-C6 cycloalkyl)$CH_2$—, (C1-C6 alkoxy)C1-C6 alkyl-, $Ar^1$, $Ar^1CH_2$—, $hetAr^1$ or $hetCyc^1$;

$Ar^1$ is phenyl which is optionally substituted with 1-5 substituents independently selected from halogen and C1-C3 alkyl;

$hetAr^1$ is a 5-6 membered heteroaryl ring having 1-2 ring nitrogen atoms and optionally substituted with 1-3 substituents independently selected from halogen and C1-C3 alkyl;

$hetCyc^1$ is a 4-6 membered saturated monocyclic heterocyclic ring having one ring oxygen atom;

$R^2$ is methyl, —$CD_3$ or HC≡C—;

$R^3$ is F, Cl, CN or methyl;

$R^4$ is H, F or Cl;

$R^5$ is H, F, Cl, methyl;

$R^6$ is C1-C6 alkyl, C1-C6 fluoroalkyl, $(Cyc^1)$C1-C6 alkyl-, (C1-C3 alkoxy)C1-C6 alkyl-, $hetAr^2$, $Ar^2$ or $R^aR^bN$—;

$Cyc^1$ is a 3-6 membered saturated carbocyclic ring;

$hetAr^2$ is a 5-6 membered heteroaryl having 1-2 ring heteroatoms independently selected from N, O and S and optionally substituted with 1-3 substituents independently selected from halogen and C1-C3 alkyl;

$Ar^2$ is phenyl optionally substituted with 1-5 substituents independently selected from halogen and C1-C6 alkyl;

$R^a$ and $R^b$ are independently C1-C3 alkyl, or $R^a$ and $R^b$ together with the nitrogen atom to which they are attached form a 5-6 membered saturated monocyclic heterocyclic ring optionally substituted with fluoro; and PG is an amine protecting group.

In one embodiment of formula (24), $R^1$ is C1-C6 alkyl.
In one embodiment of formula (24), $R^2$ is methyl.
In one embodiment of formula (24), $R^3$ is Cl.
In one embodiment of formula (24), $R^4$ is F.
In one embodiment of formula (24), $R^6$ is C1-C6 fluoroalkyl.
In one embodiment of formula (24), PG is a Boc protecting group.
In one embodiment of formula (24), $R^1$ is methyl, $R^2$ is methyl, $R^3$ is Cl, $R^4$ is F, and $R^6$ is 3-fluoropropyl. In one embodiment of formula (24), $R^1$ is methyl, $R^2$ is methyl, $R^3$ is Cl, $R^4$ is F, $R^6$ is 3-fluoropropyl, and PG is a Boc protecting group.
In one embodiment of formula (24), $R^6$ is C1-C6 alkyl, C1-C6 fluoroalkyl, $(Cyc^1)$C1-C6 alkyl-, (C1-C3 alkoxy)C1-C6 alkyl-, $hetAr^2$ or $Ar^2$.

In one embodiment of formula (24), $R^6$ is C1-C6 alkyl or C1-C6 fluoroalkyl.

Any of the aforementioned embodiments of formula (24) may be combined with each other.

In one embodiment, provided herein is a compound having the formula (45)

$$\text{(45)}$$

wherein:
$R^3$ is F, Cl, CN or methyl;
$R^4$ is H, F or Cl;
$R^5$ is H, F, Cl, methyl; and
PG is an amine protecting group.

In one embodiment of formula (45), $R^3$ is Cl.
In one embodiment of formula (45), $R^4$ is F.
In one embodiment of formula (45), $R^5$ is H.
In one embodiment of formula (45), PG is a Boc group.
In one embodiment of formula (45), $R^3$ is Cl, $R^4$ is F and $R^5$ is F. In one embodiment of formula (45), $R^3$ is Cl, $R^4$ is F, $R^5$ is F and PG is a Boc group.

Any of the aforementioned embodiments of formula (45) may be combined with each other.

In one embodiment, provided herein is a compound having the formula (51)

$$\text{(51)}$$

wherein:
$R^1$ is C1-C6 alkyl, C1-C6 deuteroalkyl, C1-C6 fluoroalkyl, C3-C6 cycloalkyl, (C3-C6 cycloalkyl)CH$_2$—, (C1-C6 alkoxy)C1-C6 alkyl-, Ar$^1$, Ar$^1$CH$_2$—, hetAr$^1$ or hetCyc$^1$;
Ar$^1$ is phenyl which is optionally substituted with 1-5 substituents independently selected from halogen and C1-C3 alkyl;
hetAr$^1$ is a 5-6 membered heteroaryl ring having 1-2 ring nitrogen atoms and optionally substituted with 1-3 substituents independently selected from halogen and C1-C3 alkyl;
hetCyc$^1$ is a 4-6 membered saturated monocyclic heterocyclic ring having one ring oxygen atom;
$R^3$ is F, Cl, CN or methyl;
$R^4$ is H, F or Cl;
$R^5$ is H, F, Cl, methyl; and
PG is an amine protecting group.

In one embodiment of formula (51), $R^1$ is C1-C6 alkyl. In one embodiment of formula (51), $R^1$ is methyl.
In one embodiment of formula (51), $R^3$ is Cl.
In one embodiment of formula (51), $R^4$ is F.
In one embodiment of formula (51), $R^5$ is H.

In one embodiment of formula (51), PG is a Boc protecting group.

In one embodiment of formula (51), $R^1$ is C1-C6 alkyl, $R^3$ is Cl, $R^4$ is F, and $R^5$ is H. In one embodiment of formula (51), $R^1$ is C1-C6 alkyl, $R^3$ is Cl, $R^4$ is F, $R^5$ is H and PG is a Boc group. In one embodiment of formula (51), $R^1$ is methyl, $R^3$ is Cl, $R^4$ is F, and $R^5$ is H. In one embodiment of formula (51), $R^1$ is methyl, $R^3$ is Cl, $R^4$ is F, $R^5$ is H and PG is a Boc group.

Any of the aforementioned embodiments of formula (51) may be combined with each other.

Also provided herein is a process for preparing of a compound of Formula I, or a pharmaceutically acceptable salt or solvate thereof which comprises:

(a) for a compound of Formula I wherein $X^1$ is CH, L is NH, and $R^1, R^2, R^3, R^4, R^5$ and $R^6$ are as defined for formula I, coupling a compound having the formula (21):

$$\text{(21)}$$

wherein $R^1$ and $R^2$ are as defined for Formula I and X is a halogen, with a compound having the formula (7):

$$\text{(7)}$$

wherein $R^3, R^4, R^5$ and $R^6$ are as defined for Formula I and PG is an amine protecting group, in the presence of a catalyst and a ligand, followed by removal of the amine protecting group; or (b) for a compound of Formula I wherein L is NH, and $X^1, R^1, R^2, R^3, R^4, R^5$ and $R^6$ are as defined for Formula I, coupling a compound having the formula (23):

$$\text{(23)}$$

wherein $R^1$ and $R^2$ are as defined for Formula I, with a compound having the formula (18)

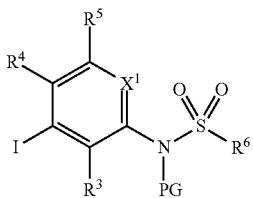

(18)

wherein $X^1$, $R^3$, $R^4$, $R^5$ and $R^6$ are as defined for Formula I and PG is an amine protecting group, in the presence of a catalyst and a ligand, followed by removal of the amine protecting group; or (c) for a compound of Formula I wherein L is O and $X^1$, $R^1$, $R^2$, $R^3$, $R^4$, $R^5$ and $R^6$ are as defined for Formula I, cyclizing a compound having the formula (33):

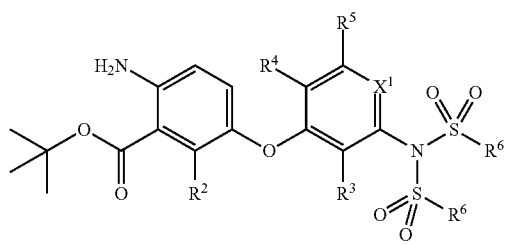

(33)

wherein $X^1$, $R^2$, $R^3$, $R^4$, $R^5$ and $R^6$ are as defined for Formula I, with N-methylformamide in the presence of an acid; or (d) for a compound of Formula I wherein $R^1$ is methyl, L is O, $X^1$ is CH, $R^3$, $R^4$, $R^5$ and $R^6$ are as defined for Formula I, coupling a compound having the formula (36)

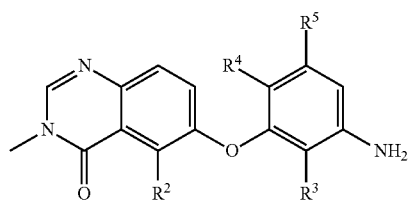

(36)

with a reagent having the formula $R^6SO_2Cl$ in the presence of an amine base, followed by hydrolysis; or (e) for a compound of Formula I wherein L is O, $R^2$ is methyl, $X^1$ is N, and $R^1$, $R^3$, $R^4$, $R^5$ and $R^6$ are as defined for Formula I, coupling a compound having the formula (38)

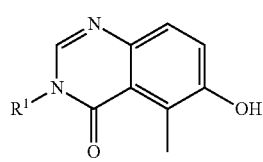

(38)

wherein $R^1$ is as defined for Formula I, with a compound having the formula (39)

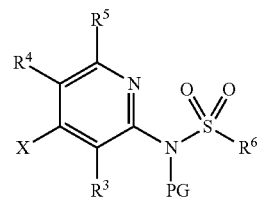

(39)

wherein X is a halogen, PG is an amine protecting group, and $R^3$, $R^4$, $R^5$ and $R^6$ are as defined for Formula I, in the presence of an alkaline carbonate base, followed by removal of the amine protecting group; or (f) for a compound of Formula I wherein $X^1$ is CH, $R^1$ is methyl, and $R^2$, $R^3$, $R^4$, $R^5$ and $R^6$ are as defined for Formula I, reacting a compound having the formula (51)

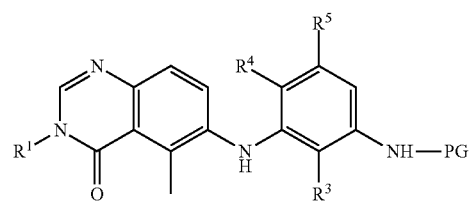

(51)

wherein $X^1$ is CH, $R^1$ is methyl, and $R^2$, $R^3$, $R^4$, $R^5$ and $R^6$ are as defined for Formula I and PG is an amine protecting group, with a compound having the formula:

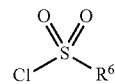

wherein $R^6$ is as defined for Formula I in the presence of a base, to provide a compound having the formula (52)

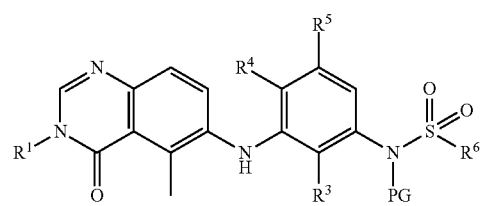

(52)

followed by removal of the amine protecting group; and
optionally forming a pharmaceutically acceptable salt or solvate thereof.

The term "amine protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amine protecting groups are t-butyloxycarbonyl ("Boc"), 2-trimethylsilylethoxymethyl (SEM), and p-methoxybenzyl (PMB). Further examples of these groups, and other protecting groups, are found in T. W. Greene, et al., Greene's Protective Groups in Organic Synthesis. New York: Wiley Interscience, 2006.

Compounds of Formula I are useful for treating diseases and disorders which can be treated with a BRAF kinase inhibitor, such as BRAF-associated diseases and disorders, e.g., proliferative disorders such as cancers, including solid tumors. The ability of test compounds to act as BRAF inhibitors may be demonstrated by the assay described in Example A. $IC_{50}$ values are shown in Table A.

In some embodiments, certain compounds of Formula I, or a pharmaceutically acceptable salt, solvate or polymorph thereof, i.e., compounds of Formula II, or a pharmaceutically acceptable salt, solvate or polymorph thereof, and Formula III, or a pharmaceutically acceptable salt, solvate or polymorph thereof, as described herein below, exhibit surprising brain and/or CNS penetrance. Such compounds are capable of crossing the BBB and inhibiting a BRAF kinase in the brain and/or other CNS structures. In some embodiments, the compounds provided herein are capable of crossing the BBB in a therapeutically effective amount. For example, treatment of a subject with cancer (e.g., a BRAF-associated cancer such as a BRAF-associated CNS cancer) can include administration (e.g., oral administration) of a compound of Formula I, or a pharmaceutically acceptable salt, solvate or polymorph thereof (i.e., compounds of Formula II and Formula III, or a pharmaceutically acceptable salt, solvate or polymorph thereof) to the subject. Accordingly, in some embodiments, compounds provided herein are useful for treating a CNS cancer.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. However, "treat" or "treatment" can also include therapeutic measures (e.g., inhibition of BRAF kinase in a BRAF-associated tumor) that temporarily worsen the appearance and/or symptoms of the subject. As used herein, the terms "treating" and "treating" when referring, e.g., to the treatment of a cancer, are not intended to be absolute terms. For example, "treatment of cancer" and "treating cancer", as used in a clinical setting, is intended to include obtaining beneficial or desired clinical results and can include an improvement in the condition of a subject having cancer. Beneficial or desired clinical results include, but are not limited to, one or more of the following: reducing the proliferation of (or destroying) neoplastic or cancerous cells, inhibiting metastasis of neoplastic cells, a decrease in metastasis in a subject, shrinking or decreasing the size of a tumor, change in the growth rate of one or more tumor(s) in a subject, an increase in the period of remission for a subject (e.g., as compared to the one or more metric(s) in a subject having a similar cancer receiving no treatment or a different treatment, or as compared to the one or more metric(s) in the same subject prior to treatment), decreasing symptoms resulting from a disease, increasing the quality of life of those suffering from a disease (e.g., assessed using FACT-G or EORTC-QLQC30), decreasing the dose of other medications required to treat a disease, delaying the progression of a disease, and/or prolonging survival of subjects having a disease. "Treatment" can also mean prolonging survival as compared to expected survival if not receiving treatment, for example, an increase in overall survival (OS) compared to a subject not receiving treatment as described herein, and/or an increase in progression-free survival (PFS) compared to a subject not receiving treatment as described herein.

As used herein, the term "subject" refers to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or prevented. In some embodiments, the subject has been identified or diagnosed as having a tumor with a BRAF mutation (a BRAF-associated tumor) (e.g., as determined using a regulatory agency-approved, e.g., FDA-approved, assay or kit). In some embodiments, the subject has a tumor that is positive for a BRAF mutation (e.g., as determined using a regulatory agency-approved assay or kit). The subject can be a subject whose tumors have a BRAF mutation (e.g., where the tumor is identified as such using a regulatory agency-approved, e.g., FDA-approved, kit or assay). In some embodiments, the subject is suspected of having a BRAF-associated tumor. In some embodiments, the subject has a clinical record indicating that the subject has a tumor that has a BRAF mutation (and optionally the clinical record indicates that the subject should be treated with any of the compositions provided herein). In some embodiments, the subject is a human. In some embodiments, the human subject is a pediatric subject.

The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E, Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula I, or pharmaceutically acceptable salts or solvates thereof are useful for preventing diseases and disorders as defined herein. The term "preventing" as used herein means the prevention of the onset, recurrence or spread, in whole or in part, of the disease or condition as described herein.

The term "BRAF-associated" with respect to a disease or disorder as used herein refers to diseases or disorders associated with or having one or more BRAF mutations.

Non-limiting examples of a BRAF-associated disease or disorder include, for example, BRAF-associated tumors.

The phrase "BRAF mutation" refers to a genetic mutation (e.g., a chromosomal translocation that results in one or more mutations in a BRAF gene that results in the expression of a BRAF protein with one or more point mutations as compared to a wild type BRAF protein.

Non-limiting examples of BRAF mutations include BRAF V600 mutations, e.g., V600E, V600K, V600R and V600S.

The term "wild type" describes a nucleic acid (e.g., a BRAF gene or a BRAF mRNA) that is typically found in a subject that does not have a disease or disorder related to the reference nucleic acid or protein.

The term "wild type BRAF" describes a BRAF nucleic acid (e.g., a BRAF gene or a BRAF mRNA) or a BRAF protein that is found in a subject that does not have a BRAF-associated disease, e.g., a BRAF-associated cancer (and optionally also does not have an increased risk of developing a BRAF-associated disease and/or is not suspected of having a BRAF-associated disease), or is found in a cell or tissue from a subject that does not have a BRAF-associated disease, e.g., a BRAF-associated cancer (and optionally also does not have an increased risk of developing a BRAF-associated disease and/or is not suspected of having a BRAF-associated disease).

The term "tumor" as used herein refers to an abnormal growth of tissue that arises from uncontrolled usually rapid cellular proliferation. The tumor may be a benign tumor (non-cancerous) or a malignant tumor (i.e., cancer). The tumor may be a solid tumor or a liquid tumor (i.e., a hematologic tumor, also known as blood cancer).

The term "BRAF-associated tumor" as used herein refers to tumors associated with or having a BRAF mutation, e.g., a BRAF V600 mutation; e.g., a BRAF V600E, V600K, V600R or V600S mutation. BRAF-associated tumors include both benign BRAF-associated tumors and malignant BRAF-associated tumors (i.e., BRAF-associated cancers).

The term "BRAF-associated cancer" as used herein refers to cancers associated with or having a BRAF mutation, e.g., a BRAF V600 mutation, e.g., a BRAF V600E, V600K, V600R or V600S mutation. Non-limiting examples of BRAF-associated cancers are described herein.

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating a BRAF-associated tumor in a subject in need of such treatment, the method comprising administering to the subject a therapeutically effective amount of a compound of Formula I, Formula II or Formula III, or a pharmaceutically acceptable salt, solvate or polymorph thereof, or a pharmaceutical composition thereof. For example, provided herein are methods for treating a BRAF-associated tumor in a subject in need of such treatment, the method comprising a) detecting a BRAF mutation in a sample from the subject; and b) administering a therapeutically effective amount of a compound of Formula I, Formula II or Formula III, or a pharmaceutically acceptable salt, solvate or polymorph thereof. In some embodiments, the BRAF mutation is V600E and/or V600K and/or V600D and/or V600R. In some embodiments, the BRAF mutation is V600E. In some embodiments, the BRAF mutation is V600K.

In some embodiments of any of the methods of use described herein, the BRAF-associated tumor is a solid tumor. In some embodiments, the tumor is intracranial. In some embodiments, the tumor is extracranial. In some embodiments of any of the methods of uses described herein, the BRAF-associated tumor is a malignant BRAF-associated tumor (i.e., a BRAF-associated cancer). In some embodiments of any of the methods of use described herein, the cancer is melanoma, colon cancer, colorectal cancer, lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), breast cancer, ovarian cancer, cancer of the CNS, bone cancer, cancer of the anus, anal canal, or anorectum, cancer of the eye, bile duct cancer, ductal carcinoma in situ, liver cancer, gallbladder, or pleura, oral cancer, oral cavity cancer, lip cancer, oropharyngeal cancer, cancer of the nose, nasal cavity or middle ear, cancer of the vulva, esophageal cancer, cervical cancer, gastrointestinal carcinoid tumor, hypopharynx cancer, kidney cancer, larynx cancer, liver cancer, lung cancer, melanoma, nasopharynx cancer, peripheral nervous system cancers (e.g., neuroblastoma), ovarian cancer, pancreatic cancer, peritoneum, omentum, and mesentery cancer, pharynx cancer, prostate, cancer, renal cancer (e.g., renal cell carcinoma (RCC)), small intestine cancer, soft tissue cancer, stomach cancer, testicular cancer, uterine cancer, ureter cancer, or urinary bladder cancer. In one embodiment, the BRAF-associated cancer is a CNS cancer, melanoma, colorectal cancer, thyroid cancer, non-small cell lung cancer, ovarian cancer, or neuroblastoma. In some embodiments, the BRAF-associated cancer is an extracranial cancer selected from melanoma, colorectal cancer, thyroid cancer, non-small cell lung cancer, ovarian cancer, and neuroblastoma. In some embodiments, the BRAF-associated cancer is melanoma. In some embodiments, the BRAF-associated cancer is colorectal cancer. In some embodiments, the BRAF-associated cancer is thyroid cancer. In some embodiments, the BRAF-associated cancer is non-small cell lung cancer. In some embodiments, the BRAF-associated cancer is ovarian cancer. In some embodiments, the BRAF-associated cancer is neuroblastoma. In some embodiments, the BRAF-associated cancer is an intracranial cancer (brain cancer). In some embodiment, the BRAF-associated cancer is a CNS cancer.

The term "metastasis" is an art known term that refers to the spread of cancer cells from the place where they first formed (the primary site) to one or more other sites in a subject (one or more secondary sites). In metastasis, cancer cells break away from the original (primary) tumor, travel through the blood or lymph system, and form a new tumor (a metastatic tumor) in other organs or tissues of the body. The new, metastatic tumor includes the same or similar cancer cells as the primary tumor. At the secondary site, the tumor cell may proliferate and begin the growth or colonization of a secondary tumor at this distant site.

The term "metastatic cancer" (also known as "secondary cancer") as used herein refers to a type of cancer that originates in one tissue type, but then spreads to one or more tissues outside of the (primary) cancer's origin. Metastatic brain cancer refers to cancer in the brain, i.e., cancer which originated in a tissue other than the brain and has metastasized to the brain.

In one embodiment, the BRAF-associated tumor is a malignant BRAF-associated CNS tumor (i.e., a BRAF-associated CNS cancer). The term "CNS cancer" or "cancer of the CNS" or as used interchangeably herein refers to a cancer (i.e., a malignant tumor) of the CNS, including cancers of the brain (also known as intracranial tumors), cancers of the spinal cord, and cancers of the meninges surrounding the brain and spinal cord. The term "BRAF-associated CNS cancer" refers to CNS cancer associated with or having a BRAF mutation. Cancers of the CNS include metastatic brain cancers and malignant primary brain tumors.

In one embodiment, the BRAF-associated CNS cancer is a BRAF-associated metastatic brain cancer. The BRAF-associated metastatic brain cancer may be the result of any cancer described herein, wherein the subject has developed at least one brain metastasis. In one embodiment, the BRAF-associated metastatic brain cancer is metastatic melanoma, metastatic colorectal cancer, or metastatic non-small cell lung cancer. In one embodiment, the BRAF-associated metastatic brain cancer is metastatic melanoma. In one embodiment, the BRAF-associated metastatic brain cancer is metastatic colorectal cancer. In one embodiment, the BRAF-associated metastatic brain cancer is metastatic non-small cell lung cancer. In one embodiment, the BRAF-associated metastatic brain cancer is metastatic ovarian cancer. In one embodiment, the metastatic brain cancer is metastatic thyroid cancer. In one embodiment, the BRAF-associated metastatic brain cancer is kidney cancer. In one embodiment, the cancer is BRAF-associated metastatic cancer with at least one brain metastasis (i.e., a metastatic brain cancer). In one embodiment, the cancer is BRAF-associated metastatic melanoma with at least one brain metastasis. In one embodiment, the cancer is BRAF-associated metastatic colorectal cancer with at least one brain metastasis. In one embodiment, the cancer is BRAF-associated metastatic non-small cell lung cancer with at least one brain metastasis. In one embodiment, the cancer is BRAF-associated metastatic ovarian cancer with at least one brain metastasis. In one embodiment, the cancer is BRAF-associated metastatic thyroid cancer with at least one brain metastasis. In one embodiment, the cancer is BRAF-associated neuroblastoma with at least one brain metastasis.

Leptomeningeal metastases (leptomeningeal disease (LMD)) represent a subset of CNS metastases that grow in the lining of the brain or spine and/or in the cerebrospinal fluid (CSF), or leptomeningeal carcinomatosis. In mammals, the meninges are the dura mater, the arachnoid mater, and the pia mater. CSF is located in the subarachnoid space between the arachnoid mater and the pia mater. The arachnoid and pia mater together are sometimes called the leptomeninges. When LMD occurs in the leptomeninges and/or CSF surrounding the spinal cord, it may be referred to as "extracranial LMD". When LMD occurs in the leptomeninges and/or CSF of the brain, it may be referred to as "intracranial LMD". Since LMD cancer cells can be suspended in the CSF, they can quickly spread throughout the CNS. As a result, LMD has a poor prognosis, with survival typically measured in months. In one embodiment, the metastatic cancer is BRAF-associated LMD. In one embodiment, the metastatic cancer is intracranial BRAF-associated LMD. In one embodiment, the metastatic cancer is extracranial BRAF-associated LMD. BRAF-associated cancers with the highest incidences of leptomeningeal metastases are lung cancer and melanoma. In one embodiment the BRAF-associated LMD is LMD derived from melanoma metastases (i.e., the LMD is metastatic melanoma). In one embodiment the BRAF-associated LMD is LMD derived from colorectal cancer metastases (i.e., the LMD is metastatic colorectal cancer). In one embodiment the BRAF-associated LMD is LMD derived from non-small cell lung cancer metastases (i.e., the LMD is metastatic non-small cell lung cancer).

In one embodiment, the cancer is a BRAF-associated cancer having a high risk of metastasis. In one embodiment, the BRAF-associated cancer having a high risk of metastasis is a cancer having a BRAF V600E, V600K, V600R and/or V600S mutation. In one embodiment, the BRAF-associated cancer having a high risk of metastasis is melanoma, colorectal cancer, thyroid cancer, non-small cell lung cancer, ovarian cancer or neuroblastoma. In one embodiment, the BRAF-associated cancer having a high risk of metastasis is melanoma, colorectal cancer, thyroid cancer, non-small cell lung cancer, ovarian cancer or neuroblastoma, each of which has a BRAF V600E, V600K, V600R and/or V600S mutation. In one embodiment, the BRAF-associated cancer having a high risk of metastasis is melanoma. In one embodiment, the BRAF-associated cancer having a high risk of metastasis is melanoma having a BRAF V600E mutation or BRAF V600K mutation. In one embodiment, the BRAF-associated cancer having a high risk of metastasis is colorectal cancer. In one embodiment, the BRAF-associated cancer having a high risk of metastasis is colorectal cancer having a BRAF V600E mutation or BRAF V600K mutation. In one embodiment, the BRAF-associated cancer having a high risk of metastasis is thyroid cancer. In one embodiment, the BRAF-associated cancer having a high risk of metastasis is thyroid cancer having a BRAF V600E mutation or BRAF V600K mutation. In one embodiment, the BRAF-associated cancer having a high risk of metastasis is non-small cell lung cancer. In one embodiment, the BRAF-associated cancer having a high risk of metastasis is non-small cell lung cancer having a BRAF V600E mutation or BRAF V600K mutation. In one embodiment, the BRAF-associated cancer having a high risk of metastasis is ovarian cancer. In one embodiment, the BRAF-associated cancer having a high risk of metastasis is ovarian cancer having a BRAF V600E mutation or BRAF V600K mutation. In one embodiment, the BRAF-associated cancer having a high risk of metastasis is neuroblastoma. In one embodiment, the BRAF-associated cancer having a high risk of metastasis is neuroblastoma having a BRAF V600E mutation or BRAF V600K mutation.

In one embodiment, the BRAF-associated CNS tumor is a BRAF-associated primary brain tumor. Primary brain tumors are tumors that start in the brain or spine and are known collectively as gliomas. The term "glioma" is used to describe tumors that originate in glial cells present in the CNS. According to the WHO classification of brain tumors, gliomas are graded by the cell activity and aggressiveness on a scale including Grade I (benign CNS tumors) and Grades II to IV (malignant CNS tumors):

Grade I glioma (Pilocytic astrocytoma): typically occurs in children in the cerebellum or brainstem, and occasionally in the cerebral hemispheres, and are slow growing. Grade I can occur in adults. Although they are benign (WHO grade I), the difficulty in curing this disease makes their growth malignant in behavior with high morbidity rates (Rostami, Acta Neurochir (Wien). 2017; 159(11): 2217-2221).

Grade II glioma (Low-grade gliomas): includes astrocytoma, oligodendroglioma, and mixed oligoastrocytoma. Grade II gliomas typically occur in young adults (20 s-50 s) and are most often found in the cerebral hemispheres. Due to the infiltrative nature of these tumors, recurrences may occur. Some grade II gliomas recur and evolve into more aggressive tumors (grade III or IV).

Grade III glioma (Malignant glioma): includes anaplastic astrocytoma, anaplastic oligodendroglioma, and anaplastic mixed oligoastrocytoma. Grade III tumors are aggressive, high-grade cancers and invade nearby brain tissue with tentacle-like projections, making complete surgical removal more difficult.

Grade IV gliomas: includes Glioblastoma multiforme (GBM) and gliosarcoma; (GBM) is a malignant glioma. GBM is the most aggressive and most common primary brain tumor. Glioblastoma multiforme usually spreads quickly and invades other parts of the brain, with tentacle-like projections, making complete surgical removal more difficult. Gliosarcoma is a malignant cancer and is defined as a glioblastoma consisting of gliomatous and sarcomatous components.

In one embodiment, the BRAF-associated primary brain tumor is a glioma.

Benign primary brain tumors can cause severe pain, permanent brain damage and death, and in some cases, become malignant. Non-limiting examples of benign primary brain tumors include Grade I gliomas, papillary craniopharyngiomas, meningioma (including rhabdoid meningioma), atypical teratoid/rhabdoid tumors, and dysembryoplastic neuroepithelial tumor (DNT), pilocytic astrocytoma, oligodendroglioma, mixed oligoastrocytoma, anaplastic astrocytoma, anaplastic oligodendroglioma, anaplastic mixed oligoastrocytoma, diffuse astrocytoma, ependymoma, a pleomorphic xanthoastrocytoma (PXA), a ganglioglioma, a gliosarcoma, or an anaplastic ganglioglioma. In one embodiment, the BRAF-associated tumor is a benign primary brain tumor.

In one embodiment, the BRAF-associate cancer is a peripheral nervous system cancer. In one embodiment, the peripheral nervous system cancer is neuroblastoma. In one embodiment, the cancer is a BRAF-associated cancer.

A subset of compounds of Formula I, that is, compounds of Formula II or pharmaceutically acceptable salts, solvates or polymorphs thereof, were found to exhibit unexpected brain and/or CNS penetrance. Such compounds are capable of crossing the BBB and inhibiting a BRAF kinase in the brain and/or other CNS structures. In some embodiments, compounds of Formula II, or pharmaceutically acceptable salts or solvates thereof, are capable of crossing the BBB in a therapeutically effective amount.

In one embodiment, provided herein are compounds of Formula II

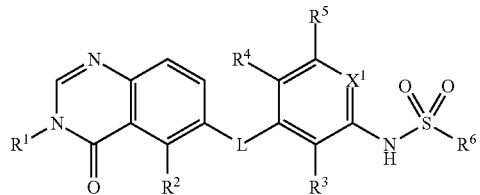

II and pharmaceutically acceptable salts, solvates or polymorphs thereof, wherein:

L is NH, or O or S;
$X^1$ is CH or N;
$R^1$ is C1-C6 alkyl, C1-C6 deuteroalkyl, C1-C6 fluoroalkyl, C3-C6 cycloalkyl, (C3-C6 cycloalkyl)CH$_2$—, Ar$^1$, Ar$^1$CH$_2$— or hetCyc$^1$;
$Ar^1$ is phenyl which is optionally substituted with 1-5 substituents independently selected from halogen and C1-C3 alkyl;
hetCyc$^1$ is a 4-6 membered saturated monocyclic heterocyclic ring having one ring oxygen atom;
$R^2$ is methyl;
$R^3$ is F or Cl;
$R^4$ is H, F or Cl;
$R^5$ is H, F, Cl or methyl;
$R^6$ is C1-C6 alkyl, C1-C6 fluoroalkyl, (Cyc$^1$)C1-C6 alkyl-, (C1-C3 alkoxy)C1-C6 alkyl-, Ar$^2$ or R$^a$R$^b$N—;
Cyc$^1$ is a 3-6 membered saturated carbocyclic ring;
$Ar^2$ is phenyl optionally substituted with 1-5 substituents independently selected from halogen and C1-C3 alkyl; and
$R^a$ and $R^b$ are independently C1-C6 alkyl, or
$R^a$ and $R^b$ together with the nitrogen atom to which they are attached form a 5-6 membered saturated monocyclic heterocyclic ring optionally substituted with 1-2 halogens;
and pharmaceutically acceptable salts and solvates thereof.

In one embodiment of Formula II, $R^1$ is C1-C6 alkyl. In one embodiment of Formula II, $R^1$ is methyl, ethyl or isopropyl. In one embodiment of Formula II, $R^1$ is methyl.

In on embodiment of Formula II, $R^1$ is C1-C6 deuteroalkyl. In on embodiment of Formula II, $R^1$ is —CD$_3$.

In one embodiment of Formula II, $R^1$ is C1-C6 fluoroalkyl. In one embodiment of Formula II, $R^1$ is 2,2,2-trifluoroethyl.

In one embodiment of Formula II, $R^1$ is C3-C6 cycloalkyl. In one embodiment of Formula II, $R^1$ is cyclopropyl, cyclobutyl or cyclopentyl.

In one embodiment of Formula II, $R^1$ is (C3-C6 cycloalkyl)CH$_2$—. In one embodiment of Formula II, $R^1$ is cyclopropylmethyl.

In one embodiment of Formula II, $R^1$ is Ar$^1$. In one embodiment of Formula II, $R^1$ is phenyl.

In one embodiment of Formula II, $R^1$ is Ar$^1$CH$_2$—. In one embodiment of Formula II, $R^1$ is benzyl.

In one embodiment of Formula II, $R^1$ is hetCyc$^1$. In one embodiment of Formula II, $R^1$ is tetrahydrofuranyl.

In one embodiment of Formula II, $R^3$ is F.
In one embodiment of Formula II, $R^3$ is Cl.
In one embodiment of Formula II, $R^4$ is H.
In one embodiment of Formula II, $R^4$ is F.
In one embodiment of Formula II, $R^4$ is Cl.
In one embodiment of Formula II, $R^1$ is H.
In one embodiment of Formula II, $R^5$ is F.
In one embodiment of Formula II, $R^5$ is Cl In one embodiment of Formula II, $R^5$ is methyl.

In one embodiment of Formula II, $R^6$ is C1-C6 alkyl. In one embodiment of Formula II, $R^6$ is ethyl, propyl, 2-methylprop-1-yl or 1-methylprop-1-yl.

In one embodiment of Formula II, $R^6$ is C1-C6 fluoroalkyl. In one embodiment of Formula II, $R^6$ is 3-fluoroprop-1-yl.

In one embodiment of Formula II, $R^6$ is (Cyc$^1$)C1-C6 alkyl-. In one embodiment of Formula II, $R^6$ is cyclopropylmethyl.

In one embodiment of Formula II, $R^6$ is (C1-C3 alkoxy) C1-C6 alkyl-. In one embodiment of Formula II, $R^6$ is (2-methoxy)ethyl.

In one embodiment of Formula II, $R^6$ is Ar$^2$. In one embodiment of Formula II, $R^6$ is phenyl optionally substituted with 1-3 halogens. In one embodiment of Formula II, $R^6$ is phenyl optionally substituted with 1-3 fluoros. In one embodiment of Formula II, $R^6$ is phenyl optionally substituted with one or two fluoros. In one embodiment of Formula II, $R^6$ is phenyl or 2,5-difluorophenyl.

In one embodiment of Formula II, $R^6$ is R$^a$R$^b$N—.

In one embodiment of Formula II, $R^6$ is R$^a$R$^b$N— wherein $R^a$ and $R^b$ are independently C1-C6 alkyl. In one embodiment of Formula II, $R^6$ is N-methyl-N-ethylamino-.

In one embodiment of Formula II, $R^6$ is $R^aR^bN$— wherein $R^a$ and $R^b$ together with the nitrogen atom to which they are attached form a 5-6 membered saturated monocyclic heterocyclic ring optionally substituted with 1-2 halogens. In one embodiment of Formula II, $R^6$ is $R^aR^bN$—, wherein $R^a$ and $R^b$ together with the nitrogen atom to which they are attached form a 5-membered saturated monocyclic heterocyclic ring optionally substituted with 1-2 halogens. In one embodiment of Formula II, $R^6$ is $R^aR^bN$—, wherein $R^a$ and $R^b$ together with the nitrogen atom to which they are attached form a 5-membered saturated monocyclic heterocyclic ring optionally substituted with 1-2 fluoros. In one embodiment of Formula II, $R^6$ is $R^aR^bN$—, wherein $R^a$ and $R^b$ together with the nitrogen atom to which they are attached form a 5-membered saturated monocyclic heterocyclic ring optionally substituted with fluoro. In one embodiment of Formula II, $R^6$ is 3-fluoropyrrolidinyl.

In one embodiment of Formula II, $R^6$ is C1-C6 alkyl, C1-C6 fluoroalkyl, (Cyc$^1$)C1-C6 alkyl-, (C1-C3 alkoxy)C1-C6 alkyl- or Ar$^2$.

Any of the aforementioned embodiments of Formula II may be combined with each other.

In one embodiment, compounds of Formula II include compounds of the formula II-A

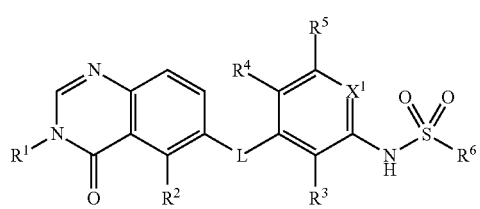

II-A and pharmaceutically acceptable salts, solvates or polymorphs thereof, wherein:

L is NH, or O or S;

$X^1$ is CH or N;

$R^1$ is C1-C6 alkyl, C1-C6 deuteroalkyl, C1-C6 fluoroalkyl, C3-C6 cycloalkyl, (C3-C6 cycloalkyl)CH$_2$—, Ar$^1$, Ar$^1$CH$_2$— or hetCyc$^1$;

Ar$^1$ is phenyl which is optionally substituted with 1-5 substituents independently selected from halogen and C1-C3 alkyl;

hetCyc$^1$ is a 4-6 membered saturated monocyclic heterocyclic ring having one ring oxygen atom;

$R^2$ is methyl;

$R^3$ is F or Cl;

$R^4$ is H, F or Cl;

$R^5$ is H, F, Cl or methyl;

$R^6$ is C1-C6 alkyl, C1-C6 fluoroalkyl, (Cyc$^1$)C1-C6 alkyl-, (C1-C3 alkoxy)C1-C6 alkyl-, Ar$^2$ or $R^aR^bN$—;

Cyc$^1$ is a 3-6 membered saturated carbocyclic ring;

Ar$^2$ is phenyl optionally substituted with 1-5 substituents independently selected from halogen and C1-C3 alkyl; and $R^a$ and $R^b$ are independently C1-C6 alkyl, or $R^a$ and $R^b$ together with the nitrogen atom to which they are attached form a 5-6 membered saturated monocyclic heterocyclic ring optionally substituted with 1-2 halogens;

wherein:

when L is NH, $X^1$ is CH and $R^3$ is F, then $R^4$ is F or H, $R^5$ is H, Cl or methyl and $R^6$ is C1-C6 alkyl, (Cyc$^1$)C1-C6 alkyl-, Ar$^2$ or $R^aR^bN$—;

when $L^1$ is NH, $X^1$ is CH, $R^3$ is Cl, $R^4$ is F and $R^5$ is F, then $R^6$ is C1-C6 alkyl, (Cyc$^1$)C1-C6 alkyl-, Ar$^2$ or $R^aR^bN$—, and when $L^1$ is NH and $X^1$ is N, then $R^3$ is Cl, $R^4$ is Cl and $R^5$ is H.

saturated monocyclic heterocyclic saturated monocyclic heterocyclic saturated monocyclic heterocyclic saturated monocyclic heterocyclic.

In one embodiment, the compounds of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82, having the following structures, respectively:

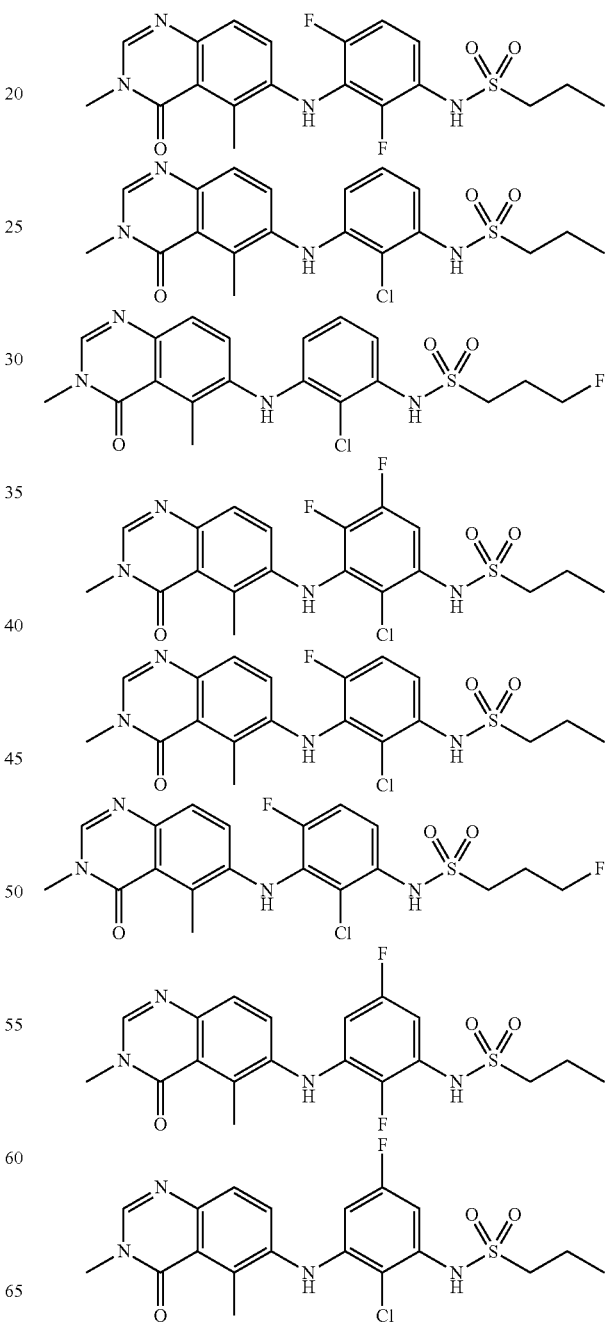

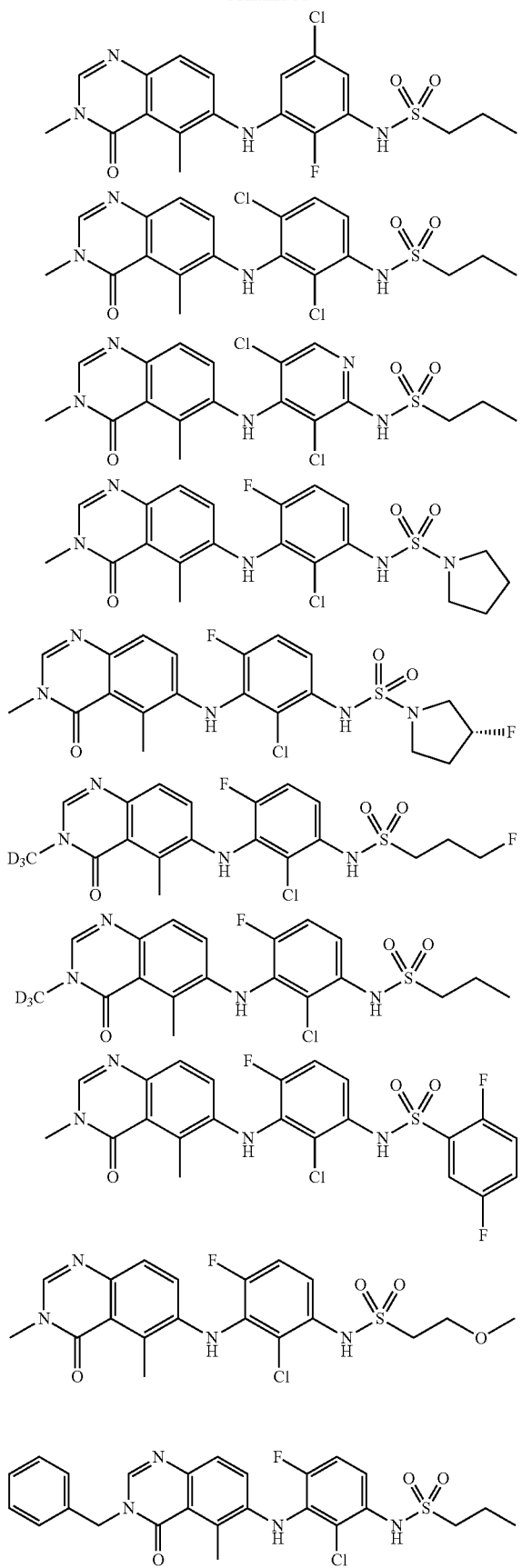
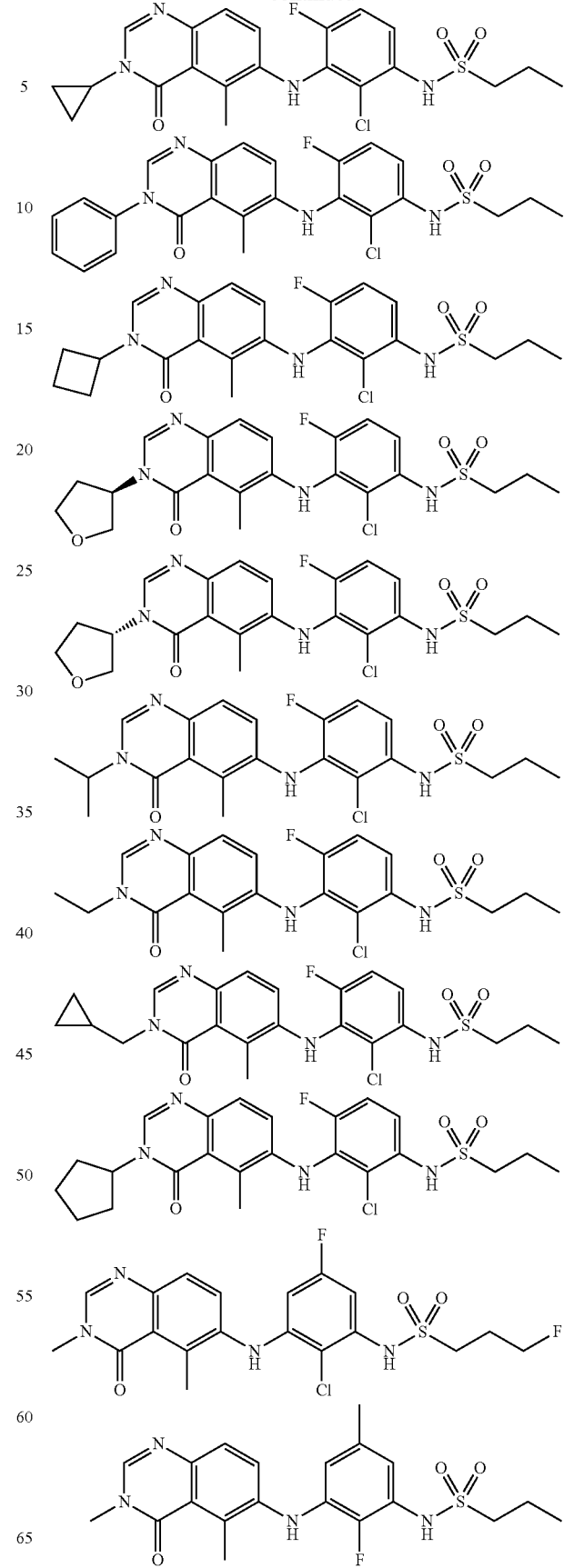

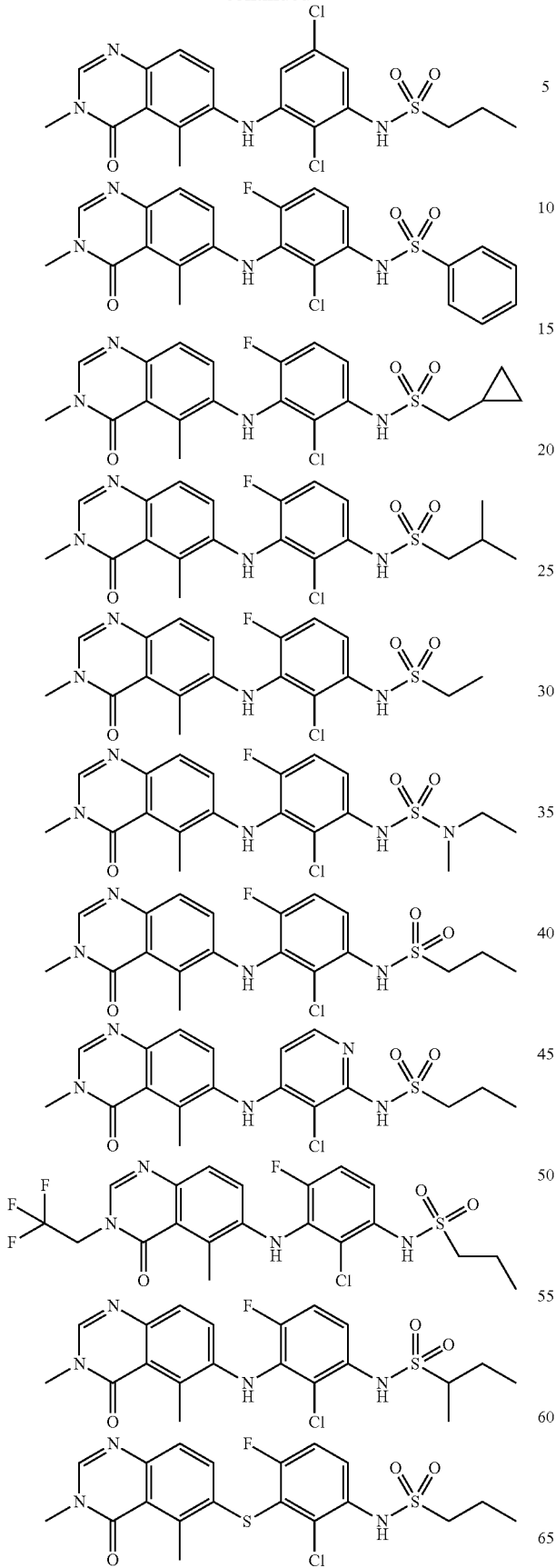
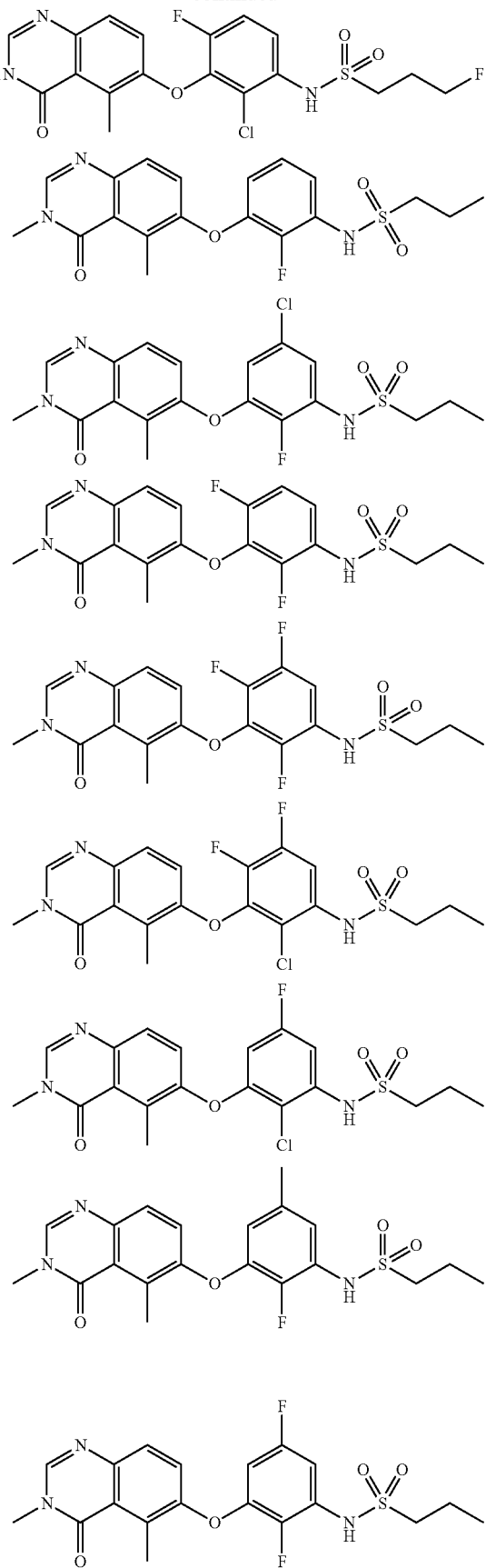

[Structures shown:]

- Quinazolinone with fluoro-difluorophenyl-O linkage and N-sulfonyl-3-fluoropropyl group
- Quinazolinone with methyl/chloro phenyl-O linkage and N-sulfonyl-propyl group
- Quinazolinone with methyl/chloro phenyl-O linkage and N-sulfonyl-3-fluoropropyl group
- Quinazolinone with methyl/fluoro phenyl-O linkage and N-sulfonyl-3-fluoropropyl group and pharmaceutically acceptable salts and solvates thereof, and

[Structure: quinazolinone-NH-linked methyl/chloro phenyl with N-sulfonyl-3-fluoropropyl group]

Form B anhydrous.

In one embodiment, the compounds of Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 are in the free base form. In one embodiment, the compounds of Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 are in the acid salt form. In one embodiment, the compounds of Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 are trifluoroacetate salts.

A particular subset of compounds of Formula II, that is, compounds of Formula III or pharmaceutically acceptable salts, solvates or polymorphs thereof, were found to have particularly unexpected CNS penetrance. In one embodiment, compounds of Formula III have particularly unexpected brain penetrance.

In one embodiment, provided herein are compounds of Formula III having the formula:

[Structure of Formula III with labels $R^1$, $R^2$, $R^3$, $R^4$, $R^5$, $R^6$, $X^1$, L]

III and pharmaceutically acceptable salts, solvates or polymorphs thereof, wherein:

L is NH or O;
$X^1$ is CH or N;
$R^1$ is C1-C6 alkyl or C1-C6 deuteroalkyl;
$R^2$ is methyl;
$R^3$ is F or Cl;
$R^4$ is H or F;
$R^5$ is H or F; and
$R^6$ C1-C6 alkyl or C1-C6 fluoroalkyl.

In one embodiment of Formula III, L is NH.
In one embodiment of Formula III, L is O.
In one embodiment of Formula III, $R^1$ is C1-C6 alkyl. In one embodiment of Formula III, $R^1$ is methyl.
In one embodiment of Formula III, $R^1$ is C1-C6 deuteroalkyl. In one embodiment of Formula III, $R^1$ is —$CD_3$.
In one embodiment of Formula III, $R^3$ is F.
In one embodiment of Formula III, $R^3$ is Cl.
In one embodiment of Formula III, $R^4$ is H.
In one embodiment of Formula III, $R^4$ is F.
In one embodiment of Formula III, $R^5$ is H.
In one embodiment of Formula III, $R^5$ is F.
In one embodiment of Formula III, $R^6$ is C1-C6 alkyl. In one embodiment of Formula III, $R^6$ is ethyl. In one embodiment of Formula III, $R^6$ is propyl.
In one embodiment of Formula III, $R^6$ is C1-C6 fluoroalkyl. In one embodiment of Formula III, $R^6$ is 3-fluoropropyl.

Any of the aforementioned embodiments of Formula III may be combined with each other.

In one embodiment, the compounds of Formula III include the compounds of Examples 1, 4, 7, 9, 10, 23, 55, 63 and 67 and pharmaceutically acceptable salts and solvates thereof, and Example 82, having the following structures, respectively:

[Three structures of quinazolinone-NH-phenyl-NH-sulfonyl compounds shown]

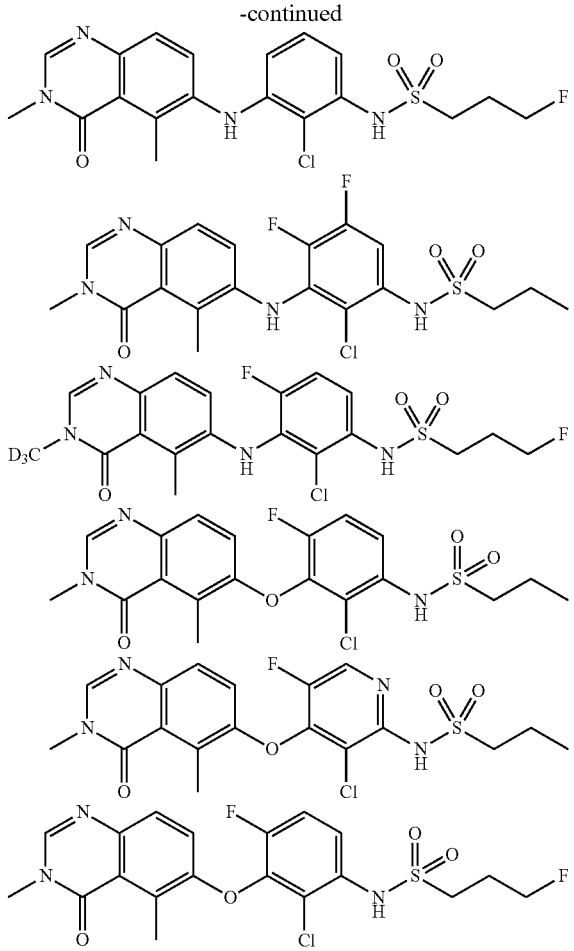

and pharmaceutically acceptable salts and solvates thereof, and

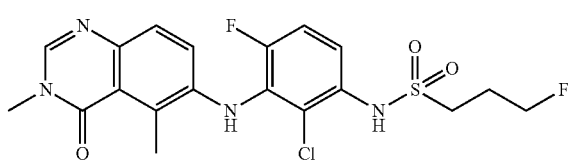 [SMILES: Cc1c(Nc2c(F)ccc(NS(=O)(=O)CCCF)c2Cl)ccc2ncn(C)c(=O)c12]

Form B anhydrous.

In one embodiment, the compounds of Examples 1, 4, 7, 9, 10, 23, 55, 63 and 67 are in the free base form. In one embodiment, the compounds of Examples 1, 4, 7, 9, 10, 23, 55, 63 and 67 are in the acid salt form. In one embodiment, the compounds of Examples 1, 4, 7, 9, 10, 23, 55, 63 and 67 are trifluoroacetate salts. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82.

In one embodiment, compounds of Formula III include compounds of Formula III-A having the formula:

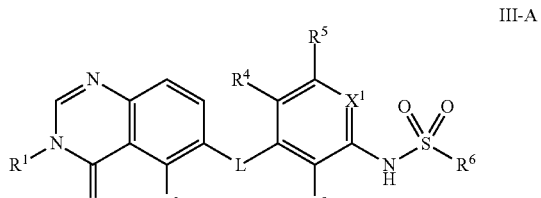

III-A and pharmaceutically acceptable salts, solvates or polymorphs thereof, wherein:

L is NH or O;
$X^1$ is CH or N;
$R^1$ is C1-C6 alkyl or C1-C6 deuteroalkyl;
$R^2$ is methyl;
$R^3$ is F or Cl;
$R^4$ is H or F;
$R^5$ is H or F; and
$R^6$ C1-C6 alkyl or C1-C6 fluoroalkyl;
wherein when $R^3$ is F and $R^4$ is F, then $R^5$ is H and $R^6$ is C1-C6 alkyl, and
when $R^3$ is Cl, $R^4$ is F and $R^5$ is F, then $R^6$ is C1-C6 alkyl.

Accordingly, compounds of Formula II or Formula III and pharmaceutically acceptable salts and solvates thereof described herein may also be used to treat BRAF-associated tumors of the CNS. For example, treatment of a subject with a BRAF-associated CNS tumor can include administration (e.g., oral administration) of a compound of Formula II or Formula III or a pharmaceutically acceptable salt, solvate or polymorph thereof to the subject. In some embodiments, the BRAF-associated CNS cancer has a BRAF V600 mutation. In some embodiments, the BRAF-associated CNS cancer has a BRAF V600E and/or V600K and/or V600D and/or V600R mutation. In some embodiments, the BRAF-associated CNS cancer has a BRAF V600E mutation. In some embodiments, the BRAF-associated CNS cancer has a BRAF V600K mutation. In some embodiments, the subject has previously been treated with one or more other anticancer therapies, e.g., an anticancer agent, surgery and/or radiotherapy, e.g., as described hereinbelow. In some embodiments, the subject is treated with a compound of Formula II or Formula III or a pharmaceutically acceptable salt, solvate or polymorph thereof in combination with one or more other anticancer therapies, e.g., an anticancer agent, surgery and/or radiotherapy, e.g., as described hereinbelow. In some embodiments, the subject is treated with one or more anticancer therapies e.g., an anticancer agent, surgery and/or radiotherapy after administration of a compound of Formula II or Formula III or a pharmaceutically acceptable salt, solvate or polymorph thereof, e.g., as described hereinbelow.

In some embodiments of any of the methods described herein, the tumor is a BRAF-associated CNS tumor and the method includes administering a compound of Formula II or Formula III or a pharmaceutically acceptable salt, solvate or polymorph thereof. In some embodiments, the BRAF-associated tumor is a CNS tumor. In some embodiments, the BRAF-associated CNS tumor is a malignant CNS tumor (CNS cancer). In some embodiments, the malignant CNS tumor is a metastatic CNS cancer. In some embodiments, the metastatic CNS cancer is selected from metastatic melanoma, metastatic colorectal cancer, metastatic non-small cell lung cancer, metastatic thyroid cancer, and metastatic ovarian cancer. In some embodiments, the metastatic CNS cancer is metastatic melanoma. In some embodiments, the metastatic CNS cancer is colorectal cancer. In some embodiments, the metastatic CNS cancer is metastatic non-small cell lung cancer. In some embodiments, the metastatic CNS cancer is metastatic thyroid cancer. In some embodiments, the metastatic CNS cancer is metastatic ovarian cancer. In some embodiments, the BRAF-associated CNS tumor is LMD. In some embodiments, the LMD is intracranial. In some embodiments, the LMD is extracranial. In some embodiments, the LMD is metastatic melanoma. In some embodiments, the LMD is selected from metastatic melanoma, metastatic colorectal cancer, and metastatic non-small cell lung cancer. In some embodiments, the LMD is metastatic colorectal cancer. In some embodiments, the LMD is metastatic non-small cell lung cancer. In some embodiments, the BRAF-associated CNS cancer is a primary brain tumor. In some embodiments, the primary brain tumor is a Grade 2 glioma. In some embodiments, the primary brain tumor is a Grade 3 glioma. In some embodiments, the primary brain tumor is a Grade 4 glioma. In some embodiments, the BRAF-associated CNS tumor is a benign tumor. In some embodiments, the benign CNS tumor is a papillary craniopharyngioma, a meningioma (including rhabdoid meningioma), an atypical teratoid/rhabdoid tumor, or a dysembryoplastic neuroepithelial tumor (DNT). In some embodiments, the compound is a compound of Formula III. In some embodiments, the compound is a compound of Formula III. In some embodiments, the compound of Formula III is selected from a compound of Examples 1, 4, 7, 9, 10, 23, 55, 63 and 67 and pharmaceutically acceptable salts and solvates thereof and Example 82.

The ability to determine whether a compound may be suitable for treating a CNS cancer may be determined, for example, by identifying if the compound is a substrate of an efflux transporter and/or measuring the cell permeability and/or measuring the free blood-to-free plasma ratio, as described herein.

In some embodiments, compounds of Formula II, or a pharmaceutically acceptable salt, solvate or polymorph thereof, or Formula III, or a pharmaceutically acceptable salt, solvate or polymorph thereof, exhibit high cell permeability. Methods for determining the permeability of a compound of Formula II or III or a pharmaceutically acceptable salt, solvate or polymorph thereof can be determined according to the assay described in Example B, and permeability coefficients for compounds of Formula I, II and III are provided in Table B1.

Certain compounds of Formula I, or a pharmaceutically acceptable salt, solvate or polymorph thereof, i.e., compounds of Formula II, or pharmaceutically acceptable salts or solvates thereof, or compounds of Formula III, or pharmaceutically acceptable salts or solvates thereof, exhibit low efflux. In vitro methods of evaluating whether compounds of Formula II, or pharmaceutically acceptable salts or solvates thereof, or Formula III, or pharmaceutically acceptable salts or solvates thereof, are substrates for the efflux transporters P-glycoprotein (P-gp or Multi-drug Resistance 1 (MDR1) protein) and Breast cancer resistance protein (BCRP) are described in Example B, and efflux ratios of compounds of Formula II are provided in Table B3. In one embodiment, compounds of Formula II and pharmaceutically acceptable salts and solvates thereof, or Formula III and pharmaceutically acceptable salts and solvates thereof, have an efflux ratio of ≤3.0 when tested in cells that express P-gp. In one embodiment, compounds of Formula II and pharmaceutically acceptable salts and solvates thereof, having an efflux ratio of ≤3.0 when tested in cells that express P-gp are selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80, and pharmaceutically acceptable salts and solvates thereof, and Example 81-86. In one embodiment, compounds of Formula II and pharmaceutically acceptable salts and solvates thereof, or Formula III and pharmaceutically acceptable salts and solvates thereof, have an efflux ratio of ≤3.0 when tested in cells that express P-gp and an efflux ratio of ≤4.5 when tested in cells that express BCRP. In one embodiment, compounds of Formula II and pharmaceutically acceptable salts and solvates thereof, or Formula III and pharmaceutically acceptable salts and solvates thereof, having an efflux ratio of ≤3.0 when tested in cells that express P-gp and an efflux ratio of ≤3.0 when tested in cells that express BCRP are selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 81-86.

In some embodiments, compounds of Formula II and pharmaceutically acceptable salts and solvates thereof, or Formula III and pharmaceutically acceptable salts and solvates thereof, exhibit medium-to-high brain (unbound)/plasma (unbound) ratios (i.e., medium-to-high free brain/plasma ratios). The ability of a compound of Formula. II and pharmaceutically acceptable salts and solvates thereof, or Formula III or a pharmaceutically acceptable salt, solvate or polymorph thereof, to penetrate the BBB of a subject (e.g., a human) can be determined in a suitable animal model (e.g., a rodent, such as a mouse). For example, the ability of certain compounds of Formula III to penetrate the BBB in mice was determined by evaluating the unbound brain-to-unbound plasma concentration (free B/P) ratio in mice e.g. as described in Example C, and the free brain-to-free plasma ratios are provided in Table C2. Free brain-to-free plasma ratios greater than 0.3 are evidence of a significant degree of free CNS penetration.

Accordingly, in some embodiments, the methods of the present invention include methods for treating a BRAF-associated CNS cancer in a subject in need thereof. In one embodiment, the method includes administration of a compound of Formula III and pharmaceutically acceptable salts and solvates thereof, or pharmaceutically composition thereof as described herein, such that at least a portion of the compound of Formula III penetrates the BBB, as demonstrated in a suitable animal model. In some embodiments, the brain/plasma ratio of total drug is at least approximately 0.3 after administration (e.g. oral or intravenous administration) to a subject. In some embodiments, the brain/plasma ratio of total drug is at least approximately 0.35 after administration (e.g. oral or intravenous administration) to a subject. In some embodiments, the brain/plasma ratio of total drug is at least approximately 0.4 after administration (e.g. oral or intravenous administration) to a subject. In some embodiments, the brain/plasma ratio of total drug is at least approximately 0.45 after administration (e.g. oral or intravenous administration) to a subject. In some embodiments, the brain/plasma ratio of total drug is at least approximately 0.5 after administration (e.g. oral or intravenous administration) to a subject. In some embodiments, the brain/plasma ratio of total drug is at least approximately 0.55 after administration (e.g. oral or intravenous administration) to a subject. In some embodiments, the brain/plasma ratio of total drug is at least approximately 0.6 after administration (e.g. oral or intravenous administration) to a subject. In some embodiments, the brain/plasma ratio of total drug is at least approximately 0.65 after administration (e.g. oral or intravenous administration) to a subject. In some embodiments, the brain/plasma ratio of total drug is at least approximately 0.7 after administration (e.g. oral or intravenous administration) to a subject. In some embodiments, the brain/plasma ratio of total drug is at least approximately 0.75 after administration (e.g. oral or intravenous administration) to a subject. In some embodiments, the brain/plasma ratio of total drug is at least approximately 0.8 after administration (e.g. oral or intravenous administration) to a subject. In some embodiments, the brain/plasma ratio of total drug is at least approximately 0.85 after administration (e.g. oral or intravenous administration) to a subject. In some embodiments, the brain/plasma ratio of total drug is at least approximately 0.9 after administration (e.g. oral or intravenous administration) to a subject. In some embodiments, the brain/plasma ratio of total drug is at least approximately 0.95 after administration (e.g. oral or intravenous administration) to a subject in some embodiments, the brain/plasma ratio of total drug is at least approximately 1.0 after administration (e.g. oral or intravenous administration) to a subject. In some embodiments, the brain/plasma ratio of total drug is at least approximately 1.0 after administration (e.g. oral or intravenous administration) to a subject. In some embodiments, the brain/plasma ratio of total drug is at least approximately 1:1 after administration (e.g. oral or intravenous administration) to a subject. In some embodiments, the brain/plasma ratio of total drug is at least approximately 1.2 after administration (e.g. oral or intravenous administration) to a subject. In some embodiments, the brain/plasma ratio of total drug is at least approximately 1.3 after administration (e.g. oral or intravenous administration) to a subject. In some embodiments, the brain/plasma ratio of total drug is at least approximately 1.4 after administration (e.g. oral or intravenous administration) to a subject. In some embodiments, the brain/plasma ratio of total drug is at least approximately 1.5 after administration (e.g. oral or intravenous administration) to a subject. In some embodiments, the brain/plasma ratio of total drug is at least approximately 1.6 after administration (e.g. oral or intravenous administration) to a subject. In some embodiments, the brain/plasma ratio of total drug is at least approximately 1.7 after administration (e.g. oral or intravenous administration) to a subject. It is to be noted that the percentage of a compound that penetrates the BBB is calculated based upon the area under the concentration-time curve for a given time period ($AUC_{0-t}$) in the brain versus the plasma. Accordingly, the percentages represent a ratio of concentrations. That is, if ($AUC_{0-24\,h}$) for a compound is 20 ng/mL in the brain and 80 ng/mL in the plasma, then the percentage of the compound that penetrates the BBB is 20% (20 ng/mL in the brain divided by the total concentration of (20 ng/mL+80 ng/mL)) (i.e., a brain-to-plasma ratio of 0.20). In some embodiments, the percentages are calculated based upon the area under the concentration-time curve for the time period from t=0 (time of dosing) to the last quantifiable concentration point, i.e., ($AUC_{0-last}$).

Mutations in the BRAF gene have been identified in malignant melanomas, papillary thyroid carcinomas, colorectal carcinomas, non-small cell lung carcinoma (NSCLC), and ovarian carcinomas and metastatic tumors thereof, and in primary brain tumors (Davies H., et al., Nature 417(6892):949-954, 2002). For example, BRAF mutations have been observed in numerous metastatic CNS tumors, including melanoma brain metastases (Flaherty K T, et al., Nat Rev Cancer (2012) 12(5):349-61), brain metastases of colorectal cancers and brain metastases of non-small cell lung cancer (Berghoff, A S, Preusser M., Curr Opin Neurol (2014) 27(6):689-696), papillary thyroid cancer (Kim, W W et al., J Otolaryngol Head Neck Surg. 2018; 47:4, 1-6), and ovarian cancer (Grisham R N., et al., Cancer. 2013; 119:548-554).

BRAF mutations have also been observed in malignant primary brain tumors, including Grade IV gliomas, e.g., glioblastomas and gliosarcomas, anaplastic astrocytomas (high-grade tumors) and WHO grade III anaplastic gangliogliomas (Berghoff, A S, Preusser M., Curr Opin Neurol (2014) 27(6):689-696); Schindler et al. (Acta Neuropathol 121(3):397-405, 2011); Behling et al. (Diagn Pathol 11(1): 55, 2016)), in pediatric and adult populations.

BRAF mutations have also been observed in benign primary brain tumors, for example in WHO Grade II astrocytomas, WHO grade II pleomorphic xanthoastrocytomas (PXAs), pleomorphic xanthoastrocytomas with anaplasia, Pilocytic astrocytoma (PA), papillary craniopharyngiomas, gangliogliomas, astroblastomas, pilocytic astrocytomas, atypical teratoid/rhabdoid tumors, rhabdoid meningiomas (Berghoff, A S, Preusser M., Curr Opin Neurol (2014) 27(6):689-696; Schindler et al. (Acta Neuropathol 121(3): 397-405, 2011); Behling et al. (Diagn Pathol 11(1):55, 2016); (Behling et al., Diagn Pathol 11(1):55, 2016; Brastianos et al., Nat Genet 46(2):161-165, 2014; Dougherty et al., Neuro Oncol 12(7):621-630, 2010; Lehman et al., Neuro Oncol 19(1):31-42, 2017; Mordechai et al., Pediatr Hematol Oncol 32(3):207-211, 2015; Myung et al., Transl Oncol 5(6):430-436, 2012; Schindler et al., Acta Neuropathol 121(3):397-405, 2011)), in pediatric and adult populations.

BRAF mutations have also been detected in relapsed neuroblastomas (Eleveld, T F, et al., Nat Genet 47(8):864-871, 2015). Neuroblastoma is a pediatric tumor of the peripheral nervous system. The majority of neuroblastoma subjects have tumors that initially respond to chemotherapy, but a large proportion of subjects will experience therapy-resistant relapses.

Accordingly, also provided herein is a method for treating a subject diagnosed with or identified as having a BRAF-associated tumor, e.g., any of the exemplary BRAF-associated tumors disclosed herein, comprising administering to the subject a therapeutically effective amount of a compound of Formula I, Formula II or Formula III, or a pharmaceutically acceptable salt, solvate or polymorph thereof, or a pharmaceutical composition thereof as defined herein. In some embodiments, the subject that has been identified or diagnosed as having a BRAF-associated tumor through the use of a regulatory agency-approved, e.g., FDA-approved test or assay for identifying BRAF mutation in a subject or a biopsy sample from the subject or by performing any of the non-limiting examples of assays described herein. In some embodiments, the test or assay is provided as a kit. For example, the BRAF-associated tumor can be a cancer that includes one or more BRAF mutations (e.g., V600E and/or V600K). In some embodiments, a compound of Formula I is selected from Examples 1-80 and pharmaceutically acceptable salts and solvates thereof, and Examples 81-86. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF associated tumor is a benign CNS tumor and the method comprises administering a compound of Formula II, or a pharmaceutically acceptable salt, solvate or polymorph thereof, or Formula III, or a pharmaceutically acceptable salt; solvate or polymorph thereof. In some embodiments, the compound is a compound of Formula II, or a pharmaceutically acceptable salt, solvate or polymorph thereof. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts or solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof: In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

Also provided are methods for treating a tumor in a subject in need thereof, comprising: (a) detecting a BRAF-associated tumor in the subject; and (b) administering to the subject a therapeutically effective amount of a compound of Formula I, Formula II or Formula III, or a pharmaceutically acceptable salt, solvate or polymorph thereof or a pharmaceutical composition thereof. In some embodiments of these methods, the tumor is a benign BRAF-associated tumor. In some embodiments of these methods, the tumor is a malignant BRAF-associated tumor. In some embodiments of these methods, the tumor is a malignant BRAF-associated tumor (e.g., any of the malignant BRAF-associated tumors described herein), and the method further include administering to the subject one or more additional anticancer therapies, e.g., surgery (e.g., at least partial resection of the tumor) and/or radiotherapy and/or an anticancer agent. In some embodiments of these methods, the tumor is a benign BRAF-associated tumor, e.g., a benign BRAF-associated CNS tumor, and the method further includes administering to the subject one or more additional anticancer therapies, e.g., surgery (e.g., at least partial resection of the tumor) and/or radiotherapy and/or an anticancer agent. In some embodiments, the subject is determined to have a BRAF-associated tumor through the use of a regulatory agency-approved, e.g., FDA-approved test or assay for identifying a BRAF mutation in a subject or a biopsy sample from the subject (e.g., a tissue or liquid biopsy) or by performing any of the non-limiting examples of assays described herein. In some embodiments, the test or assay is provided as a kit. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises administering a compound of Formula II or Formula III or a pharmaceutically acceptable salt, solvate or polymorph thereof. In some embodiments, the BRAF-associated CNS cancer is a BRAF-associated metastatic cancer, and the method comprises administering a compound of Formula II or Formula III or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor and the method comprises administering a compound of Formula II or Formula III or a pharmaceutically acceptable salt, solvate or polymorph thereof. In some embodiments, the BRAF associated tumor is a benign CNS tumor and the method comprises administering a compound of Formula II or Formula III or a pharmaceutically acceptable salt, solvate or polymorph thereof. In some embodiments, the compound is a compound of Formula III. In some embodiments, the compound is a compound of Formula III. In some embodiments, the compound of Formula III is selected from a compound of Examples 1, 4, 7, 9, 10 23, 55, 63 and 67 and pharmaceutically acceptable salts or solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

Also provided are methods of treating a subject having BRAF-associated tumor that include performing an assay on a sample obtained from the subject to determine that the subject has a tumor having a BRAF mutation, and administering a therapeutically effective amount of a compound of Formula I, Formula II or Formula III, or a pharmaceutically acceptable salt, solvate or polymorph thereof or a pharmaceutical composition thereof to the subject determined to have a BRAF mutation. In some embodiments of these methods, the BRAF-associated tumor is a malignant BRAF-associated tumor (i.e., a BRAF-associated cancer), and the method further includes administering to the subject one or more other anticancer therapies, e.g., surgery (e.g., at least partial resection of a tumor) and/or radiotherapy and/or treatment with an anticancer agent. In some embodiments of these methods, the subject was previously treated with another anticancer treatment, e.g., surgery (e.g., at least partial resection of a tumor) and/or radiotherapy and/or treatment with an anticancer agent. In some embodiments, the subject is a subject suspected of having a BRAF-associated tumor, a subject presenting with one or more symptoms of a BRAF-associated tumor, or a subject having an elevated risk of developing a BRAF-associated tumor. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the biopsy is a tissue biopsy. In some embodiments, the cancer is a CNS cancer and the biopsy is a liquid biopsy (e.g., CSF). In some embodiment, the cancer is a CNS cancer and the biopsy is a tissue biopsy (e.g., a tumor sample obtained during traditional surgery or a stereotactic needle biopsy, e.g., a stereotactic need biopsy guided by CT or MRI scanning). Additional, non-limiting assays that may be used in these methods are described herein. Additional assays are also known in the art. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated tumor is a benign CNS tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

Also provided is a compound of Formula I, Formula II or Formula III, or a pharmaceutically acceptable salt, solvate or polymorph thereof or a pharmaceutical composition thereof for use in treating a BRAF-associated tumor in a subject identified or diagnosed as having a BRAF-associated tumor through a step of performing an assay (e.g., an in vitro assay) on a sample obtained from the subject to determine that the subject has a BRAF mutation, where the presence of a BRAF mutation identifies that the subject has a BRAF-associated tumor. Also provided is the use of a compound of Formula I, Formula II or Formula III, or a pharmaceutically acceptable salt, solvate or polymorph thereof for the manufacture of a medicament for treating a BRAF-associated tumor in a subject identified or diagnosed as having a BRAF-associated tumor through a step of performing an assay on a sample obtained from the subject to determine whether the subject has a BRAF mutation identifies that the subject has a BRAF-associated tumor. Some embodiments of any of the methods or uses described herein further include recording in the subject's clinical record (e.g., a computer readable medium) that the subject is determined to have a BRAF mutation through the performance of the assay, should be administered a compound of Formula I, Formula II or Formula III, or a pharmaceutically acceptable salt, solvate or polymorph thereof or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF-associated tumor is a benign CNS tumor. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

Also provided is a compound of Formula I, Formula II or Formula III, or a pharmaceutically acceptable salt, solvate or polymorph thereof, for use in the treatment of a BRAF-associated tumor in a subject in need thereof or a subject-identified or diagnosed as having a BRAF-associated tumor. Also provided is the use of a compound of Formula I, Formula II or Formula III, or a pharmaceutically acceptable salt, solvate or polymorph thereof for the manufacture of a medicament for treating a BRAF-associated tumor in a subject identified or diagnosed as having a BRAF-associated tumor. In some embodiments, a subject is identified or diagnosed as having a BRAF-associated tumor through the use of a regulatory agency-approved, e.g., FDA-approved, kit for identifying a BRAF mutation in a subject or a biopsy sample from the subject. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises use of a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer, and the method comprises use of a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor and the method comprises use of a compound of Formula II, or a pharmaceutically acceptable salt, solvate or polymorph thereof, or Formula III, or a pharmaceutically acceptable salt, solvate or polymorph thereof. In some embodiments, the BRAF associated tumor is a benign CNS tumor and the method comprises use of a compound of Formula II, or a pharmaceutically acceptable salt, solvate or polymorph thereof, or Formula III, or a pharmaceutically acceptable salt, solvate or polymorph thereof. In some embodiments, the compound is a compound of Formula III; or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

In some embodiments of any of the methods or uses described herein, the subject has been identified or diagnosed as having a tumor with a BRAF mutation. In some embodiments of any of the methods or uses described herein, the subject has a tumor that is positive for a BRAF mutation. In some embodiments of any of the methods or uses described herein, the subject can be a subject with a tumor(s) that is positive for a BRAF mutation. In some embodiments of any of the methods or uses described herein, the subject can be a subject whose tumor(s) has a BRAF mutation. In some embodiments of any of the methods or uses described herein, the subject is suspected of having a BRAF-associated tumor. In some embodiments, provided herein are methods for treating a BRAF-associated tumor in a subject in need of such treatment, the method comprising a) detecting a BRAF mutation; and b) administering a therapeutically effective amount of a compound of Formula I, Formula II or Formula III, or a pharmaceutically acceptable salt, solvate or polymorph thereof. In some embodiments, the BRAF mutation is determined using a regulatory agency-approved, e.g., FDA-approved, assay or kit. In some embodiments, the BRAF mutation is BRAF V600E or BRAF V600K. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF-associated tumor is a benign CNS tumor. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

In some embodiments of any of the methods or uses described herein, the subject has a clinical record indicating that the subject has a tumor that has one or more BRAF mutations. In some embodiments, the clinical record indicates that the subject should be treated with one or more of the compounds of Formula I, Formula II or Formula III, or pharmaceutically acceptable salts or solvates thereof or compositions provided herein. In some embodiments, the BRAF mutation is determined using a regulatory agency-approved, e.g., FDA-approved, assay or kit. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF-associated tumor is a benign CNS tumor. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

Also provided are methods of treating a subject that include administering a therapeutically effective amount of a compound of Formula I, Formula II or Formula III, or a pharmaceutically acceptable salt, solvate or polymorph thereof to a subject having a clinical record that indicates that the subject has a BRAF mutation. Also provided is the use of a compound of Formula I, Formula II or Formula III, or a pharmaceutically acceptable salt, solvate or polymorph thereof for the manufacture of a medicament for treating a BRAF-associated tumor in a subject having a clinical record that indicates that the subject has a BRAF mutation. Some embodiments of these methods and uses can further include: a step of performing an assay (e.g., an in vitro assay) on a sample obtained from the subject to determine whether the subject has a BRAF mutation, and recording the information in a subject's clinical file (e.g., a computer readable medium) that the subject has been identified to have a BRAF mutation. In some embodiments, the assay is an in vitro assay. For example, an assay that utilizes next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated tumor is a benign CNS tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82.

In some embodiments, the subject is an adult subject. In some embodiments, the subject is a pediatric subject.

Also provided herein is a method of treating a subject. In some embodiments, the method includes performing an assay on a sample obtained from the subject to determine whether the subject has a BRAF mutation. In some such embodiments, the method also includes administering to a subject determined to have a BRAF mutation a therapeutically effective amount of a compound of Formula I, Formula II or Formula III, or a pharmaceutically acceptable salt, solvate or polymorph thereof. In some embodiments, the method includes determining that a subject has a BRAF mutation via an assay performed on a sample obtained from the subject. In such embodiments, the method also includes administering to a subject a therapeutically effective amount of a compound of Formula I, Formula II or Formula III, or a pharmaceutically acceptable salt, solvate or polymorph thereof. Some embodiments of these methods further include administering to the subject another anticancer therapy. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated tumor is a benign CNS tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

Also provided are methods (e.g., in vitro methods) of selecting a treatment for a subject identified or diagnosed as having a BRAF-associated tumor. Some embodiments can further include administering the selected treatment to the subject identified or diagnosed as having a BRAF-associated tumor. For example, the selected treatment can include administration of a therapeutically effective amount of a compound of Formula I, Formula II or Formula III, or a pharmaceutically acceptable salt, solvate or polymorph thereof. Some embodiments can further include a step of performing an assay on a sample obtained from the subject to determine that the subject has a BRAF mutation, and identifying and diagnosing a subject determined to have a BRAF mutation as having a BRAF-associated tumor. In some embodiments, the subject has been identified or diagnosed as having a BRAF-associated tumor through the use of a regulatory agency-approved, e.g., FDA-approved, kit for identifying BRAF mutation, in a subject or a biopsy sample from the subject. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated tumor is a benign CNS tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

Also provided herein are methods of selecting a treatment for a subject, wherein the methods include a step of performing an assay on a sample obtained from the subject to determine whether the subject has a BRAF mutation, and identifying or diagnosing a subject determined to have a BRAF mutation as having a BRAF-associated tumor. Some embodiments further include administering the selected treatment to the subject identified or diagnosed as having a BRAF-associated tumor. For example, the selected treatment can include administration of a therapeutically effective amount of a compound of Formula I, Formula II or Formula III, or a pharmaceutically acceptable salt, solvate or polymorph thereof to the subject identified or diagnosed as having a BRAF-associated tumor. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic, ovarian cancer. In some embodiments, the BRAF-associated metastatic cancer is intracranial LMD or extracranial LMD. In some embodiments, the BRAF-associated CNS cancer is a primary brain tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated tumor is a benign CNS tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

Also provided are methods of selecting a subject for treatment, wherein the methods include selecting, identifying, or diagnosing a subject having a BRAF-associated tumor, and selecting the subject for treatment including administration of a therapeutically-effective amount of a compound of Formula I, Formula II or Formula III, or a pharmaceutically acceptable salt, solvate or polymorph thereof. In some embodiments, identifying or diagnosing a subject as having a BRAF-associated tumor can include a step of performing an assay on a sample obtained from the subject to determine that the subject has a BRAF mutation, and identifying or diagnosing a subject determined to have a BRAF mutation as having a BRAF-associated tumor. In some embodiments, the method of selecting a subject for treatment can be used as a part of a clinical study that includes administration of various treatments of a BRAF-associated tumor. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the BRAF-associated tumor is a malignant BRAF-associated tumor (i.e., a BRAF-associated cancer). In some embodiments, the BRAF-associated cancer is a BRAF-associated CNS cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the BRAF-associated tumor is a benign CNS tumor and the method comprises administering a compound of Formula II, or a pharmaceutically acceptable salt, solvate or polymorph thereof, or Formula III, or a pharmaceutically acceptable salt, solvate or polymorph thereof. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82. In one embodiment, the compound of Formula III is Example 1 or a pharmaceutically acceptable salt or solvate thereof. In one embodiment, the compound of Formula III is Example 4 or a pharmaceutically acceptable salt or solvate thereof. In one embodiment, the compound of Formula III is Example 7 or a pharmaceutically acceptable salt or solvate thereof. In one embodiment, the compound of Formula III is Example 9 or a pharmaceutically acceptable salt or solvate thereof. In one embodiment, the compound of Formula III is Example 10 or a pharmaceutically acceptable salt or solvate thereof. In one embodiment, the compound of Formula III is Example 23 or a pharmaceutically acceptable salt or solvate thereof. In one embodiment, the compound of Formula III is Example 55 or a pharmaceutically acceptable salt or solvate thereof. In one embodiment, the compound of Formula III is Example 63 or a pharmaceutically acceptable salt or solvate thereof. In one embodiment, the compound of Formula III is Example 67 or a pharmaceutically acceptable salt or solvate thereof. In one embodiment, the compound of Formula III is Example 82. In some embodiments, the subject is an adult subject. In some embodiments, the subject is a pediatric subject.

In some embodiments of any of the methods or uses described herein, an assay used to determine whether the subject has a BRAF mutation using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting a BRAF mutation. In some embodiments, the sample is a biological sample or a biopsy sample (e.g., a paraffin-embedded biopsy sample) from the subject. In some embodiments, the subject is a subject suspected of having a BRAF-associated tumor, a subject having one or more symptoms of a BRAF-associated tumor, and/or a subject that has an increased risk of developing a BRAF-associated tumor).

In some embodiments, the biopsy is a tumor biopsy (e.g., a tumor sample obtained during traditional surgery or a stereotactic needle biopsy, e.g., a stereotactic need biopsy guided by CT or MRI scanning). Tissue biopsy methods can be used to detect total tumor burden and/or the BRAF mutation.

In some embodiments, the BRAF mutation can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.*, 3(3):36, 2016. Liquid biopsy methods can be used to detect total tumor burden and/or the BRAF mutation. Liquid biopsies can be performed on biological samples obtained relatively easily from a subject (e.g., via a simple blood draw) and are generally less invasive than traditional methods used to detect tumor burden and/or BRAF mutation. In some embodiments, liquid biopsies can be used to detect the presence of a BRAF mutation at an earlier stage than traditional methods. In some embodiments, the biological sample to be used in a liquid biopsy can include, CSF, blood, plasma, urine, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify a BRAF mutation.

In some embodiments, a BRAF mutation identified using a liquid biopsy is also present in a cancer cell that is present in the subject (e.g., in a tumor). In some embodiments, any of the types of BRAF mutations can be detected using a liquid biopsy. In some embodiments, a genetic mutation identified via a liquid biopsy can be used to identify the subject as a candidate for a particular treatment. For example, detection of a BRAF mutation in the subject can indicate that the subject will be responsive to a treatment that includes administration of a compound of Formula I, Formula II or Formula III, or a pharmaceutically acceptable salt, solvate or polymorph thereof.

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., magnetic resonance imaging (MRI) scans, computed tomography (CT), multi-detector CT (MDCT), positron emission tomography (PET), X-ray, ultrasound, or bone scan.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., MRI scans, bone scan, ultrasound, or CT.

Liquid biopsies can be performed at multiple times during a course of diagnosis, a course of monitoring, and/or a course of treatment to determine one or more clinically relevant parameters including, without limitation, progression of the disease or efficacy of a treatment, after administering a treatment to the subject. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable). In some embodiments, a treatment to be administered to a subject can include a compound of Formula I, Formula II or Formula III, or a pharmaceutically acceptable salt, solvate or polymorph thereof.

In one embodiment, a compound of Formula I, Formula II or Formula III, or a pharmaceutically acceptable salt, solvate or polymorph thereof, may be used alone or in combination with one or more different forms of treatment to treat a subject with a malignant tumor. For example, compounds of Formula I, Formula II or Formula III, or pharmaceutically acceptable salts or solvates thereof may also be used in combination with one or more additional anticancer therapies, for example surgery, radiotherapy, and/or an anticancer agent that works by the same or by a different mechanism of action. In one embodiment, treatment of a subject having a BRAF-associated malignant tumor with a compound of Formula I, Formula II or Formula III, or a pharmaceutically acceptable salt, solvate or polymorph thereof in combination with one or more additional therapies, e.g., surgery, radiotherapy, and/or an anticancer agent, can have increased therapeutic efficacy as compared to treatment of the same subject or a similar subject with a compound of Formula I, Formula II or Formula III or a pharmaceutically acceptable salt or solvate as a monotherapy.

Accordingly, in one embodiment, provided herein are methods of treating a subject having a BRAF-associated tumor (e.g., any of the BRAF-associated tumors described herein) that include: administering to the subject (i) a therapeutically effective amount of a compound of Formula I, Formula II or Formula III or a pharmaceutically acceptable salt or solvate there of as a monotherapy, or (ii) a therapeutically effective amount of a compound of Formula I, Formula II or Formula III, or a pharmaceutically acceptable salt, solvate or polymorph thereof in combination with one or more additional anticancer therapies. In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered a second anticancer therapy during said period of time. In one embodiment, the second anticancer therapy is a second anticancer agent.

Also provided herein is a compound of Formula I, Formula II or Formula III or a pharmaceutically acceptable salt, solvate or polymorph thereof, for use in combination with an additional anticancer therapy. Also provide herein is an additional anticancer therapy for use in combination with a compound of Formula I, Formula II or Formula III or a pharmaceutically acceptable salt, solvate or polymorph thereof.

Also provided herein is a compound of Formula I, Formula II or Formula III or a pharmaceutically acceptable salt, solvate or polymorph thereof, for use in treating a BRAF-associated tumor by co-administration with an additional anticancer therapy. Also provide herein is an additional anticancer therapy for use in treating a BRAF-associated tumor by co-administration with a compound of Formula I, Formula II or Formula III or a pharmaceutically acceptable salt, solvate or polymorph thereof.

In some embodiments, the subject is administered one or more anticancer therapies other than a compound of Formula I, Formula II or Formula III, or a pharmaceutically acceptable salt; solvate or polymorph thereof, prior to administration of a compound of Formula I, Formula II or Formula III, or a pharmaceutically acceptable salt, solvate or polymorph thereof. In some embodiments, the one or more anticancer therapies is selected from surgery and/or radiotherapy, and/or an anticancer agent that works by the same or by a different mechanism of action. For example, in some embodiments, a subject in need thereof may undergo at least partial resection of the tumor prior to administration of a compound of Formula I, Formula II or Formula III, or a pharmaceutically acceptable salt, solvate or polymorph thereof. In some embodiments, the treatment by at least partial resection of the tumor reduces the size of the tumor (e.g., the tumor burden) occurs prior to administration of one or more doses of a compound of Formula I, Formula II or Formula III, or a pharmaceutically acceptable salt, solvate or polymorph thereof. In some embodiments, a subject in need thereof may undergo radiotherapy prior to administration of a compound of Formula I, Formula II or Formula III, or a pharmaceutically acceptable salt, solvate or polymorph thereof. In some embodiments, a subject in need thereof may undergo treatment with one or more anticancer agents other than a compound of Formula I, Formula II or Formula III, or a pharmaceutically acceptable salt, solvate or polymorph thereof prior to administration of a compound of Formula I, Formula II or Formula III, or a pharmaceutically acceptable salt, solvate or polymorph thereof. In some embodiments, a subject has a cancer that is refractory or intolerant to the previous therapy.

Accordingly, in some embodiments provided herein are methods of treating a subject having a BRAF-associated tumor, comprising (i) administering one or more anticancer therapies to said subject during a period of time, and (ii) after (i), administering (a) a compound of Formula I, Formula II or Formula III, or a pharmaceutically acceptable salt, solvate or polymorph thereof, as monotherapy or (b) a compound of Formula I, Formula II or Formula III, or a pharmaceutically acceptable salt, solvate or polymorph thereof, in combination with one or more additional anticancer therapies.

In some embodiments, a compound of Formula I, Formula II or Formula III, or a pharmaceutically acceptable salt, solvate or polymorph thereof, can be administered prior to administration of one or more anticancer therapies (for example surgery, radiotherapy, and/or an anticancer agent that works by the same or by a different mechanism of action) to treat a subject with the tumor. For example, in some embodiments, a subject in need thereof may undergo at least partial resection of the tumor after administration of a compound of Formula I, Formula II or Formula III, or a pharmaceutically acceptable salt, solvate or polymorph thereof: In some embodiments, a subject in need thereof may undergo radiotherapy after to administration of a compound of Formula I, Formula II or Formula III, or a pharmaceutically acceptable salt, solvate or polymorph thereof. In some embodiments, a subject in need thereof may undergo treatment with a compound of Formula I, Formula II or Formula III, or a pharmaceutically acceptable salt, solvate or polymorph thereof, prior to administration of a compound one or more anticancer agents other than a compound of Formula I, Formula II or Formula III, or a pharmaceutically acceptable salt, solvate or polymorph thereof. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof: In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

Accordingly, in some embodiments provided herein are methods of treating a subject having a BRAF-associated tumor, comprising (i) administration of Formula I, Formula II or Formula III, or a pharmaceutically acceptable salt, solvate or polymorph thereof, during a period of time, and (ii) subsequent to said period of time, administration of one or more anticancer therapies. For example, a subject in need thereof can be administered one or more doses of a compound of Formula I, Formula II or Formula III, or a pharmaceutically acceptable salt, solvate or polymorph thereof for a period of time and then undergo at least partial resection of the tumor. In some embodiments, the treatment with one or more doses of a compound of Formula I, Formula II or Formula III, or a pharmaceutically acceptable salt, solvate or polymorph thereof reduces the size of the tumor (e.g., the tumor burden) prior to the at least partial resection of the tumor. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In some embodiments of any of the above described methods, the additional anticancer therapy is surgery, radiotherapy, and/or an anticancer agent that works by the same or by a different mechanism of action.

Non-limiting examples of additional anticancer agents that can be used in combination with a compound of Formula I, II or III or a pharmaceutically acceptable salt, solvate or polymorph thereof according to any of the above-described methods include additional kinase inhibitors other than compounds of Formulas I, Formula II or Formula III, or a pharmaceutically acceptable salt, solvate or polymorph thereof, including MEK inhibitors, BRAF inhibitors (e.g., BRAF inhibitors other than a compound of Formula I, II or III), EGFR inhibitors, inhibitors of HER2 and/or HER3, SHP2 inhibitors, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents including immunotherapy.

In one embodiment, the anticancer agent that can be used in combination with a compound of Formula I, II or III or a pharmaceutically acceptable salt, solvate or polymorph thereof according to any of the above-described methods is a targeted therapeutic agent. A "targeted therapeutic agent" as used herein includes, refers to a molecule that blocks the growth of cancer cells by interfering with specific targeted molecules needed for carcinogenesis and tumor growth, rather than by simply interfering with all rapidly dividing cells (e.g., with traditional cytotoxic chemotherapy), and includes but is not limited to, receptor tyrosine kinase-targeted therapeutic agents, signal transduction pathway inhibitors (for example, Ras-Raf-MEK-ERK pathway inhibitors, PI3K-Akt-mTOR-S6K pathway inhibitors ("PI3K inhibitors")), and modulators of the apoptosis pathway.

In some embodiments, the anticancer agent that can be used in combination with a compound of Formula I, II or III or a pharmaceutically acceptable salt, solvate or polymorph thereof according to any of the above-described methods is a MEK inhibitor. Non-limiting examples of MEK inhibitors include binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7 (3H,8H)-dione (TAK-733). Additional examples of MEK inhibitors include the compounds disclosed in WO 03/077914, WO 2005/023759, WO 2005/051301, U.S. Pat. Nos. 7,517,994, 7,732,616, WO 2005/051906, WO 2005/051302, WO 2005/051300, and WO 2007/044084. In some embodiments, the MEK inhibitor is binimetinib.

In some embodiments, the anticancer agent that can be used in combination with a compound of Formula I, II or III or a pharmaceutically acceptable salt, solvate or polymorph thereof according to any of the above-described methods is another BRAF inhibitor other than a compound of Formula I, Formula II or Formula III. Non-limiting examples of other BRAF inhibitors include encorafenib, dabrafenib and vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). Additional examples of BRAF inhibitors are known in the art.

In some embodiments, the anticancer agent that can be used in combination with a compound of Formula I, II or III or a pharmaceutically acceptable salt, solvate or polymorph thereof according to any of the above-described methods is an EGFR inhibitor. Non-limiting examples of EGFR inhibitors include cetuximab (Erbitux®), panitumumab (Vectibix®), osimertinib (merelectinib, Tagrisso®), erlotinib (Tarceva®), gefitinib (Iressa®), necitumumab (Portrazza™), neratinib (Nerlynx®), lapatinib (Tykerb®), vandetanib (Caprelsa®), brigatinib (Alunbrig®) and inhibitors of EGFR disclosed in PCT Publication Nos. WO 2019/071351 and WO 2017/117680, which are both incorporated herein by reference in their entirety. Additional examples of EGFR inhibitors are known in the art.

In some embodiments, the anticancer agent that can be used in combination with a compound of Formula I, II or III or a pharmaceutically acceptable salt, solvate or polymorph thereof according to any of the above-described methods is a HER2 and/or HER3 inhibitor Non-limiting examples of HER2 and/or HER3 inhibitors include lapatinib, canertinib, (E)-2-methoxy-N-(3-(4-(3-methyl-4-(6-methylpyridin-3-yloxy)phenylamino)quinazolin-6-yl)allyl)acetamide (CP-724714), sapitinib, 7-[[4-[(3-ethynylphenyl)amino]-7-methoxy-6-quinazolinyl]oxy]-N-hydroxy-heptanamide (CUDC-101), mubritinib, 6-[4-[(4-ethylpiperazin-1-yl)methyl]phenyl]-N-[(1R)-1-phenylethyl]-7H-pyrrolo[2,3-d]pyrimidin-4-amine (AEE788), irbinitinib (tucatinib), poziotinib, N-[4-[1-[4-(4-acetyl-1-piperazinyl)cyclohexyl]-4-amino-3-pyrazolo[3,4-d]pyrimidinyl]-2-methoxyphenyl]-1-methyl-2-indolecarboxamide (KIN001-111), 7-cyclopentyl-5-(4-phenoxyphenyl)-7H-pyrrolo[2,3-d]pyrimidin-4-ylamine (KIN001-051), 6,7-dimethoxy-N-(4-phenoxyphenyl)quinazolin-4-amine (KIN001-30), dasatinib and bosutinib.

In some embodiments, the anticancer agent that can be used in combination with a compound of Formula I, II or III or a pharmaceutically acceptable salt, solvate or polymorph thereof according to any of the above-described methods is a SHP2 inhibitor. Non-limiting examples of SHP2 inhibitors include 6-(4-amino-4-methylpiperidin-1-yl)-3-(2,3-dichlorophenyl)pyrazin-2-amine (SHP099), [3-[(3S,4S)-4-amino-3-methyl-2-oxa-8-azaspiro[4.5]decan-8-yl]-6-(2,3-dichlorophenyl)-5-methylpyrazin-2-yl]methanol (RMC-4550) RMC-4630, TNO155, and the compounds disclosed in WO 2015/107493, WO 2015/107494, WO 2015/107495, WO 2019/075265, PCT/US2019/056786 and PCT/IB2020/053019.

In some embodiments, a compound of Formula I, II or III or a pharmaceutically acceptable salt, solvate or polymorph thereof is administered in combination with a MEK inhibitor and a SHP2 inhibitor, e.g. any one of the MEK inhibitors and SHP2 inhibitors disclosed herein. In some embodiments, a compound of Formula I, II or III or a pharmaceutically acceptable salt, solvate or polymorph thereof is administered in combination with a MEK inhibitor which is binimetinib, and a SHP2 inhibitor, e.g. SHP2 inhibitors disclosed herein.

In some embodiments, the anticancer agent that can be used in combination with a compound of Formula I, II or III or a pharmaceutically acceptable salt, solvate or polymorph thereof according to any of the above-described methods is an Axl inhibitor. Non-limiting examples of Axl inhibitors include bemcentinib, YW327.6S2 (monoclonal antibody), GL2I.T (decoy receptor), 2-(5-chloro-2-(4-((4-methylpiperazin-1-yl)methyl)phenylamino)pyrimidin-4-ylamino)-N,N-dimethylbenzenesulfonamide (TP-0903), 3-[2-[[3-fluoro-4-(4-methyl-1-piperazinyl)phenyl]amino]-5-methyl-7Hpyrrolo[2,3-d]pyrimidin-4-yl]-benzeneacetonitrile (SGI-7079), gilteritinib, bosutinib, cabozantinib, sunitinib, foretinib, amuvatinib, glesatinib, N-(4-((2-amino-3-chloropyridin-4-yl)oxy)-3-fluorophenyl)-4-ethoxy-1-(4-fluorophenyl)-2-oxo-1,2-dihydropyridine-3-carboxamide (BMS777607), merestinib, (Z)-3-((3-((4-(morpholinomethyl)-1H-pyrrol-2-yl)methylene)-2-oxoindolin-5-yl)methyl)thiazolidine-2,4-dione (S49076), and compounds disclosed in WO 2020/047184.

In some embodiments, the anticancer agent that can be used in combination with a compound of Formula I, II or III or a pharmaceutically acceptable salt, solvate or polymorph thereof to any of the above-described methods is a SOS1 inhibitor. Non-limiting examples of SOS1 inhibitors include those disclosed in PCT Publication No. WO 2018/115380, which is incorporated herein by reference in its entirety.

In some embodiments, the anticancer agent that can be used in combination with a compound of Formula I, II or III or a pharmaceutically acceptable salt, solvate or polymorph thereof to any of the above-described methods is a PI3K inhibitor. Non-limiting examples include buparlisib (BKM120), alpelisib (BYL719), samotolisib (LY3023414), 8-[(1R)-1-[(3,5-difluorophenyl)amino]ethyl]-N,N-dimethyl-2-(morpholin-4-yl)-4-oxo-4H-chromene-6-carboxamide (AZD8186), tenalisib (RP6530), voxtalisib hydrochloride (SAR-245409), gedatolisib (PF-05212384), panulisib (P-7170), taselisib (GDC-0032), trans-2-amino-8-[4-(2-hydroxyethoxy)cyclohexyl]-6-(6-methoxypyridin-3-yl)-4-methylpyrido[2,3-d]pyrimidin-7(8H)-one (PF-04691502), duvelisib (ABBV-954), N2-[4-oxo-4-[4-(4-oxo-8-phenyl-4H-1-benzopyran-2-yl)morpholin-4-ium-4-ylmethoxy]butyryl]-L-arginyl-glycyl-L-aspartyl-L-serine acetate (SF-1126), pictilisib (GDC-0941), 2-methyl-1-[2-methyl-3-(trifluoromethyl)benzyl]-6-(morpholin-4-yl)-1H-benzimidazole-4-carboxylic acid (GSK2636771), idelalisib (GS-1101), umbralisib tosylate (TGR-1202), pictilisib (GDC-0941), copanlisib hydrochloride (BAY 84-1236), dactolisib (BEZ-235), 1-(4-[5-[5-amino-6-(5-tert-butyl-1,3,4-oxadiazol-2-yl)pyrazin-2-yl]-1-ethyl-1H-1,2,4-triazol-3-yl]piperidin-1-yl)-3-hydroxypropan-1-one (AZD-8835), 5-[6,6-dimethyl-4-(morpholin-4-yl)-8,9-dihydro-6H-[1,4]oxazino[4,3-e]purin-2-yl]pyrimidin-2-amine (GDC-0084) everolimus, rapamycin, perifosine, sirolimus, and temsirolimus.

In some embodiments, the anticancer agent that can be used in combination with a compound of Formula I, II or III or a pharmaceutically acceptable salt, solvate or polymorph thereof to any of the above-described methods is an immunotherapy. The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy that can be used in combination with a compound of Formula I, II or III or a pharmaceutically acceptable salt, solvate or polymorph thereof to any of the above-described methods is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab, amatuximab, blinatumomab (AMG103; Blincyto®) or midostaurin (Rydapt).

In some embodiments, the immunotherapy that can be used in combination with a compound of Formula I, II or III or a pharmaceutically acceptable salt, solvate or polymorph thereof to any of the above-described methods is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine.

In some embodiments, the immunotherapy that can be used in combination with a compound of Formula I, II or III or a pharmaceutically acceptable salt, solvate or polymorph thereof to any of the above-described methods includes a toxin. In some embodiments, the immunotherapy is denileukin diftitox (Ontak®).

In some embodiments, the immunotherapy that can be used in combination with a compound of Formula I, II or III or a pharmaceutically acceptable salt, solvate or polymorph thereof to any of the above-described methods is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy that can be used in combination with a compound of Formula I, II or III or a pharmaceutically acceptable salt, solvate or polymorph thereof to any of the above-described methods is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®), nivolumab (Opdivo®) and RN888. In some embodiments, the PD-L1 inhibitor is atezolizumab (Tecentriq®), avelumab (Bavencio®) or durvalumab (Imfinzi™).

In some embodiments, the immunotherapy that can be used in combination with a compound of Formula I, II or III or a pharmaceutically acceptable salt, solvate or polymorph thereof to any of the above-described methods is mRNA-based immunotherapy. In some embodiments, the mRNA-based immunotherapy is CV9104 (see, e.g., Rausch et al. (2014) Human Vaccine Immunother 10(11): 3146-52; and Kubler et al. (2015) J. Immunother Cancer 3:26).

In some embodiments, the immunotherapy that can be used in combination with a compound of Formula I, II or III or a pharmaceutically acceptable salt, solvate or polymorph thereof to any of the above-described methods is an oncolytic virus therapy. In some embodiments, the oncolytic virus therapy is talimogene alherparepvec (T-VEC; Imlygic®).

In some embodiments, the immunotherapy that can be used in combination with a compound of Formula I, II or III or a pharmaceutically acceptable salt, solvate or polymorph thereof to any of the above-described methods is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxlD®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy that can be used in combination with a compound of Formula i, II or III or a pharmaceutically acceptable salt, solvate or polymorph thereof to any of the above-described methods is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) Oncolmmunology 5(2): e1069940).

In some embodiments, the immunotherapy that can be used in combination with a compound of Formula I, II or III or a pharmaceutically acceptable salt, solvate or polymorph thereof to any of the above-described methods is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the anticancer agent that can be used in combination with a compound of Formula I, II or III or a pharmaceutically acceptable salt, solvate or polymorph thereof to any of the above-described methods is a cytotoxic chemotherapeutic. Non-limiting examples of cytotoxic chemotherapeutics include arsenic trioxide, bleomycin, cabazitaxel, capecitabine, carboplatin, cisplatin, cyclophosphamide, cytarabine, dacarbazine, daunorubicin, docetaxel, doxorubicin, etoposide, 5-fluorouracil, folinic acid, gemcitabine, irinotecan, lomustine, methotrexate, mitomycin C, oxaliplatin, paclitaxel, pemetrexed, temozolomide, and vincristine, and combinations thereof, e.g., Nordic FLOX (fluorouracil, folinic acid and oxalipiatin), FOLFOXIRI (oxaliplatin, irinotecan and fluorouracil), FOLFIRI (folinic acid, fluorouracil and irinotecan) or CAPEOX (capecitabine and oxaliplatin).

In some embodiments, the anticancer agent that can be used in combination with a compound of Formula I, II or III or a pharmaceutically acceptable salt, solvate or polymorph thereof according to any of the above-described methods is an angiogenesis-targeted therapy. Non-limiting examples of angiogenesis-targeted therapies include aflibercept and bevacizumab.

In some embodiments, the anticancer agent that can be used in combination with a compound of Formula I, II or III or a pharmaceutically acceptable salt, solvate or polymorph thereof according to any of the above-described methods includes modulators of the apoptosis pathway (e.g. obataclax).

In some embodiments, the anticancer therapy that can be used in combination with a compound of Formula I, II or III or a pharmaceutically acceptable salt, solvate or polymorph thereof to any of the above-described methods is radiotherapy. Non-limiting examples of radiotherapy include external radiation beam therapy (e.g., external beam therapy using kilovoltage X-rays or megavoltage X-rays) or internal radiotherapy. Internal radiotherapy (also called brachytherapy) can include the use of, e.g., low-dose internal radiotherapy or high-dose internal radiotherapy. Low-dose internal radiotherapy includes, e.g., inserting small radioactive pellets (also called seeds) into or proximal to a cancer tissue in the subject. High-dose internal radiotherapy includes, e.g., inserting a thin tube (e.g., a catheter) or an implant into or proximal to a cancer tissue in the subject, and delivering a high dose of radiation to the thin tube or implant using a radiation machine. Methods for performing radiotherapy on a subject having a cancer are known in the art. In embodiments wherein the tumor is a CNS tumor, the radiotherapy may include whole brain radiotherapy (WBRT) or stereotactic radiosurgery (SRS) such as Cyberknife®, XKnife®, Gamma Knife®, or ExacTrac®.

In some embodiments, the anticancer therapy that can be used in combination with a compound of Formula I, II or III or a pharmaceutically acceptable salt, solvate or polymorph thereof to any of the above-described methods is surgery. Non-limiting examples of surgery include, e.g., open surgery or minimally invasive surgery. Surgery can include, e.g., at least a partial resection of the tumor, removing an entire tumor, debulking of a tumor, or removing a tumor that is causing pain or pressure in the subject. Methods for performing open surgery and minimally invasive surgery on a subject having a cancer are known in the art.

In some embodiments, the additional therapy includes any one of the above listed therapies or anticancer agents which are standards of care in cancers wherein the cancer has a BRAF mutation.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered a MEK inhibitor (e.g., any of the MEK inhibitors disclosed herein) during said period of time. In one embodiment, the MEK inhibitor is binimetinib. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered a BRAF inhibitor (e.g., any of the BRAF inhibitors disclosed herein, including a second compound of Formula I, II or III, or a pharmaceutically acceptable salt, solvate or polymorph thereof) during said period of time. In one embodiment, the compound of Formula I is a compound selected from Examples 1-80, or a pharmaceutically acceptable salt or solvate thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37; 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt or solvate thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered an EGFR inhibitor (e.g., any of the EGFR inhibitors disclosed herein) during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82. In one embodiment, the tumor is lung cancer.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered an inhibitor of HER2 and/or HER3 during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered an Axl inhibitor (e.g., any of the Axl inhibitors disclosed herein, including compounds of Formula I and compounds other than compounds of Formula I) during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered a SOS1 inhibitor (e.g., any of the SOS1 inhibitors disclosed herein) during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered a signal transduction inhibitor (e.g., any of the signal transduction inhibitors disclosed herein) during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80, and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered a checkpoint inhibitor (e.g., any of the checkpoint inhibitors disclosed herein) during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered a modulator of the apoptosis pathway (e.g., any of the modulators of the apoptosis pathway disclosed herein) during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered a cytotoxic chemotherapeutic (e.g., any of the cytotoxic chemotherapeutics disclosed herein) during said period of time. In one embodiment, the compound of Formula I is a compound selected from Examples 1-80 pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered an angiogenesis-targeted therapy (e.g., any of the angiogenesis-targeted therapies disclosed herein) during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof, and Example 82. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In one embodiment, provided herein is a method of treating a subject having a BRAF-associated tumor (e.g., any of the BRAF-associated tumors described herein) comprising administering a therapeutically effective amount of a compound of Formula I, Formula II or Formula III, or a pharmaceutically acceptable salt, solvate or polymorph thereof for a period of time, wherein the subject is administered an immune-targeted agent (e.g., any of the immune-targeted agents disclosed herein) during said period of time. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80 and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

Also provided herein is a pharmaceutical combination for treating a BRAF-associated tumor in a subject in need thereof, which comprises (a) a compound of Formula I, Formula II or Formula III, or a pharmaceutically acceptable salt, solvate or polymorph thereof, and (b) at least one additional anticancer agent (e.g., any of the exemplary additional anticancer agents described herein or known in the art), wherein the compound of Formula I, Formula II or Formula III, or a pharmaceutically acceptable salt, solvate or polymorph thereof, and the at least one additional anticancer agent are formulated separately for simultaneous, separate or sequential use for the treatment of the tumor, wherein the amounts of the compound of Formula I, Formula II or Formula III, or pharmaceutically acceptable salt or solvate thereof, and of the additional anticancer agent are together effective in treating the tumor; (ii) the use of such a combination for the preparation of a medicament for the treatment of the tumor; and (iii) a commercial package or product comprising such a combination as a combined preparation for simultaneous, separate or sequential use; and to a method of treatment of a tumor in a subject in need thereof.

The term "pharmaceutical combination", as used herein, refers to a non-fixed combination of the active ingredients.

The term "non-fixed combination" means that a compound of Formula I, Formula II or Formula III, or a pharmaceutically acceptable salt, solvate or polymorph thereof, and at least one additional anticancer agent are formulated as separate compositions or dosages such that they may be administered to a subject in need thereof simultaneously or separately with variable intervening time limits, wherein such administration provides effective levels of the two or more compounds in the body of the subject. These also apply to cocktail therapies, e.g. the administration of three or more active ingredients. Similarly, the term "combination" when referring to a compound of Formula I, Formula II or Formula III in use with a combination of another anticancer agent refers to a non-fixed combination.

Accordingly, also provided herein is a method of treating a BRAF-associated tumor, comprising administering to a subject in need thereof a pharmaceutical combination for treating said tumor which comprises (a) a compound of Formula I, Formula II or Formula III, or a pharmaceutically acceptable salt, solvate or polymorph thereof, and (b) an additional anticancer agent for simultaneous, separate or sequential use for the treatment of the tumor, wherein the amounts of the compound of Formula I, Formula II or Formula III, or a pharmaceutically acceptable salt, solvate or polymorph thereof, and the additional anticancer agent are together effective in treating the tumor. In one embodiment, the BRAF-associated tumor is a malignant tumor, and the additional anticancer agent is an anticancer agent, e.g., any of the anticancer agents described herein. In some embodiments, the compound of Formula I, Formula II or Formula III, or pharmaceutically acceptable salt or solvate thereof, and the additional anticancer agent are administered simultaneously as separate dosages. In some embodiments, the compound of Formula I, Formula II or Formula III, or pharmaceutically acceptable salt or solvate thereof, and the additional anticancer agent are administered as separate dosages sequentially in any order, e.g. in daily or intermittent dosages, in jointly therapeutically effective amounts. The additional anticancer agents may be administered with one or more doses of the compound of Formula I, Formula II or Formula III, or a pharmaceutically acceptable salt, solvate or polymorph thereof, or pharmaceutical composition thereof, as part of the same or separate dosage forms, via the same or different routes of administration, and/or on the same or different administration schedules according to standard pharmaceutical practice known to one skilled in the art. In some embodiments, the BRAF-associated tumor is a malignant BRAF-associated tumor (i.e., a BRAF-associated cancer). In some embodiments, the BRAF-associated cancer is a BRAF-associated CNS cancer and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a BRAF-associated metastatic cancer and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic melanoma and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic colorectal cancer and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic non-small cell lung cancer and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic thyroid cancer and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is metastatic ovarian cancer and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated metastatic cancer is intracranial LMD or extracranial LMD and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated CNS cancer is a primary brain tumor and the pharmaceutical combination comprises a compound of Formula II, or a pharmaceutically acceptable salt, solvate or polymorph thereof, or Formula III, or a pharmaceutically acceptable salt, solvate or polymorph thereof. In some embodiments, the BRAF-associated tumor is a benign CNS tumor and the pharmaceutical combination comprises a compound of Formula II, or a pharmaceutically acceptable salt, solvate or polymorph thereof, or Formula III or a pharmaceutically acceptable salt, solvate or polymorph thereof. In some embodiments, the compound is a compound of Formula III, or a pharmaceutically acceptable salt, solvate or polymorph thereof. In one embodiment, the compound of Formula I is a compound selected from Examples 1-80 and pharmaceutically acceptable salts and solvates thereof, and Examples 81-86. In one embodiment, the compound is a compound of Formula II or a pharmaceutically acceptable salt, solvate or polymorph thereof. In one embodiment, the compound of Formula II is selected from Examples 1, 3, 4, 7; 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67. 68, 70, 71, 72, 73, 74, 75, 76, 77, 78, 79 and 80, and pharmaceutically acceptable salts and solvates thereof, and Example 82. In one embodiment, the compound is a compound of Formula III or a pharmaceutically acceptable salt, solvate or polymorph thereof. In one embodiment, the compound of Formula III is selected from Examples 1, 4, 7, 9, 10, 23, 55, 63 and 67 and pharmaceutically acceptable salts or solvates thereof, and Example 82.

In some embodiments of any of the methods described herein, a subject has a BRAF-associated tumor (e.g., a benign, malignant, or metastatic tumor), wherein the subject has been treated with prior therapy or standard therapy (e.g., treatment with one or more anticancer agents other than a compound of Formula I, II or III or a pharmaceutically acceptable salt, solvate or polymorph thereof and/or radiotherapy and/or surgery) wherein said BRAF-associated tumor has become refractory or intolerant to said prior therapy. In some embodiments, a subject has a BRAF-associated tumor (e.g., a locally advanced or metastatic tumor) that has no standard therapy. In one embodiment, method comprises administering a compound of Formula I selected from Examples 1-80, and pharmaceutically acceptable salts and solvates thereof, and Examples 81-86. In one embodiment, method comprises administering a compound of Formula II or a pharmaceutically acceptable salt, solvate or polymorph thereof. In one embodiment, method comprises administering a compound of Formula II selected from Examples 1, 3, 4, 7, 9, 10; 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80, and pharmaceutically acceptable salts and solvates thereof, and Example 82. In one embodiment, method comprises administering a compound of Formula III or a pharmaceutically acceptable salt, solvate or polymorph thereof. In one embodiment, method comprises administering a compound of Formula III selected from Examples 1, 4, 7, 9, 10, 23, 55, 63 and 67 and pharmaceutically acceptable salts or solvates thereof, and Example 82.

Accordingly, in one embodiment provided herein is a method of treating a subject having a BRAF-associated tumor, wherein the subject was previously treated with one or more anticancer therapies (e.g., an anticancer agent, radiotherapy and/or surgery), the method comprising administering to the subject a therapeutically effective amount of a compound of Formula I, II or III or a pharmaceutically acceptable salt, solvate or polymorph thereof.

Different BRAF-mutated tumors do not necessarily share common BRAF inhibitor resistance mechanisms, and in primary brain tumors there are limited studies describing involved resistance mechanisms. Yao, T W et al. (Oncotarget 8(1):583-595, 2017) and Ywo, Z., et al. (*Cancer Cell* 28(3): 370-383, 2015) found a hyperactivation of epidermal growth factor receptors (EGFR) in BRAF inhibitor resistant glioma cell lines, and treatment with EGFR inhibitors along with a BRAF inhibitor showed promising results on overcoming BRAF inhibitor resistance in adult and pediatric glioma cells. For thyroid cancer cells, BRAF inhibitor resistance is largely due to HER3 signaling, a common molecular pathway involved in gliomagenesis; therefore, adding the HER kinase inhibitors to treatment with a BRAF inhibitor might be also beneficial for brain tumors (Montero-Conde et al., Cancer Discov 3(5):520-533, 2013). Additionally, Yao, T W et al. (Oncotarget 8(1):583-595, 2017) found increased expression and activity of Axl to BRAF inhibitor-resistant cells with suppression of BRAF-V600E glioma using Axl inhibitors. In the same study, a resensitization of BRAF inhibitor-resistant cells after withdrawal of the BRAF inhibitor for 48 hours suggests that intermittent use of a BRAF inhibitor might decrease BRAF inhibitor resistance (Yao et al. (Oncotarget 8(1):583-595, 2017). WO 2013/070996, which is incorporated herein in its entirety, discloses a method of treating a proliferative disease (e.g., cancer, e.g. melanoma), comprising suppressing resistance to treatment with the BRAF inhibitor encorafenib by administering encorafenib on an intermittent dosing schedule. Ma, X H et al. (J Clin. Invest 124(3):1406-1417, 2014) proposed the upregulation of endoplasmic reticulum stress-induced autophagy as a mechanism of BRAF inhibitor-resistance, and Levy, J M et al. (Cancer Discov 4(7):773-780, 2014) showed clinical and radiographic improvement with the addition of the autophagy inhibitor chloroquine in a subject with brainstem ganglioglioma who previously progressed on treatment with vemurafenib.

In some embodiments, a subject having metastatic melanoma (e.g., a BRAF mutant metastatic melanoma) has received treatment with a BRAF inhibitor (e.g., a BRAF inhibitor other than a compound of Formula I, II or III, or a pharmaceutically acceptable salt, solvate or polymorph thereof) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). In one embodiment, the subject was previously treated with a BRAF inhibitor selected from encorafenib, dabrafenib and vemurafenib. In one embodiment, the subject became refractory to said prior treatment. In one embodiment, the subject developed brain metastasis during said prior treatment.

In some embodiments, a subject having metastatic melanoma (e.g., a BRAF mutant metastatic melanoma) has received treatment with a BRAF inhibitor (e.g., other than a compound of Formula I, II or III, or a pharmaceutically acceptable salt, solvate or polymorph thereof) and a MEK inhibitor prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), and a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733). In one embodiment, the subject was previously treated with a BRAF inhibitor selected from encorafenib, dabrafenib and vemurafenib and a MEK inhibitor selected from binimetinib, trametinib, and cobimetinib. In one embodiment, the subject was previously treated with encorafenib and binimetinib. In one embodiment, the subject was previously treated with dabrafenib and trametinib. In one embodiment, the subject was previously treated with vemurafenib and cobimetinib. In one embodiment, the subject became refractory to said prior treatment. In one embodiment, the subject developed brain metastasis during said prior treatment.

In some embodiments, a subject having metastatic melanoma (e.g., a BRAF mutant metastatic melanoma) has received treatment with one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with one or more checkpoint inhibitors independently selected from ipilimumab, nivolumab, pembrolizumab and avelumab. In one embodiment, the subject became refractory to said prior treatment. In one embodiment, the subject developed brain metastasis during said prior treatment.

In some embodiments, a subject having metastatic melanoma (e.g., a BRAF mutant metastatic melanoma) has received treatment with one or more inhibitors of PI3K prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with one or more PI3K inhibitors selected from buparlisib (BKM120), alpelisib (BYL719), samotolisib (LY3023414), 8-[(1R)-1-[(3,5-difluorophenyl)amino]ethyl]-N,N-dimethyl-2-(morpholin-4-yl)-4-oxo-4H-chromene-6-carboxamide (AZD8186), tenalisib (RP6530), voxtalisib hydrochloride (SAR-245409), gedatolisib (PF-05212384), panulisib (P-7170), taselisib (GDC-0032), trans-2-amino-8-[4-(2-hydroxyethoxy)cyclohexyl]-6-(6-methoxypyridin-3-yl)-4-methylpyrido[2,3-d]pyrimidin-7(8H)-one (PF-04691502), duvelisib (ABBV-954), N2-[4-oxo-4-[4-(4-oxo-8-phenyl-4H-1-benzopyran-2-yl)morpholin-4-ium-4-ylmethoxy]butyryl]-L-arginyl-glycyl-L-aspartyl-L-serine acetate (SF-1126), pictilisib (GDC-0941), 2-methyl-1-[2-methyl-3-(trifluoromethyl)benzyl]-6-(morpholin-4-yl)-1H-benzimidazole-4-carboxylic acid (GSK2636771), idelalisib (GS-1101), umbralisib tosylate (TGR-1202), pictilisib (GDC-0941), copanlisib hydrochloride (BAY 84-1236), dactolisib (BEZ-235), 1-(4-[5-[5-Amino-6-(5-tert-butyl-1,3,4-oxadiazol-2-yl)pysrazin-2-yl]-1-ethyl-1H-1,2,4-triazol-3-yl]piperidin-1-yl)-3-hydroxypropan-1-one (AZD-8835), 5-[6,6-Dimethyl-4-(morpholin-4-yl)-8,9-dihydro-6H-[1,4]oxazino[4,3-e]purin-2-yl]pyrimidin-2-amine (GDC-0084) everolimus, rapamycin, perifosine, sirolimus, and temsirolimus. In one embodiment, the subject was previously treated with buparlisib or alpelisib, alone or in combination. In one embodiment, the subject became refractory to said prior treatment. In one embodiment, the subject developed brain metastasis during said prior treatment. In one embodiment, the subject developed brain metastasis during said prior treatment.

In some embodiments, a subject having metastatic melanoma (e.g., a BRAF mutant metastatic melanoma) has received treatment with a BRAF inhibitor other than a compound of Formula I, Formula II, Formula III, or a pharmaceutically acceptable salt, solvate or polymorph thereof, and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula. II, or a pharmaceutically acceptable salt, solvate or polymorph thereof, or Formula III; or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), and one or more checkpoint inhibitors independently selected from ipilimumab, nivolumab and pembrolizumab. In one embodiment, the subject became refractory to said prior treatment. In one embodiment, the subject developed brain metastasis during said prior treatment.

In some embodiments, a subject having metastatic melanoma (e.g., a BRAF mutant metastatic melanoma) has received treatment with a BRAF inhibitor (e.g., other than a compound of Formula I, II or III, or a pharmaceutically acceptable salt, solvate or polymorph thereof), a MEK inhibitor, and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl] propane-1-sulfonamide (PLX4720), and (3R)—N-(3-[[5-(2-cyclopropylpyrimidin-5-yl)-1H-pyrrolo[2,3-b]pyridin-3-yl] carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H, 8H)-dione (TAK-733), and one or checkpoint inhibitors (e.g., any of the checkpoint inhibitors disclosed herein, e.g., a CTLA-4 inhibitor, a PD-1 inhibitor, and/or a PD-L1 inhibitor). In one embodiment, the subject was previously treated with a BRAF inhibitor selected from encorafenib, dabrafenib and vemurafenib, a MEK inhibitor selected from binimetinib, trametinib and cobimetinib, and one or more checkpoint inhibitors independently selected from ipilimumab, nivolumab, pembrolizumab and avelumab. In one embodiment, the subject became refractory to said prior treatment. In one embodiment, the subject developed brain metastasis during said prior treatment.

In some embodiments, a subject having metastatic melanoma (e.g., a BRAF mutant metastatic melanoma) has received treatment with one or more alkylating agent prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with one or more alkylating agents selected from temozolomide, fotemustine, lomustine and carmustine. In one embodiment, the subject was previously treated with temozolomide. In one embodiment, the subject became refractory to said prior treatment. In one embodiment, the subject developed brain metastasis during said prior treatment.

In some embodiments, a subject having metastatic colorectal cancer (e.g., a BRAF mutant metastatic colorectal cancer) has received treatment with a BRAF inhibitor other than a compound of Formula I, Formula II, Formula III, or a pharmaceutically acceptable salt, solvate or polymorph thereof, a MEK inhibitor and an EGFR inhibitor prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl] propane-1-sulfonamide (PLX4720), and (3R)—N-(3-[[5-(2-cyclopropylpyrimidin-5-yl)-1H-pyrrolo[2,3-b]pyridin-3-yl] carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H, 8H)-dione (TAK-733), and an EGFR inhibitor selected from cetuximab, panitumumab, osimertinib, erlotinib, gefitinib, necitumumab, neratinib, lapatinib, vandetanib and brigatinib. In one embodiment, the subject was previously treated with a BRAF inhibitor selected from encorafenib, dabrafenib and vemurafenib, a MEK inhibitor selected from binimetinib, trametinib and cobimetinib, and an EGFR inhibitor selected from cetuximab and panitumumab. In one embodiment, the subject was previously treated with encorafenib, binimetinib and cetuximab. In one embodiment, the subject was previously treated with dabrafenib, trametinib and panitumumab. In one embodiment, the subject became refractory to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with an EGFR inhibitor prior to treatment with a compound of Formula II, or a pharmaceutically acceptable salt, solvate or polymorph thereof, or Formula III, or a pharmaceutically acceptable salt, solvate or polymorph thereof. In some embodiments, a subject having a BRAF-associated metastatic colorectal cancer (e.g., a BRAF mutant metastatic colorectal cancer) has received treatment with an EGFR inhibitor selected from cetuximab, panitumumab, osimertinib, erlotinib, gefitinib, necitumumab, neratinib, lapatinib, vandetanib and brigatinib and a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b] pyridin-3-yl]carbonyl]-2,4-difluorophenyl)-3-fluoropyrrolidine-1-sulfonamide (PLX8394). In some embodiments, a subject having a BRAF-associated metastatic colorectal cancer (e.g., a BRAF mutant metastatic colorectal cancer) has received treatment with cetuximab or panitumumab prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with an EGFR inhibitor and one or more cytotoxic chemotherapy agents prior to treatment with a compound of Formula II, or a pharmaceutically acceptable salt, solvate or polymorph thereof, or Formula III, or a pharmaceutically acceptable salt, solvate or polymorph thereof. In some embodiments, a subject having a BRAF-associated metastatic colorectal cancer (e.g., a BRAF mutant metastatic colorectal cancer) has received treatment with an EGFR inhibitor selected from cetuximab, panitumumab, osimertinib, erlotinib, gefitinib, necitumumab, neratinib, lapatinib, vandetanib and brigatinib and one or more cytotoxic chemotherapeutic agents. In some embodiments, a subject having a BRAF-associated metastatic colorectal cancer (e.g., a BRAF mutant metastatic colorectal cancer) has received treatment with an EGFR inhibitor selected from cetuximab or panitumumab and one or more cytotoxic chemotherapeutic agents such as Nordic FLOX (fluorouracil, folinic acid and oxaliplatin) prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with an EGFR inhibitor and a BRAF inhibitor prior to treatment with a compound of Formula II, or a pharmaceutically acceptable salt, solvate or polymorph thereof, or Formula III, or a pharmaceutically acceptable salt, solvate or polymorph thereof. In some embodiments, a subject having a BRAF-associated metastatic colorectal cancer (e.g., a BRAF mutant metastatic colorectal cancer) has received treatment with an EGFR inhibitor selected from cetuximab, panitumumab, osimertinib, erlotinib, gefitinib, necitumumab, neratinib, lapatinib, vandetanib and brigatinib and a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). In one embodiment, the subject was previously treated with an EGFR inhibitor selected from cetuximab and panitumumab and a BRAF inhibitor selected from encorafenib, dabrafenib and vemurafenib. In one embodiment, the subject was previously treated with encorafenib and cetuximab. In one embodiment, the subject was previously treated with vemurafenib and panitumumab. In one embodiment, the subject was previously treated with dabrafenib and panitumumab. In one embodiment, the subject became refractory to said prior treatment. In one embodiment, the subject developed brain metastasis during said prior treatment.

In some embodiments, a subject having metastatic colorectal cancer (e.g., a BRAF mutant metastatic colorectal cancer) has received treatment with a MEK inhibitor and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and one or checkpoint inhibitors (e.g., any of the checkpoint inhibitors disclosed herein, e.g., a CTLA-4 inhibitor, a PD-1 inhibitor, and/or a PD-L1 inhibitor). In one embodiment, the subject was previously treated with a MEK inhibitor selected from binimetinib, trametinib and cobimetinib, and one or more checkpoint inhibitors independently selected from ipilimumab, nivolumab, pembrolizumab and avelumab. In one embodiment, the subject was previously treated with the MEK inhibitor which is binimetinib and the checkpoint inhibitors nivolumab and ipilimumab. In one embodiment, the subject was previously treated with the MEK inhibitor binimetinib and the checkpoint inhibitor pembrolizumab. In one embodiment, the subject was previously treated with the MEK inhibitor binimetinib and the checkpoint inhibitor avelumab. In one embodiment, the subject was previously treated with the MEK inhibitor trametinib and the checkpoint inhibitors nivolumab and ipilimumab. In one embodiment, the subject became refractory to said prior treatment. In one embodiment, the subject developed brain metastasis during said prior treatment.

In some embodiments, a subject having metastatic colorectal cancer (e.g., a BRAF mutant metastatic colorectal cancer) has received treatment with one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with one or more checkpoint inhibitors independently selected from ipilimumab, nivolumab, pembrolizumab and avelumab. In one embodiment, the subject was previously treated with nivolumab. In one embodiment, the subject became refractory to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with one or more cytotoxic chemotherapeutic agents prior to treatment with a compound of Formula II, or a pharmaceutically acceptable salt, solvate or polymorph thereof, or Formula III, or a pharmaceutically acceptable salt, solvate or polymorph thereof. In some embodiments, a subject having a BRAF-associated metastatic colorectal cancer (e.g., a BRAF mutant metastatic colorectal cancer) has received treatment with oxaliplatin, irinotecan, FOLFOXIRI (oxaliplatin, irinotecan and fluorouracil), FOLFIRI (folinic acid, fluorouracil and irinotecan) or CAPEOX (capecitabine and oxaliplatin) prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with an antibody therapy and one or more cytotoxic chemotherapeutic agents prior to treatment with a compound of Formula II, or a pharmaceutically acceptable salt, solvate or polymorph thereof, or Formula III, or a pharmaceutically acceptable salt, solvate or polymorph thereof. In some embodiments, a subject having a BRAF-associated metastatic colorectal cancer (e.g., a BRAF mutant metastatic colorectal cancer) has received treatment with an antibody therapy which is bevacizumab and one or more cytotoxic chemotherapeutic agents. In some embodiments, a subject having a BRAF-associated metastatic colorectal cancer (e.g., a BRAF mutant metastatic colorectal cancer) has received treatment with bevacizumab and irinotecan, bevacizumab and FOLFOXIRI (oxaliplatin, irinotecan and fluorouracil), or bevacizumab and FOLFIRI (folinic acid, fluorouracil and irinotecan) prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with an EGFR inhibitor, a BRAF inhibitor other than a compound of Formula I, Formula II or Formula III, and one or more cytotoxic chemotherapeutic agents prior to treatment with a compound of Formula, II, or a pharmaceutically acceptable salt, solvate, or polymorph thereof, or Formula III, or a pharmaceutically acceptable salt, solvate or polymorph thereof. In some embodiments, a subject having a BRAF-associated metastatic colorectal cancer (e.g., a BRAF mutant metastatic colorectal cancer) has received treatment with an EGFR inhibitor selected from cetuximab, panitumumab, osimertinib, erlotinib, gefitinib, necitumumab, neratinib, lapatinib, vandetanib and brigatinib, a BRAF inhibitor selected from a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), and one or more cytotoxic chemotherapeutic agents. In some embodiments, a subject having a BRAF-associated metastatic colorectal cancer (e.g., a BRAF mutant metastatic colorectal cancer) has received treatment with an EGFR inhibitor selected from cetuximab, and panitumumab, a BRAF inhibitor which is vemurafenib, and a cytotoxic chemotherapeutic agent which is irinotecan. In one embodiment, the subject became refractory to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with an EGFR inhibitor and one or more cytotoxic chemotherapeutic agents prior to treatment with a compound of Formula II, or a pharmaceutically acceptable salt, solvate or polymorph thereof, or Formula III, or a pharmaceutically acceptable salt, solvate or polymorph thereof. In some embodiments, a subject having a BRAF-associated metastatic colorectal cancer (e.g., a BRAF mutant metastatic colorectal cancer) has received treatment with an EGFR inhibitor selected from cetuximab, panitumumab, osimertinib, erlotinib, gefitinib, necitumumab, neratinib, lapatinib, vandetanib and brigatinib, and one or more cytotoxic chemotherapeutic agents. In some embodiments, a subject having a BRAF-associated metastatic colorectal cancer (e.g., a BRAF mutant metastatic colorectal cancer) has received treatment with an EGFR inhibitor selected from cetuximab, and panitumumab, and a cytotoxic chemotherapeutic agent which is irinotecan or FOLFIRI (folinic acid, fluorouracil and irinotecan). In one embodiment, the subject became refractory to said prior treatment. In one embodiment, the subject developed brain metastasis during said prior treatment.

In some embodiments, a subject having metastatic colorectal cancer (e.g., a BRAF mutant metastatic colorectal cancer) has received treatment with surgery prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the subject developed brain metastasis during said prior treatment.

In some embodiments, a subject having metastatic colorectal cancer (e.g., a BRAF mutant metastatic colorectal cancer) has received treatment with surgery followed by treatment with a BRAF inhibitor other than a compound of Formula I, Formula II, Formula III, or a pharmaceutically acceptable salt, solvate or polymorph thereof, a MEK inhibitor and an EGFR inhibitor prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with surgery and previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and an EGFR inhibitor selected from cetuximab, panitumumab, osimertinib, erlotinib, gefitinib, necitumumab, neratinib, lapatinib, vandetanib and brigatinib. In one embodiment, the subject was previously treated with surgery and previously treated with a BRAF inhibitor selected from encorafenib, dabrafenib and vemurafenib, a MEK inhibitor selected from binimetinib, trametinib and cobimetinib, and an EGFR inhibitor selected from cetuximab and panitumumab. In one embodiment, the subject became refractory to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with radiotherapy (e.g., whole brain radiotherapy or stereotactic radiosurgery) prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the subject developed brain metastasis during said prior treatment.

In some embodiments, a subject having metastatic colorectal cancer (e.g., a BRAF mutant metastatic colorectal cancer) has received treatment with radiotherapy (e.g., whole brain radiotherapy or stereotactic radiosurgery) followed by treatment with a BRAF inhibitor, a MEK inhibitor and an EGFR inhibitor prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with radiotherapy and previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and an EGFR inhibitor selected from cetuximab, panitumumab, osimertinib, erlotinib, gefitinib, necitumumab, neratinib, lapatinib, vandetanib and brigatinib. In one embodiment, the subject was previously treated with surgery and previously treated with a BRAF inhibitor selected from encorafenib, dabrafenib and vemurafenib, a MEK inhibitor selected from binimetinib, trametinib and cobimetinib, and an EGFR inhibitor selected from cetuximab and panitumumab. In one embodiment, the subject became refractory to said prior treatment. In one embodiment, the subject developed brain metastasis during said prior treatment.

In some embodiments, a subject having metastatic non-small cell lung cancer (e.g., a BRAF mutant metastatic non-small cell lung cancer) has received treatment with one or more EGFR inhibitors prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with one or more EGFR inhibitors independently selected from cetuximab, panitumumab, osimertinib, erlotinib, gefitinib, necitumumab, neratinib, lapatinib, vandetanib and brigatinib. In one embodiment, the subject was previously treated with erlotinib. In one embodiment, the subject was previously treated with gefitinib. In one embodiment, the subject was previously treated with erlotinib and gefitinib. In one embodiment, the subject became refractory to said prior treatment. In one embodiment, the subject developed brain metastasis during said prior treatment.

In some embodiments, a subject having metastatic non-small cell lung cancer (e.g., a BRAF mutant metastatic non-small cell lung cancer) has received treatment with a BRAF inhibitor other that a compound of Formula I, Formula II, Formula III, or a pharmaceutically acceptable salt, solvate or polymorph thereof, prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and an EGFR inhibitor selected from cetuximab, panitumumab, osimertinib, erlotinib, gefitinib, necitumumab, neratinib, lapatinib, vandetanib and brigatinib. In one embodiment, the subject was previously treated with a BRAF inhibitor selected from vemurafenib, dabrafenib and encorafenib and an EGFR inhibitor selected from cetuximab and panitumumab prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the subject developed brain metastasis during said prior treatment.

In some embodiments, a subject having metastatic thyroid cancer (e.g., a BRAF mutant metastatic thyroid cancer) has received treatment with a BRAF inhibitor (e.g., a BRAF inhibitor other than a compound of Formula I, Formula II, Formula III, or a pharmaceutically acceptable salt, solvate or polymorph thereof) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and an EGFR inhibitor selected from cetuximab, panitumumab, osimertinib, erlotinib, gefitinib, necitumumab, neratinib, lapatinib, vandetanib and brigatinib. In one embodiment, the subject was previously treated with a BRAF inhibitor selected from vemurafenib, dabrafenib and encorafenib prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the subject developed brain metastasis during said prior treatment.

In one embodiment, the subject has a BRAF-associated LMD and was previously treated with a BRAF inhibitor (e.g., a BRAF inhibitor other than a compound of Formula I, II or III, or a pharmaceutically acceptable salt, solvate or polymorph thereof) and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), and one or more checkpoint inhibitors independently selected from ipilimumab, nivolumab, pembrolizumab and avelumab. In one embodiment, the subject became refractory to said prior treatment.

In one embodiment, the subject has a BRAF-associated LMD and was previously treated with a BRAF inhibitor (e.g., a BRAF inhibitor other than a compound of Formula I, II or III, or a pharmaceutically acceptable salt, solvate or polymorph thereof), a MEK inhibitor, and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7 (3H,8H)-dione (TAK-733), and a checkpoint inhibitor (e.g., any of the checkpoint inhibitors disclosed herein, e.g., a CTLA-4 inhibitor, a PD-1 inhibitor, and/or a PD-L1 inhibitor). In one embodiment, the subject was previously treated with a BRAF inhibitor selected from encorafenib, dabrafenib and vemurafenib, a MEK inhibitor selected from binimetinib, trametinib and cobimetinib, and one or more checkpoint inhibitors independently selected from ipilimumab, nivolumab, pembrolizumab and avelumab. In one embodiment, the subject became refractory to said prior treatment.

In one embodiment, the subject has a BRAF-associated LMD and was previously treated with one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with one or more checkpoint inhibitors independently selected from ipilimumab, nivolumab, pembrolizumab and avelumab. In one embodiment, the subject became refractory to said prior treatment.

In one embodiment, the subject has a BRAF-associated glioma and was previously treated with surgery prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment; the glioma is a Grade 2, Grade 3 or Grade 4 glioma.

In one embodiment, the subject has BRAF-associated glioma and was previously treated with radiotherapy (e.g., whole brain radiotherapy or stereotactic radiosurgery) prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the glioma is a Grade 2, Grade 3 or Grade 4 glioma.

In one embodiment, the subject has a BRAF-associated glioma and was previously treated with one or more cytotoxic chemotherapy agents prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with one or more cytotoxic chemotherapy agents independently selected from cisplatin, pemetrexed, vinorelbine and paclitaxel. In one embodiment, the subject became refractory to said prior treatment. In one embodiment, the glioma is a Grade 2, Grade 3 or Grade 4 glioma.

In one embodiment, the subject has a BRAF-associated glioma and was previously treated with an ornithine decarboxylase inhibitor prior to treatment with a compound of Formula II, or a pharmaceutically acceptable salt, solvate or polymorph thereof, or Formula III, or a pharmaceutically acceptable salt, solvate or polymorph thereof. In one embodiment, the subject previously received treatment with an ornithine decarboxylase inhibitor which is eflornithine (as the racemate, or D or L enantiomer). In one embodiment, the subject became refractory to said prior treatment. In one embodiment, the glioma is a Grade 2, Grade 3 or Grade 4 glioma.

In one embodiment, the subject has a BRAF-associated glioma and was previously treated with an alkylating agent prior to treatment with a compound of Formula II, or a pharmaceutically acceptable salt, solvate or polymorph thereof, or Formula III, or a pharmaceutically acceptable salt, solvate or polymorph thereof. In one embodiment, the subject previously received treatment with an alkylating agent selected from temozolomide, lomustine, and carmustine. In one embodiment, the subject became refractory to said prior treatment. In one embodiment, the glioma is a Grade 2, Grade 3 or Grade 4 glioma.

In one embodiment, the subject has a BRAF-associated glioma and was previously treated with an alkylating agent and an ornithine decarboxylase inhibitor prior to treatment with a compound of Formula II, or a pharmaceutically acceptable salt, solvate or polymorph thereof, or Formula III, or a pharmaceutically acceptable salt, solvate or polymorph thereof. In one embodiment, the subject previously received treatment with an alkylating agent selected from temozolomide, lomustine, and carmustine, and an ornithine decarboxylase inhibitor which is eflornithine (as the racemate, or D or L enantiomer). In one embodiment, the subject became refractory to said prior treatment. In one embodiment, the glioma is a Grade 2, Grade 3 or Grade 4 glioma.

In one embodiment, the subject has a BRAF-associated glioma and was previously treated with radiotherapy (e.g., whole brain radiotherapy or stereotactic radiosurgery) and an alkylating agent prior to treatment with a compound of Formula II, or a pharmaceutically acceptable salt, solvate or polymorph thereof, or Formula III, or a pharmaceutically acceptable salt, solvate or polymorph thereof. In one embodiment, the subject previously received treatment with radiotherapy (e.g., whole brain radiotherapy or stereotactic radiosurgery) and an alkylating agent selected from temozolomide, lomustine, and carmustine. In one embodiment, the subject became refractory to said prior treatment. In one embodiment, the glioma is a Grade 2, Grade 3 or Grade 4 glioma.

In one embodiment, the subject has a BRAF-associated glioma and was previously treated with an antibody therapy prior to treatment with a compound of Formula II, or a pharmaceutically acceptable salt, solvate or polymorph thereof, or Formula III, or a pharmaceutically acceptable salt, solvate or polymorph thereof. In one embodiment, the subject previously received treatment with an antibody therapy which is bevacizumab. In one embodiment, the subject became refractory to said prior treatment. In one embodiment, the glioma is a Grade 2, Grade 3 or Grade 4 glioma.

In one embodiment, the subject has a BRAF-associated glioma and was previously treated with surgery and radiotherapy prior to treatment with a compound of Formula II, or a pharmaceutically acceptable salt, solvate or polymorph thereof, or Formula III, or a pharmaceutically acceptable salt, solvate or polymorph thereof. In one embodiment, the subject became refractory to said prior treatment. In one embodiment, the glioma is a Grade 2, Grade 3 or Grade 4 glioma.

In one embodiment, the subject has a BRAF-associated glioma and was previously treated with surgery, radiotherapy and an alkylating agent prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with surgery, radiotherapy (e.g., whole brain radiotherapy or stereotactic radiosurgery) and an alkylating agent selected from temozolomide, lomustine, and carmustine. In one embodiment, the subject became refractory to said prior treatment. In one embodiment, the glioma is a Grade 2, Grade 3 or Grade 4 glioma.

In one embodiment, the subject has a BRAF-associated glioma and was previously treated with a BRAF inhibitor (e.g., a BRAF inhibitor other than a compound of Formula I, II or III, or a pharmaceutically acceptable salt, solvate or polymorph thereof) prior to treatment with compound of Formula II, or a pharmaceutically acceptable salt, solvate or polymorph thereof, or Formula III, or a pharmaceutically acceptable salt, solvate or polymorph thereof. In one embodiment, the subject previously received treatment with a BRAF inhibitor selected from N-[3-(5-chloro-1H-pyrrolo[2,3-b]pyridin-3-ylcarbonyl)-2,4-difluorophenyl]propane-1-sulfonamide (PLX4720), vemurafenib, dabrafenib, encorafenib and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). In one embodiment, the subject became refractory to said prior treatment. In one embodiment, the glioma is a Grade 2, Grade 3 or Grade 4 glioma.

In one embodiment, the subject has a BRAF-associated glioma and was previously treated with a BRAF inhibitor (e.g., a BRAF inhibitor other than a compound of Formula I, II or III, or a pharmaceutically acceptable salt, solvate or polymorph thereof) and a MEK inhibitor prior to treatment with compound of Formula II, or a pharmaceutically acceptable salt, solvate or polymorph thereof, or Formula III, or a pharmaceutically acceptable salt, solvate or polymorph thereof. In one embodiment, the subject previously received treatment with a BRAF inhibitor selected from N-[3-(5-chloro-1H-pyrrolo[2,3-b]pyridin-3-ylcarbonyl)-2,4-difluorophenyl]propane-1-sulfonamide (PLX4720), vemurafenib, dabrafenib, encorafenib and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394) and a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7 (3H,8H)-dione (TAK-733). In one embodiment, the subject was previously treated with a BRAF inhibitor selected from encorafenib, dabrafenib and vemurafenib and a MEK inhibitor selected from binimetinib, trametinib, and cobimetinib. In one embodiment, the subject became refractory to said prior treatment. In one embodiment, the glioma is a Grade 2, Grade 3 or Grade 4 glioma.

In one embodiment, the subject has a BRAF-associated brainstem ganglioglioma and was previously treated with a BRAF inhibitor (e.g., a BRAF inhibitor other than a compound of Formula I, II or III, or a pharmaceutically acceptable salt, solvate or polymorph thereof) prior to treatment with a compound of Formula II, or a pharmaceutically acceptable salt, solvate or polymorph thereof, or Formula III, or a pharmaceutically acceptable salt, solvate or polymorph thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). In one embodiment, the subject was previously treated with a BRAF inhibitor selected from encorafenib, dabrafenib and vemurafenib. In one embodiment, the subject became refractory to said prior treatment.

Also provided herein is a method of treating a disease or disorder mediated by BRAF in a subject in need of such treatment, the method comprising administering to the subject a therapeutically effective amount of a compound of Formula I, Formula II, Formula III, or a pharmaceutically acceptable salt, solvate or polymorph thereof, or a pharmaceutical composition thereof. A disease or disorder mediated by BRAF can include any disease, disorder or condition that is directly or indirectly linked to a BRAF mutation. In some embodiments, the disease is cancer (e.g., a BRAF-associated cancer). In some embodiments, the cancer is any of the cancers or BRAF-associated cancers described herein. In some embodiments, the cancer is a CNS cancer, and the method comprises administering a compound of Formula II, or a pharmaceutically acceptable salt, solvate or polymorph thereof, or Formula III, or a pharmaceutically acceptable salt, solvate or polymorph thereof. In some embodiments, the CNS cancer is a metastatic cancer. In some embodiments, the CNS cancer is a primary brain tumor. In some embodiments, the compound is a compound of Formula III, or a pharmaceutically acceptable salt, solvate or polymorph thereof. In some embodiments, the compound of Formula III is selected from a compound of Examples 1, 4, 7, 9, 10, 23, 55, 63 and 67 and pharmaceutically acceptable salts and solvates thereof, and Example 82.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis.

Accordingly, also provided herein are methods for treating, inhibiting, preventing, aiding in the prevention, or decreasing the symptoms of metastasis of a BRAF-associated cancer in a subject in need thereof, the method comprising administering to the subject a therapeutically effective amount of a compound of Formula I, Formula II or Formula III, or a pharmaceutically acceptable salt, solvate or polymorph thereof, or a pharmaceutical composition thereof. In some embodiments, the compound of Formula I, Formula II or Formula III, or a pharmaceutically acceptable salt, solvate or polymorph thereof, is used in combination with another anticancer treatment, e.g., surgery (e.g., at least partial resection of a tumor) and/or radiotherapy and/or treatment with an anticancer agent. In one embodiment, the cancer is metastatic cancer with brain metastasis and the method comprises administering a compound of Formula II, or a pharmaceutically acceptable salt, solvate or polymorph thereof, or Formula III, or a pharmaceutically acceptable salt, solvate or polymorph thereof. In one embodiment, the cancer is metastatic melanoma with brain metastasis: In one embodiment, the cancer is metastatic colorectal cancer with brain metastasis. In one embodiment, the cancer is metastatic non-small cell lung cancer with brain metastasis. In one embodiment, the cancer is metastatic ovarian cancer with brain metastasis. In one embodiment, the cancer is metastatic thyroid cancer with brain metastasis. In one embodiment, the cancer is neuroblastoma with brain metastasis, and the method comprises administering a compound of Formula II, or a pharmaceutically acceptable salt, solvate or polymorph thereof, or Formula III, or a pharmaceutically acceptable salt, solvate or polymorph thereof. In one embodiment, the subject was previously treated with another anticancer treatment, e.g., surgery (e.g., at least partial resection of a tumor) and/or radiotherapy and/or treatment with an anticancer agent. In one embodiment, the subject became refractory to said previous treatment. In one embodiment, the subject is treated with a compound of Formula I, Formula II, Formula III, or a pharmaceutically acceptable salt, solvate or polymorph thereof, in combination with another anticancer treatment, e.g., surgery (e.g., at least partial resection of a tumor) and/or radiotherapy and/or treatment with an anticancer agent.

Also provided herein are methods for inhibiting metastasis in a subject in need thereof, the method comprising administering to the subject a therapeutically effective amount of a compound of Formula I, Formula II or Formula III, or a pharmaceutically acceptable salt, solvate or polymorph thereof, or a pharmaceutical composition thereof. In some embodiments, the compound of Formula I, Formula II or Formula III, or a pharmaceutically acceptable salt, solvate or polymorph thereof, is used in combination with another anticancer treatment, e.g., surgery (e.g., at least partial resection of a tumor) and/or radiotherapy and/or treatment with an anticancer agent. In one embodiment, the cancer is metastatic cancer with brain metastasis and the method comprises administering a compound of Formula II, or a pharmaceutically acceptable salt, solvate or polymorph thereof, or Formula III, or a pharmaceutically acceptable salt, solvate or polymorph thereof. In one embodiment, the cancer is metastatic melanoma with brain metastasis. In one embodiment, the cancer is metastatic colorectal cancer with brain metastasis. In one embodiment, the cancer is metastatic non-small cell lung cancer with brain metastasis. In one embodiment, the cancer is metastatic ovarian cancer with brain metastasis. In one embodiment, the cancer is metastatic thyroid cancer with brain metastasis. In one embodiment, the cancer is neuroblastoma with brain metastasis, and the method comprises administering a compound of Formula II, or a pharmaceutically acceptable salt, solvate or polymorph thereof, or Formula III, or a pharmaceutically acceptable salt, solvate or polymorph thereof. In one embodiment, the subject was previously treated with another anticancer treatment, e.g., surgery (e.g., at least partial resection of a tumor) and/or radiotherapy and/or treatment with an anticancer agent. In one embodiment, the subject became refractory to said previous treatment. In one embodiment, the subject is treated with a compound of Formula I, Formula II, Formula III, or a pharmaceutically acceptable salt, solvate or polymorph thereof, in combination with another anticancer treatment, e.g., surgery (e.g., at least partial resection of a tumor) and/or radiotherapy and/or treatment with an anticancer agent. In one embodiment, the anticancer therapy is an anticancer agent. In one embodiment, the anticancer agent selected from one or more of MEK inhibitors, BRAF inhibitors, EGFR inhibitors, inhibitors of HER2 and/or HER3, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents. In one embodiment, the anticancer agent is a MEK inhibitor. In one embodiment, the MEK inhibitor is selected from binimetinib, trametinib and cobimetinib. In one embodiment, the MEK inhibitor is binimetinib.

As used herein, the term "treating metastasis" means reducing the size, progression, and/or further spread of one or more metastases.

Also provide herein are methods of inhibiting metastasis in a subject in need thereof, the method comprising administering to the subject a therapeutically effective amount of a compound of Formula I, Formula II or Formula III, or a pharmaceutically acceptable salt, solvate or polymorph thereof or a pharmaceutical composition thereof. In some embodiments, the compound of Formula I, Formula II or Formula III, or a pharmaceutically acceptable salt, solvate or polymorph thereof, is used in combination with another anticancer treatment, e.g., surgery (e.g., at least partial resection of a tumor) and/or radiotherapy and/or treatment with an anticancer agent. In one embodiment, the cancer is metastatic cancer with brain metastasis and the method comprises administering a compound of Formula II or Formula III, or a pharmaceutically acceptable salt, solvate or polymorph thereof. In one embodiment, the cancer is metastatic melanoma with brain metastasis. In one embodiment, the cancer is metastatic colorectal cancer with brain metastasis. In one embodiment, the cancer is metastatic non-small cell lung cancer with brain metastasis. In one embodiment, the cancer is metastatic ovarian cancer with brain metastasis. In one embodiment, the cancer is metastatic thyroid cancer with brain metastasis. In one embodiment, the cancer is neuroblastoma with brain metastasis, and the method comprises administering a compound of Formula II, or a pharmaceutically acceptable salt, solvate or polymorph thereof, or Formula III, or a pharmaceutically acceptable salt, solvate or polymorph thereof. In one embodiment, the subject was previously treated with another anticancer treatment, e.g., surgery (e.g., at least partial resection of a tumor) and/or radiotherapy and/or treatment with an anticancer agent. In one embodiment, the subject became refractory to said previous treatment. In one embodiment, the subject is treated with a compound of Formula I, Formula II, Formula III, or a pharmaceutically acceptable salt, solvate or polymorph thereof, in combination with another anticancer treatment, e.g., surgery (e.g., at least partial resection of a tumor)

and/or radiotherapy and/or treatment with an anticancer agent. In one embodiment, the anticancer therapy is an anticancer agent. In one embodiment, the anticancer agent selected from MEK inhibitors, BRAF inhibitors, EGFR inhibitors, inhibitors of HER2 and/or HER3, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents; In one embodiment, the anticancer agent is a MEK inhibitor. In one embodiment, the MEK inhibitor is selected from binimetinib, trametinib and cobimetinib. In one embodiment, the MEK inhibitor is binimetinib.

As used herein, the term "inhibiting metastasis" means reducing the occurrence (or reoccurrence) of one or more metastases, preventing the occurrence (or reoccurrence) of one or more metastases, or reducing the spread of one or more metastases.

Also provided are methods of decreasing the risk of developing one or more metastases or one or more additional metastases in a subject having a BRAF-associated cancer that include: selecting, identifying, or diagnosing a subject as having a BRAF-associated cancer, and administering a therapeutically effective amount of a compound of Formula I, Formula II or Formula III, or a pharmaceutically acceptable salt, solvate or polymorph thereof, to the subject selected, identified, or diagnosed as having a BRAF-associated cancer. Also provided are methods of decreasing the risk of developing one or more metastases or one or more additional metastases in a subject having a BRAF-associated cancer that includes administering a therapeutically effective amount of a compound of Formula I, Formula II or Formula III, or a pharmaceutically acceptable salt, solvate or polymorph thereof, to a subject having a BRAF-associated cancer. The decrease in the risk of developing one or more metastases or one or more additional metastases in a subject having a BRAF-associated cancer can be compared to the risk of developing one or more metastases or one or more additional metastases in the subject prior to treatment, or as compared to a subject or a population of subjects having a similar or the same BRAF-associated cancer that has received no treatment or a different treatment.

The phrase "risk of developing one or more metastases" means the risk that a subject or subject having a primary tumor will develop an additional tumor (e.g., a solid tumor) at a site distant from a primary tumor in a subject or subject over a set period of time, where the additional tumor includes the same or similar cancer cells as the primary tumor. Methods for reducing the risk of developing one or more metastases in a subject or subject having a cancer are described herein.

The phrase "risk of developing additional metastases" means the risk that a subject or subject having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

Also provided herein is a method of treating a BRAF-associated tumor, metastasis of a BRAF-associated tumor, or a combination thereof, in a subject in need thereof, the method comprising administering a compound of Formula II, or a pharmaceutically acceptable salt, solvate or polymorph thereof, or Formula III, or a pharmaceutically acceptable salt, solvate or polymorph thereof, to the subject. In one embodiment, the subject has at least one metastasis or is at risk of developing at least one metastasis. In one embodiment, the subject has at least one metastasis, wherein the method comprises administering a compound of, Formula II, or a pharmaceutically acceptable salt, solvate or polymorph thereof, or Formula III, or a pharmaceutically acceptable salt, solvate or polymorph thereof. In one embodiment, the subject is at risk of developing at least one metastasis. In one embodiment, the subject is at risk of developing at least one metastasis, wherein said subject has a cancer selected, from melanoma, colorectal cancer, thyroid cancer, non-small cell lung cancer, or ovarian cancer. In one embodiment, the cancer is a BRAF mutant cancer, e.g., a BRAF V600 mutant cancer, e.g., a BRAF V600E, BRAF V600K, BRAF V600D, or BRAF V600R. In one embodiment, the subject was previously treated with another anticancer treatment, e.g., surgery (e.g., at least partial resection of a tumor) and/or radiotherapy and/or treatment with an anticancer agent. In one embodiment, the subject became refractory to said previous treatment. In one embodiment, the subject is treated with a compound of Formula I, Formula II, Formula III, or a pharmaceutically acceptable salt, solvate or polymorph thereof, in combination with another anticancer treatment, e.g., surgery (e.g., at least partial resection of a tumor) and/or radiotherapy and/or treatment with an anticancer agent. In one embodiment, the anticancer therapy is an anticancer agent selected from MEK inhibitors, BRAF inhibitors, EGFR inhibitors, SOS1 inhibitors, inhibitors of HER2 and/or HER3, Axl inhibitors, PI3K inhibitors, signal transduction pathway inhibitors, checkpoint inhibitors, modulators of the apoptosis pathway, cytotoxic chemotherapeutics, angiogenesis-targeted therapies, and immune-targeted agents. In one embodiment, the anticancer agent is a MEK inhibitor. In one embodiment, the MEK inhibitor is selected from binimetinib, trametinib and cobimetinib.

In some embodiments, a subject is administered one or more agents to ameliorate side effects of treatment (e.g., one or more of corticosteroids, serotonin antagonists, dopamine antagonists, NK-1 inhibitors, cannabinoids, anti-anxiety drugs (e.g., lorazepam or diazepam), antibiotics, anti-fungal agents, colony-stimulating factor, iron supplements, Procrit, epoetin alfa, darbepoetin alfa, anti-emetics, diuretics, NSAIDs, analgesics, methotrexate, anti-diuretics, probiotics, blood pressure medications, anti-nausea agents, laxatives, etc.).

In one embodiment, the BRAF-associated tumor is a benign tumor, and a compound of Formula I, Formula II, or Formula III, or a pharmaceutically acceptable salt, solvate or polymorph thereof, may be used alone or in combination with one or more different forms of treatment to treat a subject with a benign tumor.

In some embodiments, a subject has a CNS tumor and is administered one or more agents to ameliorate one or more symptoms associated with a CNS tumor, including, but not limited to, seizures, nausea, headaches, blurred vision, loss of vision, loss of balance, changes in fine motor skills, and drowsiness. Examples of such agents to ameliorate one or more symptoms associated with a CNS tumor include corticosteroids, anti-seizure medications (e.g., cannabidiol, gabapentin or pregabalin), pain medications (e.g., NSAIDS, acetaminophen) and anti-nausea agents.

Also provided is a method for inhibiting BRAF kinase activity in a mammalian cell, comprising contacting the cell with an effective amount of a compound of Formula I, Formula II or Formula III. In some embodiments, the contacting is in vitro. In some embodiments, the contacting is in vivo. In some embodiments, the contacting is in vivo, wherein the method comprises administering a therapeutically effective amount of a compound of Formula I, Formula II or Formula III, or a pharmaceutically acceptable salt, solvate or polymorph thereof to a subject having a cell having BRAF kinase activity. In some embodiments, the cell is a cancer cell. In some embodiments, the cancer cell is any cancer as described herein. In some embodiments, the cancer cell is a BRAF-associated cancer cell. In some embodiments, the cell is a brain cell (e.g., a neural cell or a glial cell).

Also provided is a method for inhibiting BRAF kinase activity in a mammalian cell, comprising contacting the cell with an effective amount of a compound of Formula I, Formula II or Formula III, or a pharmaceutically acceptable salt, solvate or polymorph thereof: In some embodiments, the contacting is in vitro. In some embodiments, the contacting is in vivo. In some embodiments, the contacting is in vivo, wherein the method comprises administering a therapeutically effective amount of a compound of Formula I, Formula II or Formula III, or a pharmaceutically acceptable salt, solvate or polymorph thereof, to a mammal having a cell having BRAF kinase activity. In some embodiments, the mammalian cell is a mammalian cancer cell. In some embodiments, the mammalian cancer cell is any cancer as described herein. In some embodiments, the mammalian cancer cell is a BRAF-associated cancer cell. In some embodiments, the mammalian cell is a brain cell.

As used herein, the term "contacting" refers to the bringing together of indicated moieties in an in vitro system or an in vivo system. For example, "contacting" a BRAF kinase with a compound provided herein includes contacting a cell containing a BRAF kinase with the compound provided herein, as well as, for example, introducing a compound provided herein into a sample containing a cellular or purified preparation containing the BRAF kinase.

Also provided herein is a method of inhibiting cell proliferation, in vitro or in vivo, the method comprising contacting a cell with a therapeutically effective amount of a compound of Formula I, Formula II or Formula III, or a pharmaceutically acceptable salt, solvate or polymorph thereof, or a pharmaceutical composition thereof as defined herein.

As used herein, a "therapeutically effective amount" of a compound, pharmaceutical composition thereof, or pharmaceutical combination thereof, is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include providing a therapeutic effect can include reducing the size of a tumor, inhibiting (e.g., slowing, to some extent, preferably stopping) tumor progression, inhibiting (e.g., slowing, to some extent, preferably stopping) tumor growth, inhibiting (e.g., slowing, to some extent, preferably stopping) tumor invasiveness, and/or inhibiting (e.g., slowing, to some extent, preferably stopping) tumor metastasis. The skilled person understands that tumor progression in human subjects can be determined by a variety of methods. For example, the size of a tumor close to the skin can be measured by establishing the width and depth of the tumor with calipers, and then calculating the tumor volume. Less accessible tumors, such as lung and CNS cancers can be measured by observation of the images obtained from Magnetic Resonance Imaging (MRI) scanning. CNS tumors, such as brain tumors, can be measured by a combination of MRI scanning and by monitoring neurological performance. Growth of a brain tumor is typically associated with decreasing neurological performance. Providing a therapeutic effect also includes prolonging survival of a subject or subject beyond that expected in the absence of treatment and/or relieving to some extent (or preferably eliminating) one or more signs or symptoms associated with cancer. In one embodiment, treatment of a subject or subject with a compound or combination according to an invention prolongs survival beyond that expected in the absence of treatment by 1 or months, e.g., by 3 or more months, e.g., by 6 or more months, e.g., by 1 or more years, e.g., by 2 or more years, e.g., by 3 or more years, e.g., by 5 or more years, e.g., by 10 or more years. Providing a therapeutic effect also includes reducing the number of cancer cells. Providing a therapeutic effect also includes eliminating cancer cells. Providing a therapeutic effect also includes tumor mass reduction. Providing a therapeutic effect also includes causing a cancer to go into remission. A therapeutically effective amount can be administered in one or more administrations. For purposes of this invention, dosage therapeutically effective amount of a compound, or pharmaceutical composition thereof is an amount sufficient to accomplish prophylactic or therapeutic treatment either directly or indirectly. As is understood in the clinical context, dosage therapeutically effective amount of a compound or pharmaceutical composition thereof may be achieved in conjunction with another therapy. Thus, a "therapeutically effective amount" may be considered in the context of administering one or more therapies (e.g., one or more anticancer agents), and a single agent may be considered to be given in a therapeutically effective amount if, in conjunction with one or more other agents, a desirable result may be or is achieved. In reference to the treatment of cancer, a therapeutically effective amount may also refer to that amount which has the effect of (1) reducing the size of the tumor, (2) inhibiting (that is, slowing to some extent, preferably stopping) tumor metastasis emergence, (3) inhibiting to some extent (that is, slowing to some extent, preferably stopping) tumor growth or tumor invasiveness, and/or (4) relieving to some extent (or, preferably, eliminating) one or more signs or symptoms associated with the cancer. Therapeutic or pharmacological effectiveness of the doses and administration regimens may also be characterized as the ability to induce, enhance, maintain or prolong disease control and/or overall survival in subjects with these specific tumors, which may be measured as prolongation of the time before disease progression.

In one embodiment, a subject treated according to any of the methods disclosed herein may be assessed according to one or more standard response assessment criteria known in the art, including RECIST (Response Evaluation Criteria in Solid Tumors, e.g., RECIST version 1.0, RECIST version 1.1, and modified RECIST 1.1 (mRECIST 1.1)), RANO-BM (Response Assessment in Neuro-Oncology Brain Metastases), Macdonald, RANO-LMD, and NANO (Neurologic Assessment in Neuro-Oncology). In one embodiment of any of said criteria, the tumor is assessed by an imaging study (e.g., MRI, CT, MDCT or PET). In one embodiment the treatment response is assessed in accordance with RECIST version 1.1, wherein: complete response (CR) is defined as the complete disappearance of all tumor lesions; partial response (PR) is defined as a reduction in the sum of tumor measurements by at least 30%; progressive disease (PD) is defined as at least 20% increase in the sum of tumor measurements (wherein the development of new lesions or substantial progression of non-target lesions is also was defined as PD) wherein an increase of at least 5 mm from baseline is evaluated as PD; and stable disease (SD) is defined as neither sufficient shrinkage to qualify for PR nor sufficient increase to qualify for PD, taking as reference the smallest sum diameters while on treatment. In one embodiment, assessments include intracranial response (assessed as per modified RECIST using gadolinium enhanced MRI), extracranial response, global response rate, disease control rate (DCR), duration of response (DOR), progression free survival (PFS), and overall survival (OS).

In one embodiment, the subject has a CNS tumor and has at least one measurable intracranial tumor. In one embodiment, the at least one measurable intracranial tumor is measured by MRI or CT.

A "measurable" tumor (tumor lesion) means a tumor that can be accurately measured in at least one dimension (longest diameter in the plane of measurement is not recorded) with a minimum size of: 10 mm by CT scan (CT scan slice thickness no greater than 5 mm); 10 mm caliper measurement by clinical exam; 20 mm by chest X-ray.

When employed as pharmaceuticals, the compounds of Formula I, Formula II or Formula III, including pharmaceutically acceptable salts or solvates thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula I, Formula II or Formula III, or a pharmaceutically acceptable salt, solvate or polymorph thereof, in combination with one or more pharmaceutically acceptable carriers (excipients). For example, a pharmaceutical composition prepared using a compound of Formula I, Formula II or Formula III or a pharmaceutically acceptable salt, solvate or polymorph thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula I, Formula II or Formula III, or a pharmaceutically acceptable salt, solvate or polymorph thereof with a pharmaceutically acceptable carrier. Pharmaceutical compositions containing a compound of Formula I, Formula II or Formula III, or a pharmaceutically acceptable salt, solvate or polymorph thereof as the active ingredient can be prepared by intimately mixing the compound of Formula I, Formula II or Formula III, or a pharmaceutically acceptable salt, solvate or polymorph thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems,* Volumes 1-2, edited by Lieberman et al; published by Marcel Dekker, Inc.

In preparing the compositions in oral dosage form, any of the usual pharmaceutical media can be employed. Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver a therapeutically effective amount as described herein.

The compositions comprising a compound of Formula I, Formula II or Formula III, or a pharmaceutically acceptable salt, solvate or polymorph thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other subjects, each unit containing a predetermined quantity of active material (i.e., a compound of Formula I, Formula II or Formula III or a pharmaceutically acceptable salt, solvate or polymorph thereof) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain about 10 mg, about 20 mg, about 80 mg, or about 160 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The daily dosage of the compound of Formula I, Formula II or Formula III or a pharmaceutically acceptable salt, solvate or polymorph thereof can be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 160, 200, 250 and 500 milligrams of the active ingredient for the symptomatic adjustment of the dosage to the subject to be treated. A therapeutically effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range can be from about 0.1 to about 50.0 mg/kg of body weight per day, or any amount or range therein. In another example, the range can be from about 0.1 to about 15.0 mg/kg of body weight per day, or any range therein. In yet another example, the range can be from about 0.5 to about 7.5 mg/kg of body weight per day, or any amount to range therein. Pharmaceutical compositions containing a compound of Formula I, Formula II or Formula III or a pharmaceutically acceptable salt, solvate or polymorph thereof can be administered on a regimen of 1 to 4 times per day or in a single daily dose.

The active compound may be effective over a wide dosage range and is generally administered in a therapeutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular subject being treated, including subject response, age, weight, diet, time of administration and severity of the subject's symptoms, will result in the need to adjust dosages.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily (QD) or twice-daily (BID) administration. In some embodiments, such administration can be on an intermittent dosing schedule. For example, in one embodiment the dosing schedule comprises administering a compound of: Formula I, Formula II or Formula III, or a pharmaceutically acceptable salt, solvate or polymorph thereof once-daily for a period of 1, 2, 3, 4, 5, or 6 weeks followed by a period of 1, 2, 3, 4, 5, or 6 weeks without treatment and repeating the cycle while the subject is treated with said compound. In one embodiment the dosing schedule comprises administering a compound of Formula I, Formula II or Formula III, or a pharmaceutically acceptable salt, solvate or polymorph thereof for a period of 4 weeks followed by a period of two weeks without treatment and repeating the cycle while the subject is treated with said compound. In one embodiment the dosing schedule comprises administering a compound of Formula I, Formula II or Formula III, or a pharmaceutically acceptable salt, solvate or polymorph thereof for a period of 1 week followed by a period of 1 week without treatment and repeating the cycle while the subject is treated with said compound. In one embodiment the dosing schedule comprises administering a compound of Formula I, Formula II or Formula III, or a pharmaceutically acceptable salt, solvate or polymorph thereof for a period of 2 weeks followed by a period of 1 or 2 weeks without treatment and repeating the cycle while the subject is treated with said compound. In one embodiment the dosing schedule comprises administering a compound of Formula I, Formula II or Formula III, or a pharmaceutically acceptable salt, solvate or polymorph thereof for a period of 3 weeks followed by a period of 1, 2 or 3 weeks without treatment and repeating the cycle while the subject is treated with said compound. In one embodiment the dosing schedule comprises administering a compound of Formula I, Formula II or Formula III, or a pharmaceutically acceptable salt, solvate or polymorph thereof for a period of 4 weeks followed by a period of 1, 2, 3 or 4 weeks without treatment and repeating the cycle while the subject is treated with said compound. In one embodiment the dosing schedule comprises administering a compound of Formula I, Formula II or Formula III, or a pharmaceutically acceptable salt, solvate or polymorph thereof for a period of 5 weeks followed by a period of 1, 2, 3, 4 or 5 weeks without treatment and repeating the cycle while the subject is treated with said compound. In one embodiment the dosing schedule comprises administering a compound of Formula I, Formula II or Formula III, or a pharmaceutically acceptable salt, solvate or polymorph thereof for a period of 6 weeks followed by a period of 1, 2, 3, 4, 5 or 6 weeks without treatment and repeating the cycle while the subject is treated with said compound. In any of said intermittent dosing schedules, the administration of a compound of Formula I, Formula II or Formula III, or a pharmaceutically acceptable salt, solvate or polymorph thereof is once daily (QD).

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, can be completed according to methods well known in the clinical and medical arts.

Provided herein are pharmaceutical kits useful, for example, in the treatment of BRAF-associated diseases or disorders, such as cancer, which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The following examples illustrate the invention.

Biological Examples

Example A

BRAF V600E and V600K Enzyme Assay

A competitive displacement assay was configured for B-Raf that monitors the amount of a fluorescently-tagged "tracer" bound to B-Raf via TR-FRET from an anti-tag Eu-labeled antibody also bound to B-Raf. For full-length FLAG-tagged B-Raf(V600E), the assay mixtures consisted of 25 mM K$^+$HEPES, pH 7.4, 10 mM MgCl$_2$, 0.01% Triton X-100, 1 mM DTT, 2% DMSO (from compound), 50 nM Tracer 1710 (ThermoFisher, PR9176A), 0.5 nM Eu anti-FLAG (M2)-cryptate Ab (Cisbio, 61FG2KLB) and 5 nM full-length, N-terminally FLAG-tagged B-Raf(V600E) (Origene Technologies, TP700031. When B-Raf(V600K) was assayed, the following substitutions were made: 15 nM Tracer 178 (ThermoFisher, PV5593), 2 nM Eu-anti-GST Ab (ThermoFisher, PV5595) and 5 nM N-terminally GST-tagged B-Raf(V600K) (331-end, SignalChem, B08-12DG). Compounds were typically diluted in DMSO across an 11-point dosing range created using a 3-fold serial dilution protocol at a top dose of 10 µM. The assay was run in 384-well, polystyrene, low-volume, non-treated, white microtiter plates (Costar 4512) in a final volume of 12 µL. Low control wells included 1 µM of a potent B-Raf inhibitor as a control. The assays were incubated at ambient temperature (typically 22° C.) for 60 min and then read on a PerkinElmer EnVision microplate reader using standard TRF settings ($\lambda_{Ex}$=320 nm, $\lambda_{Em}$=615 & 665 nm). The ratioed counts (665 nm/615 nm) were converted to percent of control (POC) using the following equation:

$$POC = \frac{\text{Sample} - \overline{X}_{min}}{\overline{X}_{max} - \overline{X}_{min}} \times 100$$

where:
$\overline{X}_{max}$ Average Uninhibited Controls
$\overline{X}_{min}$ Average Background
A 4-parameter logistic model was the fit to the POC data for each compound. From that fit, the IC$_{50}$ was estimated and is defined as the concentration of compound at which the best-fit curve crosses 50 POC. Averaged IC$_{50}$ values of compounds disclosed herein when tested in this assay are provided in Table A.

TABLE A

| Ex. # | structure | BRAF V600E enzyme IC$_{50}$ (nM) | BRAF V600K enzyme IC$_{50}$ (nM) |
|---|---|---|---|
| 1 | 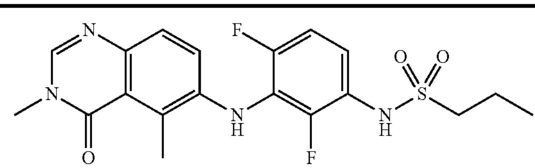 | 42.7 | 8.5 |
| 2 | 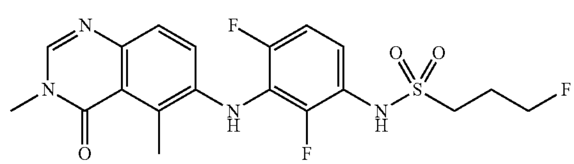 [SMILES: Cc1c(Nc2c(F)ccc(NS(=O)(=O)CCCF)c2F)ccc2ncn(C)c(=O)c12] | 14.25 | |

TABLE A-continued

| Ex. # | structure | BRAF V600E enzyme IC$_{50}$ (nM) | BRAF V600K enzyme IC$_{50}$ (nM) |
|---|---|---|---|
| 3 | 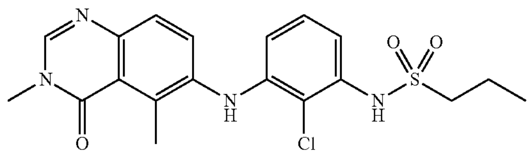 [SMILES: CCCS(=O)(=O)Nc1cccc(Nc2ccc3ncn(C)c(=O)c3c2C)c1Cl] | 70.55 | |
| 4 | 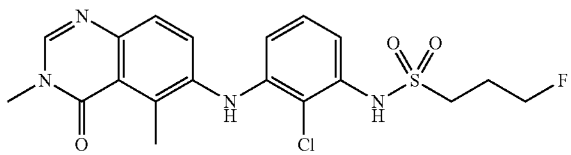 [SMILES: Cc1c(Nc2cccc(NS(=O)(=O)CCCF)c2Cl)ccc2ncn(C)c(=O)c12] | 16.1 | 8.1 |
| 5 | 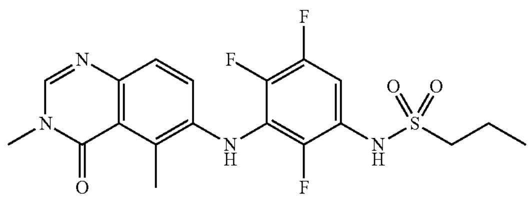 [SMILES: CCCS(=O)(=O)Nc1cc(F)c(F)c(Nc2ccc3ncn(C)c(=O)c3c2C)c1F] | 6.25 | |
| 6 | 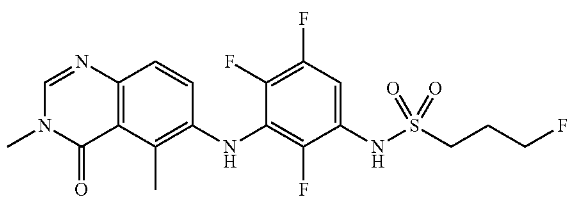 [SMILES: Cc1c(Nc2c(F)c(F)cc(NS(=O)(=O)CCCF)c2F)ccc2ncn(C)c(=O)c12] | 1.75 | |
| 7 | 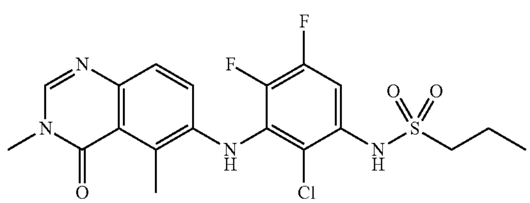 [SMILES: CCCS(=O)(=O)Nc1cc(F)c(F)c(Nc2ccc3ncn(C)c(=O)c3c2C)c1Cl] | 1.3 | 2.2 |
| 8 | 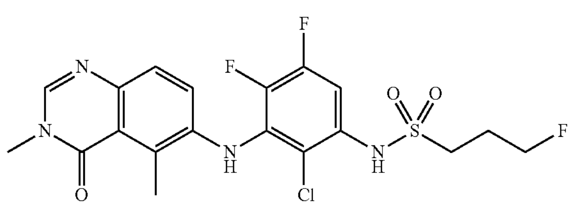 | 1.45 | |
| 9 | 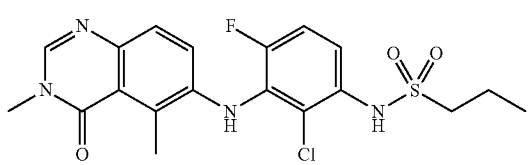 [SMILES: CCCS(=O)(=O)Nc1ccc(F)c(Nc2ccc3ncn(C)c(=O)c3c2C)c1Cl] | 19.7 | 6.5 |
| 10 | 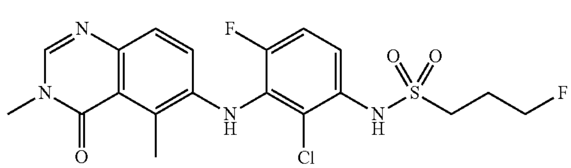 [SMILES: Cc1c(Nc2c(F)ccc(NS(=O)(=O)CCCF)c2Cl)ccc2ncn(C)c(=O)c12] | 4.25 | 2.7 |

TABLE A-continued

| Ex. # | structure | BRAF V600E enzyme IC$_{50}$ (nM) | BRAF V600K enzyme IC$_{50}$ (nM) |
|---|---|---|---|
| 11 | 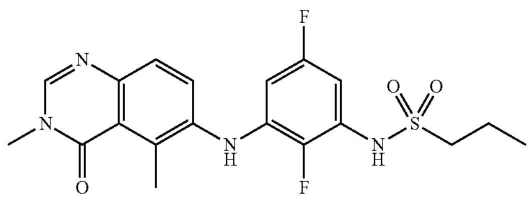 [SMILES: CCCS(=O)(=O)Nc1cc(F)cc(Nc2ccc3ncn(C)c(=O)c3c2C)c1F] | 16.1 | |
| 12 | 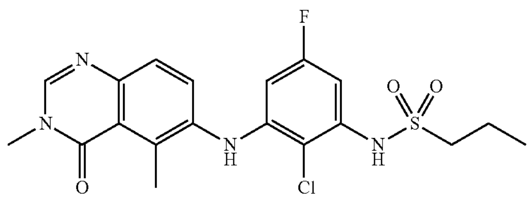 | 9.75 | |
| 13 | 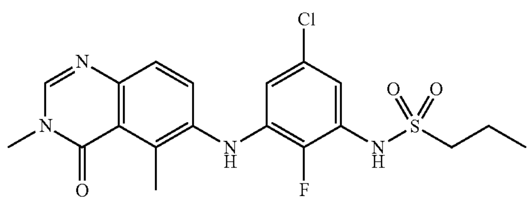 [SMILES: CCCS(=O)(=O)Nc1cc(Cl)cc(Nc2ccc3ncn(C)c(=O)c3c2C)c1F] | 4.6 | |
| 14 | 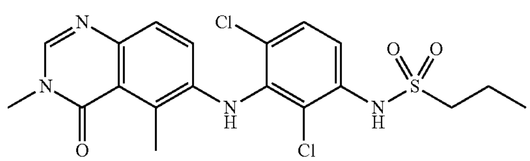 [SMILES: CCCS(=O)(=O)Nc1ccc(Cl)c(Nc2ccc3ncn(C)c(=O)c3c2C)c1Cl] | 13.95 | |
| 15 | 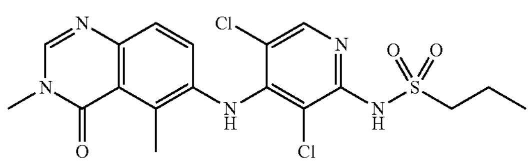 [SMILES: CCCS(=O)(=O)Nc1ncc(Cl)c(Nc2ccc3ncn(C)c(=O)c3c2C)c1Cl] | 4.55 | |
| 16 | 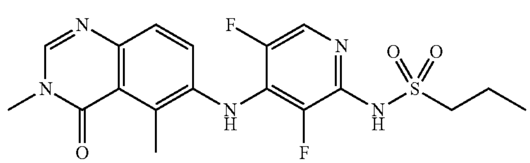 [SMILES: CCCS(=O)(=O)Nc1ncc(F)c(Nc2ccc3ncn(C)c(=O)c3c2C)c1F] | 17 | |
| 17 | 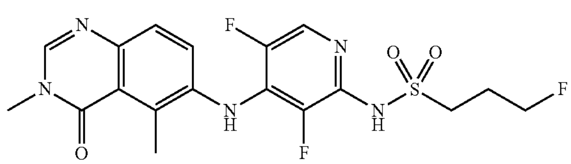 [SMILES: Cc1c(Nc2c(F)cnc(NS(=O)(=O)CCCF)c2F)ccc2ncn(C)c(=O)c12] | 9.7 | |
| 18 | 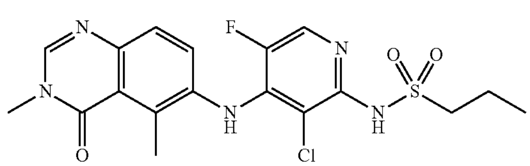 [SMILES: CCCS(=O)(=O)Nc1ncc(F)c(Nc2ccc3ncn(C)c(=O)c3c2C)c1Cl] | 7.85 | |

TABLE A-continued

| Ex. # | structure | BRAF V600E enzyme IC$_{50}$ (nM) | BRAF V600K enzyme IC$_{50}$ (nM) |
|---|---|---|---|
| 19 | 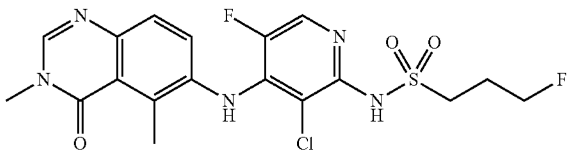 | 6.2 | |
| 20 | 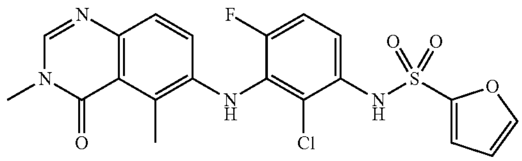 [SMILES: Cc1c(Nc2c(F)ccc(NS(=O)(=O)c3ccco3)c2Cl)ccc2ncn(C)c(=O)c12] | 0.7 | |
| 21 | 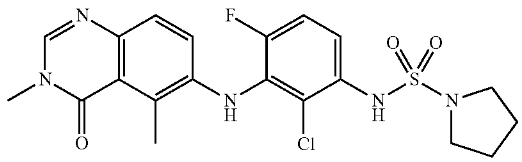 [SMILES: Cc1c(Nc2c(F)ccc(NS(=O)(=O)N3CCCC3)c2Cl)ccc2ncn(C)c(=O)c12] | 34.7 | |
| 22 | 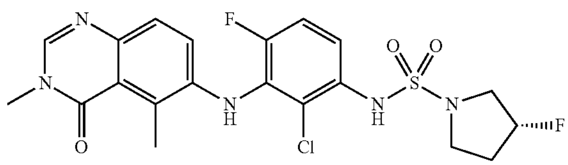 [SMILES: Cc1c(Nc2c(F)ccc(NS(=O)(=O)N3CC[C@@H](F)C3)c2Cl)ccc2ncn(C)c(=O)c12] | 13.65 | |
| 23 | 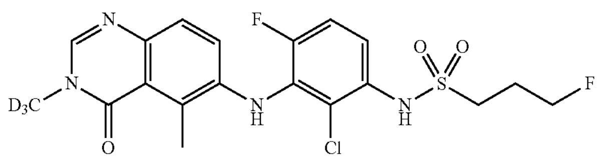 [SMILES: [2H]C([2H])([2H])n1cnc2ccc(Nc3c(F)ccc(NS(=O)(=O)CCCF)c3Cl)c(C)c2c1=O] | 3.25 | 2.7 |
| 24 | 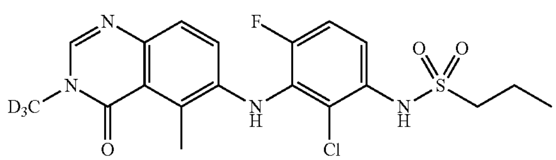 [SMILES: [2H]C([2H])([2H])n1cnc2ccc(Nc3c(F)ccc(NS(=O)(=O)CCC)c3Cl)c(C)c2c1=O] | 9.05 | |
| 25 | 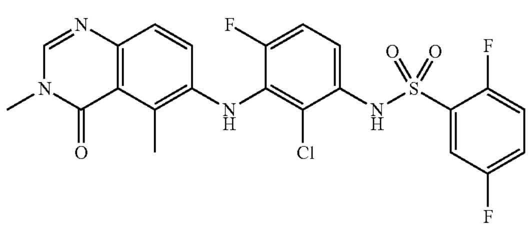 [SMILES: Cc1c(Nc2c(F)ccc(NS(=O)(=O)c3cc(F)ccc3F)c2Cl)ccc2ncn(C)c(=O)c12] | 0.34 | |
| 26 | 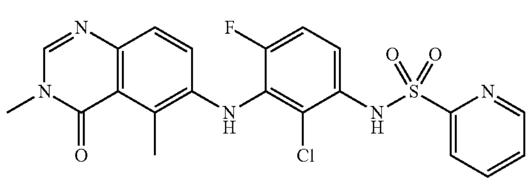 [SMILES: Cc1c(Nc2c(F)ccc(NS(=O)(=O)c3ccccn3)c2Cl)ccc2ncn(C)c(=O)c12] | 49.2 | |
| 27 | 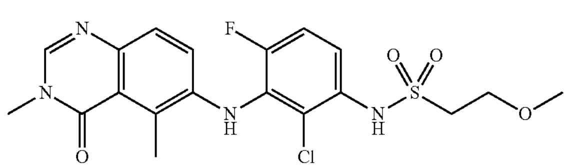 | 206.9 | |

TABLE A-continued

| Ex. # | structure | BRAF V600E enzyme IC$_{50}$ (nM) | BRAF V600K enzyme IC$_{50}$ (nM) |
|---|---|---|---|
| 28 | 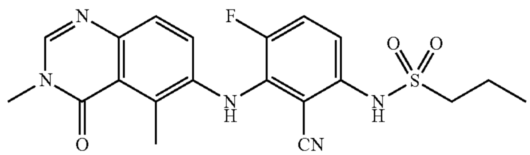 [SMILES: CCCS(=O)(=O)Nc1ccc(F)c(Nc2ccc3ncn(C)c(=O)c3c2C)c1C#N] | 2.0 | |
| 29 | 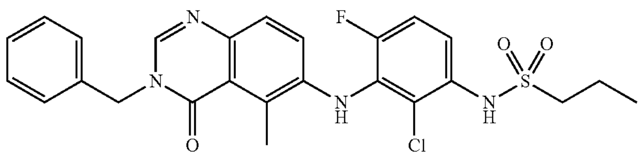 [SMILES: CCCS(=O)(=O)Nc1ccc(F)c(Nc2ccc3ncn(Cc4ccccc4)c(=O)c3c2C)c1Cl] | 173.95 | |
| 30 | 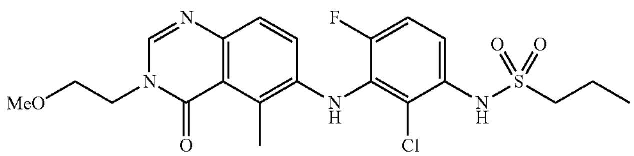 [SMILES: CCCS(=O)(=O)Nc1ccc(F)c(Nc2ccc3ncn(CCOC)c(=O)c3c2C)c1Cl] | 45.5 | |
| 31 | 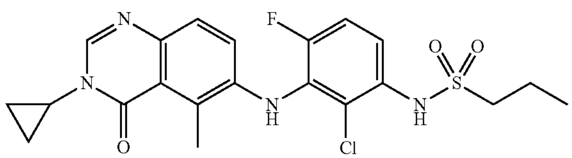 [SMILES: CCCS(=O)(=O)Nc1ccc(F)c(Nc2ccc3ncn(C4CC4)c(=O)c3c2C)c1Cl] | 25.1 | |
| 32 | 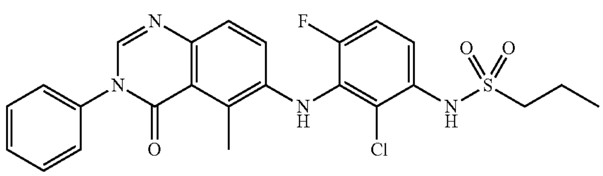 [SMILES: CCCS(=O)(=O)Nc1ccc(F)c(Nc2ccc3ncn(-c4ccccc4)c(=O)c3c2C)c1Cl] | 92.7 | |
| 33 | 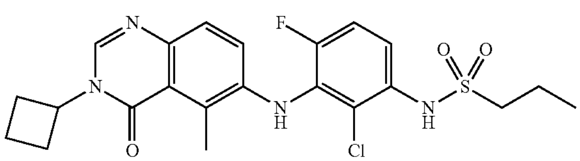 [SMILES: CCCS(=O)(=O)Nc1ccc(F)c(Nc2ccc3ncn(C4CCC4)c(=O)c3c2C)c1Cl] | 24 | |
| 34 | 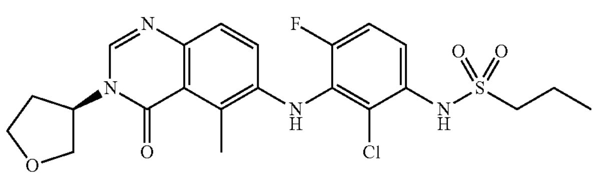 [SMILES: CCCS(=O)(=O)Nc1ccc(F)c(Nc2ccc3ncn([C@@H]4CCOC4)c(=O)c3c2C)c1Cl] | 8.9 | |
| 35 | 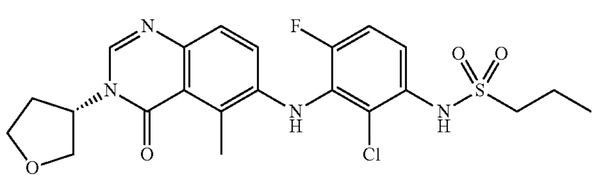 [SMILES: CCCS(=O)(=O)Nc1ccc(F)c(Nc2ccc3ncn([C@H]4CCOC4)c(=O)c3c2C)c1Cl] | 24.5 | |
| 36 | 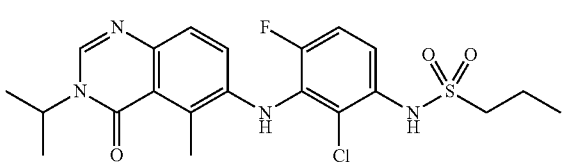 [SMILES: CCCS(=O)(=O)Nc1ccc(F)c(Nc2ccc3ncn(C(C)C)c(=O)c3c2C)c1Cl] | 26.4 | |

TABLE A-continued

| Ex. # | structure | BRAF V600E enzyme IC$_{50}$ (nM) | BRAF V600K enzyme IC$_{50}$ (nM) |
|---|---|---|---|
| 37 | 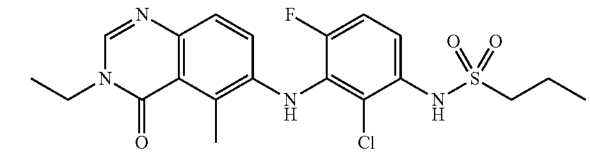 [SMILES: CCCS(=O)(=O)Nc1ccc(F)c(Nc2ccc3ncn(CC)c(=O)c3c2C)c1Cl] | 5.5 | |
| 38 | 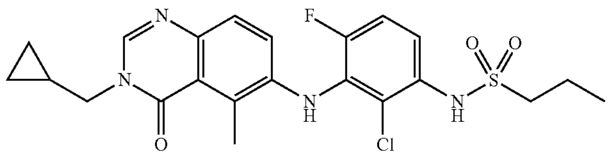 [SMILES: CCCS(=O)(=O)Nc1ccc(F)c(Nc2ccc3ncn(CC4CC4)c(=O)c3c2C)c1Cl] | 28.3 | |
| 39 | 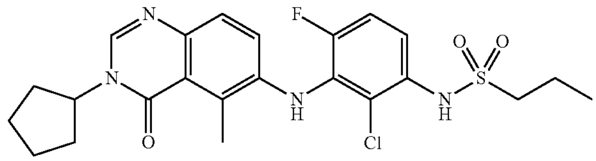 [SMILES: CCCS(=O)(=O)Nc1ccc(F)c(Nc2ccc3ncn(C4CCCC4)c(=O)c3c2C)c1Cl] | 52.6 | |
| 40 | 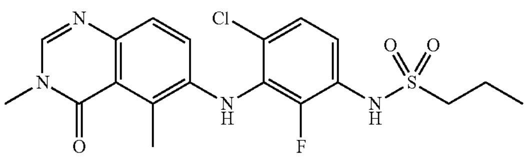 | 43.85 | |
| 41 | 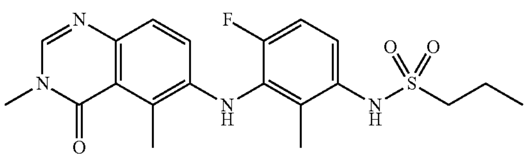 [SMILES: CCCS(=O)(=O)Nc1ccc(F)c(Nc2ccc3ncn(C)c(=O)c3c2C)c1C] | 2819 | |
| 42 | 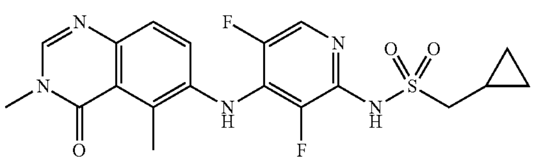 [SMILES: Cc1c(Nc2c(F)cnc(NS(=O)(=O)CC3CC3)c2F)ccc2ncn(C)c(=O)c12] | 60.3 | |
| 43 | 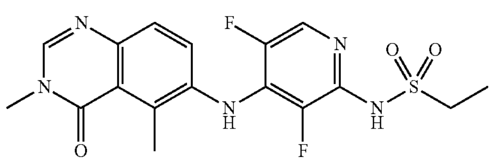 [SMILES: CCS(=O)(=O)Nc1ncc(F)c(Nc2ccc3ncn(C)c(=O)c3c2C)c1F] | 259.5 | |
| 44 | 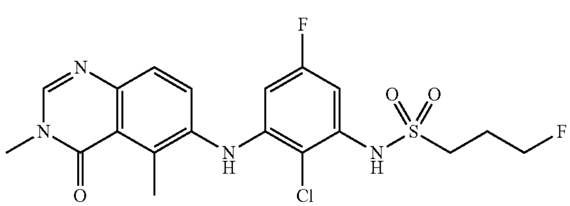 [SMILES: Cc1c(Nc2cc(F)cc(NS(=O)(=O)CCCF)c2Cl)ccc2ncn(C)c(=O)c12] | 6.05 | |
| 45 | 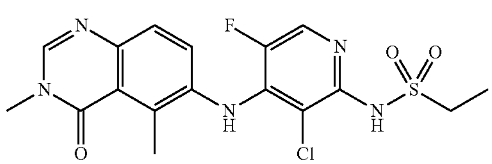 [SMILES: CCS(=O)(=O)Nc1ncc(F)c(Nc2ccc3ncn(C)c(=O)c3c2C)c1Cl] | 136.9 | |

TABLE A-continued

| Ex. # | structure | BRAF V600E enzyme IC$_{50}$ (nM) | BRAF V600K enzyme IC$_{50}$ (nM) |
|---|---|---|---|
| 46 | 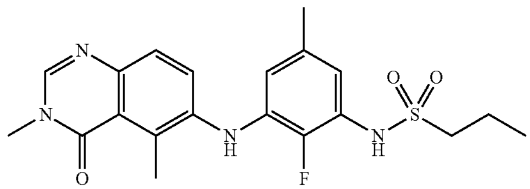 [SMILES: CCCS(=O)(=O)Nc1cc(C)cc(Nc2ccc3ncn(C)c(=O)c3c2C)c1F] | 147.8 | |
| 47 | 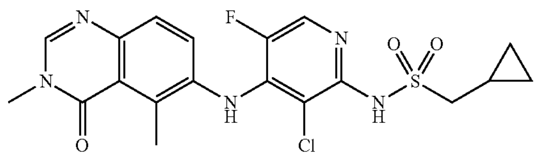 [SMILES: Cc1c(Nc2c(F)cnc(NS(=O)(=O)CC3CC3)c2Cl)ccc2ncn(C)c(=O)c12] | 41.7 | |
| 48 | 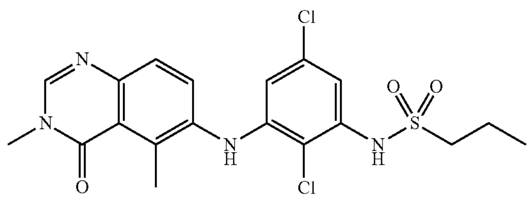 | 3 | |
| 49 | 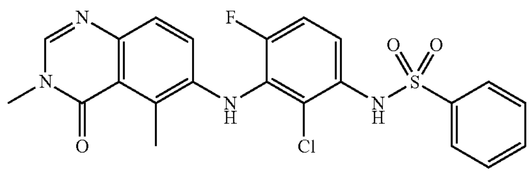 [SMILES: Cc1c(Nc2c(F)ccc(NS(=O)(=O)c3ccccc3)c2Cl)ccc2ncn(C)c(=O)c12] | 3.95 | |
| 50 | 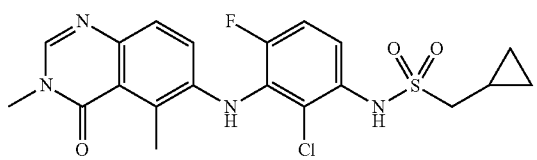 [SMILES: Cc1c(Nc2c(F)ccc(NS(=O)(=O)CC3CC3)c2Cl)ccc2ncn(C)c(=O)c12] | 66.1 | |
| 51 | 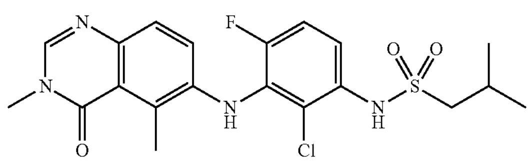 [SMILES: Cc1c(Nc2c(F)ccc(NS(=O)(=O)CC(C)C)c2Cl)ccc2ncn(C)c(=O)c12] | 63.4 | |
| 52 | 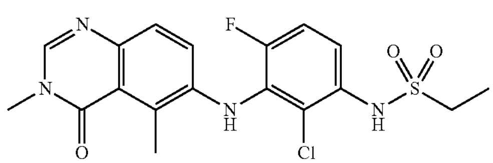 [SMILES: CCS(=O)(=O)Nc1ccc(F)c(Nc2ccc3ncn(C)c(=O)c3c2C)c1Cl] | 226.4 | |
| 53 | 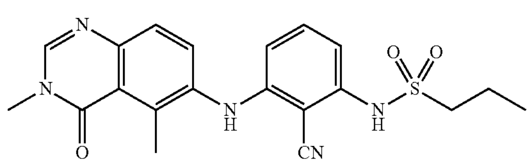 [SMILES: CCCS(=O)(=O)Nc1cccc(Nc2ccc3ncn(C)c(=O)c3c2C)c1C#N] | 9.4 | |
| 54 | 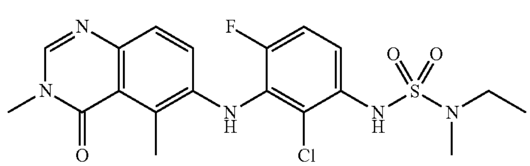 [SMILES: CCN(C)S(=O)(=O)Nc1ccc(F)c(Nc2ccc3ncn(C)c(=O)c3c2C)c1Cl] | 188.1 | |

TABLE A-continued

| Ex. # | structure | BRAF V600E enzyme IC$_{50}$ (nM) | BRAF V600K enzyme IC$_{50}$ (nM) |
|---|---|---|---|
| 55 | 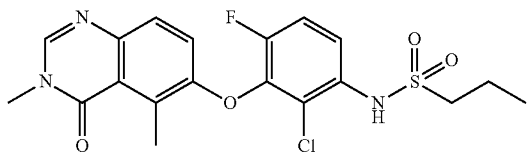 [SMILES: CCCS(=O)(=O)Nc1ccc(F)c(Oc2ccc3ncn(C)c(=O)c3c2C)c1Cl] | 5.4 | 3.1 |
| 56 | 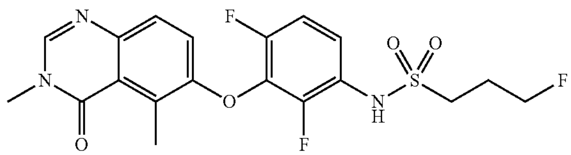 [SMILES: Cc1c(Oc2c(F)ccc(NS(=O)(=O)CCCF)c2F)ccc2ncn(C)c(=O)c12] | 12.95 | |
| 57 | 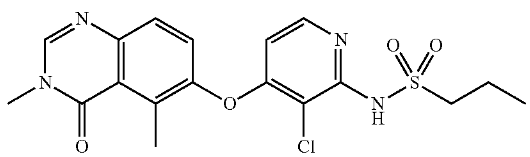 [SMILES: CCCS(=O)(=O)Nc1nccc(Oc2ccc3ncn(C)c(=O)c3c2C)c1Cl] | 96.05 | |
| 58 | 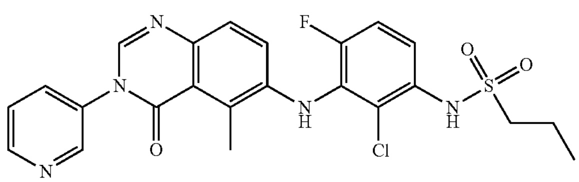 [SMILES: CCCS(=O)(=O)Nc1ccc(F)c(Nc2ccc3ncn(-c4cccnc4)c(=O)c3c2C)c1Cl] | 35.5 | |
| 59 | 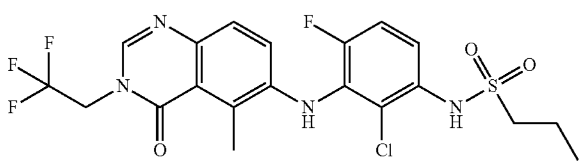 [SMILES: CCCS(=O)(=O)Nc1ccc(F)c(Nc2ccc3ncn(CC(F)(F)F)c(=O)c3c2C)c1Cl] | 3.4 | |
| 60 | 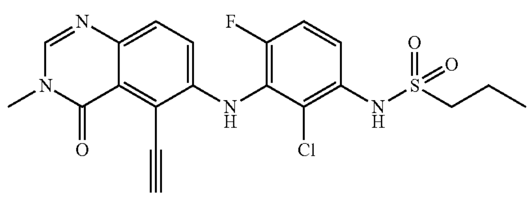 [SMILES: C#Cc1c(Nc2c(F)ccc(NS(=O)(=O)CCC)c2Cl)ccc2ncn(C)c(=O)c12] | 9.25 | |
| 61 | 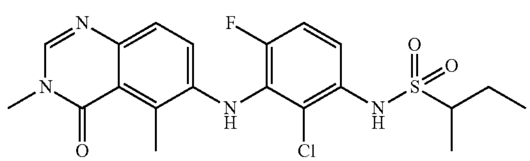 [SMILES: CCC(C)S(=O)(=O)Nc1ccc(F)c(Nc2ccc3ncn(C)c(=O)c3c2C)c1Cl] | 97.65 | |
| 62 | 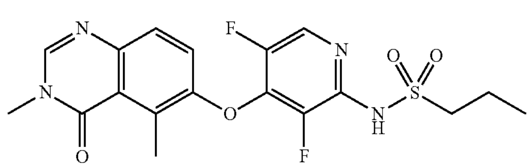 [SMILES: CCCS(=O)(=O)Nc1ncc(F)c(Oc2ccc3ncn(C)c(=O)c3c2C)c1F] | 15.8 | |
| 63 | 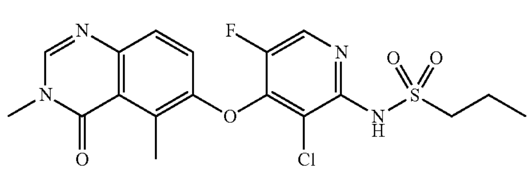 | 2.8 | 2.4 |

TABLE A-continued

| Ex. # | structure | BRAF V600E enzyme IC$_{50}$ (nM) | BRAF V600K enzyme IC$_{50}$ (nM) |
|---|---|---|---|
| 64 | 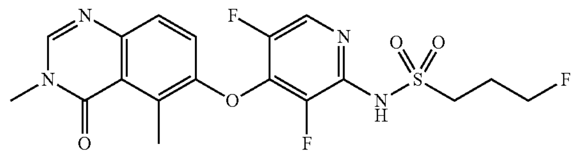 [SMILES: Cc1c(Oc2c(F)cnc(NS(=O)(=O)CCCF)c2F)ccc2ncn(C)c(=O)c12] | 10.4 | |
| 65 | 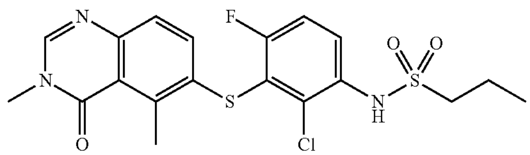 [SMILES: CCCS(=O)(=O)Nc1ccc(F)c(Sc2ccc3ncn(C)c(=O)c3c2C)c1Cl] | 92.4 | |
| 66 | 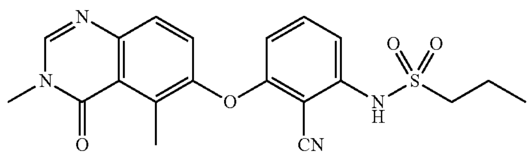 [SMILES: CCCS(=O)(=O)Nc1cccc(Oc2ccc3ncn(C)c(=O)c3c2C)c1C#N] | 4.08 | |
| 67 | 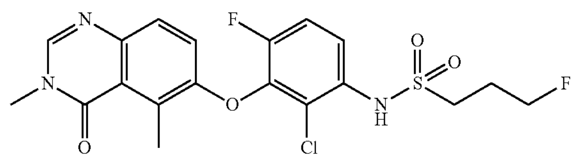 [SMILES: Cc1c(Oc2c(F)ccc(NS(=O)(=O)CCCF)c2Cl)ccc2ncn(C)c(=O)c12] | 2.0 | 2.8 |
| 68 | 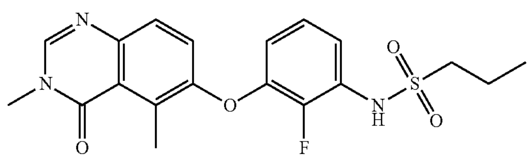 [SMILES: CCCS(=O)(=O)Nc1cccc(Oc2ccc3ncn(C)c(=O)c3c2C)c1F] | 33 | |
| 69 | 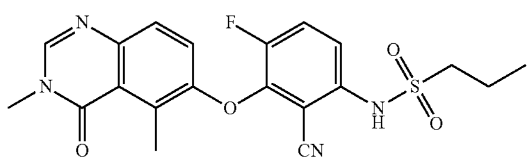 [SMILES: CCCS(=O)(=O)Nc1ccc(F)c(Oc2ccc3ncn(C)c(=O)c3c2C)c1C#N] | 0.46 | |
| 70 | 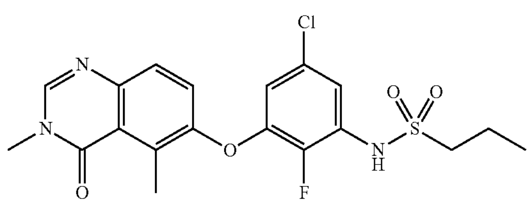 | 2.55 | |
| 71 | 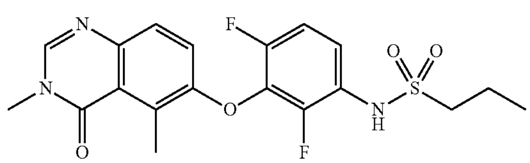 [SMILES: CCCS(=O)(=O)Nc1ccc(F)c(Oc2ccc3ncn(C)c(=O)c3c2C)c1F] | 16.4 | |
| 72 | 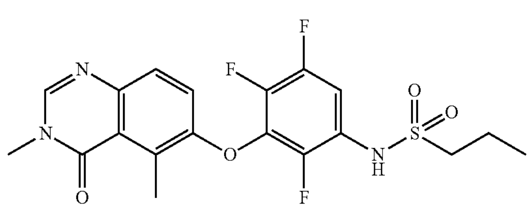 [SMILES: CCCS(=O)(=O)Nc1cc(F)c(F)c(Oc2ccc3ncn(C)c(=O)c3c2C)c1F] | 7.7 | |

TABLE A-continued

| Ex. # | structure | BRAF V600E enzyme IC$_{50}$ (nM) | BRAF V600K enzyme IC$_{50}$ (nM) |
|---|---|---|---|
| 73 | 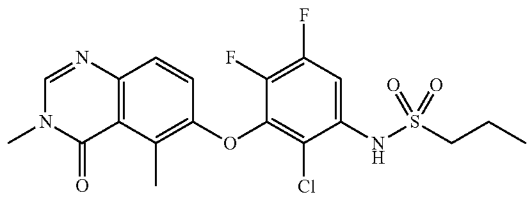 [SMILES: CCCS(=O)(=O)Nc1cc(F)c(F)c(Oc2ccc3ncn(C)c(=O)c3c2C)c1Cl] | 1.55 | |
| 74 | 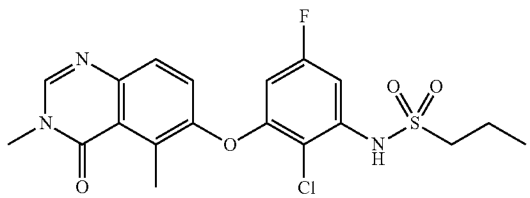 | 3.55 | |
| 75 | 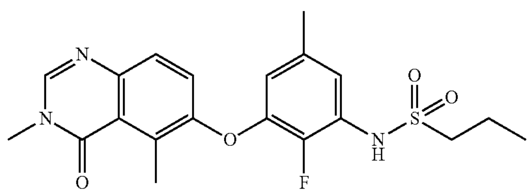 [SMILES: CCCS(=O)(=O)Nc1cc(C)cc(Oc2ccc3ncn(C)c(=O)c3c2C)c1F] | 74.85 | |
| 76 | 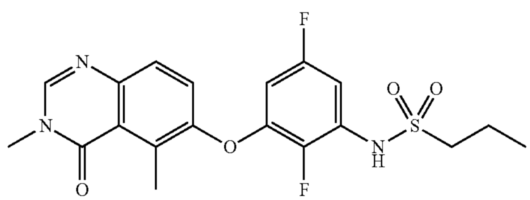 [SMILES: CCCS(=O)(=O)Nc1cc(F)cc(Oc2ccc3ncn(C)c(=O)c3c2C)c1F] | 5.1 | |
| 77 | 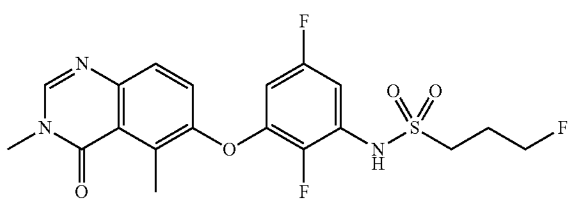 [SMILES: Cc1c(Oc2cc(F)cc(NS(=O)(=O)CCCF)c2F)ccc2ncn(C)c(=O)c12] | 4.25 | |
| 78 | 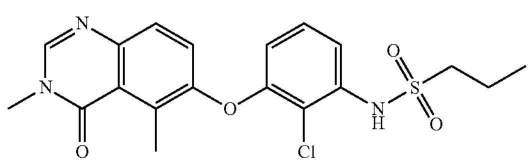 [SMILES: CCCS(=O)(=O)Nc1cccc(Oc2ccc3ncn(C)c(=O)c3c2C)c1Cl] | 10.75 | |
| 79 | 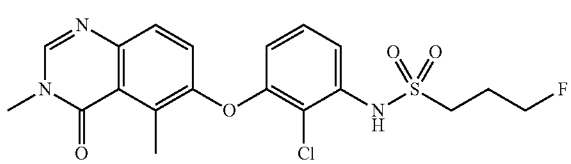 [SMILES: Cc1c(Oc2cccc(NS(=O)(=O)CCCF)c2Cl)ccc2ncn(C)c(=O)c12] | 8.55 | |
| 80 | 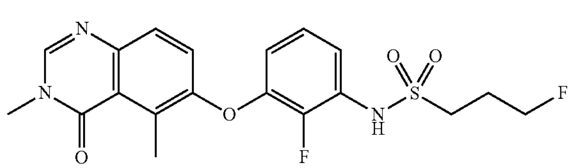 [SMILES: Cc1c(Oc2cccc(NS(=O)(=O)CCCF)c2F)ccc2ncn(C)c(=O)c12] | 20.75 | |

Example B

MDR1 LLC-PK1 and BCRP MDCKII Permeability Assay

Both LLC-PK1 and MDR1 transfected LLC-PK1 cells were cultured and plated according to manufacturer's recommendations with the exception that the passage media contained only 2% fetal bovine serum to extend passage time out to seven days.

BCRP transfected MDCKII cells were cultured and plated according to manufacturer's recommendations. Assay conditions included with and without the BCRP-specific inhibitor, K0143, at a concentration of 0.3 µM to ascertain the contribution of BCRP to the efflux value of the test compound.

Both positive and negative controls were used to assess functionality of P-gp or BCRP efflux in the assays. Stock solutions for assay controls and the test article were prepared in DMSO for final test concentrations of 10 and 1 µM, respectively. Final organic concentration in the assay was 1%. All dosing solutions contained 10 µM lucifer yellow to monitor LLC-PK1 or MDCKII cell monolayer integrity.

For the apical to basolateral determination (A to B), 75 µL of the test article in transport buffer were added to the apical side of the individual transwells and 250 µL of basolateral media, without compound or lucifer yellow, were added to each well. For the basolateral to apical determination (B to A), 250 µL of test article in transport buffer were added to each well and 75 µL transport buffer, without compound or lucifer yellow, were added to each transwell. All tests were performed in triplicate, and each compound was tested for both apical to basolateral and basolateral to apical transport. The plates were incubated for 2 hours on a Lab-Line Instruments Titer Orbital Shaker (VWR, West Chester, Pa.) at 50 rpm and 37° C. with 5% $CO_2$. All culture plates were removed from the incubator and 50 µL of media were removed from the apical and basolateral portion of each well and added to 150 µL of 1 µM labetalol in 2:1 acetonitrile (acetonitrile): $H_2O$, v/v.

The plates were read using a Molecular Devices (Sunnyvale, Calif.) Gemini Fluorometer to evaluate the lucifer yellow concentrations at excitation/emission wavelengths of 425/535 nm. These values were accepted when found to be below 2% for apical to basolateral and 5% basolateral to apical flux across the MDR1-transfected LLC-PK1 or BCRP-transfected MDCKII cell monolayers. The plates were sealed and the contents of each well analyzed by LC-MS/MS. The compound concentrations were determined from the ratio of the peak areas of the compound to the internal standard (labetalol) in comparison to the dosing solution.

LC-MS Analysis

The LC-MS/MS system was comprised of an HTS-PAL autosampler (Leap Technologies, Carrboro, N.C.), an HP1200 HPLC (Agilent, Palo Alto, Calif.), and a MDS Sciex 4000 Q Trap system (Applied Biosystems, Foster City, Calif.). Chromatographic separation of the analyte and internal standard was achieved at room temperature using a C18 column (Kinetics®, 50×300 mm, 2.6 µm particle size, Phenomenex, Torrance, Calif.) in conjunction with gradient conditions using mobile phases A (water containing 1% isopropyl alcohol and 0.1% formic acid) and B (0.1% formic acid in acetonitrile). The total run time, including re-equilibration, for a single injection was 1.2 minutes. Mass spectrometric detection of the analytes was accomplished using the ion spray positive mode. Analyte responses were measured by multiple reaction monitoring (MRM) of transitions unique to each compound (the protonated precursor ion and selected product ions for each test article and m/z 329 to m/z-162 for labetalol, the internal standard).

The permeability coefficient ($P_{app}$) is calculated from the following equation:

$$P_{app} = [((C_d * V * (1 \times 10^6))/(t * 0.12\ cm^2 * C)]$$

where $C_d$, V, t and $C_0$ are the detected concentration (µM), the volume on the dosing side (mL); the incubation time (s) and the initial dosing concentration (µM), respectively. The calculations for $P_{app}$ were made for each replicate and then averaged. Permeability coefficients for compounds of Formula I are provided in Table B1. In this assay, a compound is defined has having high permeability if the permeability is greater than $8 \times 10^{-6}$ cm/sec, a compound is defined has having medium permeability if the permeability is from $2 \times 10^{-6}$ cm/sec to $8 \times 10^{-6}$ cm/sec, and a compound is defined has having low permeability if the permeability is less than $2 \times 10^{-6}$ cm/sec.

TABLE B1

| Ex. # | Structure | Permeability ($*10^{-6}$ cm/s) |
|---|---|---|
| 1 | 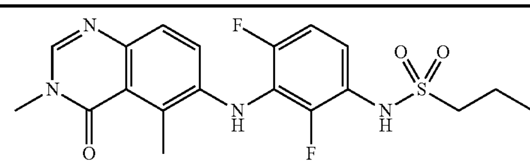 | 34.86 |
| 2 | 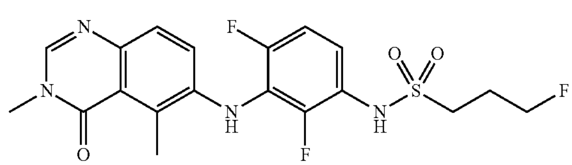 [SMILES: Cc1c(Nc2c(F)ccc(NS(=O)(=O)CCCF)c2F)ccc2ncn(C)c(=O)c12] | 30.11 |
| 3 | 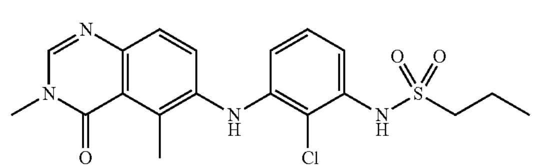 [SMILES: CCCS(=O)(=O)Nc1cccc(Nc2ccc3ncn(C)c(=O)c3c2C)c1Cl] | 25.82 |

TABLE B1-continued

| Ex. # | Structure | Permeability (*10⁻⁶ cm/s) |
|---|---|---|
| 4 | 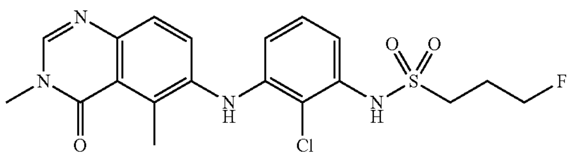 [SMILES: Cc1c(Nc2cccc(NS(=O)(=O)CCCF)c2Cl)ccc2ncn(C)c(=O)c12] | 34.55 |
| 5 | 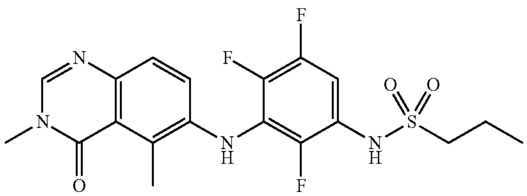 [SMILES: CCCS(=O)(=O)Nc1cc(F)c(F)c(Nc2ccc3ncn(C)c(=O)c3c2C)c1F] | 26.73 |
| 6 | 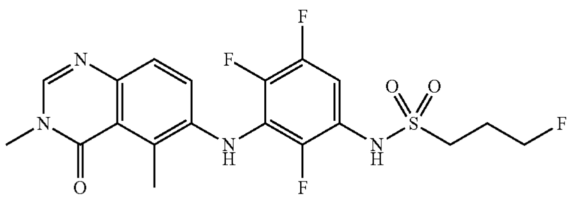 [SMILES: Cc1c(Nc2c(F)c(F)cc(NS(=O)(=O)CCCF)c2F)ccc2ncn(C)c(=O)c12] | 22.25 |
| 7 | 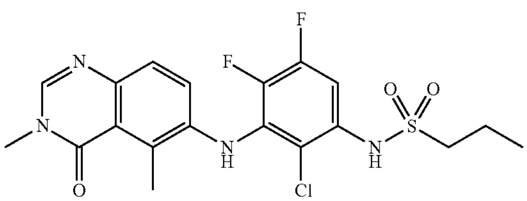 | 26.28 |
| 8 | 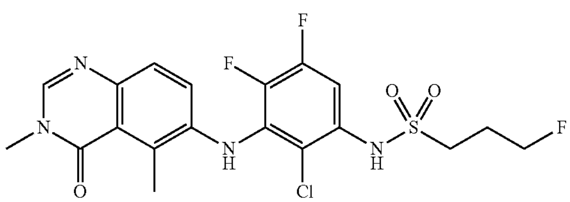 | 27.48 |
| 9 | 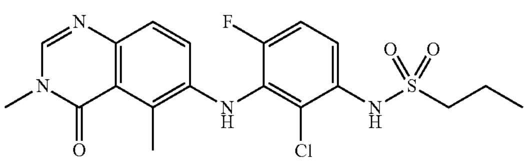 [SMILES: CCCS(=O)(=O)Nc1ccc(F)c(Nc2ccc3ncn(C)c(=O)c3c2C)c1Cl] | 27.83 |
| 10 | 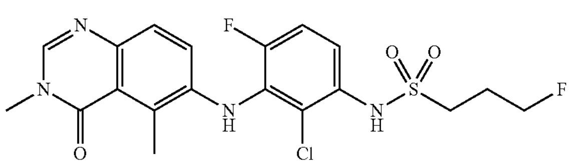 [SMILES: Cc1c(Nc2c(F)ccc(NS(=O)(=O)CCCF)c2Cl)ccc2ncn(C)c(=O)c12] | 41.05 |
| 11 | 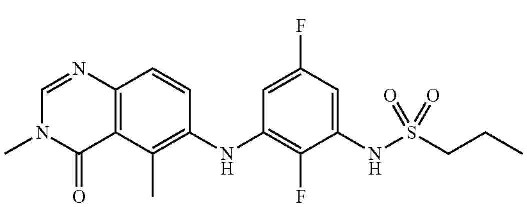 [SMILES: CCCS(=O)(=O)Nc1cc(F)cc(Nc2ccc3ncn(C)c(=O)c3c2C)c1F] | 28.64 |

TABLE B1-continued

| Ex. # | Structure | Permeability (*10⁻⁶ cm/s) |
|---|---|---|
| 12 | 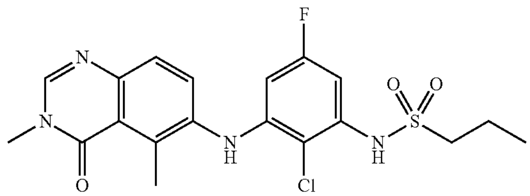 | 26.97 |
| 13 | 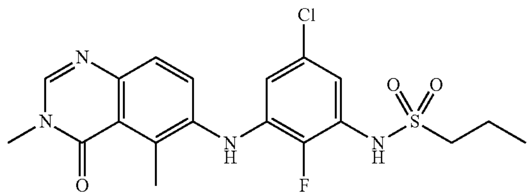 [SMILES: CCCS(=O)(=O)Nc1cc(Cl)cc(Nc2ccc3ncn(C)c(=O)c3c2C)c1F] | 24.3 |
| 14 | 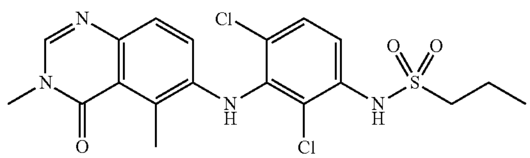 | 26.48 |
| 15 | 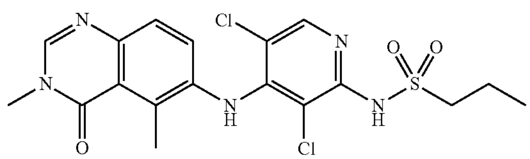 | 24.09 |
| 16 | 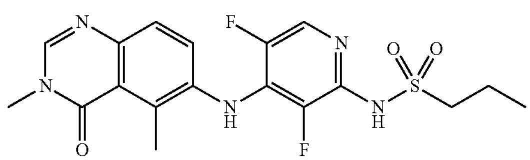 [SMILES: CCCS(=O)(=O)Nc1ncc(F)c(Nc2ccc3ncn(C)c(=O)c3c2C)c1F] | 21.29 |
| 17 | 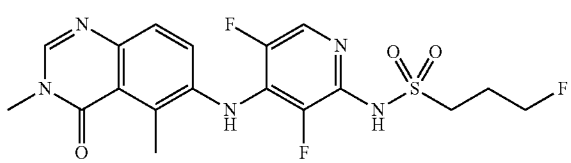 [SMILES: Cc1c(Nc2c(F)cnc(NS(=O)(=O)CCCF)c2F)ccc2ncn(C)c(=O)c12] | 6.65 |
| 18 | 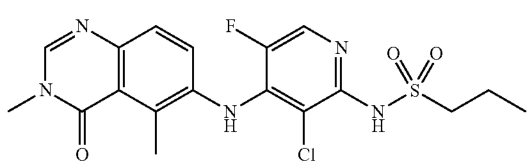 [SMILES: CCCS(=O)(=O)Nc1ncc(F)c(Nc2ccc3ncn(C)c(=O)c3c2C)c1Cl] | 27.89 |
| 19 | 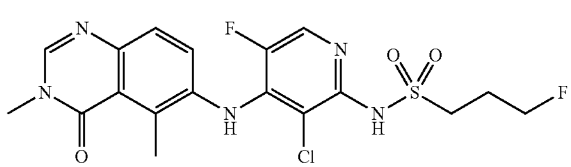 [SMILES: Cc1c(Nc2c(F)cnc(NS(=O)(=O)CCCF)c2Cl)ccc2ncn(C)c(=O)c12] | 15.93 |
| 20 | 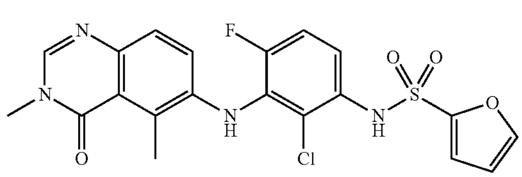 [SMILES: Cc1c(Nc2c(F)ccc(NS(=O)(=O)c3ccco3)c2Cl)ccc2ncn(C)c(=O)c12] | 32.9 |

TABLE B1-continued
| Ex. # | Structure | Permeability (*$10^{-6}$ cm/s) |
|---|---|---|
| 21 | 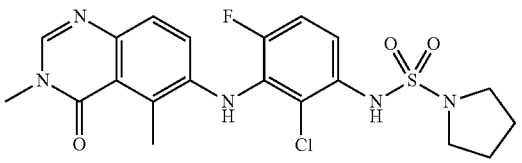 [SMILES: Cc1c(Nc2c(F)ccc(NS(=O)(=O)N3CCCC3)c2Cl)ccc2ncn(C)c(=O)c12] | 19.24 |
| 22 | 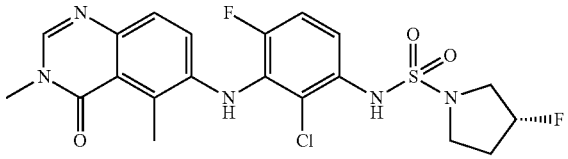 [SMILES: Cc1c(Nc2c(F)ccc(NS(=O)(=O)N3CC[C@@H](F)C3)c2Cl)ccc2ncn(C)c(=O)c12] | 34.31 |
| 23 | 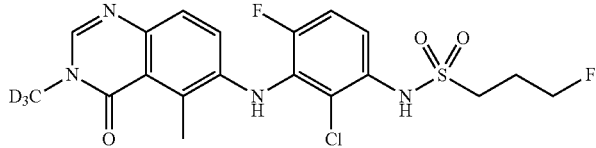 [SMILES: [2H]C([2H])([2H])n1cnc2ccc(Nc3c(F)ccc(NS(=O)(=O)CCCF)c3Cl)c(C)c2c1=O] | 39.52 |
| 24 | 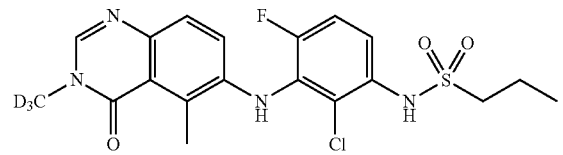 | 25.6 |
| 25 | 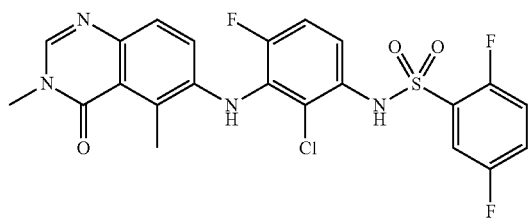 [SMILES: Cc1c(Nc2c(F)ccc(NS(=O)(=O)c3cc(F)ccc3F)c2Cl)ccc2ncn(C)c(=O)c12] | 22.07 |
| 26 | 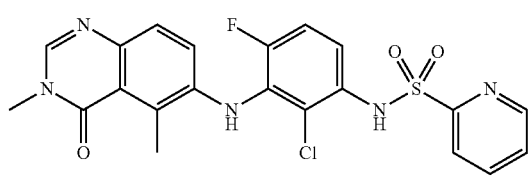 [SMILES: Cc1c(Nc2c(F)ccc(NS(=O)(=O)c3ccccn3)c2Cl)ccc2ncn(C)c(=O)c12] | 30.16 |
| 27 | 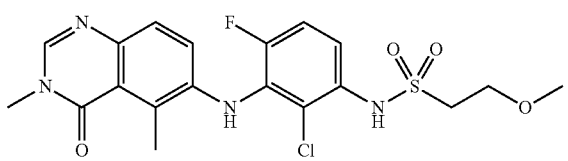 | 34.5 |
| 28 | 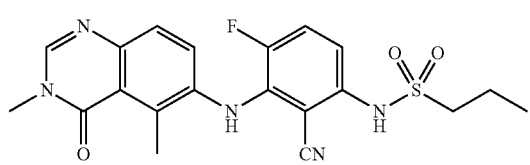 [SMILES: CCCS(=O)(=O)Nc1ccc(F)c(Nc2ccc3ncn(C)c(=O)c3c2C)c1C#N] | 26.82 |
| 29 | 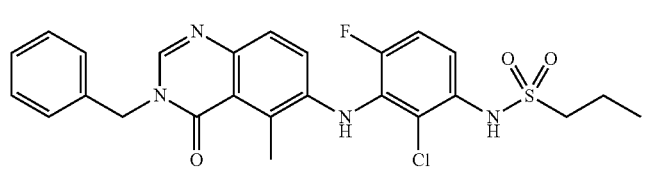 [SMILES: CCCS(=O)(=O)Nc1ccc(F)c(Nc2ccc3ncn(Cc4ccccc4)c(=O)c3c2C)c1Cl] | 11.97 |

TABLE B1-continued

| Ex. # | Structure | Permeability (*10⁻⁶ cm/s) |
|---|---|---|
| 30 | 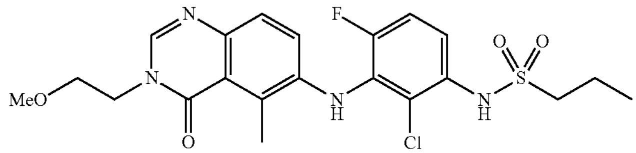 [SMILES: CCCS(=O)(=O)Nc1ccc(F)c(Nc2ccc3ncn(CCOC)c(=O)c3c2C)c1Cl] | 24.78 |
| 31 | 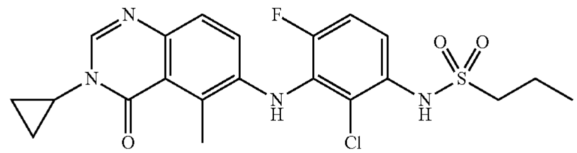 [SMILES: CCCS(=O)(=O)Nc1ccc(F)c(Nc2ccc3ncn(C4CC4)c(=O)c3c2C)c1Cl] | 24.52 |
| 32 | 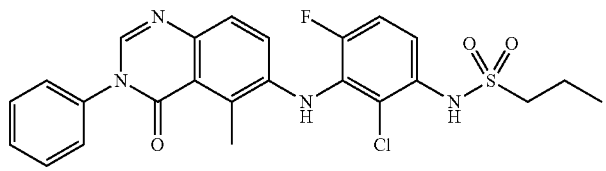 [SMILES: CCCS(=O)(=O)Nc1ccc(F)c(Nc2ccc3ncn(-c4ccccc4)c(=O)c3c2C)c1Cl] | 15.63 |
| 33 | 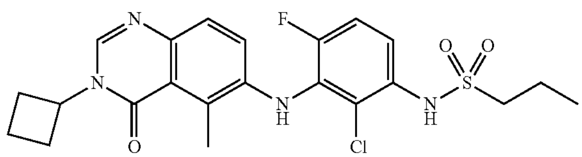 [SMILES: CCCS(=O)(=O)Nc1ccc(F)c(Nc2ccc3ncn(C4CCC4)c(=O)c3c2C)c1Cl] | 21.94 |
| 34 | 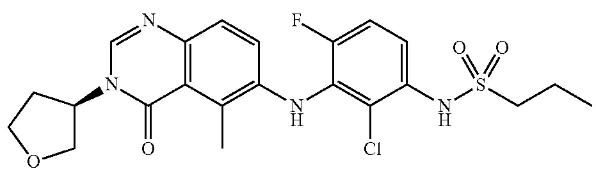 [SMILES: CCCS(=O)(=O)Nc1ccc(F)c(Nc2ccc3ncn([C@@H]4CCOC4)c(=O)c3c2C)c1Cl] | 27.67 |
| 35 | 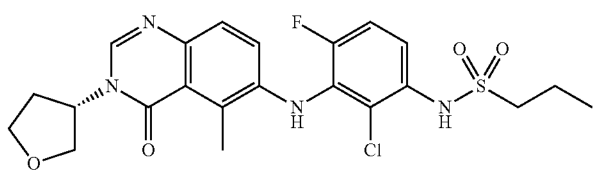 [SMILES: CCCS(=O)(=O)Nc1ccc(F)c(Nc2ccc3ncn([C@H]4CCOC4)c(=O)c3c2C)c1Cl] | 29.45 |
| 36 | 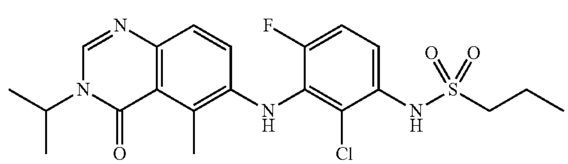 [SMILES: CCCS(=O)(=O)Nc1ccc(F)c(Nc2ccc3ncn(C(C)C)c(=O)c3c2C)c1Cl] | N/A |
| 37 | 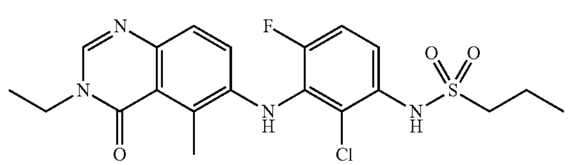 [SMILES: CCCS(=O)(=O)Nc1ccc(F)c(Nc2ccc3ncn(CC)c(=O)c3c2C)c1Cl] | 29.91 |
| 38 | 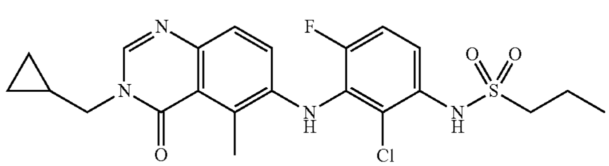 [SMILES: CCCS(=O)(=O)Nc1ccc(F)c(Nc2ccc3ncn(CC4CC4)c(=O)c3c2C)c1Cl] | 20.63 |

TABLE B1-continued

| Ex. # | Structure | Permeability (*10$^{-6}$ cm/s) |
|---|---|---|
| 39 | 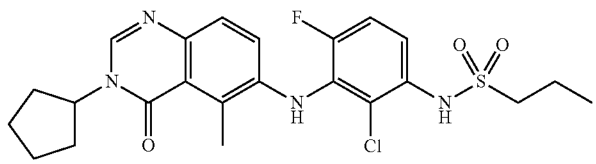 [SMILES: CCCS(=O)(=O)Nc1ccc(F)c(Nc2ccc3ncn(C4CCCC4)c(=O)c3c2C)c1Cl] | 14.16 |
| 40 | 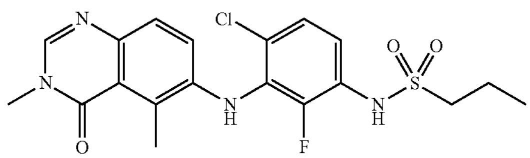 [SMILES: CCCS(=O)(=O)Nc1ccc(Cl)c(Nc2ccc3ncn(C)c(=O)c3c2C)c1F] | 28.73 |
| 41 | 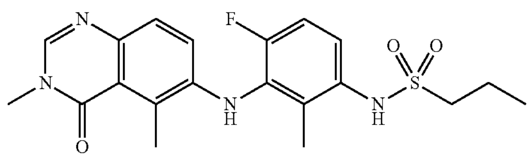 [SMILES: CCCS(=O)(=O)Nc1ccc(F)c(Nc2ccc3ncn(C)c(=O)c3c2C)c1C] | 29.79 |
| 42 | 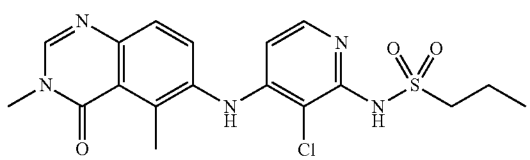 [SMILES: CCCS(=O)(=O)Nc1nccc(Nc2ccc3ncn(C)c(=O)c3c2C)c1Cl] | 18.35 |
| 43 | 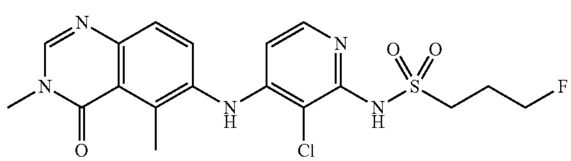 | 8.75 |
| 44 | 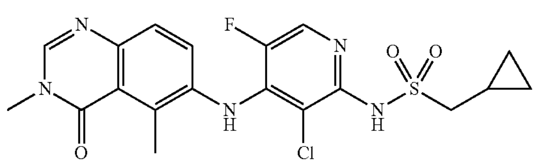 | 24.2 |
| 45 | 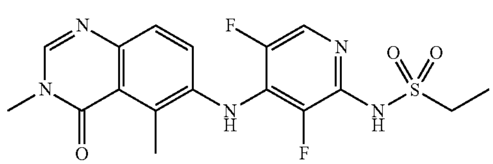 [SMILES: CCS(=O)(=O)Nc1ncc(F)c(Nc2ccc3ncn(C)c(=O)c3c2C)c1F] | 16.56 |
| 46 | 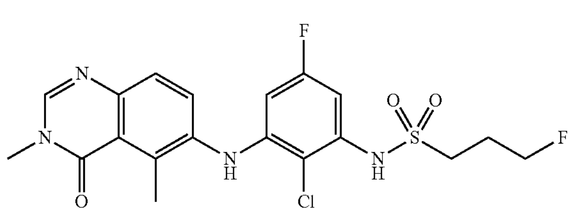 [SMILES: Cc1c(Nc2cc(F)cc(NS(=O)(=O)CCCF)c2Cl)ccc2ncn(C)c(=O)c12] | 30.74 |
| 47 | 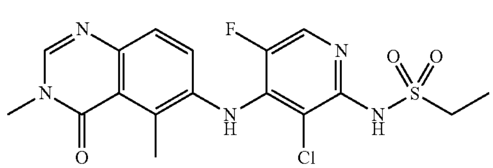 [SMILES: CCS(=O)(=O)Nc1ncc(F)c(Nc2ccc3ncn(C)c(=O)c3c2C)c1Cl] | 25.7 |

TABLE B1-continued

| Ex. # | Structure | Permeability (*10⁻⁶ cm/s) |
|---|---|---|
| 48 | (structure) | 25.83 |
| 49 | (structure) | 30.68 |
| 50 | (structure) | 21.88 |
| 51 | (structure) | 27.16 |
| 52 | (structure) | 28.91 |
| 53 | (structure) | 27.13 |
| 54 | (structure) | 35.81 |
| 55 | (structure) | 23.84 |
| 55 | (structure) | 25.46 |

TABLE B1-continued

| Ex. # | Structure | Permeability (*10⁻⁶ cm/s) |
|---|---|---|
| 56 | 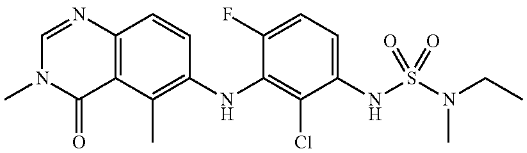 [SMILES: CCN(C)S(=O)(=O)Nc1ccc(F)c(Nc2ccc3ncn(C)c(=O)c3c2C)c1Cl] | N/A |
| 58 | 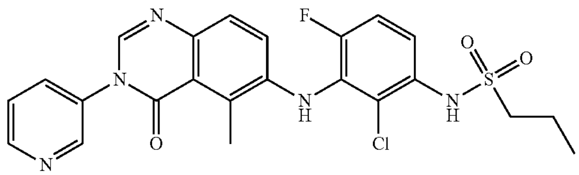 [SMILES: CCCS(=O)(=O)Nc1ccc(F)c(Nc2ccc3ncn(-c4cccnc4)c(=O)c3c2C)c1Cl] | 27.58 |
| 59 | 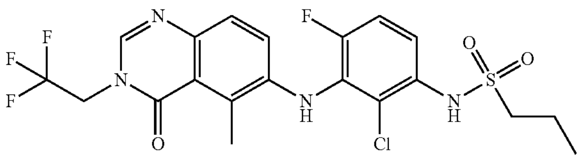 [SMILES: CCCS(=O)(=O)Nc1ccc(F)c(Nc2ccc3ncn(CC(F)(F)F)c(=O)c3c2C)c1Cl] | 25.1 |
| 60 | 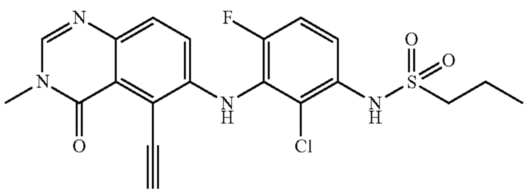 [SMILES: C#Cc1c(Nc2c(F)ccc(NS(=O)(=O)CCC)c2Cl)ccc2ncn(C)c(=O)c12] | 28.99 |
| 61 | 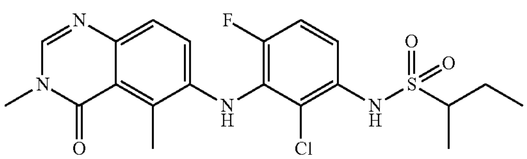 [SMILES: CCC(C)S(=O)(=O)Nc1ccc(F)c(Nc2ccc3ncn(C)c(=O)c3c2C)c1Cl] | 26.62 |
| 62 | 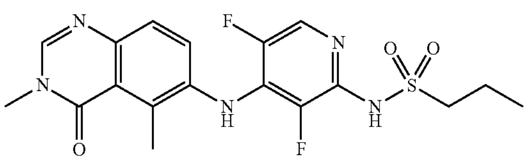 [SMILES: CCCS(=O)(=O)Nc1ncc(F)c(Nc2ccc3ncn(C)c(=O)c3c2C)c1F] | 26.34 |
| 63 | 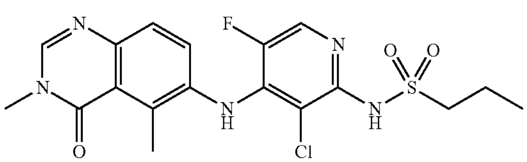 [SMILES: CCCS(=O)(=O)Nc1ncc(F)c(Nc2ccc3ncn(C)c(=O)c3c2C)c1Cl] | 26.09 |
| 64 | 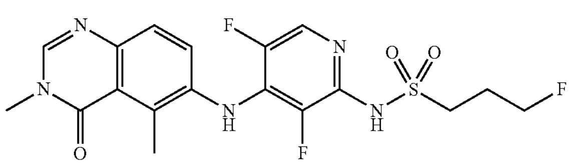 [SMILES: Cc1c(Nc2c(F)cnc(NS(=O)(=O)CCCF)c2F)ccc2ncn(C)c(=O)c12] | 9.78 |
| 65 | 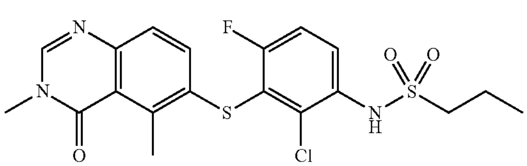 [SMILES: CCCS(=O)(=O)Nc1ccc(F)c(Sc2ccc3ncn(C)c(=O)c3c2C)c1Cl] | 176.63 |

TABLE B1-continued

| Ex. # | Structure | Permeability (*10⁻⁶ cm/s) |
|---|---|---|
| 66 | 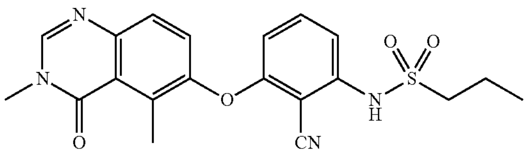 [SMILES: CCCS(=O)(=O)Nc1cccc(Oc2ccc3ncn(C)c(=O)c3c2C)c1C#N] | 23.15 |
| 67 | 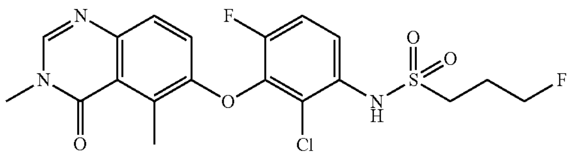 [SMILES: Cc1c(Oc2c(F)ccc(NS(=O)(=O)CCCF)c2Cl)ccc2ncn(C)c(=O)c12] | 27.55 |
| 68 | 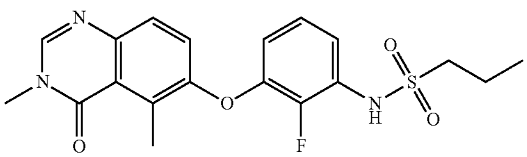 [SMILES: CCCS(=O)(=O)Nc1cccc(Oc2ccc3ncn(C)c(=O)c3c2C)c1F] | 28.47 |
| 69 | 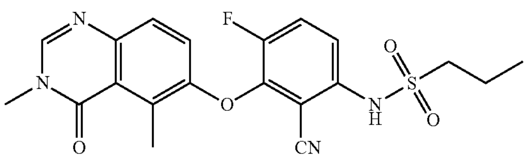 [SMILES: CCCS(=O)(=O)Nc1ccc(F)c(Oc2ccc3ncn(C)c(=O)c3c2C)c1C#N] | 24.43 |
| 70 | 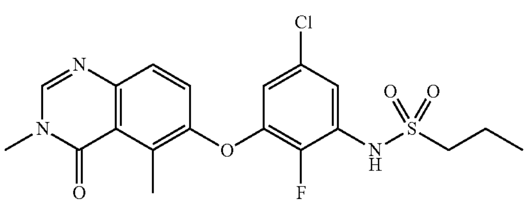 [SMILES: CCCS(=O)(=O)Nc1cc(Cl)cc(Oc2ccc3ncn(C)c(=O)c3c2C)c1F] | 19.11 |
| 71 | 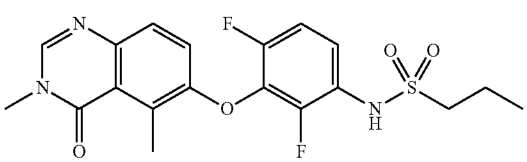 [SMILES: CCCS(=O)(=O)Nc1ccc(F)c(Oc2ccc3ncn(C)c(=O)c3c2C)c1F] | 25.09 |
| 72 | 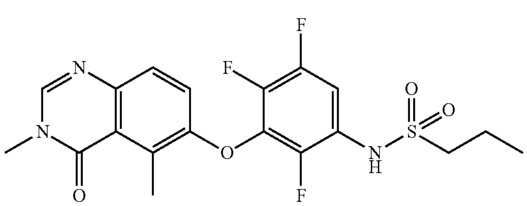 [SMILES: CCCS(=O)(=O)Nc1cc(F)c(F)c(Oc2ccc3ncn(C)c(=O)c3c2C)c1F] | 25.57 |
| 73 | 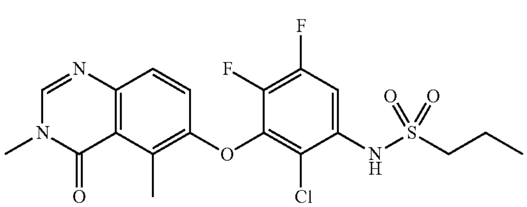 [SMILES: CCCS(=O)(=O)Nc1cc(F)c(F)c(Oc2ccc3ncn(C)c(=O)c3c2C)c1Cl] | 47.51 |

TABLE B1-continued

| Ex. # | Structure | Permeability ($*10^{-6}$ cm/s) |
|---|---|---|
| 74 | 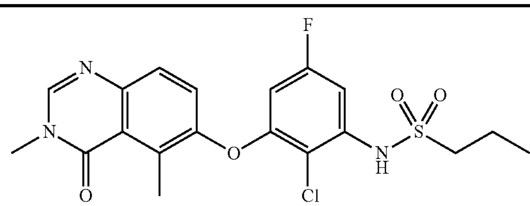 | 28.36 |
| 75 | 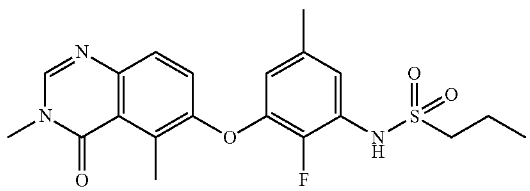 [SMILES: CCCS(=O)(=O)Nc1cc(C)cc(Oc2ccc3ncn(C)c(=O)c3c2C)c1F] | 21.51 |
| 76 | 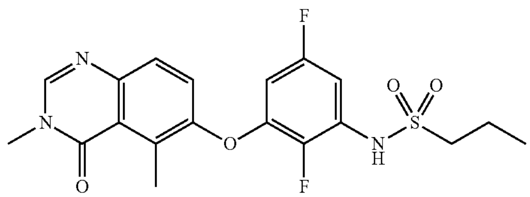 [SMILES: CCCS(=O)(=O)Nc1cc(F)cc(Oc2ccc3ncn(C)c(=O)c3c2C)c1F] | 31.8 |
| 77 | 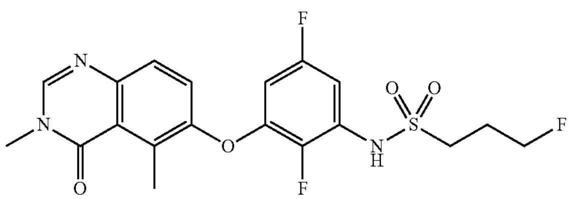 [SMILES: Cc1c(Oc2cc(F)cc(NS(=O)(=O)CCCF)c2F)ccc2ncn(C)c(=O)c12] | 25.64 |
| 78 | 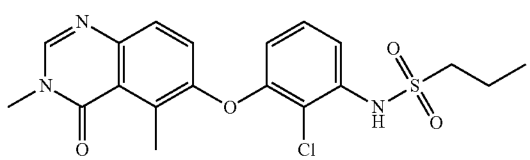 [SMILES: CCCS(=O)(=O)Nc1cccc(Oc2ccc3ncn(C)c(=O)c3c2C)c1Cl] | 29.02 |
| 79 | 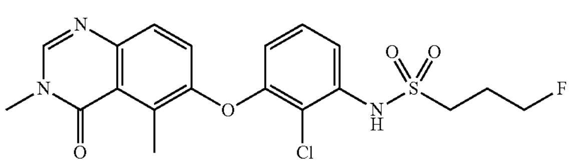 [SMILES: Cc1c(Oc2cccc(NS(=O)(=O)CCCF)c2Cl)ccc2ncn(C)c(=O)c12] | 23.12 |
| 80 | 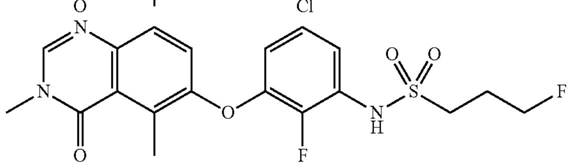 | 42.47 |

N/A: Not available

An efflux ratio is calculated from the mean apical to basolateral (A–B) $P_{app}$ data and basolateral to apical (B–A) Papp data:

Efflux ratio=$P_{app}$(B–A)/$P_{app}$(A–B)

Efflux ratios for representative compounds disclosed in WO 2012/118492, specifically the compounds of Examples 34 and 37, when tested in this assay, are shown in Table B2, and efflux ratios for compounds of Formula I (including compounds of Formula II and III) when tested in this assay are provided in Table B3. Compounds of Formula II (Examples 1, 3, 4, 7, 9, 10, 11, 12, 13, 14, 15, 21, 22, 23, 24, 25, 27, 29, 31, 32, 33, 34, 35, 36, 37, 38, 39, 44, 46, 48, 49, 50, 51, 52, 54, 55, 57, 59, 61, 65, 67, 68, 70, 71, 72, 73, 74, 75, 76, 77, 78, 79 and 80) and Formula III (Examples 1, 4, 7, 9, 10, 23, 55, 63 and 67) show a trend towards lower efflux ratios in both the MDR1 and BCRP assays compared to the representative compounds in WO 2012/118492, indicating that the compounds of Formulas II and III will have increased brain penetration compared to the representative compounds of WO 2012/118492.

TABLE B2

| Compound source | Structure | MDR1 | BCRP |
|---|---|---|---|
| WO 2012/118492 Example 34 | (structure) | 8.89 | 7.68 |
| WO 2012/118492 Ex. 37 | (structure) | 1.9 | 8.6 |

TABLE B3

| Ex. # | Structure | MDR1 | BCRP |
|---|---|---|---|
| 1 | (structure) | 1.68 | 3.4 |
| 2 | (structure) | 3.92 | 18.56 |
| 3 | (structure) | 1.37 | 0.87 |
| 4 | (structure) | 1.14 | 1.85 |
| 5 | (structure) | 2.24 | 8.33 |
| 6 | (structure) | 4.68 | 25.22 |

TABLE B3-continued

| Ex. # | Structure | MDR1 | BCRP |
|---|---|---|---|
| 7 | 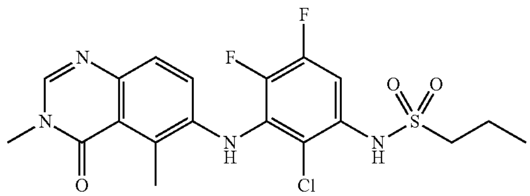 [SMILES: CCCS(=O)(=O)Nc1cc(F)c(F)c(Nc2ccc3ncn(C)c(=O)c3c2C)c1Cl] | 1.3 | 1.64 |
| 8 | 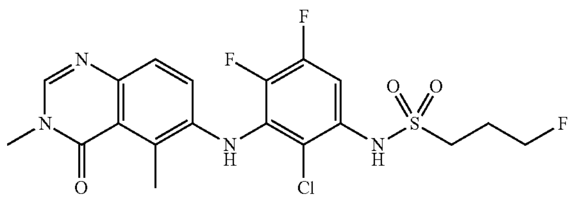 [SMILES: Cc1c(Nc2c(F)c(F)cc(NS(=O)(=O)CCCF)c2Cl)ccc2ncn(C)c(=O)c12] | 1.61 | 11.22 |
| 9 | 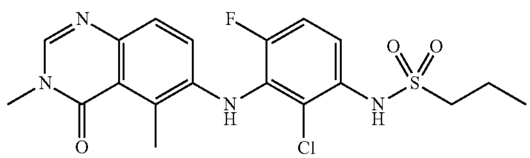 [SMILES: CCCS(=O)(=O)Nc1ccc(F)c(Nc2ccc3ncn(C)c(=O)c3c2C)c1Cl] | 1.26 | 1.23 |
| 10 | 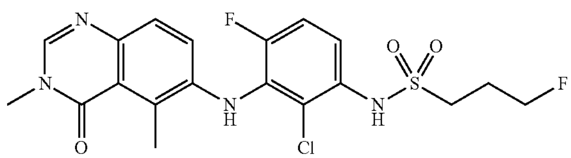 [SMILES: Cc1c(Nc2c(F)ccc(NS(=O)(=O)CCCF)c2Cl)ccc2ncn(C)c(=O)c12] | 1.15 | 4.47 |
| 11 | 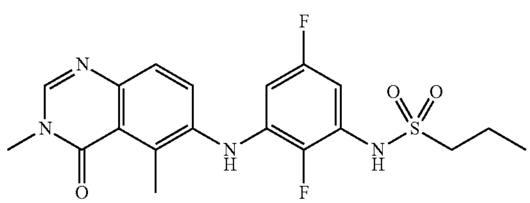 [SMILES: CCCS(=O)(=O)Nc1cc(F)cc(Nc2ccc3ncn(C)c(=O)c3c2C)c1F] | 1.65 | 2.35 |
| 12 | 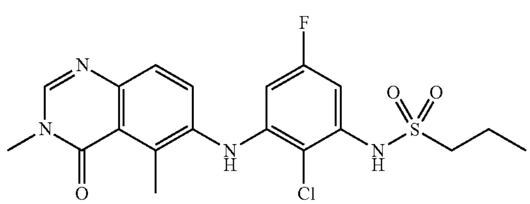 | 0.93 | 1.13 |
| 13 | 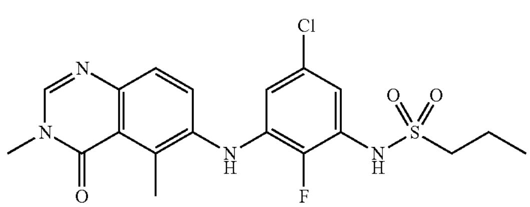 [SMILES: CCCS(=O)(=O)Nc1cc(Cl)cc(Nc2ccc3ncn(C)c(=O)c3c2C)c1F] | 1.35 | 1.51 |
| 14 | 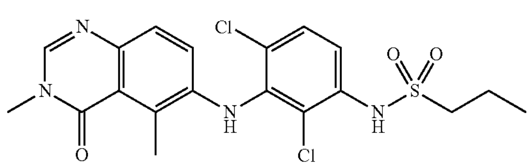 | 1.38 | 1.08 |

TABLE B3-continued

| Ex. # | Structure | MDR1 | BCRP |
|---|---|---|---|
| 15 | 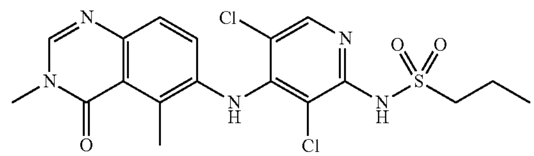 | 1.87 | 4.5 |
| 16 | 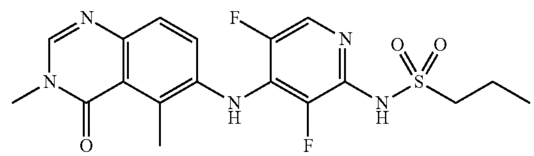 [SMILES: CCCS(=O)(=O)Nc1ncc(F)c(Nc2ccc3ncn(C)c(=O)c3c2C)c1F] | 4.76 | 20.34 |
| 17 | 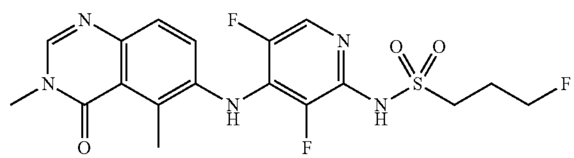 [SMILES: Cc1c(Nc2c(F)cnc(NS(=O)(=O)CCCF)c2F)ccc2ncn(C)c(=O)c12] | 5.07 | 25.3 |
| 18 | 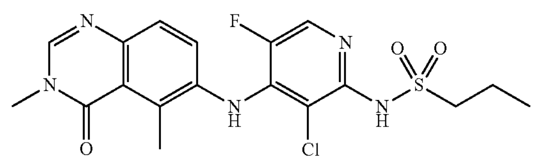 | 1.52 | 10.37 |
| 19 | 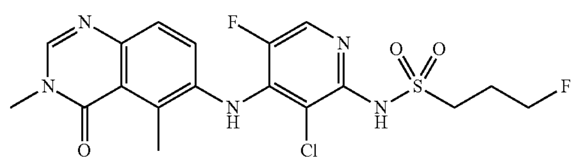 [SMILES: Cc1c(Nc2c(F)cnc(NS(=O)(=O)CCCF)c2Cl)ccc2ncn(C)c(=O)c12] | 3.24 | 21.13 |
| 20 | 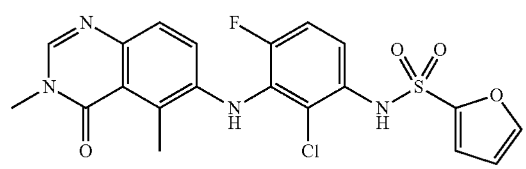 [SMILES: Cc1c(Nc2c(F)ccc(NS(=O)(=O)c3ccco3)c2Cl)ccc2ncn(C)c(=O)c12] | 1.86 | 7.43 |
| 21 | 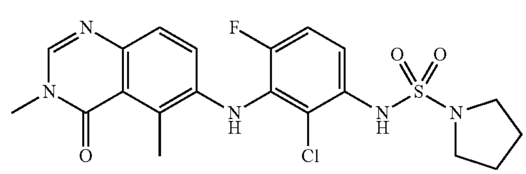 [SMILES: Cc1c(Nc2c(F)ccc(NS(=O)(=O)N3CCCC3)c2Cl)ccc2ncn(C)c(=O)c12] | 1.22 | 0.77 |
| 22 | 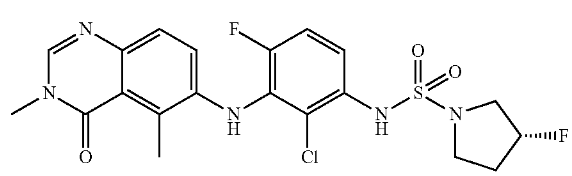 [SMILES: Cc1c(Nc2c(F)ccc(NS(=O)(=O)N3CC[C@@H](F)C3)c2Cl)ccc2ncn(C)c(=O)c12] | 1.63 | 1.49 |
| 23 | 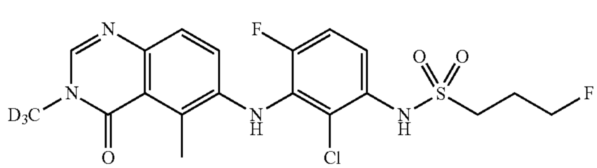 [SMILES: [2H]C([2H])([2H])n1cnc2ccc(Nc3c(F)ccc(NS(=O)(=O)CCCF)c3Cl)c(C)c2c1=O] | 1.57 | 3.49 |

TABLE B3-continued

| Ex. # | Structure | MDR1 | BCRP |
|---|---|---|---|
| 24 | 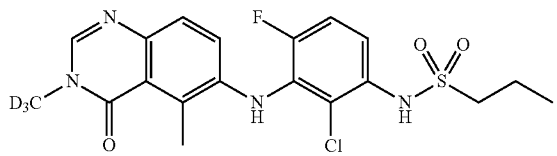 [SMILES: [2H]C([2H])([2H])n1cnc2ccc(Nc3c(F)ccc(NS(=O)(=O)CCC)c3Cl)c(C)c2c1=O] | 1.59 | 1.18 |
| 25 | 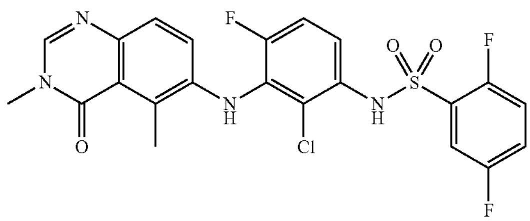 [SMILES: Cc1c(Nc2c(F)ccc(NS(=O)(=O)c3cc(F)ccc3F)c2Cl)ccc2ncn(C)c(=O)c12] | 1.82 | 1.8 |
| 26 | 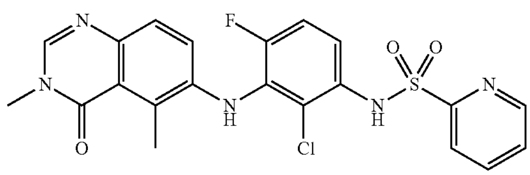 [SMILES: Cc1c(Nc2c(F)ccc(NS(=O)(=O)c3ccccn3)c2Cl)ccc2ncn(C)c(=O)c12] | 2.04 | 6.46 |
| 27 | 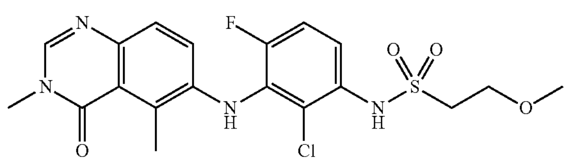 | 1.4 | 2.09 |
| 28 | 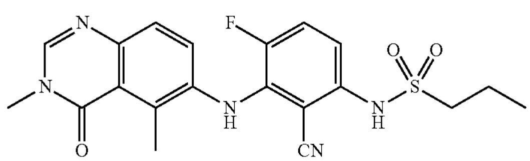 [SMILES: CCCS(=O)(=O)Nc1ccc(F)c(Nc2ccc3ncn(C)c(=O)c3c2C)c1C#N] | 6.46 | 32.97 |
| 29 | 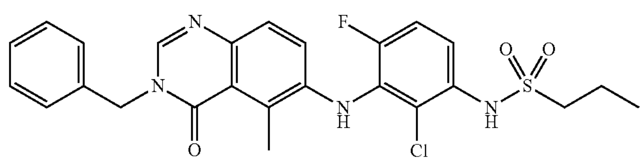 [SMILES: CCCS(=O)(=O)Nc1ccc(F)c(Nc2ccc3ncn(Cc4ccccc4)c(=O)c3c2C)c1Cl] | 1.61 | 0.87 |
| 30 | 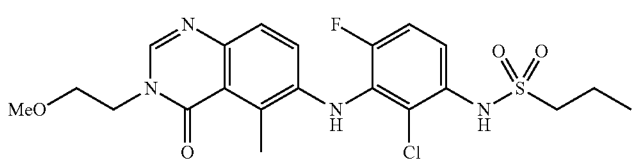 [SMILES: CCCS(=O)(=O)Nc1ccc(F)c(Nc2ccc3ncn(CCOC)c(=O)c3c2C)c1Cl] | 2.59 | 1.92 |
| 31 | 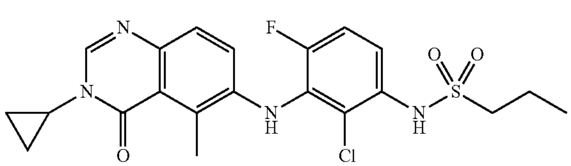 [SMILES: CCCS(=O)(=O)Nc1ccc(F)c(Nc2ccc3ncn(C4CC4)c(=O)c3c2C)c1Cl] | 1.59 | 1.64 |
| 32 | 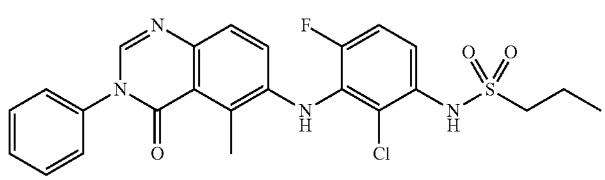 [SMILES: CCCS(=O)(=O)Nc1ccc(F)c(Nc2ccc3ncn(-c4ccccc4)c(=O)c3c2C)c1Cl] | 0.86 | 1 |

TABLE B3-continued

| Ex. # | Structure | MDR1 | BCRP |
|---|---|---|---|
| 33 | 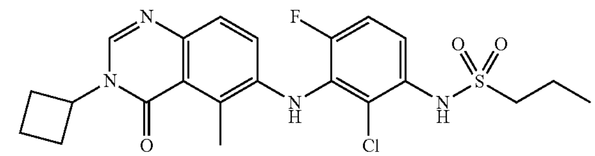 [SMILES: CCCS(=O)(=O)Nc1ccc(F)c(Nc2ccc3ncn(C4CCC4)c(=O)c3c2C)c1Cl] | 1.2 | 1.33 |
| 34 | 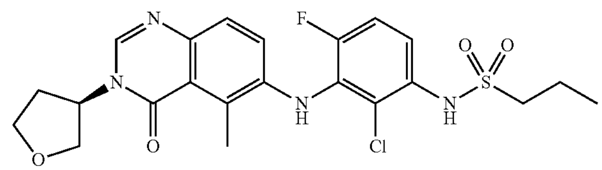 [SMILES: CCCS(=O)(=O)Nc1ccc(F)c(Nc2ccc3ncn([C@@H]4CCOC4)c(=O)c3c2C)c1Cl] | 1.81 | 2.19 |
| 35 | 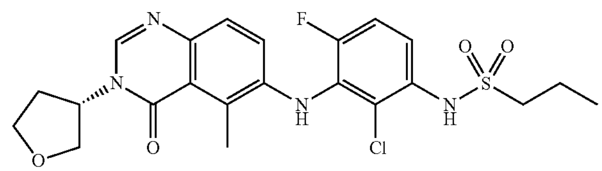 [SMILES: CCCS(=O)(=O)Nc1ccc(F)c(Nc2ccc3ncn([C@H]4CCOC4)c(=O)c3c2C)c1Cl] | 1.92 | 1.78 |
| 36 | 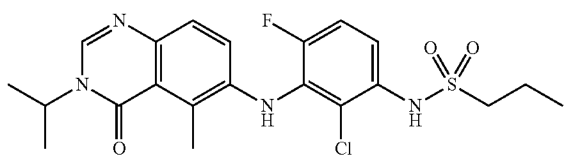 [SMILES: CCCS(=O)(=O)Nc1ccc(F)c(Nc2ccc3ncn(C(C)C)c(=O)c3c2C)c1Cl] | 1.17 | 1.22 |
| 37 | 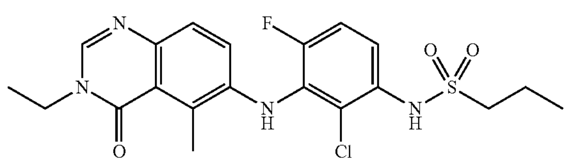 [SMILES: CCCS(=O)(=O)Nc1ccc(F)c(Nc2ccc3ncn(CC)c(=O)c3c2C)c1Cl] | 0.94 | 0.87 |
| 38 | 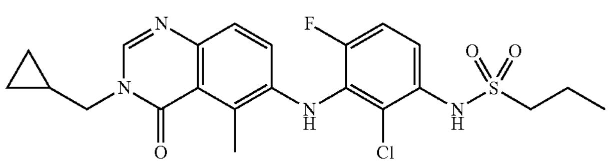 [SMILES: CCCS(=O)(=O)Nc1ccc(F)c(Nc2ccc3ncn(CC4CC4)c(=O)c3c2C)c1Cl] | 1.15 | 1.57 |
| 39 | 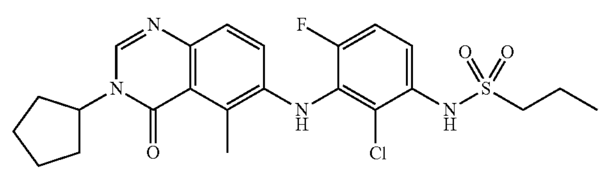 [SMILES: CCCS(=O)(=O)Nc1ccc(F)c(Nc2ccc3ncn(C4CCCC4)c(=O)c3c2C)c1Cl] | 1.29 | 1.33 |
| 40 | 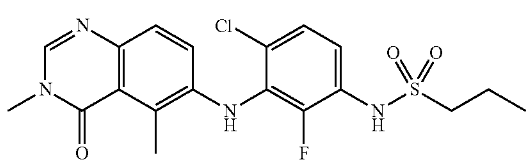 [SMILES: CCCS(=O)(=O)Nc1ccc(Cl)c(Nc2ccc3ncn(C)c(=O)c3c2C)c1F] | 2.2 | 2.87 |
| 41 | 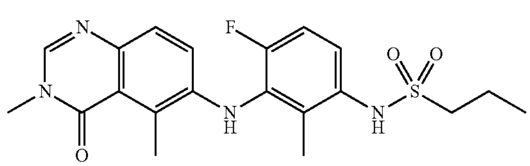 [SMILES: CCCS(=O)(=O)Nc1ccc(F)c(Nc2ccc3ncn(C)c(=O)c3c2C)c1C] | 2.79 | 3.28 |

TABLE B3-continued

| Ex. # | Structure | MDR1 | BCRP |
|---|---|---|---|
| 42 | 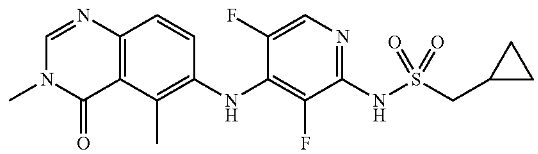 [SMILES: Cc1c(Nc2c(F)cnc(NS(=O)(=O)CC3CC3)c2F)ccc2ncn(C)c(=O)c12] | 5.26 | 23.73 |
| 43 | 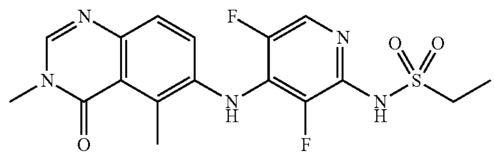 [SMILES: CCS(=O)(=O)Nc1ncc(F)c(Nc2ccc3ncn(C)c(=O)c3c2C)c1F] | 5.24 | 26.02 |
| 44 | 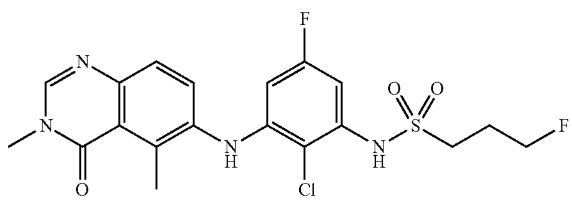 [SMILES: Cc1c(Nc2cc(F)cc(NS(=O)(=O)CCCF)c2Cl)ccc2ncn(C)c(=O)c12] | 1.05 | 2.84 |
| 45 | 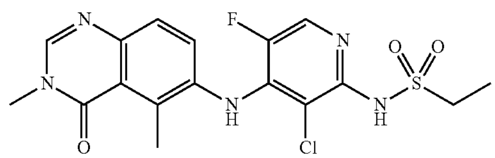 | 2.47 | 11.29 |
| 46 | 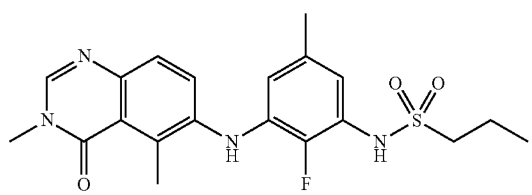 [SMILES: CCCS(=O)(=O)Nc1cc(C)cc(Nc2ccc3ncn(C)c(=O)c3c2C)c1F] | 1.43 | 1.48 |
| 47 | 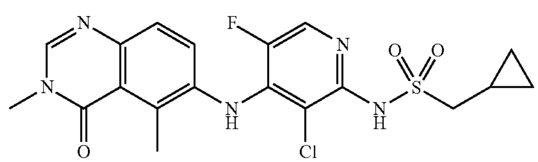 [SMILES: Cc1c(Nc2c(F)cnc(NS(=O)(=O)CC3CC3)c2Cl)ccc2ncn(C)c(=O)c12] | 1.84 | 7.93 |
| 48 | 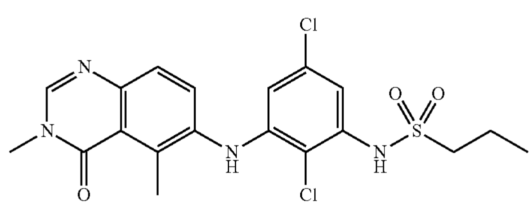 [SMILES: CCCS(=O)(=O)Nc1cc(Cl)cc(Nc2ccc3ncn(C)c(=O)c3c2C)c1Cl] | 1 | 0.9 |
| 49 | 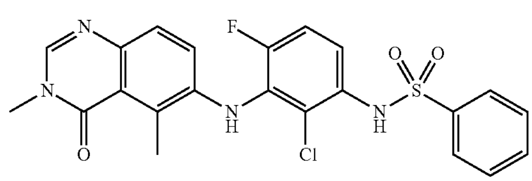 [SMILES: Cc1c(Nc2c(F)ccc(NS(=O)(=O)c3ccccc3)c2Cl)ccc2ncn(C)c(=O)c12] | 1.24 | 0.97 |
| 50 | 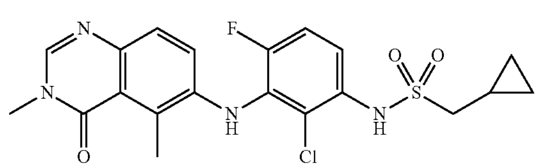 [SMILES: Cc1c(Nc2c(F)ccc(NS(=O)(=O)CC3CC3)c2Cl)ccc2ncn(C)c(=O)c12] | 1.54 | 1.13 |

TABLE B3-continued

| Ex. # | Structure | MDR1 | BCRP |
|---|---|---|---|
| 51 | 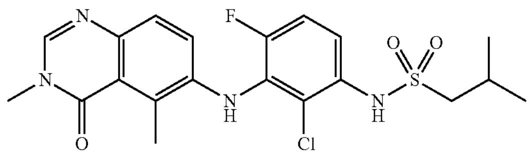 [SMILES: Cc1c(Nc2c(F)ccc(NS(=O)(=O)CC(C)C)c2Cl)ccc2ncn(C)c(=O)c12] | 1.64 | 1.28 |
| 52 | 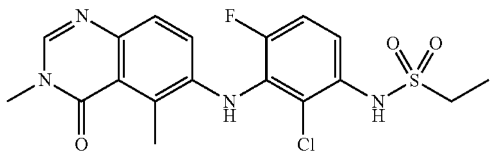 [SMILES: CCS(=O)(=O)Nc1ccc(F)c(Nc2ccc3ncn(C)c(=O)c3c2C)c1Cl] | 1.76 | 1.28 |
| 53 | 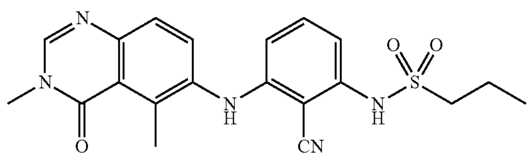 [SMILES: CCCS(=O)(=O)Nc1cccc(Nc2ccc3ncn(C)c(=O)c3c2C)c1C#N] | 2.6 | 22.97 |
| 54 | 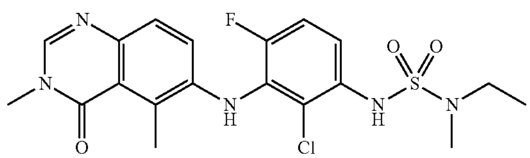 [SMILES: CCN(C)S(=O)(=O)Nc1ccc(F)c(Nc2ccc3ncn(C)c(=O)c3c2C)c1Cl] | N/A | 0.93 |
| 55 | 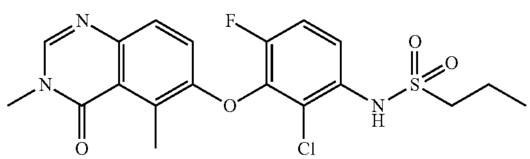 [SMILES: CCCS(=O)(=O)Nc1ccc(F)c(Oc2ccc3ncn(C)c(=O)c3c2C)c1Cl] | 1.1 | 0.83 |
| 56 | 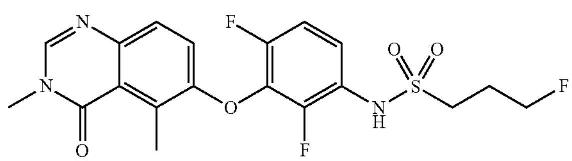 [SMILES: Cc1c(Oc2c(F)ccc(NS(=O)(=O)CCCF)c2F)ccc2ncn(C)c(=O)c12] | 2.81 | 3.14 |
| 57 | 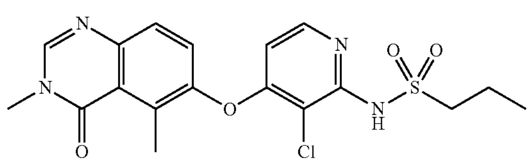 [SMILES: CCCS(=O)(=O)Nc1nccc(Oc2ccc3ncn(C)c(=O)c3c2C)c1Cl] | 0.91 | 2.08 |
| 58 | 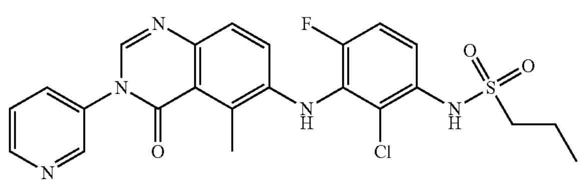 [SMILES: CCCS(=O)(=O)Nc1ccc(F)c(Nc2ccc3ncn(-c4cccnc4)c(=O)c3c2C)c1Cl] | 2.26 | 1.93 |
| 59 | 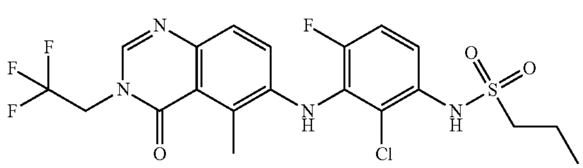 [SMILES: CCCS(=O)(=O)Nc1ccc(F)c(Nc2ccc3ncn(CC(F)(F)F)c(=O)c3c2C)c1Cl] | 1.36 | 1.08 |

TABLE B3-continued

| Ex. # | Structure | MDR1 | BCRP |
|---|---|---|---|
| 60 | 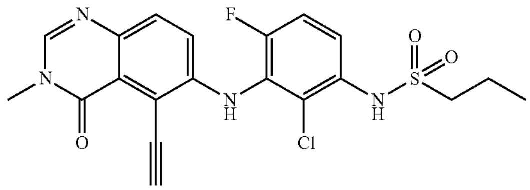 [SMILES: C#Cc1c(Nc2c(F)ccc(NS(=O)(=O)CCC)c2Cl)ccc2ncn(C)c(=O)c12] | 2.3 | 2.35 |
| 61 | 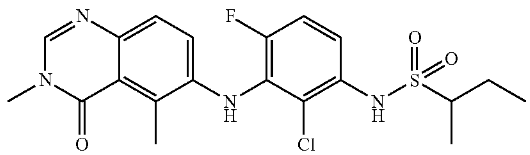 [SMILES: CCC(C)S(=O)(=O)Nc1ccc(F)c(Nc2ccc3ncn(C)c(=O)c3c2C)c1Cl] | 1.2 | 0.84 |
| 62 | 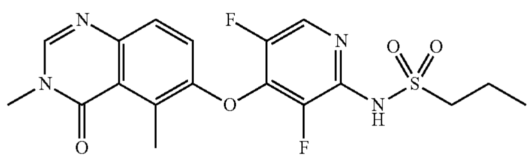 [SMILES: CCCS(=O)(=O)Nc1ncc(F)c(Oc2ccc3ncn(C)c(=O)c3c2C)c1F] | 2.3 | 22.5 |
| 63 | 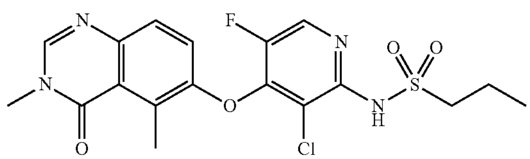 [SMILES: CCCS(=O)(=O)Nc1ncc(F)c(Oc2ccc3ncn(C)c(=O)c3c2C)c1Cl] | 1.3 | 7.7 |
| 64 | 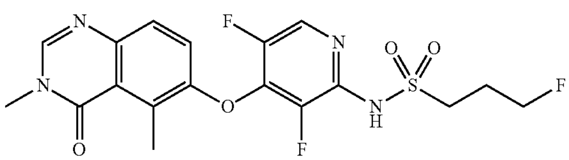 [SMILES: Cc1c(Oc2c(F)cnc(NS(=O)(=O)CCCF)c2F)ccc2ncn(C)c(=O)c12] | 10.9 | 31.0 |
| 65 | 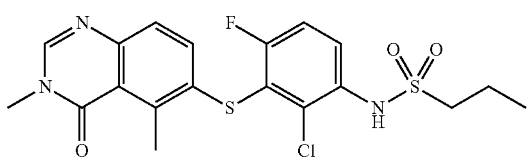 [SMILES: CCCS(=O)(=O)Nc1ccc(F)c(Sc2ccc3ncn(C)c(=O)c3c2C)c1Cl] | 1.4 | 0.9 |
| 66 | 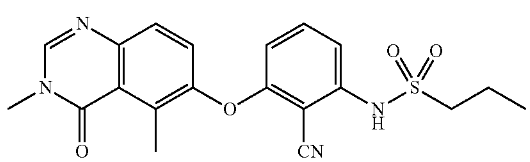 [SMILES: CCCS(=O)(=O)Nc1cccc(Oc2ccc3ncn(C)c(=O)c3c2C)c1C#N] | 1.7 | 27.9 |
| 67 | 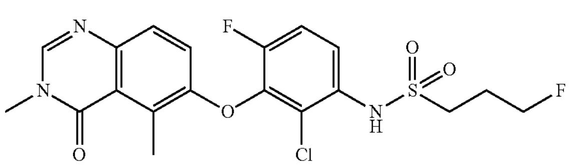 [SMILES: Cc1c(Oc2c(F)ccc(NS(=O)(=O)CCCF)c2Cl)ccc2ncn(C)c(=O)c12] | 1.8 | 1.8 |
| 68 | 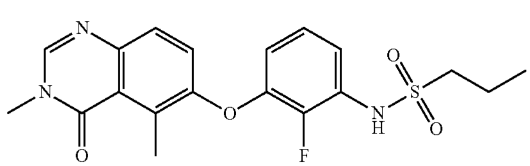 [SMILES: CCCS(=O)(=O)Nc1cccc(Oc2ccc3ncn(C)c(=O)c3c2C)c1F] | 1.2 | 1.3 |

TABLE B3-continued

| Ex. # | Structure | MDR1 | BCRP |
|---|---|---|---|
| 69 | 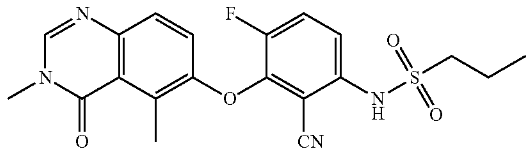 [SMILES: CCCS(=O)(=O)Nc1ccc(F)c(Oc2ccc3ncn(C)c(=O)c3c2C)c1C#N] | 4.1 | 23.8 |
| 70 | 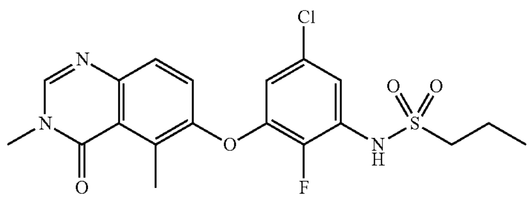 | 1.73 | 1.17 |
| 71 | 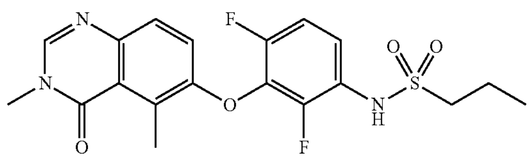 [SMILES: CCCS(=O)(=O)Nc1ccc(F)c(Oc2ccc3ncn(C)c(=O)c3c2C)c1F] | 2.4 | 0.86 |
| 72 | 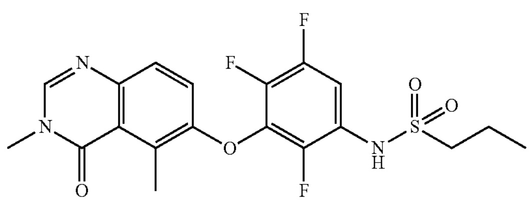 [SMILES: CCCS(=O)(=O)Nc1cc(F)c(F)c(Oc2ccc3ncn(C)c(=O)c3c2C)c1F] | 1.86 | 1.81 |
| 73 | 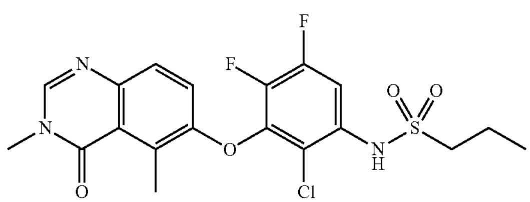 [SMILES: CCCS(=O)(=O)Nc1cc(F)c(F)c(Oc2ccc3ncn(C)c(=O)c3c2C)c1Cl] | 0.93 | 0.3 |
| 74 | 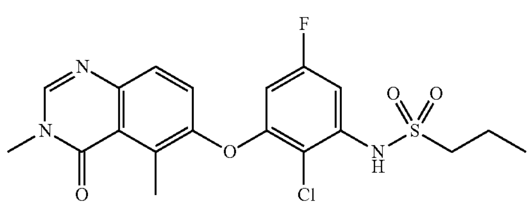 [SMILES: CCCS(=O)(=O)Nc1cc(F)cc(Oc2ccc3ncn(C)c(=O)c3c2C)c1Cl] | 1.13 | 0.92 |
| 75 | 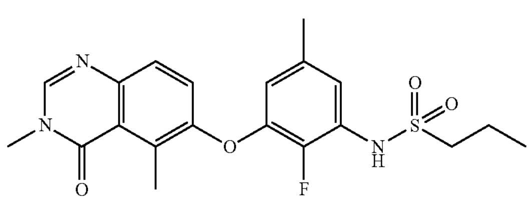 [SMILES: CCCS(=O)(=O)Nc1cc(C)cc(Oc2ccc3ncn(C)c(=O)c3c2C)c1F] | 1.57 | 0.73 |
| 76 | 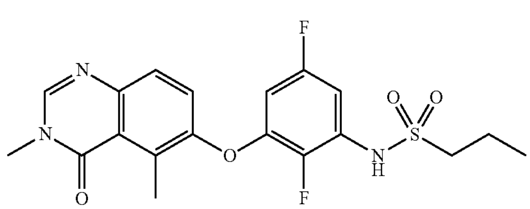 | 1.45 | 1.26 |

TABLE B3-continued

| Ex. # | Structure | MDR1 | BCRP |
|---|---|---|---|
| 77 | 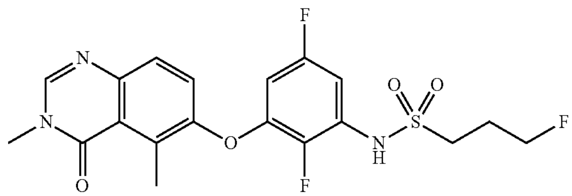 [SMILES: Cc1c(Oc2cc(F)cc(NS(=O)(=O)CCCF)c2F)ccc2ncn(C)c(=O)c12] | 1.91 | 4.24 |
| 78 | 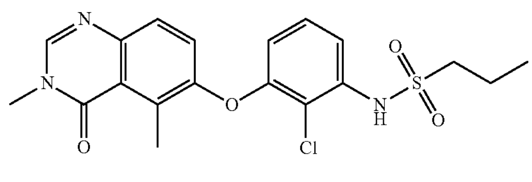 [SMILES: CCCS(=O)(=O)Nc1cccc(Oc2ccc3ncn(C)c(=O)c3c2C)c1Cl] | 1.16 | 0.96 |
| 79 | 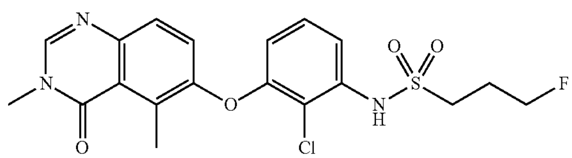 [SMILES: Cc1c(Oc2cccc(NS(=O)(=O)CCCF)c2Cl)ccc2ncn(C)c(=O)c12] | 2.14 | 1.06 |
| 80 | 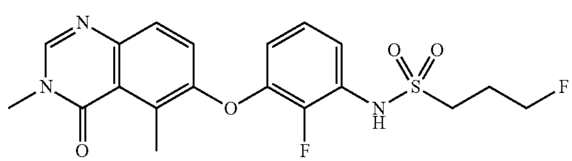 [SMILES: Cc1c(Oc2cccc(NS(=O)(=O)CCCF)c2F)ccc2ncn(C)c(=O)c12] | 1.3 | 2.03 |

N/A: Not available

Example C

PK (Free Brain-to-Free Plasma Ratio) (Mouse)

The ability of representative compounds to penetrate the BBB in mice was determined by evaluating the unbound brain-to-unbound plasma (also referred to as free brain-to-free plasma) concentration ratio in male CD-1 mice.

Brain compound levels were generated from oral mouse PK dosing with typical sampling times of 2, 4, 8, 12 and 24 hours post oral gavage dosing at 10 mg/kg. Brain samples were stored at −20±5° C. prior to analysis. Concentrations of test compound in mouse brain homogenate were determined by liquid chromatography tandem mass spectrometry (LC-MS/MS) following protein precipitation with acetonitrile. A 12-point calibration curve, ranging from 0.5 to 10,000 ng/mL, was prepared in duplicate. A solution of 400 µg/mL of test compound in dimethyl sulfoxide (DMSO) was serially diluted (3-fold) in 100% DMSO, and then 2.5 µL of each standard solution was added to 100 µL of naïve male CD-1 mice brain homogenate. To mimic the extraction in the standard curve, 2.5 µL of DMSO was added to all test samples. Both calibration and test brain homogenate samples were spiked with 10 µL of an IS (1 µg/mL of a structural analog). Brain homogenate was generated by adding 0.75 mL of 4:1 water:MeOH to each brain sample followed by homogenization for 1 minute with bead beater tubes a 6 m/s using an MP Fast Prep-24®. Proteins were precipitated from 100 µL of brain homogenate sample by the addition of 300 µL of acetonitrile. Samples were vortex-mixed for 5 minutes and spun in an Allegra X-12R centrifuge (Beckman Coulter, Fullerton, Calif.; SX4750A rotor) for 15 min at approximately 1,500×g at 4° C. A 100 µL aliquot of each supernatant was transferred via a 550 µL Personal Pipettor (Apricot Designs, Monrovia, Calif.) to 96-well plates and diluted 1:1 with HPLC grade water. The resulting plates were sealed with aluminum for LC-MS/MS analysis.

Brain-to-plasma ratios were calculated using the concentration of compound measured in the brain divided by the concentration of compound measured in the plasma. Brain-to-plasma ratios were always generated from a single animal and time point. Free brain-to-free plasma ratios were calculated by multiplying the brain-to-plasma ratio by the in vitro brain homogenate free fraction divided by the in vitro plasma free fraction using the following equation: $(B/P)*(B_{fu}/P_{fu})$.

Table C1 provides free brain-to-free plasma ratios of the compounds of Examples 34 and 37 disclosed in WO 2012/118492 when tested in the assay of Example C. Table 2 provides the free brain-to-free plasma ratios of the compounds of Examples 1, 4, 7, 9, 10, 23, 55, 63 and 67 disclosed herein. The data in Table C1 and Table C2 demonstrate the unexpected improvement in free brain-to-free plasma ratios for compounds of Examples 1, 4, 7, 9, 10, 23, 55, 63 and 67.

TABLE C1

| Compound source | Structure | B/P ratio (free) |
|---|---|---|
| WO 2012/118492 Example 34 | (structure) | 0.08-0.14 |
| WO 2012/118492 Ex. 37 | (structure) | 0.12-0.15 |

TABLE C2

| Ex. # | Structure | B/P ratio (free) |
|---|---|---|
| 1 | (structure) | 0.3-0.62 |
| 4 | (structure) | 0.35-1.60 |
| 7 | (structure) | 0.87-1.19 |
| 9 | (structure) | 0.76-1.04 |
| 10 | (structure) | 0.64-1.0 |
| 23 | (structure) | 0.44-0.59 |

TABLE C2-continued

| Ex. # | Structure | B/P ratio (free) |
|---|---|---|
| 55 | [structure] | 0.46-0.51 |
| 63 | [structure] | 0.34-0.4 |
| 67 | [structure] | 0.40-0.49 |

Example D

Intracranial A375-Luciferase Efficacy and Survival Following Treatment with N-(2-chloro-3-((3,5-dimethyl-4-oxo-3,4-dihydroquinazolin-6-yl)amino)-4-fluorophenyl)-3-fluoropropane-1-sulfonamide Form B Anhydrous (Example 82)

Female nu/nu NCr mice from Envigo (Indianapolis, Ind.) were obtained at 5-6 weeks of age and housed in groups of 5. Following a one week minimum acclimation period, mice received orthotopic (i.c.) intracranial injections of $3.0 \times 10^3$ A375-luciferase tumor cells suspended in a volume of 10 µL 0.9% sterile Dulbecco's phosphate buffered saline (DPBS) using the top-down approach (Laursen and Belknap, 1986). Seven days post cell implant (Day 1), animals were randomized and sorted into five groups (n=10/group). Mice bearing the A375-luciferase intracranial tumor xenografts were administered test compounds N-(2-chloro-3-((3,5-dimethyl-4-oxo-3,4-dihydroquinazolin-6-yl)amino)-4-fluorophenyl)-3-fluoropropane-1-sulfonamide Form B anhydrous (Example 82) and the MEK inhibitor binimetinib either as single agents or in combination.

Test compounds were given at a dose volume of 10 mL/kg, and vehicles were matched for each group to control for dosing stress, i.e. all groups received twice daily (BID) dose administration by oral gavage (PO) at the relevant dose volumes and schedule shown in Table 9. Tumor growth was monitored by measuring luciferase activity twice per week. Total flux/mouse can vary by an order of magnitude on day 1 of study start (start of dosing). The total flux was normalized per mouse by assigning the first measurement of flux on day 2 as 100%. Body weight loss as an indicator of tumor progression was determined daily during the dosing interval and then as needed (at least once weekly). Survival was evaluated through day 90 (30 days post-dosing cessation).

TABLE 9

| Group | Compound | Dose 60 days BID (mg/kg) | Route | # of Animals |
|---|---|---|---|---|
| 1 | Vehicle 1% Affinisol HPMC/0.1% SDS | 10 mL/kg | PO | 10 |
| 2 | Example 82 | 10 | PO | 10 |
| 3 | Example 82/binimetinib | 10/3.5 | PO | 10 |
| 4 | Example 82 | 30 | PO | 10 |
| 5 | Example 82/binimetinib | 30/3.5 | PO | 10 |

The doses and schedules employed in this study were well tolerated in all groups with <5% maximum body weight loss from compound administration and no deaths attributed to test article administration.

The compound of Example 82 administered as a single agent was highly effective in this model at both doses employed. Example 82 administered twice daily (BID) for 60 consecutive days by oral gavage (PO) had a significant effect on tumor growth as shown in FIG. 15.

Figure 15:
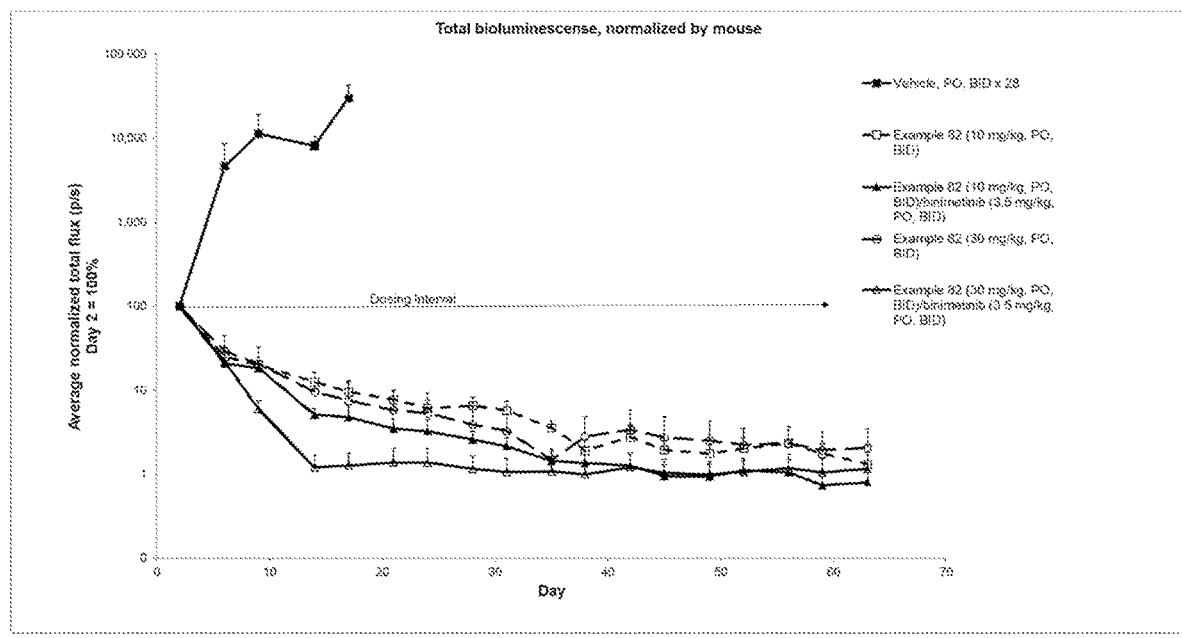
FIG. 15 is a graph showing the total bioluminescence, normalized by mouse, for days 1-60 of oral administration of the compound of Example 82 alone or in combination with binimetinib in a A375-luciferase intracranial mouse tumor model, relative to vehicle.
Figure 16:
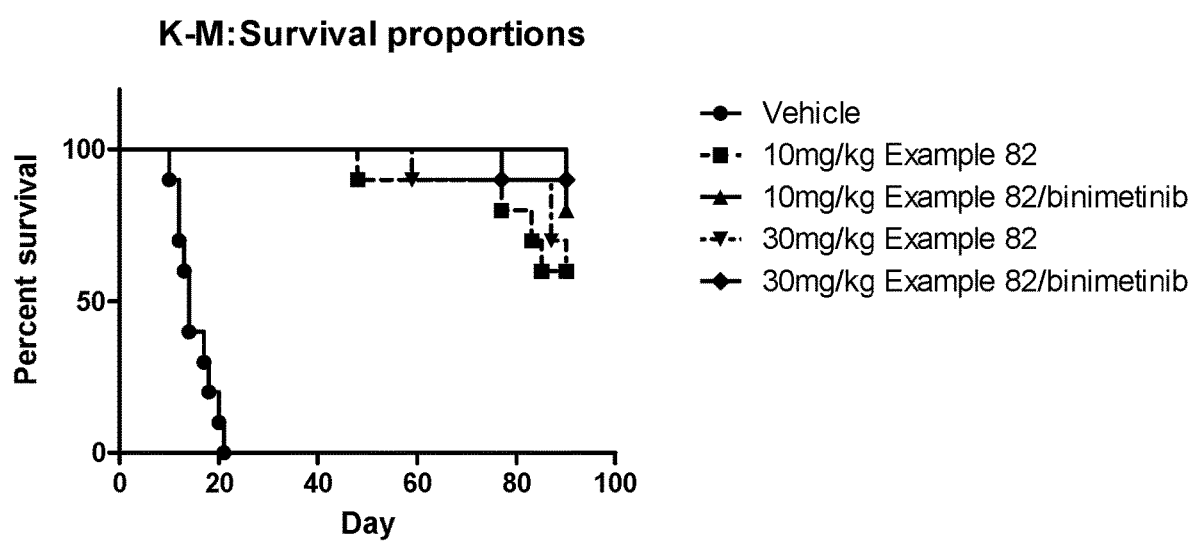
FIG. 16 is a Kaplan-Meier graph for days 1-60 of oral administration of the compound of Example 82 alone or in combination with binimetinib in a A375-luciferase intracranial mouse tumor model, relative to vehicle and for 30 days post-administration.

The compound of Example 82 and binimetinib administered in combination were significantly more effective than Example 82 alone, as shown in FIG. 15. The combination significantly increased tumor growth inhibition and improved survival in a mouse model of metastatic V600E melanoma as shown in FIG. 16 and as summarized in Table 10.

TABLE 10

| Treatment Group | Survival (# Animals on day 90) |
|---|---|
| Vehicle | 0/10 |
| Example 82 (10 mg/kg) | 6/10 |
| Example 82 (10 mg/kg) + binimetinib (3.5 mg/kg) | 8/10 |
| Example 82 (30 mg/kg) | 6/10 |
| Example 82 (30 mg/kg) + binimetinib (3.5 mg/kg) | 9/10 |

Synthetic Examples

Preparation of Synthetic Intermediates

Intermediate P1

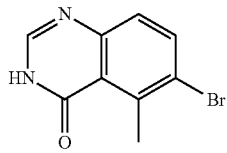

6-bromo-5-methylquinazolin-4(3H)-one

6-Amino-3-bromo-2-methylbenzoic acid (10 g, 43 mmol) and formamidine acetate (5.4 g, 52 mmol) were dissolved in ethanol (172 mL) in a 500 mL flask with a reflux condenser. The reaction mixture was heated to 80° C. for 16 hours. The mixture was cooled to ambient temperature and concentrated in vacuo. The residue was diluted with water (300 mL) and stirred vigorously for 60 minutes. The resulting solid was isolated by filtration and the filter cake was washed with water (500 mL). The solids were dried under vacuum to afford 6-bromo-5-methylquinazolin-4(3H)-one (6.9 g, 66%) as a white solid. MS (apci, m/z)=239.0, 241.0 (M+H).

Intermediate P2

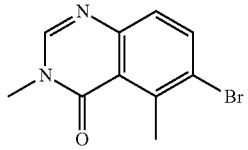

6-bromo-3,5-dimethylquinazolin-4(3H)-one

6-Bromo-5-methylquinazolin-4(3H)-one (Intermediate P1) (11 g, 46.0 mmol), potassium carbonate (14.0 g, 101 mmol) and iodomethane (13.1 g, 92.0 mmol) were dissolved in anhydrous DMF (250 mL). The reaction mixture was stirred at ambient temperature for 2 hours. The entire reaction mixture was poured directly into 900 mL water and the resulting slurry was stirred at ambient temperature for 30 minutes. The solids were collected by filtration and dried overnight under high vacuum to afford 6-bromo-3,5-dimethylquinazolin-4(3H)-one ((10.1 g, 87%) as a white solid. MS (apci, m/z)=253.0, 255.0 (M+H).

Intermediate P3

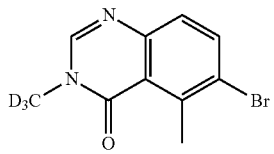

6-bromo-5-methyl-3-(methyl-d3)quinazolin-4(3H)-one

To a 50 mL flask was added 6-bromo-5-methylquinazolin-4(3H)-one (Intermediate P1) (3.37 g, 14.1 mmol), DMF (94.0 mL), potassium carbonate (4.29 g, 31.0 mmol) and iodomethane-d3 (1.75 mL, 28.2 mmol). The reaction mixture was stirred at ambient temperature for 2 hours. The reaction mixture was diluted with water and extracted with EtOAc. The organic layers were combined, dried over $Na_2SO_4$, filtered and concentrated. The crude product was purified by recrystallization from EtOAc to afford 6-bromo-5-methyl-3-(methyl-d3)quinazolin-4(3H)-one (2.94 g, 81%) as a solid. MS (apci, m/z)=256.0, 258.0 (M+H).

Intermediate P4

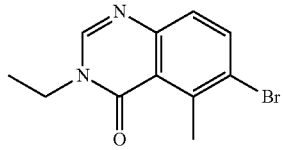

6-bromo-3-ethyl-5-methylquinazolin-4(3H)-one

To a 10 mL flask was added 6-bromo-5-methylquinazolin-4(3F)-one (Intermediate P1) (0.100 g, 0.418 mmol), iodoethane (0.101 mL, 1.25 mmol), cesium carbonate (0.204 g, 0.627 mmol) and DMF (4 mL). The flask was sealed with a rubber septum and the mixture was stirred overnight at ambient temperature. The mixture was diluted with water and ethyl acetate. The aqueous layer was extracted with EtOAc, and the combined organic extracts were washed with brine (2×), dried over $Na_2SO_4$, filtered and concentrated in vacuo. The crude material was purified by column chromatography, eluting with 30% to 70% EtOAc/hexanes to afford 6-bromo-3-ethyl-5-methylquinazolin-4(3H)-one (0.060 g, 53%) as a white solid. MS (apci, m/z)=267.0, 269.0 (M+H).

Intermediate P5

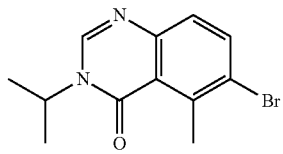 [SMILES: Cc1c(Br)ccc2ncn(C(C)C)c(=O)c12]

6-bromo-3-isopropyl-5-methylquinazolin-4(3H)-one

To a 10 mL flask was added 6-bromo-5-methylquinazolin-4(3H)-one (Intermediate P1) (0.100 g, 0.418 mmol), 2-iodopropane (0.125 mL, 1.25 mmol), cesium carbonate (0.204 g, 0.627 mmol) and DMF (4 mL). The flask was sealed with a rubber septum and the mixture was stirred overnight at ambient temperature. The mixture was diluted with water and ethyl acetate. The aqueous layer was extracted with EtOAc, and combined organic extracts were washed with brine (2×), dried over $Na_2SO_4$, filtered and concentrated in vacuo. The crude material was purified by column chromatography, eluting with 30% to 70% EtOAc/hexanes to afford 6-bromo-3-isopropyl-5-methylquinazolin-4(3H)-one (0.0716 g, 61%) as a white, solid. MS (apci, m/z),=281.0, 283.0 (M+H).

Intermediate P6

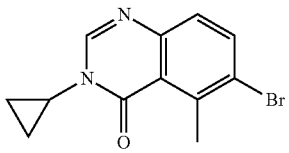 [SMILES: Cc1c(Br)ccc2ncn(C3CC3)c(=O)c12]

6-bromo-3-cyclopropyl-5-methylquinazolin-4(3H)-one

To a 10 mL flask was added cyclopropylboronic acid (0.036 g, 0.42 mmol), 6-bromo-5-methylquinazolin-4(3H)-one (Intermediate P1) (0.05 g, 0.21 mmol), cesium carbonate (0.14 g, 0.42 mmol) and dioxane (4 mL). To the suspension was added 1,10-phenanthroline (0.04 g, 0.2 mmol) and then copper(II) acetate (0.038 g, 0.21 mmol). The mixture was heated in open air at 80° C. for 40 hours and then cooled to room temperature, quenched with saturated aqueous NH₄Cl, and diluted with ethyl acetate. The aqueous layer was extracted with EtOAc (4×) and the combined organic extracts were dried over Na₂SO₄ and concentrated in vacuo. The crude material was purified by column chromatography, eluting with 30% to 70% EtOAc/hexanes to furnish 6-bromo-3-cyclopropyl-5-methylquinazolin-4(3H)-one (0.02 g, 34%) as a white solid. MS (apci, m/z)=279.0, 281.0 (M+H).

Intermediate P7

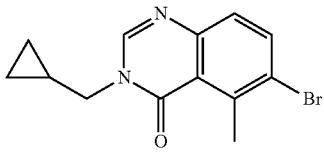 [SMILES: Cc1c(Br)ccc2ncn(CC3CC3)c(=O)c12]

6-bromo-3-(cyclopropylmethyl)-5-methylquinazolin-4(3H)-one

To a solution of 6-bromo-5-methylquinazolin-4(3H)-one (Intermediate P1) (0.100 g, 0.418 mmol) in DMF (1.67 mL) was added K₂CO₃ (0.116 g, 0.837 mmol) followed by (bromomethyl)cyclopropane (0.102 g, 0.753 mmol). The mixture was stirred for 6 hours at ambient temperature. The mixture was diluted with a saturated aqueous NH₄Cl and; extracted with EtOAc. The combined organic extracts were washed with brine and then dried over Na₂SO₄, filtered and concentrated to a solid. The crude product was purified by column chromatography, eluting with 0 to 20% EtOAc/CH₂Cl₂ to afford 6-bromo-3-(cyclopropylmethyl)-5-methylquinazolin-4(3H)-one (0.108 g, 88%) as a white solid. MS (apci, m/z)=293.0, 295.0 (M+H).

Intermediate P8

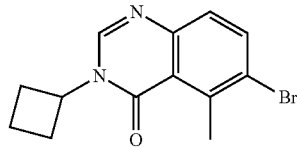 [SMILES: Cc1c(Br)ccc2ncn(C3CCC3)c(=O)c12]

6-bromo-3-cyclobutyl-5-methylquinazolin-4(3H)-one

To a 10 mL flask was added bromocyclobutane (0.118 mL, 1.26 mmol), 6-bromo-5-methylquinazolin-4(3H)-one (Intermediate P1) (0.100 g, 0.418 mmol), cesium carbonate (0.204 g, 0.627 mmol), and DMF (2.1 mL). The vessel was sealed with a rubber septum, placed under an N₂ atmosphere, stirred at ambient temperature for 17 hours and then at 70° C. for 24 hours. The mixture was cooled to room temperature, diluted with ethyl acetate, and washed with brine. The combined organic extracts were dried over Na₂SO₄, filtered and concentrated in vacuo. The crude material was purified by column chromatography, eluting with 30% to 70% EtOAc/hexanes to afford 6-bromo-3-cyclobutyl-5-methylquinazolin-4(3H)-one (0.047 g, 38%) as a white solid. MS (apci, m/z)=293.1, 295.1 (M+H).

Intermediate P9

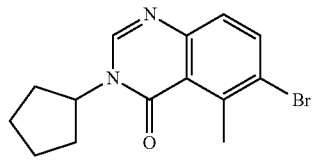 [SMILES: Cc1c(Br)ccc2ncn(C3CCCC3)c(=O)c12]

6-bromo-3-cyclopentyl-5-methylquinazolin-4(3H)-one

A round bottom flask equipped with a stir bar was charged with 6-bromo-5-methylquinazolin-4(3H)-one (Intermediate P1) (0.10 g, 0.42 mmol), dry DMA (4 mL), cesium carbonate (0.28 g, 0.84 mmol) and cyclopentyl iodide (0.12 g, 0.63 mmol). The mixture was stirred at ambient temperature for 16 hours. The mixture was diluted with water and extracted with EtOAc. The combined organic extracts were washed with brine, dried over Na₂SO₄, filtered and concentrated under reduced pressure. The crude material was purified by column chromatography, eluting with 10% to 75% EtOAc/hexanes to afford 6-bromo-3-cyclopentyl-5-methylquinazolin-4(3H)-one (0.045 g, 35%). MS (apci, m/z)=307.0, 309.0 (M+H).

Intermediate P10

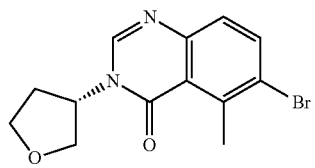 [SMILES: Cc1c(Br)ccc2ncn([C@H]3CCOC3)c(=O)c12]

(S)-6-bromo-5-methyl-3-(tetrahydrofuran-3-yl)quinazolin-4(3H)-one

A round bottom flask equipped with a stir bar and nitrogen inlet was charged with 6-bromo-5-methylquinazolin-4(3-)-one (Intermediate P1) (0.10 g, 0.418 mmol), dry DMF (4 mL), (R)-3-iodotetrahydrofuran (0.124 g, 0.627 mmol) and cesium carbonate (0.273 g, 0.837 mmol). This mixture was stirred at ambient temperature for 12 hours. After 12 hours, another 1.0 equiv. of (R)-3-iodotetrahydrofuran (0.124 g, 0.627 mmol) and 2.0 equiv. of cesium carbonate (0.273 g, 0.837 mmol) was added and the mixture was heated to 70° C. for another 24 hours. The mixture was diluted with water and extracted with EtOAc. The combined organic extracts were washed with brine, dried over $Na_2SO_4$, filtered and concentrated under reduced pressure. The crude material was purified by column chromatography, eluting with 5% to 95% EtOAc/hexanes to afford (S)-6-bromo-5-methyl-3-(tetrahydrofuran-3-yl)quinazolin-4(3H)-one (0.054 g, 41%) as a white solid. MS (apci, m/z)=309.0, 311.0 (M+H).

Intermediate P11

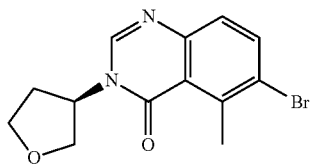 [SMILES: Cc1c(Br)ccc2ncn([C@@H]3CCOC3)c(=O)c12]

(R)-6-bromo-5-methyl-3-(tetrahydrofuran-3-yl)quinazolin-4(3H)-one

A round bottom flask equipped, with a stir bar and nitrogen inlet was charged with 6-bromo-5-methylquinazolin-4(3H)-one (Intermediate P1) (0.10 g, 0.42 mmol), dry DMF (4 mL), (S)-3-iodotetrahydrofuran (0.12 g, 0.63 mmol) and cesium carbonate (0.27 g, 0.84 mmol). This mixture was stirred at room temperature for 12 hours under a nitrogen atmosphere. After 12 hours, another 1.5 equiv. of (S)-3-iodotetrahydrofuran (0.12 g, 0.63 mmol) and 2.0 equiv. of cesium carbonate (0.27 g, 0.84 mmol) was added and the mixture was heated to 60° C. for another 24 hours. The mixture was diluted with water and extracted with EtOAc. The combined organic extracts were washed with brine, dried over $Na_2SO_4$, filtered and concentrated under reduced pressure. The crude material was purified by column chromatography, eluting with 5% to 85% EtOAc/hexanes to afford (R)-6-bromo-5-methyl-3-(tetrahydrofuran-3-yl)quinazolin-4(3H)-one (0.045 g, 35%) as a white solid. MS (apci, m/z)=309.0, 311.0 (M+H).

Intermediate P12

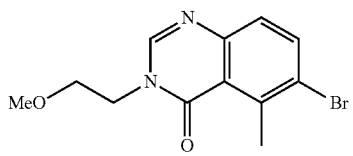 [SMILES: COCCn1cnc2ccc(Br)c(C)c2c1=O]

6-bromo-3-(2-methoxyethyl)-5-methylquinazolin-4(3H)-one

To a suspension of 6-bromo-5-methylquinazolin-4(3H)-one (Intermediate P1) (0.100 g, 0.4183 mmol) in DMF (1.67 mL) was added $K_2CO_3$ (0.1214 g, 0.8784 mmol) followed by 2-bromoethyl methyl ether (0.0786 mL, 0.8366 mmol). The mixture was stirred for 18 hours at ambient temperature. The mixture was diluted with a saturated aqueous $NH_4Cl$ and extracted with EtOAc. The combined organic extracts were washed with brine and then dried over $Na_2SO_4$, filtered and concentrated to a solid. The crude product was purified by column chromatography, eluting with 0 to 30% EtOAc/$CH_2Cl_2$ to afford 6-bromo-3-(2-methoxyethyl)-5-methylquinazolin-4(3H)-one (0.105 g, 85%) as a white solid. MS (apci, m/z)=297.0, 299.0 (M+H).

Intermediate P13

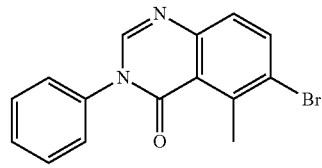 [SMILES: Cc1c(Br)ccc2ncn(-c3ccccc3)c(=O)c12]

6-bromo-5-methyl-3-phenylquinazolin-4(3H)-one

A pressure tube equipped with a stir bar was charged with 6-bromo-5-methylquinazolin-4(3H)-one (Intermediate P1) (0.050 g, 0.21 mmol), phenyl boronic acid (0.033 g, 0.27 mmol), DCM (2 mL), pyridine (0.036 g, 0.46 mmol) and copper (II) acetate (0.084 g, 0.46 mmol). The tube was capped with a rubber septum that was pierced with a needle to allow air to flow in, and the mixture was stirred at ambient temperature for 48 hours. The mixture was diluted with DCM and filtered through GF/F filter paper, and the filtrate was concentrated under reduced pressure. The crude product was purified, by column chromatography, eluting with 90% EtOAc/hexanes to afford 6-bromo-5-methyl-3-phenylquinazolin-4(3H)-one (0.020 g, 30%) as a white solid. MS (apci, m/z)=315.0, 317.0 (M+H).

Intermediate P14

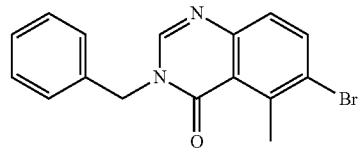 [SMILES: Cc1c(Br)ccc2ncn(Cc3ccccc3)c(=O)c12]

3-benzyl-6-bromo-5-methylquinazolin-4(3H)-one

To a solution of 6-bromo-5-methylquinazolin-4(3H)-one (Intermediate P1) (100 mg, 0.4183 mmol) in DMF (1.673 mL) was added potassium carbonate (121.4 mg, 0.8784 mmol) and benzyl bromide (74.63 µL, 0.6274 mmol) and the reaction mixture was stirred at ambient temperature for 18 hours. The mixture was diluted with a saturated aqueous $NH_4Cl$ solution and extracted with EtOAc. The combined organic extracts were washed with brine, dried over Na$_2$SO$_4$, filtered and concentrated. The crude product was purified by silica gel chromatography, eluting with 0 to 30% CH$_2$Cl$_2$/EtOAc to afford 3-benzyl-6-bromo-5-methylquinazolin-4(3H)-one (110 mg, 79%) as a white solid. MS (apci, m/z)=329.0, 331.0 (M+H).

Intermediate P15

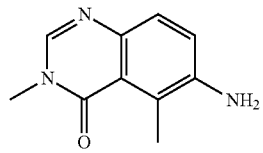

6-amino-3,5-dimethylquinazolin-4(3H)-one

Step 1: Preparation of 6-((4-methoxybenzyl)amino)-3,5-dimethylquinazolin-4(3H)-one. A solution of (4-methoxyphenyl)methanamine (1.20 mL, 9.18 mmol), 6-bromo-3,5-dimethylquinazolin-4(3H)-one (Intermediate P2) (2.02 g, 7.98 mmol), Pd$_2$(dba)$_3$ (0.364 g, 0.399 mmol), Xantphos (0.693 g, 1.20 mmol), and Cs$_2$CO$_3$ (7.80 g, 23.9 mmol) in toluene (53.2 mL) was placed in a pressure tube and sparged with argon for 10 minutes. The reaction vessel was sealed and heated to 90° C. for 60 hours. Additional Pd$_2$(dba)$_3$ (0.365 g, 0.399 mmol) and Xantphos (0.693 g, 1.20 mmol) were added and the solution was again sparged with argon for 10 minutes, sealed and heated to 90° C. for another 16 hours. The reaction mixture was cooled to ambient temperature, filtered, concentrated, and purified by column chromatography, eluting with 5 to 95% EtOAc/DCM to afford 6-((4-methoxybenzyl)amino)-3,5-dimethylquinazolin-4(3H)-one (2.4 g, 97%). MS (apci, m/z)=310.2 (M+H).

Step 2: Preparation of 6-amino-3,5-dimethylquinazolin-4(3H)-one. A solution of 6-((4-methoxybenzyl)amino)-3,5-dimethylquinazolin-4(3H)-one (2.4 g, 7.76 mmol) was stirred in 50 mL of DCM and 25 mL of TFA for 2 hours. The solution was concentrated, and the residue was dissolved in 100 mL of DCM, 10 mL of MeOH, and stirred vigorously with 4 g of K$_2$CO$_3$ for 30 minutes. The K$_2$CO$_3$ was removed by filtration and the filtrate was concentrated and the residue was purified by column chromatography, eluting with 1 to 10% MeOH/DCM (1% NH$_4$OH) to afford 6-amino-3,5-dimethylquinazolin-4(3H)-one (1.45 g, 99%). $^1$H NMR (400 MHz, CDCl$_3$) δ 8.2 (s, 1H), 7.5 (d, 1H), 7.1 (d, 1H), 4.2 (br-s, 2H), 3.6 (s, 3H), 2.8 (s, 3H); MS (apci, m/z)=190.1 (M+H).

Intermediate P16

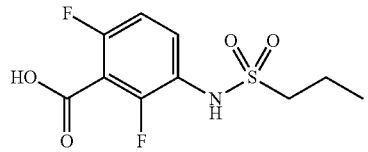

2,6-Difluoro-3-(propylsulfonamido)benzoic Acid

Step 1: Preparation of methyl 2,6-difluoro-3-nitrobenzoate. A 1 L flask was charged with 2,6-difluoro-3-nitrobenzoic acid (17.0 g, 83.7 mmol) and MeOH (170 mL). The flask was placed in an ice water bath, and an addition funnel charged with a solution of trimethylsilyl (TMS) diazomethane in hexanes (2M, 209 mL, 419 mmol) was attached to the flask. The TMS diazomethane solution was added slowly to the reaction flask over the course of 2 hours. A large excess of reagent was required for the reaction to reach completion as determined by the ceased evolution of N$_2$ upon further addition of reagent. The solution was concentrated in vacuo to afford crude methyl 2,6-difluoro-3-nitrobenzoate as a solid (18.2 g). The material was used without further purification.

Step 2: Preparation of methyl 3-amino-2,6-difluorobenzoate. To a 1 L flask charged with methyl 2,6-difluoro-3-nitrobenzoate (18.2 g, 83.8 mmol) was added 10% wt. Pd on activated carbon (4.46 g, 4.19 mmol) under a nitrogen atmosphere. To the flask was added EtOH (350 mL), and hydrogen was passed through the mixture for 15 minutes. The reaction mixture was stirred under two hydrogen balloons overnight. The balloons were recharged with H$_2$ (g) and the mixture was stirred an additional 4 hours. Upon consumption of the starting material and intermediate hydroxylamine as determined by TLC, nitrogen was flushed through the reaction mixture. The mixture was filtered through glass microfibre filter (GF/F) paper twice. The solution was concentrated to afford crude methyl 3-amino-2,6-difluorobenzoate as an oil (15.66 g). The material was used without further purification.

Step 3: Preparation of methyl 2,6-difluoro-3-(N-(propylsulfonyl)propylsulfonamido)benzoate. Propane-1-sulfonyl chloride (23.46 mL, 209.3 mmol) was slowly added to a cooled solution of methyl 3-amino-2,6-difluorobenzoate (15.66 g, 83.7 mmol) and triethylamine (35.00 mL, 251.1 mmol) in CH$_2$Cl$_2$ (175 mL). The reaction mixture was stirred for 1 hour at room temperature. Water (300 mL) was added and the organic layer was separated, washed with water (2×300 mL) and brine (200 mL), then dried (Na$_2$SO$_4$), filtered and concentrated to an oil. The crude product was purified by column chromatography, eluting with 15% EtOAc/hexanes to afford methyl 2,6-difluoro-3-(N-(propylsulfonyl)propylsulfonamido)benzoate as a solid (24.4 g, 73% for 3 steps). $^1$H NMR (400 MHz, CDCl$_3$) δ 7.52-7.45 (m, 1H), 7.08-7.02 (m, 1H), 3.97 (s, 3H), 3.68-3.59 (m, 2H), 3.53-3.45 (m, 2H), 2.02-1.89 (m, 4H), 1.10 (t, J=7.4 Hz, 6H).

Step 4: Preparation of 2,6-difluoro-3-(propylsulfonamido)benzoic acid. A 1N aqueous NaOH solution (150 mL, 150 mmol) was added to a solution of methyl 2,6-difluoro-3-(N-(propylsulfonyl)propylsulfonamido)benzoate (20.0 g, 50.1 mmol) in 4:1. THF/MeOH (250 mL). The reaction mixture was stirred at room temperature for 12 hours. The organic solvents were concentrated in vacuo to half volume (water bath temperature 35° C.). 1N HCl (150 mL) was slowly added to the mixture, and the resulting solid was filtered and rinsed with water (4×50 mL). The material was washed with Et$_2$O (4×15 mL) to give 2,6-difluoro-3-(propylsulfonamido)benzoic acid (10.7 g, 77%) as a solid. $^1$H NMR (400 MHz, (CD$_3$)$_2$SO) δ 9.74 (s, 1H), 7.57-7.50 (m, 1H), 7.23-7.17 (m, 1H), 3.11-3.06 (m, 2H), 1.79-1.69 (m, 2H), 0.98 (t, J=7.4 Hz, 3H); MS (apci, m/z)=278.0 (M−H).

Intermediate P17

2-Chloro-6-fluoro-3-(Propylsulfonamido)benzoic Acid

Step 1: Preparation of 1-(2-chloro-4-fluorophenyl)-2,5-dimethyl-1H-pyrrole. To a 20-L 4-neck round flask was added a solution of 2-chloro-4-fluorobenzenamine (1300 g, 8.82 mol) in toluene (10 L), 4-methylbenzenesulfonic acid (3.1 g, 17.84 mmol), and hexane-2,5-dione (1222.5 g, 10.62 mol). The resulting solution was heated to reflux for 1 hour, then cooled to ambient temperature. The pH of the solution was adjusted to about 8 with aqueous sodium carbonate-(1M). The resulting mixture was washed with water (5000 mL) and concentrated in vacuo. The crude product was purified by distillation at 140° C. to afford 1-(2-chloro-4-fluorophenyl)-2,5-dimethyl-1H-pyrrole (1700 g, 85%) as a solid.

Step 2: Preparation of methyl 2-chloro-3-(2,5-dimethyl-1H-pyrrol-1-yl)-6-fluorobenzoate. Into a 5000-mL 4-necked round-bottom flask, purged and maintained with an inert atmosphere of nitrogen, was placed a solution of 1-(2-chloro-4-fluorophenyl)-2,5-dimethyl-1H-pyrrole (390 g, 1.65 mol) in tetrahydrofuran (2000 mL). The reaction vessel was cooled to −78° C. A solution of n-BuLi (2.5M in hexanes, 728 mL, 1.82 mol) was added dropwise with stirring to the reaction vessel over 80 minutes, and methyl chloroformate (215.5 g, 2.27 mol) was added dropwise with stirring over 90 minutes. The reaction solution was further stirred for 60 minutes at −78° C. and quenched by the addition of NH$_4$Cl/water (1000 mL). The resulting solution was extracted with ethyl acetate (1500 mL). The organic layers were combined, washed with water (1500 mL) and aqueous sodium chloride (1500 mL), dried over anhydrous MgSO$_4$, and concentrated in vacuo to afford methyl 2-chloro-3-(2,5-dimethyl-1H-pyrrol-1-yl)-6-fluorobenzoate as an oil (crude, 566.7 g), which was used without further purification.

Step 3: Preparation of methyl 3-amino-2-chloro-6-fluorobenzoate. A solution of methyl 2-chloro-3-(2,5-dimethyl-1H-pyrrol-1-yl)-6-fluorobenzoate (1500 g, 5.05 mol) in EtOH/H$_2$O (7500/2500 mL), NH$_2$OH—HCl (5520 g, 79.20 mol), and triethylamine (2140 g, 20.98 mol) was placed into 25 L 4-neck round-bottom flasks. The resulting solution heated to reflux for 18 hours in an oil bath, cooled to room temperature, concentrated, and extracted with ethyl acetate (3×3000 mL). The organic extracts were combined, dried over anhydrous Na$_2$SO$_4$, and concentrated in vacuo. The residue was purified using a silica gel column, eluting with Et$_2$O/EtOAc (20:1 to 10:1) to afford methyl 3-amino-2-chloro-6-fluorobenzoate as an oil (980 g, 95%).

Step 4: Preparation of methyl 2-chloro-6-fluoro-3-(propylsulfonamido)benzoate. A solution of methyl 3-amino-2-chloro-6-fluorobenzoate (980 g, 4.76 mol) in dichloromethane (8000 mL) was placed into a 20 L 4-neck round-bottom flask. Triethylamine (1454 g, 14.25 mol) was added dropwise over 80 minutes to this reaction vessel with stirring at 0° C., followed by the addition of propane-1-sulfonyl chloride (1725 g, 11.94 mol). The resulting solution was stirred at room temperature for 2 hours, then diluted with water (1000 mL). The organic layer was washed with hydrogen chloride (1000 mL) and water (1000 mL), dried over Na$_2$SO$_3$, and concentrated to afford methyl 2-chloro-6-fluoro-3-(propylsulfonamido)benzoate as a solid (1500 g; 97%).

Step 5: Preparation of 2-chloro-6-fluoro-3-(propylsulfonamido)benzoic acid. A solution of methyl 2-chloro-6-fluoro-3-(propylsulfonamido)benzoate (1500 g, 4.61 mol) in THF/H$_2$O (3000 mL/3000 mL) and potassium hydroxide (1000 g, 17.68 mol) was placed into a 10 L 4-necked round-bottom flask. The resulting solution was refluxed for 2 hours, cooled to room temperature and extracted with ethyl acetate (3×2000 mL). The aqueous layers were combined, and the pH was adjusted to 2 with hydrogen chloride (2M). The resulting solution was extracted with dichloromethane (2×3000 mL). The organic layers were combined, dried over anhydrous sodium sulfate and concentrated to afford 2-chloro-6-fluoro-3-(propylsulfonamido)benzoic acid as a solid (517.5 g, 37%). $^1$H NMR (400 MHz, CDCl$_3$): □ 7.86-7.83 (d, 1H, J=14.4 Hz), 7.20-7.16 (d, 1H, J=17.2 Hz), 6.81 (s, 1H), 3.11-3.07 (m, 2H, J=15.6 Hz), 1.93-1.86 (m, 2H, J=30.8 Hz), 1.1.0-1.06 (m, 3H, J=15.2 Hz); MS (apci, m/z)=296.1 (M+H).

Intermediate P18

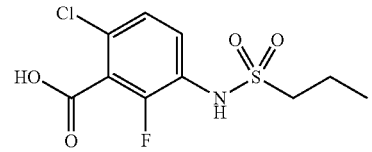 [SMILES: CCCS(=O)(=O)Nc1ccc(Cl)c(C(=O)O)c1F]

6-Chloro-2-fluoro-3-(Propylsulfonamido)benzoic Acid

Step 1: Preparation of benzyl 3-amino-6-chloro-2-fluorobenzoate. A flame dried round-bottom flask equipped with a stir bar and rubber septum was charged with 4-chloro-2-fluoroaniline (5.00 g, 34.35 mmol) and anhydrous THF (170 mL). This solution was chilled to −78° C., and n-BuLi (2.5M in hexanes, 14.7 mL, 36.75 mmol) was added over 15 minutes. This mixture was stirred at −78° C. for 20 minutes, and then a THF solution (25 mL) of 1,2-bis(chlorodimethylsilyl)ethane (7.76 g, 36.1 mmol) was added over 10 minutes to the reaction mixture. The reaction mixture was stirred at −78° C. for 1 hour, and then n-BuLi (2.5 M in hexanes, 15.11 mL, 37.79 mmol) was added slowly. The mixture to warmed to room temperature for one hour, then again cooled to −78° C. A third allotment of n-BuLi (2.5M in hexanes, 15.66 mL, 39.16 mmol) was added slowly, and the mixture was stirred at −78° C. for 75 minutes. Benzyl chloroformate (7.40 g, 41.22 mmol) was added slowly, and the mixture was stirred at −78° C. for one hour. The cooling bath was removed, and the mixture was warmed to ambient temperature for 30 minutes and then quenched with water (70 mL) and concentrated HCl (25 mL). The mixture continued to warm to room temperature. The mixture was extracted with EtOAc. The extracts were washed twice with a saturated NaHCO$_3$ solution, once with water, dried over sodium sulfate and concentrated. The residue was purified by column chromatography on (30% ethyl acetate/hexane) to afford benzyl 3-amino-6-chloro-2-fluorobenzoate (4.3 g, 0.45%) as an oil $^1$H NMR, ((CD$_3$)$_2$SO, 400 MHz) δ 7.37-7.48 (m, 5H), 7.07 (dd, 1H, J=8; 2), 6.87 (t, 1H, J=8), 5.61 (br s, 2H), 5.40 (s, 2H).

Step 2: Preparation of benzyl 6-chloro-2-fluoro-3-(N-(propylsulfonyl)propyl-sulfonamido)benzoate. Benzyl 3-amino-6-chloro-2-fluorobenzoate (4.3 g, 15.37 mmol) was dissolved in dry dichloromethane (270 mL). Triethylamine (5.36 mL, 38.43 mmol) was added and the mixture was cooled to 0° C. Propane-1-sulfonyl chloride (3.63 mL, 32.3 mmol) was added by syringe, and a precipitate resulted. After the addition was complete, the mixture was warmed to room temperature, and the starting material was consumed as determined by TLC (3:1 hexane:ethyl acetate). The mixture was diluted with dichloromethane (200 mL), washed with 2M aqueous HCl (2×100 mL), saturated aqueous NaHCO$_3$ solution, dried over sodium sulfate and concentrated. The residue was purified by column chromatography (40% ethyl acetate/hexane) to afford benzyl 6-chloro-2-fluoro-3-(N-(propylsulfonyl)propylsulfonamido)benzoate (5.5 g, 72%) as an oil that slowly solidified upon standing. NMR (CDCl$_3$, 400 MHz) δ 7.28-7.45 (m, 7H), 5.42 (s, 2H), 3.58-3.66 (m, 4H), 3.43-3.52 (m, 4H), 1.08 (t, 6H, J=8).

Step 3: Preparation of 6-chloro-2-fluoro-3-(propylsulfonamido)benzoic acid. Benzyl 6-chloro-2-fluoro-3-(N-(propylsulfonyl)propylsulfonamido) benzoate (5.4 g, 10.98 mmol) was dissolved in THF (100 mL) and 1M aqueous KOH (100 mL). The mixture was refluxed for 16 hours and then cooled to room temperature. The mixture was acidified to a pH of about 2 with 2M aqueous HCl and extracted with EtOAc (2×). The extracts were washed with water, dried over sodium sulfate and concentrated to a solid that was triturated with hexanes/Et$_2$O to afford 6-chloro-2-fluoro-3-(propylsulfonamido)benzoic acid (2.2 g, 68%) as a solid. $^1$H NMR ((CD$_3$)$_2$SO, 400 MHz) δ 9.93 (s, 1H), 7.49 (t, 1H, J=8), 7.38 (dd, 1H, J=8, 2), 3.11-3.16 (m, 2H), 1.68-1.78 (m, 2H), 0.97 (t, 3H, J=8).

Intermediate P19

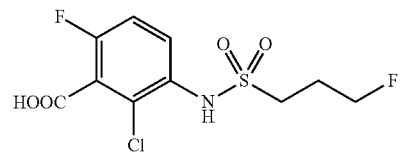 [SMILES: O=C(O)c1c(F)ccc(NS(=O)(=O)CCCF)c1Cl]

2,6-Difluoro-3-(3-fluoropropylsulfonamido)benzoic Acid

Step 1: Preparation of methyl 2,6-difluoro-3-(N-(3-fluoropropylsulfonyl)-3-fluoro-propylsulfonamido)benzoate. Methyl 2,6-difluoro-3-(N-(3-fluoropropylsulfonyl)-3-fluoropropyl-sulfonamido)benzoate was prepared according to the procedure described for Intermediate 16, Step 3, substituting 3-fluoropropyl sulfonyl chloride for propane-1-sulfonyl chloride. $^1$H NMR (400 MHz, (CD$_3$)$_2$SO). δ 8.05-7.99 (m, 1H), 7.44 (t, 1H), 4.62 (t, 2H), 4.50 (t, 2H), 3.93 (s, 3H), 3.89-3.74 (m, 4H), 2.26-2.11 (m, 4H).

Step 2: Preparation of 2,6-Difluoro-3-(3-fluoropropylsulfonamido)benzoic acid. 2,6-Difluoro-3-(3-fluoropropylsulfonamido)benzoic acid was prepared according to the procedure in Intermediate P16, Step 4, substituting methyl 2,6-difluoro-3-(N-(3-fluoropropylsulfonyl)-3-fluoropropylsulfonamido)benzoate for methyl 2,6-difluoro-3-(N-(propylsulfonyl)-propyl-sulfonamido)benzoate. $^1$H NMR (400 MHz, CD$_3$OD) δ 7.64 (m, 1H), 7.07 (m, 1H), 4.58 (m, 1H), 4.47 (m, 1H), 3.22 (m, 2H), 2.26-2.12 (m, 2H); MS (apci, m/z)=296.1 (M–H).

Intermediate P20

2-Chloro-6-fluoro-3-(3-fluoropropylsulfonamido) benzoic Acid

Step 1: Preparation of methyl 2-chloro-6-fluoro-3-(3-fluoro-N-(3-fluoropropyl-sulfonyl)propylsulfonamido)benzoate. Methyl 2-chloro-6-fluoro-3-(3-fluoro-N-(3-fluoropropyl-sulfonyl)propylsulfonamido)benzoate was prepared according to the procedure in Intermediate P16, Step 3, substituting methyl 3-amino-2-chloro-6-fluorobenzoate for methyl 3-amino-2,6-difluorobenzoate and 3-fluoropropyl sulfonyl chloride for propane-1-sulfonyl chloride.

Step 2: Preparation of 2-Chloro-6-fluoro-3-(3-fluoropropylsulfonamido)benzoic acid. 2-Chloro-6-fluoro-3-(3-fluoropropylsulfonamido)benzoic acid (93% over 2 steps) was prepared according to the procedure for Intermediate P16, Step 4, substituting methyl 2-chloro-6-fluoro-3-(3-fluoro-N-(3-fluoropropylsulfonyl)propylsulfonamido)benzoate for benzyl 6-chloro-2-fluoro-3-(N-(propylsulfonyl)propylsulfonamido)benzoate. $^1$H NMR (400 MHz, CD$_3$OD) δ 7.63 (m, 1H), 7.19 (m, 1H), 4.56 (m, 1H), 4.44 (m, 1H), 3.21 (m, 2H), 2.25-2.12 (in, 2H); MS (apci, m/z)=312.1, 314.1 (M–H).

Intermediate P21

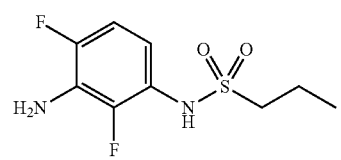

N-(3-Amino-2,4-difluorophenyl)propane-1-sulfonamide

Triethylamine (4.68 mL, 33.59 mmol) and diphenylphosphoryl azide (3.73 mL, 16.79 mmol) were added to a solution of 2,6-difluoro-3-(propylsulfonamido)benzoic acid (4.078 g, 14.6 mmol) in THF (60 mL). The reaction mixture was stirred at room temperature for 3 hours and then warmed to 80° C. for 2 hours. Water (10 mL) was added, and the mixture was stirred at 80° C. for 15 hours. The reaction mixture was diluted with EtOAc (300 mL), and the organic layer was washed with saturated aqueous NaHCO$_3$ solution and brine. The solvent was removed under reduced pressure, and the residual purified by silica gel column chromatography eluting with 30/70 EtOAc/hexane to obtain N-(3-amino-2,4-difluorophenyl)propane-1-sulfonamide (2.03 g, 55%). ¹H NMR (400 MHz, DMSO-d₆) δ 9.32 (s, 1H), 6.90-6.80 (m, 1H), 6.51 (td, J=8.7, 5.5, 1H), 5.28 (s, 2H), 3.05-2.96 (m, 2H), 1.82-1.64 (m, 2H), 1.01-0.90 (m, 3H); MS (apci, m/z)=251.1 (M+H).

Intermediate P22

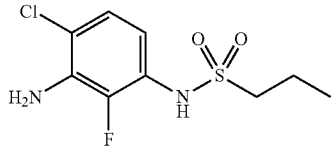 [SMILES: CCCS(=O)(=O)Nc1ccc(F)c(N)c1F]

N-(3-Amino-4-chloro-2-fluorophenyl)propane-1-sulfonamide

Triethylamine (1.84 mL, 13.2 mmol) and diphenylphosphoryl azide (1.43 mL, 6.61 mmol) were added to a solution of 6-chloro-2-fluoro-3-(propylsulfonamido)benzoic acid (1.70 g, 5.75 mmol) in THF (23 mL). The reaction mixture was stirred at room temperature for 1 hour, warmed to 70° C. and stirred for 1 hour. Water (6 mL) was added, after which the reaction mixture was stirred again at 70° C. for 3 hours. The mixture was cooled to room temperature, ethyl acetate was added, and the layers were separated. The organic phase was dried with sodium sulfate, filtered and concentrated in vacuo. The crude product was purified by flash silica gel chromatography, eluting with 0 to 50% EtOAc/heptane to afford N-(3-amino-4-chloro-2-fluorophenyl)propane-1-sulfonamide (1.01 g, 66%) as a solid. ¹H NMR (500 MHz, (CD₃)₂SO) δ 9.54 (s, 1H), 7.02 (d, 1H), 6.58 (t, 1H), 5.50 (s, 2H), 3.09-2.95 (t, 2H), 1.81-1.64 (m, 2H), 0.96 (t, 3H); MS (apci, m/z)=267.1 (M+H).

Intermediate P23

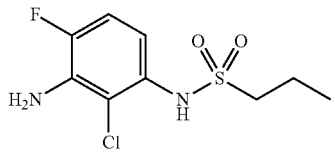 [SMILES: CCCS(=O)(=O)Nc1ccc(F)c(N)c1Cl]

N-(3-Amino-2-chloro-4-fluorophenyl)propane-1-sulfonamide

The title compound was prepared using the procedure described in Intermediate P21 using 2-chloro-6-fluoro-3-(propylsulfonamido)benzoic acid instead of 2,6-difluoro-3-(propyl-sulfonamido)benzoic acid as starting material. ¹H NMR (400 MHz, (CD₃)₂SO) δ 9.20 (s, 1H), 7.28-6.99 (m, 1H), 6.63 (td, J=8.7, 5.5, 1H), 5.45 (s, 2H), 3.07-2.99 (m, 2H), 1.88-1.69 (m, 2H), 1.03-0.95 (m, 3H); MS (apci, m/z)=267.1 (M+H).

Intermediate P24

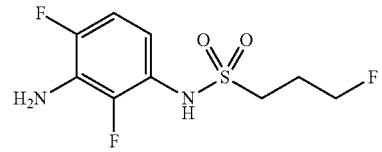 [SMILES: Nc1c(F)ccc(NS(=O)(=O)CCCF)c1F]

N-(3-Amino-2,4-difluorophenyl)-3-fluoropropane-1-sulfonamide

Triethylamine (0.682 mL, 4.89 mmol) and diphenylphosphoryl azide (0.547 mL, 2.45 mmol) were added to a solution of 2,6-difluoro-3-(3-fluoropropylsulfonamido)benzoic acid (0.485 g, 1.63 mmol) in DMF (10 mL). The reaction mixture was stirred at room temperature for 1 hour. Water (1.18 mL, 65.2 mmol) was added, and the mixture was stirred at 80° C. for 15 hours. The reaction mixture was diluted with ethyl acetate (100 mL), and the organic layer was washed with saturated aqueous NaHCO₃, dried over sodium sulfate and concentrated. The crude product was purified using silica gel chromatography, eluting with hexanes/ethyl acetate (4:1) to provide N-(3-amino-2,4-difluorophenyl)-3-fluoropropane-1-sulfonamide (0.34 g, 77%). ¹H NMR (400 MHz, (CD₃)₂SO) δ 9.49 (br-s, 1H), 6.87 (m, 1H), 6.52 (m, 1H), 5.33 (br-s, 2H), 4.60 (m, 1H), 4.48 (m, 1H), 3.14 (m, 2H), 2.16-2.03 (m, 2H); MS (apci, m/z)=267.1 (M−H).

Intermediate P25

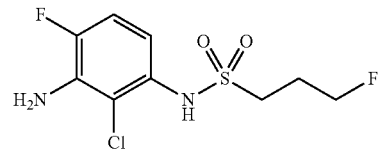 [SMILES: Nc1c(F)ccc(NS(=O)(=O)CCCF)c1Cl]

N-(3-Amino-2-chloro-4-fluorophenyl)-3-fluoropropane-1-sulfonamide

Step 1: Preparation of methyl 3-amino-2-chloro-6-fluorobenzoate. 2-Chloro-4-fluoro aniline (0.82 mL, 6.87 mmol) was dissolved in THF (54 mL) and cooled to −78° C. under a backflow of nitrogen. The reaction mixture was slowly treated with n-butyllithium (2.5 M in hexanes, 2.94 mL, 7.35 mmol) and then allowed to stir at −78° C. for 15 minutes after complete addition. The reaction mixture was treated dropwise with a 15 mL THF solution of 1,2-bis(chlorodimethylsilyl)ethane (1.55 g, 7.21 mmol) and allowed to stir at −78° C. for 15 minutes after complete addition. The reaction mixture was treated slowly with additional n-butyllithium (2.5 M in hexanes, 2.94 mL, 7.35 mmol) and the ice bath was removed after complete addition and the reaction mixture was allowed to warm for 30 minutes. The reaction mixture was cooled back to −78° C. and treated slowly with additional n-butyllithium (2.5 M in hexanes, 2.94 mL, 7.35 mmol) and allowed to stir at −78° C. for 30 minutes before being treated dropwise with methyl chloroformate (0.63 mL, 7.83 mmol). After complete addition the ice bath was removed and the reaction mixture was allowed to stir for 1 hour. The reaction mixture was treated with 4.0 M HCl and allowed to stir at ambient temperature for 30 minutes and then the reaction mixture was neutralized to about pH 8 using solid NaHCO₃. The reaction mixture was extracted with EtOAc (2×) and the organic layers were combined and washed with water and brine and then dried over Na₂SO₄, filtered, and concentrated. The residue was purified by silica gel chromatography (Hexanes/EtOAc) to provide methyl 3-amino-2-chloro-6-fluorobenzoate (1.23 g, 88%). ¹H NMR (400 MHz, DMSO-d6) δ 7.08 (t, 1H), 6.95 (t, 1H), 5.51 (s, 2H), 3.89 (s, 3H).

Step 2: Preparation of 2-chloro-6-fluoro-3-((3-fluoro-N-((3-fluoropropyl)sulfonyl)propyl)-sulfonamido)benzoate.

To a 250 mL flask was added methyl 3-amino-2-chloro-6-fluorobenzoate (5.09 g, 25.0 mmol), dichloromethane (125 mL), and triethylamine (10.5 mL, 75.0 mmol) under nitrogen. The solution was cooled to 0° C. and treated with 3-fluoropropane-1-sulfonyl chloride (6.25 mL, 52.5 mmol) over 20 minutes. The reaction mixture was allowed to stir for 15 hours at ambient temperature after complete addition. The reaction mixture was concentrated and reconstituted with EtOAc, which was washed with a 0.1N HCl aqueous solution, then with brine. The organic layer was dried over Na₂SO₄ and concentrated, then purified by silica gel chromatography (EtOAc/Hexane) to afford methyl 2-chloro-6-fluoro-3-((3-fluoro-N-((3-fluoropropyl)sulfonyl)-propyl)sulfonamido)benzoate as a brown liquid (10.1 g, 90%). ¹H NMR (400 MHz, CDCl₃) δ 7.49-7.52 (dd, 1H), 7.16 (t, 1H), 4.63 (t, 2H), 4.53 (t, 2H), 3.99 (s, 3H), 3.74-3.85 (m, 4H), 2.29-2.39 (m, 4H).

Step 3: Preparation of 2-chloro-6-fluoro-3-((3-fluoropropyl)sulfonamido)benzoic acid. To a 250 mL flask was added methyl 2-chloro-6-fluoro-3-((3-fluoro-N-((3-fluoropropyl)sulfonyl)-propyl)sulfonamido)benzoate (4.0 g, 8.85 mmol), tetrahydrofuran (59.0 mL), methanol (9.84 mL), and 2.0 M potassium hydroxide (26.6 mL, 53.1 mmol). The reaction mixture was stirred at 50° C. for 14 hours. The reaction mixture was concentrated, and the residue was dissolved in EtOAc and the pH was adjusted to about 2 with a 1M aqueous HCl solution. The aqueous layer was extracted with EtOAc and the combined organic layers were washed with a brine solution. The organic layer was dried over Na₂SO₄ and concentrated to produce 2-chloro-6-fluoro-3-((3-fluoropropyl)sulfonamido)benzoic acid a brown solid (2.15 g, 77%). ¹H NMR (400 MHz, CDCl₃) δ 7.58-7.61 (dd, 1H), 7.03 (t, 1H), 4.51 (t, 1H), 4.42 (t, 1H), 3.13 (t, 2H), 2.10-2.21 (m, 2H); MS (apci, m/z)=312.1 (M−H).

Step 4: Preparation of N-(3-amino-2-chloro-4-fluorophenyl)-3-fluoropropane-1-sulfonamide. To a 100 mL flask was added 2-chloro-6-fluoro-3-((3-fluoropropyl)sulfonamido)benzoic acid (2.15 g, 6.854 mmol), DMF (11.42 mL), and triethylamine (2.866 mL, 20.56 mmol) under nitrogen. Diphenylphosphoryl azide (2.216 mL, 10.28 mmol) was added and the reaction mixture was allowed to stir at ambient temperature for 90 minutes, at which time water (18.28 mL, 6.854 mmol) was added and the reaction mixture was heated to 80° C. for 15 hours. The reaction mixture was diluted with EtOAc and washed with saturated aqueous NaHCO₃. The aqueous layer was extracted with EtOAc (×4), and the combined organic layers were washed with brine, dried over Na₂SO₄ and concentrated. The crude material was purified using silica gel chromatography, eluting with EtOAc/hexanes to afford N-(3-amino-2-chloro-4-fluorophenyl)-3-fluoropropane-1-sulfonamide (0.91 g, 47%). ¹H NMR (400 MHz, CDCl₃) δ 6.94-7.02 (m, 2H), 6.55 (br-s, 1H), 4.58 (t, 1H), 4.48 (t, 1H), 4.22 (br-s, 2H), 3.22 (t, 2H), 2.16-2.27 (m, 2H); MS (apci, m/z)=283.0 (M−H).

Intermediate P26

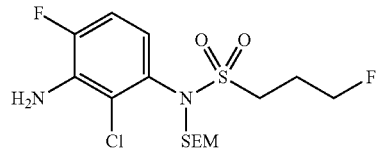 [SMILES: C[Si](C)(C)CCOCN(c1ccc(F)c(N)c1Cl)S(=O)(=O)CCCF]

N-(3-amino-2-chloro-4-fluorophenyl)-3-fluoro-N-((2-(trimethylsilyl)ethoxy)methyl)propane-1-sulfonamide To a 100 mL flask was added N-(3-amino-2-chloro-4-fluorophenyl)-3-fluoropropane-1-sulfonamide (Intermediate P25) (2.04 g, 7.17 mmol) and DMF (28.7 mL) under nitrogen. The solution was cooled to 0° C. and treated with 60% sodium hydride in mineral oil (0.387 g, 9.67 mmol). The reaction mixture was allowed to stir at 0° C. for 15 minutes before 2-(trimethylsilyl)ethoxymethyl chloride (1.53 mL, 8.60 mmol) was added dropwise over 5 minutes. The reaction mixture was monitored by TLC until all of the starting material was consumed. The reaction mixture was diluted with EtOAc and water. The aqueous layer was extracted with EtOAc and the combined organic layers were washed with brine, dried over Na₂SO₄ and concentrated. The crude material was purified using silica gel chromatography, eluting with EtOAc/hexanes to afford N-(3-amino-2-chloro-4-fluorophenyl)-3-fluoro-N-((2-(trimethylsilyl)-ethoxy)methyl)-propane-1-sulfonamide (2.83 g, 95%) as a white solid. ¹H NMR (400 MHz, CDCl₃) δ 6.99-6.94 (dd, 1H), 6.88-6.84 (dd, 1H), 5.24 (d, 1H), 4.68 (d, 1H), 4.62 (t, 1H), 4.50 (t, 1H), 4.22 (s, 2H), 3.69-3.58 (m, 2H), 3.29 (dd, 2H), 2.34-2.21 (m, 2H), 0.94-0.88 (m, 2H), 0.00 (s, 9H).

Intermediate P27

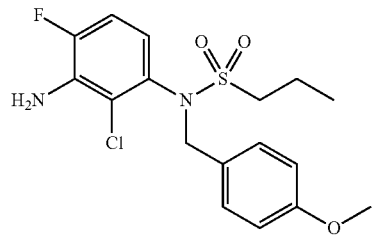 [SMILES: CCCS(=O)(=O)N(Cc1ccc(OC)cc1)c1ccc(F)c(N)c1Cl]

N-(3-Amino-2-chloro-4-fluorophenyl)-N-(4-methoxybenzyl)propane-1-sulfonamide

N-(3-Amino-2-chloro-4-fluorophenyl)propane-1-sulfonamide (75 g, 280 mmol) was dissolved in DMF (200 mL). A 60% sodium hydride suspension in mineral oil (11.85 g, 296 mmol) was added in multiple portions over 15 minutes. The reaction mixture was stirred at room temperature for 90 minutes and was warmed to 40° C. for two hours. This homogeneous mixture was cooled to 0° C., and p-methoxybenzyl chloride (40.03 mL, 295.25 mmol) was added over 5 minutes. The reaction mixture was left to stir and warm to room temperature. After 14 hours, the reaction mixture was poured into a dilute ammonium chloride solution (1750 mL), and the water layer was decanted to leave an oil. This oil was triturated three times with water (2 L). The remaining product was transferred into a 1 L beaker, diluted with water (800 mL), sonicated for 30 minutes and then stirred at room temperature for 1 hour. The resulting solid was collected by filtration and dried by lyophilization to give N-(3-amino-2-chloro-4-fluorophenyl)-N-(4-methoxybenzyl)propane-1-sulfonamide (111.9 g, 99%). $^1$H NMR (500 MHz, $(CD_3)_2SO$) δ=7.11 (d, J=8.6, 2H), 6.96 (dd, J=10.6, 8.8, 1H), 6.81 (t, J=5.7, 2H), 6.51 (dd, J=8.7, 5.1, 1H), 5.42 (s, 2H), 4.71 (d, J=14.4, 1H), 4.57 (d, J=14.4, 1H), 3.70 (s, 3H), 3.21 (td, J=6.7, 1.4, 2H), 1.77 (dd, J=15.3, 7.5, 2H), 1.00 (t, J=7.4, 3H).

Intermediate P28

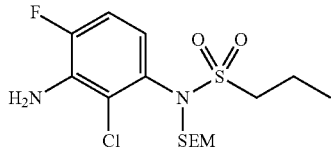 [SMILES: CCCS(=O)(=O)N(COCC[Si](C)(C)C)c1ccc(F)c(N)c1Cl]

N-(3-amino-2-chloro-4-fluorophenyl)-N-((2-(trimethylsilyl)ethoxy)methyl) propane-1-sulfonamide To a solution of N-(3-amino-2-chloro-4-fluorophenyl) propane-1-sulfonamide (Intermediate P27) (10.0 g, 37.5 mmol) in DMF (187 mL) at 0° C. was added 60% sodium hydride suspension in mineral oil (1.65 g, 41.2 mmol) and (2-(chloromethoxy)ethyl)trimethylsilane (6.58 mL, 39.4 mmol) and the solution was allowed to stir at ambient temperature for 4 hours. The reaction mixture was quenched with water and extracted with EtOAc. The combined organic extracts were washed with brine, dried over $Na_2SO_4$, filtered and concentrated in vacuo. The crude product was purified by silica gel chromatography, eluting with 5% to 35% EtOAc/hexanes to give N-(3-amino-2-chloro-4-fluorophenyl)-N-((2-(trimethylsilyl)ethoxy)methyl)propane-1-sulfonamide (12.7 g, 85%) as a white solid. $^1$H NMR (400 MHz, $CDCl_3$) δ 6.97 (m, 1H), 6.87 (m, 1H), 5.23 (d, 1H), 4.69 (d, 1H), 4.2 (s, 2H), 3.65 (m, 2H), 3.1 (t, 2H), 1.92 (m, 2H), 1.05 (t, 3H), 0.91 (m, 2H), 0.01 (s, 9H).

Intermediate P29

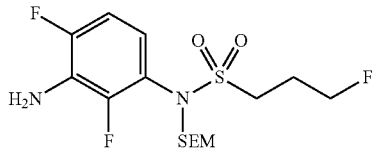 [SMILES: C[Si](C)(C)CCOCN(c1ccc(F)c(N)c1F)S(=O)(=O)CCCF]

N-(3-amino-2,4-difluorophenyl)-3-fluoro-N-((2-(trimethylsilyl)ethoxy)methyl)propane-1-sulfonamide To a 10 mL flask was added N-(3-amino-2,4-difluorophenyl)-3-fluoropropane-1-sulfonamide (Intermediate P24) (204 mg, 0.764 mmol) and DMF (3.0 mL) under nitrogen. The solution was cooled to 0° C. and treated with 60% sodium hydride in mineral oil (41.3 mg, 1.03 mmol). The reaction mixture was stirred at 0° C. for 15 minutes before 2-(trimethylsilyl)ethoxymethyl chloride (0.163 mL, 0.917 mmol) was added dropwise over the course of 5 minutes. The reaction mixture was monitored by TLC until all of the starting material was consumed. The reaction mixture was diluted with EtOAc and water. The aqueous layer was extracted with EtOAc and the combined organic layers were washed with brine, dried over $Na_2SO_4$, filtered and concentrated. The crude material was purified using silica gel chromatography, eluting with EtOAc/hexanes to afford N-(3-amino-2,4-difluorophenyl)-3-fluoro-N-((2-(trimethylsilyl)-ethoxy)methyl)propane-1-sulfonamide (59.3 mg, 20%) as a white solid. $^1$H NMR (400 MHz, $CDCl_3$) δ (ppm) 6.73-6.86 (m, 2H), 4.96 (s, 2H), 4.61 (t, 1H), 4.50 (t, 1H), 3.83 (s, 2H), 3.65 (t, 2H), 3.26 (t, 2H), 2.18-2.31 (m, 2H), 0.92 (t, 2H), 0.01 (s, 9H).

Intermediate P30

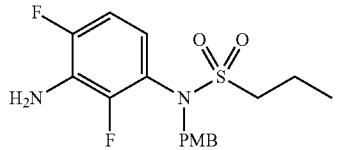

N-(3-amino-2,4-difluorophenyl)-N-(4-methoxybenzyl) propane-1-sulfonamide

To a solution of N-(3-amino-2,4-difluorophenyl)propane-1-sulfonamide (1.05 g, 4.196 mmol) in DMF (20 mL) at 0° C. was added 60% sodium hydride suspension in mineral oil (0.1678 g, 4.196 mmol) and the mixture was stirred at 0° C. for 15 minutes. To the reaction mixture was added 1-(chloromethyl)-4-methoxybenzene (0.5694 mL, 4.196 mmol) and the reaction mixture was stirred for at ambient temperature for 1 hour. The solution was quenched with water and extracted with EtOAc. The organic layers were washed with brine, dried with $Na_2SO_4$, filtered, concentrated, and purified by silica gel chromatography, eluting with 5% to 50% EtOAc/hexanes to afford N-(3-amino-2,4-difluorophenyl)-N-(4-methoxybenzyl)propane-1-sulfonamide (0.789 g, 51%). $^1$H NMR (400 MHz, $CDCl_3$) δ 7.14 (d, 2H), 6.78 (d, 2H), 6.67 (m, 1H), 6.42 (m, 1H), 4.69 (s, 2H), 3.77 (s, 3H), 3.06 (t, 2H), 1.92 (m, 2H), 1.06 (t, 3H).

Intermediate P31

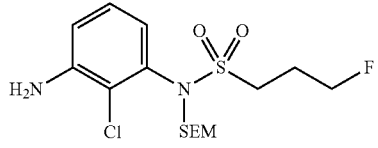 [SMILES: C[Si](C)(C)CCOCN(c1cccc(N)c1Cl)S(=O)(=O)CCCF]

N-(3-amino-2-chlorophenyl)-3-fluoro-N-((2-(trimethylsilyl)ethoxy)methyl)propane-1-sulfonamide Step 1: Preparation of N-(2-chloro-3-nitrophenyl)-3-fluoro-N-((3-fluoropropyl)sulfonyl)propane-1-sulfonamide.

A solution of 2-chloro-3-nitroaniline (1.0 g, 5.79 mmol) in CH₂Cl₂ (29.0 mL) was treated with triethylamine (1.01 mL, 7.24 mmol) followed by 3-fluoro-propane-1-sulfonyl chloride (1.47 mL, 11.6 mmol) and the mixture was stirred at ambient temperature for 2 hours. Additional triethylamine (1.01 mL, 7.24 mmol) and 3-fluoro-propane-1-sulfonyl chloride (1.47 mL, 11.6 mmol) were added and the mixture was stirred at ambient temperature for 30 minutes. 50 mL of a 0.5 N HCl solution was added and the layers were mixed and separated-. The organic layer was dried over Na₂SO₄, filtered and concentrated to afford N-(2-chloro-3-nitrophenyl)-3-fluoro-N-((3-fluoropropyl)sulfonyl)propane-1-sulfonamide (2.44 g, 99%), and used without further purification.

Step 2: Preparation of N-(2-chloro-3-nitrophenyl)-3-fluoropropane-1-sulfonamide. To a solution of N-(2-chloro-3-nitrophenyl)-3-fluoro-N-((3-fluoropropyl)sulfonyl)propane-1-sulfonamide (2.44 g, 5.80 mmol) in THF (11.6 mL) and MeOH (3.87 mL) was added NaOH (5.80 mL, 11.6 mmol, 2.0M aqueous) and the mixture was stirred at ambient temperature for 30 minutes. The reaction mixture was quenched by the addition of 1N HCl (10 mL) and the mixture was concentrated to remove MeOH. The mixture was extracted with EtOAc and the combined extracts were dried over Na₂SO₄, filtered and concentrated. The crude product was purified by column chromatography, eluting with 5% EtOAc/DCM to provide N-(2-chloro-3-nitrophenyl)-3-fluoropropane-1-sulfonamide (0.933 g, 54%) as a yellow solid.

Step 3: Preparation of N-(3-amino-2-chlorophenyl)-3-fluoropropane-1-sulfonamide. To a solution of N-(2-chloro-3-nitrophenyl)-3-fluoropropane-1-sulfonamide (0.933 g, 3.14 mmol) in EtOH (15.7 mL) and water (3.93 mL) was added iron powder (1.76 g, 31.4 mmol) in one portion followed by NH₄Cl (0.168 g, 3.14 mmol). The mixture was heated to 80° C. for 2.5 hours. The mixture was filtered through Celite®, washed with MeOH, and the filtrate was concentrated. The crude residue was dissolved in EtOAc, then washed with water and dried over Na₂SO₄, filtered and concentrated. The crude product was purified by column chromatography, eluting with 5% to 40% EtOAc/hexanes to afford N-(3-amino-2-chlorophenyl)-3-fluoropropane-1-sulfonamide as an orange oil (0.711 g, 84%).

Step 4: Preparation of N-(3-amino-2-chlorophenyl)-3-fluoro-N-((2-(trimethylsilyl)ethoxy)-methyl)propane-1-sulfonamide. A solution of N-(3-amino-2-chlorophenyl)-3-fluoropropane-1-sulfonamide (0.679 g, 2.55 mmol) in DMF (10.2 mL) was cooled to 0° C. in a water/ice bath. The solution was treated with 60% sodium hydride in mineral oil (0.137 g, 3.44 mmol) and the mixture was stirred for 15 minutes. Then 2-(trimethylsilyl)ethoxymethyl chloride (0.541 mL, 3.05 mmol) was added dropwise and the mixture was stirred for an additional 1 hour at 0° C. The reaction mixture was quenched by the addition of a saturated aqueous NH₄Cl solution and the mixture was warmed to ambient temperature and extracted with EtOAc. The combined organic extracts were dried over Na₂SO₄, filtered and concentrated. The crude product was purified by column chromatography, eluting with 10% to 30% EtOAc/hexanes to afford N-(3-amino-2-chlorophenyl)-3-fluoro-N-((2-(trimethylsilyl)ethoxy)methyl)propane-1-sulfonamide (0.726 g, 71%) as a thick pale yellow oil. ¹H NMR (400 MHz, CDCl₃) δ 7.09 (t, 1H); 6.90 (dd, 1H); 6.80 (dd, 1H); 5.26 (br-m, 1H); 4.74 (br-m, 1H); 4.62 (t, 1H); 4.51 (t, 1H); 4.18 (br-s, 2H); 3.65 (br-m, 2H); 3.31 (m, 2H); 2.29 (m, 2H); 0.92 (m, 2H); 0.01 (s, 9H).

Intermediate P32

N-(3-amino-4-fluoro-2-methylphenyl)-N-((2-(trimethylsilyl)ethoxy)methyl)propane-1-sulfonamide Step 1: Preparation of 6-fluoro-2-methyl-3-(propylsulfonamido)benzoic acid. To a solution of methyl 3-amino-6-fluoro-2-methylbenzoate (900 mg, 4.913 mmol) and triethylamine (2.05 mL, 14.74 mmol) in dichloromethane (19.6 mL) was added propane-1-sulfonyl chloride (1.38 mL, 12.28 mmol) and the mixture was stirred at ambient temperature for 30 minutes. The reaction mixture was quenched with saturated aqueous NaHCO₃ and extracted with DCM. The combined organic extracts were dried over Na₂SO₄, filtered and concentrated. The residue was dissolved in tetrahydrofuran (19.6 mL) and methanol (4.9 mL) and treated with 2.0 M potassium hydroxide (14.7~mL, 29.48 mmol) at 50° C. for 60 hours. The solution was concentrated and washed with Et₂O. The aqueous layer was adjusted to about pH 2 with concentrated HCl and extracted with 4:1 DCM/IPA. The organic layers were dried with Na₂SO₄, filtered, and concentrated to give 6-fluoro-2-methyl-3-(propylsulfonamido)benzoic acid (1.13 g, 84%). ¹H NMR (400 MHz, DMSO) δ 9.2 (s, 1H), 7.35 (m, 1H), 7.15 (t, 1H), 3.08 (m, 2H), 2.3 (s, 3H), 1.73 (m, 2H), 0.99 (t, 3H).

Step 2: Preparation of N-(3-amino-4-fluoro-2-methylphenyl)propane-1-sulfonamide. To a solution of 6-fluoro-2-methyl-3-(propylsulfonamido)benzoic acid (1.13 g, 4.105 mmol) in DMF (41.05 mL) was added triethylamine (1.716 mL, 12.31 mmol) and diphenyl phosphoryl azide (1.33 mL, 6.157 mmol). The solution was stirred at ambient temperature for 1 hour. Then water (5.86 mL, 4.105 mmol) was added and the solution was heated to 80° C. overnight. The solution was quenched with water and extracted with EtOAc. The organic layers were washed with brine, dried with Na₂SO₄, filtered, concentrated, and purified by column chromatography, eluting with 10:90 EtOAc/hexanes to give N-(3-amino-4-fluoro-2-methylphenyl)propane-1-sulfonamide (0.88 g, 87%). MS (apci, m/z)=247.1 [M+H].

Step 3: To a solution of N-(3-amino-4-fluoro-2-methylphenyl)propane-1-sulfonamide (880 mg, 3.57 mmol) in DMF (23.8 mL) at 0° C. was added sodium hydride (60% suspension in mineral oil, 193 mg, 4.82 mmol) and (2-(chloromethoxy)ethyl)trimethylsilane (717 μL, 4.29 mmol) and the reaction was stirred at ambient temperature overnight. The reaction mixture was quenched with water and extracted with EtOAc. The organic layers were washed with brine, dried with Na₂SO₄, filtered, concentrated, and purified by 60% sodium hydride suspension in mineral oil, eluting with 10% to 50% EtOAc/hexanes to afford N-(3-amino-4-fluoro-2-methylphenyl)-N-((2-(trimethylsilyl)ethoxy)-methyl)propane-1-sulfonamide (590 mg, 44%). ¹H NMR (400 MHz, CDCl₃) δ 6.87 (m, 1H), 6.78 (m, 1H), 5.2 (d, 1H), 4.48 (d, 1H), 3.58 (t, 2H), 3.14 (t, 2H), 2.19 (s, 3H), 1.89 (m, 2H), 1.15 (t, 3H), 0.94 (m, 2H), 0.01 (s, 9H).

Intermediate P33

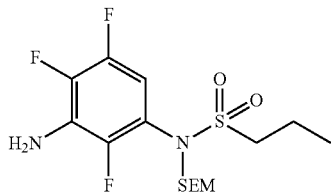 [SMILES: CCCS(=O)(=O)N(COCC[Si](C)(C)C)c1cc(F)c(F)c(N)c1F]

N-(3-amino-2,4,5-trifluorophenyl)-N-((2-(trimethyl-silyl)ethoxy)methyl)propane-1-sulfonamide Step 1: Preparation of methyl 3-amino-2,5,6-trifluorobenzoate. 2,4,5-Trifluoroaniline (3.00 g, 20.394 mmol) was dissolved in THF (100 mL) and cooled to −78° C. under a backflow $N_2$. The reaction mixture was treated slowly with n-butyllithium (2.5 M in hexanes, 8.97 mL, 22.434 mmol) and stirred at −78° C. for 15 minutes. The reaction mixture was treated dropwise with a THF solution (50 mL) of 1,2-bis(chlorodimethylsilyl)ethane (4.61 g, 21.414 mmol) and stirred at −78° C. for 15 minutes after complete addition. The reaction mixture was treated slowly with an additional n-butyllithium (2.5 M in hexanes, 8.97 mL, 22.434 mmol). The ice bath was removed and the reaction mixture allowed to warm for 30 minutes. The reaction mixture was cooled back to −78° C. and treated slowly with an additional n-butyllithium (2.5 M in hexanes, 8.97 mL, 22.434 mmol) and stirred at −78° C. for 30 minutes. The reaction mixture was treated dropwise with methyl chloroformate (2.36 mL, 30.591 mmol). The cold bath was removed and the mixture was stirred for 1 hour. The reaction mixture was quenched with water and acidified to about pH 1 using 4.0 M HCl and stirred at room temperature for 30 minutes. The reaction mixture was adjusted to about pH 8 using solid $NaHCO_3$ and extracted with EtOAc (2×). The combined organic extracts were washed with water, brine, dried over $Na_2SO_4$, filtered, and concentrated. The crude product was purified by silica gel chromatography, eluting with 5:95 hexanes/ethyl acetate, followed by reverse phase C18 chromatography, eluting with 5:95 water/acetonitrile with 0.1% TFA. The product was partitioned between DCM and saturated aqueous $NaHCO_3$. The organic layers were washed with brine, dried with $Na_2SO_4$, filtered, and concentrated give methyl 3-amino-2,5,6-trifluorobenzoate (2.34 g, 56%). $^1$H NMR (400 MHz, DMSO) δ 6.88 (m, 1H), 5.58 (s, 2H), 3.87 (s, 3H).

Step 2: Preparation of methyl 2,3,6-trifluoro-5-(N-(propylsulfonyl)propylsulfonamido)benzoate. To a solution of methyl 3-amino-2,5,6-trifluorobenzoate (2.32 g, 11.31 mmol) and triethylamine (4.729 mL, 33.93 mmol) in dichloromethane (45.24 mL) was added propane-1-sulfonyl chloride (3.170 mL, 28.27 mmol) and the mixture was stirred at ambient temperature for 30 minutes. The reaction mixture was quenched with water and extracted with DCM. The organic layers were washed with brine, filtered, concentrated, and purified by silica gel chromatography, eluting with 5% to 50% EtOAc/hexanes to give methyl 2,3,6-trifluoro-5-(N-(propylsulfonyl)-propylsulfonamido)benzoate (3.08 g, 65%). $^1$H NMR (400 MHz, $CDCl_3$) δ 7.37 (m, 1H), 3.99 (s, 3H), 3.63 (m, 2H), 3.49 (m, 2H), 1.94 (m, 4H), 1.1 (t, 6H).

Step 3: Preparation of 2,3,6-trifluoro-5-(propylsulfonamido)benzoic acid. To a solution of methyl 2,3,6-trifluoro-5-(N-(propylsulfonyl)propylsulfonamido)benzoate (3.08 g, 7.38 mmol) in methanol (8.20 mL) and tetrahydrofuran (49.2 mL) was added 2.0 M potassium hydroxide (22.1 mL, 44.3 mmol) and the mixture was heated to 50° C. overnight. The THF/MeOH was removed under vacuum and the residue was diluted with water and washed with ether. The aqueous layer was adjusted to about pH 2 with concentrated HCl and extracted with 4:1 DCM/IPA. The organic layers were dried with $Na_2SO_4$, filtered, and concentrated to give 2,3,6-trifluoro-5-(propylsulfonamido)benzoic acid (1.6 g, 73%). MS (apci, m/z)=296.1 [M−H].

Step 4: Preparation of N-(3-amino-2,4,5-trifluorophenyl)propane-1-sulfonamide. To a solution of 2,3,6-trifluoro-5-(propylsulfonamido)benzoic acid (1.6 g, 5.383 mmol) in DMF (53.83 mL) was added triethylamine (2.251 mL, 16.15 mmol) and diphenyl phosphoryl azide (1.740 mL, 8.074 mmol). The solution was stirred at ambient temperature for 1 hour. Then water (7.690 mL, 5.383 mmol) was added and the reaction mixture was heated to 80° C. for 24 hours. The solution was quenched with water and extracted with EtOAc. The organic layers were washed with brine, dried with $Na_2SO_4$, filtered, concentrated, and purified by silica gel chromatography, eluting with 50% EtOAc/hexanes to give N-(3-amino-2,4,5-trifluorophenyl)propane-1-sulfonamide (0.733 g, 51%). MS (apci, m/z)=267.0 [M−H].

Step 5: Preparation of N-(3-amino-2,4,5-trifluorophenyl)-N-((2-(trimethylsilyl)ethoxy)methyl)-propane-1-sulfonamide. To a solution of N-(3-amino-2,4,5-trifluorophenyl)propane-1-sulfonamide (733 mg, 2.73 mmol) in DMF (13.7 mL) at 0° C. was added 60% sodium hydride suspension in mineral oil (148 mg, 3.69 mmol) and (2-(chloromethoxy)ethyl)trimethylsilane (582 μL, 3.28 mmol) and the reaction mixture was stirred at ambient temperature for 30 minutes. The reaction mixture was quenched with water and extracted with EtOAc. The organic layers were washed with brine, dried with $Na_2SO_4$, filtered, concentrated and the residue was purified by silica gel chromatography, eluting with 5% to 50% EtOAc/hexanes to give N-(3-amino-2,4,5-trifluorophenyl)-N-((2-(trimethylsilyl)ethoxy)methyl)propane-1-sulfonamide (1.02 g, 94%). $^1$H NMR (400 MHz, $CDCl_3$) δ 6.66 (m, 1H), 4.93 (s, 2H), 3.97 (br-s, 2H), 3.65 (m, 2H), 3.07 (m, 2H), 1.88 (m, 2H), 1.04 (t, 3H), 0.91 (m, 2H), 0.02 (s, 9H).

Intermediate P34

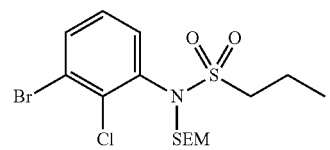 [SMILES: CCCS(=O)(=O)N(COCC[Si](C)(C)C)c1cccc(Br)c1Cl]

N-(3-bromo-2-chlorophenyl)-N-((2-(trimethylsilyl)ethoxy)methyl)propane-1-sulfonamide Step 1: Preparation of N-(3-bromo-2-chlorophenyl)-N-(propylsulfonyl)propane-1-sulfonamide. 3-bromo-2-chloroaniline (2.026 g, 9.813 mmol) was dissolved in DCM (20 mL) and treated with triethylamine (4.103 mL, 29.44 mmol). 1-Propanesulfonyl chloride (2.420 mL, 21.59 mmol) was added and the reaction mixture was stirred at ambient temperature for 16 hours. After 16 hours additional triethylamine (2.05 mL, 14.72 mmol, 1.5 equiv.) and 1-propanesulfonyl chloride (1.21 mL, 10.79 mmol, 1.1 equiv.) were added and the reaction mixture was stirred at ambient temperature for 2 hours. The reaction mixture was diluted with DCM (20 mL) and washed with a saturated aqueous solution of NaHCO$_3$ (50 mL). The organic phase was separated and dried over Na$_2$SO$_4$, filtered, and concentrated to afford N-(3-bromo-2-chlorophenyl)-N-(propylsulfonyl)-propane-1-sulfonamide (4.1 g, 99%). The material was used directly in Step 2 without further purification.

Step 2: Preparation of N-(3-bromo-2-chlorophenyl)propane-1-sulfonamide. N-(3-bromo-2-chlorophenyl)-N-(propylsulfonyl)propane-1-sulfonamide (4.1 g, 9.81 mmol) was dissolved in THF (50 mL) and treated with 1.0 M sodium hydroxide (19.63 mL, 19.63 mmol). The reaction mixture was stirred at ambient temperature for 2 hours. The reaction mixture was diluted with water and adjusted to about pH 4 using 4.0 M HCl. The aqueous phase was extracted with DCM (2×50 mL). The organic phases were combined, dried over Na$_2$SO$_4$, filtered, and concentrated to a brown oil. The crude material was purified using silica gel chromatography, eluting with 14% EtOAc/86% hexanes to afford N-(3-bromo-2-chlorophenyl)propane-1-sulfonamide as a yellow solid (2.90 g, 95%). $^1$H NMR (400 MHz, CDCl$_3$) δ 7.66 (dd, 1H), 7.43 (dd, 1H), 7.16 (t, 1H), 6.85 (s, 1H), 3.11-3.05 (m, 2H), 1.91-1.81 (m, 2H), 1.04 (t, 3H).

Step 3: Preparation of N-(3-bromo-2-chlorophenyl)-N-((2-(trimethylsilyl)ethoxy)methyl)propane-1-sulfonamide. N-(3-bromo-2-chlorophenyl)propane-1-sulfonamide (1.063 g, 3.40 mmol) was dissolved in DMF (18 mL) and cooled in an ice/water bath for 10 minutes under argon. To the reaction mixture was added 60% sodium hydride suspension in mineral oil (0.1428 g, 3.57 mmol) and the reaction mixture was stirred for about 15 minutes until gas evolution ceased. (2-(Chloromethoxy)ethyl)trimethylsilane (0.724 mL, 4.08 mmol) was added and the reaction mixture was allowed to warm to ambient temperature under argon for 45 minutes. The solution was quenched with H$_2$O (50 mL) and the product was extracted with EtOAc (50 mL). The organic phase was washed with brine, dried with Na$_2$SO$_4$, filtered, concentrated and the residue was purified by silica gel chromatography, eluting with 5% to 50% EtOAc/hexanes to afford N-(3-bromo-2-chlorophenyl)-N-((2-(trimethylsilyl)ethoxy)methyl)propane-1-sulfonamide as a light yellow oil (1.38 g, 92%). $^1$H NMR (400 MHz, CDCl$_3$) δ 7.56 (dd, 1H), 7.47 (dd, 1H), 7.19 (t, 1H), 5.22 (d, 1H), 4.78 (d, 1H), 3.67 (d, 2H), 3.13-3.06 (m, 2H), 1.98-1.84 (m, 2H), 1.05 (t, 3H), 0.99-0.81 (m, 2H), 0.01 (s, 9H).

Intermediate P35

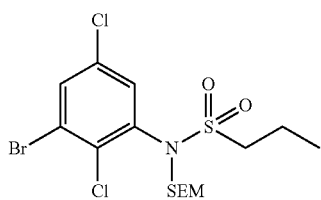

N-(3-bromo-2,5-dichlorophenyl)-N-((2-(trimethylsilyl)ethoxy)methyl)propane-1-sulfonamide Step 1: Preparation of N-(3-bromo-2,5-dichlorophenyl)-N-(propylsulfonyl)propane-1-sulfonamide. Triethylamine (1.794 mL, 12.87 mmol) was added to 3-bromo-2,5-dichloroaniline (1.0 g, 4.151 mmol) and propane-1-sulfonyl chloride (1.070 mL, 9.547 mmol) in DCM (30 mL) and the mixture was stirred at ambient temperature for 60 hours. The reaction mixture was quenched with water (100 mL) and the aqueous layer was extracted with DCM (2×40 mL). The organic layers were combined, washed with brine, dried over Na$_2$SO$_4$, filtered and concentrated to afford N-(3-bromo-2,5-dichlorophenyl)-N-(propylsulfonyl)propane-1-sulfonamide (1.87 g, 99%) that was used directly in the next step without purification.

Step 2: Preparation of N-(3-bromo-2,5-dichlorophenyl)propane-1-sulfonamide. To a solution of N-(3-bromo-2,5-dichlorophenyl)-N-(propylsulfonyl)propane-1-sulfonamide (1.87 g, 4.13 mmol, 1.92 M) in acetonitrile (40 mL) was added sodium carbonate monohydrate (15 mL, 28.9 mmol) and the reaction mixture was heated to 80° C. for 6 hours. The reaction mixture was concentrated to remove acetonitrile and 10% aqueous citric acid was added to adjust the pH adjusted to about 3. The product was extracted with DCM (3×50 mL) and the organic layers were combined, dried over Na$_2$SO$_4$, filtered and concentrated to give a dark brown solid that was purified by silica gel chromatography eluting with 20% EtOAc/hexanes to afford N-(3-bromo-2,5-dichlorophenyl)propane-1-sulfonamide as a light brown solid (700 mg, 49%). MS (apci, m/z)=343.9 (M–H).

Step 3: Preparation of N-(3-bromo-2,5-dichlorophenyl)-N-((2-(trimethylsilyl)ethoxy)methyl)-propane-1-sulfonamide. N-(3-bromo-2,5-dichlorophenyl)propane-1-sulfonamide (645 mg, 1.859 mmol) was dissolved in DMF (9.2 mL) under argon and the mixture was cooled in an ice/water bath. To the reaction mixture was added (81.77 mg, 2.044 mmol) and the reaction mixture was stirred at 0° C. for 30 minutes. (2-(Chloromethoxy)ethyl)trimethylsilane (395.6 μL, 2.230 mmol) was added and the reaction mixture was warmed to ambient temperature overnight. The solution was quenched with H$_2$O (50 mL) and the product was extracted with EtOAc (50 mL). The organic phase was washed with brine, dried with Na$_2$SO$_4$, filtered, and concentrated. The residue was purified by silica gel chromatography (5-50% EtOAc/hex) to afford N-(3-bromo-2,5-dichlorophenyl)-N-((2-(trimethylsilyl)ethoxy)methyl)-propane-1-sulfonamide as a yellow oil (575.8 mg, 65%). $^1$H NMR (400 MHz, CDCl$_3$) δ 7.68 (d, 1H), 7.47 (d, 1H), 5.21 (d, 1H), 4.74 (d, 1H), 3.67 (d, 2H), 3.14-3.05 (m, 2H), 1.98-1.85 (m, 2H), 1.06 (t, 3H), 0.99-0.82 (m, 2H), 0.02 (s, 9H).

Intermediate P36

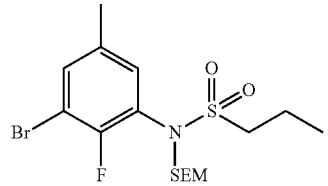 [SMILES: CCCS(=O)(=O)N(COCC[Si](C)(C)C)c1cc(C)cc(Br)c1F]

N-(3-bromo-2-fluoro-5-methylphenyl)-N-((2-(trimethylsilyl)ethoxy)methyl)propane-1-sulfonamide Step 1: Preparation of N-(3-bromo-2-fluoro-5-methylphenyl)-N-(propylsulfonyl)propane-1-sulfonamide. Triethylamine (1059 μL, 7:596 mmol) was added to a solution of 3-bromo-2-fluoro-5-methylaniline (500 mg, 2.450 mmol) and propane-1-sulfonyl chloride (631.8 µL, 5.636 mmol) in DCM (24.5 mL) and the mixture was stirred at ambient temperature for 16 hours. The reaction mixture was quenched with 100 mL of water and the aqueous layer was extracted with DCM (2×40 mL). The combined organic extracts were washed with brine, dried with $Na_2SO_4$ and concentrated to afford N-(3-bromo-2-fluoro-5-methylphenyl)-N-(propylsulfonyl)propane-1-sulfonamide (1.01 g, 99%) as an orange solid that was used directly in the next step.

Step 2: Preparation of N-(3-bromo-2-fluoro-5-methylphenyl)propane-1-sulfonamide. To a solution of N-(3-bromo-2-fluoro-5-methylphenyl)-N-(propylsulfonyl)propane-1-sulfonamide (1.01 g, 2.40 mmol) in acetonitrile (25 mL) was added sodium carbonate (15 mL, 18.16 mmol, 1.2M) and the reaction mixture was heated to 80° C. for one hour. The reaction mixture was concentrated to remove acetonitrile and 10% aqueous citric acid was added to adjust the pH to about 3. The product was extracted with DCM (3×50 mL) and the combined organic layers were dried over $Na_2SO_4$, filtered and concentrated to give a dark brown solid which was purified by silica gel chromatography, eluting with 10% EtOAc/DCM, to afford N-(3-bromo-2-fluoro-5-methylphenyl)propane-1-sulfonamide as a white solid (650.9 mg, 81%). $^1$H NMR (400 MHz, CDCl$_3$) δ 7.37-7.32 (m, 1H), 7.17-7.12 (m, 1H), 6.48 (s, 1H), 3.12-3.05 (m, 2H), 2.31 (s, 3H), 1.93-1.81 (m, 2H), 1.05 (t, 3H).

Step 3: Preparation of N-(3-bromo-2-fluoro-5-methylphenyl)-N-((2-(trimethylsilyl)ethoxy)-methyl)propane-1-sulfonamide. N-(3-bromo-2-fluoro-5-methylphenyl)propane-1-sulfonamide (524 mg, 1.689 mmol) was dissolved in DMF (8.45 mL) under argon and the mixture was cooled in an ice/water bath. To the reaction mixture was added 60% sodium hydride suspension in mineral oil (74.32 mg, 1.858 mmol) and the reaction mixture was stirred at 0° C. for 30 minutes. (2-(Chloromethoxy)ethyl)trimethylsilane (359.5 µL, 2.027 mmol) was added and the reaction mixture was warmed to ambient temperature for 1 hour. The reaction mixture was quenched with 10% aqueous citric acid (50 mL) and the aqueous layer was extracted with EtOAc (50 mL). The organic phase was washed with brine, dried over $Na_2SO_4$, filtered and concentrated to give a yellow oil, which was purified by silica gel chromatography, eluting with 20% EtOAc/hexanes, to afford N-(3-bromo-2-fluoro-5-methylphenyl)-N-((2-(trimethylsilyl)ethoxy)methyl)propane-1-sulfonamide as white crystals (588.4 mg, 79%). $^1$H NMR (400 MHz, CDCl$_3$) δ 7.40-7.36 (m, 1H), 7.20-7.16 (m, 1H), 4.98 (s, 2H), 3.72-3.66 (m, 2H), 3.10-3.03 (m, 2H), 2.33 (s, 3H), 1.95-1.83 (m, 2H), 1.06 (t, 3H), 0.95-0.88 (m, 2H), 0.01 (s, 9H).

N-(3-bromo-5-chloro-2-fluorophenyl)-N-((2-(trimethylsilyl)ethoxy)methyl)propane-1-sulfonamide Step 1: Preparation of N-(3-bromo-5-chloro-2-fluorophenyl)-N-(propylsulfonyl)propane-1-sulfonamide. Triethylamine (1733 µL, 12.43 mmol) was added to 3-bromo-5-chloro-2-fluoroaniline (900 mg, 4.010 mmol) and propane-1-sulfonyl chloride (1034 µL, 9.222 mmol) in DCM (30 mL) and the mixture was stirred at room temperature for 16 hours. The reaction mixture was quenched with 100 mL of water and the aqueous layer was extracted with DCM (2×40 mL). The organic layers were combined, washed with brine, dried with $Na_2SO_4$, filtered and concentrated to afford N-(3-bromo-5-chloro-2-fluorophenyl)-N-(propylsulfonyl)propane-1-sulfonamide (1.7 g, 95%) that was used directly in the next step without purification.

Step 2: Preparation of N-(3-bromo-5-chloro-2-fluorophenyl)propane-1-sulfonamide. To a solution of N-(3-bromo-5-chloro-2-fluorophenyl)-N-(propylsulfonyl)propane-1-sulfonamide (1.7 g, 4.01 mmol) in acetonitrile (30 mL) was added sodium carbonate (15 mL, 28.5 mmol, 1.9 M) and the reaction was heated to 80° C. for 1 hour. The reaction mixture was concentrated and the pH adjusted to about 3 with 10% aqueous citric acid (50 mL) and EtOAc (50 mL). The layers were separated and the aqueous layer was extracted with EtOAc (3×50 mL). The organic layers were combined, washed with brine (25 mL), dried over $Na_2SO_4$, filtered and concentrated to give a light brown solid which was purified by silica gel chromatography, eluting with hexanes/EtOAc (9:1), to afford N-(3-bromo-5-chloro-2-fluorophenyl)propane-1-sulfonamide as a white solid (1.3 g, 97%). MS (apci, m/z)=327.9, 329.9 (M−H).

Step 3: Preparation of N-(3-bromo-5-chloro-2-fluorophenyl)-N-((2-(trimethylsilyl)-ethoxy)methyl)propane-1-sulfonamide. N-(3-bromo-5-chloro-2-fluorophenyl)propane-1-sulfonamide (1 g, 3.025 mmol) was dissolved in DMF (15 mL) under argon and cooled in an ice bath for 5 minutes. To the reaction mixture was added 60% sodium hydride suspension in mineral oil (0.1331 g, 3.327 mmol) and the reaction mixture was stirred at 0° C. for 30 minutes. (2-(chloromethoxy)ethyl)trimethylsilane (0.644 mL, 3.630 mmol) was added and the ice bath was removed and the reaction mixture was warmed to ambient temperature for 1 hour. The reaction mixture was quenched by the addition of water (50 mL) and the product was extracted with EtOAc (3×50 mL). The organic phases were combined, washed with brine (50 mL), dried over $Na_2SO_4$, filtered and concentrated to give a brown oil, which was purified with silica gel chromatography, eluting with Hexanes/EtOAc (9:1), to afford N-(3-bromo-5-chloro-2-fluorophenyl)-N-((2-(trimethylsilyl)ethoxy)methyl)propane-1-sulfonamide as a clear oil (751.9 mg, 54%). $^1$H NMR (400 MHz, CDCl$_3$) δ 7.60-7.56 (m, 1H), 7.43-7.39 (m, 1H), 4.97 (s, 2H), 3.71-3.63 (m, 2H), 3.12-3.04 (m, 2H), 1.95-1.83 (m, 2H), 1.07 (t, 3H), 0.96-0.88 (m, 2H), 0.02 (s, 9H).

Intermediate P37

Intermediate P38

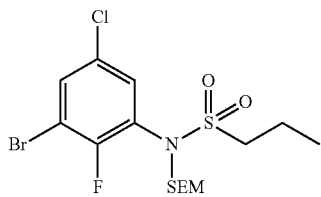 [SMILES: CCCS(=O)(=O)N(COCC[Si](C)(C)C)c1cc(Cl)cc(Br)c1F]

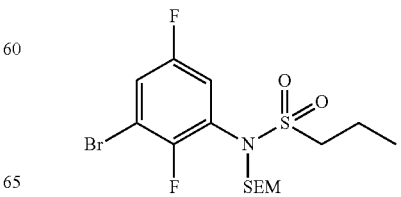

N-(3-bromo-2,5-difluorophenyl)-N-((2-(trimethylsilyl)ethoxy)methyl)propane-1-sulfonamide Step 1: Preparation of N-(3-bromo-2,5-difluorophenyl)-N-(propylsulfonyl)propane-1-sulfonamide. Triethylamine (1.768 mL, 12.68 mmol) was added to a solution of 3-bromo-2,5-difluoroaniline hydrochloride (1 g, 4.091 mmol) and propane-1-sulfonyl chloride (0.963 mL, 8.59 mmol) in DCM (41 mL). The reaction mixture was stirred at ambient temperature for 16 hours then quenched with water (100 mL). The layers were separated, and the aqueous layer was extracted with DCM (2×40 mL). The organic layers were combined, washed with brine (50 mL) and dried over $Na_2SO_4$, filtered and concentrated to afford N-(3-bromo-2,5-difluorophenyl)-N-(propylsulfonyl)propane-1-sulfonamide (1.6 g, 93%) that was used directly in the next step.

Step 2: Preparation of N-(3-bromo-2,5-difluorophenyl)propane-1-sulfonamide. To a solution of N-(3-bromo-2,5-difluorophenyl)-N-(propylsulfonyl)propane-1-sulfonamide (1.6 g, 3.81 mmol) in acetonitrile (30 mL) was added sodium carbonate (15 mL, 26.6 mmol, 1.77 M) and the reaction mixture was heated to 80° C. for 1 hour. The reaction mixture was concentrated to remove acetonitrile the pH adjusted to about 3 with 10% aqueous citric acid (50 mL) and EtOAc (50 mL). The layers were separated, and the aqueous layer was extracted with EtOAc (3×50 mL). The organic layers were combined, washed with brine and dried over $Na_2SO_4$, filtered and concentrated to give a light brown solid that was purified on silica gel, eluting with hexanes/EtOAc (9:1), to afford N-(3-bromo-2,5-difluorophenyl)propane-1-sulfonamide as a white solid (844 mg, 71%). MS (apci, m/z)=311.9, 313.9 (M−H).

Step 3: Preparation of N-(3-bromo-2,5-difluorophenyl)-N-((2-(trimethylsilyl)ethoxy)-methyl)propane-1-sulfonamide. N-(3-bromo-2,5-difluorophenyl)propane-1-sulfonamide (700 mg, 2.228 mmol) was dissolved in DMF (11 mL) under argon and cooled in an ice/water bath for 5 minutes. A 60% sodium hydride suspension in mineral oil (93.58 mg, 2.340 mmol) was added and the reaction mixture was stirred until gas evolution ceased. (2-(Chloromethoxy)ethyl)trimethylsilane (474.3 µL, 2.674 mmol) was added and the reaction mixture was warmed to ambient temperature over 16 hours. The reaction mixture was quenched with water (50 mL) and EtOAc (50 mL). The organic phase was washed with brine, dried over $Na_2SO_4$, filtered, and concentrated to give a brown solid. The solid was purified by silica gel chromatography, eluting with hexanes/EtOAc (1:1) to afford N-(3-bromo-2,5-difluorophenyl)-N-((2-(trimethylsilyl)ethoxy)-methyl)propane-1-sulfonamide as white crystals (801.4 mg, 81%). 1H NMR (400 MHz, $CDCl_3$) δ 7.37-7.32 (m, 1H), 7.21-7.16 (m, 1H), 4.98 (s, 2H), 3.70-3.64 (m, 2H), 3.11-3.05 (m, 2H), 1.94-1.84 (m, 2H), 1.07 (t, 3H), 0.95-0.88 (m, 2H), 0.02 (s, 9H).

Intermediate P39

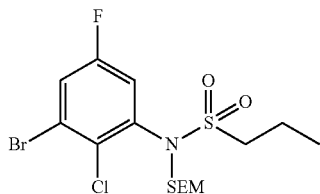 [SMILES: CCCS(=O)(=O)N(COCC[Si](C)(C)C)c1cc(F)cc(Br)c1Cl]

N-(3-bromo-2-chloro-5-fluorophenyl)-N-((2-(trimethylsilyl)ethoxy)methyl)propane-1-sulfonamide Step 1: Preparation of N-(3-bromo-2-chloro-5-fluorophenyl)propane-1-sulfonamide. 3-Bromo-2-chloro-5-fluoroaniline (2.38 g, 10.60 mmol) was dissolved in DCM (105 mL) and then treated sequentially with triethylamine (4.434 mL, 31.81 mmol) and 1-propanesulfonyl chloride (2.615 mL, 23.33 mmol). The reaction mixture was stirred at ambient temperature for 1.5 hours. The reaction mixture was diluted with DCM (250 mL), washed with saturated $NaHCO_3$, dried over $Na_2SO_4$, filtered, and concentrated to dryness. The residue was dissolved in THF (50 mL) and treated with potassium hydroxide (15.91 mL, 31.81 mmol) and allowed to stir at ambient temperature for 30 minutes. The reaction mixture was acidified to about pH 4 using 4.0 M HCl and then extracted with DCM (2×200 mL). The organic layers were combined and dried over $Na_2SO_4$, filtered, and concentrated to dryness. The residue was purified by silica gel chromatography (Hexanes/EtOAc) to provide N-(3-bromo-2-chloro-5-fluorophenyl)propane-1-sulfonamide (3.14 g, 90%). $^1$H NMR (500 MHz, $(CD_3)_2SO$) δ=9.83 (s, 1H), 7.67-7.64 (dd, 1H), 7.40-7.36 (dd, 1H), 3.23-3.19 (m, 2H), 1.79-1.69 (m, 2H), 0.99-0.95 (t, 3H).

Step 2: Preparation of N-(3-bromo-2-chloro-5-fluorophenyl)-N-((2-(trimethylsilyl)ethoxy)-methyl)propane-1-sulfonamide. N-(3-bromo-2-chloro-5-fluorophenyl)propane-1-sulfonamide (3.14 g, 9.50 mmol) was dissolved in DMF (48 mL), cooled with an ice/water bath. A 60% sodium hydride suspension in mineral oil (0.570 g, 14.2 mmol) was added and the reaction stirred until gas evolution ceased. 2-(Trimethylsilyl)ethoxymethyl chloride (2.02 mL, 11.4 mmol) was added and the reaction mixture was warmed to ambient temperature and stirred for 16 hours. The reaction mixture was treated with water (50 mL) and extracted with EtOAc (2×250 mL) and then the combined organic layers were washed with water (3×100 mL) and brine (1×50 mL) and then dried over $Na_2SO_4$, filtered, and concentrated to dryness. The residue was purified by silica gel chromatography, eluting with hexanes/EtOAc to provide N-(3-bromo-2-chloro-5-fluorophenyl)-N-((2-(trimethylsilyl)ethoxy)methyl)propane-1-sulfonamide (4.00 g, 91%). $^1$H NMR (500 MHz, $(CD_3)_2SO$) δ=7.96-7.93 (dd, 1H), 7.63-7.60 (dd, 1H), 5.15-5.10 (m, 1H), 4.83-4.78 (m, 1H), 3.68-3.60 (m, 2H), 3.37-3.28 (m, 2H), 1.83-1.73 (m, 2H), 1.03-1.00 (t, 3H), 0.88-0.84 (t, 2H), 0.00 (s, 9H).

Intermediate P40

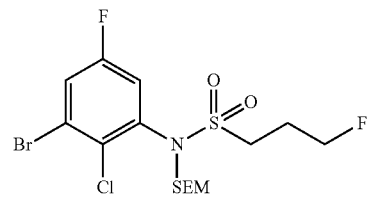 [SMILES: C[Si](C)(C)CCOCN(c1cc(F)cc(Br)c1Cl)S(=O)(=O)CCCF]

N-(3-bromo-2-chloro-5-fluorophenyl)-3-fluoro-N-((2-(trimethylsilyl)ethoxy)methyl)propane-1-sulfonamide Step 1: Preparation of N-(3-bromo-2-chloro-5-fluorophenyl)-3-fluoropropane-1-sulfonamide. 3-Bromo-2-chloro-5- fluoroaniline (1.10 g, 4.90 mmol) was dissolved in DCM (50 mL) and then treated sequentially with triethylamine (2.05 mL, 14.7 mmol) and 3-fluoro-propane-1-sulfonyl chloride (1.28 mL, 10.8 mmol). The reaction mixture was stirred at ambient temperature for 1 hour. The reaction mixture was diluted with additional DCM (100 mL) and washed with saturated NaHCO$_3$ (1×100 mL) and then dried over Na$_2$SO$_4$, filtered, and concentrated to dryness. The residue was dissolved in THF (50 mL) and treated with 2.0 M potassium hydroxide (7.35 mL, 14.7 mmol) and stirred at ambient temperature for 30 minutes. The reaction mixture was acidified to about pH 4 using 4.0 M HCl and then extracted with DCM (2×200 mL) and then the combined organic layers were dried over Na$_2$SO$_4$, filtered, and concentrated to dryness. The residue was purified by silica gel chromatography, eluting with hexanes/EtOAc to provide N-(3-bromo-2-chloro-5-fluorophenyl)-3-fluoropropane-1-sulfonamide (1.29 g, 76%). $^1$H NMR (500 MHz, (CD$_3$)$_2$SO) δ=10.00 (s, 1H), 7.70-7.67 (dd, 1H), 7.41-7.38 (dd, 1H), 4.61-4.58 (t, 1H), 4.49-4.47 (t, 1H), 3.35-3.31 (m, 2H), 2.18-2.05 (m, 2H).

Step 2: Preparation of N-(3-bromo-2-chloro-5-fluorophenyl)-3-fluoro-N-((2-(trimethylsilyl)-ethoxy)methyl)propane-1-sulfonamide. N-(3-bromo-2-chloro-5-fluorophenyl)-3-fluoropropane-1-sulfonamide (1.29 g, 3.70 mmol) was dissolved in DMF (19 mL), cooled to 0° C., and then treated sequentially with sodium hydride (60% suspension in mineral oil, 0.222 g, 5.55 mmol) and 2-(trimethylsilyl)ethoxymethyl chloride (0.788 mL, 4.44 mmol). The reaction mixture was allowed to warm to ambient temperature and stirred for 16 hours. The reaction mixture was treated with water (50 mL) and extracted with EtOAc (2×200 mL) and then the combined organic layers were washed with water (3×100 mL) and brine (1×50 mL) and then dried over Na$_2$SO$_4$, filtered, and concentrated to dryness. The residue was purified by silica gel chromatography (Hexanes/EtOAc) to provide N-(3-bromo-2-chloro-5-fluorophenyl)-3-fluoro-N-((2-(trimethylsilyl)ethoxy)methyl)-propane-1-sulfonamide (1.24 g, 70%). $^1$H NMR (500 MHz, (CD$_3$)$_2$SO) δ=7.98-7.95 (dd, 1H), 7.66-7.63 (dd, 1H), 5.17-5.14 (m, 1H), 4.83-4.80 (m, 1H), 4.65-4.62 (t, 1H), 4.53-4.50 (t, 1H), 3.69-3.60 (m, 2H), 3.51-3.42 (m, 2H), 2.20-2.10 (m, 2H), 0.89-0.85 (m, 2H), 0.00 (s, 9H).

Intermediate P41

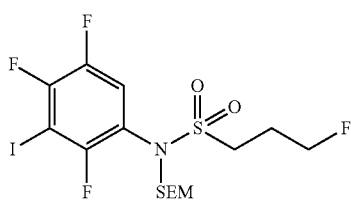 [SMILES: C[Si](C)(C)CCOCN(c1cc(F)c(F)c(I)c1F)S(=O)(=O)CCCF]

3-fluoro-N-(2,4,5-trifluoro-3-iodophenyl)-N-((2-(trimethylsilyl)ethoxy)methyl)propane-1-sulfonamide Step 1: Preparation of 2,4,5-trifluoro-3-iodoaniline. A solution of 2,4,5-trifluoroaniline (3.0 g, 20.394 mmol) in 150 mL of THF was cooled to −78° C. under nitrogen and the solution was treated slowly with n-butyllithium (2.5 M in hexanes, 8.97 mL, 22.43 mmol) and stirred at −78° C. for 15 minutes. Then a solution of 1,2-bis(chlorodimethylsilyl)ethane (4.61 g, 21.4 mmol) in 50 mL THF was slowly added to the reaction and stirred for 15 minutes. Then n-butyllithium (2.5 M in hexanes, 8.97 mL, 22.43 mmol) was slowly added and the reaction mixture was removed from the −78° C. bath and allowed to warm for 30 minutes. The reaction mixture was cooled back to −78° C. and n-butyllithium (2.5 M in hexanes, 8.97 mL, 22.43 mmol) was slowly added and allowed to stir at −78° C. for 30 minutes. Then a solution of iodine (7.764 g, 30.59 mmol) in 50 mL of THF was slowly added and the reaction mixture was allowed to stir at ambient temperature for 1 hour. The solution was quenched with ~10 mL of 4M HCl and stirred for 30 minutes. Then 20 mL of saturated sodium thiosulfate was added and the solution was adjusted to about pH 8 with solid NaHCO$_3$ and stirred for 15 minutes. The solution was quenched with water and extracted with EtOAc. The organic layers were washed with water, brine, dried with Na$_2$SO$_4$, filtered, and concentrated. The crude product was purified by silica, eluting with 10% to 50% EtOAc/hexanes to give 2,4,5-trifluoro-3-iodoaniline (5.1 g, 92%). $^1$H NMR (400 MHz, CDCl$_3$) δ 6.66 (m, 1H), 3.78 (br-s, 2H).

Step 2: Preparation of 3-fluoro-N-(2,4,5-trifluoro-3-iodophenyl)propane-1-sulfonamide. To a solution of 2,4,5-trifluoro-3-iodoaniline (2.5 g, 9.16 mmol) in dichloromethane (45.8 mL) at 0° C. was added 3-fluoropropane-1-sulfonyl chloride (2.29 mL, 19.2 mmol) and triethylamine (3.83 mL, 27.5 mmol) and the mixture was stirred at ambient temperature for 30 minutes. The reaction mixture was quenched with water and extracted with DCM. The organic layers were washed with brine, dried with Na$_2$SO$_4$, filtered, and concentrated. The residue was dissolved in acetonitrile (45.8 mL) and treated with 2.0 M Na$_2$CO$_3$ (36.6 mL, 73.3 mmol) at 60° C. for 45 minutes. The pH was adjusted to about 3 with 10% citric acid. The reaction mixture was quenched with water and extracted with DCM. The organic layers were washed with brine, dried with Na$_2$SO$_4$, filtered, and concentrated to give 3-fluoro-N-(2,4,5-trifluoro-3-iodophenyl)propane-1-sulfonamide (2.72 g, 75%). MS (apci, m/z)=395.9 [M−H].

Step 3: Preparation of 3-fluoro-N-(2,4,5-trifluoro-3-iodophenyl)-N-((2-(trimethylsilyl)ethoxy)-methyl)propane-1-sulfonamide. To a solution of 3-fluoro-N-(2,4,5-trifluoro-3-iodophenyl)-propane-1-sulfonamide (2.72 g, 6.85 mmol) in DMF (34.2 mL) at 0° C. was added sodium hydride (60% suspension in mineral oil, 0.370 g, 9.25 mmol) and (2-(chloromethoxy)ethyl)trimethylsilane (1.46 mL, 8.22 mmol) and the reaction mixture was stirred at ambient temperature for 30 minutes. The reaction mixture was quenched with water and extracted with EtOAc. The organic layers were washed with brine, dried with Na$_2$SO$_4$, filtered, concentrated and the residue was purified by silica gel chromatography, eluting with 5% to 50% EtOAc/hexanes to give 3-fluoro-N-(2,4,5-trifluoro-3-iodophenyl)-N-((2-(trimethylsilyl)ethoxy)methyl)propane-1-sulfonamide (3.11 g, 86%). $^1$H NMR (400 MHz, CDCl$_3$) δ 7.39 (m, 1H), 4.95 (s, 2H), 4.62 (t, 1H), 4.51 (t, 1H), 3.66 (t, 2H), 3.24 (t, 2H), 2.25 (m, 2H), 0.93 (t, 2H), 0.03 (s, 9H).

Intermediate P42

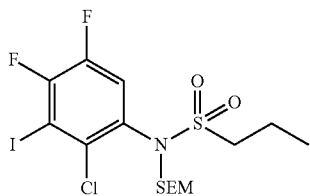 [SMILES: CCCS(=O)(=O)N(COCC[Si](C)(C)C)c1cc(F)c(F)c(I)c1Cl]

N-(2-chloro-4,5-difluoro-3-iodophenyl)-N-((2-(trimethylsilyl)ethoxy)methyl)propane-1-sulfonamide Step 1: Preparation of 2-chloro-4,5-difluoro-3-iodoaniline. 2-Chloro-4,5-difluoroaniline (5.08 g, 31.06 mmol) was dissolved in THF (200 mL) and cooled to −78° C. under a backflow of N₂. The reaction mixture was treated slowly with n-butyllithium (2.5 M in hexanes, 13.667 mL, 34.167 mmol) and allowed to stir at −78° C. for 15 minutes. The reaction mixture was treated dropwise with a THF solution (50 mL) of 1,2-bis(chlorodimethylsilyl)ethane (7.021 g, 32.61 mmol) and allowed to stir at −78° C. for 15 minutes after complete addition. The reaction mixture was treated with additional n-butyllithium (2.5 M in hexanes, 13.667 mL, 34.167 mmol). The ice bath was removed and the reaction mixture allowed to warm for 30 minutes. The reaction mixture was cooled back to −78° C. and treated slowly with additional n-butyllithium (2.5 M in hexanes, 13.667 mL, 34.167 mmol) and allowed to stir at −78° C. for 30 minutes. The reaction mixture was treated dropwise with a THF solution (100 mL) of iodine (11.825 g, 46.591 mmol) and the reaction mixture was allowed to stir at ambient temperature for 1 hour. The solution was quenched with 4M HCl to about pH 1 and stirred for 30 minutes. The solution was adjusted to about pH 8 with solid NaHCO₃ and stirred for 15 minutes. The reaction mixture was treated with 3.0 M sodium thiosulfate and extracted with EtOAc (2×). The organic layers were washed with water, brine, dried with Na₂SO₄, filtered, and concentrated. The crude product was purified by silica gel chromatography (5-50% EtOAc/hex) to give 2-chloro-4,5-difluoro-3-iodoaniline (4.86 g, 54%). ¹H NMR (400 MHz, DMSO) δ 6.83 (m, 1H) 5.75 (s, 2H).

Step 2: Preparation of N-(2-chloro-4,5-difluoro-3-iodophenyl)-N-(propylsulfonyl) propane-1-sulfonamide. To a solution of 2-chloro-4,5-difluoro-3-iodoaniline (2.1 g, 7.255 mmol) in dichloromethane (36.28 mL) at 0° C. was added propane-1-sulfonyl chloride (1.708 mL, 15.24 mmol) and triethylamine (3.034 mL, 21.77 mmol) and the reaction mixture was stirred at ambient temperature for 30 minutes. The reaction mixture was quenched with water and extracted with DCM. The organic layers were washed with brine, dried with Na₂SO₄, filtered, and concentrated to give N-(2-chloro-4,5-difluoro-3-iodophenyl)-N-(propylsulfonyl)propane-1-sulfonamide (3.1 g, 85%) that was used without purification.

Step 3: Preparation of N-(2-chloro-4,5-difluoro-3-iodophenyl)propane-1-sulfonamide. A solution of N-(2-chloro-4,5-difluoro-3-iodophenyl)-N-(propylsulfonyl)propane-1-sulfonamide (3.1 g, 6.2 mmol) in acetonitrile (31 mL) and 2.0 M sodium carbonate (25 mL, 49 mmol) was heated to 60° C. for 90 minutes. The solution was adjusted to about pH 4 with 10% citric acid. The reaction mixture was quenched with water and extracted with DCM. The organic layers were washed with brine, dried with Na₂SO₄, filtered, concentrated, and purified by silica gel chromatography, eluting with 1% to 20% EtOAc/DCM to give N-(2-chloro-4,5-difluoro-3-iodophenyl)propane-1-sulfonamide (0.91 g, 37%). MS (apci, m/z)=393.9 [M−H].

Step 4: Preparation of N-(2-chloro-4,5-difluoro-3-iodophenyl)-N-((2-(trimethylsilyl)ethoxy)-methyl)propane-1-sulfonamide. To a solution of N-(2-chloro-4,5-difluoro-3-iodophenyl)propane-1-sulfonamide (910 mg, 2.30 mmol) in DMF (11.5 mL) at 0° C. was added sodium hydride (60% suspension in mineral oil, 124.2 mg, 3.106 mmol) and (2-(chloromethoxy)ethyl)trimethylsilane (489.6 µL, 2.760 mmol) and the reaction mixture was stirred at 0° C. for 1 hour. The reaction mixture was quenched with water and extracted with EtOAc. The organic layers were washed with brine, dried with Na₂SO₄, filtered, concentrated and the residue was purified by silica gel chromatography, eluting with 5% to 50% EtOAc/hexanes to give N-(2-chloro-4,5-difluoro-3-iodophenyl)-N-((2-(trimethylsilyl)ethoxy)methyl)propane-1-sulfonamide (1118 mg, 92%). ¹H NMR (400 MHz, CDCl₃) δ 7.44 (m, 1H), 5.21 (d, 1H), 4.78 (d, 1H), 3.7 (m, 2H), 3.05 (m, 2H), 1.95 (m, 2H), 1.16 (t, 3H), 1.0 (m, 2H) 0.03 (s, 9H).

Intermediate P44

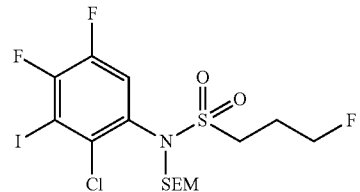 [SMILES: C[Si](C)(C)CCOCN(c1cc(F)c(F)c(I)c1Cl)S(=O)(=O)CCCF]

N-(2-chloro-4,5-difluoro-3-iodophenyl)-3-fluoro-N-((2-(trimethylsilyl)ethoxy)methyl)propane-1-sulfonamide Step 1: Preparation of 2-chloro-4,5-difluoro-3-iodoaniline. 2-Chloro-4,5-difluoroaniline (5.08 g, 31.060 mmol) was dissolved in THF (200 mL) and cooled to −78° C. under a backflow of nitrogen. The reaction mixture was treated slowly with n-butyllithium (2.5 M in hexanes, 13.667 mL, 34.167 mmol) and allowed to stir at −78° C. for 15 minutes. The reaction mixture was treated dropwise with a THF solution (50 mL) of 1,2-bis(chlorodimethylsilyl)ethane (7.021 g, 32.614 mmol) and allowed to stir at −78° C. for 15 minutes after complete addition. The reaction mixture was treated with additional n-butyllithium (2.5 M in hexanes, 13.667 mL, 34.167 mmol) The ice bath was removed and the reaction mixture allowed to warm for 30 minutes. The reaction mixture was cooled back to −78° C. and treated slowly with additional n-butyllithium (2.5 M in hexanes, 13.667 mL, 34.167 mmol) and allowed to stir at −78° C. for 30 minutes. The reaction mixture was treated dropwise with a THF solution (100 mL) of iodine (11.825 g, 46.591 mmol) and the reaction mixture was allowed to stir at ambient temperature for 1 hour. The solution was quenched with 4M HCl to about pH 1 and stirred for 30 minutes. The reaction mixture was adjusted to about pH 8 using solid NaHCO₃. The reaction mixture was treated with 3.0 M sodium thiosulfate and extracted with EtOAc (2×). The organic layers were washed with water, brine, dried with Na₂SO₄, filtered, and concentrated. The crude product was purified by silica gel chromatography, eluting with 5% to 50% EtOAc/hexanes to give 2-chloro-4,5-difluoro-3-iodoaniline (4.86 g, 54%). $^1$H NMR (400 MHz, DMSO) δ 6.83 (m, 1H) 5.75 (s, 2H).

Step 2: Preparation of N-(2-chloro-4,5-difluoro-3-iodophenyl)-3-fluoro-N-((3-fluoropropyl)-sulfonyl)propane-1-sulfonamide. To a solution of 2-chloro-4,5-difluoro-3-iodoaniline (2.1 g, 7.26 mmol) in dichloromethane (36.3 mL) at 0° C. was added 3-fluoropropane-1-sulfonyl chloride (1.81 mL, 15.2 mmol) and triethylamine (3.03 mL, 21.8 mmol). The reaction mixture was stirred at ambient temperature for 45 minutes. The reaction mixture was quenched with water and extracted with DCM. The organic layers were washed with brine, dried with Na$_2$SO$_4$, filtered, and concentrated to give N-(2-chloro-4,5-difluoro-3-iodophenyl)-3-fluoro-N-((3-fluoropropyl)-sulfonyl)propane-1-sulfonamide (3.8 g, 97%) that was used directly in the next step without purification.

Step 3: Preparation of N-(2-chloro-4,5-difluoro-3-iodophenyl)-3-fluoropropane-1-sulfonamide. A solution of N-(2-chloro-4,5-difluoro-3-iodophenyl)-3-fluoro-N-((3-fluoropropyl)sulfonyl)-propane-1-sulfonamide (3.8 g, 7.07 mmol) in acetonitrile (35.3 mL) and 2.0 M sodium carbonate (28.3 mL, 56.5 mmol) was heated to 60° C. for 1 hour. The solution was adjusted to about pH 4 with 10% citric acid. The reaction mixture was quenched with water and extracted with DCM. The organic layers were washed with brine, dried with Na$_2$SO$_4$, filtered, concentrated, and purified by silica, eluting with 1% to 20% EtOAc/DCM to give N-(2-chloro-4,5-difluoro-3-iodophenyl)-3-fluoropropane-1-sulfonamide (2:89 g, 99%). MS (apci, m/z)=411.9 [M–H].

Step 4: Preparation of N-(2-chloro-4,5-difluoro-3-iodophenyl)-3-fluoro-N-((2-(trimethylsilyl)-ethoxy)methyl)propane-1-sulfonamide. To a solution of N-(2-chloro-4,5-difluoro-3-iodophenyl)-3-fluoropropane-1-sulfonamide (2.89 g, 6.99 mmol) in DMF (34.9 mL) at 0° C. was added sodium hydride (60% suspension in mineral oil, 0.377 g, 9.43 mmol) and (2-(chloromethoxy)ethyl)trimethylsilane (1.49 ml, 8.39 mmol) and the reaction mixture was stirred at 0° C. for 45 minutes. The reaction mixture was quenched with water and extracted with EtOAc. The organic layers were washed with brine, dried with Na$_2$SO$_4$, filtered, concentrated and the residue was purified by silica gel chromatography, eluting with 5% to 50% EtOAc/hexanes to give N-(2-chloro-4,5-difluoro-3-iodophenyl)-3-fluoro-N-((2-(trimethylsilyl)ethoxy)methyl)propane-1-sulfonamide (3.46 g, 91%). $^1$H NMR (400 MHz, CDCl$_3$) δ 7.48 (m, 1H), 5.21 (d, 1H), 4.78 (d, 1H), 4.65 (t, 1H), 4.58 (t, 1H), 3.7 (m, 2H), 3.3 (t, 2H), 2.3 (m, 2H), 0.95 (m, 2H), 0.02 (s, 9H).

Intermediate P45

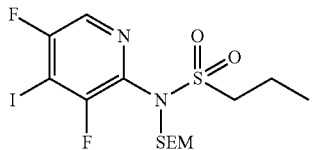 [SMILES: CCCS(=O)(=O)N(COCC[Si](C)(C)C)c1ncc(F)c(I)c1F]

N-(3,5-difluoro-4-iodopyridin-2-yl)-N-((2-(trimethylsilyl)ethoxy)methyl)propane-1-sulfonamide Step 1: Preparation of 3,5-difluoro-4-iodopyridin-2-amine-2-Amino-3,5-difluoropyridine (7.07 g, 54.3 mmol) was dissolved in THF (250 mL) and cooled to –78° C. The reaction mixture was treated with a 2.5 M solution of n-butyllithium in hexanes (54.3 mL, 136 mmol) and allowed to stir at –78° C. for 1 hour after complete addition. The reaction mixture was treated dropwise with a 50 mL THF solution of iodine (41.4 g, 163 mmol) and stirred at ambient temperature for 30 minutes. The reaction mixture was quenched with 10% sodium thiosulfate and extracted with EtOAc (2×). The organic layers were washed with water and brine. The organic layers were dried over Na$_2$SO$_4$, filtered, concentrated, and purified by silica gel chromatography, eluting with 5% to 60% hexanes/acetone) to give 3,5-difluoro-4-iodopyridin-2-amine (8.5 g, 61%). MS (apci, m/z)=257.0 [M+H].

Step 2: Preparation of N-(3,5-difluoro-4-iodopyridin-2-yl)-N-(propylsulfonyl)propane-1-sulfonamide. Triethylamine (1.134 mL, 8.138 mmol) was added to 3,5-difluoro-4-iodopyridin-2-amine (0.992 g, 3.875 mmol) and propane-1-sulfonyl chloride (0.912 mL, 8.138 mmol) in DCM (38.75 mL) and the mixture was stirred at ambient temperature overnight. The reaction mixture was quenched with water and extracted with DCM. The organic extracts were washed with brine and dried with Na$_2$SO$_4$ and concentrated to give N-(3,5-difluoro-4-iodopyridin-2-yl)-N-(propylsulfonyl)propane-1-sulfonamide (1.8 g, 99%) that was used directly in the next step without purification.

Step 3: Preparation of N-(3,5-difluoro-4-iodopyridin-2-yl)propane-1-sulfonamide. A solution of N-(3,5-difluoro-4-iodopyridin-2-yl)-N-(propylsulfonyl)propane-1-sulfonamide (1.8 g, 3.84 mmol) in acetonitrile (19.2 mL) and 2.0 M sodium carbonate (13.5 mL, 26.9 mmol) was heated to 80° C. for 1 hour. The solution was adjusted to about pH 3 with 10% citric acid. The reaction mixture was quenched with water and extracted with DCM. The organic layers were washed with brine, dried with Na$_2$SO$_4$, filtered, concentrated, and purified by silica gel chromatography, eluting with 5% to 95% EtOAc/DCM to give N-(3,5-difluoro-4-iodopyridin-2-yl)propane-1-sulfonamide (0.664 g, 48%). MS (apci, m/z)=363.0 [M+H].

Step 4: Preparation of N-(3,5-difluoro-4-iodopyridin-2=yl)-N-((2-(trimethylsilyl)ethoxy)-methyl)propane-1-sulfonamide. To a solution of N-(3,5-difluoro-4-iodopyridin-2-yl)propane-1-sulfonamide (661 mg, 1.83 mmol) in DMF (9.1 mL) at 0° C. was added 60% sodium hydride as a suspension in mineral oil (98.6 mg, 2.46 mmol) and (2-(chloromethoxy)ethyl)trimethylsilane (388 μL, 2.19 mmol) and the reaction mixture was stirred at room temperature for 1 hour. The reaction mixture was quenched with water and extracted with EtOAc. The organic layers were washed with brine, dried with Na$_2$SO$_4$, filtered, concentrated and the residue was purified by silica gel chromatography, eluting with 5% to 50% EtOAc/hexanes to give N-(3,5-difluoro-4-iodopyridin-2-yl)-N-((2-(trimethylsilyl)ethoxy)methyl)propane-1-sulfonamide (808 mg, 90%) as an oil. $^1$H NMR (400 MHz, CDCl$_3$) δ 8.07 (s, 1H), 5.10 (s, 2H), 3.68 (t, 2H), 3.34 (t, 2H), 1.95 (m, 2H) 1.09 (t, 2H), 0.89 (t, 3H), 0.02 (s, 9H); MS (apci, m/z)=493.1 [M+H].

Intermediate P46

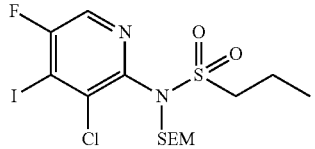

N-(3,5-difluoro-4-iodopyridin-2-yl-N-((2-(trimethylsilyl)ethoxy)methyl)propane-1-sulfonamide Step 1: Preparation of 3-chloro-5-fluoro-4-iodopyridin-2-amine. To a 500 mL flask was added 3-chloro-5-fluoropyridin-2-amine (5.67 g, 38.7 mmol) and tetrahydrofuran (193 mL). The solution was cooled to −78° C. and was treated with the dropwise addition of a 2.5 M solution of n-butyllithium in hexanes (38.7 mL, 96.7 mmol) and stirred at −78° C. for 1 hour. A solution of iodine (29.5 g, 116 mmol) in tetrahydrofuran (59.3 mL) was added dropwise from an addition funnel. The reaction mixture was allowed to warm to ambient temperature and stirred for 30 minutes. The reaction mixture was quenched with saturated aqueous Na$_2$S2O$_3$ and extracted with EtOAc. The organic layers were washed with brine, dried over Na$_2$SO$_4$, filtered, concentrated, and purified by silica gel chromatography, eluting with 0% to 95% acetone/DCM to give 3-chloro-5-fluoro-4-iodopyridin-2-amine (5.7 g, 54%). MS (apci, m/z)=272.9 [M+H].

Step 2: Preparation of N-(3-chloro-5-fluoro-4-iodopyridin-2-yl)-N-(propylsulfonyl)propane-1-sulfonamide. To a solution of 3-chloro-5-fluoro-4-iodopyridin-2-amine (4.0 g, 14.68 mmol) and propane-1-sulfonyl chloride (3.456 mL, 30.83 mmol) in dichloromethane (73.41 mL) was added triethylamine (4.297 mL, 30.83 mmol) and the mixture was stirred at ambient temperature overnight. The reaction mixture was quenched with water and extracted with DCM. The organic layers were washed with brine, dried with Na$_2$SO$_4$, filtered, and concentrated to give N-(3-chloro-5-fluoro-4-iodopyridin-2-yl)-N-(propylsulfonyl)propane-1-sulfonamide (7 g, 98%) which was used directly in the next step without purification. MS (apci, m/z)=485.0 [M+H].

Step 3: Preparation of N-(3-chloro-5-fluoro-4-iodopyridin-2-yl)propane-1-sulfonamide. A solution of N-(3-chloro-5-fluoro-4-iodopyridin-2-yl)-N-(propylsulfonyl)propane-1-sulfonamide (7.0 g, 14 mmol) in acetonitrile (72 mL) and 2.0 M Na$_2$CO$_3$ (51 mL, 101 mmol) was stirred at ambient temperature for 60 hours and then heated to 70° C. for 90 minutes. The solution was adjusted to about pH 3 with 10% citric acid. The reaction mixture was quenched with water and extracted with DCM. The reaction mixture was The organic layers were washed with brine, dried with Na$_2$SO$_4$, filtered, concentrated, and purified by silica, eluting with 5% to 75% EtOAc/hexanes to give N-(3-chloro-5-fluoro-4-iodopyridin-2-yl)propane-1-sulfonamide (4.3 g, 79%). MS (apci, m/z)=378.9 [M+H].

Step 4: Preparation of N-(3-chloro-5-fluoro-4-iodopyridin-2-yl)-N-((2-(trimethylsilyl)-ethoxy)methyl)propane-1-sulfonamide. To a solution of N-(3-chloro-5-fluoro-4-iodopyridin-2-yl)propane-1-sulfonamide (4.30 g, 11.4 mmol) in DMF (56.8 mL) at 0° C. was added 60% sodium hydride as a suspension in mineral oil (0.613 g, 15.3 mmol) and (2-(chloromethoxy)ethyl)trimethylsilane (2.42 mL, 13.6 mmol) and the reaction mixture was stirred at room temperature for 1 hour. The reaction mixture was quenched with water and extracted with EtOAc. The organic layers were washed with brine, dried with Na$_2$SO$_4$, filtered, concentrated and the residue was purified by silica gel chromatography, eluting with 5% to 50% EtOAc/hexanes to give N-(3-chloro-5-fluoro-4-iodopyridin-2-yl)-N-((2-(trimethylsilyl)ethoxy)methyl)propane-1-sulfonamide (4.08 g, 71%) as an oil. $^1$H NMR (400 MHz, CDCl$_3$) δ 8.13 (s, 1H), 5.06 (s, 2H), 3.68 (t, 2H), 3.38 (t, 2H), 1.95 (m, 2H) 1.09 (t, 2H), 0.89 (t, 3H), 0.02 (s, 9H); MS (apci, m/z)=509.1 [M+H].

Intermediate P47

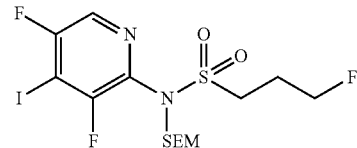 [SMILES: C[Si](C)(C)CCOCN(c1ncc(F)c(I)c1F)S(=O)(=O)CCCF]

N-(3,5-difluoro-4-iodopyridin-2-yl)-3-fluoro-N-((2-(trimethylsilyl)ethoxy)methyl)propane-1-sulfonamide Step 1: Preparation of 3,5-difluoro-4-iodopyridin-2-amine. 2-Amino-3,5-difluoropyridine (7.07 g, 54.3 mmol) was dissolved in THF (250 mL) and cooled to −78° C. The reaction mixture was treated with a 2.5 M solution of n-butyllithium in hexanes (54.3 mL, 136 mmol) and allowed to stir at −78° C. for 1 hour after complete addition. The reaction mixture was treated dropwise with a 50 mL THF solution of iodine (41.4 g, 163 mmol) and stir at ambient temperature for 30 minutes. The reaction mixture was quenched with 10% sodium thiosulfate and extracted with EtOAc (2×). The organic layers were washed with water and brine. The organic layers were dried over Na$_2$SO$_4$, filtered, concentrated, and purified by silica gel chromatography, eluting with 5% to 60% hexanes/acetone to give 3,5-difluoro-4-iodopyridin-2-amine (8.5 g, 61%). MS (apci, m/z)=257.0 [M+H].

Step 2: Preparation of N-(3,5-difluoro-4-iodopyridin-2-yl)-3-fluoro-N-((3-fluoropropyl)-sulfonyl)propane-1-sulfonamide. To a solution of 3,5-difluoro-4-iodopyridin-2-amine (1.40 g, 5.47 mmol) and 3-fluoropropane-1-sulfonyl chloride (1.43 mL, 12.0 mmol) in dichloromethane (27.3 mL) was added triethylamine (2.29 mL, 16.4 mmol) and the mixture was stirred at ambient temperature for 45 minutes. The reaction mixture was quenched with water and extracted with DCM. The organic layers were washed with brine, dried with Na$_2$SO$_4$, filtered, and concentrated to give N-(3,5-difluoro-4-iodopyridin-2-yl)-3-fluoro-N-((3-fluoropropyl)sulfonyl)propane-1-sulfonamide (2.7 g, 98%) that was used directly in the next step without purification. MS (apci, m/z)=504.9 [M+H].

Step 3: Preparation of N-(3,5-difluoro-4-iodopyridin-2-yl)-3-fluoropropane-1-sulfonamide. A solution of N-(3,5-difluoro-4-iodopyridin-2-yl)-3-fluoro-N-((3-fluoropropyl)sulfonyl)propane-1-sulfonamide (2.7 g, 5.4 mmol) in acetonitrile (27 mL) and 2.0 M sodium carbonate (21 mL, 43 mmol) was heated to 60° C. for 90 minutes. The solution was adjusted to about pH 4 with 10% citric acid. The reaction mixture was quenched with water and extracted with DCM. The organic layers were washed with brine, dried with Na$_2$SO$_4$, filtered, concentrated, and purified by silica gel chromatography, eluting with 1% to 20% EtOAc/DCM to give N-(3,5-difluoro-4-iodopyridin-2-yl)-3-fluoropropane-1-sulfonamide (1.6 g, 79%). MS (apci, m/z)=380.9 [M+H].

Step 4: Preparation of N-(3,5-difluoro-4-iodopyridin-2-yl)-3-fluoro-N-((2-(trimethylsilyl)-ethoxy)methyl)propane-1-sulfonamide. To a solution of N-(3,5-difluoro-4-iodopyridin-2-yl)-3-fluoropropane-1-sulfonamide (1.6 g, 4.209 mmol) in DMF (21.05 mL) at 0° C. was added sodium hydride (60% suspension in mineral oil, 0.2273 g, 5.682 mmol) and then (2-(chloromethoxy)ethyl)trimethylsilane (0.8959 mL, 5.051 mmol) and the reaction mixture was stirred at 0° C. for 30 minutes. The reaction mixture was quenched with water and extracted with EtOAc. The organic layers were washed with brine, dried with Na₂SO₄, filtered, concentrated and the residue was purified by silica gel chromatography, eluting with 5% to 50% EtOAc/hexanes to give N-(3,5-difluoro-4-iodopyridin-2-yl)-3-fluoro-N-((2-(trimethylsilyl)ethoxy)methyl)propane-1-sulfonamide (1.97 g, 92%) as an oil. ¹H NMR (400 MHz, CDCl₃) δ 8.08 (s, 1H), 5.10 (s, 2H), 4.66 (t, 1H), 4.54 (t, 1H), 3.68 (t, 2H), 3.55 (t, 2H), 2.34 (m, 2H) 1.09 (t, 2H), 0.89 (t, 3H) 0.01 (s, 9H); MS (apci, m/z)=511.0 [M+H].

Intermediate P48

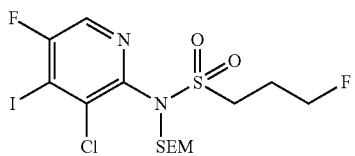 [SMILES: C[Si](C)(C)CCOCN(c1ncc(F)c(I)c1Cl)S(=O)(=O)CCCF]

N-(3-chloro-5-fluoro-4-iodopyridin-2-yl)-3-fluoro-
N-((2-(trimethylsilyl)ethoxy)methyl)propane-1-
sulfonamide Step 1: Preparation of 3-chloro-5-fluoro-4-iodopyridin-2-amine. To a 500 mL flask was added 3-chloro-5-fluoropyridin-2-amine (5.67 g, 38.7 mmol) and tetrahydrofuran (193 mL). The solution was cooled to −78° C. and was treated with the dropwise addition of a 2.5 M solution of n-butyllithium in hexanes (38.7 mL, 96.7 mmol) and stirred at −78° C. for 1 hour. Then a solution of iodine (29.5 g, 116 mmol) in tetrahydrofuran (59.3 mL) was added dropwise from an addition funnel and the reaction mixture was allowed to warm to ambient temperature and stirred for 30 minutes. The reaction mixture was quenched with saturated aqueous Na₂S₂O₃ and extracted with EtOAc. The organic layers were washed with brine, dried over Na₂SO₄, filtered, concentrated, and purified by silica gel chromatography, eluting with 0 to 95% acetone/DCM) to give 3-chloro-5-fluoro-4-iodopyridin-2-amine (5.7 g, 54%). MS (apci, m/z)=272.9 [M+H].

Step 2: Preparation of N-(3-chloro-5-fluoro-4-iodopyridin-2-yl)-3-fluoro-N-((3-fluoropropyl)-sulfonyl)propane-1-sulfonamide. To a solution of 3-chloro-5-fluoro-4-iodopyridin-2-amine (1.28 g, 4.698 mmol) and 3-fluoropropane-1-sulfonyl chloride (1.362 mL, 11.75 mmol) in dichloromethane (23.49 mL) was added triethylamine (1.637 mL, 11.75 mmol) and the mixture was stirred at ambient temperature for 1 hour. The reaction mixture was quenched with water and extracted with DCM. The reaction mixture was The organic layers were washed with brine, dried with Na₂SO₄, filtered, and concentrated to give N-(3-chloro-5-fluoro-4-iodopyridin-2-yl)-3-fluoro-N-((3-fluoropropyl)sulfonyl)propane-1-sulfonamide (1.85 g, 76%) that was used directly in the next step without purification. MS (apci, m/z)=520.9 [M+H].

Step 3: Preparation of N-(3-chloro-5-fluoro-4-iodopyridin-2-yl)-3-fluoropropane-1-sulfonamide. A solution of N-(3-chloro-5-fluoro-4-iodopyridin-2-yl)-3-fluoro-N-((3-fluoropropyl)sulfonyl)-propane-1-sulfonamide (1.85 g, 3.55 mmol) in acetonitrile (17.8 mL) and 2.0 M Na₂CO₃ (12.4 mL, 24.9 mmol) was heated to 60° C. for 90 minutes. The solution was adjusted to about pH 3 with 10% citric acid. The reaction mixture was quenched with water and extracted with DCM. The organic layers were washed with brine, dried with Na₂SO₄, filtered, concentrated, and purified by silica gel chromatography, eluting with 5% to 95% EtOAc/hexanes to give N-(3-chloro-5-fluoro-4-iodopyridin-2-yl)-3-fluoropropane-1-sulfonamide (1.01 g, 72%). MS (apci, m/z)=396.9 [M+H].

Step 4: Preparation of N-(3-chloro-5-fluoro-4-iodopyridin-2-yl)-3-fluoro-N-((2-(trimethylsilyl)-ethoxy)methyl)propane-1-sulfonamide. To a solution of N-(3-chloro-5-fluoro-4-iodopyridin-2-yl)-3-fluoropropane-1-sulfonamide (1.01 g, 2.55 mmol) in DMF (12.7 mL) at 0° C. was added sodium hydride (60% suspension in mineral oil, 0.138 g, 3.44 mmol) and (2-(chloromethoxy)ethyl)trimethylsilane (0.542 mL, 3.06 mmol) and The reaction mixture was stirred at 0° C. for 2 hours. The reaction mixture was quenched with water and extracted with EtOAc. The organic layers were washed with brine, dried with Na₂SO₄, filtered, concentrated and the residue was purified by silica gel chromatography, eluting with 5% to 50% EtOAc/hexanes to give N-(3-chloro-5-fluoro-4-iodopyridin-2-yl)-3-fluoro-N-((2-(trimethylsilyl)ethoxy)methyl)propane-1-sulfonamide (0.912 g, 68%) as an oil. ¹H NMR (400 MHz, CDCl₃) δ 8.14 (s, 1H), 5.06 (s, 2H), 4.65 (t, 1H), 4.54, (t, 1H), 3.66 (t, 2H), 3.59 (t, 2H), 2.34 (m, 2H) 1.09 (t, 2H), 0.89 (t, 3H) 0.01 (s, 9H); MS (apci, m/z)=526.9 [M+H].

Intermediate P49

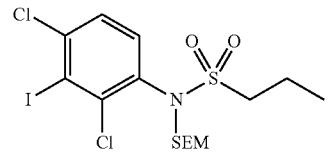 [SMILES: CCCS(=O)(=O)N(COCC[Si](C)(C)C)c1ccc(Cl)c(I)c1Cl]

N-(2,4-dichloro-3-iodophenyl)-N-((2-(trimethylsilyl)
ethoxy)methyl)propane-1-sulfonamide Step 1: Preparation of 2,4-dichloro-3-iodoaniline. A solution of 2,4-dichloroaniline (2.0 g, 12.345 mmol) in 80 mL of THF was cooled to −78° C. under nitrogen and the solution was treated slowly with n-butyllithium (2.5 M in hexanes, 5.432 mL, 13.579 mmol) and stirred at −78° C. for 15 minutes. Then a solution of 1,2-bis(chlorodimethylsilyl)ethane (2.790 g, 12.962 mmol) in 30 mL of THF was added to the reaction and the mixture was stirred at −78° C. for 15 minutes n-butyllithium (2.5 M in hexanes, 5.432 mL, 13.579 mmol) was slowly added and the reaction mixture was removed from the −78° C. bath and allowed to warm for 30 minutes. The reaction mixture was cooled back to −78° C. and n-butyllithium (2.5 M in hexanes, 5.432 mL, 13.579 mmol) was slowly added and allowed to stir at −78° C. for 20 minutes. Then a solution of iodine (4.70 g, 18.517 mmol) in 30 mL of THF was slowly added and the reaction mixture was allowed to stir at ambient temperature for 1 hour. The solution was quenched with −10 mL of 4M HCl and stirred for 30 minutes. Then 20 mL of saturated sodium thiosulfate was added and the solution was adjusted to about pH 8 with solid NaHCO₃ and stirred for 15 minutes. The reaction mixture was quenched with water and extracted with EtOAc. The organic layers were washed with water, brine, dried with Na₂SO₄, filtered; and concentrated. The crude product was purified by silica gel chromatography, eluting with 10% to 50% EtOAc/hexanes to give 2,4-dichloro-3-iodoaniline (1.35 g, 38%). MS (apci, m/z)=287.9 [M+H].

Step 2: Preparation of N-(2,4-dichloro-3-iodophenyl)propane-1-sulfonamide. To a solution of 2,4-dichloro-3-iodoaniline (1.35 g, 4:69 mmol) in dichloromethane (23.4 mL) at 0° C. was added triethylamine (1.96 mL, 14.1 mmol) and propane-1-sulfonyl chloride (1.11 mL-9.85 mmol) and the mixture was stirred at ambient temperature for 1 hour. The reaction mixture was quenched with water and extracted with DCM. The combined organic layers were concentrated, and the residue was dissolved in acetonitrile (23.4 mL), treated with 2.0 M $Na_2CO_3$ (18.8 mL, 37.5 mmol) and stirred at 60° C. for 16 hours. The solution was adjusted to about pH 5 with 10% citric acid. The reaction mixture was quenched with water and extracted with DCM. The organic layers were washed with brine, dried with $Na_2SO_4$, filtered, and concentrated to give N-(2,4-dichloro-3-iodophenyl)propane-1-sulfonamide (1.8 g, 97%). MS (apci, m/z)=391.9 [M−H].

Step 3: Preparation of N-(2,4-dichloro-3-iodophenyl)-N-((2-(trimethylsilyl)ethoxy)methyl)-propane-1-sulfonamide. To a solution of N-(2,4-dichloro-3-iodophenyl)propane-1-sulfonamide (1.8 g, 4.57 mmol) in DMF (30.5 mL) at 0° C. was added sodium hydride (60% suspension in mineral oil, 0.247 g, 6.17 mmol) and then (2-(chloromethoxy)ethyl)trimethylsilane (0.917 mL, 5.48 mmol) and the solution was allowed to stir at ambient temperature for 45 minutes. The reaction mixture was quenched with water and extracted with EtOAc. The combined organic layers were concentrated and the residue was purified by silica gel chromatography, eluting with 10% to 50% EtOAc/hexanes to give N-(2,4-dichloro-3-iodophenyl)-N-((2-(trimethylsilyl)ethoxy)methyl)propane-1-sulfonamide (2.3 g, 96%). $^1$H NMR (400 MHz, $CDCl_3$) δ 7.45 (s, 1H), 7.25 (s, 1H), 5.21 (d, 1H), 4.77 (d, 1H), 3.68 (m, 2H), 3.09 (t, 2H), 1.91 (m, 2H), 1.05 (t, 3H), 0.91 (m, 2H), 0.01 (s, 9H).

Intermediate P50

N-(3,5-dichloro-4-iodopyridin-2-yl)-N-((2-(trimethylsilyl)ethoxy)methyl)propane-1-sulfonamide Step 1: Preparation of 3,5-dichloro-4-iodopyridin-2-amine. A solution of 3,5-dichloropyridin-2-amine (2.9 g, 17.791 mmol) in 150 mL of THF was cooled to −78° C. under $N_2$ and the solution was treated slowly with n-butyllithium (2.5 M in hexanes, 7.83 mL, 19.570 mmol) and stirred at −78° C. for 15 minutes. Then a solution of 1,2-bis(chlorodimethylsilyl)ethane (4.021 g, 18.681 mmol) in 50 mL of THF was slowly added to the reaction and the mixture was stirred at −78° C. for 15 minutes. Then n-butyllithium (2.5 M in hexanes, 7.83 mL, 19.570 mmol) was slowly added and the reaction mixture was removed from the −78° C. bath and allowed to warm for 30 minutes. The reaction mixture was cooled back to −78° C. and n-butyllithium (2.5 M in hexanes, 7.83 mL, 19.570 mmol) was slowly added and the mixture was stirred at −78° C. for 20 minutes. A solution of iodine (6.773 g, 26.687 mmol) in 50 mL of THF was slowly added and the reaction mixture was allowed to stir at ambient temperature for 1 hour. The solution was quenched with about 10 mL of 4M HCl and stirred for 30 minutes. Then 20 mL of saturated sodium thiosulfate was added and the solution was adjusted to about pH 8 with solid $NaHCO_3$ and stirred for 15 minutes. The reaction mixture was quenched with water and extracted with EtOAc. The organic layers were washed with water, brine, dried with $Na_2SO_4$, filtered, and concentrated. The crude was purified by silica gel chromatography (10-50% EtOAc/hex) to give 3,5-dichloro-4-iodopyridin-2-amine (3.35 g, 65%). MS (apci, m/z)=288.9 [M+H].

Step 2: Preparation of N-(3,5-dichloro-4-iodopyridin-2-yl)propane-1-sulfonamide. To a solution of 3,5-dichloro-4-iodopyridin-2-amine (3.35 g, 11.6 mmol) in dichloromethane (58.0 mL) at 0° C. was added propane-1-sulfonyl chloride (2.73 mL, 24.4 mmol) and triethylamine (4.85 mL, 34.8 mmol) and the mixture was stirred at ambient temperature for 16 hours. The reaction mixture was quenched with water and extracted with DCM. The combined organic layers were concentrated and the residue was dissolved in acetonitrile (58.0 mL) and treated with 2.0 M $Na_2CO_3$ (46.4 mL, 92.8 mmol) at 60° C. for 4 hours. The solution was adjusted to pH ~5 with 10% citric acid. The reaction mixture was quenched with water and extracted with DCM. The combined organic layers were concentrated and the residue was purified by silica gel chromatography, eluting with 5% to 50% EtOAc/hexanes to give N-(3,5-dichloro-4-iodopyridin-2-yl)propane-1-sulfonamide (1.85 g, 40%). MS (apci, m/z)=394.9 [M+H].

Step 3: Preparation of N-(3,5-dichloro-4-iodopyridin-2-yl)-N-((2-(trimethylsilyl)ethoxy)-methyl)propane-1-sulfonamide. To a solution of N-(3,5-dichloro-4-iodopyridin-2-yl)propane-1-sulfonamide (1.85 g, 4.68 mmol) in DMF (23.4 mL) at 0° C. was added sodium hydride (60% suspension in mineral oil, 0.253 g, 6.32 mmol) and (2-(chloromethoxy)ethyl)trimethylsilane (0.997 mL, 5.62 mmol) and the reaction mixture was stirred at ambient temperature for 30 minutes. The reaction mixture was quenched with water and extracted with EtOAc. The organic layers were washed with brine, dried with $Na_2SO_4$, filtered, concentrated and the residue was purified by silica gel chromatography, eluting with 5% to 50% EtOAc/hexanes to give N-(3,5-dichloro-4-iodopyridin-1-yl)-N-((2-(trimethylsilyl)ethoxy)methyl)propane-1-sulfonamide (1.94 g, 79%). MS (apci, m/z)=525.0 [M+H].

Intermediate P51

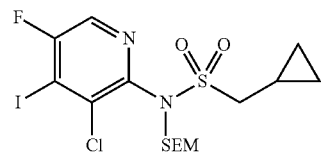 [SMILES: C[Si](C)(C)CCOCN(c1ncc(F)c(I)c1Cl)S(=O)(=O)CC1CC1]

N-(3-chloro-5-fluoro-4-iodopyridin-2-yl)-1-cyclopropyl-N-((2-(trimethylsilyl)ethoxy)-methyl)methanesulfonamide Step 1: Preparation of N-(3-chloro-5-fluoro-4-iodopyridin-2-yl)-1-cyclopropyl-N-((cyclopropyl-methyl)sulfonyl)

methanesulfonamide. Triethylamine (1.586 mL, 11.38 mmol) was added to a solution of 3-chloro-5-fluoro-4-iodopyridin-2-amine (1 g, 3.670 mmol) and cyclopropylmethanesulfonyl chloride (0.9008 mL, 7.708 mmol) in DCM (37 mL) at 0° C. The reaction mixture was stirred at 0° C. for 10 minutes then heated to 40° C. for 16 hours. The reaction mixture was quenched with 100 mL of water and extracted with DCM (2×40 mL). The organic layers were combined, washed with brine and dried with $Na_2SO_4$. The solution was filtered and concentrated to give N-(3-chloro-5-fluoro-4-iodopyridin-2-yl)-1-cyclopropyl-N-((cyclopropylmethyl)-sulfonyl)methanesulfonamide (1.68 g, 90%) that was used directly in the next step without purification.

Step 2: Preparation of N-(3-chloro-5-fluoro-4-iodopyridin-2-yl)-1-cyclopropylmethane-sulfonamide. A solution of N-(3-chloro-5-fluoro-4-iodopyridin-2-yl)-1-cyclopropyl-N-((cyclopropylmethyl)sulfonyl)methanesulfonamide (1.68 g, 3.30 mmol) in acetonitrile (40 mL) and sodium carbonate monohydrate (15 mL, 23.1 mmol, 1.54 M) was heated to 80° C. for one hour. The reaction mixture was concentrated to remove acetonitrile and the pH was adjusted to about 3 with 10% citric acid in water. The product was extracted with DCM (3×50 mL) and the organic extracts were combined, dried over sodium sulfate, filtered and concentrated to give a dark brown solid that was purified by silica gel chromatography eluting with 90% DCM/10% EtOAc to afford N-(3-chloro-5-fluoro-4-iodopyridin-2-yl)-1-cyclopropyl-methanesulfonamide (400 mg, 31%). MS (apci, m/z)=390.9 (M+H).

Step 3: Preparation of N-(3-chloro-5-fluoro-4-iodopyridin-2-yl)-1-cyclopropyl-N-((2-(trimethyl-silyl)ethoxy)methyl)methanesulfonamide. N-(3-chloro-5-fluoro-4-iodopyridin-2-yl)-1-cyclo-propylmethanesulfonamide (400 mg, 1.024 mmol) was dissolved in DMF (5.1 mL). The solution was cooled to 0° C. using an ice bath and sodium hydride (60% suspension in mineral oil, 43.01 mg, 1.075 mmol) was added. The reaction mixture was allowed to stir at 0° C. for 15 min and (2-(chloromethoxy)ethyl)trimethylsilane (218.0 μL, 1.229 mmol) was added dropwise. The reaction mixture was stirred at ambient temperature for 2 hours and then quenched with water and extracted with EtOAc. The organic phase was dried over $Na_2SO_4$, filtered and concentrated. The crude mixture was purified silica gel chromatography, eluting with 0 to 100% EtOAc/Hex to afford N-(3-chloro-5-fluoro-4-iodopyridin-2-yl)-1-cyclopropyl-N-((2-(trimethylsilyl)ethoxy)methyl)-methanesulfonamide as a yellow oil (317.3 mg, 59%). MS (apci, m/z) =521.0 (M+H).

4-iodopyridin-2-amine (1 g, 3.670 mmol) and ethanesulfonyl chloride (0.7303 mL, 7.708 mmol) in DCM (37 mL) at 0° C. The reaction mixture was stirred at 0° C. for 10 minutes and then allowed to warm to ambient temperature overnight. The reaction mixture was quenched with water (100 mL) and the aqueous layer was extracted with DCM (2×40 mL). The organic layers were combined and washed with brine and then dried over $Na_2SO_4$, filtered, and concentrated to give N-(3-chloro-5-fluoro-4-iodopyridin-2-yl)-N-(ethylsulfonyl)ethanesulfonamide (1.5 g, 89%) that was used directly in the next step without purification.

Step 2: Preparation of N-(3-chloro-5-fluoro-4-iodopyridin-2-yl)ethanesulfonamide. To a solution of N-(3-chloro-5-fluoro-4-iodopyridin-2-yl)-N-(ethylsulfonyl)ethanesulfonamide (1.5 g, 3.29 mmol) in acetonitrile (30 mL) was added a 15 mL aqueous solution of sodium carbonate mono hydrate (2.9 g, 23.0 mmol) and the reaction mixture was heated to 80° C. for 1 hour. The reaction mixture was cooled to ambient temperature and concentrated to remove acetonitrile and then treated with a 10% aqueous citric acid solution (50 mL) followed by EtOAc (50 mL). The layers were separated and the aqueous was extracted with additional EtOAc and the organic extracts were combined and washed with brine and dried over $Na_2SO_4$, filtered, and concentrated to give a light brown solid that was purified with silica gel chromatography (DCM/EtOAc) to afford N-(3-chloro-5-fluoro-4-iodopyridin-2-yl)ethanesulfonamide (623 mg, 41%). MS (apci, m/z)=364.8 (M+H).

Step 3: Preparation of N-(3-chloro-5-fluoro-4-iodopyridin-2-yl)-N-((2-(trimethylsilyl)ethoxy)-methyl)ethanesulfonamide. N-(3-chloro-5-fluoro-4-iodopyridin-2-yl)ethanesulfonamide (623 mg, 1.71 mmol) was dissolved in DMF (11 mL) and cooled in an ice water bath for 5 minutes under an argon atmosphere. Sodium hydride (60% suspension in mineral oil, 75.19 mg, 1.88 mmol) was added to the solution and the reaction mixture was stirred until gas evolution ceased and then treated with (2-(chloromethoxy)ethyl)trimethylsilane (363.7 μL, 2.05 mmol). The reaction mixture was allowed to warm to ambient temperature and stirred for 74 hour, then heated to 40° C. for 6 hours. The reaction mixture was quenched with water (50 mL) and then extracted EtOAc (50 mL). The organic phase was washed with brine, dried with $Na_2SO_4$, filtered, and concentrated. The crude reaction mixture was purified with silica gel chromatography, eluting with hexanes/EtOAc to afford N-(3-chloro-5-fluoro-4-iodopyridin-2-yl)-N-((2-(trimethylsilyl)ethoxy)-methyl)ethanesulfonamide as a yellow oil (751.8 mg, 89%). MS (apci, m/z)=495.0 (M+H).

Intermediate P52

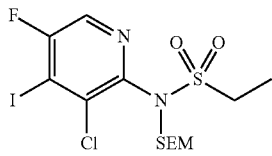 [SMILES: CCS(=O)(=O)N(COCC[Si](C)(C)C)c1ncc(F)c(I)c1Cl]

N-(3-chloro-5-fluoro-4-iodopyridin-2-yl)-N-((2-(trimethylsilyl)ethoxy)methyl)ethane-sulfonamide Step 1: Preparation of N-(3-chloro-5-fluoro-4-iodopyridin-2-yl)-N-(ethylsulfonyl)ethane-sulfonamide. Triethylamine (1.586 mL, 11.38 mmol) was added to 3-chloro-5-fluoro- Intermediate P53

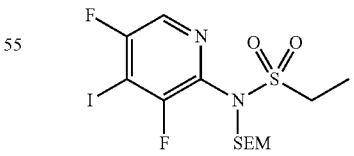

N-(3,5-difluoro-4-iodopyridin-2-yl)-N-((2-(trimethylsilyl)ethoxy)methyl)ethanesulfonamide Step 1: Preparation of N-(3,5-difluoro-4-iodopyridin-2-yl)-N-(ethylsulfonyl)ethanesulfonamide. To a solution of 3,5-difluoro-4-iodopyridin-2-amine (400 mg, 1.563 mmol)

and ethane sulfonyl chloride (0.370 mL, 3.906 mmol) in dichloromethane (7.81 mL) was added triethylamine (0.653 mL, 4.688 mmol) and the mixture was stirred at ambient temperature overnight. The reaction mixture was diluted with EtOAc and then washed with water followed by brine. The organic extracts were combined and dried over Na$_2$SO$_4$, filtered, and concentrated to give N-(3,5-fluoro-4-iodopyridin-2-yl)-N-(ethylsulfonyl)ethanesulfonamide (0.500 g, 73%) that was used directly in the next step without purification. MS (apci, m/z)=440.9 (M+H).

Step 2: Preparation of N-(3,5-fluoro-4-iodopyridin-2-yl)ethanesulfonamide. A solution of N-(3,5-difluoro-4-iodopyridin-2-yl)-N-(ethylsulfonyl)ethanesulfonamide (0.50 g, 1.14 mmol) in acetonitrile (5.68 mL) and 2.0 M aqueous sodium carbonate (4.5 mL, 9.09 mmol) was heated to 60° C. for 90 minutes. The reaction mixture was cooled to ambient temperature and acidified to about pH 3 with 10% aqueous citric acid. The reaction mixture was extracted with EtOAc and the combined organic layers were washed with water followed by brine. The organic layers were dried over Na$_2$SO$_4$, filtered, and concentrated. The residue was purified by silica gel chromatography, eluting with hexanes/EtOAc to give N-(3,5-fluoro-4-iodopyridin-2-yl)ethanesulfonamide (0.364 g, 92%). MS (apci, m/z)=349.0 (M+H).

Step 3: Preparation of N-(3,5-difluoro-4-iodopyridin-2-yl)-N-((2-(trimethylsilyl)ethoxy)-methyl)ethanesulfonamide. To a solution of N-(3,5-difluoro-4-iodopyridin-2-yl)ethane-sulfonamide (0.364 g, 1.05 mmol) in DMF (4.2 mL) at 0° C. was added 60% sodium hydride as a suspension in mineral oil (56.5 mg, 1.41 mmol). After 15 minutes the reaction mixture was treated with (2-(chloromethoxy)ethyl)trimethylsilane (0.223 mL, 1.25 mmol) and the reaction mixture was allowed to warm to ambient temperature and stirred for 1 hour. The reaction mixture was treated with water and extracted with EtOAc, and the combined organic layers were washed with water followed by brine. The organic extracts were dried over Na$_2$SO$_4$, filtered, and concentrated. The residue was purified by silica gel chromatography, eluting with hexanes/EtOAc to give N-(3,5-difluoro-4-iodopyridin-2-yl)-N-((2-(trimethylsilyl)ethoxy)methyl)ethane-sulfonamide (0.343 g, 69%) as an oil. $^1$H NMR (400 MHz, CDCl$_3$) δ 8.06 (s, 1H), 5.09 (s, 2H), 3.69-3.65 (dd, 2H), 3.37 (q, 2H), 1.46 (t, 3H), 0.86-0.90 (dd, 2H), 0.01 (s, 9H).

Intermediate P54

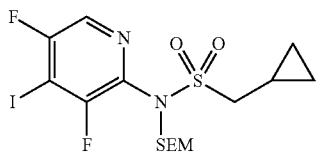 [SMILES: C[Si](C)(C)CCOCN(c1ncc(F)c(I)c1F)S(=O)(=O)CC1CC1]

1-cyclopropyl-N-(3,5-difluoro-4-iodopyridin-2-yl)-N-((2-(trimethylsilyl)ethoxy)methyl)-methanesulfonamide Step 1: Preparation of 1-cyclopropyl-N-((cyclopropylmethyl)sulfonyl)-N-3,5-difluoro-4-iodopyridin-2-yl)methanesulfonamide. To a solution of 3,5-difluoro-4-iodopyridin-2-amine (500 mg, 1.95 mmol) and cyclopropylmethanesulfonyl chloride (0.656 mL, 5.86 mmol) in dichloromethane (9.8 mL) was added triethylamine (1.089 mL; 7.81 mmol) and the mixture was stirred at ambient temperature overnight. The reaction mixture was diluted with EtOAc and washed with water, followed by brine. The combined organic layers were dried with Na$_2$SO$_4$, filtered, and concentrated to give 1-cyclopropyl-N-((cyclopropylmethyl)sulfonyl)-N-3,5-difluoro-4-iodopyridin-2-yl)methanesulfonamide (0.915 g, 95%) that was used directly in the next step without purification.

Step 2: Preparation of 1-cyclopropyl-N-(3,5-fluoro-4-iodopyridin-2-yl)methanesulfonamide. A solution of 1-cyclopropyl-N-((cyclopropylmethyl)sulfonyl)-N-3,5-difluoro-4-iodopyridin-2-yl)methanesulfonamide (0.915 g, 1.86 mmol) in acetonitrile (9.3 mL) and 2.0 M aqueous sodium carbonate (7.4 mL, 14.9 mmol) was heated to 60° C. for 90 minutes. The reaction mixture was cooled to ambient temperature and acidified to about pH 3 with 10% aqueous citric acid. The reaction mixture was diluted with water and extracted with EtOAc and the combined organic layers were washed with water followed by brine. The organic layers were dried over Na$_2$SO$_4$, filtered, and concentrated. The residue was purified by silica gel chromatography, eluting with hexanes/EtOAc to give 1-cyclopropyl-N-(3,5-fluoro-4-iodopyridin-2-yl)methanesulfonamide (0.680 g, 98%). MS (apci, m/z)=372.9 (M−H).

Step 3: Preparation of 1-cyclopropyl-N-(3,5-difluoro-4-iodopyridin-2-yl)-N-((2-(trimethylsilyl)-ethoxy)methyl)methanesulfonamide. To a solution of 1-cyclopropyl-N-(3,5-fluoro-4-iodopyridin-2-yl)methanesulfonamide (0.680 g, 1.82 mmol) in DMF (7.2 mL) at 0° C. was added 60% sodium hydride as a suspension in mineral oil (98.1 mg, 2.45 mmol). After 15 minutes the reaction mixture was treated with (2-(chloromethoxy)ethyl)trimethylsilane (0.387 mL, 2.18 mmol) and the reaction mixture was allowed to warm to ambient temperature and stir for 1 hour. The reaction mixture was treated with water and extracted with EtOAc and then the combined organic layers were washed with water followed by brine. The organic layers were, dried over Na$_2$SO$_4$, filtered, concentrated. The residue was purified by silica gel chromatography (Hexanes/EtOAc) to give 1-cyclopropyl-N-(3,5-difluoro-4-iodopyridin-2-yl)-N-((2-(trimethylsilyl)ethoxy)methyl)-methanesulfonamide (0.682 g, 74%) as an oil. $^1$H NMR (400 MHz, CDCl$_3$) δ 8.04 (s, 1H), 5.13 (s, 2H), 3.73-3.68 (dd, 2H), 3.24-3.23 (d, 2H), 1.27-1.24 (m, 1H), 0.91-0.86 (dd, 2H), 0.74-0.69 (m, 2H), 0.52-0.48 (m, 2H), 0.01 (s, 9H).

Intermediate P55

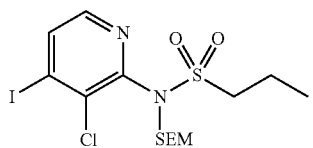 [SMILES: CCCS(=O)(=O)N(COCC[Si](C)(C)C)c1nccc(I)c1Cl]

N-(3-chloro-4-iodopyridin-2-yl)-N-((2-(trimethylsilyl)ethoxy)methyl)propane-1-sulfonamide Step 1: Preparation of N-(3-chloro-4-iodopyridin-2-yl)-N-(propylsulfonyl)propane-1-sulfonamide. To a solution of 3-chloro-iodopyridin-2-amine (243 mg, 0.953 mmol) and 1-propanesulfonyl chloride (0.246 mL, 2.19 mmol) in dichloromethane (4.77 mL) was added triethylamine (0.399 mL, 2.86 mmol) and the mixture was stirred at ambient temperature overnight. The reaction mixture was diluted with EtOAc and washed with water followed by brine and then The organic layers were dried over Na₂SO₄, filtered, and concentrated to give N-(3-chloro-4-iodopyridin-2-yl)-N-(propylsulfonyl)propane-1-sulfonamide (0.189 g, 43%) that was used directly in the next step without purification. MS (apci, m/z)=466.9 (M+H).

Step 2: Preparation of N-(3-chloro-4-iodopyridin-2-yl)propane-1-sulfonamide. A solution of N-(3-chloro-4-iodopyridin-2-yl)-N-(propylsulfonyl)propane-1-sulfonamide (0.189 g, 0.405 mmol) in acetonitrile (2.03 mL) and 2.0 M aqueous sodium carbonate (1.6 mL, 3.24 mmol) was heated to 60° C. for 90 minutes. The reaction mixture was cooled to ambient temperature and acidified to about pH 3 with 10% aqueous citric acid. The reaction mixture was diluted with water and extracted with EtOAc and the combined organic layers were washed with water followed by brine. The organic layers were dried over Na₂SO₄, filtered, and concentrated. The residue was purified by silica gel chromatography, eluting with hexanes/EtOAc to give N-(3-chloro-4-iodopyridin-2-yl)propane-1-sulfonamide (0.121 g, 83%). MS (apci, m/z)=360.9 (M+H).

Step 3: Preparation of N-(3-chloro-4-iodopyridin-2-yl)-N-((2-(trimethylsilyl)ethoxy)methyl)-propane-1-sulfonamide. To a solution of N-(3-chloro-4-iodopyridin-2-yl)propane-1-sulfonamide (0.121 g, 0.336 mmol) in DMF (1.3 mL) at 0° C. was added 60% sodium hydride as a suspension in mineral oil (16.1 mg, 0.403 mmol). After 15 minutes the reaction mixture was treated with (2-(chloromethoxy)ethyl)trimethylsilane (0.080 mL, 0.453 mmol). The reaction mixture was allowed to stir at ambient temperature for 1 hour. The reaction mixture was treated with water and extracted with EtOAc and then the combined organic extracts were washed with water followed by brine. The organic layers were dried over Na₂SO₄, filtered, and concentrated. The residue was purified by silica gel chromatography, eluting with hexanes/EtOAc to give N-(3-chloro-4-iodopyridin-2-yl)-N-((2-(trimethylsilyl)ethoxy)methyl)propane-1-sulfonamide (0.13 g, 79%) as an oil. $^1$H NMR (400 MHz, CDCl₃) δ 8.00 (d, 1H), 7.80 (d, 1H), 5.09 (s, 2H), 3.67-3.63 (dd, 2H), 3.45-3.41 (dd, 2H), 2.01-1.91 (m, 2H), 1.08 (t, 3H), 0.91-0.86 (dd, 2H), 0.01 (s, 9H).

followed by brine. The organic extracts were dried over Na₂SO₄, filtered, and concentrated to give N-(3-chloro-4-iodopyridin-2-yl)-3-fluoro-N-((3-fluoropropyl)sulfonyl)propane-1-sulfonamide (0.433 g, 86%) that was used directly in the next step without purification. MS (apci, m/z)=502.9 (M+H).

Step 2: Preparation of N-(3-chloro-4-iodopyridin-2-yl)-3-fluoropropane-1-sulfonamide. A solution of N-(3-chloro-4-iodopyridin-2-yl)-3-fluoro-N-((3-fluoropropyl)sulfonyl)propane-1-sulfonamide (0.433 g, 0.861 mmol) in acetonitrile (4.31 mL) and 2.0 M aqueous sodium carbonate (3.45 mL, 6.89 mmol) was heated to 60° C. for 90 minutes. The reaction mixture was cooled to ambient temperature and acidified to about pH 3 with 10% aqueous citric acid. The reaction mixture was diluted with water and extracted with EtOAc and the combined organic layers were washed with water followed by brine. The organic layers were dried with Na₂SO₄, filtered, and concentrated. The residue was purified by silica gel chromatography, eluting with hexanes/EtOAc to give N-(3-chloro-4-iodopyridin-2-yl)-3-fluoropropane-1-sulfonamide (0.292 g, 90%). MS (apci, m/z)=379.0 (M+H).

Step 3: Preparation of N-(3-chloro-4-iodopyridin-2-yl)-3-fluoro-N-((2-(trimethylsilyl)ethoxy)-methyl)propane-1-sulfonamide. To a solution of N-(3-chloro-4-iodopyridin-2-yl)-3-fluoropropane-1-sulfonamide (0.292 g, 0.771 mmol) in DMF (3.09 mL) at 0° C. was added 60% sodium hydride as a suspension in mineral oil (41.6 mg, 1.04 mmol). After 15 minutes the reaction mixture was treated with (2-(chloromethoxy)ethyl)trimethylsilane (0.164 mL, 0.926 mmol) was added and the reaction mixture was allowed to stir at ambient temperature for 1 hour. The reaction mixture was treated with water and extracted with EtOAc and then the combined organic layers were washed with water followed by brine. The organic layers were dried over Na₂SO₄, filtered, and concentrated. The residue was purified by silica gel chromatography, eluting with hexanes/EtOAc to give N-(3-chloro-4-iodopyridin-2-yl)-3-fluoro-N-((2-(trimethylsilyl)-ethoxy)methyl)propane-1-sulfonamide (0.200 g, 51%) as an oil. $^1$H NMR (400 MHz, CDCl₃) δ 8.00 (d, 1H), 7.81 (d, 1H), 5.09 (s, 2H), 4.65 (t, 1H), 4.53 (t, 1H), 3.66-3.61 (dd, 4H), 2.41-2.27 (m, 2H), 0.90-0.86 (dd, 2H), 0.01 (s, 9H).

Intermediate P56

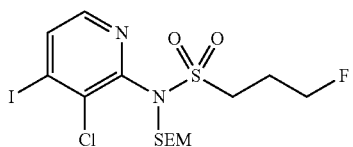 [SMILES: C[Si](C)(C)CCOCN(c1nccc(I)c1Cl)S(=O)(=O)CCCF]

N-(3-chloro-4-iodopyridin-2-yl)-3-fluoro-N-((2-(trimethylsilyl)ethoxy)methyl)propane-1-sulfonamide Step 1: Preparation of, N-(3-chloro-4-iodopyridin-2-yl)-3-fluoro-N-((3-fluoropropyl)sulfonyl)-propane-1-sulfonamide. To a solution of 3-chloro-iodopyridin-2-amine (256 mg, 1.01 mmol) and 3-fluoropropane-1-sulfonyl chloride (0.275 mL, 2.31 mmol) in dichloromethane (5.03 mL) was added triethylamine (0.421 mL, 3.02 mmol) and the mixture was stirred at ambient temperature overnight. The reaction mixture was diluted with EtOAc and washed with water Intermediate P57

N-(2-chloro-4-fluoro-3-iodophenyl)-3-fluoro-N-((2-(trimethylsilyl)ethoxy)methyl)propane-1-sulfonamide Step 1: Preparation of 2-chloro-4-fluoro-3-iodoaniline. 2-Chloro-4-fluoroaniline (2.44 g, 16.76 mmol) was dissolved in THF (100 mL) and cooled to −78° C. under a backflow of N₂. The reaction mixture was slowly treated with n-butyllithium (2.5 M in hexanes, 7.38 mL, 18.44 mmol) and then allowed to stir at −78° C. for 15 minutes after complete addition. The reaction mixture was treated dropwise with a 50 mL THF solution of 1,2-bis(chlorodimethylsilyl)ethane (3.79 g, 17.60 mmol) and allowed to stir at −78° C. for 15 minutes after complete addition. The reaction mixture was treated slowly with additional n-butyllithium (2.5 M in hexanes, 7.38 mL, 18.44 mmol) and the ice bath was removed after complete addition and the reaction mixture was allowed to warm for 30 minutes. The reaction mixture was cooled back to −78° C. and treated slowly with additional n-butyllithium (2.5 M in hexanes, 7.38 mL, 18.44 mmol) and allowed to stir at −78° C. for 30 minutes before being treated dropwise with a 50 mL THF solution of iodine (6.38 g, 25.14 mmol). After complete addition the ice bath was removed and the reaction mixture was allowed to stir for 1 hour. The reaction mixture was treated with water and then acidified to about pH 1 using 4.0 M HCl and allowed to stir at ambient temperature for 30 minutes. The reaction mixture was neutralized to about pH 8 using solid NaHCO$_3$ and then treated with an aqueous 3.0 M sodium thiosulfate solution. The reaction mixture was extracted with EtOAc (2×250 mL). The organic layers were combined and washed with water (1×100 mL) and brine (1×100 mL) and then dried over Na$_2$SO$_4$, filtered, and concentrated. The residue was purified by silica gel chromatography (Hexanes/EtOAc) followed by reverse phase C18 chromatography, eluting with water/acetonitrile with 0.1% TFA. The desired fractions were combined and partitioned between 4:1 DCM/IPA and saturated NaHCO$_3$ (1×100 mL). The organic layers were dried over Na$_2$SO$_4$, filtered, and concentrated to provide 2-chloro-4-fluoro-3-iodoaniline (2.70 g, 59%). $^1$H NMR (400 MHz, DMSO-d$_6$) δ 6.99-6.95 (m, 1H), 6.83-6.79 (m, 1H), 5.44 (s, 2H).

Step 2: Preparation of N-(2-chloro-4-fluoro-3-iodophenyl)-3-fluoro-N-((3-fluoropropyl)sulfonyl)-propane-1-sulfonamide. To a solution of 2-chloro-4-fluoro-3-iodoaniline (1.7 g, 6.262 mmol) and 3-fluoropropane-1-sulfonyl chloride (1.815 mL, 15.66 mmol) in dichloromethane (31.31 mL) was added triethylamine (2.182 mL, 15.66 mmol) and the mixture was stirred at ambient temperature for 1 hour. The reaction mixture was treated with water and extracted with DCM (2×) and then the combined organic extracts were washed with brine. The organic extracts were dried over Na$_2$SO$_4$, filtered, and concentrated to give N-(2-chloro-4-fluoro-3-iodophenyl)-3-fluoro-N-((3-fluoropropyl)sulfonyl)propane-1-sulfonamide (3.0 g, 92%) that was used directly in the next step without purification.

Step 3: Preparation of N-(2-chloro-4-fluoro-3-iodophenyl)-3-fluoropropane-1-sulfonamide. A solution of N-(2-chloro-4-fluoro-3-iodophenyl)-3-fluoro-N-((3-fluoropropyl)sulfonyl)propane-1-sulfonamide (3.0 g, 5.8 mmol) in acetonitrile (29 mL) and 2.0 M aqueous sodium carbonate (20 mL, 40 mmol) was heated to 60° C. for 90 minutes. The reaction mixture was cooled to ambient temperature and then acidified to about pH 3 with 10% aqueous citric acid. The reaction mixture was diluted with water and extracted with DCM (2×) and the combined organic layers were washed with brine. The organic layers were dried over Na$_2$SO$_4$, filtered, and concentrated. The residue was purified by silica gel chromatography, hexanes/EtOAc to give N-(2-chloro-4-fluoro-3-iodophenyl)-3-fluoropropane-1-sulfonamide (2.1 g, 92%). MS (apci, m/z)=393.9 (M−H).

Step 4: Preparation of N-(2-chloro-4-fluoro-3-iodophenyl)-3-fluoro-N-((2-. (trimethylsilyl)ethoxy)-methyl)propane-1-sulfonamide. To a solution of N-(2-chloro-4-fluoro-3-iodophenyl)-3-fluoropropane-1-sulfonamide (2.1 g, 5.31 mmol) in DMF (26.5 mL) at 0° C. was added sodium hydride (60% suspension in mineral oil, 0.287 g, 7.17 mmol) followed by (2-(chloromethoxy)ethyl)trimethylsilane (1.13 mL, 6.37 mmol) and The reaction mixture was stirred at 0° C. for 30 minutes. The reaction mixture was treated with water and extracted with EtOAc and then the combined organic layers were washed with water followed by brine. The organic layers were dried over Na$_2$SO$_4$, filtered, and concentrated. The residue was purified by silica gel chromatography, hexanes/EtOAc to give N-(2-chloro-4-fluoro-3-iodophenyl)-3-fluoro-N-((2-(trimethylsilyl)ethoxy)methyl)propane-1-sulfonamide (2.7 g, 97%). $^1$H NMR (500 MHz, CDCl$_3$) δ 7.52 (dd, 1H), 7.07 (dd, 1H), 5.21 (d, 1H), 4.71 (d, 1H), 4.62 (t, 1H), 4.52 (t, 1H), 3.73 (m, 1H), 3.59 (m, 1H), 3.28 (t, 2H), 2.28 (m, 2H), 0.88, (t, 2H), 0.02 (s, 9H).

Intermediate P58

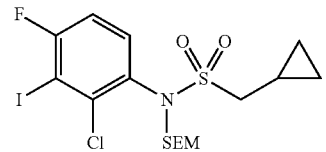 [SMILES: C[Si](C)(C)CCOCN(c1ccc(F)c(I)c1Cl)S(=O)(=O)CC1CC1]

N-(2-chloro-4-fluoro-3-iodophenyl)-1-cyclopropyl-N-((2-(trimethylsilyl)ethoxy)methyl)-methanesulfonamide Step 1: Preparation of N-(2-chloro-4-fluoro-3-iodophenyl)-1-cyclopropyl-N-((cyclopropyl-methyl)sulfonyl)methanesulfonamide. To a solution of 2-chloro-4-fluoro-3-iodoanaline (150 mg, 0.553 mmol) and cyclopropanemethanesulfonyl chloride (0.186 mL, 1.66 mmol) in dichloromethane (2.76 mL) was added triethylamine (0.308 mL, 2.21 mmol) and the mixture was stirred at ambient temperature overnight. The reaction mixture was treated with water and extracted with EtOAc (2×). The combined organic layers were washed with brine and dried over Na$_2$SO$_4$, filtered, and concentrated to give N-(2-chloro-4-fluoro-3-iodophenyl)-1-cyclopropyl-N-((cyclopropylmethyl)sulfonyl)methanesulfonamide (0.281 g, 99%) that was used directly in the next step without purification.

Step 2: Preparation of N-(2-chloro-4-fluoro-3-iodophenyl)-1-cyclopropylmethanesulfonamide. A solution of N-(2-chloro-4-fluoro-3-iodophenyl)-1-cyclopropyl-N-((cyclopropylmethyl)sulfonyl)-methanesulfonamide (0.281 g, 0.553 mmol) in acetonitrile (2.77 mL) and 2.0 M aqueous sodium carbonate (2.21 mL, 4.43 mmol) was heated to 60° C. for 90 minutes. The reaction mixture was cooled to ambient temperature and then acidified to about pH 3 with 10% aqueous citric acid. The reaction mixture was diluted with water and extracted with EtOAc and the combined organic layers were washed with water followed by brine. The organic layers were dried over Na$_2$SO$_4$, filtered, and concentrated. The residue was purified by silica gel chromatography (Hexanes/EtOAc) to give N-(2-chloro-4-fluoro-3-iodophenyl)-1-cyclopropylmethanesulfonamide (0.192 g, 89%). $^1$H NMR (400 MHz, CDCl$_3$) δ 7.76-7.69 (m, 1H), 7.06-6.99 (m, 1H), 3.03 (d, 2H), 1.14-1.06 (m, 1H), 0.71-0.63 (m, 2H), 0.33-0.25 (m, 2H).

Step 3: Preparation of N-(2-chloro-4-fluoro-3-iodophenyl)-1-cyclopropyl-N-((2-(trimethylsilyl)-ethoxy)methyl) methanesulfonamide. To a solution of N-(2-chloro-4-fluoro-3-iodophenyl)-1-cyclopropylmethanesulfonamide (0.192 g, 0.493 mmol) in DMF (1.9 mL) at 0° C. was added 60% sodium hydride as a suspension in mineral oil (26.6 mg, 0.665 mmol). After 15 minutes the reaction mixture was treated with (2-(chloromethoxy)ethyl)trimethylsilane (0.105 mL, 0.591 mmol) and the reaction mixture was allowed to stir at ambient temperature for 1 hour. The reaction mixture was treated with water and extracted with EtOAc and then the combined organic layers were washed with water followed by brine. The organic layers were dried over Na$_2$SO$_4$, filtered, and concentrated. The residue was purified by silica gel chromatography (Hexanes/EtOAc) to give N-(2-chloro-4-fluoro-3-iodophenyl)-1-cyclopropyl-N-((2-(trimethyl-silyl)ethoxy)methyl)methanesulfonamide (0.16 g, 63%) as an off white solid. $^1$H NMR (400 MHz, CDCl$_3$) δ 7.51 (d, 1H), 7.05 (d, 1H), 5.23 (d, 1H), 4.73 (d, 1H), 3.77-3.54 (m, 2H), 3.12-2.97 (m, 2H), 1.28-1.18 (m, 1H), 0.95-0.85 (m, 2H), 0.74-0.69 (m, 2H), 0.44-0.40 (m, 2H), 0.01 (s, 9H).

Intermediate P59

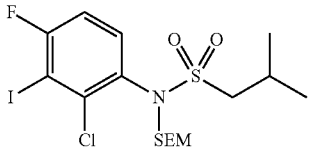

N-(2-chloro-4-fluoro-3-iodophenyl)-2-methyl-N-((2-(trimethylsilyl)ethoxy)methyl)propane-1-sulfonamide Step 1: Preparation of N-(2-chloro-4-fluoro-3-iodophenyl)-N-(isobutylsulfonyl)-2-methylpropane-1-sulfonamide. To a solution of 2-chloro-4-fluoro-3-iodoanaline (152 mg, 0.560 mmol) and 2-methylpropane-1-sulfonyl chloride (0.183 mL, 1.4 mmol) in dichloromethane (2.8 mL) was added triethylamine (0.234 mL, 1.68 mmol) and the reaction mixture was heated to 50° C. for 15 hours. The reaction mixture was cooled to ambient temperature and concentrated, then treated with water and extracted with EtOAc. The combined organic extracts were washed with brine and then dried over Na$_2$SO$_4$, filtered, and concentrated to give N-(2-chloro-4-fluoro-3-iodophenyl)-N-(isobutylsulfonyl)-2-methylpropane-1-sulfonamide (0.274 g, 96%) that was used directly in the next step without purification.

Step 2: Preparation of N-(2-chloro-4-fluoro-3-iodophenyl)-2-methylpropane-1-sulfonamide. A solution of N-(2-chloro-4-fluoro-3-iodophenyl)-N-(isobutylsulfonyl)-2-methylpropane-1-sulfonamide (0.274 g, 0.536 mmol) in acetonitrile (2.68 mL) and 2.0 M aqueous sodium carbonate (2.14 mL, 4.28 mmol) was heated to 60° C. for-90 minutes. The reaction mixture was cooled to ambient temperature and then acidified to about pH 3 with 10% aqueous citric acid. The reaction mixture was diluted with water and extracted with EtOAc and the combined organic extracts were washed with water followed by brine. The organic layers were dried over Na$_2$SO$_4$, filtered, and concentrated. The residue was purified by silica gel chromatography, eluting with hexanes/EtOAc to give N-(2-chloro-4-fluoro-3-iodophenyl)-2-methylpropane-1-sulfonamide (0.138 g, 63%). $^1$H NMR (400 MHz, CDCl$_3$) δ 7.72-7.67 (m, 1H), 7.09-7.02 (m, 1H), 6.67 (bs, 1H), 2.94 (d, 2H), 2.35-2.23 (m, 1H), 1.09 (d, 6H).

Step 3: Preparation of N-(2-chloro-4-fluoro-3-iodophenyl-2-methyl-N-((2-(trimethylsilyl)ethoxy)-methyl)propane-1-sulfonamide. To a solution of N-(2-chloro-4-fluoro-3-iodophenyl)-2-methylpropane-1-sulfonamide (0.138 g, 0.352 mmol) in DMF (1.4 mL) at 0° C. was added 60% sodium hydride as a suspension in mineral oil (19.0 mg, 0.476 mmol). After 15 minutes, the reaction mixture was treated with (2-(chloromethoxy)ethyl)trimethylsilane (0.075 mL, 0.423 mmol) The reaction mixture was and allowed to stir at ambient temperature for 1 hour. The reaction mixture was treated with water and extracted with EtOAc and then the combined organic layers were washed with water followed by brine. The organic layers were dried over Na$_2$SO$_4$, filtered, and concentrated. The residue was purified by silica gel chromatography (Hexanes/EtOAc) to give N-(2-chloro-4-fluoro-3-iodophenyl-2-methyl-N-((2-(trimethylsilyl)ethoxy)methyl)propane-1-sulfonamide (0.113 g, 61%) as an off white solid. $^1$H NMR (400 MHz, CDCl$_3$) δ 7.52-7.49 (dd, 1H), 7.07-7.04 (dd, 1H), 5.21 (d, 1H), 4.70 (d, 1H), 3.76-3.55 (m, 2H), 3.01 (d, 2H), 2.38-2.28 (m, 1H), 1.10 (d, 6H), 0.95-0.85 (m, 2H), 0.01 (s, 9H).

Intermediate P60

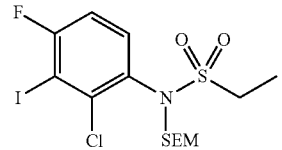

N-(2-chloro-4-fluoro-3-iodophenyl)-N-((2-(trimethylsilyl)ethoxy)methyl)ethanesulfonamide Step 1: Preparation of N-(2-chloro-4-fluoro-3-iodophenyl)-N-(ethylsulfonyl)ethylsulfonamide. To a solution of 2-chloro-4-fluoro-3-iodoaniline (150 mg, 0.553 mmol) and ethanesulfonyl chloride (0.157 mL, 1.66 mmol) in dichloromethane (2.8 mL) was added triethylamine (0.308 mL, 2.21 mmol) and the mixture was stirred at ambient temperature for 15 hours. The reaction mixture was treated with water and extracted with EtOAc and then the combined organic extracts were washed with brine then dried over Na$_2$SO$_4$, filtered, and concentrated to give N-(2-chloro-4-fluoro-3-iodophenyl)-N-(ethylsulfonyl)ethylsulfonamide (0.250 g, 99%) that was used directly in the next step without purification.

Step 2: Preparation of N-(2-chloro-4-fluoro-3-iodophenyl)ethanesulfonamide. A solution of N-(2-chloro-4-fluoro-3-iodophenyl)-N-(ethylsulfonyl)ethyanesulfonamide (0.250 g, 0.45 mmol) in acetonitrile (2.3 mL) and 2.0 M aqueous sodium carbonate (1.8 mL, 3.6 mmol) was heated to 60° C. for 90 minutes. The reaction mixture was cooled to ambient temperature and then acidified to about pH 3 with 10% aqueous citric acid. The reaction mixture was diluted with water and extracted with EtOAc and the combined organic layers were washed with water followed by brine. The organic layers were dried over Na$_2$SO$_4$, filtered, and concentrated. The residue was purified by silica gel chromatography, eluting with hexanes/EtOAc to give N-(2-chloro-4-fluoro-3-iodophenyl)ethanesulfonamide (0.158 g, 63%). $^1$H NMR (400 MHz, CDCl$_3$) δ 7.73-7.68 (m, 1H), 7.07-7.01 (m, 1H), 3.10 (q, 2H), 1.37 (t, 3H).

Step 3: Preparation of N-(2-chloro-4-fluoro-3-iodophenyl-N-((2-(trimethylsilyl)ethoxy)-methyl)ethanesulfonamide. To a solution of N-(2-chloro-4-fluoro-3-iodophenyl)-ethanesulfonamide (0.158 g, 0.435 mmol) in DMF (1.7 mL) at 0° C. was added 60% sodium hydride as a suspension in mineral oil (23.5 mg, 0.587 mmol). After 15 minutes the reaction mixture was treated with (2-(chloromethoxy)ethyl)trimethylsilane (0.093 mL, 0.521 mmol) and the reaction mixture was allowed to stir at ambient temperature for 1 hour. The reaction mixture was treated with water and extracted with EtOAc and then the combined organic layers were washed with water followed by brine. The organic layers were dried over Na$_2$SO$_4$, filtered, and concentrated. The residue was purified by silica gel chromatography, eluting with hexanes/EtOAc to give N-(2-chloro-4-fluoro-3-iodophenyl-N-((2-(trimethylsilyl)ethoxy)methyl)ethanesulfonamide (0.166 g, 77%) as an off white solid. $^1$H NMR (400 MHz, CDCl$_3$) δ 7.53-7.49 (dd, 1H), 7.07-7.04 (dd, 1H), 5.20 (d, 1H), 4.74 (d, 1H), 3.78-3.71 (m, 1H), 3.63-3.56 (m, 1H), 3.14 (q, 2H), 1.45 (t, 3H), 0.97-0.84 (m, 2H), 0.01 (s, 9H).

Intermediate P61

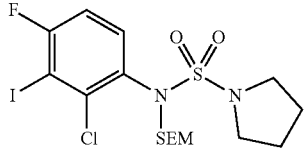 [SMILES: C[Si](C)(C)CCOCN(c1ccc(F)c(I)c1Cl)S(=O)(=O)N1CCCC1]

N-(2-chloro-4-fluoro-3-iodophenyl)-N-((2-(trimethylsilyl)ethoxy)methyl)pyrrolidine-1-sulfonamide Step 1: Preparation of N-(2-chloro-4-fluoro-3-iodophenyl)-N-(pyrrolindin-1-ylsulfonyl)pyrrolidine-1-sulfonamide. To a solution of 2-chloro-4-fluoro-3-iodoanaline (150 mg, 0.553 mmol) in pyridine (2.8 mL) was added pyrrolidine-1-sulfonyl chloride (0.070 mL, 0.608 mmol) and the mixture was stirred at ambient temperature for 15 hours. The reaction mixture was treated with water and extracted with EtOAc. The organic layers were washed with brine and then dried over Na$_2$SO$_4$, filtered, and concentrated to give N-(2-chloro-4-fluoro-3-iodophenyl)-N-(pyrrolindin-1-ylsulfonyl)pyrrolidine-1-sulfonamide (0.290 g, 98%) that was used directly in the next step without purification.

Step 2: Preparation of N-(2-chloro-4-fluoro-3-iodophenyl)pyrrolidine-1-sulfonamide. A solution of N-(2-chloro-4-fluoro-3-iodophenyl)-N-(pyrrolindin-1-ylsulfonyl)pyrrolidine-1-sulfonamide (0.290 g, 0.539 mmol) in acetonitrile (2.7 mL) and 2.0 M aqueous sodium carbonate (2.2 mL, 4.3 mmol) was heated to 60° C. for 90 minutes. The reaction mixture was cooled to ambient temperature and then acidified to about pH 3 with 10% aqueous citric acid. The reaction mixture was diluted with water and extracted with EtOAc and the combined organic layers were washed with water followed by brine. The organic layers were dried over Na$_2$SO$_4$, filtered, and concentrated. The residue was purified by silica gel chromatography, eluting with hexanes/EtOAc to give N-(2-chloro-4-fluoro-3-iodophenyl)pyrrolidine-1-sulfonamide (0.093 g, 42%).

Step 3: Preparation of N-(2-chloro-4-fluoro-3-iodophenyl)-N-((2-(trimethylsilyl)ethoxy)methyl)-pyrrolidine-1-sulfonamide. To a solution of N-(2-chloro-4-fluoro-3-iodophenyl)pyrrolidine-1-sulfonamide (0.093 g, 0.229 mmol) in DMF (0.92 mL) at 0° C. was added 60% sodium hydride as a suspension in mineral oil (12.4 mg, 0.309 mmol). After 15 minutes the reaction mixture was treated with (2-(chloromethoxy)ethyl)trimethylsilane (0.049 mL, 0.275 mmol) and the reaction mixture was allowed to stir at ambient temperature for 1 hour. The reaction mixture was treated with water and extracted with EtOAc and then the combined organic layers were washed with water followed by brine. The organic layers were dried over Na$_2$SO$_4$, filtered, and concentrated. The residue was purified by silica gel chromatography, eluting with hexanes/EtOAc) to give N-(2-chloro-4-fluoro-3-iodophenyl)-N-((2-(trimethylsilyl)ethoxy)methyl)pyrrolidine-1-sulfonamide (0.087 g, 71%) as an off white solid. $^1$H NMR (400 MHz, CDCl$_3$) δ 7.68-7.64 (dd, 1H), 7.05-7.02 (dd, 1H), 5.19 (d, 1H), 4.68 (d, 1H), 3.78-3.72 (m, 1H), 3.64-3.58 (m, 1H), 3.37 (d, 2H), 3.21 (d, 2H), 1.89-1.83 (m, 4H), 0.93-0.88 (m, 2H), 0.01 (s, 9H).

Intermediate P62

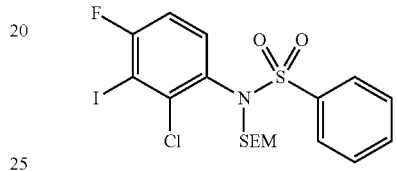

N-(2-chloro-4-fluoro-3-iodophenyl)-N-((2-(trimethylsilyl)ethoxy)methyl)benzenesulfonamide Step 1: Preparation of N-(2-chloro-4-fluoro-3-iodophenyl)-N-(phenylsulfonyl). To a solution of 2-chloro-4-fluoro-3-iodoaniline (152 mg, 0.560 mmol) in tetrahydrofuran (1.4 mL) and pyridine (1.4 mL) was added phenylsulfonyl chloride (0.079 mL, 0.62 mmol) and the mixture was stirred at ambient temperature for 15 hours. The reaction mixture was concentrated to give N-(2-chloro-4-fluoro-3-iodophenyl)-N-(phenylsulfonyl)benzenesulfonamide (0.240 g, 104%) that was used directly in the next step without purification.

Step 2: Preparation of N-(2-chloro-4-fluoro-3-iodophenyl)-benzenesulfonamide. A solution of N-(2-chloro-4-fluoro-3-iodophenyl)-N-(phenylsulfonyl)benzenesulfonamide (0.240 g, 0.45 mmol) in 4:1 THF/MeOH (2.3 mL) was treated with a 2.0 M aqueous KOH solution (1.3 mL, 2.25 mmol) and the mixture was heated to 60° C. for 1 hour. The reaction mixture was cooled to ambient temperature and then acidified to about pH 3 with 10% aqueous citric acid. The reaction mixture was diluted with water and extracted with EtOAc and the combined organic layers were washed with water followed by brine. The organic layers were dried over Na$_2$SO$_4$, filtered, and concentrated to afford N-(2-chloro-4-fluoro-3-iodophenyl)-benzenesulfonamide (0.220 g, 95%) that was used directly in the next step without purification.

Step 3: Preparation of N-(2-chloro-4-fluoro-3-iodophenyl)-N-((2-(trimethylsilyl)ethoxy)-methyl)benzenesulfonamide. To a solution of N-(2-chloro-4-fluoro-3-iodophenyl)-benzenesulfonamide (0.220 g, 0.534 mmol) in DMF (2.1 mL) at 0° C. was added 60% sodium hydride as a suspension in mineral oil (28.9 mg, 0.722 mmol). After 15 minutes the reaction mixture was treated with (2-(chloromethoxy)ethyl)trimethylsilane (0.114 mL, 0.641 mmol). The reaction mixture was allowed to stir at ambient temperature for 1 hour. The reaction mixture was treated with water and extracted with EtOAc and then the combined organic layers were washed with water followed by brine. The organic layers were dried with Na$_2$SO$_4$, filtered, and concentrated. The residue was purified by silica gel chromatography, hexanes/EtOAc to give N-(2-chloro-4-fluoro-3-iodophenyl)-N-((2-(trimethylsilyl)ethoxy)methyl)benzenesulfonamide (0.180 g, 62%) as an off white solid. ¹H NMR (400 MHz, CDCl₃) δ 7.74-7.71 (m, 2H), 7.61-7.56 (m, 1H), 7.49-7.44 (m, 2H), 7.23-7.19 (dd, 1H), 6.99-6.94 (dd, 1H), 5.32 (d, 1H), 4.73 (d, 1H), 3.70-3.58 (m, 2H), 0.92-0.82 (m, 2H), 0.01 (s, 9H).

Intermediate P63

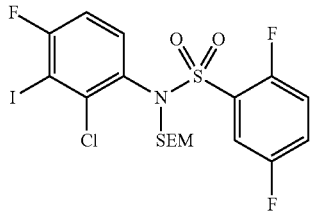 [SMILES: C[Si](C)(C)CCOCN(c1ccc(F)c(I)c1Cl)S(=O)(=O)c1cc(F)ccc1F]

N-(2-chloro-4-fluoro-3-iodophenyl)-2,5-difluoro-N-((2-(trimethylsilyl)ethoxy)methyl)benzenesulfonamide Step 1: Preparation of N-(2-chloro-4-fluoro-3-iodophenyl)-N-((2,5-difluorophenyl)sulfonyl)-2,5-difluorobenzenesulfonamide. To a solution of 2-chloro-4-fluoro-3-iodoaniline (150 mg, 0.553 mmol) in tetrahydrofuran (1.4 mL) and pyridine (1.4 mL) was added 2,5-difluorobenzenesulfonyl chloride (0.082 mL, 0.608 mmol) and the mixture was stirred at ambient temperature for 15 hours. The reaction mixture was concentrated to give N-(2-chloro-4-fluoro-3-iodophenyl)-N-((2,5-difluorophenyl)sulfonyl)-2,5-difluorobenzenesulfonamide (0.253 g, 73%) that was used directly in the next step without purification.

Step 2: Preparation of N-(2-chloro-4-fluoro-3-iodophenyl)-2,5-difluorobenzenesulfonamide. A solution of N-(2-chloro-4-fluoro-3-iodophenyl)-N-((2,5-difluorophenyl)sulfonyl)-2,5-difluoro-benzenesulfonamide (0.253 g, 0.41 mmol) in 4:1 THF/MeOH (2.03 mL) was treated with a 2.0 M aqueous KOH solution (1.03 mL, 2.05 mmol) and the reaction mixture was heated to 60° C. for 1 hour. The reaction mixture was cooled to ambient temperature and then acidified to about pH 3 with 10% aqueous citric acid. The reaction mixture was diluted with water and extracted with EtOAc and the combined organic layers were washed with water followed by brine. The organic layers were dried-over Na₂SO₄, filtered, and concentrated to afford N-(2-chloro-4-fluoro-3-iodophenyl)-2,5-difluorobenzenesulfonamide (0.173 g, 70%) that was used directly in the next step without purification.

Step 3: Preparation of N-(2-chloro-4-fluoro-3-iodophenyl)-2,5-difluoro-N-((2-(trimethylsilyl)-ethoxy)methyl)benzenesulfonamide. To a solution of N-(2-chloro-4-fluoro-3-iodophenyl)-2,5-difluorobenzenesulfonamide (0.173 g, 0.387 mmol) in DMF (1.5 mL) at 0° C. was added 60% sodium hydride as a suspension in mineral oil (20.9 mg, 0.522 mmol). After 15 minutes the reaction mixture was treated with (2-(chloromethoxy)ethyl)trimethylsilane (0.082 mL, 0.464 mmol) and allowed to stir at ambient temperature for 1 hour. The reaction mixture was treated with water and extracted with EtOAc and then the combined organic layers were washed with water followed by brine. The organic layers were dried over Na₂SO₄, filtered, and concentrated. The residue was purified by silica gel chromatography, hexanes/EtOAc to give N-(2-chloro-4-fluoro-3-iodophenyl)-2,5-difluoro-N-((2-(trimethylsilyl)ethoxy)methyl)benzenesulfonamide (0.118 g, 53%) as an off white solid. ¹H NMR (400 MHz, CDCl₃) δ 7.41-7.34 (m, 2H), 7.29-7.22 (m, 1H), 7.21-7.14 (m, 1H), 7.05-6.99 (m, 1H), 5.43 (d, 1H), 4.91 (d, 1H), 3.82-3.63 (m, 2H), 0.98-0.83 (m, 2H), 0.02 (s, 9H).

Intermediate P64

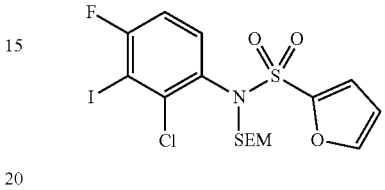

N-(2-chloro-4-fluoro-3-iodophenyl)-N-((2-(trimethylsilyl)ethoxy)methyl)furan-2-sulfonamide Step 1: Preparation of N-(2-chloro-4-fluoro-3-iodophenyl)-N-(furan-2-ylsulfonyl)furan-2-sulfonamide. To a solution of 2-chloro-4-fluoro-3-iodoanaline (150 mg, 0.553 mmol) in dichloromethane (2.8 mL) and triethylamine (0.231 mL, 1.66 mmol) was added furan-2-sulfonyl chloride (0.193 mg, 1.16 mmol) and the mixture was stirred at ambient temperature for 16 hours. The reaction mixture was concentrated to give N-(2-chloro-4-fluoro-3-iodophenyl)-N-(furan-2-ylsulfonyl)furan-2-sulfonamide (0.061 g, 21%) that was used directly in the next step without purification.

Step 2: Preparation of N-(2-chloro-4-fluoro-3-iodophenyl)furan-2-sulfonamide. A solution of N-(2-chloro-4-fluoro-3-iodophenyl)-N-(furan-2-ylsulfonyl)furan-2-sulfonamide (0.061 g, 0.115 mmol) in 4:1 THF/MeOH (0.692 mL) was treated with a 2.0 M aqueous KOH solution (0.290 mL, 0.577 mmol) and the mixture was stirred at ambient temperature for 18 hours. The reaction mixture was cooled to ambient temperature and then acidified to about pH 3 was about pH with 10% aqueous citric acid. The reaction mixture was diluted with water and extracted with EtOAc and the combined organic layers were washed with water followed by brine. The organic layers were dried over Na₂SO₄, filtered, and concentrated to afford N-(2-chloro-4-fluoro-3-iodophenyl)furan-2-sulfonamide (0.035 g, 76%) that was used directly in the next step without purification.

Step 3: Preparation of N-(2-chloro-4-fluoro-3-iodophenyl-N-((2-(trimethylsilyl)ethoxy)-methyl)furan-2-sulfonamide. To a solution of N-(2-chloro-4-fluoro-3-iodophenyl)furan-2-sulfonamide (0.035 g, 0.0879 mmol) in DMF (0.35 mL) at 0° C. was added 60% sodium hydride as a suspension in mineral oil (4.75 mg, 0.119 mmol). After 15 minutes the reaction mixture was treated with (2-(chloromethoxy)ethyl)trimethylsilane (0.019 mL, 0.105 mmol) and the reaction mixture was allowed to stir at ambient temperature for 1 hour. The reaction mixture was treated with water and extracted with EtOAc and then the combined organic layers were washed with water followed by brine. The organic layers were dried over Na₂SO₄, filtered, and concentrated. The residue was purified by silica gel chromatography, eluting with hexanes/EtOAc to give N-(2-chloro-4-fluoro-3-iodophenyl-N-((2-(trimethylsilyl)ethoxy)methyl)furan-2-sulfonamide (0.032 g, 68%) as an off white solid. ¹H NMR (400 MHz, CDCl₃) δ 7.60-7.59 (dd, 1H), 7.30-7.26 (dd, 1H), 7.03-6.99 (dd, 1H), 6.91-6.90 (dd, 1H), 6.51-6.50 (dd, 1H), 5.30 (d, 1H), 4.87 (d, 1H), 3.76-3.63 (m, 2H), 0.96-0.82 (m, 2H), 0.01 (s, 9H).

Intermediate P65

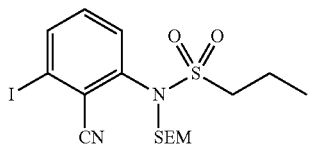 [SMILES: CCCS(=O)(=O)N(COCC[Si](C)(C)C)c1cccc(I)c1C#N]

N-(2-cyano-3-iodophenyl)-N-((2-(trimethylsilyl) ethoxy)methyl) propane-1-sulfonamide Step 1: Preparation of N-(2-cyano-3-iodophenyl)propane-1-sulfonamide. To a solution of propane-1-sulfonamide (46 mg, 0.37 mmol) in DMF (810 µL) was added sodium hydride (60% suspension in mineral oil, 15 mg, 0.37 mmol) and the mixture was heated to 40° C. for 15 minutes. The reaction mixture was treated with 2-fluoro-6-iodobenzonitrile (40 mg, 0.16 mmol) and was heated to 90° C. for 2 hours and then allowed to stir at ambient temperature for 16 hours. The reaction mixture was acidified to about pH 3 with 10% aqueous citric acid and extracted with EtOAc (2×) and the combined organic layers were washed with water and brine then dried over Na$_2$SO$_4$, filtered, and concentrated. The residue was were purified by silica gel chromatography, eluting with hexanes/EtOAc to afford N-(2-cyano-3-iodophenyl)propane-1-sulfonamide (51 mg, 90%). $^1$H NMR (400 MHz, CDCl$_3$) δ 7.76 (d, 1H), 7.68 (d, 1H), 7.28 (t, 1H), 6.89 (br-s, 1H), 3.17 (t, 2H), 1.91 (m, 2H), 1.07 (t, 3H).

Step 2: Preparation of N-(2-cyano-3-iodophenyl)-N-((2-(trimethylsilyl)ethoxy)methyl)propane-1-sulfonamide. To a solution of N-(2-cyano-3-iodophenyl)propane-1-sulfonamide (50 mg, 0.143 mmol) in DMF (952 µL) at 0° C. was added sodium hydride (60% suspension in mineral oil, 7.71 mg, 0.193 mmol), and (2-(chloromethoxy)ethyl)trimethylsilane (28.7 µL, 0.171 mmol) and the reaction mixture was stirred at 0° C. for 1 hour. The reaction mixture was treated with water and extracted with EtOAc (2×) and then the combined organic layers were washed with water followed by brine and then dried over Na$_2$SO$_4$, filtered, and concentrated. The residue was purified by silica gel chromatography, eluting with hexanes/EtOAc) to give N-(2-cyano-3-iodophenyl)-N-((2-(trimethylsilyl)ethoxy)methyl)propane-1-sulfonamide (50 mg, 73%). $^1$H NMR (400 MHz, CDCl$_3$) δ 7.93 (d, 1H), 7.56 (d, 1H), 7.33 (t, 1H), 5.08 (s, 2H), 3.70 (t, 2H), 3.16 (t, 2H), 1.94 (m, 2H), 1.08 (t, 3H), 0.92 (t, 2H), 0.01 (s, 9H).

Intermediate P66

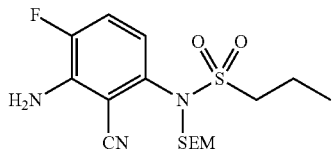 [SMILES: CCCS(=O)(=O)N(COCC[Si](C)(C)C)c1ccc(F)c(N)c1C#N]

N-(3-amino-2-cyano-4-fluorophenyl)-N-((2-(trimethylsilyl)ethoxy)methyl)propane-1-sulfonamide Step 1: Preparation of N-(3-amino-2-cyano-4-fluorophenyl)propane-1-sulfonamide. To a solution of propane-1-sulfonamide (232 mg, 1.88 mmol) in DMSO (2 mL) was added sodium hydride (60% suspension in mineral oil, 82.4 mg, 2.06 mmol) and the mixture was stirred at ambient temperature for 30 minutes. The reaction mixture was treated with a 2 mL DMSO solution of 2-amino-3,6-difluorobenzonitrile (138 mg, 0.895 mmol) and then the reaction mixture was heated to 100° C. for 16 hours and then at 120° C. for 24 hours. The reaction mixture was cooled to ambient temperature and treated with 0.5 M aqueous NaOH and then extracted with EtOAc (2×). The aqueous layer was acidified to about pH 4 and extracted with EtOAc (2×) and then the combined organic layers were washed with brine then dried over Na$_2$SO$_4$, filtered, and concentrated. The residue was purified by silica gel chromatography, eluting with hexanes/EtOAc to give N-(3-amino-2-cyano-4-fluorophenyl)propane-1-sulfonamide (26 mg, 11%). $^1$H NMR (400 MHz, CDCl$_3$) δ 7.15 (dd, 1H), 6.92 (dd, 1H), 6.54 (br-s, 1H), 4.58 (br-s, 2H), 3.12 (t, 2H), 1.91 (m, 2H), 1.06 (t, 3H).

Step 2: Preparation of N-(3-amino-2-cyano-4-fluorophenyl)-N-((2-(trimethylsilyl)ethoxy)-methyl)propane-1-sulfonamide. To a solution of N-(3-amino-2-cyano-4-fluorophenyl)propane-1-sulfonamide (25 mg, 0.0972 mmol) in DMF (648 µL) at 0° C. was added sodium hydride (60% suspension in mineral oil, 4.28 mg, 0.107 mmol) and then (2-(chloromethoxy)ethyl)trimethylsilane (17.1 µL, 0.102 mmol) and the reaction mixture was stirred at 0° C. for 30 minutes The reaction mixture was treated with water and extracted with EtOAc (2×) and then the combined organic layers were washed with water followed by brine and then dried over Na$_2$SO$_4$, filtered, and concentrated. The residue was purified by silica gel chromatography, eluting with hexanes/EtOAc to give N-(3-amino-2-cyano-4-fluorophenyl)-N-((2-(trimethylsilyl)ethoxy)methyl)propane-1-sulfonamide (16 mg, 43%). $^1$H NMR (400 MHz, CDCl$_3$) δ 7.17 (dd, 1H), 6.81 (dd, 1H), 5.01 (s, 2H), 4.60 (br-s, 2H), 3.69 (t, 2H), 3.12 (t, 2H), 1.92 (m, 2H), 1.06 (t, 3H), 0.93 (t, 2H), 0.02 (s, 9H).

Intermediate P67

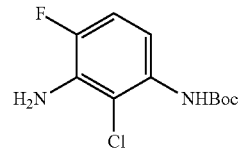

Tert-butyl (3-amino-2-chloro-4-fluorophenyl)carbamate

Step 1: Preparation of methyl 3-((tert-butoxycarbonyl)amino)-2-chloro-6-fluorobenzoate. Methyl 3-amino-2-chloro-6-fluorobenzoate (5.06 g, 24.9 mmol) was dissolved in DCM (250 mL), and cooled to 0° C. The reaction mixture was sequentially treated with triethylamine (10.4 mL, 74.6 mmol), 4-(dimethylamino)pyridine (0.304 g, 2.49 mmol), and then di-tert-butyl dicarbonate (13.6 g, 62.1 mmol) and allowed to stir at ambient temperature for 16 hours. The reaction mixture was concentrated and the residue was purified by silica gel chromatography, eluting with hexanes/acetone to provide methyl 3-((tert-butoxycarbonyl)amino)-2-chloro-6-fluorobenzoate (7.55 g, 100%) which was used immediately in the next step as a mixture of mono/bis-Boc products.

Step 2: Preparation of 3-((tert-butoxycarbonyl)amino)-2-chloro-6-fluorobenzoic acid. Methyl 3-((tert-butoxycarbonyl)amino)-2-chloro-6-fluorobenzoate (7.55 g, 24.9 mmol) was dissolved in 1:1 THF/MeOH (120 mL) and then treated with 2.0 M aqueous NaOH (37.3 mL, 74.6 mmol) and allowed to stir at ambient temperature for 16 hours. The reaction mixture was diluted with additional water and extracted with Et$_2$O (2×250 mL). The Et$_2$O organics were combined and washed with 1.0 M NaOH (1×50 mL) and then the combined aqueous layers were acidified to about pH 4 using 4.0 M HCl and then extracted with 4:1 DCM/IPA (2×250 mL). The DCM/IPA organic layers Were combined and dried over Na$_2$SO$_4$, filtered, and concentrated to provide 3-((tert-butoxycarbonyl)amino)-2-chloro-6-fluorobenzoic acid (5.53 g, 77%) that was used directly in the next step without purification.

Step 3: Preparation of tert-butyl (3-amino-2-chloro-4-fluorophenyl)carbamate. 3-((Tert-butoxycarbonyl)amino)-2-chloro-6-fluorobenzoic acid (5.53 g, 19.1 mmol) was dissolved in DMF (100 mL) and treated sequentially with triethylamine (7.98 mL, 57.27 mmol) then diphenylphosphoryl azide (6.17 mL, 28.63 mmol) and stirred at ambient temperature for 1 hour. The reaction mixture was treated with water (20 mL) and heated to 80° C. for 16 hours. The reaction mixture was cooled to ambient temperature and diluted with additional water (50 mL) and then extracted with EtOAc (2×250 mL). The organic extracts were combined and washed with water (3×100 mL) and brine (1×50 mL) then dried over Na$_2$SO$_4$, filtered, and concentrated. The residue was purified by silica gel chromatography, eluting with hexanes/Acetone and, then again with hexanes/MTBE to provide tert-butyl (3-amino-2-chloro-4-fluorophenyl)carbamate (1.05 g, 21%). $^1$H NMR (400 MHz, DMSO-d$_6$) δ 8.41 (s, 1H), 6.99-6.94 (m, 1H), 6.69-6.66 (m, 1H), 5.34 (s, 2H), 1.43 (s, 9H).

Intermediate P68

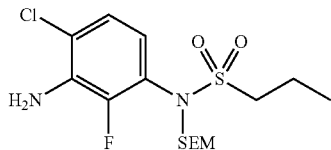 [SMILES: CCCS(=O)(=O)N(COCC[Si](C)(C)C)c1ccc(Cl)c(N)c1F]

N-(3-amino-4-chloro-2-fluorophenyl)-N-((2-(trimethylsilyl)ethoxy)methyl) propane-1-sulfonamide To a solution of N-(3-amino-4-chloro-2-fluorophenyl)propane-1-sulfonamide (3.0 g, 11.2 mmol) in DMF (45.0 mL) at 0° C. was added 60% sodium hydride as a suspension in mineral oil (607 mg, 15.2 mmol). After 15 minutes the reaction mixture was treated dropwise with (2-(chloromethoxy)ethyl)trimethylsilane (2.4 mL, 13.5 mmol) and the reaction mixture was allowed to stir at ambient temperature for 1 hour. The reaction mixture was treated with water and extracted with EtOAc (2×) and then the combined organic layers were washed with water followed by brine and then dried over Na$_2$SO$_4$, filtered, and concentrated. The residue was purified by silica gel chromatography, eluting with hexanes/EtOAc to give N-(3-amino-4-chloro-2-fluorophenyl)-N-((2-(trimethylsilyl)ethoxy)methyl)propane-1-sulfonamide (3.85 g, 86%) as an off white solid. $^1$H NMR (400 MHz, CDCl$_3$) δ 7.08 (d, 1H), 6.75 (dd, 1H), 4.97 (s, 2H), 4.16 (s, 2H), 3.65 (dd, 2H), 3.08 (dd, 2H), 1.93-1.83 (m, 2H), 1.05 (t, 3H), 0.91 (dd, 2H), 0.01 (s, 9H).

Intermediate P69

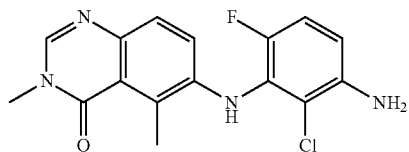 [SMILES: Cc1c(Nc2c(F)ccc(N)c2Cl)ccc2ncn(C)c(=O)c12]

6-((3-amino-2-chloro-6-fluorophenyl)amino)-3,5-dimethylquinazolin-4(3H1)-one

Step 1: Preparation of tert-butyl (2-chloro-3-((3,5-dimethyl-4-oxo-3,4-dihydroquinazolin-6-yl)amino)-4-fluorophenyl)carbamate. Tert-butyl (3-amino-2-chloro-4-fluorophenyl)carbamate (56.7 mg, 0.217 mmol), 6-bromo-3,5-dimethylquinazolin-4(3H)-one (50 mg, 0.198 mmol), cesium carbonate (193 mg, 0.593 mmol), Xantphos (17.1 mg, 0.0296 mmol) and tris(dibenzylideneacetone)dipalladium (0) (9.05 mg, 0.0099) were combined in a vial then degassed under reduced pressure and backfilled with argon gas. Toluene (0.988 mL) was added and the solution was sparged with argon for 5 minutes before the vial was sealed and heated to 100° C. for 16 hours. The reaction mixture was cooled to ambient temperature and was filtered through a pad of Celite® and purified by silica gel chromatography, eluting with DCM/EtOAc to provide tert-butyl (2-chloro-3-((3,5-dimethyl-4-oxo-3,4-dihydroquinazolin-6-yl)amino)-4-fluorophenyl)-carbamate as an off white solid (81 mg, 95%). MS (apci, m/z)=333.1 (M-Boc).

Step 2: Preparation of 6-((3-amino-2-chloro-6-fluorophenyl)amino)-3,5-dimethylquinazolin-4(3H)-one. Tert-butyl (2-chloro-3-((3,5-dimethyl-4-oxo-3,4-dihydroquinazolin-6-yl)amino)-4-fluorophenyl)carbamate (81 mg, 0.187 mmol) was dissolved in DCM (4.7 mL) and treated with trifluoroacetic acid (1.5 mL) and the reaction mixture was allowed to stir at ambient temperature for 1 hour. The reaction mixture was concentrated and the residue was purified by silica gel chromatography, eluting with DCM/MeOH and 1% NH$_4$OH to obtain 6-((3-amino-2-chloro-6-fluorophenyl)amino)-3,5-dimethylquinazolin-4(3H)-one as a light yellow solid (37 mg, 56%). $^1$H NMR (400 MHz, CDCl$_3$) δ 7.99 (s, 1H), 7.38 (d, 1H), 7.02 (d, 1H), 6.86 (dd, 1H), 6.51 (dd, 1H), 3.50 (s, 3H), 2.90 (s, 3H); MS (apci; m/z)=333.1 (M+H).

Intermediate P70

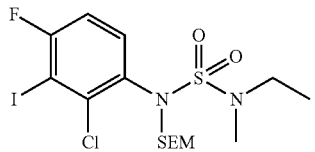 [SMILES: CCN(C)S(=O)(=O)N(COCC[Si](C)(C)C)c1ccc(F)c(I)c1Cl]

N-(2-chloro-4-fluoro-3-iodophenyl)-N-((2-(trimethylsilyl)ethoxy)methyl)-N-ethyl-N-methyl-1-sulfonamide Step 1: Preparation of N-(2-chloro-4-fluoro-3-iodophenyl)-N-ethyl-N-methyl-1-sulfonamide. To a solution of 2-chloro-4-fluoro-3-iodoaniline (145 mg, 0.534 mmol) in pyridine (2671 µL) was added ethyl(methyl)sulfamoyl chloride (177 mg, 1.12 mmol) and the reaction mixture was stirred overnight at ambient temperature. The reaction mixture was treated with 10% aqueous citric acid and extracted with EtOAc (2×) and the combined organic layers were washed with water and brine then dried over Na₂SO₄, filtered, and concentrated. The residue was purified by silica gel chromatography, eluting with hexanes/EtOAc and then the isolated product was dissolved in acetonitrile (2671 µL) and 2.0 M aqueous Na₂CO₃ (2671 µL, 5.34 mmol) and heated to 65° C. for 2 hours. The reaction mixture was purified by reverse-phase C18 chromatography, eluting with H₂O/acetonitrile with 0.1% TFA and the isolated product was dissolved in DCM and washed with saturated NaHCO₃ followed by brine. The organic layers were dried over Na₂SO₄, filtered, and concentrated to give N-(2-chloro-4-fluoro-3-iodophenyl)-N-ethyl-N-methyl-1-sulfonamide (21 mg, 10%). ¹H NMR (400 MHz, CDCl₃) δ 7.64 (dd, 1H), 7.02 (dd, 1H), 6.71 (br-s, 1H), 3.22 (q, 2H), 2.81 (s, 3H), 1.01 (t, 3H).

Step 2: Preparation of N-(2-chloro-4-fluoro-3-iodophenyl)-N-((2-(trimethylsilyl)ethoxy)methyl)-N-ethyl-N-methyl-1-sulfonamide. To a solution of N-(2-chloro-4-fluoro-3-iodophenyl)-N-ethyl-N-methyl-1-sulfonamide (21 mg, 0.0535 mmol) in DMF (357 µL) at 0° C. was added 60% sodium hydride in mineral oil (2.57 mg, 0.0642 mmol) and then (2-(chloromethoxy)ethyl)trimethylsilane (9.39 µL, 0.0562 mmol) and the solution was allowed to stir at ambient temperature for 30 minutes. The reaction mixture was treated with water and extracted with EtOAc (2×) and then the combined organic layers were washed with water followed by brine and then dried over Na₂SO₄, filtered, and concentrated. The residue was purified by silica gel chromatography, eluting with hexanes/EtOAc) to give N-(2-chloro-4-fluoro-3-iodophenyl)-N-((2-(trimethylsilyl)ethoxy)methyl)-N-ethyl-N-methyl-1-sulfonamide (27.5 mg, 98%). ¹H NMR (400 MHz, CDCl₃) δ 7.66 (dd, 1H), 7.04 (dd; 1H),5.19 (d, 1H), 4.68 (d, 1H), 3.64 (t, 2H), 3.14 (1, 2H), 2.80 (s, 3H), 0.92 (m, 5H), 0.01 (s, 9H).

Intermediate P71

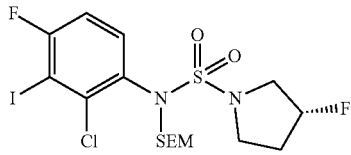 [SMILES: C[Si](C)(C)CCOCN(c1ccc(F)c(I)c1Cl)S(=O)(=O)N1CC[C@@H](F)C1]

(R)—N-(2-chloro-4-fluoro-3-iodophenyl)-3-fluoro-N-((2-(trimethylsilyl)ethoxy)methyl)-pyrrolidine-1-sulfonamide Step 1: Preparation of (R)—N-(2-chloro-4-fluoro-3-iodophenyl)-3-fluoropyrrolidine-1-sulfonamide. To a solution of 2-chloro-4-fluoro-3-iodoaniline (197 mg, 0.726 mmol) in pyridine (3629 µL) was added (R)-3-fluoropyrrolidine-1-sulfonyl chloride (286 mg, 1.52 mmol) and the reaction mixture was stirred at ambient temperature for 48 hours. The reaction mixture was treated with 10% aqueous citric acid and extracted with EtOAc (2×) and the combined organic layers were washed with water and brine then dried over Na₂SO₄, filtered, and concentrated. The residue was purified by reverse-phase C18 chromatography, eluting with H₂O/acetonitrile with 0.1% TFA and the isolated product was dissolved in DCM and washed with saturated NaHCO₃ followed by brine. The organic layers were dried over Na₂SO₄, filtered, and concentrated to give (R)—N-(2-chloro-4-fluoro-3-iodophenyl)-3-fluoropyrrolidine-1-sulfonamide (200 mg, 43%). ¹H NMR (400 MHz, CDCl₃) δ 7.68 (dd, 1H), 7.02 (dd, 1H), 6.78 (br-s, 1H), 3.59 (m, 3H), 3.47 (m, 2H), 2.24 (m, 1H), 2.05 (m, 1H).

Step 2: Preparation of (R)—N-(2-chloro-4-fluoro-3-iodophenyl)-3-fluoro-N-((2-(trimethylsilyl)-ethoxy)methyl)pyrrolidine-1-sulfonamide. To a solution of (R)—N-(2-chloro-4-fluoro-3-iodophenyl)-3-fluoropyrrolidine-1-sulfonamide (132 mg, 0.312 mmol) in DMF (2082 µL) at 0° C. was added 60% sodium hydride in mineral oil (15.0 mg, 0.375 mmol) and then (2-(chloromethoxy)ethyl)trimethylsilane (54.8 µL, 0.328 mmol) and the solution was allowed to stir at ambient temperature for 30 minutes. The reaction mixture was treated with water and extracted with EtOAc (2×) and then the combined organic layers were washed with water followed by brine and then dried over Na₂SO₄, filtered, and concentrated. The residue was purified by silica gel chromatography, eluting with hexanes/EtOAc and then re-purified by reverse-phase C18 chromatography (H₂O/acetonitrile with 0.1% TFA) and then the isolated product was dissolved in DCM and washed with saturated NaHCO₃ followed by brine, then dried over Na₂SO₄, filtered, and concentrated to give (R)—N-(2-chloro-4-fluoro-3-iodophenyl)-3-fluoro-N-((2-(trimethylsilyl)ethoxy)methyl)pyrrolidine-1-sulfonamide (25.2 mg, 15%). ¹H NMR (400 MHz, CDCl₃) δ 7.64 (m, 1H), 7.04 (dd, 1H), 5.29 (m, 1H), 5.18 (m, 1H), 3.64 (m, 4H), 3.49 (m, 3H), 2.24 (m, 1H), 2.09 (m, 1H), 0.91 (t, 2H), 0.01 (s, 9H).

Intermediate P72

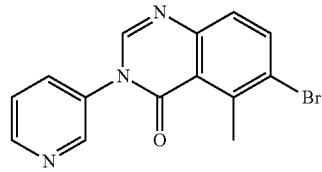 [SMILES: Cc1c(Br)ccc2ncn(-c3cccnc3)c(=O)c12]

6-bromo-5-methyl-3-(pyridin-3-yl)quinazolin-4(3H)-one

Pyridin-3-ylboronic acid (51.4 mg, 0.418 mmol), copper (II) acetate (38.0 mg, 0.209 mmol) and 15 mg crushed 4 angstrom mol sieves were suspended in anhydrous DCM (3 mL). The slurry was stirred for 5 minutes at ambient temperature under an oxygen balloon. 6-Bromo-5-methylquinazolin-4(3H)-one (50 mg, 0.209 mmol) and pyridine (33.8 µL, 0.418 mmol) were added and the reaction was stirred at 40° C. for 42 hours under an oxygen balloon. The reaction was diluted with DCM (15 mL), and solids were removed by filtration and washed with DCM (10 mL). The organic filtrate was washed with aqueous saturated sodium bicarbonate (3×25 mL). The aqueous washes were combined and extracted with DCM:IPA (4:1) (2×10 mL). The organics phases were combined and dried over sodium sulfate, filtered, and concentrated to obtain a green oil that was purified by silica gel chromatography eluting with DCM and MeOH (0%-10% MeOH, with 1% NH₄OH) to afford 6-bromo-5-methyl-3-(pyridin-3-yl)quinazolin-4(3H)-one (38.7 mg, 59%) as a white solid. MS (apci, m/z)=316.0, 318.0 (M+H).

Intermediate P73

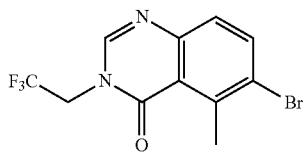 [SMILES: Cc1c(Br)ccc2ncn(CC(F)(F)F)c(=O)c12]

6-bromo-5-methyl-3-(2,2,2-trifluoroethyl)quinazolin-4(3H)-one

To a solution of 6-bromo-5-methylquinazolin-4(3H)-one (50 mg, 0.2091 mmol) in DMF (2.1 mL) was added K₂CO₃ (115.6 mg, 0.8366 mmol) and the reaction mixture was stirred under argon at ambient temperature for 5 minutes. 2,2,2-Trifluoroethyl trifluoromethanesulfonate (33.14 μL, 0.2301 mmol) was added and the reaction was stirred overnight at ambient temperature. The reaction mixture was quenched with water (15 mL) and extracted with EtOAc (3×15 mL). The organic phases were combined, dried over sodium sulfate, and concentrated to afford a white solid that was purified by silica gel chromatography eluting with hexanes and EtOAc (0-30% EtOAc) to afford 6-bromo-5-methyl-3-(2,2,2-trifluoroethyl)quinazolin-4(3H)-one (60 mg, 89%) as a waxy white solid. MS (apci, m/z)=321.0, 323.0 (M+H).

Intermediate P74

5-bromo-6-chloro-3-methylquinazolin-4(3H)-one

Step 1: Preparation of 5-bromo-6-chloroquinazolin-4(3H)-one. A solution of 6-amino-2-bromo-3-chlorobenzoic acid (1.21 g, 4.831 mmol), formamide (0.288 mL, 7.246 mmol) and POCl₃ (2.25 mL, 24.15 mmol) was heated to 95° C. for 2 hours. The reaction mixture was cooled to ambient temperature and then concentrated to remove excess POCl₃ and the residue was carefully quenched with water. The resulting yellow suspension was stirred at ambient temperature for 30 minutes and the solids were collected by filtration, washed with water and dried in vacuo to afford 5-bromo-6-chloroquinazolin-4(3H)-one (1.20 g, 96%) which was used directly in the next step without purification. MS (apci, m/z)=259.0, 261.0 (M+H).

Step 2: Preparation of 5-bromo-6-chloro-3-methylquinazolin-4(3H)-one. To a solution of 5-bromo-6-chloroquinazolin-4(3H)-one (1.2 g, 4.62 mmol) in DMF (20 mL) was added potassium carbonate (1.41 g, 10.2 mmol) followed by iodomethane (0.576 mL, 9.25 mmol), and the reaction mixture was stirred at ambient temperature for 16 hours. The reaction mixture was diluted with 100 mL of water and extracted with EtOAc (×4). The organic phases were combined, washed with brine, dried over Na₂SO₄, then concentrated. The crude product was purified via column chromatography, eluting with 10-50% acetone in DCM to give 5-bromo-6-chloro-3-methylquinazolin-4(3H)-one (0.78 g, 62%). MS (apci, m/z)=274.9, 276.9 (M+H).

Intermediate P75

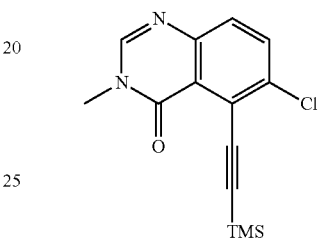

6-chloro-3-methyl-5-((trimethylsilyl)ethynyl)quinazolin-4(3H)-one

5-Bromo-6-chloro-3-methylquinazolin-4(3H)-one (276.5 mg, 1.011 mmol) was dissolved in dioxane (10 mL) and treated with trimethylsilylacetylene (171.44 μL, 1.213 mmol), bis(triphenylphosphine)palladium(II)chloride (141.91 mg, 0.202 mmol), copper (I) iodide (38.506 mg, 0.202 mmol), and triethylamine (563.62 μL, 4.044 mmol) and then sparged with argon for 5 minutes, sealed, and heated to 70° C. for 16 hours. The reaction mixture was cooled to ambient temperature, concentrated and purified by silica gel chromatography (Hexanes/Acetone) followed by reverse phase C18 chromatography (water-acetonitrile with 0.1% TFA). The desired fractions were then concentrated to dryness and the resulting residue was dissolved in 4:1 DCM:IPA and washed with saturated NaHCO₃ (1×). The organic fractions were combined and dried over Na₂SO₄, filtered, and concentrated to provide 6-chloro-3-methyl-5-((trimethylsilyl)ethynyl)quinazolin-4(3H)-one (115.4 mg, 39%). MS (apci, m/z)=291.1, 293.1 (M−H).

Intermediate P76

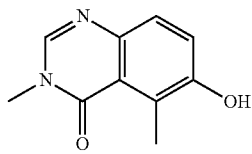

6-hydroxy-3,5-dimethylquinazolin-4(3H)-one

Step 1: Preparation of 3,5-dimethyl-6-(4,4,5,5-tetramethyl-1,3,2-dioxaborolan-2-yl)quinazolin-4(3H)-one. To a vial was added 6-bromo-3,5-dimethylquinazolin-4(3H)-one (2.70 g, 10.7 mmol), bis(pinacolato)diboron (3.25 g, 12.8 mmol), KOAc (3.14 g, 320 mmol) and DMSO (26.7 mL). The slurry was purged with bubbling Ar for 5 minutes, then dichloro[1,1'-bis(diphenylphosphino)ferrocene]palladium (II) dichloromethane adduct (0.263 g, 0.320 mmol) was added in one portion and the vial was sealed. The mixture was heated to 90° C. for 15 hours. The mixture was cooled to ambient temperature, diluted with water (150 mL) and stirred for 15 minutes. The resulting solid was isolated by vacuum filtration and washed with additional water. The resulting solid was dissolved in EtOAc (150 mL) and the solution was dried over $Na_2SO_4$. The mixture was then filtered directly through a silica plug and the desired product was eluted with EtOAc. The filtrate was concentrated to afford 3,5-dimethyl-6-(4,4,5,5-tetramethyl-1,3,2-dioxaborolan-2-yl)quinazolin-4(3H)-one as a tan solid (2.48 g, 77%). MS (apci, m/z)=301.1 (M+H).

Step 2: Preparation of 6-hydroxy-3,5-dimethylquinazolin-4(3H)-one. A solution of 3,5-dimethyl-6-(4,4,5,5-tetramethyl-1,3,2-dioxaborolan-2-yl)quinazolin-4(3H)-one (2.48 g, 8.26 mmol) in THF (41.3 mL) was cooled to 0° C. in an ice/water bath, then NaOH (2.0 M aqueous, 20.7 mL, 41.3 mmol) was added dropwise. Hydrogen peroxide (35% wt, aqueous, 5.68 mL, 66.1 mmol) was added slowly. The reaction mixture was stirred at 0° C. for 2.5 hours and then quenched by the addition of sodium thiosulfate (3.0 M aqueous, 24.8 mL, 74.4 mmol) and the reaction mixture was allowed to warm to ambient temperature and stirred for 1 hour. The reaction mixture was diluted with 0.1 N aqueous NaOH and washed with MTBE (2×). The aqueous layer was adjusted to about pH 4 with solid citric acid. The resulting solid was isolated by vacuum filtration, washed with additional water and then dried overnight under vacuum at ambient temperature to afford 6-hydroxy-3,5-dimethylquinazolin-4(3H)-one as an off-white solid (1.49 g, 94%). MS (apci, m/z)=191.1 (M+H).

Intermediate P77

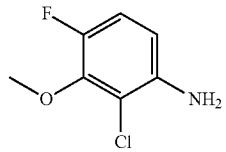

N-(2-chloro-4-fluoro-3-iodophenyl)-N-((2-(trimethylsilylethoxy)methyl)butane-2-sulfonamide Step 1: Preparation of N-(2-chloro-4-fluoro-3-iodophenyl)butane-2-sulfonamide. To a solution of 2-chloro-4-fluoro-3-iodoaniline (250 mg, 0.921 mmol) in dichloromethane (4.6 mL) at 0° C. was added triethylamine (385 µL, 2.76 mmol) and butane-2-sulfonyl chloride (303 mg, 1.93 mmol) and the reaction mixture was stirred overnight at ambient temperature. The reaction mixture was diluted with DCM and washed with water (1×) and brine (1×). The organic layer was dried over $Na_2SO_4$, filtered, and concentrated. The residue was purified by silica gel chromatography (10-75% EtOAc/hexane) to afford N-(2-chloro-4-fluoro-3-iodophenyl)butane-2-sulfonamide (250 mg, 52%). $^1$H NMR (400 MHz, $CDCl_3$) δ 7.75 (dd, 1H), 7.02 (dd, 1H), 2.99 (m, 1H), 1.37 (d, 3H), 1.14 (m, 2H), 1.01 (t, 3H).

Step 2: Preparation of N-(2-chloro-4-fluoro-3-iodophenyl)-N-((2-(trimethylsilyl)ethoxy)methyl)butane-2-sulfonamide. To a solution of N-(2-chloro-4-fluoro-3-iodophenyl)butane-2-sulfonamide (188 mg, 0.480 mmol) in N,N-dimethylformamide (32 mL) at 0° C. was added 60% sodium hydride in mineral oil (23.0 mg, 0.576 mmol) followed by (2-(chloromethoxy)ethyl)trimethylsilane (84.3 µL, 0.504 mmol). The ice bath was removed, and the solution was allowed to stir at ambient temperature for 30 minutes. The solution was then diluted with EtOAc and quenched with water. The organic layer was washed with water (1×) and brine (1×), dried over $Na_2SO_4$, filtered and concentrated. The residue was purified by reverse-phase chromatography (5-95% MeCN/water, 0.1% TFA). The isolated product was dissolved in DCM and washed with saturated $NaHCO_3$. The organic layer was washed with brine, dried over $Na_2SO_4$, filtered, and concentrated to afford N-(2-chloro-4-fluoro-3-iodophenyl)-N-((2-(trimethylsilyl)ethoxy)methyl)butane-2-sulfonamide (185 mg, 52%). $^1$H NMR (400 MHz, $CDCl_3$) δ 7.51 (dd, 1H), 7.05 (dd, 1H), 5.16 (dd, 1H), 4.81 (dd, 1H), 3.69 (m, 2H), 2.94 (m, 1H), 1.40 (dd, 3H), 1.13 (m, 2H), 1.03 (m, 3H), 0.89 (m, 2H), 0.02 (s, 9H).

Intermediate P78

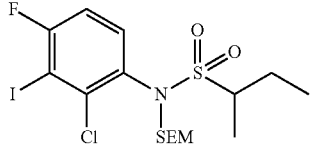 [SMILES: CCC(C)S(=O)(=O)N(COCC[Si](C)(C)C)c1ccc(F)c(I)c1Cl]

2-chloro-4-fluoro-3-methoxyaniline

Step 1: Preparation of 2-chloro-4-fluoro-3-methoxybenzaldehyde. N,N,N'-trimethylethylenediamine (1.77 mL, 13.6 mmol) was dissolved in THF (50 mL) and cooled to −42° C. under a backflow of nitrogen then treated with n-butyllithium (2.5 M in hexanes, 5.45 mL, 13.6 mmol) and allowed to stir at −42° C. for 30 minutes after complete addition. The reaction mixture was then cooled to −78° C. and treated, with a 50 mL THF solution of 4-fluoro-3-methoxybenzaldehyde (2.0 g, 13.0 mmol) and then warmed to −42° C. and stirred for 30 minutes. The reaction mixture was cooled to −78° C. and treated with n-butyllithium (2.5 M in hexanes, 5.45 mL, 13.6 mmol) and then warmed to −42° C. and allowed to stir for 1 hr. The reaction mixture was transferred quickly via cannula to 50 mL THF solution of hexachloroethane (6.14 g, 26.0 mmol) at ambient temperature and allowed to stir at ambient temperature for 2 hours. The reaction mixture was treated with 4.0 M HCl and extracted with $Et_2O$ (2×250 mL). The organic phases were combined and washed with 1.0 M NaOH (1×100 mL), 1.0 M HCl (1×100 mL), and brine (1×50 mL) and then dried over $Na_2SO_4$, filtered, and concentrated. The residue was purified by reverse phase C18 chromatography (water/acetonitrile with 0.1% TFA) and the fractions containing the desired product were combined and partitioned between 4:1 DCM:IPA and saturated $NaHCO_3$ (1×100 mL), dried over $Na_2SO_4$, filtered, and concentrated to afford 2-chloro-4-fluoro-3-methoxybenzaldehyde (1.12 g, 46%) $^1$H NMR (400 MHz, DMSO-d6) δ 10.26 (s, 1H), 7.70-7.67 (m, 1H), 7.52-7.48 (t, 1H), 3.94 (s, 3H).

Step 2: Preparation of 2-chloro-4-fluoro-3-methoxybenzoic acid. 2-Chloro-4-fluoro-3-methoxybenzaldehyde (1.07 g, 5.67 mmol) was dissolved in acetonitrile (57 mL) and treated with an aqueous 1.0 M dibasic sodium phosphate solution (8.51 mL, 8.51 mmol) and then cooled to 0° C. The reaction mixture was treated with an aqueous 35% wt hydrogen peroxide solution (0.732 mL, 8.51 mmol) followed by dropwise addition of an aqueous 1.0 M sodium chlorite solution (8.51 mL, 8.51 mmol) and then allowed to warm to ambient temperature and stirred for 16 hours. The reaction mixture was treated with a 3.0 M sodium thiosulfate solution and diluted with 1.0 M NaOH, then washed with Et₂O (2×250 mL). The aqueous layer was acidified to about pH 2 using 4.0 M HCl and extracted with 4:1 DCM:IPA (2×250 mL). The organic extracts were combined and dried over Na₂SO₄, filtered, and concentrated to provide 2-chloro-4-fluoro-3-methoxybenzoic acid (1.16 g, 99%). ¹H NMR (400 MHz, DMSO-d6) δ 13.45 (br-s, 1H), 7.59-7.56 (m, 1H), 7.40-7.36 (t, 1H), 3.89 (s, 3H).

Step 3: Preparation of 2-chloro-4-fluoro-3-methoxyaniline. 2-Chloro-4-fluoro-3-methoxybenzoic acid (1.16 g, 5.670 mmol) was dissolved in DMF (57 mL) and treated with triethylamine (2.37 mL, 17.01 mmol) followed by diphenylphosphoryl azide (1.83 mL, 8.51 mmol) and allowed to stir at ambient temperature for 1 hour. The reaction mixture was treated with 10 mL water and heated to 80° C. for 16 hours. The reaction mixture was cooled to ambient temperature, diluted with water, and extracted with EtOAc (2×250 mL). The organic phases were combined and washed with water (3×100 mL) and brine (1×50 mL), dried over Na₂SO₄, filtered, and concentrated. The residue was purified by silica gel chromatography (Hexanes/EtOAc) to provide 2-chloro-4-fluoro-3-methoxyaniline (640.9 mg, 64%). 1H NMR (400 MHz, DMSO-d6) δ 6.98-6.94 (t, 1H), 6.52-6.49 (m, 1H), 5.24 (br-s, 2H), 3.82 (s, 3H).

Intermediate P79

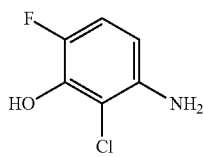

3-amino-2-chloro-6-fluorophenol

To a solution of 2-chloro-4-fluoro-3-methoxyaniline (400 mg, 2.2 mmol) in DCM (10 mL) was added BBr₃ (4.5 mL, 1.0 M in DCM, 4.5 mmol) at 0° C., and the reaction mixture was stirred at ambient temperature for 16 hours. The reaction mixture was quenched with methanol (3 mL) and then poured into cold water (75 mL) and extracted with ethyl acetate (100 mL×2). The organic layers were washed with water (2×50 mL) and brine (50 mL), dried over anhydrous sodium sulfate, filtered and evaporated under reduced pressure. The crude product was purified by silica gel column chromatography (10% ethyl acetate in hexanes) to provide 3-amino-2-chloro-6-fluorophenol as off white solid (220 mg, 60%). ¹H NMR (400 MHz, DMSO-d₆) δ 9.87 (br-s, 1H), 6.83 (dd, 1H), 6.22-60.18 (m, 1H), 5.03 (br-s, 2H). MS (m/z)=159.8 (M−H).

Intermediate P80

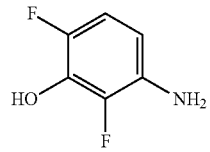

3-amino-2,6-difluorophenol

Step 1: Preparation of 2-(2,4-difluoro-3-methoxyphenyl)isoindoline-1,3-dione. A mixture of 2,4-difluoro-3-methoxyaniline (4.89 g, 30.7 mmol), isobenzofuran-1,3-dione (4.55 g, 30.7 mmol) and triethylamine (4.28 mL, 30.7 mmol) in toluene (76.8 mL) was heated to reflux with a dean stark trap for 16 hours. The reaction mixture was cooled to ambient temperature and concentrated. The residue was diluted with EtOAc and quenched with water. The organic phase was washed with water (1×) and brine (1×), dried over Na₂SO₄, filtered, and concentrated, and the residue was purified by silica gel chromatography (100% DCM) to give 2-(2,4-difluoro-3-methoxyphenyl)isoindoline-1,3-dione (8.0 g, 90%). ¹H NMR (400 MHz, DMSO-d₆) δ 8.0 (m, 2H), 7.95 (m, 2H), 7.35 (m, 2H), 3.98 (s, 3H).

Step 2: Preparation of 2-(2,4-difluoro-3-hydroxyphenyl)isoindoline-1,3-dione. To a solution of 2-(2,4-difluoro-3-methoxyphenyl)isoindoline-1,3-dione (7.6 g, 26 mmol) in dichloromethane (131 mL) at 0° C. was added 1.0 M tribromoborane (34 mL, 34 mmol) and the reaction was allowed to warm to ambient temperature and stirred for 4 hours. The solution was poured onto ice and stirred for 2 hours. The resulting solids were collected by filtration and dried in vacuo to give 2-(2,4-difluoro-3-hydroxyphenyl)isoindoline-1,3-dione (6.2 g, 86%). MS (apci, m/z)=274.1 [M−H].

Step 3: Preparation of 3-amino-2,6-difluorophenol. A solution of 2-(2,4-difluoro-3-hydroxyphenyl)isoindoline-1,3-dione (200 mg, 0.727 mmol) and 1.0 M hydrazine (1453 μL, 1.45 mmol) in methanol (1453 μL) was stirred at ambient temperature overnight. The solution was concentrated, and the residue was purified by silica gel chromatography (1-20% MeOH/DCM, 1% NH₄OH) to give 3-amino-2,6-difluorophenol (91 mg, 86%). ¹H NMR (400 MHz, CD₃OD) δ 6.62 (m, 1H), 6.24 (in, 1H); MS (apci, m/z)=146.1 [M+H].

Intermediate P81

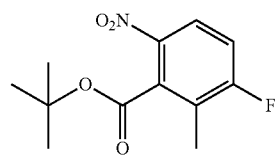 [SMILES: Cc1c(F)ccc([N+](=O)[O-])c1C(=O)OC(C)(C)C]

Tert-butyl 3-fluoro-2-methyl-6-nitrobenzoate

To a stirred solution of 3-fluoro-2-methyl-6-nitrobenzoic acid (800 mg, 4.02 mmol) in a mixture of tert-BuOH and DCM (1:1, 5 mL) was added Boc₂O (1.38 mL, 6.03 mmol)

followed by DMAP (147 mg, 1.2 mmol), and the reaction mixture was stirred at ambient temperature for 16 hours under a nitrogen atmosphere. The reaction mixture was concentrated and: the crude residue was quenched with water (150 mL) and extracted with ethyl acetate (2×150 mL). The combined organic layers were washed with water (2×100 mL), brine (100 mL), dried over anhydrous sodium sulfate, filtered, and concentrated under reduced pressure. The crude product was purified by silica gel column chromatography using 15-20% ethyl acetate in hexanes to provide tert-butyl 3-fluoro-2-methyl-6-nitrobenzoate as colorless liquid (600 mg, 60%). $^1$H NMR (400 MHz, CDCl$_3$) δ 8.10-8.07 (dd, 1H), 7.34 (t, 1H), 2.30 (s, 3H), 1.60 (s, 9H).

Intermediate P82

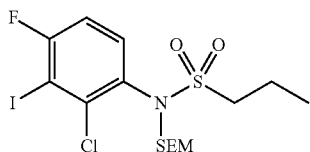 [SMILES: CCCS(=O)(=O)N(COCC[Si](C)(C)C)c1ccc(F)c(I)c1Cl]

N-(2-chloro-4-fluoro-3-iodophenyl)-N-((2-(trimethylsilyl)ethoxy)methyl)propane-1-sulfonamide Step 1: Preparation of N-(2-chloro-4-fluoro-3-iodophenyl)-N-(propylsulfonyl)propane-1-sulfonamide. To a solution of 2-chloro-4-fluoro-3-iodoaniline (2.0 g, 7.4 mmol) in DCM (50 mL) at 0° C. was added triethyl amine (2.6 mL, 18.5 mmol) and propane 1-sulfonyl chloride (2.1 mL, 18.5 mmol) and the reaction was stirred at ambient temperature for 16 hours under nitrogen. The reaction mixture was poured into water and extracted with DCM (3×20 mL). The combined organic layers were dried over anhydrous sodium sulfate, filtered and concentrated under reduced pressure. The crude product was purified by silica gel column chromatography using 20% ethyl acetate in hexane to provide N-(2-chloro-4-fluoro-3-iodophenyl)-N-(propylsulfonyl)propane-1-sulfonamide (2.5 g, 70%) as a brown solid. $^1$H NMR (400 MHz, CDCl$_3$) δ 7.48-7.39 (m, 1H), 7.12-7.03 (m, 1H), 3.73-3.61 (m, 2H), 3.62-3.49 (m, 2H), 2.06-1.88 (m, 4H), 1.09 (t, J=7.4 Hz, 6H).

Step 2: Preparation of N-(2-chloro-4-fluoro-3-iodophenyl)propane-1-sulfonamide. To a solution of N-(2-chloro-4-fluoro-3-iodophenyl)-N-(propylsulfonyl)propane-1-sulfonamide (8.0 g, 16.59 mmol) in acetonitrile (100 mL) was added sodium bicarbonate (17.5 g, 170 mmol) and 25 mL water and the reaction mixture was heated at 70° C. for 16 hours. The reaction mixture was cooled to ambient temperature, acidified to about pH 1 with saturated citric acid solution and extracted with ethyl acetate (3×50 mL). The combined organic layers were dried over anhydrous sodium sulfate, filtered and concentrated under reduced pressure. The crude product was purified by silica gel column chromatography eluting with 20% ethyl acetate in hexane to provide N-(2-chloro-4-fluoro-3-iodophenyl)propane-1-sulfonamide (5.0 g, 80%) as a brown solid. $^1$H NMR (400 MHz, CDCl$_3$) δ 7.74-7.66 (m, 1H), 7.09-7.00 (m, 1H), 6.67 (s, 1H), 3.08-2.99 (m, 2H), 1.92-1.78 (m, 2H), 1.03 (t, J=7.5 Hz, 3H); MS (m/z) 377.9 (M+H).

Step 3: Preparation of N-(2-chloro-4-fluoro-3-iodophenyl)-N-((2-(trimethylsilyl)ethoxy)methyl)propane-1-sulfonamide. To a solution of N-(2-chloro-4-fluoro-3-iodophenyl)propane-1-sulfonamide (2.0 g, 7.38 mmol) in DMF (10 mL) at 0° C. was added 60% sodium hydride in mineral oil (396 mg, 9.88 mmol) portionwise and the reaction mixture was stirred at 0° C. for 30 minutes. To this was added 2-(trimethylsilyl)ethoxymethyl chloride (1.5 mL, 8.85 mmol) and the reaction mixture was stirred at ambient temperature for 1 hour. The reaction mixture was poured into cold water and extracted with ethyl acetate (100 mL×3). The combined organic layers were dried over anhydrous sodium sulfate, filtered and concentrated under reduced pressure. The crude product was purified by silica gel column chromatography using 5% ethyl acetate in hexane to provide N-(2-chloro-4-fluoro-3-iodophenyl)-N-((2-(trimethylsilyl)ethoxy)methyl)propane-1-sulfonamide (3.2 g, 85%) as white solid. $^1$H NMR (400 MHz, DMSO-d$_6$) δ 7.67-7.58 (m, 1H), 7.41-7.30 (m, 1H), 5.09 (d, J=11.1 Hz, 1H), 4.71 (d, J=11.1 Hz, 1H), 3.60 (q, J=7.7 Hz, 2H), 3.31-3.15 (m, 2H), 1.75 (q, J=7.5 Hz, 2H), 0.99 (t, J=7.4 Hz, 3H), 0.83 (t, J=8.2 Hz, 2H), −0.02 (s, 9H).

Intermediate P83

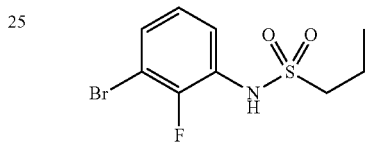

N-(3-bromo-2-fluorophenyl)propane-1-sulfonamide

To a solution of 3-bromo-2-fluoroaniline (1.0 g, 5.26 mmol) in pyridine (10 mL) was added propane-1-sulfonyl chloride (5.92 mL, 52.62 mmol) and the reaction mixture was stirred at 60° C. for 3 hours under argon atmosphere. The reaction mixture was cooled to ambient temperature and the solvent was removed under reduced pressure. The crude product was purified by silica gel column chromatography (5% ethyl acetate in hexane) to provide N-(3-bromo-2-fluorophenyl)propane-1-sulfonamide as a pale yellow solid (950 mg, 60%). $^1$H NMR (400 MHz, DMSO-d$_6$) δ 9.86 (s, 1H), 7.57-7.48 (m, 1H), 7.46-7.37 (m, 1H), 7.19-7.10 (m, 1H), 3.16-3.08 (m, 2H), 1.80-1.66 (m, 2H), 0.97 (t, J=7.4 Hz, 3H).

Intermediate P84

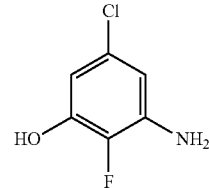

3-amino-5-chloro-2-fluorophenol

Step 1: Preparation of 5-chloro-2-fluoro-3-(4,4,5,5-tetramethyl-1,3,2-dioxaborolan-2-yl)aniline. A solution of 3-bromo-5-chloro-2-fluoroaniline (184 mg, 0.82 mmol), 4,4,4',4',5,5,5',5'-octamethyl-2,2'-bi(1,3,2-dioxaborolane) (271 mg, 1.07 mmol), PdCl$_2$(dppf)-dcm (18 mg, 0.025 mmol), and potassium acetate (161 mg, 1.64 mmol) in N,N-dimethylformamide (1949 µL) was sparged with Argon for 10 minutes and heated to 100° C. under an Argon balloon for 16 hours. The reaction mixture was cooled to ambient temperature, diluted with water and extracted with EtOAc (3×). The combined organic layers were dried over Na$_2$SO$_4$, filtered and concentrated. The crude product was purified by silica gel chromatography (5-50% EtOAc/hexane) to afford 5-chloro-2-fluoro-3-(4,4,5,5-tetramethyl-1,3,2-dioxaborolan-2-yl)aniline (169 mg, 76%).

Step 2: Preparation of 3-amino-5-chloro-2-fluorophenol. To a solution of 5-chloro-2-fluoro-3-(4,4,5,5-tetramethyl-1,3,2-dioxaborolan-2-yl)aniline (134 mg, 0.494 mmol) in tetrahydrofuran (4935 µL) at 0° C. was added 2.0 M sodium hydroxide (1234 µL, 2.47 mmol) and 35% hydrogen peroxide (340 µL, 3.95 mmol) and the reaction mixture was stirred at 0° C. for 30 minutes. The reaction mixture was quenched with 5 mL of saturated sodium thiosulfate and stirred at ambient temperature for 30 minutes. The reaction mixture was acidified to about pH 5 with 10% citric acid, diluted with water and extracted with EtOAc (3×). The combined organic layers were washed With brine, dried with Na$_2$SO$_4$, filtered, concentrated, and purified by silica gel chromatography (5-95% EtOAc/hexane) to give 3-amino-5-chloro-2-fluorophenol (63 mg, 79%). $^1$H NMR (400 MHz, CDCl$_3$) δ 6.39 (m, 1H), 6.33 (m, 1H), 5.02 (m, 1H), 3.79 (br-s, 2H).

Intermediate P85

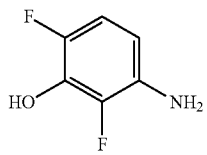

3-amino-2,6-difluorophenol

Step 1: Preparation of 2-(2,4-difluoro-3-methoxyphenyl)isoindoline-1,3-dione. A mixture of 2,4-difluoro-3-methoxyaniline (4.4 g, 28 mmol), isobenzofuran-1,3-dione (4.1 g, 28 mmol) and triethylamine (3.9 mL, 28 mmol) in 69 mL of toluene was heated to reflux with a Dean Stark trap for 16 hours. The reaction mixture was cooled to ambient temperature, diluted with water and extracted with EtOAc (3×). The combined organic layers were washed with water, brine, dried with Na$_2$SO$_4$, filtered, concentrated, and purified by reverse-phase chromatography (5-95% ACN/water, 0.1% TFA). The isolated product was dissolved in DCM and washed with saturated aqueous NaHCO$_3$. The combined organic layers were washed with brine, dried with Na$_2$SO$_4$, filtered, concentrated to give 2-(2,4-difluoro-3-methoxyphenyl)isoindoline-1,3-dione (6.3 g, 79%). $^1$H NMR (400 MHz, CDCl$_3$) δ 7.02 (m, 4H), 6.69 (m, 1H), 6.38 (m, 1H), 3.98 (s, 3H).

Step 2: Preparation of 2-(2,4-difluoro-3-hydroxyphenyl)isoindoline-1,3-dione. To a solution of 2-(2,4-difluoro-3-methoxyphenyl)isoindoline-1,3-dione (6.1 g, 21.1 mmol) in 70 mL of dichloromethane at 0° C. was added 1.0 M tribromoborane (27.4 mL, 27.4 mmol) in DCM and the reaction was allowed to warm to ambient temperature and stirred for 16 hours. The solution was poured onto ice and the resulting solids were collected by filtration and dried in vacuo to give 2-(2,4-difluoro-3-hydroxyphenyl)isoindoline-1,3-dione (4.29 g, 74%). $^1$H NMR (400 MHz, CDCl$_3$) δ 7.97 (m, 2H), 7.82 (m, 2H), 7.05 (m, 1H), 6.88 (m, 1H).

Step 3: Preparation of 3-amino-2,6-difluorophenol. A solution of 2-(2,4-difluoro-3-hydroxyphenyl)isoindoline-1,3-dione (4.29 g, 15.6 mmol) and 1.0 M hydrazine (31.2 mL, 31.2 mmol) was stirred in methanol (31.2 mL) at ambient temperature for 16 hours. The reaction mixture was filtered through Celite, the Celite was rinsed with methanol, and the filtrate was concentrated under reduce pressure. The residue was adjusted to about pH 5 with citric acid in water and extracted with EtOAc (3×). The combined organic layers were washed with brine, dried with Na$_2$SO$_4$, filtered, concentrated, and purified by silica gel chromatography (5-95% EtOAc/hexane) to give 3-amino-2,6-difluorophenol (2.11 g, 93%). MS (apci, m/z)=146.1 (M+H).

Intermediate P86

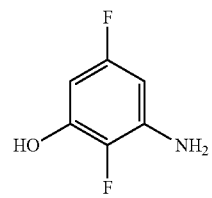

3-amino-2,5-difluorophenol

A solution of 2,5-difluoro-3-(4,4,5,5-tetramethyl-1,3,2-dioxaborolan-2-yl)aniline (0.500 g, 1.960 mmol) in THF (9.80 mL) was cooled to 0° C. in an ice/water bath and 2.0 M NaOH (4.90 mL, 9.801 mmol) was added dropwise. To this was slowly added 35 wt % hydrogen peroxide (1.35 mL, 15.68 mmol) and the mixture was stirred at 0° C. for 2.5 hours. The reaction was quenched by 3.0 M sodium thiosulfate (5.88 mL, 17.64 mmol) and the mixture was allowed to warm to ambient temperature and stirred for 0.5 hour. The mixture was diluted with 0.1N NaOH and the mixture was extracted with MTBE (2×). The aqueous layer was treated with solid citric acid to about pH 4-5. The mixture was extracted with EtOAc (3×) and the combined organic layers were dried over Na$_2$SO$_4$, filtered and concentrated to afford 3-amino-2,5-difluorophenol (0.236 g, 82%). $^1$H NMR (400 MHz, DMSO-d$_6$) δ 9.75 (s, 1H), 5.97 (ddd, J=10.6, 6.3, 3.1 Hz, 1H), 5.87 (ddd, J=9.4, 6.3, 3.1 Hz, 1H), 5.28 (brs, 2H).

Intermediate P87

3-amino-2-fluorophenol

To a solution of 2-fluoro-3-methoxyaniline (2 g, 14.18 mmol) in DCM (15 mL) was added BBr$_3$ (29 mL, 1M in DCM, 28.36 mmol) at 0° C. and the reaction mixture was stirred at ambient temperature for 16 hours. The reaction mixture was quenched with methanol (30 mL) and concentrated. The residue was poured in cold water (20 mL) and extracted with ethyl acetate (2×200 mL). The combined organic layers were washed with water (2×100 mL) and brine (100 mL), dried over anhydrous $Na_2SO_4$, filtered and concentrated. The crude product was purified by silica gel column chromatography (10% EtOAc/hexane) to provide 3-amino-2-fluorophenol (1.6 g, 88%) as brown solid. $^1H$ NMR (400 MHz, DMSO-$d_6$) δ 9.28 (s-br, 1H), 6.60 (t, J=8.1 Hz, 1H), 6.18 (t, J=7.9 Hz, 1H), 6.11 (t, J=7.9 Hz, 1H), 4.93 (s-br, 2H). MS (apci, m/z)=126.0 (M−H).

Intermediate P88

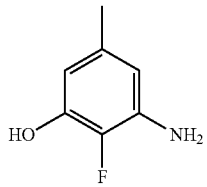

3-amino-2-fluoro-5-methylphenol

Step 1: Preparation of tert-butyl(2-fluoro-5-methylphenoxy)dimethylsilane. To a solution of 2-fluoro-5-methylphenol (12 g, 95.23 mmol) in N,N-dimethylformamide (30 mL) was added 1H-imidazole (9.71 g, 142.85 mmol) and the reaction mixture was cooled to 0° C. To this was added tert-butyl dimethylsilyl chloride (21.42 g, 142.85 mmol) and the reaction mixture was stirred at ambient temperature for 16 hours. The reaction mixture was diluted with cold water and extracted with ethyl acetate (3×100 mL). The combined organic layers-were dried over anhydrous $Na_2SO_4$, filtered and concentrated. The crude product was purified by silica gel column chromatography (5% EtOAc/hexane) to afford tert-butyl(2=fluoro-5-methylphenoxy)dimethylsilane as a colorless oil (21.3 g, 94%). $^1H$ NMR (400 MHz, CDCl$_3$) δ 6.88-6.93 (m, 1H), 6.67-6.72 (m, 2H), 2.25 (s, 3H), 1.00 (s, 9H), 0:19 (s, 6H).

Step 2: Preparation of 3-((tert-butyldimethylsilyl)oxy)-2-fluoro-5-methylbenzaldehyde. To a stirred solution of tert-butyl(2-fluoro-5-methylphenoxy)dimethylsilane (5.0 g, 20.83 mmol) in THF (100 mL) was added N,N,N',N'',N''-pentamethyldiethylenetriamine (PMDTA, 2.6 mL, 12.5 mmol) and the reaction mixture was cooled to −78° C. To this was added n-BuLi (1.6 M in Hexane, 14 mL, 22.91 mmol) dropwise and the reaction mixture was stirred at −35° C. for 1 hour. The reaction mixture was cooled to −78° C. and N,N-dimethylformamide (9.7 mL, 125 mmol) was added dropwise. The reaction mixture was slowly warmed up to room temperature, stirred for 1 hour and quenched with saturated aqueous ammonium chloride solution (70 mL). The resulting mixture was extracted with ethyl acetate (3×100 mL) and the organic layer was washed with cold water (2×20 mL). The combined organic layers were dried over anhydrous $Na_2SO_4$, filtered and concentrated. The crude product was purified by silica gel column chromatography (10% EtOAc/hexane) to provide 3-((tert-butyldimethylsilyl)oxy)-2-fluoro-5-methylbenzaldehyde as a colorless viscous liquid (3.5 g, 63%). $^1H$ NMR (400 MHz, DMSO-$d_6$) δ 10.15 (s, 1H), 7.15-7.20 (m, 2H), 2.29 (s, 3H), 0.97 (s, 9H), 0.19 (s, 6H).

Step 3: Preparation of 2-fluoro-3-hydroxy-5-methylbenzoic acid. To a solution of 3-((tert-butyldimethylsilyl)oxy)-2-fluoro-5-methylbenzaldehyde (11.0 g, 41.04 mmol) in acetonitrile (40 mL) was added saturated aqueous solution of dibasic sodium phosphate (9.6 g, 61.56 mmol) and the reaction mixture was cooled to 0° C. To this was added aqueous hydrogen peroxide (30% w/w; 6.9 mL, 61.56 mmol) followed by dropwise addition of saturated aqueous sodium chlorite (5.54 g, 61.56 mmol) solution and the reaction mixture was stirred at ambient temperature for 16 hours. The reaction mixture was treated with saturated aqueous sodium thiosulfate solution (100 mL), basified to about pH 9 with 2N NaOH (50 mL) and extracted with ethyl acetate (3×30 mL). The aqueous layer was acidified with 4N HCl (50 mL) solution and extracted with ethyl acetate (3×200 mL). The combined organic layers were dried over anhydrous $Na_2SO_4$, filtered and concentrated to provide crude 2-fluoro-3-hydroxy-5-methylbenzoic acid as a brown solid (4.5 g, 64%) that was used as such in the next step. $^1H$ NMR (400 MHz, DMSO-$d_6$) δ 13.00 (s-br, 1H), 9.93 (s-br, 1H); 7.01 (d, J=5.2 Hz, 1H), 6.94 (d, J=8 Hz, 1H), 2.21 (s, 3H); MS (m/z)=168.9 (M−H).

Step 4: Preparation of methyl 2-fluoro-3-methoxy-5-methylbenzoate. To a solution of 2-fluoro-3-hydroxy-5-methylbenzoic acid (4.5 g, 26.47 mmol) in N,N-dimethylformamide (10 mL) at 0° C. was added potassium carbonate (14.61 g, 105.88 mmol) and methyl iodide (9.9 mL, 158.82 mmol) and the reaction mixture was stirred at ambient temperature for 3 hours. The reaction mixture was diluted with water (30 mL) and extracted with ethyl acetate (3×100 mL). The combined organic layers were washed with cold water (2×30 mL), dried over anhydrous $Na_2SO_4$, filtered and concentrated. The crude product was purified by silica gel column chromatography (10% EtOAc/hexane) to provide methyl 2-fluoro-3-methoxy-5-methylbenzoate as a brown liquid (2.75 g, 52%). $^1H$ NMR (400 MHz, DMSO-$d_6$) δ 7.22-7.24 (m, 1H), 6.91 (d, J=8 Hz, 1H), 3.89, (s, 3H). 3.86 (s, 3H), 2.31 (s, 3H); MS (m/z)=199.3 (M+H).

Step 5: Preparation of 2-fluoro-3-methoxy-5-methylbenzoic acid. To a solution of methyl 2-fluoro-3-methoxy-5-m ethylbenzoate (4.0 g, 20.20 mmol) in THF and water (4:1, 50 mL) was added lithium hydroxide monohydrate (3.8 g, 90.90 mmol) and the reaction mixture was stirred at ambient temperature for 3 hours. The reaction mixture was cooled to 0° C., quenched with aqueous 1N HCl to about pH 1 and extracted with ethyl acetate (3×100 mL). The combined organic layers were dried over anhydrous $Na_2SO_4$, filtered and concentrated to provide crude 2-fluoro-3-methoxy-5-methylbenzoic acid as a white solid (3.0 g, 80%) that was used as such in the next step. $^1H$ NMR (400 MHz, DMSO-$d_6$) δ 13.12 (s-br, 1H), 7.14-7.21 (m, 2H), 3.83 (s, 3H), 1.90 (s, 3H); MS (m/z)=183.2 (M-1).

Step 6: Preparation of tert-butyl (2-fluoro-3-methoxy-5-methylphenyl)carbamate. To a stirred solution of 2-fluoro-3-methoxy-5-methylbenzoic acid (3.0 g, 16.30 mmol) in tert-BuOH/toluene mixture (1:1, 60 mL) was added N,N-diisopropylethyl amine (DIPEA, 4.5 mL, 26.08 mmol) and the mixture was cooled to 0° C. To this was added diphenylphosphoric azide (DPPA, 5.25 mL, 24.45 mmol) and the reaction was warmed to ambient temperature and then refluxed at 110° C. for 16 hour. The reaction mixture was cooled to ambient temperature, diluted with water (20 mL) and extracted with ethyl acetate (3×100 mL). The combined organic layers were dried over anhydrous $Na_2SO_4$, filtered and concentrated. The crude product was purified by silica gel column chromatography (10% EtOAc/hexane) to provide tert-butyl (2-fluoro-3-methoxy-5-methylphenyl)carbamate as a colorless solid (1.7 g, 41%). $^1$H NMR (400 MHz, DMSO-d$_6$) δ 8.80 (s-br, 1H), 6.95 (d, J=8 Hz, 1H), 6.69 (d, J=8 Hz, 1H), 3.78 (s, 3H), 2.23 (s, 3H), 1.44 (s, 9H).

Step 7: Preparation of 3-amino-2-fluoro-5-methylphenol. To a solution of tert-butyl (2-fluoro-3-methoxy-5-methylphenyl)carbamate (1.7 g, 6.66 mmol) in DCM (10 mL) at 0° C. was added boron tribromide (17 mL, 1M in DCM, 16.66 mmol) and the reaction mixture was stirred at ambient temperature for 16 hours. The reaction mixture was quenched with methanol (30 mL) and then concentrated. The residue was treated with saturated aqueous sodium bicarbonate to about pH 5 and extracted with ethyl acetate (2×200 mL). The combined organic layers were washed with water (100 mL), dried over anhydrous Na$_2$SO$_4$, filtered and concentrated to provide crude 3-amino-2-fluoro-5-methylphenol as a brown solid (1.2 g, crude) that was used as it is without purification. MS (m/z)=140.0 (M−H).

Intermediate P89

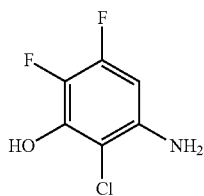

3-amino-2-chloro-5,6-difluorophenol

Step 1: Preparation of 3,4-difluoro-2-methoxyaniline. To a suspension of Fe-powder (26 g, 465.61 mmol) in methanol (70 mL) and water (30 mL) was added concentrated HCl (4 mL) dropwise and the mixture was heated to 75° C. To this was added a solution of 1,2-difluoro-3-methoxy-4-nitrobenzene (22 g, 116.40 mmol) in methanol (30 mL) dropwise over the period of 30 minutes and the mixture was stirred at 75° C. for 4 hours. The reaction mixture was cooled to ambient temperature, filtered through Celite and the Celite was washed with DCM (2×250 mL). The filtrate was concentrated, and the crude residue was diluted with water (250 mL) and extracted with DCM (2×500 mL). The organic layer was washed with water (2×100 mL) and brine (100 mL), dried over anhydrous Na$_2$SO$_4$, filtered and concentrated. The crude product was purified by silica gel column chromatography (20% EtOAc/hexane) to provide 3,4-difluoro-2-methoxyaniline as a light yellow liquid (15 g, 81%). $^1$H NMR (400 MHz, DMSO-d$_6$) δ 6.83 (q, J=9.0 Hz, 1H), 6.47-6.38 (m, 1H), 5.01 (s-br, 2H), 3.78 (s, 3H).

Step 2: Preparation of 6-bromo-3,4-difluoro-2-methoxyaniline. To a solution of 3,4-difluoro-2-methoxyaniline (15.0 g, 94.3 mmol) in DCM (50 mL) was added a solution of N-bromosuccinimide (16.6 g, 94.3 mmol) in DMF (10 mL) and the reaction mixture was stirred at 0° C. for 30 minutes. The reaction mixture was concentrated, and the residue was diluted with water and extracted with ethyl acetate (2×500 mL). The combined organic layers were washed with saturated Na$_2$S$_2$O$_3$ (4×150 mL), water (3×75 mL) and brine (2×100 mL), dried over anhydrous Na$_2$SO$_4$, filtered and concentrated. The crude product was purified by amine silica column chromatography (5% EtOAc/hexane) to provide 6-bromo-3,4-difluoro-2-methoxyaniline (10.0 g, 44%). $^1$H NMR (400 MHz, DMSO-d$_6$) δ 7.35 (dd, J=7.9, 10.2 Hz, 1H), 5.14 (s-br, 2H), 3.83 (s, 3H); MS (m/z)=238.0, 240.0 [M+H].

Step 3: Preparation of 1-bromo-2-chloro-4,5-difluoro-3-methoxybenzene. To a mixture of anhydrous cupric chloride (1.01 g, 7.56 mmol) and 6-bromo-3,4-difluoro-2-methoxyaniline (1.2 g, 5.04 mmol) in anhydrous acetonitrile (10 mL) was added t-butyl nitrite (1.04 g, 10.08 mmol) dropwise at 55° C. during a period of 5 minutes. The reaction mixture was stirred at 55° C. for another 10 minutes and was quenched with chilled 10% aqueous HCl (10 mL) and extracted with ethyl acetate (2×100 mL). The combined organic layers were washed with water (2×50 mL) and brine (50 mL), dried over anhydrous Na$_2$SO$_4$, filtered and concentrated. The crude product was purified by silica gel-column chromatography (hexane) to provide 1-bromo-2-chloro-4,5-difluoro-3-methoxybenzene as a light yellow liquid (1.0 g, 77%). $^1$H NMR (400 MHz, DMSO-d$_6$) δ 7.84 (t, J=8.8 Hz, 1H), 3.98 (s, 3H).

Step 4: Preparation of 2-chloro-4,5-difluoro-3-methoxyaniline. To a solution of 1-bromo-2-chloro-4,5-difluoro-3-methoxybenzene (6.0 g, 23.34 mmol), benzophenone imine (8.46 g, 46.69 mmol), and NaO$^t$Bu (3.37 g, 35.01 mmol) in toluene (15 mL) was added Pd$_2$(dba)$_3$ (1.07 g, 1.17 mmol) and BINAP (1.45 g, 2.34 mmol) and the reaction mixture was sparged with Ar for 15 minutes, sealed and then heated at 11.0° C. for 16 hours. The reaction mixture was cooled to ambient temperature and concentrated under reduced pressure. The residue was diluted with water and extracted with ethyl acetate (2×250 mL). The combined organic layers were washed with water (2×75 mL) and brine (2×50 mL), dried over anhydrous Na$_2$SO$_4$, filtered and concentrated to afford crude N-(2-chloro-4,5-difluoro-3-methoxyphenyl)-1,1-diphenylmethanimine (7.0 g) that was immediately used in the next step without further purification.

Step 5: Preparation of 2-chloro-4,5-difluoro-3-methoxyaniline: To a solution of N-(2-chloro-4,5-difluoro-3-methoxyphenyl)-1,1-diphenylmethanimine (7.0 g) in THF (10 mL) was added 1N HCl (10 mL, 10 mmol) dropwise and the reaction mixture was stirred at ambient temperature for 1 hour. The reaction mixture was concentrated, and the residue was dissolved in water and the pH was adjusted to about 7 with solid NaHCO$_3$. The aqueous layer was extracted with ethyl acetate (2×250 mL) and the combined organic layers were washed with water (2×50 mL) and brine (50 mL), dried over anhydrous Na$_2$SO$_4$, filtered and concentrated. The crude product was purified by amine silica column chromatography (10% EtOAc/hexane) to provide 2-chloro-4,5-difluoro-3-methoxyaniline as a pale yellow liquid (1.85 g, 22%). $^1$H NMR (400 MHz, DMSO-d$_6$) δ 6.51 (dd, J=7.3, 12.8 Hz, 1H), 5.55 (s-br, 2H), 3.88 (s, 3H).

Step 6: Preparation of 3-amino-2-chloro-5,6-difluorophenol. To a solution of 2-chloro-4,5-difluoro-3-methoxyaniline (2.2 g, 9.24 mmol) in DCM (30 mL) was added a solution of 1N BBr$_3$ in DCM (28.0 mL, 27.73 mmol) at 0° C. The reaction mixture was stirred at 0° C. for 1 hour and then at 25° C. for 16 hours under Ar. The reaction mixture was concentrated, and the residue was dissolved in MeOH at 0° C. and the pH was adjusted to about 7 with saturated NaHCO$_3$. The reaction mixture was concentrated, and the aqueous layer was extracted with ethyl acetate (2×250 mL). The combined organic layers were washed with water (2×50 mL) and brine (50 mL), dried over anhydrous Na$_2$SO$_4$, filtered and concentrated to provide 3-amino-2-chloro-5,6-difluorophenol as a pale brown solid. (1.1 g, 66%). $^1$H NMR (400 MHz, DMSO-d$_6$) δ 5.96 (dd, J=6.9, 12.8 Hz, 1H), 5.03 (s-br, 2H). MS (m/z)=177.8 [M−H].

Intermediate P90

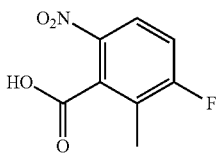

3-fluoro-2-methyl-6-nitrobenzoic Acid

To an ice cold solution of 3-fluoro-2-methylbenzoic acid (5 g, 32.4 mmol) in concentrated $H_2SO_4$ (50 mL) was added concentrated $HNO_3$ (3.5 mL) slowly and the reaction mixture was stirred at ambient temperature for 6 hours. The reaction mixture was poured into ice cold water and the solid was collected by filtration, washed with water (2×50 mL) and dried under reduced pressure to get 3-fluoro-2-methyl-6-nitrobenzoic acid as off white solid (3.0 g, 47%). $^1$H NMR (400 MHz, MeOD) δ 8.11-8.07 (m, 1H), 7.34 (t, 1H), 2.32 (s, 3H); MS (m/z)=197.6 (M–H).

Intermediate P91

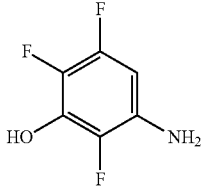 [SMILES: Nc1cc(F)c(F)c(O)c1F]

3-amino-2,5,6-trifluorophenol

Step 1: Preparation of tert-butyl (2,4,5-trifluoro-3-methoxyphenyl)carbamate. To a solution of 2,4,5-trifluoro-3-methoxybenzoic acid (5.0 g, 24.27 mmol) in a mixture of toluene:tert-butanol (1:1, 20 mL) was added N,N-diisopropylethylamine (5.7 mL, 31.55 mmol) and the mixture was cooled to 0° C. To this was added diphenylphosphoryl azide (7.8 mL, 36.4 mmol) and the reaction mixture was warmed to ambient temperature and then stirred at 100° C. for 16 hours. The reaction mixture was cooled to ambient temperature, diluted with water and extracted with ethyl acetate (3×50 mL). The combined organic layers were dried with $Na_2SO_4$, filtered and concentrated. The crude product was purified by silica gel column chromatography (10% EtOAc/hexane) to provide tert-butyl (2,4,5-trifluoro-3-methoxyphenyl)carbamate as a colorless solid (5.0 g, 74%). $^1$H NMR (400 MHz, CDCl$_3$) δ 7.73 (s-br, 1H), 6.60 (s, 1H), 4.01 (s, 3H), 1.51 (s, 9H); MS (m/z)=278.0 (M+H).

Step 2: Preparation of 2,4,5-trifluoro-3-methoxyaniline. To a solution of tert-butyl (2,4,5-trifluoro-3-methoxyphenyl) carbamate (5.0 g, 18.0 mmol) in 1,4-dioxane (20 mL) was added 4N HCl in dioxane (22.5 mL, 90.25 mmol) and the reaction mixture was stirred at ambient temperature for 16 hours. The reaction mixture was concentrated, and the pH was adjusted to about 7 with saturated aqueous sodium bicarbonate. The aqueous layer was extracted with ethyl acetate (3×100 mL) and the combined organic layers were dried with $Na_2SO_4$, filtered and concentrated to provide 2,4,5-trifluoro-3-methoxyaniline as a brownish semi-solid (2.5 g, 60%) which was used directly in the next step. $^1$H NMR (400 MHz, CDCl$_3$) δ 6.33-6.21 (m, 1H), 3.99 (s, 3H), 3.66 (s-br, 2H); MS (m/z)=175.9 (M–H).

Step 3: Preparation of 3-amino-2,5,6-trifluorophenol. To a stirred solution of 2,4,5-trifluoro-3-methoxyaniline (2.5 g, 17.73 mmol) in dichloromethane (20 mL) was added 1.0 M boron tribromide in DCM (35.5 mL, 35.46 mmol) at 0° C. The reaction mixture was stirred at ambient temperature for 16 hours. The reaction mixture was quenched with methanol (50 mL), concentrated under reduced pressure and the pH was adjusted to about 6 with saturated sodium bicarbonate solution (10 mL). The aqueous layer was extracted with ethyl acetate (2×50 mL) and the combined organic layers were dried with $Na_2SO_4$, filtered and concentrated to provide 3-amino-2,5,6-trifluorophenol as a brown solid (1.75 g, 61%) which was used directly in the next step. $^1$H NMR (400 MHz, DMSO-d$_6$) δ 10.27 (s-br, 1H), 6.36-5.85 (m, 1H), 5.14 (s-br, 2H); MS (m/z)=161.9 (M–H).

Preparation of Synthetic Examples

Example 1

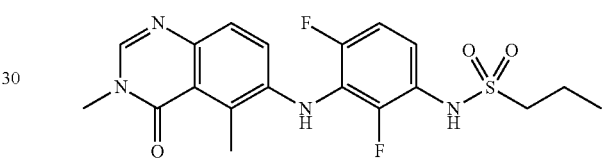

N-(3-((3,5-dimethyl-4-oxo-3,4-dihydroquinazolin-6-yl)amino)-2,4-difluorophenyl)propane-1-sulfonamide Step 1: Preparation of N-(3-((3,5-dimethyl-4-oxo-3,4-dihydroquinazolin-6-yl)amino-2,4-difluorophenyl)-N-(4-methoxybenzyl)propane-1-sulfonamide. N-(3-amino-2,4-difluorophenyl)-N-(4-methoxybenzyl)propane-1-sulfonamide (83.7 mg, 0.226 mmol), 6-bromo-3,5-dimethylquinazolin-4(3H)-one (52 mg, 0.205 mmol), cesium carbonate (201 mg, 0.616 mmol), Xantphos (17.8 mg, 0.0308 mmol), and tris(dibenzylideneacetone)dipalladium (0) (9.41 mg, 0.0103) were combined in a vial then degassed under reduced pressure and backfilled with argon gas. Toluene (0.1.03 mL) was added and the solution was sparged with argon for 5 minutes before the vial was sealed and heated to 90° C. for 16 hours. The reaction mixture was cooled to ambient temperature and was filtered through a pad of Celite® and purified by silica gel chromatography, eluting with DCM/EtOAc to provide N-(3-((3,5-dimethyl-4-oxo-3,4-dihydroquinazolin-6-yl)amino-2,4-difluorophenyl)-N-(4-methoxybenzyl)propane-1-sulfonamide as a white solid (65 mg, 58%). MS (apci, m/z)=543.2 (M+H).

Step 2: Preparation of N-(3-((3,5-dimethyl-4-oxo-3,4-dihydroquinazolin-6-yl)amino-2,4-difluorophenyl)propane-1-sulfonamide. N-(3-((3,5-dimethyl-4-oxo-3,4-dihydroquinazolin-6-yl)amino-2,4-difluorophenyl)-N-(4-methoxybenzyl)propane-1-sulfonamide (65 mg, 0.12 mmol) was dissolved in DCM (3.0 mL) and treated with trifluoroacetic acid (1.0 mL) and the reaction mixture was allowed to stir at ambient temperature for 1 hour. The reaction mixture was concentrated and the residue was purified by silica gel chromatography, eluting with DCM/MeOH with 1% NH₄OH to afford N-(3-((3,5-dimethyl-4-oxo-3,4-dihydroquinazolin-6-yl)amino)-2,4-difluorophenyl)propane-1-sulfonamide as a white solid (37.5 mg, 43%). ¹H NMR (400 MHz; CDCl₃) δ 7.94 (s, 1H), 7.45 (d, 1H), 7.29-7.23 (m, 1H), 7.16-7.12 (m, 1H), 6.98 (t, 1H), 6.62 (br-s, 1H), 5.41 (br-s, 1H), 3.54 (s, 3H), 3.07 (dd, 2H), 2.95 (s, 3H), 1.92-1.83 (m, 2H), 1.05 (t, 3H); MS (apci, m/z)=423.1 (M+H).

Example 2

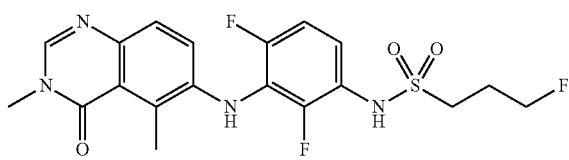

N-(3-((3,5-dimethyl-4-oxo-3,4-dihydroquinazolin-6-yl)amino)-2,4-difluorophenyl)-3-fluoropropane-1-sulfonamide Step 1: Preparation of N-(3-((3,5-dimethyl-4-oxo-3,4-dihydroquinazolin-6-yl)amino)-2,4-difluorophenyl)-N-((2-(trimethylsilyl)ethoxy)methyl))propane-1-sulfonamide. N-(3-amino-2,4-difluorophenyl)-3-fluoro-N-((2-(trimethylsilyl)ethoxy)methyl))propane-1-sulfonamide (34.6 mg, 0.087 mmol), 6-bromo-3,5-dimethylquinazolin-4(3H)-one (20 mg, 0.079 mmol), cesium carbonate (77 mg, 0.237 mmol), Xantphos (6.9 mg, 0.012 mmol), and tris(dibenzylideneacetone)dipalladium (0) (3.62 mg, 0.00395) were combined in a vial then degassed under reduced pressure and backfilled with argon gas. Toluene (0.395 mL) was added and the solution was sparged with argon for 5 min before the vial was sealed and heated to 90° C. for 16 hours. The reaction mixture was cooled to ambient temperature and was filtered through a pad of Celite® and purified by silica gel chromatography (DCM/EtOAc) to provide N-(3-((3,5-dimethyl-4-oxo-3,4-dihydroquinazolin-6-yl)amino)-2,4-difluorophenyl)-N-((2-(trimethylsilyl)-ethoxy)methyl))propane-1-sulfonamide as a white solid (35.6 mg, 79%). MS (apci, m/z)=571.2 (M+H).

Step 2: Preparation of N-(3-((3,5-dimethyl-4-oxo-3,4-dihydroquinazolin-6-yl)amino)-2,4-difluorophenyl)3-fluoropropane-1-sulfonamide. N-(3-((3,5-dimethyl-4-oxo-3,4-dihydro-quinazolin-6-yl)amino-2,4-difluorophenyl)-N-((2-(trimethylsilyl)ethoxy)methyl))propane-1-sulfonamide (35.6 mg, 0.0624 mmol) was dissolved in DCM (1.5 mL) and treated with trifluoroacetic acid (0.5 mL) and the reaction mixture was allowed to stir at ambient temperature for 1 hour. The reaction mixture was concentrated and the residue was purified by silica gel chromatography (DCM/MeOH with 1% NH₄OH) to obtain N-(3-((3,5-dimethyl-4-oxo-3,4-dihydroquinazolin-6-yl)amino)-2,4-difluorophenyl)3-fluoropropane-1-sulfonamide as a white solid (16.0 mg, 46%). ¹H NMR (400 MHz, CDCl₃) δ 7.90 (s, 1H), 7.42 (d, 1H), 7.17-7.22 (m, 1H), 7.09-7.12 (m, 1H), 6.92-6.97 (m, 1H), 5.49 (br-s, 1H), 4.57 (t, 1H), 4.45 (t, 1H), 3.51 (s, 3H), 3.21 (dd, 2H), 2.91 (s, 3H), 2.15-2.27 (m, 2H). MS (apci, m/z)=441.1 (M+H).

Example 3

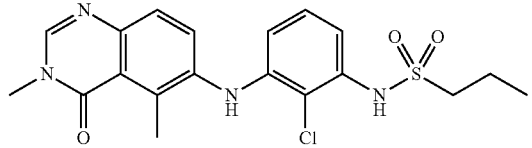 [SMILES: CCCS(=O)(=O)Nc1cccc(Nc2ccc3ncn(C)c(=O)c3c2C)c1Cl]

N-(2-chloro-3-((3,5-dimethyl-4-oxo-3,4-dihydroquinazolin-6-yl)amino)phenyl)propane-1-sulfonamide Step 1: Preparation of N-(2-chloro-3-((3,5-dimethyl-4-oxo-3,4-dihydroquinazolin-6-yl)amino)phenyl)-N-((2-(trimethylsilyl)ethoxy)methyl)propane-1-sulfonamide. A solution of N-(3-bromo-2-chlorophenyl)-N-((2-(trimethylsilyl)ethoxy)methyl)propane-1-sulfonamide (41 mg, 0.093 mmol), 6-amino-3,5-dimethylquinazolin-4(3H)-one (Intermediate P15) (18 mg, 0.093 mmol), tris(dibenzylideneacetone)dipalladium (0) (4.2 mg, 0.0046 mmol), Xantphos (8.0 mg, 0.014 mmol), and cesium carbonate (90 mg, 0.28 mmol) in toluene (617 μL) was sparged with argon for 10 minutes then sealed and heated in a vial to 90° C. overnight. The reaction mixture was cooled to ambient temperature and purified by silica gel chromatography, eluting with DCM/EtOAc to give N-(2-chloro-3-((3,5-dimethyl-4-oxo-3,4-dihydroquinazolin-6-yl)amino)phenyl)-N-((2-(trimethylsilyl)ethoxy)methyl)propane-1-sulfonamide. MS (apci, m/z)=551.2 [M+H].

Step 2: Preparation of N-(2-chloro-3-((3,5-dimethyl-4-oxo-3,4-dihydroquinazolin-6-yl)amino)phenyl)propane-1-sulfonamide. A solution of N-(2-chloro-3-((3,5-dimethyl-4-oxy-3,4-dihydroquinazolin-6-yl)amino)phenyl)-N-((2-(trimethylsilyl)ethoxy)methyl)propane-1-sulfonamide was stirred in 1 mL of DCM and 0.2 mL of trifluoroacetic acid for 45 minutes. The reaction mixture was concentrated and dissolved in 1 mL of THF and 1 mL of saturated NaHCO₃ and stirred for 30 minutes. The reaction mixture was diluted with additional saturated NaHCO₃ and extracted with DCM (2×) and then the combined organic layers were dried over Na₂SO₄, filtered, and concentrated. The residue was purified by reverse-phase C18 chromatography (H₂O/acetonitrile with 0.1% TFA) and the isolated product was dissolved in DCM and washed with saturated NaHCO₃ followed by brine. The organic layers were dried over Na₂SO₄, then filtered, and concentrated to give N-(2-chloro-3-((3,5-dimethyl-4-oxo-3,4-dihydroquinazolin-6-yl)amino)phenyl)propane-1-sulfonamide (17 mg, 44% over 2 steps). ¹H NMR (400 MHz, CDCl₃) δ 8.01 (s, 1H), 7.62 (d, 1H), 7.57 (d, 1H), 7.15 (d, 1H), 7.07 (t, 1H), 6.78 (s-br, 1H), 6.47 (d, 1H), 5.98 (s-br, 1H), 3.57 (s, 3H), 3.14 (t, 2H), 2.82 (s, 3H), 1.90 (m, 2H), 1.06 (t, 3H). MS (apci, m/z)=421.1 [M+H].

Example 4

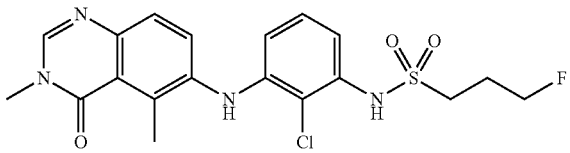 [SMILES: Cc1c(Nc2cccc(NS(=O)(=O)CCCF)c2Cl)ccc2ncn(C)c(=O)c12]

N-(2-chloro-3-((3,5-dimethyl-4-oxo-3,4-dihydroquinazolin-6-ylamino)phenyl)-3-fluoropropane-1-sulfonamide Step 1: Preparation of N-(2-chloro-3-((3,5-dimethyl-4-oxo-3,4-dihydroquinazolin-6-yl)amino)phenyl)-3-fluoro-N-((2-(trimethylsilyl)ethoxy)methyl)propane-1-sulfonamide. A suspension of N-(3-amino-2-chlorophenyl)-3-fluoro-N-((2-(trimethylsilyl)ethoxy)methyl)-propane-1-sulfonamide (0.045 g, 0.11 mmol), 6-bromo-3,5-dimethylquinazolin-4 (3H)-one (0.026 g, 0.10 mmol); tris(dibenzylideneacetone)dipalladium (0) (0.0047 g, 0.0051 mmol), Xantphos (0.0089 g, 0.015 mmol) and cesium carbonate (0.10 g, 0.31 mmol) in toluene (1.0 mL) was sparged with bubbling argon for 5 minutes. The vial was sealed and the mixture was heated at 90° C. overnight. The mixture was cooled to ambient temperature and diluted with a saturated aqueous NH₄Cl solution and the mixture was extracted with EtOAc (3×). The combined organic layers were dried over Na₂SO₄, filtered and concentrated. The crude product was purified by column chromatography, eluting with DCM/EtOAc to afford N-(2-chloro-3-((3,5-dimethyl-4-oxo-3,4-dihydroquinazolin-6-yl)amino)phenyl)-3-fluoro-N-((2-(trimethylsilyl)ethoxy)methyl)propane-1-sulfonamide as a pale yellow solid foam (0.055 g, 94%). MS (apci, m/z)=569.2 [M+H].

Step 2: Preparation of N-(2-chloro-3-((3,5-dimethyl-4-oxo-3,4-dihydroquinazolin-6-yl)amino)phenyl)-3-fluoro-propane-1-sulfonamide. To a vial containing N-(2-chloro-3-((3,5-dimethyl-4-oxo-3,4-dihydroquinazolin-6-yl)amino)phenyl)-3-fluoro-N-((2-(trimethylsilyl)-ethoxy)methyl)propane-1-sulfonamide (0.055 g, 0.097 mmol) was added CH₂Cl₂ (0.483 mL) and the solution was treated with trifluoroacetic acid (0.185 mL, 2.42 mmol). The solution was stirred at ambient temperature for 2 hours. The mixture was added to a saturated aqueous NaHCO₃ solution and the mixture was extracted with CHCl₃. The combined organic extracts were dried over Na₂SO₄, filtered and concentrated. The crude product was purified by column chromatography (DCM/MeOH) to afford N-(2-chloro-3-((3,5-dimethyl-4-oxo-3,4-dihydroquinazolin-6-yl)amino)phenyl)-3-fluoro-propane-1-sulfonamide as an off-white solid (0.026 g, 58%). ¹H NMR (400 MHz, CDCl₃) δ 8.00 (s, 1H); 7.59 (m, 2H); 7.15 (dd, 1H); 7.08 (t, 1H); 6.80 (brs, 1H); 6.49 (dd, 1H); 5.98 (brs, 1H); 4.63 (t, 1H); 4.51 (t, 1H); 3.56 (s, 3H); 3.32 (m, 2H); 2.83 (s, 3H); 2.27 (m, 2H); MS (apci, m/z)=439.0 [M+H].

Example 5

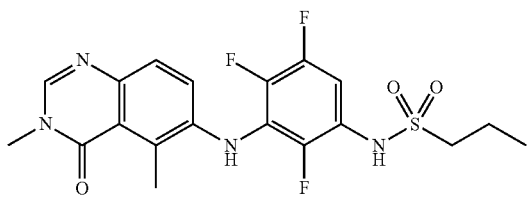

N-(3-((3,5-dimethyl-4-oxo-3,4-dihydroquinazolin-6-yl)amino)-2,4,5-trifluorophenyl)propane-1-sulfonamide Step 1: Preparation of N-(3-((3,5-dimethyl-4-oxo-3,4-dihydroquinazolin-6-yl)amino)-2,4,5-trifluorophenyl)-N-((2-(trimethylsilyl)ethoxy)methyl)propane-1-sulfonamide. A solution of N-(2,4,5-trifluoro-3-iodophenyl)-N-((2-(trimethylsilyl)ethoxy)methyl)propane-1-sulfonamide (105 mg, 0.206 mmol), 6-amino-3,5-dimethylquinazolin-4(3H)-one (Intermediate P15) (39.0 mg, 0.206 mmol), tris(dibenzylideneacetone)dipalladium (0) (9.44 mg, 0.0103 mmol), Xantphos (17.9 mg, 0.0309 mmol), and cesium carbonate (201 mg, 0.618 mmol) in toluene (1374 µL) was sparged with argon for 10 minutes and then heated in a sealed flask to 90° C. for 3 hours. The reaction mixture was cooled to ambient temperature and then purified by silica gel chromatography, eluting with DCM/EtOAc to give N-(3-((3,5-dimethyl-4-oxo-3,4-dihydroquinazolin-6-yl)amino)-2,4,5-trifluorophenyl)-N-((2-(trimethylsilyl)ethoxy)methyl)propane-1-sulfonamide (59 mg, 50%). MS (apci, m/z)=571.2 [M+H].

Step 2: Preparation of N-(3-((3,5-dimethyl-4-oxo-3,4-dihydroquinazolin-6-yl)amino)-2,4,5-trifluorophenyl)propane-1-sulfonamide. A solution of N-(3-((3,5-dimethyl-4-oxo-3,4-dihydro-quinazolin-6-yl)amino)-2,4,5-trifluorophenyl)-N-((2-(trimethylsilyl)ethoxy)methyl)propane-1-sulfonamide (96 mg, 0.168 mmol) in dichloromethane (1 mL) and trifluoroacetic acid (0.5 mL) was stirred for 30 minutes at ambient temperature. The solution was concentrated and then dissolved in tetrahydrofuran (1 mL) and saturated NaHCO₃ (1 mL) and stirred at ambient temperature for 20 minutes. The reaction mixture was diluted with additional saturated NaHCO₃ and extracted with DCM (2×) and then the combined organic layers were dried over Na₂SO₄, filtered, and concentrated. The organic layers were purified by silica gel chromatography, eluting with DCM/EtOAc to give N-(3-((3,5-dimethyl-4-oxo-3,4-dihydroquinazolin-6-yl)amino)-2,4,5-trifluorophenyl)propane-1-sulfonamide (47.5 mg, 64%). ¹H NMR (400 MHz, CDCl₃) δ 9.37 (s, 1H), 7.71 (d, 1H), 7.27 (m, 2H), 6.52 (s-br, 1H), 5.63 (br-s, 1H), 3.79 (s, 3H), 3.16 (t, 2H), 2.94 (s, 3H), 1.90 (m, 2H), 1.09 (t, 3H); MS (apci, m/z)=441.1 [M+H].

Example 6

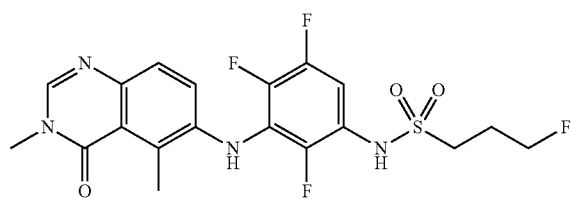 [SMILES: Cc1c(Nc2c(F)c(F)cc(NS(=O)(=O)CCCF)c2F)ccc2ncn(C)c(=O)c12]

N-(3-((3,5-dimethyl-4-oxo-3,4-dihydroquinazolin-6-yl)amino)-2,4,5-trifluorophenyl)-3-fluoropropane-1-sulfonamide Step 1: Preparation of N-(3-((3,5-dimethyl-4-oxo-3,4-dihydroquinazolin-6-yl)amino-2,4,5-trifluorophenyl)-3-fluoro-N-((2-(trimethylsilyl)ethoxy)methyl))propane-1-sulfonamide. 3-fluoro-N-(2,4,5-trifluoro-3-iodophenyl)-N-((2-(trimethylsilyl)ethoxy)methyl))propane-1-sulfonamide (39 mg, 0.074 mmol), 6-amino-3,5-dimethylquinazolin-4 (3H)-one (Intermediate P15) (14 mg, 0.074 mmol), cesium carbonate (72 mg, 0.22 mmol), Xantphos (9.0 mg, 0.016 mmol), and tris(dibenzylideneacetone)dipalladium (0) (4.7 mg, 0.0052) were combined in a vial then degassed under reduced pressure and backfilled with argon gas. Toluene (0.395 mL) was added and the solution was sparged with argon for 5 minutes before the vial was sealed and heated to 110° C. for 16 hours. The reaction mixture was cooled to ambient temperature and was filtered through a pad of Celite® and purified by silica gel chromatography, eluting with DCM/EtOAc to provide N-(3-((3,5-dimethyl-4-oxo-3,4-dihydroquinazolin-6-yl)amino-2,4,5-trifluorophenyl)-3-fluoro-N-((2-(trimethylsilyl)ethoxy)methyl))propane-1-sulfonamide as a white solid (28.9 mg, 66%). MS (apci, m/z)=589.2 (M+H).

Step 2: Preparation of N-(3-((3,5-dimethyl-4-oxo-3,4-dihydroquinazolin-6-yl)amino)-2,4,5-trifluorophenyl)-3-fluoropropane-1-sulfonamide. N-(3-((3,5-dimethyl-4-oxo-3,4-dihydroquin-azolin-6-yl)amino)-2,4,5-trifluorophenyl)-3-fluoro-N-((2-(trimethylsilyl)ethoxy)methyl))propane-1-sulfonamide (28.9 mg, 0.0491 mmol) was dissolved in DCM (1.2 mL) and treated with trifluoroacetic acid (0.41 mL) and the reaction mixture was allowed to stir at ambient temperature for 1 hour. The reaction mixture was concentrated and the residue was purified by reverse phase C18 chromatography ($H_2O$/acetonitrile with 0.1% TFA) and then the isolated product was dissolved in DCM and washed with saturated $NaHCO_3$ followed by brine, then dried over $Na_2SO_4$, filtered, and concentrated to obtain N-(3-((3,5-dimethyl-4-oxo-3,4-dihydroquinazolin-6-yl)amino)-2,4,5-trifluorophenyl)-3-fluoropropane-1-sulfonamide as a white solid (8.20 mg, 24%). $^1$H NMR (400 MHz, $CDCl_3$) δ 7.89 (s, 1H), 7.35 (d, 1H), 7.13 (d, 1H), 6.98-7.05 (m, 1H), 6.02 (br-s, 1H), 4.51 (t, 1H), 4.39 (t, 1H), 3.46 (s, 3H), 3.15 (dd, 2H), 2.82 (s, 3H), 2.06-2.19 (m, 2H); MS (apci, m/z)=459.1 (M+H).

Example 7

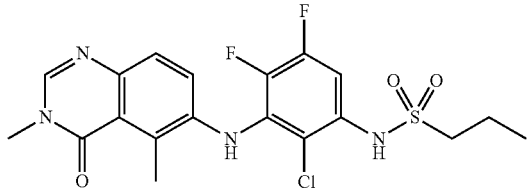 [SMILES: CCCS(=O)(=O)Nc1cc(F)c(F)c(Nc2ccc3ncn(C)c(=O)c3c2C)c1Cl]

N-(2-chloro-3-((3,5-dimethyl-4-oxo-3,4-dihydroquinazolin-6-yl)amino)-4,5-difluorophenyl)propane-1-sulfonamide Step 1: Preparation of N-(2-chloro-3-((3,5-dimethyl-4-oxo-3,4-dihydroquinazolin-6-yl)amino)-4,5-difluorophenyl)-N-((2-(trimethylsilyl)ethoxy)methyl)propane-1-sulfonamide. A solution of N-(2-chloro-4,5-difluoro-3-iodophenyl)-N-((2-(trimethylsilyl)ethoxy)methyl)propane-1-sulfonamide (39 mg, 0.074 mmol), 6-amino-3,5-dimethylquinazolin-4(3H)-one (Intermediate P15) (14 mg, 0.074 mmol), tris(dibenzylideneacetone)dipalladium (0) (3.4 mg, 0.0037 mmol), Xantphos (6.4 mg, 0.011 mmol), and cesium carbonate (72 mg, 0.22 mmol) in toluene (494 µL) was sparged with argon for 10 minutes and then heated in a sealed vial to 90° C. overnight. The reaction mixture was cooled to ambient temperature and purified by silica gel chromatography, eluting with DCM/EtOAc to give N-(2-chloro-3-((3,5-dimethyl-4-oxo-3,4-dihydroquinazolin-6-yl)amino)-4,5-difluorophenyl)-N-((2-(trimethylsilyl)ethoxy)methyl)propane-1-sulfonamide (33 mg, 75%). MS (apci, m/z)=587.2 [M+H].

Step 2: Preparation of N-(2-chloro-3-((3,5-dimethyl-4-oxo-3,4-dihydroquinazolin-6-yl)amino)-4,5-difluorophenyl)propane-1-sulfonamide. A solution of N-(2-chloro-3-((3,5-dimethyl-4-oxo-3,4-dihydroquinazolin-6-yl)amino)-4,5-difluorophenyl)-N-((2-(trimethylsilyl)ethoxy)methyl)-propane-1-sulfonamide (33 mg, 0.567 mmol) in 1 mL of DCM and 0.2 mL of trifluoroacetic acid was stirred at ambient temperature for 1 hour. The solution was concentrated and dissolved in 1 mL of THF and 1 mL of saturated $NaHCO_3$ and stirred at ambient temperature for 30 minutes. The reaction mixture was diluted with additional saturated $NaHCO_3$ and extracted with DCM (2×) and then the combined organic layers were dried over $Na_2SO_4$, filtered, and concentrated. The residue was purified by reverse-phase chromatography ($H_2O$/acetonitrile with 0.1% TFA) and then the isolated product was dissolved in DCM and washed with saturated $NaHCO_3$ followed by brine, then dried over $Na_2SO_4$, filtered, and concentrated to give N-(2-chloro-3-((3,5-dimethyl-4-oxo-3,4-dihydroquinazolin-6-yl)amino)-4,5-difluorophenyl)propane-1-sulfonamide (15 mg, 44%). $^1$H NMR (400 MHz, $CDCl_3$) δ 7.96 (s, 1H), 7.48 (d, 1H), 7:31 (dd, 1H), 7.18 (dd, 1H), 6.72 (br-s, 1H), 5.69 (br-s, 1H), 3.56 (s, 3H), 3.12 (t, 2H), 2.96 (s, 3H), 1.88 (m, 2H), 1.07 (t, 3H); MS (apci, m/z)=457.1 [M+H].

Example 8

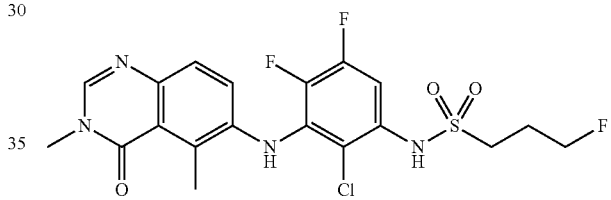

N-(2-chloro-3-((3,5-dimethyl-4-oxo-3,4-dihydroquinazolin-6-yl)amino)-4,5-difluorophenyl)-3-fluoropropane-1-sulfonamide Step 1: Preparation of N-(2-chloro-3-((3,5-dimethyl-4-oxo-3,4-dihydroquinazolin-6-yl)amino)-4,5-difluorophenyl)-3-fluoro-N-((2-(trimethylsilyl)ethoxy)methyl))propane-1-sulfonamide. N-(2-chloro-4,5-difluoro-3-iodophenyl)-3-fluoro-N-((2-(trimethylsilyl)ethoxy)methyl))propane-1-sulfonamide (52 mg, 0.095 mmol), 6-amino-3,5-dimethylquinazolin-4(3H)-one (Intermediate P15) (18 mg, 0.095 mmol), cesium carbonate (93 mg, 0.29 mmol), Xantphos (14.0 mg, 0.024 mmol), and tris(dibenzylideneacetone) dipalladium (0) (7.4 mg, 0.0081) were combined in a vial then degassed under reduced pressure and backfilled with argon gas. Toluene (0.475 mL) was added and the solution was sparged with argon for 5 minutes before the vial was sealed and heated to 110° C. for 16 hours. The reaction mixture was cooled to ambient temperature and filtered through a pad of Celite® then purified by silica gel chromatography (DCM/EtOAc) to provide N-(2-chloro-3-((3,5-dimethyl-4-oxo-3,4-dihydroquinazolin-6-yl)amino)-4,5-difluorophenyl)-3-fluoro-N-((2-(trimethylsilyl)ethoxy)methyl))propane-1-sulfonamide as a white solid (34.5 mg, 60%). MS (apci, m/z)=605.2 (M+H).

Step 2: Preparation of N-(2-chloro-3-((3,5-dimethyl-4-oxo-3,4-dihydroquinazolin-6-yl)amino)-4,5-difluorophenyl)-3-fluoropropane-1-sulfonamide. N-(2-chloro-3-((3,5- dimethyl-4-oxo-3,4-dihydroquinazolin-6-yl)amino)-4,5-difluorophenyl)-3-fluoro-N-((2-(trimethylsilyl)ethoxy)-methyl))propane-1-sulfonamide (34.5 mg, 0.057 mmol) was dissolved in DCM (1.4 mL) and treated with trifluoroacetic acid (0.48 mL) and the reaction mixture was allowed to stir at ambient temperature for 1 hour. The reaction mixture was concentrated and the residue was purified by reverse phase chromatography (H$_2$O/acetonitrile with 0.1% TFA) and then the isolated product was dissolved in DCM and washed with saturated NaHCO$_3$ followed by brine then dried over Na$_2$SO$_4$, filtered, and concentrated to obtain N-(2-chloro-3-((3,5-dimethyl-4-oxo-3,4-dihydroquinazolin-6-yl)amino)-4,5-difluorophenyl)-3-fluoropropane-1-sulfonamide as a white solid (20.5 mg, 45%). $^1$H NMR (400 MHz, CDCl$_3$) δ 7.95 (s, 1H), 7.49 (d, 1H), 7:30 (d, 1H), 7.17 (dd, 1H), 6.72 (br-s, 1H), 5.69 (br-s, 1H), 4.63 (t, 1H), 4.51 (t, 1H), 3.55 (s, 3H), 3.29 (dd, 2H), 2.95 (s, 3H), 2.18-2.32 (m, 2H); MS (apci, m/z) 475.1 (M+H).

Example 9

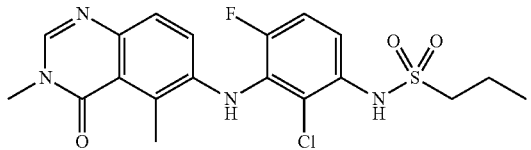

N-(2-chloro-3-((3,5-dimethyl-4-oxo-3,4-dihydroquinazolin-6-yl)amino)-4-fluorophenyl)propane-1-sulfonamide Step 1: Preparation of N-(2-chloro-3-((3,5-dimethyl-4-oxo-3,4-dihydroquinazolin-6-yl)amino)-4-fluorophenyl)-N-(4-methoxybenzyl)propane-1-sulfonamide. A solution of N-(3-amino-2-chloro-4-fluorophenyl)-N-(4-methoxybenzyl)propane-1-sulfonamide (42 mg, 0.11 mmol), 6-bromo-3,5-dimethylquinazolin-4(3H)-one (27 mg, 0.11 mmol), tris(dibenzylideneacetone)dipalladium (0) (5.0 mg, 0.0054 mmol), Xantphos (9.4 mg, 0.016 mmol), and cesium carbonate (106 mg, 0.33 mmol) in toluene (724 μL) was sparged with argon for 10 minutes and then heated in a sealed vial to 90° C. overnight. The reaction mixture was cooled to ambient temperature and purified by silica gel chromatography (DCM/EtOAc) to give N-(2-chloro-3-((3,5-dimethyl-4-oxo-3,4-dihydroquinazolin-6-yl)amino)-4-fluorophenyl)-N-(4-methoxybenzyl)propane-1-sulfonamide (43 mg, 70%). MS (apci, m/z)=559.2 [M+H].

Step 2: Preparation of N-(2-chloro-3-((3,5-dimethyl-4-oxo-3,4-dihydroquinazolin-6-yl)amino)-4-fluorophenyl)propane-1-sulfonamide. A solution of N-(2-chloro-3-((3,5-dimethyl-4-oxo-3,4-dihydroquinazolin-6-yl)amino)-4-fluorophenyl)-N-(4-methoxybenzyl)propane-1-sulfonamide (43 mg, 0.077 mmol) in 1 mL of DCM and 0.2 mL of trifluoroacetic acid was stirred at ambient temperature for 3 hours. The reaction mixture was concentrated and the residue was purified by reverse-phase C18 chromatography (H$_2$O/acetonitrile with 0.1% TFA) and then the isolated product was dissolved in DCM and washed with saturated NaHCO$_3$ followed by brine then dried over Na$_2$SO$_4$, filtered, and concentrated to give N-(2-chloro-3-((3,5-dimethyl-4-oxo-3,4-dihydroquinazolin-6-yl)amino)-4-fluorophenyl)propane-1-sulfonamide (23 mg, 48%). $^1$H NMR (400 MHz, CDCl$_3$) δ 7.94 (s, 1H), 7.44 (d, 1H), 7.41 (dd, 1H), 7.11 (d, 1H), 7.08 (d, 1H), 6.76 (br-s, 1H), 5.61 (br-s, 1H), 3.55 (s, 3H), 3.10 (t, 2H), 2.97 (s, 3H), 1.88 (m, 2H), 1.05 (t, 3H); MS (apci, m/z)=439.1 [M+H].

Example 10

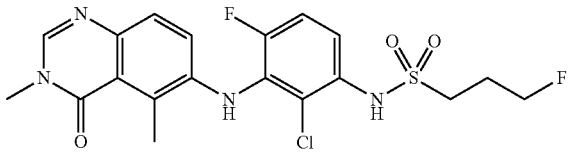 [SMILES: Cc1c(Nc2c(F)ccc(NS(=O)(=O)CCCF)c2Cl)ccc2ncn(C)c(=O)c12]

N-(2-chloro-3-((3,5-dimethyl-4-oxo-3,4-dihydroquinazolin-6-yl)amino)-4-fluorophenyl)-3-fluoropropane-1-sulfonamide Method A Step 1: Preparation of N-(2-chloro-3-((3,5-dimethyl-4-oxo-3,4-dihydroquinazolin-6-yl)amino)-4-fluorophenyl)-3-fluoro-N-((2-(trimethylsilyl)ethoxy)methyl)propane-1-sulfonamide. A solution of N-(3-amino-2-chloro-4-fluorophenyl)-3-fluoro-N-((2-(trimethylsilyl)ethoxy)methyl)propane-1-sulfonamide (Intermediate P26; 150 mg, 0.361 mmol), 6-bromo-3,5-dimethylquinazolin-4(3H)-one (Intermediate P2; 91.5 mg, 0.361 mmol), tris(dibenzylideneacetone)dipalladium (0) (16.6 mg, 0.0181 mmol), Xantphos (31.4 mg, 0.0542 mmol), and cesium carbonate (353 mg, 1.08 mmol) in toluene (2410 μL) was sparged with argon for 10 minutes and then heated in a sealed vial to 90° C. overnight. The reaction mixture was cooled to ambient temperature and purified by silica gel chromatography (DCM/EtOAc) to give N-(2-chloro-3-((3,5-dimethyl-4-oxo-3,4-dihydroquinazolin-6-yl)amino)-4-fluorophenyl)-3-fluoro-N-((2-(trimethylsilyl)ethoxy)methyl)propane-1-sulfonamide (200 mg, 94%). MS (apci, m/z)=587.2 [M+H].

Step 2: Preparation of N-(2-chloro-3-((3,5-dimethyl-4-oxo-3,4-dihydroquinazolin-6-yl)amino)-4-fluorophenyl)-3-fluoropropane-1-sulfonamide. A solution of N-(2-chloro-3-((3,5-dimethyl-4=oxo-3,4-dihydroquinazolin-6-yl)amino)-4-fluorophenyl)-3-fluoro-N-((2-(trimethylsilyl)ethoxy)-methyl)propane-1-sulfonamide (200 mg, 0.34 mmol) was stirred in 2 mL of DCM and 0.5 mL of trifluoroacetic acid at ambient temperature for 45 minutes. The reaction mixture was concentrated, and the residue was purified by silica gel chromatography (DCM/MeOH with 1% NH$_4$OH) and reverse-phase C18 chromatography (H$_2$O/acetonitrile with 0.1% TFA) The fractions containing the desired product were dissolved in DCM and washed with saturated NaHCO$_3$ followed by brine. The organic layers were dried over Na$_2$SO$_4$, filtered, and concentrated to give N-(2-chloro-3-((3,5-dimethyl-4-oxo-3,4-dihydroquinazolin-6-yl)amino)-4-fluorophenyl)-3-fluoropropane-1-sulfonamide (65 mg, 39%). $^1$H NMR (400 MHz, CDCl$_3$) δ 7.93 (s, 1H), 7.44 (d, 1H), 7.41 (dd, 1H), 7.12 (d, 1H), 7.08 (d, 1H), 6.79 (br-s, 1H), 5.61 (br-s, 1H), 4.61 (t, 1H), 4.50 (t, 1H), 3.55 (s, 3H), 3.28 (t, 2H), 2.98 (s, 3H), 2.25 (t, 2H); MS (apci, m/z)=457.1 [M+H].

Method B

Step A: Preparation of 5-methylquinazolin-4(3H)-one. A solution of 2-amino-6-methylbenzoic acid (74.7 g, 494 mmol) and formamidine acetate (61.7 g, 593 mmol) in ethanol (1.2 L) was heated at reflux under a nitrogen atmosphere for 18 hours. The reaction mixture was cooled to ambient temperature to afford a thick slurry. The solids were isolated by filtration and washed with ethanol (500 mL) and dried in a vacuum oven at 50° C. for 18 hours. The filtrate was concentrated to 500 mL, then diluted with water (1 L) and allowed to stand at ambient temperature for 18 hours to afford a thick slurry. The solids were isolated by filtration and dried in a vacuum oven at 50° C. for 18 hours. The solids from the first filtration and the second filtration were combined to afford 5-methylquinazolin-4(3H)-one (63.3 g, 80%) as a white solid. $^1$H NMR (400 MHz, DMSO-d$_6$) δ 12.01 (br-s, 1H), 8.00 (s, 1H), 7.63 (t, 1H), 7.47 (d, 1H), 7.26 (d, 1H), 2.78 (s, 3H); MS (apci, m/z)=161.2 (M+H).

Step B: Preparation of 5-methyl-6-nitroquinazolin-4(3H)-one. A solution of 5-methylquinazolin-4(3H)-one (50 g, 312.2 mmol) in concentrated sulfuric acid (555 mL) was cooled to an internal temperature of 10° C. with an external ice water bath. To the reaction mixture was added a solution of nitric acid (5M solution in concentrated sulfuric acid, 68.67 mL, 343.4 mmol). The rate of addition was controlled to maintain an internal reaction temperature below 30° C. The reaction mixture was stirred for 20 minutes and then diluted with ice water (5.5 L) and cooled with an external ice water bath until the internal temperature of the reaction mixture was <25° C. The pH of the reaction mixture was adjusted to 4 by slow addition of 10 M aqueous NaOH (2 L) to afford a thick yellow slurry. The solids were isolated by filtration and washed with water (1 L) to afford a filter cake. The filter cake was suspended in methanol (7 L) and ethyl acetate (500 mL) then heated to 55° C. to afford an orange solution. Upon cooling to ambient temperature over 18 hours a suspension of yellow crystals formed. The crystals were filtered, washed with methanol (1 L), and dried in a high vacuum oven at 50° C. for 18 hours to afford 5-methyl-6-nitroquinazolin-4(3H)-one (59.94 g, 94%) as yellow crystals. $^1$H NMR (400 MHz, DMSO-d$_6$) δ 12.50 (br-s, 1H), 8.18 (s, 1H), 8.13 (d, 1H), 7.63 (d, 1H), 2.82 (s, 3H); MS (apci, m/z)=206.1 (M+H).

Step C: Preparation of 3,5-dimethyl-6-nitroquinazolin-4 (3H)-one. A solution of 5-methyl-6-nitroquinazolin-4(3H)-one (59.94 g, 292.1 mmol) in DMF (0.2 M, 1.5 L) was cooled in an external ice water bath. To the reaction mixture was added K$_2$CO$_3$ (80.75 g, 584.3 mmol) and iodomethane (27.28 mL, 438.2 mmol). The reaction mixture was stirred for 3 hours at ambient temperature then diluted into water (7.5 L) to afford a thick yellow slurry that was stirred for 1 hour at ambient temperature. The solids were isolated by filtration, washed with water (1 L) and dried under vacuum for 18 hours to afford 3,5-dimethyl-6-nitroquinazolin-4 (3H)-one (45.85 g 72%) as a faint yellow solid. $^1$H NMR (400 MHz, DMSO-d$_6$) δ 8.49 (s, 1H), 8.13 (d, 1H), 7.63 (d, 1H), 3.47 (s, 3H), 2.81 (s, 3H); MS (apci, m/z)=220.1 (M+H)

Step D: Preparation of 6-amino-3,5-dimethylquinazolin-4(3H)-one: A suspension of 3,5-dimethyl-6-nitroquinazolin-4(3H)-one (45.85 g, 209.2 mmol) and palladium on carbon (11.13 g, 5.229 mmol) in methanol (3 L) was sparged with nitrogen for 30 minutes and then placed under a hydrogen balloon. The reaction mixture was stirred at ambient temperature for 18 hours, then sparged with nitrogen and filtered through a pad of diatomaceous earth. The filtrate was concentrated to afford 6-amino-3,5-dimethylquinazolin-4 (3H)-one (37.59 g, 95%) as a yellow solid. $^1$H NMR (400 MHz, DMSO-d$_6$) δ 8.02 (s, 1H), 7.26 (d, 1H), 7.13 (d, 1H), 5.28 (br-s, 2H), 3.39 (s, 3H), 2.62 (s, 3H); MS (apci, m/z)=190.1 (M+H)

Step E: Preparation of 2-Chloro-4-fluoro-3-iodoaniline. In a 5-L 4-neck flask equipped with 3 addition funnels, an internal temperature probe, and a magnetic stir bar, 2-chloro-4-fluoroaniline (82.03 mL, 687.00 mmol) was dissolved in THF (1.5 L) under a backflow of N$_2$ and cooled to −78° C. The reaction mixture was then treated dropwise with n-butyllithium (2.5 M in hexanes) (299.53 mL, 748.82 mmol) and allowed to stir at −78° C. for 15 minutes after complete addition. The reaction mixture was treated dropwise with a THF solution (500 mL) of 1,2-bis(chlorodimethylsilyl)ethane (155.28 g, 721.35 mmol) and allowed to stir at −78° C. for 30 minutes after complete addition. The reaction mixture was treated dropwise with additional n-butyllithium (2.5 M in hexanes) (299.53 mL, 748.82 mmol) and then the ice bath was removed after complete addition and the reaction mixture allowed to stir for 1 hour. The reaction mixture was then cooled back to −78° C. and treated dropwise with additional n-butyllithium (2.5 M in hexanes) (299.53 mL, 748.82 mmol) and allowed to stir at −78° C. for 30 minutes after complete addition. The reaction mixture was treated dropwise with a THF solution (600 mL) of iodine (249.34 g, 982.40 mmol) and the ice bath was removed, and reaction mixture allowed to warm to ambient temperature and stir for 16 hours. The reaction mixture was treated with 1 L of water followed by hydrochloric acid (4.0 M aqueous solution) (601.12 mL, 2404.5 mmol) and allowed to stir at ambient temperature for 1 hour. The reaction mixture was neutralized to about pH 8 using solid NaHCO$_3$ and then treated with sodium thiosulfate (3.0 M aqueous solution) (801.49 mL, 2404.5 mmol) and allowed to stir at ambient temperature for 30 minutes. The reaction mixture was transferred to a 6 L extraction funnel, rinsing the flask with MTBE and water, and the layers were separated. The aqueous layer was extracted with MTBE (1×) and the organic layers were combined, washed with brine (1×), dried over Na$_2$SO$_4$, filtered, and concentrated to provide 2-chloro-4-fluoro-3-iodoaniline (186.49 g, 100%) that was used directly in the next step. $^1$H NMR (400 MHz, DMSO-d$_6$) δ 7.08-7.04 (m, 1H), 6.91-6.88 (m, 1H), 5.52 (br-s, 2H). MS (apci, m/z)=271.9, 273.9 (M+H).

Step F: Preparation of bis-tert-butyl (2-chloro-4-fluoro-3-iodophenyl)carbamate. In a 3-L 1 neck flask, 2-chloro-4-fluoro-3-iodoaniline (186.49 g, 687.0 mmol) was dissolved in THF (2.0 L) and treated with 4-(dimethylamino)pyridine (8.393 g, 68.7 mmol) followed by the addition of di-tert-butyl dicarbonate (314.87 g, 1442.7 mmol). The reaction mixture was stirred at ambient temperature for 1 hour open to air with a Vigreux column. The reaction mixture was then concentrated to dryness and the resulting solids were suspended in heptane (1 L) and stirred for 30 minutes. The resulting solids were collected by filtration, rinsed with additional heptane (250 mL×2) to provide bis-tert-butyl (2-chloro-4-fluoro-3-iodophenyl)carbamate (150.7 g, 47%) as light tan solids. $^1$H NMR (400 MHz, DMSO-d$_6$) δ 7.55-7.51 (m, 1H), 7.32-7.27 (m, 1H), 1.33 (s, 18H).

Step G: Preparation of Tert-butyl (2-chloro-4-fluoro-3-iodophenyl)carbamate. Bis-tert-butyl (2-chloro-4-fluoro-3-iodophenyl)carbamate (150.7 g, 319.5 mmol) was dissolved in MeOH (800 mL) and treated with potassium carbonate (48.57 g, 351.4 mmol) and the reaction mixture was heated to 65° C. for 1 hour. The reaction mixture was then cooled to ambient temperature and poured into 3.0 L of water and stirred for 30 minutes. The resulting solids were collected by filtration and rinsed with additional water (1 L). The solids were then dissolved in DCM (1 L), diluted with hexanes (1 L) and filtered through a plug of silica gel (500 g) eluting with additional 1:1 DCM:Hexanes (4.0 L). The fractions containing the desired product were concentrated to provide tert-butyl (2-chloro-4-fluoro-3-iodophenyl)carbamate (101.0 g; 85%). ¹H NMR (400 MHz, DMSO-d₆) δ 8.82 (br-s, 1H), 7.53-7.49 (m, 1H), 7.27-7.20 (m, 1H), 1.42 (s, 9H).

Step H: Preparation of tert-butyl (2-chloro-3-((3,5-dimethyl-4-oxo-3,4-dihydroquinazolin-6-yl)amino)-4-fluorophenyl)carbamate. In a 3 L flask equipped with a reflux condenser and magnetic stir bar, 6-amino-3,5-dimethylquinazolin-4(3H)-one (50.5 g, 266.9 mmol) was dissolved in toluene (1065 mL) and treated with tert-butyl (2-chloro-4-fluoro-3-iodophenyl)carbamate (109.1 g, 293.6 mmol), tris(dibenzylideneacetone)dipalladium (0) (2.44 g, 2.67 mmol), Xantphos (3.86 g, 6.67 mmol), and cesium carbonate (173.9 g, 533.78 mmol). The reaction mixture was sparged with argon for 15 minutes and then heated to 110° C. under an argon balloon for 24 hours. The reaction mixture was cooled to ambient temperature and then diluted with DCM (2.0 L) and stirred for 30 minutes. The reaction mixture was filtered through Celite® and the filtrate was concentrated. The resulting solids were dissolved in DCM (2.5 L) and then poured into a stirring solution of heptane (12.5 L) and allowed to stir at ambient temperature for 30 minutes. The resulting solids were collected by filtration, rinsed with additional heptane (1.5 L), to provide tert-butyl (2-chloro-3-((3,5-dimethyl-4-oxo-3,4-dihydroquinazolin-6-yl)amino)-4-fluorophenyl)carbamate (95.3 g, 83%). ¹H NMR (400 MHz, DMSO-d₆) δ 8.70 (s, 1H), 8.15 (s, 1H), 7.36-7.23 (m, 4H), 6.81-6.79 (m, 1H), 3.43 (s, 3H), 2.81 (s, 3H), 1.45 (s, 9H); MS (apci, m/z)=433.2, 435.2 (M+H).

Step I: Preparation of tert-butyl (2-chloro-3-((3,5-dimethyl-4-oxo-3,4-dihydroquinazolin-6-yl)amino)-4-fluorophenyl)((3-fluoropropyl)sulfonyl)carbamate. In a 5 L 3-neck flask equipped with 2 addition funnels, an internal temperature probe, a magnetic stir bar, and nitrogen inlet, tert-butyl (2-chloro-3-((3,5-dimethyl-4-oxo-3,4-dihydroquinazolin-6-yl)amino)-4-fluorophenyl)carbamate (95.3 g, 220 mmol) was dissolved in THF (2.2 L) and cooled to 5° C. under a backflow of N₂. The reaction mixture was treated dropwise with 1.0 M sodium bis(trimethylsilyl)amide solution in THF (209 mL, 209 mmol) and then allowed to stir for 15 minutes after complete addition. The reaction mixture was treated dropwise with a 150 mL THF solution of 3-fluoropropane-1-sulfonyl chloride (33.6 g, 209 mmol) and the ice bath was then removed, and the reaction mixture allowed to stir at ambient temperature for 1 hour. The reaction mixture was concentrated to provide tert-butyl (2-chloro-3-((3,5-dimethyl-4-oxo-3,4-dihydroquinazolin-6-yl)amino)-4-fluorophenyl)((3-fluoropropyl)sulfonyl)carbamate (123 g, 100%) that was used directly in the next step. ¹H NMR (400 MHz, DMSO-d₆) δ 8.17 (s, 1H), 7.53 (s, 1H), 7.40 (s, 1H), 7.39 (s, 1H), 7.33-7.31 (d, 1H), 6.80-6.78 (d, 1H), 4.67-4.64 (t, 1H), 4.55-4.52 (t, 1H), 4.00-3.93 (m, 1H), 3.85-3.77 (m, 1H), 3.43 (s, 3H), 2.80 (s, 3H), 2.25-2.19 (m, 2H), 1.41 (s, 9H). MS (m/z)=557.2, 559.2 (M+H).

Step J: Preparation of N-(2-chloro-3-((3,5-dimethyl-4-oxo-3,4-dihydroquinazolin-6-yl)amino)-4-fluorophenyl)-3-fluoropropane-1-sulfonamide. To a solution of tert-butyl (2-chloro-3-((3,5-dimethyl-4-oxo-3,4-dihydroquinazolin-6-yl)amino)-4-fluorophenyl)carbamate (123 g, 221.0 mmol) in DCM (500 mL) was added a steady stream of 500 mL trifluoroacetic acid and the mixture was stirred at ambient temperature for 1 hour after complete addition. The reaction mixture was concentrated, and the resulting residue was dissolved in DCM (1500 mL), treated with 1500 mL water and neutralized to about pH 7-8 using solid NaHCO₃ The solution was then filtered, and the layers were partitioned and the aqueous NaHCO₃ layer was extracted with DCM (1×). The combined the organic layers were washed with saturated NaHCO₃ (1×) and then with 1.0 M NaOH (3×). The combined aqueous NaOH layers were washed with DCM (1×) and the NaOH aqueous layer was transferred to a flask and diluted with 4:1 DCM:IPA (1000 mL) and acidified to about pH 2 using 4.0 M HCl. The layers were separated and the aqueous HCl layer was extracted with 4:1 DCM:IPA (2×). The combined 4:1 DCM:IPA layers were dried over Na₂SO₄, filtered, and concentrated. The resulting residue was dissolved in DCM (2000 mL) and stirred with SiliaMetS Thiol (100 grams) at ambient temperature for 16 hours. The mixture was loaded onto a plug of silica gel (500 g) and eluted with EtOAc (8.0 L). The filtrate was concentrated to provide N-(2-chloro-3-((3,5-dimethyl-4-oxo-3,4-dihydroquinazolin-6-yl)amino)-4-fluorophenyl)-3-fluoropropane-1-sulfonamide (78.9 g, 78.4%). ¹H NMR (400 MHz, DMSO-d₆) δ 9.64 (br-s, 1H), 8.16 (s, 1H), 7.34-7.25 (m, 4H), 6.88-6.85 (d, 1H), 4.62-4.59 (t, 1H), 4.50-4.47 (t, 1H), 3.43 (s, 3H), 3.25-3.21 (m, 2H), 2.81 (s, 3H), 2.19-2.06 (m, 2H). MS (m/z)=457.1, 459.1 (M+H).

Example 11

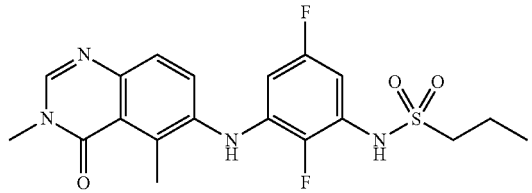 [SMILES: CCCS(=O)(=O)Nc1cc(F)cc(Nc2ccc3ncn(C)c(=O)c3c2C)c1F]

N-(3-((3,5-dimethyl-4-oxo-3,4-dihydroquinazolin-6-yl)amino)-2,5-difluorophenyl)propane-1-sulfonamide Step 1: Preparation of N-(3-((3,5-dimethyl-4-oxo-3,4-dihydroquinazolin-6-yl)amino)-2,5-difluorophenyl)-N-((2-(trimethylsilyl)ethoxy)methyl)propane-1-sulfonamide. A solution of N-(3-bromo-2,5-difluorophenyl)-N-((2-(trimethylsilyl)ethoxy)methyl)propane-1-sulfonamide (72.6 mg, 0.163 mmol), 6-amino-3,5-dimethylquinazolin-4(3H)-one (Intermediate P15) (30.9 mg, 0.163 mmol), tris(dibenzylideneacetone)dipalladium (0) (10.5 mg, 0.0114 mmol), Xantphos (19.8 mg, 0.0343 mmol), and cesium carbonate (160 mg, 0.490 mmol) in toluene (4 mL) was sparged with argon for 5 minutes and then heated at 100° C. for 18 hours in a 15 mL sealed tube. The reaction mixture was cooled to ambient temperature then diluted with water (25 mL) and 4:1 DCM:IPA (25 mL). The layers were separated and the organic phase was dried over Na₂SO₄, filtered, and concentrated to give a brown oil that was purified by silica gel chromatography (DCM/EtOAc) to afford N-(3-((3,5-dimethyl-4-oxo-3,4-dihydroquinazolin-6-yl)amino)-2,5-difluorophenyl)-N-((2-(trimethylsilyl)ethoxy)methyl)propane-1-sulfonamide (62.9 mg, 70%) as an off-white foam. MS (apci, m/z)=553.2 (M+H)

Step 2: Preparation of N-(3-((3,5-dimethyl-4-oxo-3,4-dihydroquinazolin-6-yl)amino)-2,5-difluorophenyl)propane-1-sulfonamide. N-(3-((3,5-dimethyl-4-oxo-3,4-dihydroquinazolin-6-yl)amino)-2,5-difluorophenyl)-N-((2-(trimethylsilyl)ethoxy)methyl)propane-1-sulfonamide (62.9 mg, 0.114 mmol) was dissolved in DCM (5 mL) and neat trifluoroethanoic acid (3507 µL) and the reaction mixture was stirred at ambient temperature for 1.5 hours. The reaction mixture was concentrated and then purified by silica gel chromatography (DCM/EtOAc) then by reverse phase C18 chromatography (H₂O/acetonitrile with 0.1% TFA) and then the isolated product was dissolved in 4:1 DCM:IPA and washed with saturated NaHCO₃ then dried over Na₂SO₄, filtered, and concentrated to afford N-(3-((3,5-dimethyl-4-oxo-3,4-dihydroquinazolin-6-yl)amino)-2,5-difluorophenyl)propane-1-sulfonamide (13.6 mg, 28%). ¹H NMR (400 MHz, CDCl₃) δ 8.01 (s, 1H), 7.64-7.56 (m, 1H), 6.82-6.75 (m, 1H), 6.55 (s, 1H), 6.19-6.13 (m, 1H), 5.74 (s, 1H), 3.56 (s, 3H), 3.21-3.14 (m, 2H), 2.84 (s, 3H), 1.97-1.86 (m, 2H), 1.09 (t, 3H); MS (apci, m/z)=423.1 (M+H).

Example 12

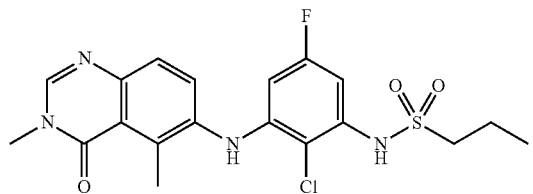 [SMILES: CCCS(=O)(=O)Nc1cc(F)cc(Nc2ccc3ncn(C)c(=O)c3c2C)c1Cl]

N-(2-chloro-3-((3,5-dimethyl-4-oxo-3,4-dihydroquinazolin-6-yl)amino)-5-fluorophenyl)propane-1-sulfonamide Step 1: Preparation of N-(2-chloro-3-((3,5-dimethyl-4-oxo-3,4-dihydroquinazolin-6-yl)amino)-5-fluorophenyl)-N-((2-(trimethylsilyl)ethoxy)methyl)propane-1-sulfonamide. A solution of N-(3-bromo-2-chloro-5-fluorophenyl)-N-((2-(trimethylsilyl)ethoxy)methyl)propane-1-sulfonamide (47 mg, 0.102 mmol), 6-amino-3,5-dimethylquinazolin-4(3H)-one (Intermediate P15) (19.3 mg, 0.102 mmol), tris(dibenzylideneacetone)dipalladium (0) (7.00 mg, 0.00765 mmol), Xantphos (13.3 mg, 0.0229 mmol), and cesium carbonate (99.7 mg, 0.306 mmol) in toluene (4 mL) was sparged with argon for 10 minutes and then heated to 110° C. overnight under an argon balloon. The reaction mixture was cooled to ambient temperature and concentrated. The crude product was purified by silica gel chromatography (DCM/Acetone) to give N-(2-chloro-3-((3,5-dimethyl-4-oxo-3,4-dihydroquinazolin-6-yl)amino)-5-fluorophenyl)-N-((2-(trimethylsilyl)ethoxy)methyl)-propane-1-sulfonamide (38 mg, 66%). MS (apci, m/z)=569.2 (M+H).

Step 2: Preparation of N-(2-chloro-3-((3,5-dimethyl-4-oxo-3,4-dihydroquinazolin-6-yl)amino)-5-fluorophenyl)propane-1-sulfonamide. A solution of N-(2-chloro-3-((3,5-dimethyl-4-oxo-3,4-dihydroquinazolin-6-yl)amino)-5-fluorophenyl)-N-((2-(trimethylsilyl)ethoxy)methyl)propane-1-sulfonamide (0.038 g, 0.067 mmol) in trifluoroacetic acid (4 mL) was stirred at ambient temperature for 1 hour. The reaction mixture was concentrated and the residue was treated with THF and saturated NaHCO₃ (4 mL, 1:1) for 30 minutes. The reaction mixture was partitioned between ethyl acetate and water. The organic layers were separated, dried over Na₂SO₄, filtered and concentrated. The crude product was purified by silica gel chromatography (DCM/Acetone) to give N-(2-chloro-3-((3,5-dimethyl-4-oxo-3,4-dihydroquinazolin-6-yl)amino)-5-fluorophenyl)propane-1-sulfonamide (13 mg, 44%). ¹H NMR (400 MHz, CDCl₃) δ 8.03 (s, 1H), 7.60 (s, 2H), 6.91 (dd, 1H), 6.86 (br-s, 1H), 6.09-6.05 (m, 2H), 3.56 (s, 3H), 3.19-3.14 (m, 2H), 2.81 (s, 3H), 1.95-1.85 (m, 2H), 1.07 (t, 3H); MS (apci, m/z)=439.1 (M+H).

Example 13

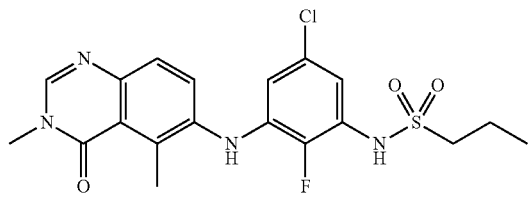

N-(5-chloro-3-((3,5-dimethyl-4-oxo-3,4-dihydroquinazolin-6-yl)amino)-2-fluorophenyl)propane-1-sulfonamide Step 1: Preparation of N-(5-chloro-3-((3,5-dimethyl-4-oxo-3,4-dihydroquinazolin-6-yl)amino)-2-fluorophenyl)-N-((2-(trimethylsilyl)ethoxy)methyl)propane-1-sulfonamide. A solution of N-(3-bromo-5-chloro-2-fluorophenyl)-N-((2-(trimethylsilyl)ethoxy)methyl)propane-1-sulfonamide (75.2 mg, 0.163 mmol), 6-amino-3,5-dimethylquinazolin-4(3H)-one (Intermediate P15) (29.9 mg, 0.158 mmol), tris(dibenzylideneacetone)dipalladium (0) (10.1 mg, 0.0111 mmol), Xantphos (19.2 mg, 0.0332 mmol), and cesium carbonate (154 mg, 0.474 mmol) in toluene (1.5 mL) was sparged with argon for 5 minutes and then heated to 100° C. for 18 hours under argon in a 15 mL sealed tube. The reaction mixture was diluted with water (25 mL) and 4:1 DCM:IPA (25 mL). The layers were separated and the organic phase was dried over Na₂SO₄, filtered, and concentrated then purified by silica gel chromatography (DCM/EtOAc) to afford N-(5-chloro-3-((3,5-dimethyl-4-oxo-3,4-dihydroquinazolin-6-yl)amino)-2-fluorophenyl)-N-((2-(trimethylsilyl)ethoxy)methyl)-propane-1-sulfonamide (60.0 mg, 67%) as a yellow oil. MS (apci, m/z)=569.2 (M+H).

Step 2: Preparation of N-(5-chloro-3-((3,5-dimethyl-4-oxo-3,4-dihydroquinazolin-6-yl)amino)-2-fluorophenyl)propane-1-sulfonamide. N-(5-chloro-3-((3,5-dimethyl-4-oxo-3,4-dihydroquinazolin-6-yl)amino)-2-fluorophenyl)-N-((2-(trimethylsilyl)ethoxy)methyl)propane-1-sulfonamide (60 mg, 0.105 mmol) was dissolved in DCM (5 mL) and trifluoroacetic acid (3249 µL) at 0° C. then warmed to ambient temperature and stirred for 30 minutes. The solvent was removed in vacuo and the yellow oil was dissolved in DCM (25 mL) and stirred with a saturated aqueous NaHCO₃ solution (15 mL) for 30 minutes. The layers were separated and the organic phase was dried over Na₂SO₄, filtered, and concentrated then purified with silica gel chromatography (DCM/EtOAc) to afford N-(5-chloro-3-((3,5-dimethyl-4-oxo-3,4-dihydroquinazolin-6-yl)amino)-2-fluorophenyl)-propane-1-sulfonamide (13.6 mg, 29%) as a white solid. ¹H NMR (400 MHz, CDCl₃) δ 8.01 (s, 1H), 7.62-7.56 (m, 2H), 7.04 (dd, 1H), 6.52 (d, 1H), 6.42 (dd, 1H), 5.69 (d, 1H), 3.56 (s, 3H), 3.21-3.14 (m, 2H), 2.84 (s, 3H), 1.97-1.86 (m, 2H), 1.09 (t, 3H); MS (apci, m/z)=439.0 (M+H).

Example 14

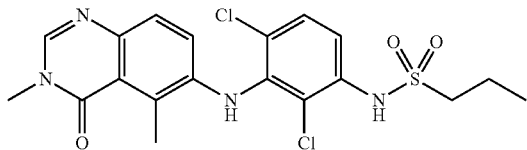 [SMILES: CCCS(=O)(=O)Nc1ccc(Cl)c(Nc2ccc3ncn(C)c(=O)c3c2C)c1Cl]

N-(2,4-dichloro-3-((3,5-dimethyl-4-oxo-3,4-dihydro-quinazolin-6-yl)amino)phenyl)propane-1-sulfonamide Step 1: Preparation of N-(2,4-dichloro-3-((3,5-dimethyl-4-oxo-3,4-dihydroquinazolin-6-yl)amino)phenyl)-N-((2-(trimethylsilyl)ethoxy)methyl)propane-1-sulfonamide. A solution of N-(2,4-dichloro-3-iodophenyl)-N-((2-(trimethylsilyl)ethoxy)methyl)propane-1-sulfonamide (50 mg, 0.095 mmol), 6-amino-3,5-dimethylquinazolin-4(3H)-one (Intermediate P15) (18 mg, 0.095 mmol), tris(dibenzylideneacetone)dipalladium (0) (4.4 mg, 0.0048 mmol), Xantphos (8.3 mg, 0.014 mmol), and cesium carbonate (93 mg, 0.29 mmol) in toluene (636 µL) was sparged with argon for 10 minutes and then sealed and heated in a vial to 90° C. overnight. The reaction mixture was cooled to ambient temperature, concentrated, and purified by silica gel chromatography (DCM/EtOAc) to give N-(2,4-dichloro-3-((3,5-dimethyl-4-oxo-3,4-dihydroquinazolin-6-yl)amino)phenyl)-N-((2-(trimethylsilyl)ethoxy)methyl)propane-1-sulfonamide (45 mg, 80%). MS (apci, m/z)=585.1 [M+H].

Step 2: Preparation of N-(2,4-dichloro-3-((3,5-dimethyl-4-oxo-3,4-dihydroquinazolin-6-yl)amino)phenyl)propane-1-sulfonamide. A solution of N-(2,4-dichloro-3-((3,5-dimethyl-4-oxo-3,4-dihydroquinazolin-6-yl)amino)phenyl)-N-((2 (trimethylsilyl)ethoxy)methyl)propane-1-sulfonamide (45 mg, 0.077 mmol) in 1 mL of DCM and 0.2 mL of trifluoroacetic acid was stirred at ambient temperature for 30 minutes. The solution was concentrated and then dissolved in 1 mL of THF and 1 mL of saturated NaHCO$_3$ and stirred at ambient temperature for 20 minutes. The reaction mixture was diluted with additional water and extracted with DCM (2×) and the combined organic layers were dried over Na$_2$SO$_4$, filtered, and concentrated. The residue was purified by silica gel chromatography (DCM/MeOH) to give N-(2,4-dichloro-3-((3,5-dimethyl-4-oxo-3,4-dihydroquinazolin-6-yl)amino)phenyl)propane-1-sulfonamide (23 mg, 53%). $^1$H NMR (400 MHz, CDCl$_3$) δ 7.92 (s, 1H), 7.48 (d, 1H), 7.41 (t, 1H), 6.88 (d, 1H), 6.79 (br-s, 1H), 5.72 (br-s, 1H), 3.55 (s, 3H), 3.11 (t, 2H), 3.00 (s, 3H), 1.88 (m, 2H), 1.04 (t, 3H); MS (apci, m/z)=455.1 [M+H].

Example 15

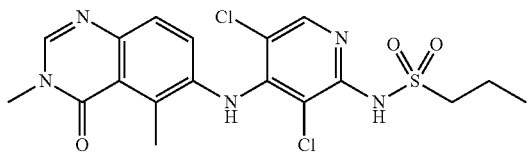 [SMILES: CCCS(=O)(=O)Nc1ncc(Cl)c(Nc2ccc3ncn(C)c(=O)c3c2C)c1Cl]

N-(3,5-dichloro-4-((3,5-dimethyl-4-oxo-3,4-dihydro-quinazolin-6-yl)amino)pyridin-2-yl)propane-1-sulfonamide Step 1: Preparation of N-(3,5-dichloro-4-((3,5-dimethyl-4-oxo-3,4-dihydroquinazolin-6-yl)amino)pyridin-2-yl)-N-((2-(trimethylsilyl)ethoxy)methyl)propane-1-sulfonamide. A solution of N-(3,5-dichloro-4-iodopyridin-2-yl)-N-((2-(trimethylsilyl)ethoxy)methyl)propane-1-sulfonamide (40 mg, 0.076 mmol), 6-amino-3,5-dimethylquinazolin-4(3H)-one (Intermediate P15) (14 mg, 0.076 mmol), tris(dibenzylideneacetone)dipalladium (0) (3.5 mg, 0.0038 mmol), Xantphos (6.6 mg, 0.011 mmol), and cesium carbonate (74 mg, 0.23 mmol) in toluene (508 µL) was sparged with argon for 10 minutes and then sealed and heated in a vial to 90° C. overnight. The reaction mixture was cooled to ambient temperature and purified by silica gel chromatography (DCM/EtOAc) to give N-(3,5-dichloro-4-((3,5-dimethyl-4-oxo-3,4-dihydroquinazolin-6-yl)amino)pyridin-2-yl)-N-((2-(trimethylsilyl)ethoxy)methyl)propane-1-sulfonamide (20 mg, 44%). MS (apci, m/z)=586.1 [M+H].

Step 2: Preparation of N-(3,5-dichloro-4-((3,5-dimethyl-4-oxo-3,4-dihydroquinazolin-6-yl)amino)pyridin-2-yl)propane-1-sulfonamide. A solution of N-(3,5-dichloro-4-((3,5-dimethyl-4-oxo-3,4-dihydroquinazolin-6-yl)amino)pyridin-2-yl)-N-((2-(trimethylsilyl)ethoxy)methyl)-propane-1-sulfonamide (20 mg, 0.034 mmol) in 1 mL of DCM and 0.2 mL of trifluoroacetic acid was stirred at ambient temperature for 45 minutes. The solution was concentrated and the residue was purified by silica gel chromatography (DCM/MeOH with 1% NH$_4$OH) to give N-(3,5-dichloro-4-((3,5-dimethyl-4-oxo-3,4-dihydroquinazolin-6-yl)amino)pyridin-2-yl)propane-1-sulfonamide (13 mg, 37%). $^1$H NMR (400 MHz, CDCl$_3$) δ 8.12 (s, 1H), 8.01 (s, 1H), 7.50 (d, 1H), 7.24 (d, 1H), 7.21 (br-s, 1H), 6.25 (br-s, 1H), 3.66 (t, 2H), 3.56 (s, 3H), 2.91 (s, 3H), 1.92 (m, 2H), 1.09 (t, 3H); MS (apci, m/z)=456.1 [M+H].

Example 16

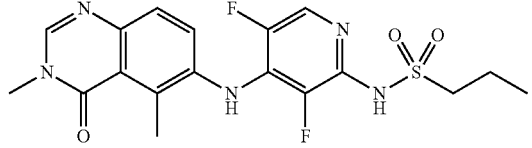

N-(4-((3,5-dimethyl-4-oxo-3,4-dihydroquinazolin-6-yl)amino)-3,5-difluoropyridin-2-yl)propane-1-sulfonamide Step 1: Preparation of N-(4-((3,5-dimethyl-4-oxo-3,4-dihydroquinazolin-6-yl)amino)-3,5-difluoropyridin-2-yl)-N-((2-(trimethylsilyl)ethoxy)methyl)propane-1-sulfonamide. A solution of N-(3,5-difluoro-4-iodopyridin-2-yl)-N-((2-(trimethylsilyl)ethoxy)methyl)propane-1-sulfonamide (38 mg, 0.077 mmol), 6-amino-3,5-dimethylquinazolin-4(3H)-one (Intermediate P15) (15 mg, 0.077 mmol), tris(dibenzylideneacetone)dipalladium (0) (3.5 mg, 0.0039 mmol), Xantphos (6.7 mg, 0.012 mmol), and cesium carbonate (75 mg, 0.23 mmol) in toluene (514 µL) was sparged with argon for 10 minutes and then sealed and heated in a vial to 90° C. overnight. The reaction mixture was cooled to ambient temperature, concentrated, and purified by silica gel chromatography (DCM/EtOAc) to give N-(4-((3,5-dimethyl-4-oxo-3,4-dihydroquinazolin-6-yl)amino)-3,5-difluoropyridin-2-yl)-N-((2-(trimethylsilyl)ethoxy)methyl)propane-1-sulfonamide (35 mg, 81%). MS (apci, m/z)=554.2 [M+H].

Step 2: Preparation of N-(4-((3,5-dimethyl-4-oxo-3,4-dihydroquinazolin-6-yl)amino)-3,5-difluoropyridin-2-yl)propane-1-sulfonamide. A solution of N-(4-((3,5-dimethyl-4-oxo-3,4-dihydroquinazolin-6-yl)amino)-3,5-difluoropyridin-2-yl)-N-((2-(trimethylsilyl)ethoxy)methyl)-propane-1-sulfonamide (35 mg, 0.063 mmol) in 1 mL of DCM and 0.2 mL of trifluoroacetic acid was stirred at ambient temperature for 45 minutes. The reaction mixture was concentrated and the residue was purified by reverse-phase C18 chromatography (H$_2$O/acetonitrile with 0.1% TFA) and then the isolated product was dissolved in DCM and washed with saturated NaHCO$_3$ followed by brine then dried over Na$_2$SO$_4$, filtered, and concentrated to give N-(4-((3,5-dimethyl-4-oxo-3,4-dihydroquinazolin-6-yl)amino)-3,5-difluoropyridin-2-yl)propane-1-sulfonamide (21 mg, 64%). $^1$H NMR (400 MHz, CDCl$_3$) δ 8.04 (s, 1H), 7.94 (s, 1H), 7.48 (d, 1H), 7.41 (d, 1H), 5.93 (s, 1H), 3.62 (t, 2H), 3.54 (s, 3H), 2.89 (s, 3H), 1.93 (m, 2H), 1.08 (t, 3H); MS (apci, m/z)=424.1 [M+H].

Example 17

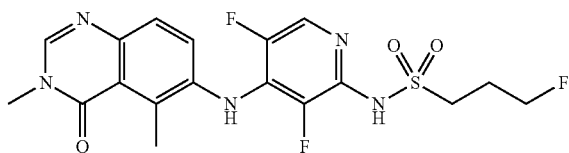 [SMILES: Cc1c(Nc2c(F)cnc(NS(=O)(=O)CCCF)c2F)ccc2ncn(C)c(=O)c12]

N-(4-((3,5-dimethyl-4-oxo-3,4-dihydroquinazolin-6-yl)amino)-3,5-difluoropyridin-2-yl)-3-fluoropropane-1-sulfonamide Step 1: Preparation of N-(4-((3,5-dimethyl-4-oxo-3,4-dihydroquinazolin-6-yl)amino)-3,5-difluoropyridin-2-yl)-3-fluoro-N-((2-(trimethylsilyl)ethoxy)methyl)propane-1-sulfonamide. A solution of N-(3,5-difluoro-4-iodopyridin-2-yl)-3-fluoro-N-((2-(trimethylsilyl)ethoxy)methyl)propane-1-sulfonamide (44 mg, 0.086 mmol), 6-amino-3,5-dimethylquinazolin-4(3H)-one (Intermediate P15) (16 mg, 0.086 mmol), tris(dibenzylideneacetone)dipalladium (0) (3.9 mg, 0.0043 mmol), Xantphos (7.5 mg, 0.013 mmol), and cesium carbonate (84 mg, 0.26 mmol) in toluene (575 µL) was sparged with argon for 10 minutes and then sealed and heated in a vial to 90° C. overnight. The reaction mixture was cooled to ambient temperature, concentrated, and purified by silica gel chromatography (DCM/EtOAc), to give N-(4-((3,5-dimethyl-4-oxo-3,4-dihydroquinazolin-6-yl)amino)-3,5-difluoropyridin-2-yl)-3-fluoro-N-((2-(trimethylsilyl)ethoxy)-methyl)propane-1-sulfonamide (37 mg, 76%). MS (apci, m/z)=572.2 [M+H].

Step 2: Preparation of N-(4-((3,5-dimethyl-4-oxo-3,4-dihydroquinazolin-6-yl)amino)-3,5-difluoropyridin-2-yl)-3-fluoropropane-1-sulfonamide. A solution of N-(4-((3,5-dimethyl-4-oxo-3,4-dihydroquinazolin-6-yl)amino)-3,5-difluoropyridin-2-yl)-3-fluoro-N-((2-(trimethylsilyl)-ethoxy)methyl)propane-1-sulfonamide (37 mg, 0.065 mmol) in 1 mL of DCM and 0.2 mL of trifluoroacetic acid was stirred at ambient temperature for 30 minutes. The reaction mixture was concentrated and the residue was purified by silica gel chromatography (DCM/MeOH with 1% NH$_4$OH) to give N-(4-((3,5-dimethyl-4-oxo-3,4-dihydroquinazolin-6-yl)amino)-3,5-difluoropyridin-2-yl)-3-fluoropropane-1-sulfonamide (18 mg, 47%). $^1$H NMR (400 MHz, CDCl$_3$) δ 8.02 (s, 1H), 7.94 (s, 1H), 7.52 (d, 1H), 7.42 (d, 1H), 5.92 (br-s, 1H), 4.66 (t, 1H), 4.54 (t, 1H), 3.80 (t, 2H), 3.55 (s, 3H), 2.90 (s, 3H), 2.31 (m, 2H); MS (apci, m/z)=442.1 [M+H].

Example 18

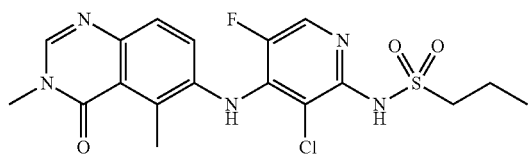

N-(3-chloro-4-((3,5-dimethyl-4-oxo-3,4-dihydroquinazolin-6-yl)amino)-5-fluoropyridin-2-yl)propane-1-sulfonamide Step 1: Preparation of N-(3-chloro-4-((3,5-dimethyl-4-oxo-3,4-dihydroquinazolin-6-yl)amino)-5-fluoropyridin-2-yl)-N-((2-(trimethylsilyl)ethoxy)methyl)propane-1-sulfonamide. A solution of N-(3-chloro-5-fluoro-4-iodopyridin-2-yl)-N-((2-(trimethylsilyl)ethoxy)methyl)propane-1-sulfonamide (105 mg, 0.206 mmol), 6-amino-3,5-dimethylquinazolin-4(3H)-one (Intermediate P15) (39.0 mg, 0.206 mmol), tris(dibenzylideneacetone)dipalladium (0) (9.45 mg, 0.0103 mmol), Xantphos (17.9 mg, 0.0310 mmol), and cesium carbonate (202 mg, 0.619 mmol) in toluene (1376 µL) was sparged with argon for 10 minutes and then heated in a sealed flask to 90° C. overnight. The reaction mixture was cooled to ambient temperature, filtered, concentrated, and then purified by silica gel chromatography (DCM/EtOAc) to give N-(3-chloro-4-((3,5-dimethyl-4-oxo-3,4-dihydroquinazolin-6-yl)amino)-5-fluoropyridin-2-yl)-N-((2-(trimethylsilyl)ethoxy)methyl)-propane-1-sulfonamide (111 mg, 94%). MS (apci, m/z)=570.2 [M+H].

Step 2: Preparation of N-(3-chloro-4-((3,5-dimethyl-4-oxo-3,4-dihydroquinazolin-6-yl)amino)-5-fluoropyridin-2-yl)propane-1-sulfonamide. A solution of N-(3-chloro-4-((3,5-dimethyl-4-oxo-3,4-dihydroquinazolin-6-yl)amino)-5-fluoropyridin-2-yl)-N-((2-(trimethylsilyl)ethoxy)methyl)-propane-1-sulfonamide (111 mg; 0.19 mmol) in 1 mL of DCM and 0.5 mL of trifluoroacetic acid was stirred at ambient temperature for 30 minutes. The reaction mixture was concentrated and dissolved in DCM and washed with saturated aqueous NaHCO$_3$ and then dried over Na$_2$SO$_4$, filtered, and concentrated. The residue was purified by silica gel chromatography (DCM/EtOAc) to give N-(3-chloro-4-((3,5-dimethyl-4-oxo-3,4-dihydroquinazolin-6-yl)amino)-5-fluoropyridin-2-yl)propane-1-sulfonamide (71 mg, 78%). $^1$H NMR (400 MHz, CDCl$_3$) δ 8.04 (s, 1H), 7.96 (d, 1H), 7.54 (d, 1H), 7.40 (d, 1H), 6.11 (br-s, 1H), 3.66 (t, 2H), 3.56 (s, 3H), 2.89 (s, 3H), 1.95 (m, 2H), 1.09 (t, 3H); MS (apci, m/z)=440.1 [M+H].

Example 19

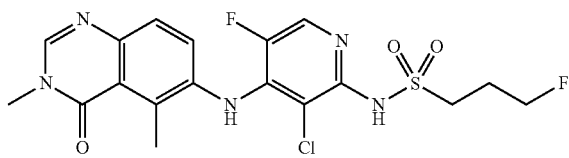

N-(3-chloro-4-((3,5-dimethyl-4-oxo-3,4-dihydroquinazolin-6-yl)amino)-5-fluoropyridin-2-yl)-3-fluoropropane-1-sulfonamide Step 1: Preparation of N-(3-chloro-4-((3,5-dimethyl-4-oxo-3,4-dihydroquinazolin-6-yl)amino)-5-fluoropyridin-2-yl)-3-fluoro-N-((2-(trimethylsilyl)ethoxy)methyl))propane-1-sulfonamide. N-(3-chloro-5-fluoro-4-iodopyridin-2-yl)-3-fluoro-N-((2-(trimethylsilyl)ethoxy)methyl))propane-1-sulfonamide (53 mg, 0.101 mmol), 6-amino-3,5dimethylquinazolin-4(3H)-one (17.4 mg, 0.092 mmol), cesium carbonate (90 mg, 0.276 mmol), Xantphos (8.0 mg, 0.0138 mmol), and tris(dibenzylideneacetone)dipalladium (0) (4.2 mg, 0.0046) were combined in a vial then degassed under reduced pressure and backfilled with argon gas. Toluene (0.46 mL) was added and the solution was sparged with argon for 5 minutes before the vial was sealed and heated to 100° C. for 16 hours. The reaction mixture was cooled to ambient temperature, filtered through a pad of Celite® and purified by silica gel chromatography (DCM/EtOAc) to provide N-(3-chloro-4-((3,5-dimethyl-4-oxo-3,4-dihydroquinazolin-6-yl)amino)-5-fluoropyridin-2-yl)-3-fluoro-N-((2-(trimethylsilyl)ethoxy)methyl))propane-1-sulfonamide as a white solid (34.5 mg, 63%). MS (apci, m/z)=588.2 (M+H).

Step 2: Preparation of N-(3-chloro-4-((3,5-dimethyl-4-oxo-3,4-dihydroquinazolin-6-yl)amino)-5-fluoropyridin-2-yl)-3-fluoropropane-1-sulfonamide. N-(3-chloro-4-((3,5-dimethyl-4-oxo-3,4-dihydroquinazolin-6-yl)amino)-5-fluoropyridin-2-yl)-3-fluoro-N-((2-(trimethylsilyl)ethoxy)methyl))propane-1-sulfonamide (34.5 mg, 0.057 mmol) was dissolved in DCM (1.4 mL) and treated with trifluoroacetic acid (0.48 mL) and the reaction mixture was allowed to stir at ambient temperature for 1 hour. The reaction mixture was concentrated and the residue was purified by reverse phase C18 chromatography (H$_2$O/acetonitrile with 0.1% TFA). The isolated product was dissolved in DCM and washed with saturated NaHCO$_3$ followed by brine then dried over Na$_2$SO$_4$, filtered, and concentrated to obtain N-(3-chloro-4-((3,5-dimethyl-4-oxo-3,4-dihydroquinazolin-6-yl)amino)-5-fluoropyridin-2-yl)-3-fluoropropane-1-sulfonamide as a white solid (12.1 mg, 29%). $^1$H NMR (400 MHz, CDCl$_3$) δ 7.94 (s, 1H), 7.76 (d, 1H), 7.37 (d, 1H), 7.31 (dd, 1H), 4.52 (t, 1H), 4.41 (t, 1H), 3.87 (s, 3H), 3.64 (t, 2H), 3.43 (s, 3H), 2.22-2.09 (m, 2H); MS (apci, m/z)=458.0 (M+H).

Example 20

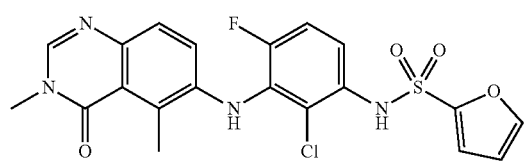 [SMILES: Cc1c(Nc2c(F)ccc(NS(=O)(=O)c3ccco3)c2Cl)ccc2ncn(C)c(=O)c12]

N-(2-chloro-3-((3,5-dimethyl-4-oxo-3,4-dihydroquinazolin-6-yl)amino)-4-fluorophenyl)furan-2-sulfonamide Step 1: Preparation of N-(2-chloro-3-((3,5-dimethyl-4-oxo-3,4-dihydroquinazolin-6-yl)amino)-4-fluorophenyl)-N-((2-(trimethylsilyl)ethoxy)methyl)furan-2-sulfonamide. N-(2-chloro-4-fluoro-3-iodophenyl)-N-((2-trimethylsilyl)ethoxy)methyl)furan-2-sulfonamide (31.2 mg, 0.0587 mmol), 6-amino-3,5-dimethylquinazolin-4(3H)-one (Intermediate P15) (10 mg, 0.0534 mmol), cesium carbonate (52 mg, 0.16 mmol), Xantphos (4.6 mg, 0.00801 mmol), and tris(dibenzylideneacetone)dipalladium (0) (2.4 mg, 0.00267) were combined in a vial then degassed under reduced pressure and backfilled with argon gas. Toluene (0.356 mL) was added and the solution was sparged with argon for 5 minutes before the vial was sealed and heated to 90° C. for 16 hours. The reaction mixture was cooled to ambient temperature then filtered through a pad of Celite® and purified by silica gel chromatography (DCM/EtOAc) to provide N-(2-chloro-3-((3,5-dimethyl-4-oxo-3,4-dihydroquinazolin-6-yl)amino)-4-fluorophenyl)-N-((2-(trimethylsilyl)ethoxy)methyl)furan-2-sulfonamide as a white solid (15.3 mg, 48%). MS (apci, m/z)=593.1 (M+H).

Step 2: Preparation of N-(2-chloro-3-((3,5-dimethyl-4-oxo-3,4-dihydroquinazolin-6-yl)amino)-4-fluorophenyl)furan-2-sulfonamide. N-(2-chloro-3-((3,5-dimethyl-4-oxo-3,4-dihydroquinazolin-6-yl)amino)-4-fluorophenyl)-N-((2-(trimethylsilyl)ethoxy)methyl)furan-2-sulfonamide (15.3 mg, 0.0258 mmol) was dissolved in DCM (0.65 mL) and treated with trifluoroacetic acid (0.215 mL) and the reaction mixture was allowed to stir at ambient temperature for 1 hour. The reaction mixture was concentrated and the residue was purified by silica gel chromatography, eluting with DCM/MeOH with a 1% NH$_4$OH to obtain N-(2-chloro-3-((3,5-dimethyl-4-oxo-3,4-dihydroquinazolin-6-yl)amino)-4-fluorophenyl)furan-2-sulfonamide as a white solid (8.4 mg, 32%). $^1$H NMR (400 MHz, CDCl$_3$) δ 7.93 (s, 1H), 7.55 (q, 1H), 7.40-7.36 (m, 2H), 7.07 (dd, 2H), 7.00 (dd, 1H), 6.89 (s, 1H), 6.48 (dd, 1H), 5.51 (br-s, 1H), 3.54 (s, 3H), 2.93 (s, 3H); MS (apci, m/z)=463.0 (M+H).

Example 21

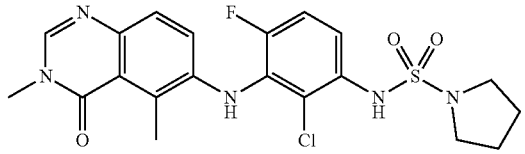 [SMILES: Cc1c(Nc2c(F)ccc(NS(=O)(=O)N3CCCC3)c2Cl)ccc2ncn(C)c(=O)c12]

N-(2-chloro-3-((3,5-dimethyl-4-oxo-3,4-dihydroquinazolin-6-yl)amino)-4-fluorophenyl)pyrrolidine-1-sulfonamide Step 1: Preparation of N-(2-chloro-3-((3,5-dimethyl-4-oxo-3,4-dihydroquinazolin-6-yl)amino-4-fluorophenyl)-N-((2-trimethylsilyl)ethoxy)methyl)pyrrolidine-1-sulfonamide. N-(2-chloro-4-fluoro-3-iodophenyl)-N-((2-trimethylsilyl)ethoxy)methyl)pyrrolidine-1-sulfonamide (52 mg, 0.097 mmol), 6-amino-3,5-dimethylquinazolin-4(3H)-one (Intermediate P15) (16.6 mg, 0.088 mmol), cesium carbonate (86 mg, 0.263 mmol), Xantphos (7.61 mg, 0.0132 mmol), and tris(dibenzylideneacetone)dipalladium (0) (4.0 mg, 0.00439) were combined in a vial then degassed under reduced pressure and backfilled with argon gas. Toluene (0.585 mL) was added and the solution was sparged with argon for 5 min before the vial was sealed and heated to 90° C. for 16 hours. The reaction mixture was cooled to ambient temperature, filtered through a pad of Celite® and purified by silica gel chromatography (DCM/EtOAc) to provide N-(2-chloro-3-((3,5-dimethyl-4-oxo-3,4-dihydroquinazolin-6-yl)amino-4-fluorophenyl)-N-((2-trimethylsilyl)-ethoxy)methyl)pyrrolidine-1-sulfonamide as a white solid (36 mg, 69%). MS (apci, m/z)=596.2 (M+H).

Step 2: Preparation. of N-(2-chloro-3-((3,5-dimethyl-4-oxo-3,4-dihydroquinazolin-6-yl)amino)-4-fluorophenyl) pyrrolidine-1-sulfonamide. N-(2-chloro-3-((3,5-dimethyl-4-oxo-3,4-dihydroquinazolin-6-yl)amino-4-fluorophenyl)-N-((2-trimethylsilyl)ethoxy)methyl)pyrrolidine-1-sulfonamide (36 mg, 0.0604 mmol) was dissolved in DCM (1.5 mL) and treated with trifluoroacetic acid (0.500 mL) and the reaction mixture was allowed to stir at ambient temperature for 1 hour. The reaction mixture was concentrated and the residue was purified by reverse phase C18 chromatography (H$_2$O/acetonitrile with 0.1% TFA) and then the isolated product was dissolved in DCM and washed with saturated NaHCO$_3$ followed by brine then dried over Na$_2$SO$_4$, filtered, and concentrated to obtain N-(2-chloro-3-((3,5-dimethyl-4-oxo-3,4-dihydroquinazolin-6-yl)amino)-4-fluorophenyl)pyrrolidine-1-sulfonamide as a white solid (4.2 mg, 10%). $^1$H NMR (400 MHz, CDCl$_3$) δ 7.93 (s, 1H), 7.44 (d, 1H), 7.41 (dd, 1H), 7.08 (d, 1H), 7.03 (dd, 1H), 6.73 (s, 1H), 5.58 (br-s, 1H), 3.54 (s, 3H), 3.36-3.33 (m, 4H), 2.97 (s, 3H), 1.89-1.86 (m, 4H); MS (apci, m/z)=466.1 (M+H).

Example 22

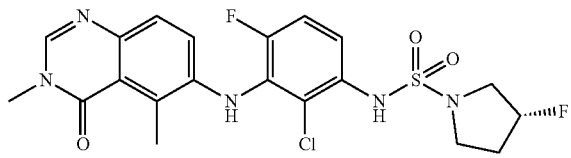 [SMILES: Cc1c(Nc2c(F)ccc(NS(=O)(=O)N3CC[C@@H](F)C3)c2Cl)ccc2ncn(C)c(=O)c12]

(R)—N-(2-chloro-3-((3,5-dimethyl-4-oxo-3,4-dihydroquinazolin-6-yl)amino)-4-fluorophenyl)-3-fluoropyrrolidine-1-sulfonamide Step 1: Preparation of (R)—N-(2-chloro-3-((3,5-dimethyl-4-oxo-3,4-dihydroquinazolin-6-yl)amino)-4-fluorophenyl)-3-fluoro-N-((2-(trimethylsilyl)ethoxy)methyl)pyrrolidine-1-sulfonamide. A solution of (R)—N-(2-chloro-4-fluoro-3-iodophenyl)-3-fluoro-N-((2-(trimethyl-silyl)ethoxy)methyl)pyrrolidine-1-sulfonamide (25 mg, 0.045 mmol), 6-amino-3,5-dimethylquinazolin-4(3H)-one (Intermediate P15) (8.6 mg, 0.045 mmol), tris(dibenzylideneacetone)dipalladium (0) (2.1 mg, 0.0023 mmol), Xantphos (3.9 mg, 0.0068 mmol), and cesium carbonate (44 mg, 0.14 mmol) in toluene (301 μL) was sparged with argon for 10 minutes and then sealed in a vial and heated to 90° C. for 24 hours. The reaction mixture was cooled to ambient temperature then filtered through Celite® and concentrated to give (R)—N-(2-chloro-3-((3,5-dimethyl-4-oxo-3,4-dihydroquinazolin-6-yl)amino)-4-fluorophenyl)-3-fluoro-N-((2-(trimethylsilyl)ethoxy)methyl)pyrrolidine-1-sulfonamide (25 mg, 90%) which was used in the next step without purification. MS (apci, m/z)=614.2 (M+H).

Step 2: Preparation of (R)—N-(2-chloro-3-((3,5-dimethyl-4-oxo-3,4-dihydroquinazolin-6-yl)amino)-4-fluorophenyl)-3-fluoropyrrolidine-1-sulfonamide. (R)—N-(2-chloro-3-((3,5-dimethyl-4-oxo-3,4-dihydroquinazolin-6-yl)amino)-4-fluorophenyl)-3-fluoro-N-((2-(trimethylsilyl)-ethoxy)methyl)pyrrolidine-1-sulfonamide (25 mg, 0.041 mmol) was stirred in 0.2 mL of trifluoroacetic acid and 0.2 mL of DCM for 30 minutes. The reaction mixture was concentrated and dissolved in 0.2 mL of THF and then treated with 0.2 mL of saturated NaHCO$_3$ and stirred at ambient temperature for 20 minutes. The reaction mixture was diluted with water and extracted with DCM (2×) and then the combined organic layers were dried over Na$_2$SO$_4$, filtered, and concentrated. The organic layers were purified by reverse-phase C18 chromatography (H$_2$O/acetonitrile with 0.1% TFA). The isolated product was dissolved in DCM and washed with saturated NaHCO$_3$ followed by brine, then dried over Na$_2$SO$_4$, filtered, and concentrated to give (R)—N-(2-chloro-3-((3,5-dimethyl-4-oxo-3,4-dihydroquinazolin-6-yl)amino)-4-fluorophenyl)-3-fluoropyrrolidine-1-sulfonamide (13 mg, 59%). $^1$H NMR (400 MHz, CDCl$_3$) δ 7.92 (s, 1H), 7.42 (m, 2H), 7.06 (m, 2H), 6.75 (br-s, 1H), 5.57 (br-s, 1H), 3.63 (m, 3H), 3.55 (s, 3H), 3.49 (m, 2H), 2.98 (s, 3H), 2.26 (m, 1H), 2.09 (m, 1H); MS (apci, m/z)=484.1 [M+H].

Example 23

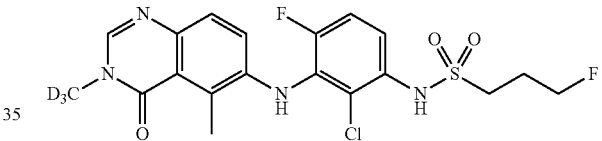

N-(2-chloro-4-fluoro-3-((5-methyl-3-(methyl-d3)-4-oxo-3,4-dihydroquinazolin-6-yl)amino)-phenyl)-3-fluoropropane-1-sulfonamide Step 1: Preparation of N-(2-chloro-4-fluoro-3-((5-methyl-3-(methyl-d3)-4-oxo-3,4-dihydroquinazolin-6-yl)amino)phenyl)-3-fluoro-N-((2-(trimethylsilyl)ethoxy)methyl))propane-1-sulfonamide. N-(3-amino-2-chloro-4-fluorophenyl)-3-fluoro-N-((2-(trimethylsilyl)ethoxy)-methyl))propane-1-sulfonamide (533 mg, 1.283 mmol), 6-bromo-5-methyl-3-(methyl-d3)quinazolin-4(3H)-one (298.8 mg, 1.167 mmol), cesium carbonate (1140 mg, 3.5 mmol), Xantphos (101 mg, 0.175 mmol), and tris(dibenzylideneacetone)dipalladium (0) (53.4 mg, 0.0583) were combined in a vial then degassed under reduced pressure and backfilled with argon gas. Toluene (5.83 mL) was added and the solution was sparged with argon for 5 minutes before the vial was sealed and heated to 100° C. for 18 hours. The reaction mixture was cooled to ambient temperature, filtered through a pad of Celite® and purified by silica gel chromatography, eluting with DCM/EtOAc to provide N-(2-chloro-4-fluoro-3-((5-methyl-3-(methyl-d3)-4-oxo-3,4-dihydroquinazolin-6-yl)amino)phenyl)-3-fluoro-N-((2-(trimethylsilyl)ethoxy)methyl))propane-1-sulfonamide as a white solid (670 mg, 97%). MS (apci, m/z)=590.2 (M+H).

Step 2: Preparation of N-(2-chloro-4-fluoro-3-((5-methyl-3-(methyl-d3)-4-oxo-3,4-dihydroquinazolin-6-yl)amino)phenyl)-3-fluoropropane-1-sulfonamide. N-(2-chloro-4-fluoro-3-((5-methyl-3-(methyl-d3)-4oxo-3,4- dihydroquinazolin-6-yl)amino)phenyl)-3-fluoro-N-((2-(trimethylsilyl)ethoxy)methyl))propane-1-sulfonamide (670 mg, 1.135 mmol) was dissolved in DCM (28 mL) and treated with trifluoroacetic acid (9.5 mL) and the reaction mixture was allowed to stir at ambient temperature for 1 hour. The reaction mixture was quenched with an aqueous solution of saturated NaHCO₃ and extracted with EtOAc (3×): The combined organic extracts were dried over Na₂SO₄, filtered, and concentrated. The residue was purified by reverse phase C18 chromatography (H₂O/acetonitrile with 0.1% TFA) and then the isolated product was dissolved in DCM and washed with saturated NaHCO₃ followed by brine, then dried over Na₂SO₄, filtered, and concentrated to obtain N-(2-chloro-4-fluoro-3-((5-methyl-3-(methyl-d3)-4-oxo-3,4-dihydroquinazolin-6-yl)amino)phenyl)-3-fluoro-propane-1-sulfonamide as a white solid (319 mg, 60%) ¹H NMR (400 MHz, CDCl₃) δ 7.92 (s, 1H), 7.46 (d, 1H), 7.40 (dd, 1H), 7.12 (d, 1H), 7.07 (dd, 1H), 6.65 (br-s, 1H), 5.60 (br-s, 1H), 4.62 (t, 1H), 4.50 (t, 1H), 3.27 (dd, 2H), 2.98 (s, 3H), 2.31-2.18 (m, 2H); MS (apci, m/z)=460.1 (M+H).

Example 24

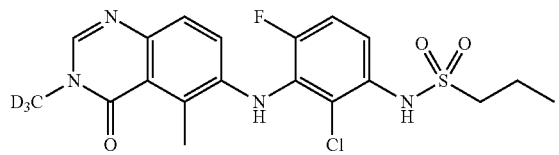 [SMILES: [2H]C([2H])([2H])n1cnc2ccc(Nc3c(F)ccc(NS(=O)(=O)CCC)c3Cl)c(C)c2c1=O]

N-(2-chloro-4-fluoro-3-((5-methyl-3-(methyl-d3)-4-oxo-3,4-dihydroquinazolin-6-yl)amino)phenyl)propane-1-sulfonamide Step 1: Preparation of N-(2-chloro-4-fluoro-3-((5-methyl-3-(methyl-d3)-4-oxo-3,4-dihydroquinazolin-6-yl)amino)phenyl)-N-(4-methoxybenzyl)propane-1-sulfonamide. N-(3-amino-2-chloro-4-fluorophenyl)-N-(methoxybenzyl) propane-1-sulfonamide (116 mg, 0.301 mmol), 6-bromo-5-methyl-3-(methyl-d3)quinazolin-4(3H)-one (70 mg, 0.273 mmol), cesium carbonate (267 mg, 0.820 mmol), Xantphos (23.7 mg, 0.0410 mmol), and tris(dibenzylideneacetone) dipalladium (0) (12.5 mg, 0.0137) were combined in a vial then degassed under reduced pressure and backfilled with argon gas. Toluene (1.37 mL) was added and the solution was sparged with argon for 5 minutes before the vial was sealed and heated to 90° C. for 16 hours. The reaction mixture was cooled to ambient temperature then filtered through a pad of Celite® and purified by silica gel chromatography, eluting with DCM/EtOAc to provide N-(2-chloro-4-fluoro-3-((5-methyl-3-(methyl-d3)-4-oxo-3,4-dihydroquinazolin-6-yl)amino)phenyl)-N-(4-methoxybenzyl)propane-1-sulfonamide as a white solid (144 mg, 94%). MS (apci, m/z)=562.2 (M+H).

Step 2: Preparation of N-(2-chloro-4-fluoro-3-((5-methyl-3-(methyl-d3)-4-oxo-3,4-dihydroquinazolin-6-yl)amino) phenyl)-propane-1-sulfonamide. N-(2-chloro-4-fluoro-3-((5-methyl-3-(methyl-d3)-4-oxo-3,4-dihydroquinazolin-6-yl)amino)phenyl)-N-(4-methoxybenzyl)propane-1-sulfonamide (144 mg, 0.256 mmol) was dissolved in DCM (6.4 mL) and treated with trifluoroacetic acid (2.1 mL) and the reaction mixture was allowed to stir at ambient temperature for 1 hour. The reaction mixture was quenched with an aqueous solution of saturated NaHCO₃ and extracted with EtOAc (3×). The combined organic fractions were dried over Na₂SO₄, filtered, and concentrated. The crude mixture was purified by silica gel chromatography (DCM/MeOH with a 1% NH₄OH) to obtain N-(2-chloro-4-fluoro-3-((5-methyl-3-(methyl-d3)-4-oxo-3,4-dihydroquinazolin-6-yl) amino)phenyl)-propane-1=sulfonamide as a yellow solid (66 mg; 55%)¹H NMR (400 MHz; CDCl₃) δ 7.92 (s, 1H), 7.45 (d, 1H), 7.41 (dd, 1H), 7.11 (d, 1H), 7.06 (dd, 1H), 6.62 (br-s, 1H), 5.60 (br-s, 1H), 3.10 (dd, 2H), 2.98 (s, 3H), 1.93-1.83 (m, 2H), 1.05 (t 3H); MS (apci, m/z)=442.1 (M+H).

Example 25

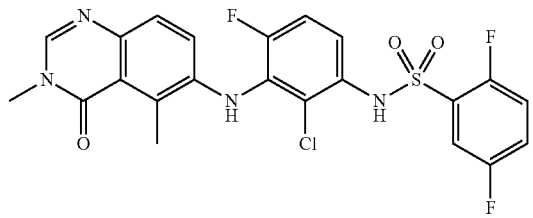 [SMILES: Cc1c(Nc2c(F)ccc(NS(=O)(=O)c3cc(F)ccc3F)c2Cl)ccc2ncn(C)c(=O)c12]

N-(2-chloro-3-((3,5-dimethyl-4-oxo-3,4-dihydroquinazolin-6-yl)amino)-4-fluorophenyl)-2,5-difluorobenzenesulfonamide Step 1: Preparation of N-(2-chloro-3-((3,5-dimethyl-4-oxo-3,4-dihydroquinazolin-6-yl)amino)-4-fluorophenyl)-2,5-difluoro-N-((2-(trimethylsilyl)ethoxy)methyl) benzenesulfonamide. N-(2-chloro-4-fluoro-3-iodophenyl)-2,5-difluoro-N-((2-trimethylsilyl)ethoxy)methyl) benzenesulfonamide (63 mg, 0.109 mmol), 6-amino-3,5-dimethylquinazolin-4(3H)-one (intermediate P15) (18.8 mg, 0.0994 mmol), cesium carbonate (97 mg, 0.298 mmol), Xantphos (8.6 mg; 0.0149 mmol), and tris(dibenzylideneacetone)dipalladium (0) (4.6 mg, 0.00497) were combined in a vial then degassed under reduced pressure and backfilled with argon gas. Toluene (0.662 mL) was added and the solution was sparged with argon for 5 minutes before the vial was sealed and heated to 90° C. for 18 hours. The reaction mixture was cooled to ambient temperature was filtered through a pad of Celite® and purified by silica gel chromatography (DCM/EtOAc) to provide N-(2-chloro-3-((3,5-dimethyl-4-oxo-3,4-dihydroquinazolin-6-yl)amino)-4-fluorophenyl)-2,5-difluoro-N-((2-(trimethylsilyl)ethoxy) methyl)benzenesulfonamide as a white solid (15.1 mg, 24%). MS (apci, m/z)=639.2 (M+H).

Step 2: Preparation of N-(2-chloro-3-((3,5-dimethyl-4-oxo-3,4-dihydroquinazolin-6-yl)amino)-4-fluorophenyl)-2,5-difluorobenzenesulfonamide. N-(2-chloro-3-((3,5-dimethyl-4-oxo-3,4-dihydroquinazolin-6-yl)amino)-4-fluorophenyl)-2,5-difluoro-N-((2-(trimethylsilyl)ethoxy) methyl) benzene-sulfonamide (15.1 mg, 0.0236 mmol) was dissolved in DCM (0.47 mL) and treated with trifluoroacetic acid (0.197 mL-) and the reaction mixture was allowed to stir at ambient temperature for 1 h. The reaction mixture was concentrated and the residue was purified by silica gel chromatography, eluting with DCM/MeOH with 1% NH₄OH to provide N-(2-chloro-3-((3,5-dimethyl-4-oxo-3, 4-dihydroquinazolin-6-yl)amino)-4-fluorophenyl)-2,5-difluorobenzenesulfonamide as an off white solid (2.4 mg, 5.0%). ¹H NMR (400 MHz, CDCl₃) δ 7.86 (s, 1H), 7.45-

7.40 (m, 1H), 7.29 (d, 1H), 7.22-7.14 (m, 2H), 7.11-7.04 (m, 1H), 6.95 (t, 1H), 6.82-6.77 (m, 1H), 5.63 (br-s, 1H), 3.47 (s, 3H), 2.81 (s, 3H); MS (apci, m/z)=509.1 (M+H).

Example 26

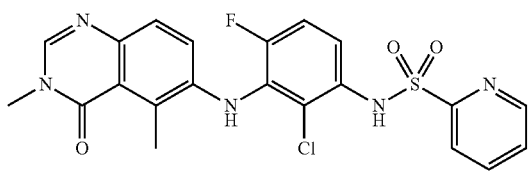 [SMILES: Cc1c(Nc2c(F)ccc(NS(=O)(=O)c3ccccn3)c2Cl)ccc2ncn(C)c(=O)c12]

N-(2-chloro-3-((3,5-dimethyl-4-oxo-3,4-dihydroquinazolin-6-yl)amino)-4-fluorophenyl)pyridine-2-sulfonamide To a solution of 6-((amino-2-chloro-6-fluorophenyl)amino)-3,5-dimethylquinazolin-4(3H)-one (18 mg, 0.054 mmol) and triethylamine (0.030 mL, 0.216 mmol) in DCM (0.540 mL) was added pyridine-2-sulfonyl chloride (20.2 mg, 0.114 mmol). The reaction mixture was allowed to stir at ambient temperature for 16 hours then quenched with water. The aqueous layer was extracted with EtOAc (3×) and the combined organic layers were washed with brine (1×), dried over Na$_2$SO$_4$, filtered, and concentrated. The crude product was purified by reverse phase C18 chromatography. (H$_2$O/acetonitrile with 0.1% TFA) and then the isolated product was dissolved in DCM and washed with saturated NaHCO$_3$ followed by brine then dried over Na$_2$SO$_4$, filtered, and concentrated to obtain N-(2-chloro-3-((3,5-dimethyl-4-oxo-3,4-dihydroquinazolin-6-yl)amino)-4-fluorophenyl)pyridine-2-sulfonamide as a white solid (2.75 mg, 11%). $^1$H NMR (400 MHz, CD$_3$OD) δ 8.63 (d, 1H), 8.11 (s, 1H), 8.01 (t, 1H), 7.92-7.89 (m, 1H), 7.62-7.59 (m, 1H), 7.36 (dd, 1H), 7.32 (d, 1H), 7.14 (t, 1H), 6.77 (d, 1H), 3.52 (s, 3H), 2.83 (s, 3H); MS (apci, m/z)=474.1 (M+H).

Example 27

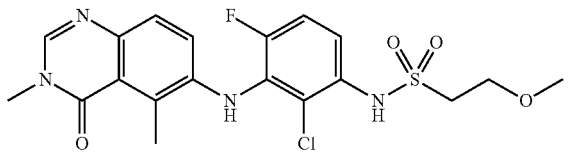

N-(2-chloro-3-((3,5-dimethyl-4-oxo-3,4-dihydroquinazolin-6-yl)amino)-4-fluorophenyl)-2-methoxyethane-1-sulfonamide Step 1: Preparation of N-(2-chloro-3-((3,5-dimethyl-4-oxo-3,4-dihydroquinazolin-6-yl)amino)-4-fluorophenyl)-2-methoxy-N-((2-methoxyethyl)sulfonyl)ethane-1-sulfonamide, To a solution of 6-((3-amino-2-chloro-6-fluorophenyl)amino)-3,5-dimethylquinazolin-4(3H)-one (15.3 mg, 0.046 mmol) and triethylamine (0.026 ml, 0.184 mmol) in DCM (0.115 mL) at 0.0° C. was added 2-methoxyethylsulfonyl chloride (0.011, mL, 0.0966 mmol). The reaction mixture was allowed to warm to ambient temperature and stir for 16 hours then quenched with water. The aqueous layer was extracted with EtOAc (3×) and the combined organic layers were washed with brine (1×), dried over Na$_2$SO$_4$, filtered, and concentrated. The crude product was purified by silica gel chromatography, eluting with DCM/MeOH with 1% NH$_4$OH to obtain N-(2-chloro-3-((3,5-dimethyl-4-oxo-3,4-dihydroquinazolin-6-yl)amino)-4-fluorophenyl)-2-methoxy-N-((2-methoxyethyl)sulfonyl)ethane-1-sulfonamide (18 mg, 68%). MS (apci, m/z)=577.1 (M+H).

Step 2: Preparation of N-(2-chloro-3-((3,5-dimethyl-4-oxo-3,4-dihydroquinazolin-6-yl)amino)-4-fluorophenyl)-2-methoxyethane-1-sulfonamide. N-(2-chloro-3-((3,5-dimethyl-4-oxo-3,4-dihydroquinazolin-6-yl)amino)-4-fluorophenyl)-2-methoxy-N-((2-methoxyethyl)sulfonyl)ethane-1-sulfonamide (18 mg, 0.033 mmol) was dissolved in MeCN (0.165 mL) and treated with a 2.0 M aqueous Na$_2$CO$_3$ solution (0.132 mL, 0.263 mmol) then heated to 60° C. for 1 hour. The reaction mixture was cooled to ambient temperature and then treated with water and extracted with EtOAc (3×). The combined organic extracts were dried over Na$_2$SO$_4$, filtered, and concentrated. The crude product was purified by silica gel chromatography (DCM/MeOH with 1% NH$_4$OH) to obtain N-(2-chloro-3-((3,5-dimethyl-4-oxo-3,4-dihydroquinazolin-6-yl)amino)-4-fluorophenyl)-2-methoxyethane-1-sulfonamide as a white solid (1.9 mg, 13%). $^1$H NMR (400 MHz, CDCl$_3$) δ 7.92 (s, 1H), 7.47-7.44 (m, 2H), 7.11-7.05 (m, 2H), 6.96 (br-s, 1H), 5.60 (br-s, 1H), 3.83 (t, 2H), 3.55 (s, 3H), 3.40-3.38 (m, 2H), 3.35 (s, 3H), 2.97 (s, 3H); MS (apci, m/z)=455.1 (M+H).

Example 28

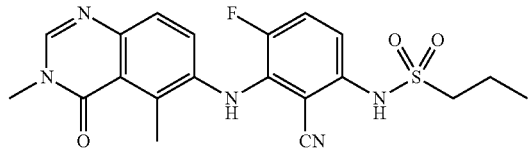

N-(2-cyano-3-((3,5-dimethyl-4-oxo-3,4-dihydroquinazolin-6-yl)amino)-4-fluorophenyl)propane-1-sulfonamide Step 1: Preparation of N-(2-cyano-3-((3,5-dimethyl-4-oxo-3,4-dihydroquinazolin-6-yl)amino)-4-fluorophenyl)-N-((2-(trimethylsilyl)ethoxy)methyl)propane-1-sulfonamide. A solution of N-(3-amino-2-cyano-4-fluorophenyl)-N-((2-(trimethylsilyl)ethoxy)methyl)propane-1-sulfonamide (16 mg, 0.041 mmol), 6-bromo-3,5-dimethylquinazolin-4(3H)-one (10 mg, 0.041 mmol), tris(dibenzylideneacetone)dipalladium (0) (1.9 mg, 0.0021 mmol), Xantphos (3.6 mg, 0.0062 mmol), and cesium carbonate (40 mg, 0.12 mmol) in toluene (275 µL) was sparged with argon for 10 minutes and then sealed and heated in a vial to 90° C. for 18 hours. The reaction mixture was cooled to ambient temperature and then diluted with water and extracted with DCM (2×) and the combined organic layers were washed with brine, dried over Na$_2$SO$_4$, filtered, concentrated. The residue was taken forward as the crude N-(2-cyano-3-((3,5-dimethyl-4-oxo-3,4-dihydroquinazolin-6-yl)amino)-4-fluorophenyl)-N-((2-(trimethylsilyl)ethoxy)methyl)propane-1-sulfonamide without purification. MS (apci, m/z)=560.2 [M+H].

Step 2: Preparation of N-(2-cyano-3-((3,5-dimethyl-4-oxo-3,4-dihydroquinazolin-6-yl)amino)-4-fluorophenyl)

propane-1-sulfonamide. A solution of N-(2-cyano-3-((3,5-dimethyl-4-oxo-3,4-dihydroquinazolin-6-yl)amino)-4-fluorophenyl)-N-((2-(trimethylsilyl)ethoxy)methyl)propane-1-sulfonamide was stirred in 0.5 mL of DCM and 0.2 mL of trifluoroacetic acid for 30 minutes. The reaction mixture was concentrated and the residue was purified by reverse-phase C18 chromatography (H$_2$O/acetonitrile with 0.1% TFA) and then the isolated product was dissolved in DCM and washed with saturated NaHCO$_3$ followed by brine then dried over Na$_2$SO$_4$, filtered, and concentrated to give N-(2-cyano-3-((3,5-dimethyl-4-oxo-3,4-dihydroquinazolin-6-yl)amino)-4-fluorophenyl)propane-1-sulfonamide (6.4 mg, 36%). $^1$H NMR (400 MHz, CDCl$_3$) δ 8.01 (s, 1H), 7.55 (d, 1H), 7.40 (d, 1H), 7.26 (dd, 1H), 7.18 (dd, 1H), 6.58 (br-s, 1H), 5.94 (br-s, 1H), 3.56 (s, 3H), 3.13 (m, 2H), 2.91 (s, 3H), 1.88 (m, 2H), 1.06 (t, 3H); MS (apci, m/z)=430.2 [M+H].

The compounds in Table 1 were prepared using a similar method to that described for the synthesis of N-(3-((3,5-dimethyl-4-oxo-3,4-dihydroquinazolin-6-yl)amino-2,4-difluorophenyl)propane-1-sulfonamide (Example 1) employing the following modifications: in Step 1, replacing 6-bromo-3,5dimethylquinazolin-4(3H)-one and/or N-(3-amino-2,4-difluorophenyl)-N-(4-methoxybenzyl)propane-1-sulfonamide with appropriate 3,5-substituted 6-bromo-quinazolin-4(3H)-one and SEM or PMB-protected aniline; and in Step 2, replacing N-(3-((3,5-dimethyl-4-oxo-3,4-dihydroquinazolin-6-yl)amino-2,4-difluorophenyl)-N-(4-methoxybenzyl)propane-1-sulfonamide with appropriate SEM or PMB-protected coupling product from Step 1. The compounds in Table 1 that are TFA salts were isolated upon purification of the crude material by reverse-phase C18 chromatography, eluting with H$_2$O/acetonitrile with 0.1% TFA, followed by concentrating fractions containing the desired product.

TABLE 1

| Ex. # | Structure | Name | MS (apci) m/z |
|---|---|---|---|
| 29 | 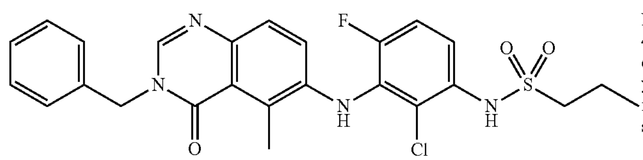 | N-(3-((3-benzyl-5-methyl-4-oxo-3,4-dihydroquinazolin-6-yl)amino)-2-chloro-4-fluorophenyl)propane-1-sulfonamide | 515.1 (M + H) |
| 30 | 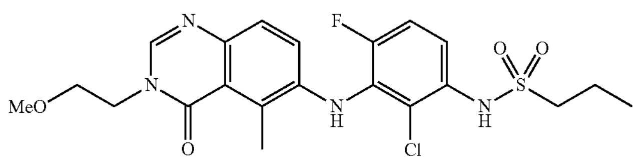 [SMILES: CCCS(=O)(=O)Nc1ccc(F)c(Nc2ccc3ncn(CCOC)c(=O)c3c2C)c1Cl] | N-(2-chloro-4-fluoro-3-((3-(2-methoxyethyl)-5-methyl-4-oxo-3,4-dihydroquinazolin-6-yl)amino)phenyl)propane-1-sulfonamide | 483.1 (M + H) |
| 31 | 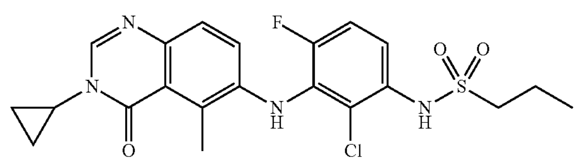 | N-(2-chloro-3-((3-cyclopropyl-5-methyl-4-oxo-3,4-dihydroquinazolin-6-yl)amino)-4-fluorophenyl)propane-1-sulfonamide trifluoroacetate | 465.1 (M + H) |
| 32 | 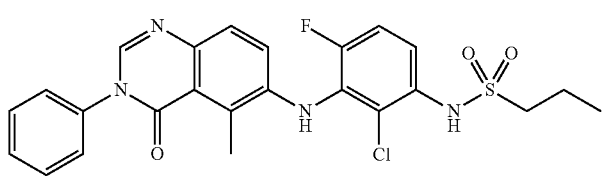 | N-(2-chloro-4-fluoro-3-((5-methyl-4-oxo-3-phenyl-3,4-dihydroquinazolin-6-yl)amino)phenyl)propane-1-sulfonamide trifluoroacetate | 501.2 (M + H) |
| 33 | 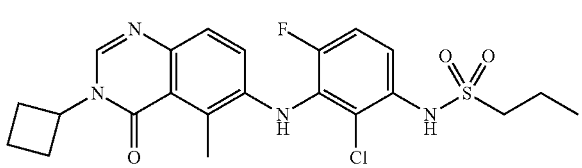 | N-(2-chloro-3-((3-cyclobutyl-5-methyl-4-oxo-3,4-dihydroquinazolin-6-yl)amino)-4-fluorophenyl)propane-1-sulfonamide trifluoroacetate | 479.1 (M + H) |

TABLE 1-continued

| Ex. # | Structure | Name | MS (apci) m/z |
|---|---|---|---|
| 34 | 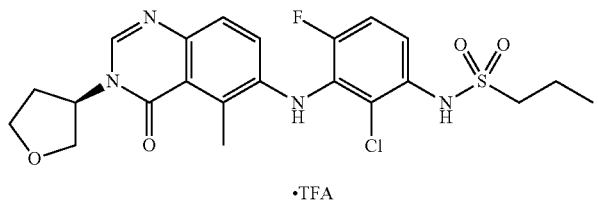 [SMILES: CCCS(=O)(=O)Nc1ccc(F)c(Nc2ccc3ncn([C@@H]4CCOC4)c(=O)c3c2C)c1Cl] •TFA | (R)-N-(2-chloro-4-fluoro-3-((5-methyl-4-oxo-3-(tetrahydrofuran-3-yl)-3,4-dihydroquinazolin-6-yl)amino)phenyl)propane-1-sulfonamide trifluoroacetate | 495.1 (M + H) |
| 35 | 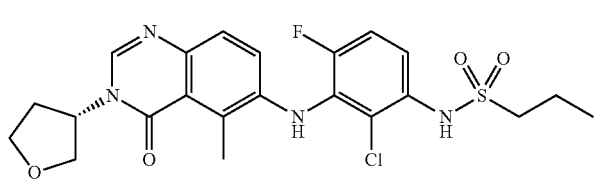 •TFA | (S)-N-(2-chloro-4-fluoro-3-((5-methyl-4-oxo-3-(tetrahydrofuran-3-yl)-3,4-dihydroquinazolin-6-yl)amino)phenyl)propane-1-sulfonamide trifluoroacetate | 495.1 (M + H) |
| 36 | 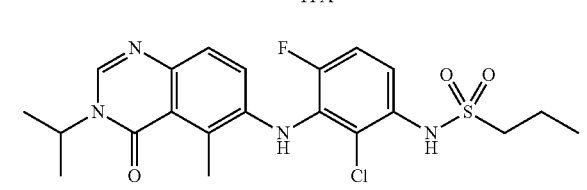 •TFA | N-(2-chloro-4-fluoro-3-((3-isopropyl-5-methyl-4-oxo-3,4-dihydroquinazolin-6-yl)amino)phenyl)propane-1-sulfonamide trifluoroacetate | 467.1 (M + H) |
| 37 | 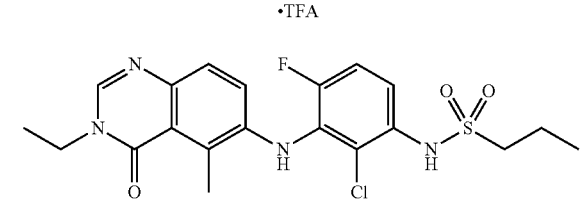 •TFA | N-(2-chloro-3-((3-ethyl-5-methyl-4-oxo-3,4-dihydroquinazolin-6-yl)amino)-4-fluorophenyl)propane-1-sulfonamide trifluoroacetate | 453.1 (M + H) |
| 38 | 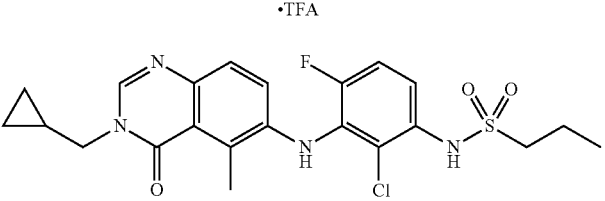 | N-(2-chloro-3-((3-(cyclopropylmethyl)-5-methyl-4-oxo-3,4-dihydroquinazolin-6-yl)amino)-4-fluorophenyl)propane-1-sulfonamide | 479.1 (M + H) |
| 39 | 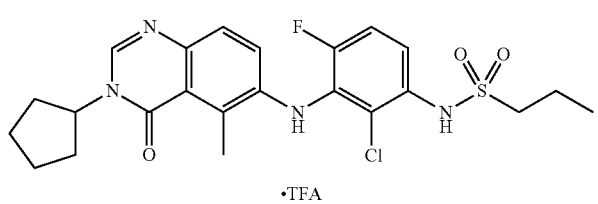 [SMILES: CCCS(=O)(=O)Nc1ccc(F)c(Nc2ccc3ncn(C4CCCC4)c(=O)c3c2C)c1Cl] •TFA | N-(2-chloro-3-((3-cyclopentyl-5-methyl-4-oxo-3,4-dihydroquinazolin-6-yl)amino)-4-fluorophenyl)propane-1-sulfonamide trifluoroacetate | 493.1 (M + H) |
| 40 | 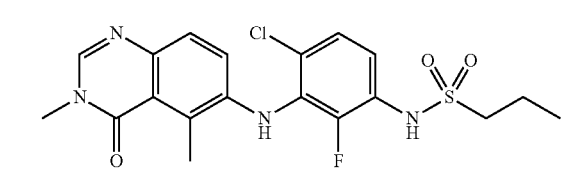 [SMILES: CCCS(=O)(=O)Nc1ccc(Cl)c(Nc2ccc3ncn(C)c(=O)c3c2C)c1F] | N-(4-chloro-3-((3,5-dimethyl-4-oxo-3,4-dihydroquinazolin-6-yl)amino)-2-fluorophenyl)propane-1-sulfonamide | 439.1 (M + H) |
| 41 | 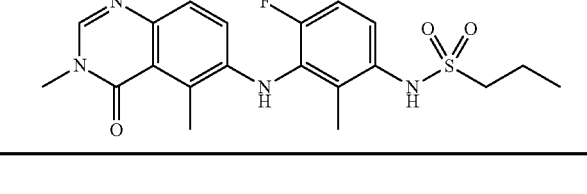 | N-(3-((3,5-dimethyl-4-oxo-3,4-dihydroquinazolin-6-yl)amino)-4-fluoro-2-methylphenyl)propane-1-sulfonamide | 419.1 (M + H) |

The compounds in Table 2 were prepared using a similar method to that described for the synthesis of N-(3-((3,5-dimethyl-4-oxo-3,4-dihydroquinazolin-6-yl)amino)-2,5-difluorophenyl)propane-1-sulfonamide (Example 11) employing the following modifications: in Step 1, replacing N-(3-bromo-2,5-difluorophenyl)-N-((2-(trimethylsilyl)ethoxy)methyl)propane-1-sulfonamide and/or 6-amino-3,5-dimethylquinazolin-4(3H)-one (Intermediate P15) with appropriate 35-substituted 6-amino-quinazolin-4(3H)-one and SEM or PMB-protected aryl or heteroaryl halide; and in Step 2, replacing N-(3-((3,5-dimethyl-4-oxo-3,4-dihydroquinazolin-6-yl)amino)-2,5-difluorophenyl)-N-((2-(trimethylsilyl)ethoxy)methyl)propane-1-sulfonamide (Example 11, Step 1) with appropriate SEM or PMB-protected coupling product.

TABLE 2

| Ex. # | Structure | Name | MS (apci) m/z |
| --- | --- | --- | --- |
| 42 | 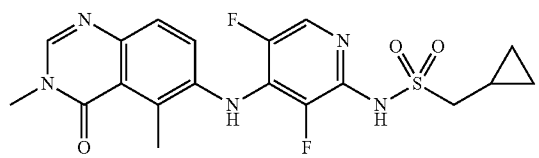 [SMILES: Cc1c(Nc2c(F)cnc(NS(=O)(=O)CC3CC3)c2F)ccc2ncn(C)c(=O)c12] | 1-cyclopropyl-N-(4-((3,5-dimethyl-4-oxo-3,4-dihydroquinazolin-6-yl)amino)-3,5-difluoropyridin-2-yl)methanesulfonamide | 436.1 (M + H) |
| 43 | 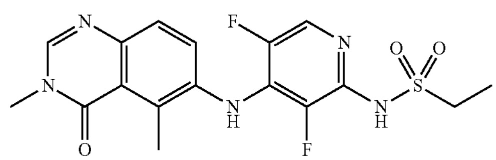 [SMILES: CCS(=O)(=O)Nc1ncc(F)c(Nc2ccc3ncn(C)c(=O)c3c2C)c1F] | N-(4-((3,5-dimethyl-4-oxo-3,4-dihydroquinazolin-6-yl)amino)-3,5-difluoropyridin-2-yl)ethanesulfonamide | 410.1 (M + H) |
| 44 | 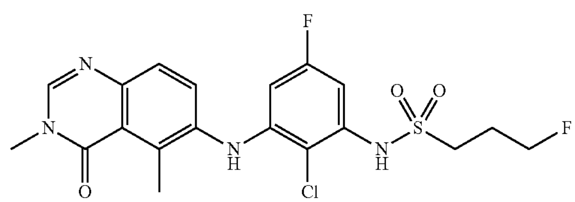 [SMILES: Cc1c(Nc2cc(F)cc(NS(=O)(=O)CCCF)c2Cl)ccc2ncn(C)c(=O)c12] | N-(2-chloro-3-((3,5-dimethyl-4-oxo-3,4-dihydroquinazolin-6-yl)amino)-5-fluorophenyl)-3-fluoropropane-1-sulfonamide | 457.1 (M + H) |
| 45 | 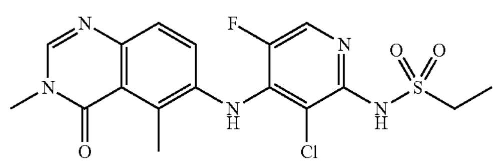 [SMILES: CCS(=O)(=O)Nc1ncc(F)c(Nc2ccc3ncn(C)c(=O)c3c2C)c1Cl] | N-(3-chloro-4-((3,5-dimethyl-4-oxo-3,4-dihydroquinazolin-6-yl)amino)-5-fluoropyridin-2-yl)ethanesulfonamide | 426.1 (M + H) |
| 46 | 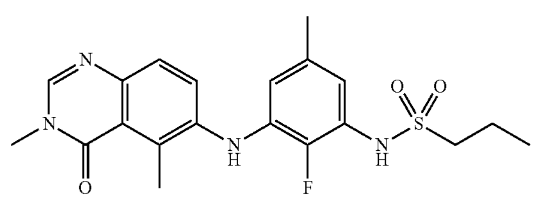 [SMILES: CCCS(=O)(=O)Nc1cc(C)cc(Nc2ccc3ncn(C)c(=O)c3c2C)c1F] | N-(3-((3,5-dimethyl-4-oxo-3,4-dihydroquinazolin-6-yl)amino)-2-fluoro-5-methylphenyl)propane-1-sulfonamide | 419.1 (M + H) |
| 47 | 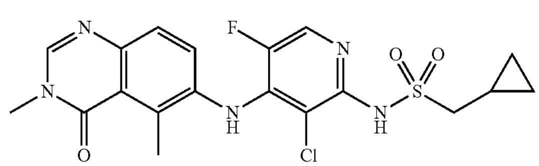 [SMILES: Cc1c(Nc2c(F)cnc(NS(=O)(=O)CC3CC3)c2Cl)ccc2ncn(C)c(=O)c12] | N-(3-chloro-4-((3,5-dimethyl-4-oxo-3,4-dihydroquinazolin-6-yl)amino)-5-fluoropyridin-2-yl)-1-cyclopropylmethanesulfonamide | 452.1 (M + H) |
| 48 | 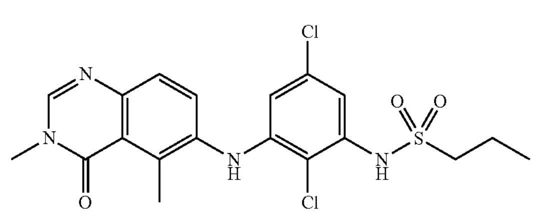 | N-(2,5-dichloro-3-((3,5-dimethyl-4-oxo-3,4-dihydroquinazoli-6-yl)amino)phenyl)propane-1-sulfonamide | 455.1 (M + H) |

TABLE 2-continued

| Ex. # | Structure | Name | MS (apci) m/z |
|---|---|---|---|
| 49 | 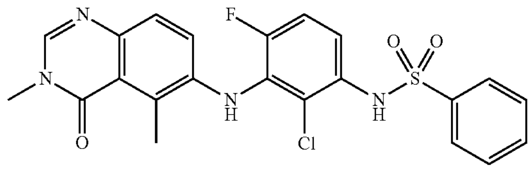 [SMILES: Cc1c(Nc2c(F)ccc(NS(=O)(=O)c3ccccc3)c2Cl)ccc2ncn(C)c(=O)c12] | N-(2-chloro-3-((3,5-dimethyl-4-oxo-3,4-dihydroquinazolin-6-yl)amino)-4-fluorophenyl)benzenesulfonamide | 473.1 (M + H) |
| 50 | 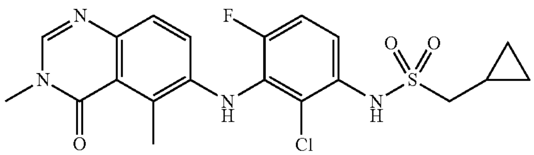 [SMILES: Cc1c(Nc2c(F)ccc(NS(=O)(=O)CC3CC3)c2Cl)ccc2ncn(C)c(=O)c12] | N-(2-chloro-3-((3,5-dimethyl-4-oxo-3,4-dihydroquinazolin-6-yl)amino)-4-fluorophenyl)-1-cyclopropylmethanesulfonamide | 451.1 (M + H) |
| 51 | 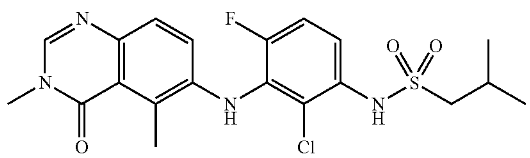 [SMILES: Cc1c(Nc2c(F)ccc(NS(=O)(=O)CC(C)C)c2Cl)ccc2ncn(C)c(=O)c12] | N-(2-chloro-3-((3,5-dimethyl-4-oxo-3,4-dihydroquinazolin-6-yl)amino)-4-fluorophenyl)-2-methylpropane-1-sulfonamide | 453.1 (M + H) |
| 52 | 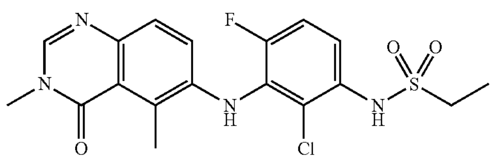 [SMILES: CCS(=O)(=O)Nc1ccc(F)c(Nc2ccc3ncn(C)c(=O)c3c2C)c1Cl] | N-(2-chloro-3-((3,5-dimethyl-4-oxo-3,4-dihydroquinazolin-6-yl)amino)-4-fluorophenyl)ethanesulfonamide | 425.1 (M + H) |
| 53 | 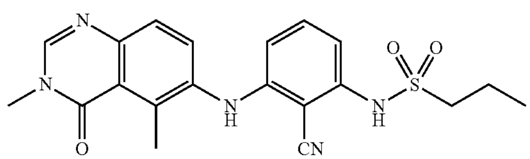 | N-(2-cyano-3-((3,5-dimethyl-4-oxo-3,4-dihdyroquinazolin-6-yl)amino)phenyl)propane-1-sulfonamide | 412.1 (M + H) |
| 54 | 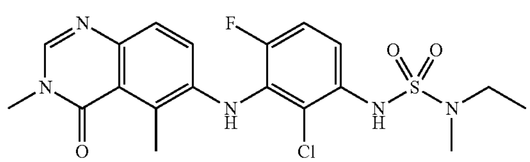 [SMILES: CCN(C)S(=O)(=O)Nc1ccc(F)c(Nc2ccc3ncn(C)c(=O)c3c2C)c1Cl] | N-(2-chloro-3-((3,5-dimethyl-4-oxo-3,4-dihydroquinazolin-6-yl)amino)-4-fluorophenyl)-N-ethyl-N-methylamino-1-sulfonamide | 454.1 (M + H) |

Example 55

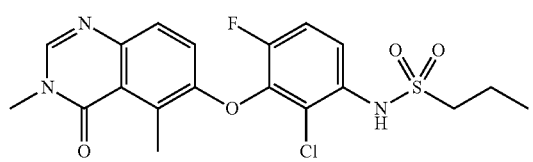 [SMILES: CCCS(=O)(=O)Nc1ccc(F)c(Oc2ccc3ncn(C)c(=O)c3c2C)c1Cl]

N-{2-chloro-3-[(3,5-dimethyl-4-oxo-3,4-dihydroquinazolin-6-yl)oxy]-4-fluorophenyl}propane-1-sulfonamide Step 1: Preparation of tert-butyl 3-(3-amino-2-chloro-6-fluorophenoxy)-2-methyl-6-nitrobenzoate. To a solution of 3-amino-2-chloro-6-fluorophenol-(100 mg, 0.62 mmol) in DMF (3.0 mL) was added $Cs_2CO_3$ (505 mg, 1.55 mmol) followed by tert-butyl 3-fluoro-2-methyl-6-nitrobenzoate (136 mg, 0.68 mmol) and the reaction mixture was heated at 100° C. for 2 hours in a sealed tube. The reaction mixture was cooled to ambient temperature, quenched with water and extracted with ethyl acetate (2×100 mL). The organic layers were washed with water (2×50 mL), brine (50 mL), dried over anhydrous sodium sulfate, filtered, and evaporated under reduced pressure. The crude product was purified by silica gel column chromatography (50% ethyl acetate in hexanes) to provide tert-butyl 3-(3-amino-2-chloro-6-fluorophenoxy)-2-methyl-6-nitrobenzoate as light yellow solid (140 mg, 56%). $^1$H NMR (400 MHz, DMSO-$d_6$) δ 8.04 (d, 1H), 7.21 (t, 1H), 6.79-6.73 (m, 2H), 5.57 (br-s, 2H), 2.37 (s, 3H), 1.58 (s, 9H); MS (m/z)=394.9 (M−H).

Step 2: Preparation of tert-butyl 3-{2-chloro-6-fluoro-3-[N-(propane-1-sulfonyl)propane-1-sulfonamido]-phenoxy}-2-methyl-6-nitrobenzoate. To a stirred solution of tert-butyl 3-(3-amino-2-chloro-6-fluorophenoxy)-2-methyl-6-nitrobenzoate (140.0 mg, 0.35 mmol) in dichloromethane (6 mL) was added triethylamine (0.15 mL, 1.06 mmol) under nitrogen. The solution was cooled to 0° C. and treated with propane-1-sulfonyl chloride (0.09 mL, 0.74 mmol) and was allowed to stir for 6 hours at ambient temperature. The reaction mixture was concentrated under reduced pressure, diluted with water and extracted with ethyl acetate (2×100 mL). The organic layers were washed with water (2×50 mL)

and brine (50 mL), dried over anhydrous sodium sulfate, filtered, and evaporated under reduced pressure. The crude product was purified by silica gel column chromatography (50% ethyl acetate in hexanes) to provide tert-butyl 3-{2-chloro-6-fluoro-3-[N-(propane-1-sulfonyl)propane-1-sulfonamido]-phenoxy}-2-methyl-6-nitrobenzoate as a light yellow solid (160 mg, 60%). $^1$H NMR (400 MHz, DMSO-d$_6$) δ 8.10 (d, 1H), 7.88-7.84 (m, 1H), 7.70 (t, 1H), 6.75 (d, 1H), 3.77-3.76 (m, 4H), 2.40 (s, 3H), 1.87-1.80 (m, 4H), 1.58 (s, 9H), 1.01 (t, 6H).

Step 3: Preparation of tert-butyl-6-amino-3-{2-chloro-6-fluoro-3-[N-(propane-1-sulfonyl)propane-1-sulfonamido]phenoxy}-2-methylbenzoate. To a solution of tert-butyl-3-{2-chloro-6-fluoro-3-[N-(propane-1-sulfonyl)propane-1-sulfonamido]-phenoxy}-2-methyl-6-nitrobenzoate (160 mg, 0.23 mmol) in a mixture of methanol (3 mL) and water (0.5 mL) at ambient temperature was added ammonium chloride (70 mg, 1.3 mmol), followed by Fe-powder (147 mg, 2.6 mmol). The reaction mixture was allowed to stir at ambient temperature for 16 hours. The reaction mixture was filtered through Celite®, washed with DCM (2×30 mL) and concentrated under reduced pressure. The residue was diluted with water (30 mL) and extracted with DCM (2×100 mL). The organic layer was washed with water (2×50 mL) and brine (100 mL), dried over anhydrous sodium sulfate, filtered, and concentrated under reduced pressure. The crude material was purified by silica gel column chromatography (5-10% ethyl, acetate in hexanes) to provide tert-butyl-6-amino-3-{2-chloro-6-fluoro-3-[N-(propane-1-sulfonyl)propane-1-sulfonamido]phenoxy}-2-methylbenzoate as light yellow solid (80 mg, 53%). $^1$H NMR (400 MHz, DMSO-d$_6$) δ 7.69-7.66 (dd, 1H), 7.52 (t, 1H), 6.52 (d, 1H), 6.33 (d, 1H), 5.16 (br-s, 2H), 3.78-3.63 (m, 4H), 2.30 (s, 3H), 1.85-1.83 (m, 4H), 1.56 (s, 9H), 1.01 (t, 6H).

Step 4: Preparation of N-{2-chloro-3-[(3,5-dimethyl-4-oxo-3,4-dihydroquinazolin-6-yl)oxy]-4-fluorophenyl}propane-1-sulfonamide. To a solution of tert-butyl-6-amino-3-{2-chloro-6-fluoro-3-[N-(propane-1-sulfonyl)propane-1-sulfonamido]phenoxy}-2-methylbenzoate (55 mg, 0.12 mmol) in N-methyl formamide (1.5 mL) was added formic acid (0.004 mL, 0.11 mmol) and the reaction mixture was heated to 180° C. for 2 hours. The reaction mixture was allowed to cool to ambient temperature, diluted with water and extracted with ethyl acetate (2×80 mL). The organic layer was washed with water (2×50 mL), brine (50 mL), dried over anhydrous sodium sulfate, filtered, and concentrated under reduced pressure. The crude material was purified by silica gel column chromatography (50% ethyl acetate in hexanes) followed by trituration with diethyl ether to provide N-{2-chloro-3-[(3,5-dimethyl-4-oxo-3,4-dihydroquinazolin-6-yl)oxy]-4-fluorophenyl}propane-1-sulfonamide as off white solid (25 mg, 56%). $^1$H NMR (400 MHz, DMSO-d$_6$) δ 9.66 (br-s, 1H), 8.27 (s, 1H), 7.50-7.43 (m, 3H), 7.00 (d, 1H), 3.45 (s, 3H), 3.13 (t, 2H), 2.90 (s, 3H), 1.78-1.72 (m, 2H), 0.97 (t, 3H). MS (m/z)=440.1 [M+H].

Example 56

N-(3-((3,5-dimethyl-4-oxo-3,4-dihydroquinazolin-6-yl)oxy)-2,4-difluorophenyl)-3-fluoropropane-1-sulfonamide Step 1: Preparation of tert-butyl 3-(3-amino-2,6-difluorophenoxy)-2-methyl-6-nitrobenzoate. To a solution of 3-amino-2,6-difluorophenol (70 mg, 0.482 mmol) in N,N-dimethylformamide (2.4 mL) was added cesium carbonate (393 mg, 1.21 mmol) and tert-butyl 3-fluoro-2-methyl-6-nitrobenzoate (135 mg, 0.531 mmol) and the reaction was heated to 1.00° C. under nitrogen for 2 hours. The solution was cooled to ambient temperature, diluted with water and extracted with EtOAc. The organic layer was washed with brine, dried over Na$_2$SO$_4$ filtered, and concentrated. The crude material was purified by silica gel chromatography (5-95% EtOAc/hexane) to give tert-butyl 3-(3-amino-2,6-difluorophenoxy)-2-methyl-6-nitrobenzoate (134 mg, 73%). $^1$H NMR (400 MHz, CDCl$_3$) δ 7.94 (d, 1H), 6.85 (m, 1H), 6.67 (m, 2H), 2.44 (s, 3H), 1.64 (s, 9H).

Step 2: Preparation of tert-butyl 3-(2,6-difluoro-3-((3-fluoro-N-((3-fluoropropyl)sulfonyl)propyl)sulfonamido)phenoxy)-2-methyl-6-nitrobenzoate. To a solution of tert-butyl 3-(3-amino-2,6-difluorophenoxy)-2-methyl-6-nitrobenzoate (134 mg, 0.352 mmol) in dichloromethane (3.5 mL) at 0° C. was added triethylamine (147 µL, 1.06 mmol) and 3-fluoropropane-1-sulfonyl chloride (92.2 µL, 0.775 mmol) and the reaction mixture was allowed to stir at ambient temperature for 16 hours. The reaction mixture was diluted with water and extracted with DCM. The organic layer was washed with brine, dried over Na$_2$SO$_4$, filtered, and concentrated. The crude material was purified by silica gel chromatography (5-95% EtOAc/hexanes) to give tert-butyl 3-(2,6-difluoro-3-((3-fluoro-N-((3-fluoropropyl)sulfonyl)propyl)sulfonamido)phenoxy)-2-methyl-6-nitrobenzoate (208 mg, 94%). 1H NMR (400 MHz, CDCl$_3$) δ 7.98 (d, 1H), 7.35 (m, 1H), 7.18 (m, 1H), 6.63 (d, 1H), 4.64 (t, 2H), 4.51 (t, 2H), 3.73 (m, 4H), 2.46 (s, 3H), 2.32 (m, 4H), 1.65 (s, 9H).

Step 3: Preparation of 6-amino-3-(2,6-difluoro-3-((3-fluoro-N-((3-fluoropropyl)sulfonyl)propyl)sulfonamido)phenoxy)-2-methylbenzoate. A solution of tert-butyl 3-(2,6-difluoro-3-(63-fluoro-N-((3-fluoropropyl)sulfonyl) propyl)sulfonamido)phenoxy)-2-methyl-6-nitrobenzoate (170 mg, 0.270 mmol) and 10% palladium on carbon (28.8 mg, 0.0270 mmol) in methanol (2.7 mL) was stirred at ambient temperature under a balloon of hydrogen for 8 hours. The solution was filtered through Celite® and concentrated to give tert-butyl 6-amino-3-(2,6-difluoro-3-((3-fluoro-N-((3-fluoropropyl)sulfonyl)propyl)sulfonamido)phenoxy)-2-methylbenzoate (122 mg, 75%). $^1$H NMR (400 MHz, CDCl$_3$) δ 7.18 (m 1H), 7.06 (m, 1H), 6.54 (d, 1H), 6.46 (d, 1H), 4.62 (t, 2H), 4.51 (t, 2H), 3.72 (m, 4H), 2.42 (s, 3H), 2.32 (m, 4H), 1.61 (s, 9H); MS (apci, m/z)=599.2 (M+H).

Step 4: Preparation of N-(3-((3,5-dimethyl-4-oxo-3,4-dihydroquinazolin-6-yl)oxy)-2,4-difluorophenyl)-3-fluoropropane-1-sulfonamide. A solution of tert-butyl 6-amino-3-(2,6-difluoro-3-((3-fluoro-N-((3-fluoropropyl)sulfonyl propyl)sulfonamido)phenoxy)-2-methylbenzoate (34 mg, 0.057 mmol) in N-methylformamide (568 µL) and formic acid (2.9 µL, 0.062 mmol) was heated to 180° C. for 90 minutes. The reaction mixture was cooled to ambient temperature and purified by reverse-phase chromatography (5-95% MeCN/water, 0.1% TFA). The product was then partitioned between DCM and saturated aqueous NaHCO$_3$. The organic layer was washed with brine, dried over Na$_2$SO$_4$, filtered, and concentrated to give N-(3-((3,5-dimethyl-4-oxo-3,4-dihydroquinazolin-6-yl)oxy)-2,4-difluorophenyl)-3-fluoropropane-1-sulfonamide (7 mg, 28%). $^1$H NMR (400 MHz, CDCl$_3$) δ 7.98 (s, 1H), 7.42 (m, 2H), 7.04 (m, 2H), 6.78 (br-s, 1H), 4.61 (t, 1H), 4.49 (t, 1H), 3.55 (s, 3H), 3.26 (t, 2H), 2.98 (s, 3H), 2.22 (m, 2H); MS (apci, m/z)=442.2 (M+H).

Example 57

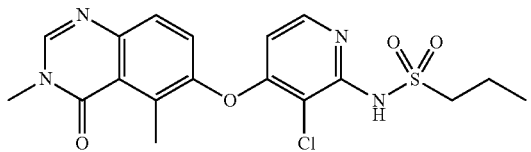 [SMILES: CCCS(=O)(=O)Nc1nccc(Oc2ccc3ncn(C)c(=O)c3c2C)c1Cl]

N-(3-chloro-4-((3,5-dimethyl-4-oxo-3,4-dihydroquinazolin-6-yl)oxy)pyridin-2-yl)propane-1-sulfonamide Step 1: Preparation of 6-((2,3-dichloropyridin-4-yl)oxy)-3,5-dimethylquinazolin-4(3H)-one. To a vial was added 6-hydroxy-3,5-dimethylquinazolin-4(3H)-one (0.050 g, 0.26 mmol), 2,3-dichloro-4-iodopyridine (0.086 g, 0.32 mmol) and DMF (1.3 mL). The resulting solution was treated with cesium carbonate (0.13 g, 0.39 mmol) and the reaction mixture was warmed to 100° C. and stirred for 7 hours. The mixture was cooled to ambient temperature and diluted with water (3 mL). The resulting solid was collected by vacuum filtration, washed with additional water, and dried in vacuo. The crude product was purified via column chromatography (50-100%/EtOAc/DCM) to afford 6-((2,3-dichloropyridin-4-yl)oxy)-3,5-dimethylquinazolin-4(3H)-one as a white solid (0.061 g, 69%). MS (apci, m/z)=336.0, 338.0 (M+H).

Step 2: Preparation of N-(3-chloro-4-((3,5-dimethyl-4-oxo-3,4-dihydroquinazolin-6-yl)oxy)pyridin-2-yl)propane-1-sulfonamide. To a vial was added 6-((2,3-dichloropyridin-4-yl)oxy)-3,5-dimethylquinazolin-4(3H)-one (0.060 g, 0.18 mmol), propane-1-sulfonamide (0.033 g, 0.27 mmol), tris(dibenzylideneacetone)dipalladium (0) (0.016 g, 0.018 mmol), Xantphos (0.026 g, 0.045 mmol) and cesium carbonate (0.17 g, 0.54 mmol). Dioxane (1.8 mL) was added and the mixture was purged with bubbling argon for 10 minutes. The vial was sealed and the mixture was heated at 90° C. for 14 hours and then at 110° C. for another 8 hours. The mixture was then cooled to ambient temperature, diluted with saturated aqueous NH$_4$Cl solution and extracted with 5% IPA/CHCl$_3$ (3×). The combined organic layers were dried over Na$_2$SO$_4$, filtered, and concentrated. The crude product was then purified via silica gel column chromatography (0-4% MeOH/DCM) to afford N-(3-chloro-4-((3,5-dimethyl-4-oxo-3,4-dihydroquinazolin-6-yl)oxy)pyridin-2-yl)propane-1-sulfonamide as an off-white solid (0.054 g, 68%). MS (apci, m/z)=423.1, 425.1 (M+H).

The following were prepared using a similar method to that described for the synthesis of N-(3-((3,5-dimethyl-4-oxo-3,4-dihydroquinazolin-6-yl)amino-2,4-difluorophenyl)propane-1-sulfonamide (Example 1)

| Ex# | structure | Chemical Name | MS (apci) m/z |
|---|---|---|---|
| 58 | 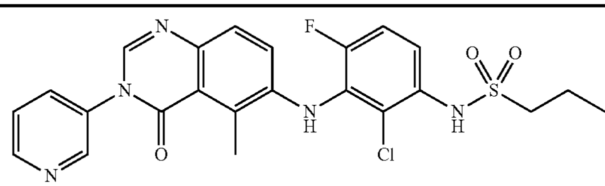 | N-(2-chloro-4-fluoro-3-((5-methyl-4-oxo-3-(pyridin-3-yl)-3,4-dihydroquinazolin-6-yl)amino)phenyl)propane-1-sulfonamide | 502.1, 504.1 (M + H) |
| 59 | 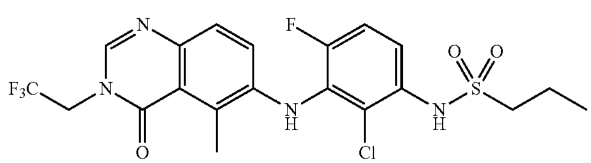 [SMILES: CCCS(=O)(=O)Nc1ccc(F)c(Nc2ccc3ncn(CC(F)(F)F)c(=O)c3c2C)c1Cl] | N-(2-chloro-4-fluoro-3-((5-methyl-4-oxo-3-(2,2,2-trifluoroethyl)-3,4-dihydroquinazolin-6-yl)amino)phenyl)propane-1-sulfonamide | 507.1, 509.1 (M + H) |
| 60 | 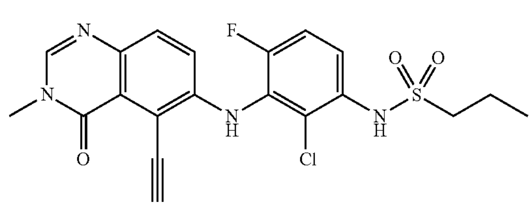 [SMILES: C#Cc1c(Nc2c(F)ccc(NS(=O)(=O)CCC)c2Cl)ccc2ncn(C)c(=O)c12] | N-(2-chloro-3-((5-ethynyl-3-methyl-4-oxo-3,4-dihydroquinazolin-6-yl)amino)-4-fluorophenyl)propane-1-sulfonamide | 449.1, 451.1 (M + H) |

The following compound was prepared using a similar method to that described for the synthesis of N-(3-((3,5-dimethyl-4-oxo-3,4-dihydroquinazolin-6-yl)amino)-2,5-difluorophenyl)propane-1-sulfonamide (Example 11).

| Ex# | structure | Chemical Name | MS (apci) m/z |
|---|---|---|---|
| 61 | 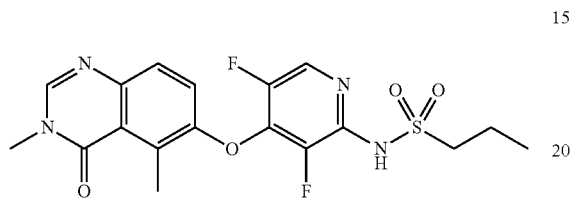 | N-(2-chloro-3-((3,5-dimethyl-4-oxo-3,4-dihydroquinazolin-6-yl)amino)-4-fluorophenyl)butane-2-sulfonamide | 453.1, 455.1 (M + H) |

Example 62

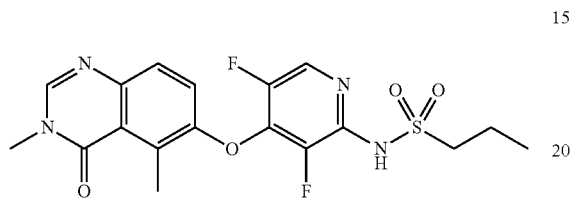

N-(4-((3,5-dimethyl-4-oxo-3,4-dihydroquinazolin-6-yl)oxy)-3,5-difluoropyridin-2-yl)propane-1-sulfonamide Step 1: Preparation of N-(4-((3,5-dimethyl-4-oxo-3,4-dihydroquinazolin-6-yl)oxy)-3,5-difluoropyridin-2-yl)-N-((2-(trimethylsilyl)ethoxy)methyl)propane-1-sulfonamide. To a solution of 6-hydroxy-3,5-dimethylquinazolin-4(3H)-one (0.040 g, 0.21 mmol) and N-(3,5-difluoro-4-iodopyridin-2-yl)-N-((2-(trimethylsilyl)ethoxy)methyl)propane-1-sulfonamide (0.12 g, 0.25 mmol) in DMF (2.1 mL) was added cesium carbonate (0.14 g, 0.42 mmol) and the mixture was heated to 100° C. for 1 hour. The reaction mixture was cooled to ambient temperature and partitioned between ethyl acetate and water. The combined organic layers were washed with brine, dried over Na₂SO₄, filtered and concentrated. The crude product was purified by reverse phase chromatography, eluting with 5-95% acetonitrile in water (0.1% TFA). The crude product was dissolved in DCM/IPA (4:1), washed with saturated NaHCO₃, brine, dried over Na₂SO₄, filtered, and concentrated to afford to afford N-(4-((3,5-dimethyl-4-oxo-3,4-dihydroquinazolin-6-yl)oxy)-3,5-difluoropyridin-2-yl)-N-((2-(trimethylsilyl)ethoxy)methyl)propane-1-sulfonamide (0.073 g, 63%). MS (apci, m/z)=555.2 (M+H).

Step 2: Preparation of N-(4-((3,5-dimethyl-4-oxo-3,4-dihydroquinazolin-6-yl)oxy)-3,5-difluoropyridin-2-yl)propane-1-sulfonamide. A solution of N-(4-((3,5-dimethyl-4-oxo-3,4-dihydroquinazolin-6-yl)oxy)-3,5-difluoropyridin-2-yl)-N-((2-(trimethylsilyl)ethoxy)methyl)propane-1-sulfonamide (0.073 g, 0.13 mmol) in TFA (4 mL) was stirred at ambient temperature for 1 hour. The reaction mixture was concentrated, and the crude product was purified by reverse phase chromatography, eluting with 5-95% acetonitrile in water (0.1% TFA). The isolated product was dissolved in DCM/IPA (4:1), washed with saturated NaHCO₃, brine, dried over Na₂SO₄, filtered, and concentrated to afford to afford N-(4-((3,5-dimethyl-4-oxo-3,4-dihydroquinazolin-6-yl)oxy)-3,5-difluoropyridin-2-yl)propane-1-sulfonamide (15 mg, 27%). MS (apci, m/z)=425.1 (M+H).

Example 63

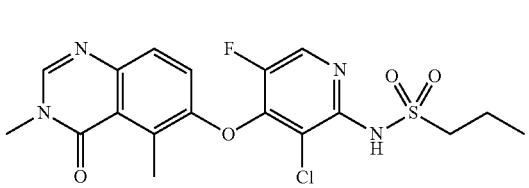

N-(3-chloro-4-((3,5-dimethyl-4-oxo-3,4-dihydroquinazolin-6-yl)oxy)-5-fluoropyridin-2-yl)propane-1-sulfonamide To a solution of 6-hydroxy-3,5-dimethylquinazolin-4(3H)-one (0.043 g, 0.23 mmol) and N-(3-chloro-5-fluoro-4-iodopyridin-2-yl)-N-((2-(trimethylsilyl)ethoxy)methyl)propane-1-sulfonamide (0.14 g, 0.27 mmol) in DMF (2.3 mL) was added cesium carbonate (0.15 g, 0.45 mmol) and the mixture was heated to 100° C. for 16 hours. The reaction mixture was cooled to ambient temperature and partitioned between ethyl acetate and water. The combined organic layers were washed with brine, dried over Na₂SO₄, filtered and concentrated. The crude product was purified by reverse phase chromatography, eluting with 5-95% acetonitrile in water (0.1% TFA). The isolated product was dissolved in DCM/IPA (4:1), washed with saturated NaHCO₃, brine, dried over Na₂SO₄, filtered, and concentrated to afford to afford N-(3-chloro-4-((3,5-dimethyl-4-oxo-3,4-dihydroquinazolin-6-yl)oxy)-5-fluoropyridin-2-yl)propane-1-sulfonamide (15 mg, 15%). MS (apci, m/z)=441.1, 443.1 (M+H).

Example 64

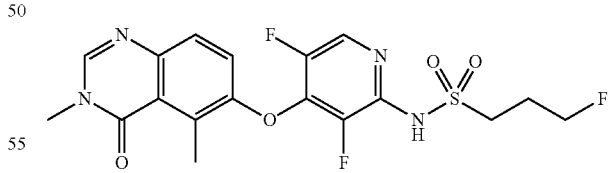

N-(4-((3,5-dimethyl-4-oxo-3,4-dihydroquinazolin-6-yl)oxy)-3,5-difluoropyridin-2-yl)-3-fluoropropane-1-sulfonamide Step 1: Preparation of N-(4-((3,5-dimethyl-4-oxo-3,4-dihydroquinazolin-6-yl)oxy)-3,5-difluoropyridin-2-yl)-3-fluoro-N-((2-(trimethylsilyl)ethoxy)methyl)propane-1-sulfonamide. To a solution of 6-hydroxy-3,5-dimethylquinazolin-4(3H)-one (0.050 g, 0.26 mmol), N-(3, 5-difluoro-4-iodopyridin-2-yl)-3-fluoro-N-((2-(trimethylsilyl)ethoxy)methyl)propane-1-sulfonamide (0.15 g, 0.29 mmol) in DMF (2.6 mL) was added cesium carbonate (0.17 g, 0.53 mmol) and the reaction mixture was stirred at 100° C. for 3 hours. The reaction mixture was cooled to ambient temperature and partitioned between ethyl acetate and water. The combined organic layers were washed with brine, dried over $Na_2SO_4$, filtered and concentrated under reduced pressure. The crude product was purified by reverse phase chromatography, eluting with 5-95% acetonitrile in water (0.1% TFA). The isolated product was dissolved in DCM/IPA (4:1), washed with saturated $NaHCO_3$, brine, dried over $Na_2SO_4$, filtered, and concentrated to afford N-(4-((3,5-dimethyl-4-oxo-3,4-dihydroquinazolin-6-yl)oxy)-3,5-difluoropyridin-2-yl)-3-fluoro-N-((2-(trimethylsilyl)ethoxy)methyl)propane-1-sulfonamide (0.029 g, 19%). MS (apci, m/z)=573.2 (M+H).

Step 2: Preparation of N-(4-((3,5-dimethyl-4-oxo-3,4-dihydroquinazolin-6-yl)oxy)-3,5-difluoropyridin-2-yl)-3-fluoropropane-1-sulfonamide. A solution of N-(4-((3,5-dimethyl-4-oxo-3,4-dihydroquinazolin-6-yl)oxy)-3,5-difluoropyridin-2-yl)-3-fluoro-N-((2-(trimethylsilyl)ethoxy)methyl)propane-1-sulfonamide (0.029 g, 0.051 mmol) in TFA (4 mL) was stirred at ambient temperature for 2 hours. The reaction mixture was concentrated and purified by reverse phase chromatography (5 to 95% acetonitrile in water, 0.1% TFA). The isolated product was dissolved in DCM/IPA (4:1), washed with saturated $NaHCO_3$, brine, dried over $Na_2SO_4$, filtered, and concentrated to afford N-(4-((3,5-dimethyl-4-oxo-3,4-dihydroquinazolin-6-yl)oxy)-3,5-difluoropyridin-2-yl)-3-fluoropropane-1-sulfonamide (3 mg, 13%). MS (apci, m/z)=443.1 (M+H).

Example 65

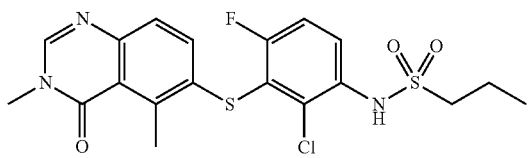

N-(2-chloro-3-((3,5-dimethyl-4-oxo-3,4-dihydroquinazolin-6-yl)thio)-4-fluorophenyl)propane-1-sulfonamide Step 1: Preparation of 2-ethylhexyl 3-((3,5-dimethyl-4-oxo-3,4-dihydroquinazolin-6-yl)thio)propanoate. To a solution of 6-bromo-3,5-dimethylquinazolin-4(3H)-one (600.0 mg, 2.37 mmol), 2-ethylhexyl 3-mercaptopropanoate (1.06 mL, 4.74 mmol) and N,N-diisopropylethylamine (0.83 mL, 4.74 mmol) in dioxane (6 mL) was added Xantphos (411.50 mg, 0.71 mmol) and Pd(OAc)$_2$ (160.00 mg, 0.71 mmol). The reaction mixture was degassed with argon for 10 minutes, sealed and then heated at 140° C. for 48 hours. After completion of the reaction, the reaction mixture was concentrated under reduced pressure, diluted with water and extracted with ethyl acetate (2×100 mL). The organic layers were washed with water (2×50 mL), brine (50 mL), dried over anhydrous sodium sulfate, filtered and evaporated under reduced pressure. The crude product was purified by silica gel column chromatography (60% ethyl acetate in hexane) to provide 2-ethylhexyl 3-((3,5-dimethyl-4-oxo-3,4-dihydroquinazolin-6-yl)thio)propanoate as a yellow liquid (800 mg, 86%). $^1$H NMR (400 MHz, DMSO-d$_6$) δ 8.31 (s, 1H), 7.79 (d, J=8.6 Hz, 1H), 7.48 (d, J=8.6 Hz, 1H), 3.92 (d, J=5.8 Hz, 2H), 3.43 (s, 3H), 3.19 (t, J=6.8 Hz, 2H), 2.89 (s, 3H), 2.60 (t, J=6.7 Hz, 2H), 1.54-1.44 (m, 1H), 1.34-1.19 (m, 8H), 0.87-0.78 (m, 6H); MS (apci, m/z)=390.8 (M+H).

Step 2: Preparation of 6-mercapto-3,5-dimethylquinazolin-4(3H)-one. To a solution of 2-ethylhexyl-3-((3,5-dimethyl-4-oxo-3,4-dihydroquinazolin-6-yl)thio)propanoate (280.0 mg, 0.72 mmol) in THF (3 mL) at 0° C. was added sodium ethoxide (53.7 mg, 0.79 mmol) and the reaction mixture was stirred at 0° C. under nitrogen atmosphere for 30 minutes. After completion of the reaction, the solvent was evaporated and the solid was washed with DCM. The resulting solid was then dissolved in water and 2N HCl was added to adjust the pH to about 7 with. The precipitate was collected by filtration and dried in vacuum to provide 6-mercapto-3,5-dimethylquinazolin-4(3H)-one as a light yellow solid (130 mg, 87%). $^1$H NMR (400 MHz, DMSO-d$_6$) δ 8.27 (s, 1H), 7.80 (d, J=8.5 Hz, 1H), 7.38 (d, J=8.6 Hz, 1H), 5.61 (s, 1H), 3.43 (s, 3H), 2.80 (s, 3H); MS (apci, m/z)=207.0 (M+H).

Step 3: Preparation of N-(2-chloro-3-((3,5-dimethyl-4-oxo-3,4-dihydroquinazolin-6-yl)thio)-4-fluorophenyl)propane-1-sulfonamide. To a solution of 6-mercapto-3,5-dimethylquinazolin-4(3H)-one (54.00 mg, 0.26 mmol), N-(2-chloro-4-fluoro-3-iodophenyl)-N-((2-(trimethylsilyl)ethoxy)methyl)propane-1-sulfonamide (132.72 mg, 0.26 mmol) and tripotassium phosphate (111.14 mg, 0.52 mmol) in DMA (1.0 mL) was added DMEDA (0.01 mL, 0.11 mmol) and CuI (9.97 mg, 0.05 mmol). The reaction mixture was degassed with Ar for 10 minutes, sealed and heated at 130° C. for 16 hours. After completion of the reaction, the reaction mixture was concentrated under reduced pressure, diluted with water and extracted with ethyl acetate (2×25 mL). The organic layers were washed with water (2×10 mL), brine (10 mL), dried over anhydrous sodium sulfate, filtered and evaporated under reduced pressure. The crude product was purified by silica gel column chromatography (40% ethyl acetate in hexane) to provide N-(2-chloro-3-((3,5-dimethyl-4-oxo-3,4-dihydroquinazolin-6-yl)thio)-4-fluorophenyl)propane-1-sulfonamide as light brown solid (14 mg, 12%). $^1$H NMR (400 MHz, DMSO-d$_6$) δ 9.63 (s, 1H), 8.32 (s, 1H), 7.68-7.57 (m, 1H), 7.41 (t, J=8.9 Hz, 2H), 7.21 (d, J=8.7 Hz, 1H), 3.44 (s, 3H), 3.15-3.06 (m, 2H), 2.98 (s, 3H), 1.79-1.65 (m, 2H), 0.94 (t, J=7.4 Hz, 3H); MS (apci, m/z)=456.1 (M+H).

Example 66

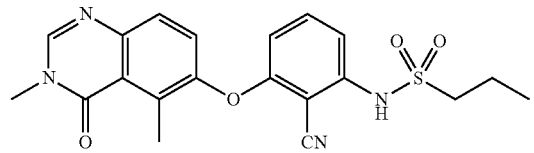 [SMILES: CCCS(=O)(=O)Nc1cccc(Oc2ccc3ncn(C)c(=O)c3c2C)c1C#N]

N-{2-Cyano-3-[(3,5-dimethyl-4-oxo-3,4-dihydroquinazolin-6-yl)oxy]phenyl}propane-1-sulfonamide Step 1: Preparation of 2-[(3,5-dimethyl-4-oxo-3,4-dihydroquinazolin-6-yl)oxy]-6-fluorobenzonitrile. To a cold (0° C.) solution of 6-hydroxy-3,5-dimethyl-3H-quinazolin-4-one (233 mg, 1.22 mmol) in DMF (4 mL) was added 60% NaH in mineral oil (49.0 mg, 1.22 mmol) and the reaction mixture was stirred at 0° C. for 30 minutes. To this was added 2,6-difluoro-benzonitrile (170.41 mg, 1.22 mmol) and the mixture was stirred at ambient temperature for 16 hours. The reaction mixture was quenched with ice-cooled water and extracted with ethyl acetate (2×100 mL). The organic layer was washed with brine, dried over anhydrous Na$_2$SO$_4$, filtered and concentrated under reduced pressure. The crude product was purified by silica gel column chromatography using 50% ethyl acetate/hexane to afford 2-[(3,5-dimethyl-4-oxo-3,4-dihydroquinazolin-6-yl)oxy]-6-fluorobenzonitrile (151 mg, 39%) as an off white solid. $^1$H NMR (400 MHz, DMSO-d$_6$) δ 8.39 (s, 1H), 7.70-7.58 (m, 3H), 7.22 (t, J=8.7 Hz, 1H), 6.53 (d, J=8.7 Hz, 1H), 3.47 (s, 3H), 2.66 (s, 3H).

Step 2: Preparation of N-{2-cyano-3-[(3,5-dimethyl-4-oxo-3,4-dihydroquinazolin-6-yl)oxy]phenyl}propane-1-sulfonamide. To a solution of propane-1-sulfonic acid amide (120.2 mg, 0.98 mmol) in NMP (5 mL) in a sealed tube was added NaH (60% in mineral oil, 39.1 mg, 0.98 mmol) and the reaction mixture was stirred at 60° C. for 40 minutes. To this was added 2-[(3,5-dimethyl-4-oxo-3,4-dihydroquinazolin-6-yl)oxy]-6-fluorobenzonitrile (151.0 mg, 0.49 mmol) and the reaction mixture was stirred at 130° C. for 18 hours. The reaction mixture was cooled to ambient temperature and diluted with 0.5M NaOH solution. The aqueous layer was washed with ethyl acetate (2×15 mL), and then acidified to about pH 5 with 6N HCl. The aqueous layer was extracted with ethyl acetate (3×15 mL), the combined organic layers were washed with water and brine, dried over anhydrous Na$_2$SO$_4$, filtered and concentrated under reduced pressure. The crude product was purified by reverse phase chromatography (20-95/o acetonitrile/water, 20 mM NH$_4$CO$_3$) to afford N-{2-cyano-3-[(3,5-dimethyl-4-oxo-3,4-dihydroquinazolin-6-yl)oxy]phenyl}propane-1-sulfonamide (100 mg, 49%) as a white solid. $^1$H NMR (400 MHz, DMSO-d$_6$) δ 10.24 (s, 1H), 8.37 (s, 1H), 7.64-7.54 (m, 2H), 7.54-7.44 (m, 1H), 7.17 (d, J=8.3 Hz, 1H), 6.43 (s, 1H), 3.47 (s, 3H), 3.20 (m, 2H), 2.66 (s, 3H), 1.80 (q, J=7.7 Hz, 2H), 1.01 (t, J=7.4 Hz, 3H); MS (m/z)=413.3 (M+H).

Example 67

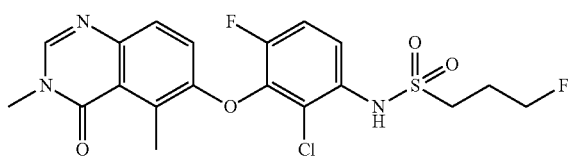 [SMILES: Cc1c(Oc2c(F)ccc(NS(=O)(=O)CCCF)c2Cl)ccc2ncn(C)c(=O)c12]

N-{2-chloro-3-[(3,5-dimethyl-4-oxo-3,4-dihydroquinazolin-6-yl)oxy]-4-fluorophenyl}-3-fluoropropane-1-sulfonamide Step 1: Preparation of tert-butyl-3-{2-chloro-6-fluoro-3-[N-(3-fluoropropanesulfonyl)-3-fluoropropanesulfonamido]phenoxy}2-methyl-6-nitrobenzoate. To a solution of tert-butyl 3-(3-amino-2-chloro-6-fluorophenoxy)-2-methyl-6-nitro benzoate (500.0 mg, 1.26 mmol) in dichloromethane (15 mL) was added triethylamine (0.53 mL, 3.78 mmol) under nitrogen. The solution was cooled to 0° C. and treated with 3-fluoropropane-1-sulfonyl chloride (505 mg, 3.15 mmol) and the reaction mixture was stirred for 6 hours at ambient temperature. After completion of the reaction, the reaction mixture was concentrated under reduced pressure, diluted with water and extracted with ethyl acetate (2×100 mL). The organic layers were washed with water (2×50 mL), brine (50 mL), dried over anhydrous sodium sulfate, filtered and evaporated under reduced pressure. The crude product was purified by silica gel column chromatography (50% ethyl acetate in hexane) to provide tert-butyl-3-{2-chloro-6-fluoro-3-[N-(3-fluoropropanesulfonyl)-3-fluoropropanesulfonamido]phenoxy}2-methyl-6-nitrobenzoate as a light yellow solid (600 mg, 73%). $^1$H NMR (400 MHz, CDCl$_3$) δ 7.96 (d, J=9.1 Hz, 1H), 7.47-7.39 (m, 1H), 7.29 (t, J=8.8 Hz, 1H), 6.50 (d, J=9.2 Hz, 1H), 4.64 (t, J=5.6 Hz, 2H), 4.52 (t, J=5.6 Hz, 2H), 3.89-3.71 (m, 4H), 2.46 (s, 3H), 2.50-2:26 (m, 4H), 1.65 (s, 9H).

Step 2: Preparation of tert-butyl-6-amino-3-{2-chloro-6-fluoro-3-[N-(3-fluoropropanesulfonyl)3-fluoropropanesulfonamido]phenoxy}-2-methylbenzoate. To a solution of tert-butyl-3-{2-chloro-6-fluoro-3-[N-(3-fluoropropanesulfonyl)3-fluoropropanesulfonamido]phenoxy}2-methyl-6-nitrobenzoate (600 mg, 0.93 mmol) in a mixture of methanol (10 mL) and water (3 mL) at ambient temperature were added ammonium chloride (250 mg, 4.6 mmol) and iron powder (520 mg, 9.3 mmol). The reaction mixture was stirred at ambient temperature for 16 hours. After completion of reaction, the reaction mixture was filtered through Celite®, washed with DCM (2×30 mL) and concentrated under reduced pressure. The crude residue was diluted with water (30 mL) and extracted with DCM (2×100 mL). The organic layer was washed with water (2×50 mL), brine (100 mL), dried over anhydrous sodium sulfate, filtered and concentrated. The crude product was purified by silica gel column chromatography (5-10% ethyl acetate in hexane) to provide tert-butyl-6-amino-3-{2-chloro-6-fluoro-3-[N-(3-fluoropropanesulfonyl)3-fluoropropanesulfonamido]phenoxy}-2-methylbenzoate as brown sticky solid (300 mg, 53%). $^1$H NMR (400 MHz, DMSO-d$_6$) δ 9.82-9.70 (m, 1H), 7.79-7.70 (m, 1H), 7.56 (t, J=9.5 Hz, 1H), 7.46-7.34 (m, 1H), 6.51 (t, J=9.1 Hz, 1H), 6.35 (t, J=8.3 Hz, 1H), 5.22-5.08 (m, 2H), 4.67-4.56 (m, 2H), 4.55-4.44 (m, 2H), 3.96-3.75 (m, 2H), 3.29-3.20 (m, 1H), 2.38-2.23 (m, 4H), 2.27-2.16 (m, 1H), 2.20-2.03 (m, 1H), 1.56 (s, 9H).

Step 3: Preparation of N-{2-chloro-3-[(3,5-dimethyl-4-oxo-3,4-dihydroquinazolin-6-yl)oxy]-4-fluorophenyl}-3-fluoropropane-1-sulfonamide. To a solution of tert-butyl-6-amino-3-{2-chloro-6-fluoro-3-[N-(3-fluoropropanesulfonyl)3-fluoropropanesulfonamido] phenoxy}-2-methylbenzoate (250 mg, 0.82 mmol) in N-Methyl formamide (4 mL) was added formic acid (0.031 mL, 0.82 mmol) and the reaction mixture was heated to 180° C. for 2 hours. After completion of reaction, the reaction mixture was cooled to ambient temperature, diluted with water and extracted with ethyl acetate (2×80 mL). The organic layer was washed with water (2×50 mL), brine (50 mL), dried over anhydrous sodium sulfate, filtered and evaporated under reduced pressure. The crude product was purified by silica gel column chromatography (50% ethyl acetate in hexane) followed by triturating with diethyl ether to provide N-{2-chloro-3-[(3,5-dimethyl-4-oxo-3,4-dihydroquinazolin-6-yl)oxy]-4-fluorophenyl}-3-fluoropropane-1-sulfonamide as an off white solid (70 mg, 20%). $^1$H NMR (400 MHz, DMSO-d$_6$) δ 9.82 (s, 1H), 8.28 (s, 1H), 7.54-7.40 (m, 3H), 7.00 (d, J=9.0 Hz, 1H), 4.60 (t, J=6.0 Hz, 1H), 4.49 (t, J=6.0 Hz, 1H), 3.46 (s, 3H), 3.27 (t, J=7.9 Hz, 2H), 2.91 (s, 3H), 2.22-2.04 (m, 2H); MS (apci, m/z)=458.1 (M+H).

Example 68

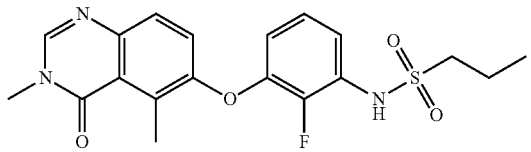 [SMILES: CCCS(=O)(=O)Nc1cccc(Oc2ccc3ncn(C)c(=O)c3c2C)c1F]

N-(3-((3,5-dimethyl-4-oxo-3,4-dihydroquinazolin-6-yl)oxy)-2-fluorophenyl)propane-1-sulfonamide A solution of N-(3-bromo-2-fluorophenyl)propane-1-sulfonamide (1.2 g, 4.05 mmol), 6-hydroxy-3,5-dimethylquinazolin-4(3H)-one (1.2 g, 6.07 mmol), $K_3PO_4$ (2.58 g, 12.15 mmol), picolinic acid (498 mg, 4.05 mmol) and CuI (772 mg, 4.05 mmol) in DMSO (12 mL) was degassed for 15 minutes by purging with argon. The reaction mixture was sealed and heated to 150° C. for 16 hours. After completion of reaction, the reaction mixture was concentrated under reduced pressure, diluted with water and extracted with ethyl acetate (2×100 mL). The organic layers were washed with water (2×50 mL), brine (100 mL), dried over anhydrous sodium sulfate, filtered and evaporated under reduced pressure. The crude material was purified by reverse phase chromatography (30-95% acetonitrile/water, 20 mM $NH_4HCO_3$) to afford N-(3-((3,5-dimethyl-4-oxo-3,4-dihydroquinazolin-6-yl)oxy)-2-fluorophenyl)propane-1-sulfonamide (66 mg, 4%). $^1$H NMR (400 MHz, DMSO-$d_6$) δ 9.80 (s, 1H), 8.33 (s, 1H), 7.53 (d, J=8.8 Hz, 1H), 7.38 (d, J=8.8 Hz, 1H), 7.17 (t, J=7.6 Hz, 1H), 7.09 (t, J=8.3 Hz, 1H), 6.69 (t, J=7.7 Hz, 1H), 3.46 (s, 3H), 3.18-3.09 (m, 2H), 2.74 (s, 3H), 1.81-1.69 (m, 2H), 0.98 (t, J=7.5 Hz, 3H); MS (m/z)=406.3 (M+H).

Example 69

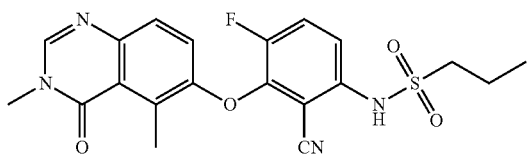 [SMILES: CCCS(=O)(=O)Nc1ccc(F)c(Oc2ccc3ncn(C)c(=O)c3c2C)c1C#N]

N-(2-cyano-3-((3,5-dimethyl-4-oxo-3,4-dihydroquinazolin-6-yl)oxy)-4-fluorophenyl)propane-1-sulfonamide Step 1: Preparation of 2-((3,5-dimethyl-4-oxo-3,4-dihydroquinazolin-6-yl)oxy)-3,6-difluorobenzonitrile. To a stirred solution of 6-hydroxy-3,5-dimethylquinazolin-4(3H)-one (250 mg, 1.31 mmol) in DMF (5.0 mL) was added 60% NaH in mineral oil (62 mg, 1.579 mmol)) at 0° C. and the reaction mixture was stirred for 30 minutes at ambient temperature. Then 2,3,6-trifluorobenzonitrile (206.69 mg, 1.31 mmol) was added and the reaction mixture was stirred for 2 hours at ambient temperature. After completion of the reaction, the reaction mixture was cooled to 5° C. and the reaction mixture was quenched with saturated aqueous solution of $NH_4Cl$ (15 mL), diluted with water and extracted with DCM (2×50 mL). The organic layers were washed with water (2×25 mL), brine (25 mL), dried over anhydrous sodium sulfate, filtered and evaporated under reduced pressure. The crude product was purified by silica gel column chromatography (30% ethyl acetate in hexane) to provide 2-((3,5-dimethyl-4-oxo-3,4-dihydroquinazolin-6-yl)oxy)-3,6-difluorobenzonitrile as off white solid (300 mg, 77%). $^1$H NMR (400 MHz, DMSO-$d_6$) δ 8.32 (s, 1H), 7.95-7.83 (m, 1H), 7.54-7.43 (m, 2H), 7.41 (d, J=9.0 Hz, 1H), 3.46 (s, 3H), 2.87 (s, 3H).

Step 2: Preparation of N-(2-cyano-3-((3,5-dimethyl-4-oxo-3,4-dihydroquinazolin-6-yl)oxy)-4-fluorophenyl)propane-1-sulfonamide. To a stirred solution of propane-1-sulfonamide (210 mg, 1.71 mmol) in DMF (5.0 mL) was added 60% NaH in mineral oil (92 mg, 2.28 mmol)) at 0° C. and the reaction mixture was stirred for 1 hour at ambient temperature. 2-(3,5-Dimethyl-4-oxo-3,4-dihydroquinazolin-6-yl)oxy)-3,6-difluorobenzonitrile (350 mg, 1.06 mmol) was added and the reaction mixture was stirred for 2 hours at 100° C. The reaction mixture was allowed to cool to 5° C. and the reaction mixture was quenched with saturated aqueous solution of $NH_4Cl$ (20 mL), diluted with water and extracted with DCM (3×50 mL). The organic layers were washed with water (2×30 mL), brine (30 mL), dried over anhydrous sodium sulfate, filtered and evaporated under reduced pressure. The crude product was purified by reverse phase chromatography (10-95% acetonitrile/water, 20 mM $NH_4HCO_3$) to provide N-(2-cyano-3-((3,5-dimethyl-4-oxo-3,4-dihydroquinazolin-6-yl)oxy)-4-fluorophenyl)propane-1-sulfonamide as a white solid (70 mg, 15%). $^1$H NMR (400 MHz, DMSO-$d_6$) δ 10.24 (s, 1H), 8.37 (s, 1H), 7.81-7.75 (m, 1H), 7.50-7.47 (m, 1H), 7.42-7.38 (m, 1H), 7.25 (d, J=8.3 Hz, 1H), 3.47 (s, 3H), 3.20 (m, 2H), 2.90 (s, 3H), 1.80 (q, J=7.7 Hz, 2H), 1.01 (t, J=7.4 Hz, 3H); MS (m/z)=431.3 (M+H).

Example 70

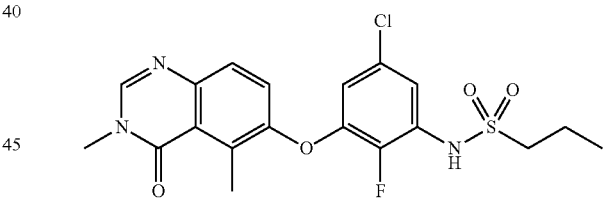

N-(5-chloro-3-((3,5-dimethyl-4-oxo-3,4-dihydroquinazolin-6-yl)oxy)-2-fluorophenyl) propane-1-sulfonamide Step 1: Preparation of tert-butyl 3-(3-amino-5-chloro-2-fluorophenoxy)-2-methyl-6-nitrobenzoate. To a solution of 3-amino-5-chloro-2-fluorophenol (61 mg, 0.38 mmol) in N,N-dimethylformamide (1888 μL) was added cesium carbonate (308 mg, 0.94 mmol) and tert-butyl 3-fluoro-2-methyl-6-nitrobenzoate (106 mg, 0.42 mmol) and the reaction was heated to 100° C. under nitrogen for 90 minutes. The solution was cooled to room temperature, diluted with water and extracted with EtOAc (3×). The combined organic layers were washed with brine, dried with $Na_2SO_4$, filtered and concentrated. The crude product was purified by silica gel chromatography (5-95% EtOAc/hexane) and then by reverse-phase chromatography (5-95% MeCN/water, 0.1% TFA). The isolated product was dissolved in DCM and washed with saturated aqueous NaHCO₃. The combined organic layers were washed with brine, dried with Na₂SO₄, filtered, concentrated to give tert-butyl 3-(3-amino-5-chloro-2-fluorophenoxy)-2-methyl-6-nitrobenzoate (90 mg, 60%). ¹H NMR (400 MHz, CDCl₃) δ 7.98 (d, 1H), 6.78 (d, 1H), 6.66 (dd, 1H), 6.43 (dd, 1H), 2.39 (s, 3H), 1.64 (s, 9H).

Step 2: Preparation of tert-butyl 6-amino-3-(3-amino-5-chloro-2-fluorophenoxy)-2-methylbenzoate. A solution of, tert-butyl 3-(3-amino-5-chloro-2-fluorophenoxy)-2-methyl-6-nitrobenzoate (47 mg, 0.12 mmol), zinc dust (77 mg, 1.2 mmol), and NH₄Cl (127 mg, 2.4 mmol) in methanol (592 µL) was stirred at ambient temperature for 30 minutes. The solution was filtered through Celite, the Celite was rinsed with MeOH and the filtrate was concentrated. The crude product was purified by reverse-phase chromatography (5-95%. MeCN/water, 0.1% TFA). The isolated product was dissolved in DCM and washed with saturated aqueous NaHCO₃. The combined organic layers were washed with brine, dried with Na₂SO₄, filtered, concentrated to give tert-butyl 6-amino-3-(3-amino-5-chloro-2-fluorophenoxy)-2-methylbenzoate (20 mg, 46%). MS (apci, m/z)=367.1 (M+H).

Step 3: Preparation of 6-(3-amino-5-chloro-2-fluorophenoxy)-3,5-dimethylquinazolin-4(3H)-one. A solution of tert-butyl 6-amino-3-(3-amino-5-chloro-2-fluorophenoxy)-2-methylbenzoate (20 mg, 0.055 mmol) in N-methylformamide (545 µL, 0.055 mmol) and formic acid (2.8 µL, 0.060 mmol) was heated to 180° C. for 16 hours. The reaction mixture was cooled to ambient temperature, diluted with saturated aqueous NaHCO₃ and extracted with DCM (3×). The combined organic layers were washed with brine, dried with Na₂SO₄, filtered concentrated and purified by silica gel chromatography (5-95% EtOAc/DCM) to give 6-(3-amino-5-chloro-2-fluorophenoxy)-3,5-dimethylquinazolin-4(3H)-one (7.2 mg, 40%). MS (apci, m/z)=334.0, 336.0 (M+H).

Step 4: Preparation of N-(5-chloro-3-((3,5-dimethyl-4-oxo-3,4-dihydroquinazolin-6-yl)oxy)-2-fluorophenyl)propane-1-sulfonamide. To a solution of 6-(3-amino-5-chloro-2-fluorophenoxy)-3,5-dimethylquinazolin-4(3H)-one (7.2 mg, 0.02157 mmol) in dichloromethane (215.7 µL) at 0° C. was added triethylamine (9.021 µL, 0.06472 mmol) and propane-1-sulfonyl chloride (5.342 µL, 0.04746 mmol) and the reaction was stirred at ambient temperature for 1 hour. The reaction mixture was diluted with water and extracted with DCM (3×). The combined organic layers were washed with brine, dried with Na₂SO₄, filtered and concentrated. The residue was dissolved in acetonitrile (107.9 µL) and heated to 60° C. with 2 M Na₂CO₃ (107.9 µL, 0.02157 mmol) for 1 hour. The solution was brought to about pH 5 with 10% citric acid, diluted with water and extracted with DCM (3×). The combined organic layers were washed with brine, dried with Na₂SO₄, filtered, concentrated and purified by reverse-phase chromatography (5-95% MeCN/water, 0.1% TFA). The isolated product was dissolved in DCM and washed with saturated aqueous NaHCO₃. The combined organic layers were washed with brine, dried with Na₂SO₄, filtered, concentrated to give N-(5-chloro-3-((3,5-dimethyl-4-oxo-3,4-dihydroquinazolin-6-yl)oxy)-2-fluorophenyl)propane-1-sulfonamide (4.5 mg, 47%). ¹H NMR (400 MHz, CDCl₃) δ 8.02 (s, 1H), 7.58 (d, 1H), 7.33 (m, 2H), 6.41 (m, 1H), 3.57 (s, 3H), 3.18 (t, 2H), 2.80 (s, 3H), 1.92 (m, 2H), 1.08 (t, 3H).

Example 71

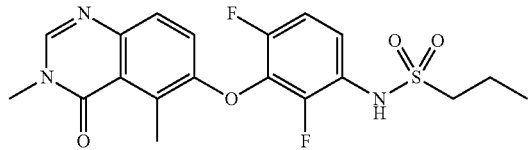 [SMILES: CCCS(=O)(=O)Nc1ccc(F)c(Oc2ccc3ncn(C)c(=O)c3c2C)c1F]

N-(3-((3,5-dimethyl-4-oxo-3,4-dihydroquinazolin-6-yl)oxy)-2,4-difluorophenyl)propane-1-sulfonamide Step 1: Preparation of tert-butyl 3-(3-amino-2,6-difluorophenoxy)-2-methyl-6-nitrobenzoate. To a solution of 3-amino-2,6-difluorophenol (271 mg, 1.87 mmol) in N,N-dimethylformamide (9338 µL) was added cesium carbonate (1521 mg, 4.67 mmol) and tert-butyl 3-fluoro-2-methyl-6-nitrobenzoate (524 mg, 2.05 mmol) and the reaction was heated to 100° C. under nitrogen for 90 minutes. The solution was cooled to ambient temperature, diluted with water and extracted with EtOAc (3×). The combined organic layers were washed with brine, dried with Na₂SO₄, filtered, concentrated, and purified by silica gel chromatography (5-50% EtOAc/hexane) to give tert-butyl 3-(3-amino-2,6-difluorophenoxy)-2-methyl-6-nitrobenzoate (681 mg, 96%). ¹H NMR (400 MHz, CDCl₃) δ 7.96 (d, 1H), 6.86 (m, 1H), 6.65 (m, 2H), 2.45 (s, 3H), 1.65 (s, 9H).

Step 2: Preparation of tert-butyl 6-amino-3-(3-amino-2,6-difluorophenoxy)-2-methylbenzoate. A solution of tert-butyl 3-(3-amino-2,6-difluorophenoxy)-2-methyl-6-nitrobenzoate (681 mg, 1.79 mmol) and 10% palladium on carbon (191 mg, 0.179 mmol) in methanol (11936 µL, 1.79 mmol) was purged with argon for 10 minutes and then stirred under a hydrogen balloon for 90 minutes. The palladium was removed by filtration and the filtrate was concentrated to give tert-butyl 6-amino-3-(3-amino-2,6-difluorophenoxy)-2-methylbenzoate (529 mg, 84%). MS (apci, m/z)=351.1 (M+H).

Step 3: Preparation of 6-(3-amino-2,6-difluorophenoxy)-3,5-dimethylquinazolin-4(3H)-one. A solution of tert-butyl 6-amino-3-(3-amino-2-fluoro-6-methylphenoxy)-2-methylbenzoate (150 mg, 0.433 mmol) in N-methylformamide (4330 µL, 0.433 mmol) was heated to 180° C. for 3 ours. The solution was cooled to ambient temperature, diluted with water and extracted with EtOAc (3×). The organics were concentrated and heated to 90° C. in a solution of 3 mL of dioxane and 3 mL of 6 M NaOH for 16 hours. The solution was cooled to ambient temperature and brought to about pH 5 with 10% citric acid. The reaction mixture was diluted with water and extracted with DCM (3×). The combined organic layers were washed with brine, dried with Na₂SO₄, filtered, concentrated and purified by silica gel chromatography (5-95% EtOAc/DCM) to give 6-(3-amino-2,6-difluorophenoxy)-3,5-dimethylquinazolin-4(3H)-one (79 mg, 58%). MS (apci, m/z)=318.1 (M+H).

Step 4: Preparation of N-(3-((3,5-dimethyl-4-oxo-3,4-dihydroquinazolin-6-yl)oxy)-2,4-difluorophenyl)propane-1-sulfonamide. To a solution of 6-(3-amino-2,6-difluorophenoxy)-3,5-dimethylquinazolin-4(3H)-one (76 mg, 0.2395 mmol) in dichloromethane (2395 µL) was added triethylamine (100.2 µL, 0.7186 mmol) and propane-1-sulfonyl chloride (59.31 µL, 0.5270 mmol) and the reaction was stirred at ambient temperature for 30 minutes. The reaction mixture was diluted with water and extracted with DCM (3×). The combined organic layers were washed with brine, dried with Na₂SO₄, filtered, concentrated. The residue was dissolved in 1 mL of MeCN and 1 mL of 2 M Na₂CO₃ and heated to 80° C. for 30 minutes. The solution was cooled to ambient temperature and brought to about pH 5 with 10% citric acid. The reaction mixture was diluted with water and extracted with EtOAc (3×). The combined organic layers were washed with brine, dried with Na₂SO₄, filtered, concentrated and purified by silica gel chromatography (5-95% EtOAc/DCM) to give N-(3-((3,5-dimethyl-4-oxo-3,4-dihydroquinazolin-6-yl)oxy)-2,4-difluorophenyl)propane-1-sulfonamide (55 mg, 54%). ¹H NMR (400 MHz, CDCl₃) δ 7.97 (s, 1H), 7.42 (m, 2H), 7.03 (m, 2H), 6.48 (br-s, 1H), 3.55 (s, 3H), 3.09 (m, 2H), 2.99 (s, 3H), 1.88 (m, 2H), 1.05 (t, 3H). MS (apci, m/z)=424.1 (M+H).

Example 72

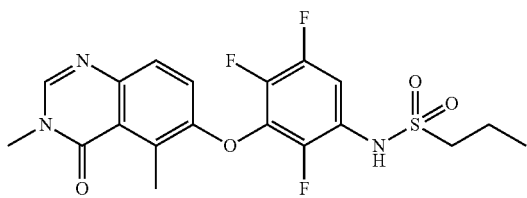 [SMILES: CCCS(=O)(=O)Nc1cc(F)c(F)c(Oc2ccc3ncn(C)c(=O)c3c2C)c1F]

N-(3-((3,5-dimethyl-4-oxo-3,4-dihydroquinazolin-6-yl)oxy)-2,4,5-trifluorophenyl)propane-1-sulfonamide Step 1: Preparation of tert-butyl 3-(3-amino-2,5,6-trifluorophenoxy)-2-methyl-6-nitrobenzoate. To a solution of 3-amino-2,5,6-trifluorophenol (1.0 g, 6.1 mmol) in DMF (5 mL) was added potassium carbonate (2.54 g, 18.4 mmol) and a solution of tert-butyl 3-fluoro-2-methyl-6-nitrobenzoate (1.87 g, 7.36 mmol) in DMF (3 mL) and the reaction mixture was stirred at ambient temperature for 16 hours. The reaction mixture was poured into ice water (20 mL) and extracted with ethyl acetate (3×50 mL). The combined organic layers were dried over Na₂SO₄, filtered, concentrated and purified by silica gel chromatography (10% EtOAc/hexane) to provide tert-butyl 3-(3-amino-2,5,6-trifluorophenoxy)-2-methyl-6-nitrobenzoate as a brown solid (1.0 g, 41%). ¹H NMR (400 MHz, DMSO-d₆) δ 8.05 (d, J=9.1 Hz, 1H), 7.04 (d, J=9.1 Hz, 1H), 6.80-6.68 (m, 1H), 5.66 (s-br, 2H), 2.37 (s, 3H), 1.58 (s, 9H).

Step 2: Preparation of tert-butyl (2-methyl-6-nitro-3-(2,3,6-trifluoro-5-(N-(propylsulfonyl)propylsulfonamido)phenoxy)benzoate. To, a solution of tert-butyl 3-(3-amino-2,5,6-trifluorophenoxy)-2-methyl-6-nitrobenzoate (1.0 g, 2.5 mmol) in dichloromethane (10 mL) at 0° C. was added triethyl amine (1.0 mL, 7.5 mmol) and propane sulphonyl chloride (0.75 mL, 6.2 mmol) and the reaction mixture was stirred at ambient temperature for 6 hours. The reaction mixture was quenched with cold water (10 mL) and extracted with dichloromethane (3×30 mL). The combined organic layers were washed with water (10 mL), dried over Na₂SO₄, filtered, and concentrated. The crude product was purified by silica gel column chromatography (20% EtOAc/hexane) to provide tert-butyl (2-methyl-6-nitro-3-(2,3,6-trifluoro-5-(N-(propylsulfonyl)propylsulfonamido)phenoxy)benzoate as a brown semi-solid (1.0 g, 65%). ¹H NMR (400 MHz, DMSO-d₆) δ 8.15-8.04 (m, 2H), 7.12 (dd, J=3.6, 9.7 Hz, 1H), 3.78-3.56 (m, 4H), 2.40 (s, 3H), 1.92-1.67 (m, 4H), 1.58 (s, 9H), 1.05-0.95 (m, 6H).

Step 3: Preparation of tert-butyl 6-amino-2-methyl-3-(2,3,6-trifluoro-5-(N-(propylsulfonyl)propylsulfonamido) phenoxy) benzoate. To a solution of tert-butyl 2-methyl-6-nitro-3-(2,3,6-trifluoro-5-(N-(propylsulfonyl)propylsulfonamido) phenoxy)benzoate (1.0 g, 1.63 mmol) in methanol (50 mL) was added 10% Pd on carbon (50% moist support) (500 mg, 50% loading) and the mixture was sparged with argon for 10 minutes. The reaction mixture was placed under a H₂ balloon and stirred at ambient temperature for 3-days. The reaction mixture was filtered through a bed of Celite and the filtrate was concentrated. The crude product was purified by silica gel column chromatography (30% EtOAc/hexane) to provide tert-butyl 6-amino-2-methyl-3-(2,3,6-trifluoro-5-(N-(propylsulfonyl)propylsulfonamido) phenoxy) benzoate as a brown sticky liquid (300 mg, 31%). ¹H NMR (400 MHz, DMSO-d₆) δ 7.94-7.83 (m, 1H), 6.66 (d, J=8.9 Hz, 1H), 6.55 (d, J=9.0 Hz, 1H), 5.27 (s-br, 2H), 3.75-3.55 (m, 4H), 2.29 (s, 3H), 1.90-1.70 (m, 4H), 1.56 (s, 9H), 1.00 (t, J=7.4 Hz, 6H); MS (m/z)=581.2 (M+H).

Step 4: Preparation of N-(3-((3,5-dimethyl-4-oxo-3,4-dihydroquinazolin-6-yl)oxy)-2,4,5-trifluorophenyl)propane-1-sulfonamide. To a solution of tert-butyl 6-amino-2-methyl-3-(2,3,6-trifluoro-5-(N-(propylsulfonyl) propylsulfonamido)phenoxy)benzoate (400 mg, 0.086 mmol) in N-methylformamide (2 mL) was added formic acid (0.5 mL). The reaction tube was flushed with argon for 10 minutes, then sealed and the reaction mixture was stirred at 180° C. for 3 hours. The reaction mixture was cooled to ambient temperature, diluted with water and extracted with ethyl acetate (3×20 mL). The combined organic layers were dried over Na₂SO₄, filtered, and concentrated. The crude product was purified by reverse phase column chromatography (30-100% ACN/water with 10 mM ammonium bicarbonate) to provide N-(3-((3,5-dimethyl-4-oxo-3,4-dihydroquinazolin-6-yl)oxy)-2,4,5-trifluorophenyl)propane-1-sulfonamide as an off-white solid (99 mg, 32%). ¹H NMR (400 MHz, DMSO-d₆) δ 10.02 (s-br, 1H), 8.30 (s, 1H), 7.50-7.36 (m, 2H), 7.34 (d, J=9.0 Hz, 1H), 3.46 (s, 3H), 3.19-3.11 (m, 2H), 2.88 (s, 3H), 1.70 (q, J=7.6 Hz, 2H), 0.99-0.89 (m, 3H); MS (m/z)=442.4 (M+H).

Example 73

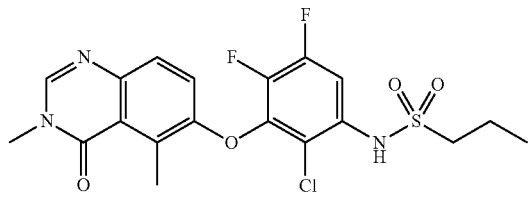 [SMILES: CCCS(=O)(=O)Nc1cc(F)c(F)c(Oc2ccc3ncn(C)c(=O)c3c2C)c1Cl]

N-(2-chloro-3-((3,5-dimethyl-4-oxo-3,4-dihydroquinazolin-6-yl)oxy)-4,5-difluorophenyl)propane-1-sulfonamide Step 1: Preparation of tert-butyl 3-(3-amino-2-chloro-5,6-difluorophenoxy)-2-methyl-6-nitrobenzoate. To a solution of 3-amino-2-chloro-5,6-difluorophenol (550 mg, 3.07 mmol) in DMF (10.0 mL) was added K₂CO₃ (848.00 mg, 6.15 mmol) followed by tert-butyl 3-fluoro-2-methyl-6-nitrobenzoate (783 mg, 3.07 mmol) and the reaction mixture was heated at 90° C. for 16 hours in a sealed tube. The reaction mixture was cooled to ambient temperature, diluted with water and extracted with ethyl acetate (4×100 mL). The combined organic layers were washed with water (4×50 mL) and brine (2×25 mL), dried over Na$_2$SO$_4$, filtered, and concentrated. The crude product was purified by silica gel column chromatography (10% EtOAc/hexane) to provide tert-butyl 3-(3-amino-2-chloro-5,6-difluorophenoxy)-2-methyl-6-nitrobenzoate (450 mg, 35%). $^1$H NMR (400 MHz, DMSO-d$_6$) δ 8.03 (d, J=9.2 Hz, 1H), 6.90 (d, J=9.2 Hz, 1H), 6.78 (dd, J=7.4, 12.9 Hz, 1H), 5.88 (s-br, 2H), 2.38 (s, 3H), 1.58 (s, 9H); MS (m/z)=412.5 (M–H).

Step 2: Preparation of tert-butyl-3-(2-chloro-5,6-difluoro-3-propylsulfonamido)phenoxy)-2-methyl-6-nitrobenzoate. To a solution of tert-butyl 3-(3-amino-2-chloro-5,6-difluorophenoxy)-2-methyl-6-nitrobenzoate (500 mg, 1.21 mmol) in dichloromethane (10 mL) at 0° C. was added triethylamine (2.40 mL, 18.12 mmol) followed by propane-1-sulfonyl chloride (0.80 mL, 8.45 mmol) and the reaction mixture was stirred for 1 hours at ambient temperature. The reaction mixture was concentrated under reduced pressure, diluted with water and extracted with ethyl acetate (3×100 mL). The combined organic layers were washed with water (2×50 mL) and brine (50 mL), dried over anhydrous Na$_2$SO$_4$, filtered and evaporated under reduced pressure. The crude product was purified by silica gel column chromatography (10% EtOAc/hexane) to provide tert-butyl-3-(2-chloro-5,6-difluoro-3-propylsulfonamido)phenoxy)-2-methyl-6-nitrobenzoate as a light yellow solid (600 mg, 95%). MS (m/z) =518.7 [M–H].

Step 3: Preparation of tert-butyl-6-amino-3-(2-chloro-5,6-difluoro-3-(propylsulfonamido)phenoxy)-2-(methyl)benzoate. To a solution of tert-butyl-3-(2-chloro-5,6-difluoro-3-propylsulfonamido)phenoxy)-2-methyl-6-nitrobenzoate (300 mg, 0.57 mmol) in a mixture of methanol (10 mL) and water (5 mL) were added ammonium chloride (153.00 mg, 2.89 mmol), followed by Fe-powder (224.00 mg, 8.67 mmol) and the reaction mixture was stirred at 75° C. for 4 hours. The reaction mixture was cooled to ambient temperature, filtered through Celite, the Celite was washed with DCM (2×50 mL) and the filtrate was concentrated under reduced pressure. The crude residue was diluted with water (50 mL) and extracted with DCM (2×100 mL). The organic layer was washed with water (2×50 mL) and brine (100 mL), dried over anhydrous Na$_2$SO$_4$, filtered and concentrated. The crude product was purified by silica gel column chromatography (20% EtOAc/hexane) to provide tert-butyl-6-amino-3-(2-chloro-5,6-difluoro-3-(propylsulfonamido)phenoxy)-2-(methyl)benzoate as a white solid (200 mg, 72%). MS (m/z)=488.9 [M–H].

Step 4: Preparation of N-(2-chloro-3-((3,5-dimethyl-4-oxo-3,4-dihydroquinazolin-6-yl)oxy)-4,5-difluorophenyl) propane-1-sulfonamide. To a solution of tert-butyl-6-amino-3-(2-chloro-5,6-difluoro-3-(propylsulfonamido)phenoxy)-2-(methyl)benzoate (300 mg, 0.61 mmol) in N-methylformamide (3.0 mL) was added formic acid (catalytic amount) and the reaction mixture was heated to 180° C. for 2 hours. The reaction mixture was cooled to ambient temperature, diluted with water and extracted with ethyl acetate (3×100 mL). The organic layer was washed with water (2×50 mL) and brine (50 mL), dried over anhydrous Na$_2$SO$_4$, filtered and concentrated. The crude product was purified by silica gel column chromatography (50% EtOAc/hexane) followed by triturating with diethyl ether to provide N-(2-chloro-3-((3,5-dimethyl-4-oxo-3,4-dihydroquinazolin-6-yl)oxy)-4,5-difluorophenyl)propane-1-sulfonamide as an off white solid (70 mg, 25%). $^1$H NMR (400 MHz, DMSO-d$_6$) δ 9.85 (s-br, 1H), 8.29 (s, 1H), 7.53 (dd, J=7.5, 11.7 Hz, 1H), 7.44 (d, J=9.0 Hz, 1H), 7.17 (d, J=8.9 Hz, 1H), 3.46 (s, 3H), 3.22-3.17 (m, 2H), 2.90 (s, 3H), 1.75 (q, J=7.6 Hz, 2H), 0.97 (t, J=7.4 Hz, 3H); MS (m/z)=458.4, 460.3 [M+H].

Example 74

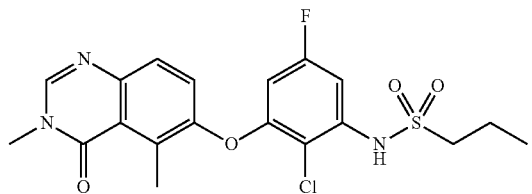

N-(2-chloro-3-((3,5-dimethyl-4-oxo-3,4-dihydroquinazolin-6-yl)oxy)-5-fluorophenyl)propane-1-sulfonamide Step 1: Preparation of 6-(3-amino-2-chloro-5-fluorophenoxy)-3,5-dimethylquinazolin-4(3H)-one. To a stirred solution of 6-hydroxy-3,5-dimethylquinazolin-4(3H)-one (1.0 g, 5.25 mmol), 3-bromo-2-chloro-5-fluoroaniline (1.77 g, 7.88 mmol) and potassium triphosphate (3.3 g, 15.77 mmol) in DMSO (10 mL) in a seal tube was added picolinic acid (65 mg, 0.52 mmol) and CuI (301 mg, 1.57 mmol). The reaction mixture was sparged with argon for 10 minutes; sealed and heated at 140° C. for 18 hours. The reaction mixture was cooled to ambient temperature, filtered through a bed of Celite and the Celite was washed with ethyl acetate. The filtrate was diluted with water and extracted with ethyl acetate (2×100 mL). The combined organic layers were washed with water (2×50 mL) and brine (50 mL), dried over Na$_2$SO$_4$, filtered, and concentrated. The crude product was purified by column chromatography over amine silica (50% EtOAc/hexane) to provide 6-(3-amino-2-chloro-5-fluorophenoxy)-3,5-dimethylquinazolin-4(3H)-one (170 mg, 10%) as a brown solid. $^1$H NMR (400 MHz, DMSO-d$_6$) δ 8.32 (s, 1H), 7.53 (d, J=8.8 Hz, 1H), 7.38 (d, J=8.8 Hz, 1H), 6.35 (dd, J=2.9, 10.9 Hz, 1H), 5.91 (s-br, 2H), 5.67 (dd, J=2.8, 9.9 Hz, 1H), 3.45 (s, 3H), 2.67 (s, 3H); MS (m/z) =334.1 (M+H).

Step 2: Preparation of N-(2-chloro-3-((3,5-dimethyl-4-oxo-3,4-dihydroquinazolin-6-yl)oxy)-5-fluorophenyl)-N-(propylsulfonyl)propane-1-sulfonamide. To a solution 6-(3-amino-2-chloro-5-fluorophenoxy)-3,5-dimethylquinazolin-4(3H)-one (170 mg, 0.51 mmol) in DCM (10 mL) was added triethylamine (0.3 mL, 2.24 mmol) followed by propane-1-sulfonyl chloride (0.21 mL, 1.87 mmol) and the reaction mixture was stirred at ambient temperature for 6 hours under nitrogen atmosphere. The reaction mixture was diluted with water and extracted with ethyl acetate (2×50 mL). The combined organic layers were washed with water (2×25 mL) and brine (25 mL), dried over Na$_2$SO$_4$, filtered and concentrated. The crude product was purified by column chromatography over amine silica (50% EtOAc/hexane) to provide N-(2-chloro-3-((3,5-dimethyl-4-oxo-3,4-dihydroquinazolin-6-yl)oxy)-5-fluorophenyl)-N-(propylsulfonyl)propane-1-sulfonamide (116 mg, 42%) as a yellow solid. $^1$H NMR (400 MHz, DMSO-d$_6$) δ 8.37 (s, 1H), 7.59 (d, J=8.8 Hz, 1H), 7.53 (dd, J=2.9, 8.5 Hz, 1H), 7.48 (d, J=8.8 Hz, 1H), 6.85 (dd, J=2.9, 9.5 Hz, 1H), 3.87-3.75 (m, 2H), 3.74-3.62 (m, 2H), 3.47 (s, 3H), 2.67 (s, 3H), 1.94-1.74 (m, 4H), 1.04 (t, J=7.4 Hz, 6H); MS (m/z)=546.2 (M+H).

Step 3: Preparation of N-(2-chloro-3-((3,5-dimethyl-4-oxo-3,4-dihydroquinazolin-6-yl)oxy)-5-fluorophenyl)propane-1-sulfonamide. To a stirred solution of N-(2-chloro-3-((3,5-dimethyl-4-oxo-3,4-dihydroquinazolin-6-yl)oxy)-5-fluorophenyl)-N-(propylsulfonyl)propane-1-sulfonamide (7) (116 mg, 0.212 mmol) in a mixture of acetonitrile (12 mL) and water (4 mL) was added sodium bicarbonate (139 mg, 1.66 mmol) and the reaction mixture was heated at 80° C. for 3 hours. The reaction mixture was cooled to ambient temperature and concentrated. The residue was diluted with water and extracted with ethyl acetate (3×20 mL). The combined organic layers were washed with water (2×20 mL) and brine (20 mL), dried over Na$_2$SO$_4$, filtered and concentrated. The crude product was purified by reverse phase column chromatography (20-100% ACN/water with 10 mM ammonium bicarbonate) to afford N-(2-chloro-3-((3,5-dimethyl-4-oxo-3,4-dihydroquinazolin-6-yl)oxy)-5-fluorophenyl)propane-1-sulfonamide (14 mg, 15%) as a white solid. $^1$H NMR (400 MHz, DMSO-d$_6$) δ 9.78 (s-br, 1H), 8.35 (s, 1H), 7.56 (d, J=8.8 Hz, 1H), 7.45 (d, J=8.9 Hz, 1H), 7.10 (dd, J=2.9, 10.2 Hz, 1H), 6.49-6.41 (m, 1H), 3.46 (s, 3H), 3.23 (t, J=7.7 Hz, 2H), 2.68 (s, 3H), 1.76 (p, J=7.5 Hz, 2H), 0.99 (t, J=7.4 Hz, 3H); MS (m/z)=440.3, 442.3 (M+H).

Example 75

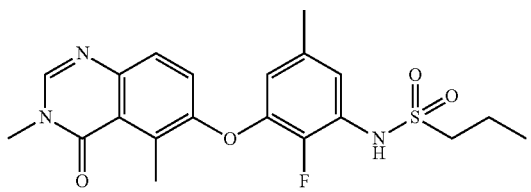 [SMILES: CCCS(=O)(=O)Nc1cc(C)cc(Oc2ccc3ncn(C)c(=O)c3c2C)c1F]

N-(3-((3,5-dimethyl-4-oxo-3,4-dihydroquinazolin-6-yl)oxy)-2-fluoro-5-methylphenyl)propane-1-sulfonamide Step 1: Preparation of tert-butyl 3-(3-amino-2-fluoro-5-methylphenoxy)-2-methyl-6-nitrobenzoate. To a solution of 3-amino-2-fluoro-5-methylphenol (1.2 g, crude) in DMF (7 mL) was added K$_2$CO$_3$ (4.69 g, 34 mmol) followed by a solution of tert-butyl 3-fluoro-2=methyl-6-nitrobenzoate (2.6 g, 10.21 mmol) in DMF (3 mL) and the reaction mixture was stirred at ambient temperature for 16 hours. The reaction mixture was poured into ice water and extracted with ethyl acetate (3×100 mL). The organic layer was dried over Na$_2$SO$_4$, filtered and concentrated. The crude was purified by silica gel column chromatography (10% EtOAc/hexane) to provide tert-butyl 3-(3-amino-2-fluoro-5-methylphenoxy)-2-methyl-6-nitrobenzoate as a brown semi-solid (1.5 g, 47%). $^1$H NMR (400 MHz, DMSO-d$_6$) δ 8.06 (d, J=8 Hz, 1H), 6.84 (d, J=12 Hz, 1H), 6.50 (d, J=4 Hz, 1H), 6.23 (d, J=4 Hz, 1H), 5.37 (s-br, 2H), 2.31 (s, 3H), 2.15 (s, 3H), 1.57 (s, 9H).

Step 2: Preparation of tert-butyl 6-amino-3-(3-amino-2-fluoro-5-methylphenoxy)-2-methylbenzoate. To a solution of tert-butyl 3-(3-amino-2-fluoro-5-methylphenoxy)-2-methyl-6-nitrobenzoate (1.5 g, 4.29 mmol) in methanol-water (1:1; 60 mL) at ambient temperature was added ammonium chloride (1.13 g, 21.49 mmol) and Fe-powder (2.39 g, 42.98 mmol) and the reaction mixture was stirred at 80° C. for 2 hours. The reaction mixture was filtered through a pad of Celite, the Celite was washed with dichloromethane and the filtrate was concentrated. The residue was extracted with dichloromethane (3×50 mL) and the combined organic layers were washed with water, dried over Na$_2$SO$_4$, filtered and concentrated. The crude product was purified by silica gel column chromatography (20% EtOAc/hexane) to provide tert-butyl 6-amino-3-(3-amino-2-fluoro-5-methylphenoxy)-2-methylbenzoate as a white solid (800 mg, 54%). NMR (400 MHz, DMSO-d$_6$) δ 6.69-6.83 (m, 1H), 6.60-6.65 (m, 1H), 6.21 (d, J=4 Hz, 1H), 5.60 (J=8 Hz, 1H), 5.35 (s-br, 1H), 5.13 (s-br, 1H), 2.10 (s, 3H), 2.01 (s, 3H), 1.54 (s, 9H); MS (m/z)=347.3 (M+H).

Step 3: Preparation of 6-(3-amino-2-fluoro-5-methylphenoxy)-3,5-dimethylquinazolin-4(3H)-one. A solution of tert-butyl 6-amino-3-(3-amino-2-fluoro-5-methylphenoxy)-2-methylbenzoate (800 mg, 2.31 mmol) in N-methylformamide (2 mL) was stirred at 180° C. in a sealed tube under argon for 3 hours. The reaction mixture was cooled to ambient temperature, diluted with water and extracted by ethyl acetate (3×30 mL). The combined organic layers were dried over Na$_2$SO$_4$, filtered and concentrated to afford crude 6-(3-amino-2-fluoro-5-methylphenoxy)-3,5-dimethylquinazolin-4(3H)-one (500 mg) that was used in the next step without further purification. MS (m/z)=314.2 (M+H).

Step 4: Preparation of N-(3-((3,5-dimethyl-4-oxo-3,4-dihydroquinazolin-6-yl)oxy)-2-fluoro-5-methylphenyl)-N-(propylsulfonyl)propane-1-sulfonamide. To a solution of 6-(3-amino-2-fluoro-5-methylphenoxy)-3,5-dimethylquinazolin-4(3H)-one (500 mg, crude) in dichloromethane (10 mL) at 0° C. was added triethylamine (0.67 mL, 4.79 mmol) and 1-propanesulphonyl chloride (0.47 mL, 3.99 mmol) and the reaction mixture was stirred at ambient temperature for 6 hours. The reaction mixture was quenched with water (10 mL) and extracted with dichloromethane (3×20 mL). The combined organic layers were washed with water (20 mL), dried over Na$_2$SO$_4$, filtered and concentrated to afford crude N-(3-((3,5-dimethyl-4-oxo-3,4-dihydroquinazolin-6-yl)oxy)-2-fluoro-5-methylphenyl)-N-(propylsulfonyl)propane-1-sulfonamide (900 mg) that was used in the next step without further purification. MS (m/z)=526.2 (M+H).

Step 5: Preparation of N-(3-((3,5-dimethyl-4-oxo-3,4-dihydroquinazolin-6-yl)oxy)-2-fluoro-5-methylphenyl)propane-1-sulfonamide. To a solution of N-(3-((3,5-dimethyl-4-oxo-3,4-dihydroquinazolin-6-yl)oxy)-2-fluoro-5-methylphenyl)-N-(propylsulfonyl)propane-1-sulfonamide (900 mg, crude) in a 1:1 mixture of acetonitrile/water (40 mL) was added sodium carbonate (1.26 g, 12 mmol) and the reaction mixture was stirred at 80° C. for 2 hours. The reaction mixture was cooled to ambient temperature and the pH was adjust to about 7 with 10% aqueous citric acid solution. The aqueous layer was extracted with ethyl acetate (3×20 mL) and the combined organic layers were dried over Na$_2$SO$_4$, filtered and concentrated. The crude product was purified by reverse phase column chromatography (30-95% ACN/water with 20 mM ammonium bicarbonate) to provide N-(3-((3,5-dimethyl-4-oxo-3,4-dihydroquinazolin-6-yl)oxy)-2-fluoro-5-methylphenyl)propane-1-sulfonamide as an off white solid (70 mg, 10%). $^1$H NMR (400 MHz, DMSO-d$_6$) δ 9.71 (s-br, 1H), 8.32 (s, 1H), 7.52 (d, J=8.8 Hz, 1H), 7.36 (d, J=8.8 Hz, 1H), 6.96 (d, J=5.7 Hz, 1H), 6.50 (d, J=6.5 Hz, 1H), 3.45 (s, 3H), 3.12 (t, J=7.7 Hz, 2H) 2.73 (s, 3H), 2.18 (s, 3H), 1.73 (m, 2H), 0.97 (t, J=7.4 Hz, 3H); MS (m/z)=420.2 (M+H).

Example 76

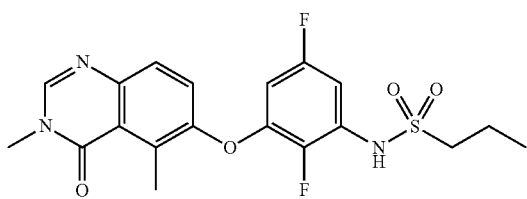 [SMILES: CCCS(=O)(=O)Nc1cc(F)cc(Oc2ccc3ncn(C)c(=O)c3c2C)c1F]

N-(3-((3,5-dimethyl-4-oxo-3,4-dihydroquinazolin-6-yl)oxy)-2,5-difluorophenyl)propane-1-sulfonamide Step 1: Preparation of tert-butyl 3-(3-amino-2,5-difluorophenoxy)-2-methyl-6-nitrobenzoate. To a solution of 3-amino-2,5-difluorophenol (0.100 g, 0.689 mmol) and tert-butyl 3-fluoro-2-methyl-6-nitrobenzoate (0.193 g, 0.758 mmol) in DMF (2.76 mL) was added cesium carbonate (0.561 g, 1.72 mmol) and the mixture was warmed to 100° C. where it stirred for 2 hours. The mixture was cooled to ambient temperature and diluted with water. The mixture was extracted with EtOAc (3×) and the combined organic layers were dried over $Na_2SO_4$, filtered and concentrated. The crude product was purified by silica gel chromatography (10-20% EtOAc/hexanes) to afford tert-butyl 3-(3-amino-2,5-difluorophenoxy)-2-methyl-6-nitrobenzoate as a yellow solid (0.254 g, 96%). $^1$H NMR (400 MHz, CDCl$_3$) δ 7.97 (d, J=9.0 Hz, 1H), 6.79 (d, J=9.0 Hz, 1H), 6.39 (ddd, J=9.4, 6.3, 2.7 Hz, 1H), 6.17 (ddd, J=8.6, 5.5, 2.7 Hz, 1H), 3.99 (brs, 2H), 2.39 (s, 3H), 1.65 (s, 9H).

Step 2: Preparation of tert-butyl 6-amino-3-(3-amino-2,5-difluorophenoxy)-2-methylbenzoate. To a solution of tert-butyl 3-(3-amino-2,5-difluorophenoxy)-2-methyl-6-nitrobenzoate (0.246 g, 0.647 mmol) in EtOAc (3.23 mL) and MeOH (3.23 mL) was added palladium (0.0688 g, 0.0323 mmol, Pd/C, 10 wt %, Degussa type). The system was purged with $H_2$ gas and then stirred under an atmosphere of $H_2$ (balloon pressure) for 3 hours. The mixture was filtered through a nylon filter and the solid was washed with additional MeOH and EtOAc. The filtrate was concentrated to provide tert-butyl 6-amino-3-(3-amino-2,5-difluorophenoxy)-2-methylbenzoate (0.230 g, 99%) as a thick yellow oil. $^1$H NMR (400 MHz, CDCl$_3$) δ 6.87 (d, J=8.6 Hz, 1H), 6.53 (d, J=8.6 Hz, 1H), 6.13 (ddd, J=9.4, 6.3, 3.1 Hz, 1H), 5.73 (ddd, J=9.7, 6.3, 2.7 Hz, 1H), 2.25 (s, 3H), 1.60 (s, 9H).

Step 3: Preparation of 6-(3-amino-2,5-difluorophenoxy)-3,5-dimethylquinazolin-4(3H)-one. A mixture of tert-butyl 6-amino-3-(3-amino-2,5-difluorophenoxy)-2-methylbenzoate (0.227 g, 0.648 mmol) and methylformamide (1.89 mL, 32.4 mmol) was heated to 150° C. where it stirred for 22 hours. The mixture was cooled to ambient temperature and then diluted with water (15 mL) which produced a milky, tan suspension. The mixture was diluted with 5 mL of a saturated aqueous NaHCO$_3$ solution and then extracted with EtOAc (3×). The combined organic extracts were washed with brine and dried over $Na_2SO_4$, filtered and concentrated. The crude product was purified by silica gel chromatography (20-50% EtOAc/DCM) to afford 6-(3-amino-2,5-difluorophenoxy)-3,5-dimethylquinazolin-4(3H)-one (0.138 g, 67%) as a cream colored solid. MS (apci, m/z)=318.1 (M+H).

Step 4: Preparation of N-(3-((3,5-dimethyl-4-oxo-3,4-dihydroquinazolin-6-yl)oxy)-2,5-difluorophenyl)-N-(propylsulfonyl)propane-1-sulfonamide. To a vial was added 6-(3-amino-2,5-difluorophenoxy)-3,5-dimethylquinazolin-4(3H)-one (0.040 g, 0.1261 mmol) and CH$_2$Cl$_2$ (1.26 mL) and the suspension was cooled to 0° C. Triethylamine (0.053 mL, 0.378 mmol) was added followed by 1-propanesulfonyl chloride (0.031 mL, 0.277 mmol) and the mixture was stirred at 0° C. for 1 hour. The mixture was diluted with a saturated aqueous NH$_4$Cl solution and extracted with EtOAc (3×). The combined organic extracts were dried over Na$_2$SO$_4$, filtered and concentrated to afford the crude N-(3-((3,5-dimethyl-4-oxo-3,4-dihydroquinazolin-6-yl)oxy)-2,5-difluorophenyl)-N-(propylsulfonyl)propane-1-sulfonamide as a beige foam, which was used in step 5 without purification. MS (apci, m/z)=530.1 (M+H).

Step 5: Preparation of N-(3-((3,5-dimethyl-4-oxo-3,4-dihydroquinazolin-6-yl)oxy)-2,5-difluorophenyl)propane-1-sulfonamide. To a vial containing N-(3-((3,5-dimethyl-4-oxo-3,4-dihydroquinazolin-6-yl)oxy)-2,5-difluorophenyl)-N-(propylsulfonyl)propane-1-sulfonamide (0.067 g, 0.13 mmol) was added CH$_3$CN (0.63 mL) followed by 2M Na$_2$CO$_3$ (0.63 mL, 1.3 mmol). The mixture was warmed to 40° C. and stirred for 3 hours and then warmed to 50° C. where it stirred for an additional 3 hours. The mixture was cooled to ambient temperature, diluted with water and the pH was adjusted to about 5 with solid citric acid (0.24 g, 1.3 mmol). The mixture was extracted with EtOAc (3×) and the combined organic extracts were dried over Na$_2$SO$_4$, filtered and concentrated. The crude product was purified by silica gel chromatography (10-30% EtOAc/DCM) to afford N-(3 (3,5-dimethyl-4-oxo-3,4-dihydroquinazolin-6-yl)oxy)-2,5-difluorophenyl)propane-1-sulfonamide (0.043 g, 78%) as a white solid. MS (apci, m/z)=424.1 (M+H).

Example 77

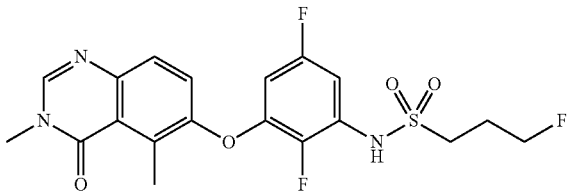 [SMILES: Cc1c(Oc2cc(F)cc(NS(=O)(=O)CCCF)c2F)ccc2ncn(C)c(=O)c12]

N-(3-((3,5-dimethyl-4-oxo-3,4-dihydroquinazolin-6-yl)oxy)-2,5-difluorophenyl)-3-fluoropropane-1-sulfonamide Step 1: Preparation of N-(3-((3,5-dimethyl-4-oxo-3,4-dihydroquinazolin-6-yl)oxy)-2,5-difluorophenyl)-3-fluoro-N-((3-fluoropropyl)sulfonyl)propane-1-sulfonamide. To a vial was added 6-(3-amino-2,5-difluorophenoxy)-3,5-dimethylquinazolin-4(3H)-one (0.040 g, 0.126 mmol) and CH$_2$Cl$_2$ (1.26 mL) and the suspension was cooled to 0° C. Triethylamine (0.053 mL, 0.378 mmol) was added followed by 3-fluoropropane-1-sulfonyl chloride (0.035 mL, 0.277 mmol) and the mixture was stirred at 0° C. for 1 hour. The mixture was diluted with a saturated aqueous NH$_4$Cl solution and extracted with EtOAc (3×). The combined organic extracts were dried over Na$_2$SO$_4$, filtered and concentrated to afford the crude N-(3-((3,5-dimethyl-4-oxo-3,4-dihydroquinazolin-6-yl)oxy)-2,5-difluorophenyl)-3-fluoro-N-((3-fluoropropyl)sulfonyl)propane-1-sulfonamide as a beige foam, that was used directly in the step 2. MS (apci, m/z)=566.1 (M+H).

Step 2: Preparation of N-(3-((3,5-dimethyl-4-oxo-3,4-dihydroquinazolin-6-yl)oxy)-2,5-difluorophenyl)-3-fluoropropane-1-sulfonamide. To a vial containing crude N-(3-((3,5-dimethyl-4-oxo-3,4-dihydroquinazolin-6-yl)oxy)-2,5-difluorophenyl)-3-fluoro-N-((3-fluoropropyl)sulfonyl)propane-1-sulfonamide (0.071 g, 0.126 mmol) was added CH$_3$CN (0.628 mL) followed by 2M Na$_2$CO$_3$ (0.628 mL, 1.26 mmol). The mixture was warmed to 50° C. where it stirred for 1 hour. The mixture was cooled to ambient temperature and diluted with water and the pH was adjusted to about 5 with solid citric acid (0.241 g, 1.26 mmol). The mixture was extracted with EtOAc (3×) and the combined organic extracts were dried over Na$_2$SO$_4$, filtered and 1-5 concentrated. The crude product was purified by silica gel chromatography (10-30% EtOAc/DCM) to afford N-(3-((3,5-dimethyl-4-oxo-3,4-dihydroquinazolin-6-yl)oxy)-2,5-difluorophenyl)-3-fluoropropane-1-sulfonamide (0.046 g, 82%) as an off-white solid. MS (apci, m/z)=442.1 (M+H).

Example 78

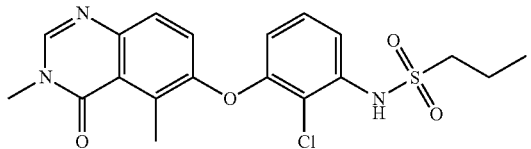

N-(2-chloro-3-((3,5-dimethyl-4-oxo-3,4-dihydroquinazolin-6-yl)oxy)phenyl)propane-1-sulfonamide Step 1: Preparation of 6-(3-amino-2-chlorophenoxy)-3,5-dimethylquinazolin-4(3H)-one. A solution of 6-bromo-3,5-dimethylquinazolin-4(3H)-one (300.0 mg, 1.18 mmol), 3-amino-2-chlorophenol (339.1 mg, 2.37 mmol), tripotassium phosphate (1.0 g, 4.74 mmol), picolinic acid (43.76 mg, 0.36 mmol) and CuI (112.6 mg, 0.59 mmol) in DMSO (6 mL) was sparged with Ar for five minutes. The reaction mixture was sealed and heated at 130° C. for 48 hours. After the reaction was complete, the reaction mixture was concentrated under reduced pressure, diluted with water and extracted with ethyl acetate (2×100 mL). The combined organic layers were washed with water (2×50 mL) and brine (50 mL), dried over anhydrous sodium sulfate, filtered and evaporated under reduced pressure. The crude product was purified by silica gel column chromatography (60% ethyl acetate in hexane) to provide 6-(3-amino-2-chlorophenoxy)-3,5-dimethylquinazolin-4(3H)-one as light brown solid (260 mg, 69%). $^1$H NMR (400 MHz, DMSO-d) δ 8.31 (s, 1H), 7.51 (d, J=8.7 Hz, 1H), 7.32-7.25 (m, 1H), 6.92 (t, J=8.1 Hz, 1H), 6.58-6.54 (m, 1H), 5.92-5.88 (m, 1H), 5.57 (s, 2H), 3.45 (s, 3H), 2.70 (s, 3H); MS (m/z)=316.0 (M+H).

Step 2: Preparation of N-(2-chloro-3-((3,5-dimethyl-4-oxo-3,4-dihydroquinazolin-6-yl)oxy)phenyl)=N-(propylsulfonyl)propane-1-sulfonamide and N-(2-chloro-3-((3,5-dimethyl-4-oxo-3,4-dihydroquinazolin-6-yl)oxy)phenyl)propane-1-sulfonamide. To a solution of 6-(3-amino-2-chlorophenoxy)-3,5-dimethylquinazolin-4(3H)-one (200 mg, 0.64 mmol) in DCM (5.0 mL) was added triethylamine (1.26 mL, 9.52 mmol) followed by propane-1-sulfonyl chloride (0.42 mL, 4.44 mmol). The reaction mixture was stirred at ambient temperature for 1 hour under nitrogen atmosphere. After the reaction was complete, the reaction mixture was diluted with water and extracted with ethylacetate (2×250 mL). The combined organic layers were washed with water (2×100 mL) and brine (100 mL), dried over anhydrous sodium sulfate, filtered and evaporated under reduced pressure. The crude product was purified by silica gel column chromatography (40% ethyl acetate in hexane) to provide a mixture of N-(2-chloro-3-((3,5-dimethyl-4-oxo-3,4-dihydroquinazolin-6-yl)oxy)phenyl)-N-(propylsulfonyl)propane-1-sulfonamide and N-(2-chloro-3-((3,5-dimethyl-4-oxo-3,4-dihydroquinazolin-6-yl)oxy)phenyl)propane-1-sulfonamide as pale white solid (200 mg). MS (m/z)=528.2, 422.4 (M+H).

Step 3: Preparation of N-(2-chloro-3-((3,5-dimethyl-4-oxo-3,4-dihydroquinazolin-6-yl)oxy)phenyl)propane-1-sulfonamide. To a solution of N-(2-chloro-3-((3,5-dimethyl-4-oxo-3,4-dihydroquinazolin-6-yl)oxy)phenyl)-N-(propylsulfonyl)propane-1-sulfonamide and N-(2-chloro-3-((3,5-dimethyl-4-oxo-3,4-dihydro quinazolin-6-yl)oxy)phenyl)propane-1-sulfonamide (240 mg) in MeOH was added sodium hydroxide (36.43 mg, 0.91 mmol). The reaction mixture was stirred at ambient temperature for 1 hour. After the reaction was complete, the reaction mixture was evaporated to dryness under reduced pressure. The reaction mixture was diluted with water and extracted with ethyl acetate (2×50 mL) and the combined organic layers were washed with water (2×25 mL) and brine (25 mL), dried over anhydrous sodium sulfate, filtered and evaporated under reduced pressure. The crude product was purified by silica gel column chromatography (80% ethyl acetate in hexane) to provide N-(2-chloro-3-((3,5-dimethyl-4-oxo-3,4-dihydroquinazolin-6-yl)oxy)phenyl)propane-1-sulfonamide as white solid (70.0 mg, 36%). $^1$H NMR (400 MHz, DMSO-d$_6$) δ 9.57 (s, 1H), 8.34 (s, 1H), 7.55 (d, J=8.7 Hz, 1H), 7.36 (d, J=8.8 Hz, 1H), 7.25 (d, J=5.0 Hz, 2H), 6.65-6.57 (m, 1H), 3.46 (s, 3H), 3.19-3.14 (m, 2H), 2.69 (s, 3H), 1.78 (q, J=7.5 Hz, 2H), 0.99 (t, J=7.4 Hz, 3H); MS (m/z)=422.4 (M+H).

Example 79

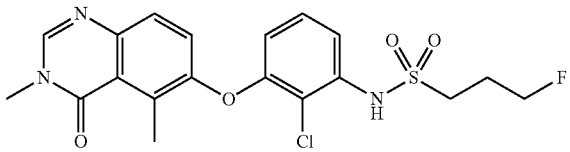 [SMILES: Cc1c(Oc2cccc(NS(=O)(=O)CCCF)c2Cl)ccc2ncn(C)c(=O)c12]

N-(2-chloro-3-((3,5-dimethyl-4-oxo-3,4-dihydroquinazolin-6-yl)oxy)phenyl)-3-fluoropropane-1-sulfonamide Step 1: Preparation of tert-butyl 3-(3-amino-2-chlorophenoxy)-2-methyl-6-nitrobenzoate. To a stirred solution of 3-amino-2-chlorophenol (500 mg, 3.84 mmol) in DMF (10 mL) was added cesium carbonate (2.84 g, 8.74 mmol) and tert-butyl 3-fluoro-2-methyl-6-nitrobenzoate (934 mg, 3.84 mmol). The reaction mixture was heated at 120° C. for 2 hours. After the reaction was complete, the reaction mixture was poured into ice cold water (30 mL) and extracted with ethyl acetate (3×40 mL). The combined organic layers were dried over anhydrous sodium sulfate, filtered and concentrated under reduced pressure. The crude product was purified by silica gel column chromatography using 10% ethyl acetate in hexane to provide tert-butyl 3-(3-amino-2-chlorophenoxy)-2-methyl-6-nitrobenzoate (800 mg, 60%) as yellow liquid. $^1$H NMR (400 MHz, CDCl$_3$) δ 7.92 (d, J=9.2

Hz, 1H), 7.08 (t, J=8.1 Hz, 1H), 6.71-6.60 (m, 2H), 6.44 (d, J=9.2 Hz, 1H), 5.29 (s, 1H), 4.22 (s, 2H), 2.41 (s, 3H), 1.64 (s, 9H).

Step 2: Preparation of tert-butyl 3-(2-chloro-3-((3-fluoro-N-((3-fluoropropyl)sulfonyl)propyl)sulfonamido)phenoxy)-2-methyl-6-nitrobenzoate. To a stirred solution of tert-butyl 3-(3-amino-2-chlorophenoxy)-2-methyl-6=nitrobenzoate (300 mg, 0.794 mmol) in: DCM (15 mL) at 0° C. was added triethyl amine (0.330 mL, 2.38 mmol) and 3-fluoropropane-sulphonyl chloride (0.317 mg, 1.98 mmol) sequentially. The reaction mixture was stirred at ambient temperature for 6 hours and the solvent was evaporated under reduced pressure. The residue was diluted with water (10 mL) and extracted with DCM (3×20 mL). The combined organic layers were dried over anhydrous sodium sulfate, filtered and concentrated under reduced pressure. The crude product was purified by silica gel column chromatography using 5% ethyl acetate in hexane to provide tert-butyl 3-(2-chloro-3-((3-fluoro-N-((3-fluoropropyl)sulfonyl)propyl)sulfonamido)phenoxy)-2-methyl-6-nitrobenzoate (400 mg, 80%) as a brown liquid. $^1$H NMR (400 MHz, CDCl$_3$) δ 7.97 (d, J=9.1 Hz, 1H), 7.47-7.34 (m, 2H), 7.22-7.18 (m, 1H), 6.64 (d, J=9.1 Hz, 1H), 4.64 (t, J=5.6 Hz, 2H), 4.53 (t, J=5.7 Hz, 2H), 3.91-3.73 (m, 4H), 2.44-2.26 (m, 4H), 2.03 (s, 3H), 1.64 (s, 9H).

Step 3: Preparation of tert-butyl 6-amino-3-(2-chloro-3-((3-fluoro-N-((3-fluoropropyl)sulfonyl)propyl) sulfonamido)phenoxy)-2-methylbenzoate. To a stirred solution of tert-butyl 3-(2-chloro-3-((3-fluoro-N-((3-fluoropropyl)sulfonyl)propyl)sulfonamido)phenoxy)-2-methyl-6-nitrobenzoate (1.0 g, 1.59 mmol) in a mixture of methanol/water (2:1) at ambient temperature were added ammonium chloride (426 mg, 7.97 mmol) and iron powder (890 mg, 15.94 mmol) and the reaction mixture was stirred at ambient temperature for 16 hours. After reaction completion, the reaction mixture was filtered through Celite, the Celite was washed with DCM and the filtrate was concentrated under reduced pressure. The residue was diluted with water (10 mL) and extracted with DCM (3×20 mL). The combined organic layers were dried over anhydrous sodium sulfate, filtered and concentrated under reduced pressure. The crude product was purified by silica gel column chromatography using 10% ethyl acetate in hexane to provide tert-butyl 6-amino-3-(2-chloro-3-((3-fluoro-N-((3-fluoropropyl)sulfonyl)propyl)sulfonamido)phenoxy)-2-methylbenzoate (650 mg, 68%) as a white solid. $^1$H NMR (400 MHz, CDCl$_3$) δ 7.25 (s, 1H), 7.17 (t, J=8.2 Hz, 1H), 7.08 (dd, J=1.5, 7.9 Hz, 1H), 6.86 (d, J=8.7 Hz, 1H), 6.74 (dd, J=1.5, 8.3 Hz, 1H), 6.55 (d, J=8.7 Hz, 1H), 4.72 (s, 2H), 4.65 (t, J=5.7 Hz, 2H), 4.53 (t, J=5.7 Hz, 2H), 3.93-3.75 (m, 4H), 2.46-2.28 (m, 4H), 2.21 (s, 3H), 1.59 (s, 9H).

Step 4: Preparation of N-(2-chloro-3-((3,5-dimethyl-4-oxo-3,4-dihydroquinazolin-6-yl)oxy)phenyl)-3-fluoropropane-1-sulfonamide. A mixture of tert-butyl 6-amino-3-(2-chloro-3-((3-fluoro-N-((3-fluoropropyl)sulfonyl)propyl) sulfonamido)phenoxy)-2-methylbenzoate (350 mg, 0.60 mmol), N-methyl formamide (1 mL) and formic acid (0.5 mL) was heated to 180° C. in a sealed tube for 2 hours. After reaction completion, the reaction mixture was cooled to ambient temperature, diluted with water (30 mL) and extracted with DCM (2×50 mL). The combined organic layers were washed with water (2×25 mL) and brine (25 mL), dried over anhydrous sodium sulfate, filtered and evaporated under reduced pressure. The crude product was purified by silica gel column chromatography using 50% ethyl acetate in hexane to provide N-(2-chloro-3-((3,5-dimethyl-4-oxo-3,4-dihydroquinazolin-6-yl)oxy)phenyl)-3-fluoropropane-1-sulfonamide (60 mg, 23%) as a white solid. $^1$H NMR (400 MHz, DMSO-d$_6$) δ 9.72 (s, 1H), 8.33 (s, 1H), 7.55 (d, J=8.8 Hz, 1H), 7.36 (d, J=8.8 Hz, 1H), 7.31-7.21 (m, 2H), 6.67-6.59 (m, 1H), 4.62 (t, J=5.9 Hz, 1H), 4.50 (t, J=6.0 Hz, 1H), 3.46 (s, 3H), 3.30-3.25 (m, 2H), 2.69 (s, 3H), 2.24-2.06 (m, 2H); MS (m/z)=440.3 (M+H).

Example 80

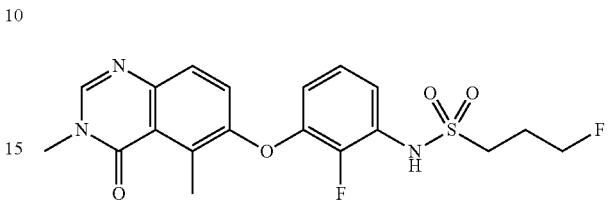

N-(3-((3,5-dimethyl-4-oxo-3,4-dihydroquinazolin-6-yl)oxy)-2-fluorophenyl)-3-fluoropropane-1-sulfonamide Step 1: Preparation of tert-butyl 3-(3-amino-2-fluorophenoxy)-2-methyl-6-nitrobenzoate. To a stirred solution of 3-amino-2-fluorophenol (1 g, 6.21 mmol) in DMF (5 mL) was added K$_2$CO$_3$ (3.26 g, 23.62 mmol) and a solution of tert-butyl 3-fluoro-2-methyl-6-nitrobenzoate (2.4 g, 7.45 mmol) in DMF (3 mL). The reaction mixture was stirred at ambient temperature for 16 hours, poured into ice water and extracted with ethyl acetate (3×20 mL). The combined, organic layers were dried over anhydrous Na$_2$SO$_4$, filtered and concentrated. The crude product was purified by silica gel column chromatography (10% EtOAc/hexane) to provide tert-butyl 3-(3-amino-2-fluorophenoxy)-2-methyl-6-nitrobenzoate (2.5 g, 87%) as a light yellow solid. 1H NMR (400 MHz, DMSO-d$_6$) δ 8.07 (d, J=9.2 Hz, 1H), 6.99-6.90 (m, 1H), 6.84 (d, J=9.2 Hz, 1H), 6.76-6.67 (m, 1H), 6.47-6.37 (m, 1H), 5.47 (s-br, 2H), 2.33 (s, 3H), 1.58 (s, 9H); MS (apci, m/z)=361.3 (M−H).

Step 2: Preparation of tert-butyl 3-(2-fluoro-3-((3-fluoro-N-((3-fluoropropyl)sulfonyl)propyl)sulfonamido)phenoxy)-2-methyl-6-nitrobenzoate. To a solution of tert-butyl 3-(3-amino-2-fluorophenoxy)-2-methyl-6-nitrobenzoate (2.5 g, 6.86 mmol) in DCM (15 mL) at 0° C. was added triethyl-amine (3.4 mL, 23.9 mmol) followed by 3-fluoropropane-sulphonyl chloride (2.74 g, 17.17 mmol) and the reaction mixture was stirred at ambient temperature for 6 hours under nitrogen atmosphere. The reaction mixture was quenched with water (10 mL) and extracted with DCM (2×20 mL). The combined organic layers were washed with water (10 mL), dried over anhydrous Na$_2$SO$_4$, filtered and concentrated. The crude product was purified by silica gel column chromatography (10% EtOAc/hexane) to provide tert-butyl 3-(2-fluoro-3-((3-fluoro-N-((3-fluoropropyl)sulfonyl)propyl)sulfonamido)phenoxy)-2-methyl-6-nitrobenzoate (2.2 g, 52%) as a brown semi-solid. $^1$H NMR (400 MHz, DMSO-d$_6$) δ 8.10 (d, J=9.1 Hz, 1H), 7.72-7.57 (m, 2H), 7.45 (t, J=0.8 Hz, 1H), 6.88 (d, J=9.0 Hz, 1H), 4.62 (t, J=5.7 Hz, 2H), 4.50 (t, J=5.7 Hz, 2H), 3.91-3.72 (m, 4H), 2.36 (s, 3H), 2.29-2.05 (m, 4H), 1.58 (s, 9H).

Step 3: Preparation of tert-butyl 6-amino-3-(2-fluoro-3-((3-fluoro-N-((3-fluoropropyl)sulfonyl)propyl)sulfonamido)phenoxy)-2-methylbenzoate. To a solution of tert-butyl 3-(2-fluoro-3-((3-fluoro-N-((3-fluoropropyl)sulfonyl) propyl)sulfonamido)phenoxy)-2-methyl-6-nitrobenzoate (1.0 g, 1.63 mmol) in MeOH (10 mL) was added 10% Pd/C (about 50% moist) (500.0 mg; 50% w/w) and the reaction mixture was sparged with argon for 10 minutes. The reaction mixture was stirred under a hydrogen balloon at ambient temperature for 12 hours, filtered through Celite and the filtrate was concentrated. The crude product was purified by silica gel column chromatography to provide tert-butyl 6-amino-3-(2-fluoro-3-((3-fluoro-N-((3-fluoropropyl)sulfonyl)propyl)sulfonamido)phenoxy)-2-methylbenzoate (700 mg, 73%) as a colorless gummy liquid. MS (apci, m/z)=581.3 (M+H).

Step 4: Preparation of N-(3-((3,5-dimethyl-4-oxo-3,4-dihydroquinazolin-6-yl)oxy)-2-fluorophenyl)-3-fluoropropane-1-sulfonamide. A solution of tert-butyl 6-amino-3-(2-fluoro-3-((3-fluoro-N-((3-fluoropropyl)sulfonyl)propyl)sulfonamido)phenoxy)-2-methylbenzoate (400 mg, 0.689 mmol), N-methyl formamide (2 mL) and formic acid (10 mL) was heated at 180° C. in a sealed tube for 2 hours. The reaction mixture was cooled to ambient temperature, diluted with water (30 mL) and extracted with DCM (2×50 mL). The combined organic layers were washed with water (2×25 mL) and brine (25 mL), dried over anhydrous $Na_2SO_4$, filtered and concentrated. The crude product was purified by reverse-phase chromatography (20-95% MeCN/water, 20 mM ammonium bicarbonate) to provide N-(3-((3,5-dimethyl-4-oxo-3,4-dihydroquinazolin-6-yl)oxy)-2-fluorophenyl)-3-fluoropropane-1-sulfonamide (155 mg, 53%) as a white solid. $^1$H NMR (400 MHz, DMSO-$d_6$) δ 9.93 (s, 1H), 8.32 (s, 1H), 7.53 (d, J=8.9 Hz, 1H), 7.38 (d, J=8.9 Hz, 1H), 7.18 (t, J=7.4 Hz, 1H), 7.11 (t, J=8.2 Hz, 1H), 6.71 (t, J=8.0 Hz, 1H), 4.61 (t, J=5.9 Hz, 1H), 4.49 (t, J=5.9 Hz, 1H), 3.46 (s, 3H), 3.30-3.25 (m, 2H), 2.74 (s, 3H), 2.21-2.03 (m, 2H). MS (m/z)=424.4 (M+H).

Example 81

Methods of Preparing N-(2-chloro-3-((3,5-dimethyl-4-oxo-3,4-dihydroquinazolin-6-yl)amino)-4-fluorophenyl)-3-fluoropropane-1-sulfonamide Form A Anhydrous Method 1A: N-(2-chloro-3-((3,5-dimethyl-4-oxo-3,4-dihydroquinazolin-6-yl)amino)-4-fluorophenyl)-3-fluoropropane-1-sulfonamide Form C was dissolved in 20% water/EtOH (12 vol) and heated to reflux. The solution was slowly transferred dropwise-into water (10 vol). The slurry was stirred for 2 h, then filtered and dried to provide N-(2-chloro-3-((3,5-dimethyl-4-oxo-3,4-dihydroquinazolin-6-yl)amino)-4-fluorophenyl)-3-fluoropropane-1-sulfonamide Form A anhydrous. The XRPD scan is shown in FIG. 1 and the peak assignments are shown in Table 3. A representative DSC thermogram is shown in FIG. 2.

Method 2A: N-(2-chloro-3-((3,5-dimethyl-4-oxo-3,4-dihydroquinazolin-6-yl)amino)-4-fluorophenyl)-3-fluoropropane-1-sulfonamide Form C was taken up in EtOH (44 vol) and heated to 78° C. until complete dissolution was achieved. Water (73 vol) was quickly added and the slurry was cooled to 22° C. and held at 5° C. for 15 h. The solids were filtered and dried to provide N-(2-chloro-3-((3,5-dimethyl-4-oxo-3,4-dihydroquinazolin-6-yl)amino)-4-fluorophenyl)-3-fluoropropane-1-sulfonamide Form A anhydrous.

Figure 17:
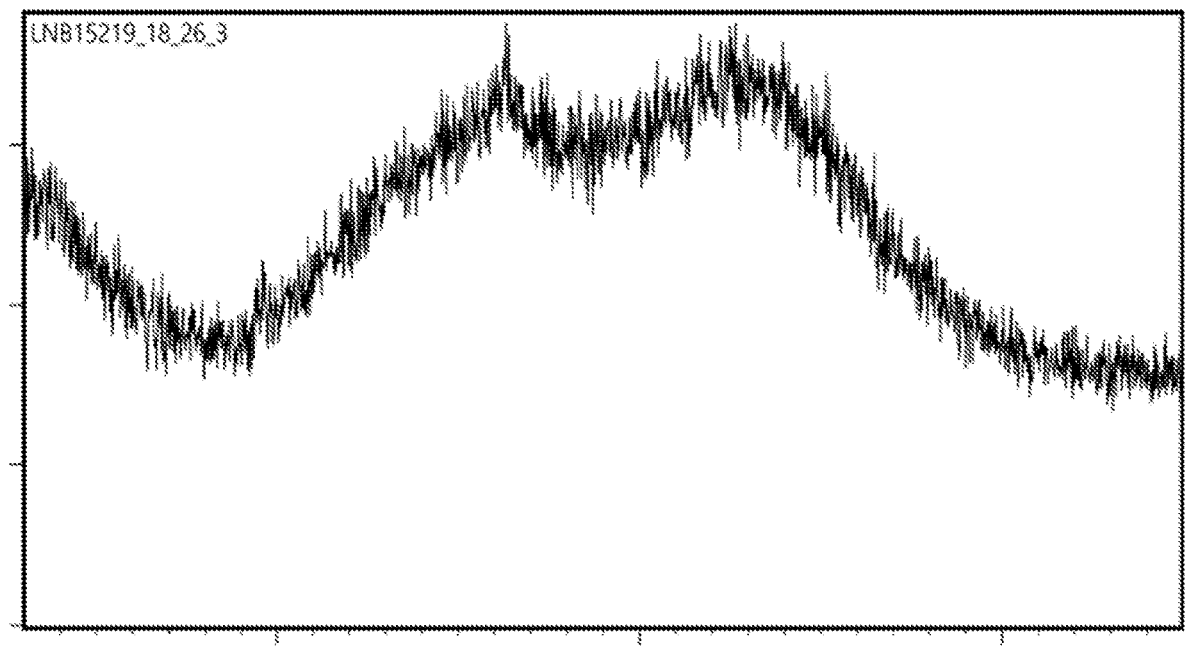
FIG. 17 illustrates an X-ray powder diffraction (XRPD) pattern of amorphous N-(2-chloro-3-((3,5-dimethyl-4-oxo-3,4-dihydroquinazolin-6-yl)amino)-4-fluorophenyl)-3-fluoropropane-1-sulfonamide, according to one embodiment.

Method 3A: Amorphous N-(2-chloro-3-((3,5-dimethyl-4-oxo-3,4-dihydroquinazolin-6-yl)amino)-4-fluorophenyl)-3-fluoropropane-1-sulfonamide was prepared by dissolving N-(2-chloro-3-((3,5-dimethyl-4-oxo-3',4-dihydroquinazolin-6-yl)amino)-4-fluorophenyl)-3-fluoropropane-1-sulfonamide Form B anhydrous in 1,4-dioxane and then lyophilizing, and repeating this process was repeated until the material was deemed completely amorphous by XRPD (FIG. 17). To amorphous N-(2-chloro-3-((3,5-dimethyl-4-oxo-3,4-dihydroquinazolin-6-yl)amino)-4-fluorophenyl)-3-fluoropropane-1-sulfonamide (20 mg) was added 2 drops of a super saturated THF solution and 2×2.8 mm bead mill beads. The sample was loaded into a bead mill and shaken in 3×60 second intervals with a 10 second pause between each interval. The isolated wet solids were dried to provide N-(2-chloro-3-((3,5-dimethyl-4-oxo-3,4-dihydroquinazolin-6-yl)amino)-4-fluorophenyl)-3-fluoropropane-1-sulfonamide Form A anhydrous.

Method 4A: N-(2-chloro-3-((3,5-dimethyl-4-oxo-3,4-dihydroquinazolin-6-yl)amino)-4-fluorophenyl)-3-fluoropropane-1-sulfonamide Form F was dried in a vacuum oven for 12 h at 40° C. to provide N-(2-chloro-3-((3,5-dimethyl-4-oxo-3,4-dihydroquinazolin-6-yl)amino)-4-fluorophenyl)-3-fluoropropane-1-sulfonamide Form A anhydrous.

Method 5A: A saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in 1,4-dioxane was stored at 2-8° C. for 72 hours. The resulting solids were filtered to provide N-(2-chloro-3-((3,5-dimethyl-4-oxo-3,4-dihydroquinazolin-6-yl)amino)-4-fluorophenyl)-3-fluoropropane-1-sulfonamide Form A anhydrous.

Example 82

Methods of Preparing N-(2-chloro-3-((3,5-dimethyl-4-oxo-3,4-dihydroquinazolin-6-yl)amino)-4-fluorophenyl)-3-fluoropropane-1-sulfonamide Form B Anhydrous Method 1B: In this procedure, S=a scaling factor (g/g). N-(2-chloro-3-((3,5-dimethyl-4-oxo-3,4-dihydroquinazolin-6-yl)amino)-4-fluorophenyl)-3-fluoropropane-1-sulfonamide (either in the amorphous form or as Form A or Form C) was dissolved in ethanol (9.4 S) and deionized water (3.0 S) at 65-75° C. The solution was polish filtered at 65-75° C. The reactor was rinsed forward with a hot (65-75° C.) solution of ethanol (1.3 S) and water (0.4 S). Water (5.6 S) was added to the filtered solution at 65-75° C. over 30-120 minutes and the temperature was lowered to 60-65° C. The solution was seeded with N-(2-chloro-3-((3,5-dimethyl-4-oxo-3,4-dihydroquinazolin-6-yl)amino)-4-fluorophenyl)-3-fluoropropane-1-sulfonamide Form B (0.001S) and the temperature was lowered to 20-25° C. over 4-8 h. The slurry was aged 10-24 h at 20-25° C. The solids were isolated by centrifugation, washed with a mixture of cold ethanol (0.7 S) and deionized water (0.9 S), pure deionized water (2.5 S) and dried at 28-32° C. for a minimum of 16 h to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous. The XRPD scan is shown in FIG. 4 and the peak assignments are shown in Table 4. A representative DSC thermogram is shown in FIG. 5, having a melt maxima temperature of about 151.39° C. FIG. 6 is an overlay of differential scanning calorimetry scan and a thermogravimetric analysis scan of N-(2-chloro-3-((3,5-dimethyl-4-oxo-3,4-dihydroquinazolin-6-yl)amino)-4-fluorophenyl)-3-fluoropropane-1-sulfonamide Form B anhydrous. TG/DSC analysis found a small weight loss of 0.2 wt. % during the endothermic event observed in the DSC trace which had an onset of 148° C. and a peak at 152° C. which was the melt of Form B anhydrous. The weight loss was most likely due to sample movement during the melting. No further weight losses, or events were observed until the material began to degrade at approximately 250° C.

Method 2B: To amorphous N-(2-chloro-3-((3,5-dimethyl-4-oxo-3,4-dihydroquinazolin-6-yl)amino)-4-fluorophenyl)-3-fluoropropane-1-sulfonamide (20 mg; prepared as described in Example 81, Method 3A) was added 2 drops of a supersaturated 2-ethoxyethanol, chloroform, 2-propanol, ethanol, ethanol/water, ethyl acetate, heptane, isopropyl acetate, methanol, 2-methyl THF, methylisobutyl ketone or a trifluoroethanol solution and 2×2.8 mm bead mill beads. The samples were loaded into the bead mill and shaken in 3×60 second intervals with a 10 second pause between each interval, and the resulting solids were isolated to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Method 3B: N-(2-chloro-3-((3,5-dimethyl-4-oxo-3,4-dihydroquinazolin-6-yl)amino)-4-fluorophenyl)-3-fluoropropane-1-sulfonamide Form D was dried in a vacuum oven for 12 h at 40° C. to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Method 4B: A saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in trifluoroethanol was stored at 2-8° C. for 72 hours. The resulting solids were filtered to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Method 5B: A saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in trifluoroethanol was stored at −10° C. for 72 hours. The resulting solids were filtered to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Method 6B: A saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in 2-ethoxyethanol, acetic acid, acetone, anisole, benzyl alcohol, chloroform, dichloromethane, 2-propanol, ethanol, ethanol/water, ethyl acetate, heptane, isopropyl acetate, methanol, 2-methyl THF, methylisobutyl ketone, tert-butyl methyl ether, trifluoroethanol or water was heat cycled between 20° C. and 40° C. in 4-hour cycles for 48 hours with agitation. The solids were isolated and dried to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Method 7B: A saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in 2-ethoxyethanol, N,N'-dimethylformamide, N,N'-dimethylacetamide or trifluoroethanol was transferred to 2 mL vials. The vials were then uncapped and the solvent allowed to evaporate at ambient temperature. The resulting solid material was isolated to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Method 8B: Tert-butyl methyl ether was added dropwise with stirring to a saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in N,N'-dimethylformamide. The slurry was then uncapped and allowed to evaporate at ambient temperature. The resulting solids were recovered to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Method 9B: Tert-butyl methyl ether was added dropwise with stirring to a saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in N,N'-dimethylacetamide. The slurry was then uncapped and allowed to evaporate at ambient temperature. The resulting solids were recovered to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Method 10B: Water was added dropwise with stirring to a saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in acetone. The slurry was then uncapped and allowed to evaporate at ambient temperature. The resulting solids were recovered to provide N-(2-chloro-3-((3,5-dimethyl-4-oxo-3,4-dihydroquinazolin-6-yl)amino)-4-fluorophenyl)-3-fluoropropane-1-sulfonamide Form B anhydrous.

Example 83

Methods of Preparing N-(2-chloro-3-((3,5-dimethyl-4-oxo-3,4-dihydroquinazolin-6-yl)amino)-4-fluorophenyl)-3-fluoropropane-1-sulfonamide Form C Mono-anisole To amorphous N-(2-chloro-3-((3,5-dimethyl-4-oxo-3,4-dihydroquinazolin-6-yl)amino)-4-fluorophenyl)-3-fluoropropane-1-sulfonamide (20 mg; prepared as described in Example 81, Method 3A) was added 2 drops of a supersaturated anisole solution and 2×2.8 mm bead mill beads. The samples were loaded into the bead mill and shaken in 3×60 second intervals with a 10 second pause between each interval, and the resulting solids were isolated to provide N-(2-chloro-3-((3,5-dimethyl-4-oxo-3,4-dihydroquinazolin-6-yl)amino)-4-fluorophenyl)-3-fluoropropane-1-sulfonamide Form C mono-anisole. The XRPD scan is shown in FIG. 7 and the peak assignments are shown in Table 5. FIG. 8 is an overlay of a differential scanning calorimetry (DSC) scan and a thermogravimetric (TG) analysis scan of N-(2-chloro-3-((3,5-dimethyl-4-oxo-3,4-dihydroquinazolin-6-yl)amino)-4-fluorophenyl)-3-fluoropropane-1-sulfonamide Form C mono-anisole. TG/DSC analysis showed an 18.4% weight loss from 92° C. to 122° C. This was equal to 0.95 equiv. of anisole. Due to the low amounts of material available for analysis (0.2 mg) and the time exposed to ambient conditions prior to analysis, the amount of anisole present in the thermogram may not be accurately represented but this information appeared to suggest that Form C was a mono-anisole solvate. Upon drying, Form C mono-anisole converted to poorly crystalline Form B.

Example 84

Methods of Preparing N-(2-chloro-3-((3,5-dimethyl-4-oxo-3,4-dihydroquinazolin-6-yl)amino)-4-fluorophenyl)-3-fluoropropane-1-sulfonamide Form D Hemi-dichloromethane Solvate Method 1D: To amorphous N-(2-chloro-3-((3,5-dimethyl-4-oxo-3,4-dihydroquinazolin-6-yl)amino)-4-fluorophenyl)-3-fluoropropane-1-sulfonamide (20 mg; prepared as described in Example 81, Method 3A) was added 2 drops of a super saturated dichloromethane solution and 2×2.8 mm bead mill beads. The sample was loaded into the bead mill and shaken in 3×60 second intervals with a 10 second pause between each interval, and the resulting solids were isolated to provide N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane. The XRPD scan is shown in FIG. 9 and the peak assignments are shown in Table 6. FIG. 10 is an overlay of a differential scanning calorimetry scan and a thermogravimetric analysis scan of N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane. Thermogravimetric analysis (TGA) of Form D showed a 10.2% weight loss between 61° C. and 88° C. This was equivalent to 0.61 equiv. of dichloromethane. Differential thermal analysis showed a small endothermic event with an onset of 147° C. and a peak at 150° C. This was followed by another small endothermic event with an onset of 164° C. and a peak at 165° C. This was consistent with Form A (onset at 162° C. and peak at 165° C.). Upon drying, Form D hemi-dichloromethane converted to crystalline Form B.

Method 2D: Amorphous N-(2-chloro-3-((3,5-dimethyl-4-oxo-3,4-dihydroquinazolin-6-yl)amino)-4-fluorophenyl)-3-fluoropropane-1-sulfonamide was dissolved in dichloromethane. The solution was concentrated and the solids were isolated to provide N-(2-chloro-3-((3,5-dimethyl-4-oxo-3,4-dihydroquinazolin-6-yl)amino)-4-fluorophenyl)-3-fluoropropane-1-sulfonamide Form D hemi-dichloromethane.

Example 85

Methods of Preparing N-(2-chloro-3-((3,5-dimethyl-4-oxo-3,4-dihydroquinazolin-6-yl)amino)-4-fluorophenyl)-3-fluoropropane-1-sulfonamide Form E Mono-toluene Solvate Method 1E: To amorphous N-(2-chloro-3-((3,5-dimethyl-4-oxo-3,4-dihydroquinazolin-6-yl)amino)-4-fluorophenyl)-3-fluoropropane-1-sulfonamide (20 mg; prepared as described in Example 81, Method 3A) was added 2 drops of a supersaturated toluene solution of N-(2-chloro-3-((3,5-dimethyl-4-oxo-3,4-dihydroquinazolin-6-yl)amino)-4-fluorophenyl)-3-fluoropropane-1-sulfonamide and 2×2.8 mm bead mill beads. The sample was loaded into the bead mill and shaken in 3×60 second intervals with a 10 second pause between each interval and the resulting wet solids were isolated to provide N-(2-chloro-3-((3,5-dimethyl-4-oxo-3,4-dihydroquinazolin-6-yl)amino)-4-fluorophenyl)-3-fluoropropane-1-sulfonamide Form E toluene. The XRPD scan is shown in FIG. 11 and the peak assignments are shown in Table 7: FIG. 12 is an overlay of a differential scanning calorimetry scan and a thermogravimetric analysis scan of N-(2-chloro-3-((3,5-dimethyl-4-oxo-3,4-dihydroquinazolin-6-yl)amino)-4-fluorophenyl)-3-fluoropropane-1-sulfonamide Form E. Thermogravimetric analysis (TGA) showed a 17.1% weight loss between 87 and 128° C. This was equivalent to 1.02 equiv. of toluene. During this weight loss a change in baseline was observed. The event was observed with an onset of 93° C. and a peak at 103° C. Following this, an endothermic event was observed with an onset of 164° C. and a peak at 165° C. This was consistent with Form A (onset at 162° C. and peak at 165° C.).

Method 2E: A saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in toluene was heat cycled between 20° C. and 40° C. in 4-hour cycles for 48 hours with agitation. The resulting solids were isolated to provide N-(2-chloro-3-((3,5-dimethyl-4-oxo-3,4-dihydroquinazolin-6-yl)amino)-4-fluorophenyl)-3-fluoropropane-1-sulfonamide Form E toluene.

Example 86

Methods of Preparing N-(2-chloro-3-((3,5-dimethyl-4-oxo-3,4-dihydroquinazolin-6-yl)amino)-4-fluorophenyl)-3-fluoropropane-1-sulfonamide Form F 1,4 dioxane Method 1F: A saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in 1,4-dioxane was stored at 2-8° C. for 72 hours. The resulting solids were filtered to provide N-(2-chloro-3-((3,5-dimethyl-4-oxo-3,4-dihydroquinazolin-6-yl)amino)-4-fluorophenyl)-3-fluoropropane-1-sulfonamide Form F 1,4 dioxane. The XRPD scan is shown in FIG. 13 and the peak assignments are shown in Table 8. FIG. 14 is an overlay of a differential scanning calorimetry scan and a thermogravimetric analysis scan of N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane. TG/DSC analysis of Form F showed a 23.7% weight loss from 49 to 89° C. which was equal to 1.6 equivalents of 1,4-dioxane. This weight loss appeared to represent N-(2-chloro-3-((3,5-dimethyl-4-oxo-3,4-dihydroquinazolin-6-yl)amino)-4-fluorophenyl)-3-fluoropropane-1-sulfonamide Form F 1,4-dioxane desolvating to N-(2-chloro-3-((3,5-dimethyl-4-oxo-3,4-dihydroquinazolin-6-yl)amino)-4-fluorophenyl)-3-fluoropropane-1-sulfonamide Form A as the Form A melting endothermic event was observed in the DSC trace with an onset of 161° C. and a peak at 164° C.

Method 2F: A saturated solution of amorphous N-(2-chloro-3-((3,5-dimethyl-4-oxo-3,4-dihydroquinazolin-6-yl)amino)-4-fluorophenyl)-3-fluoropropane-1-sulfonamide in 1,4-dioxane was stored at −10° C. for 72 hours. The resulting solids were filtered to provide N-(2-chloro-3-((3,5-dimethyl-4-oxo-3,4-dihydroquinazolin-6-yl)amino)-4-fluorophenyl)-3-fluoropropane-1-sulfonamide Form F 1,4 dioxane.

What is claimed is:
1. A compound of Formula III

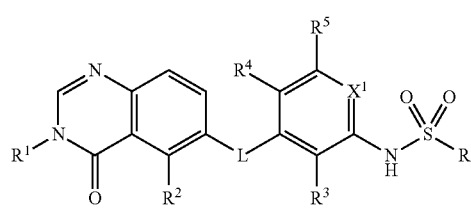

or a pharmaceutically acceptable salt thereof, wherein:
L is NH or O;
$X^1$ is CH or N;
$R^1$ is C1-C6 alkyl or C1-C6 deuteroalkyl;
$R^2$ is methyl;
$R^3$ is F or Cl;
$R^4$ is H or F;
$R^5$ is H or F; and
$R^6$ is C1-C6 alkyl or C1-C6 fluoroalkyl.

2. The compound according to claim 1, selected from the group consisting of:

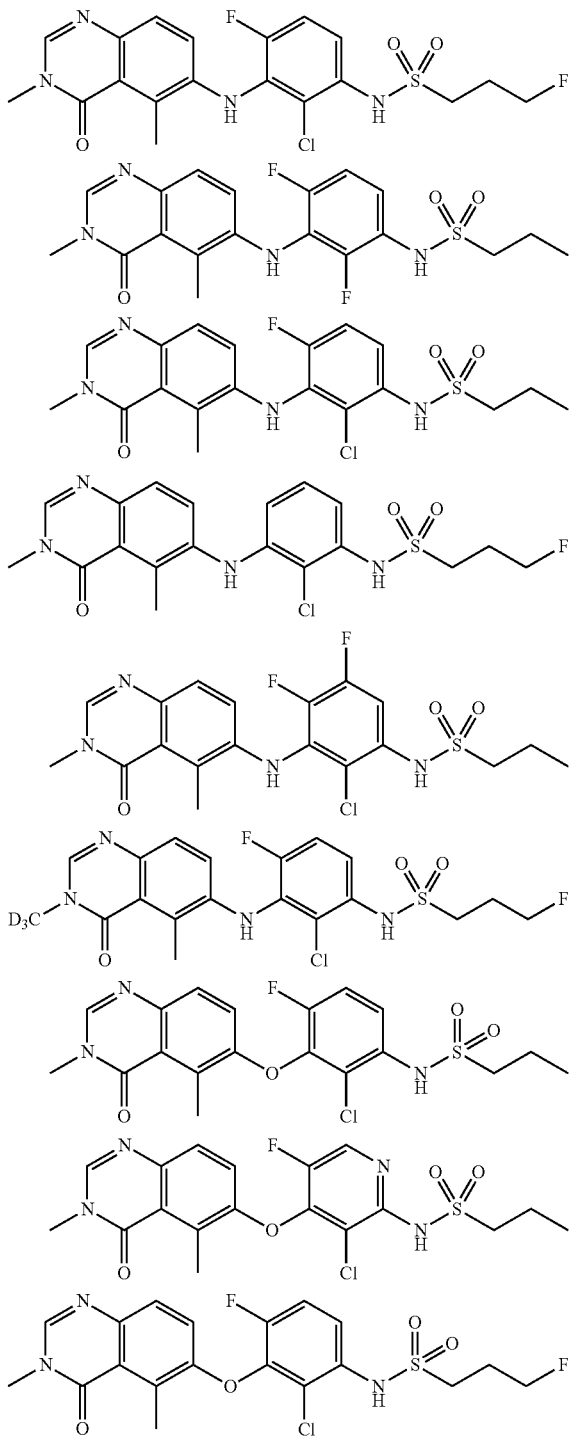

and a pharmaceutically acceptable salt thereof.

3. A compound which is
N-(2-chloro-3-((3,5-dimethyl-4-oxo-3,4-dihydroquinazolin-6-yl)amino)-4-fluorophenyl)-3-fluoropropane-1-sulfonamide having the structure

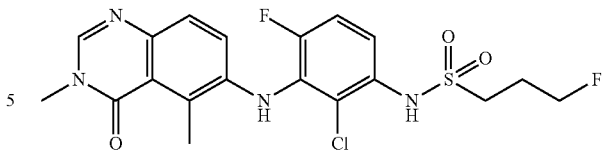

or a pharmaceutically acceptable salt thereof.

4. A compound which is a crystalline form of N-(2-chloro-3-((3,5-dimethyl-4-oxo-3,4-dihydroquinazolin-6-yl)amino)-4-fluorophenyl)-3-fluoropropane-1-sulfonamide Form B anhydrous.

5. A compound which is a crystalline form of N-(2-chloro-3-((3,5-dimethyl-4-oxo-3,4-dihydroquinazolin-6-yl)amino)-4-fluorophenyl)-3-fluoropropane-1-sulfonamide Form B anhydrous, characterized by having an XRPD pattern comprising peaks at 2θ values of 17.23, 22.93, 25.54, 26.22 and 27.69 (±0.2° 2θ).

6. A compound which is a crystalline form of N-(2-chloro-3-((3,5-dimethyl-4-oxo-3,4-dihydroquinazolin-6-yl)amino)-4-fluorophenyl)-3-fluoropropane-1-sulfonamide Form A anhydrous.

7. A compound which is crystalline form of N-(2-chloro-3-((3,5-dimethyl-4-oxo-3,4-dihydroquinazolin-6-yl)amino)-4-fluorophenyl)-3-fluoropropane-1-sulfonamide Form A anhydrous, characterized by having an XRPD pattern comprising peaks at 2θ values of 10.4, 10.8, 12.3, 14.2, 14.5, 16.3, 20.5, and 23.6 (±0.2° 2θ).

8. A pharmaceutical composition comprising a compound according to claim 1 in admixture with a pharmaceutically acceptable diluent or carrier.

9. A compound which is N-(2-chloro-3-((3,5-dimethyl-4-oxo-3,4-dihydroquinazolin-6-yl)amino)-4-fluorophenyl)-3-fluoropropane-1-sulfonamide having the structure

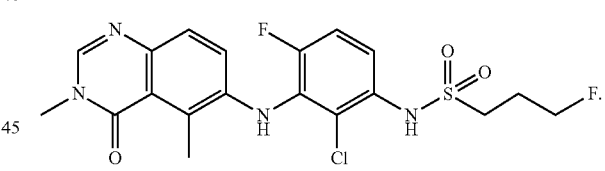

10. A pharmaceutical composition comprising a compound according to claim 3 in admixture with a pharmaceutically acceptable diluent or carrier.

11. A pharmaceutical composition comprising a compound according to claim 9 in admixture with a pharmaceutically acceptable diluent or carrier.

12. A pharmaceutical composition comprising a compound according to claim 4 in admixture with a pharmaceutically acceptable diluent or carrier.

13. A pharmaceutical composition comprising a compound according to claim 6 in admixture with a pharmaceutically acceptable diluent or carrier.

14. A pharmaceutically acceptable salt of N-(2-chloro-3-((3,5-dimethyl-4-oxo -3,4-dihydroquinazolin-6-yl)amino)-4-fluorophenyl)-3-fluoropropane-1-sulfonamide having the structure 331 332
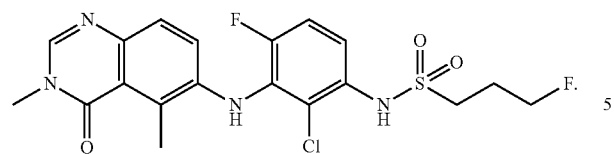
* * * * *